United States Patent
Hirst et al.

(10) Patent No.: US 6,713,474 B2
(45) Date of Patent: *Mar. 30, 2004

(54) PYRROLOPYRIMIDINES AS THERAPEUTIC AGENTS

(75) Inventors: Gavin C. Hirst, Malborough, MA (US); David Calderwood, Framingham, MA (US); Rainer Munschauer, Neustadt (DE); Lee D. Arnold, Westborough, MA (US); David N. Johnston, Nottingham (GB); Paul Rafferty, Nottingham (GB)

(73) Assignee: Abbott GmbH & Co. KG, Wiesbaden (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 9 days.

(21) Appl. No.: 09/537,167

(22) Filed: Mar. 29, 2000

(65) Prior Publication Data

US 2003/0153752 A1 Aug. 14, 2003

Related U.S. Application Data

(63) Continuation-in-part of application No. PCT/US00/21560, filed on Sep. 17, 1999.
(60) Provisional application No. 60/100,832, filed on Sep. 18, 1998, provisional application No. 60/100,833, filed on Sep. 18, 1998, provisional application No. 60/100,834, filed on Sep. 18, 1998, and provisional application No. 60/100,946, filed on Sep. 18, 1998.

(51) Int. Cl.$^7$ .................. C07D 487/04; A61K 31/505; A61D 35/00

(52) U.S. Cl. ............ 514/218; 514/228.5; 514/234.2; 514/252.16; 514/252.18; 514/252.19; 514/252.2; 514/258; 540/575; 544/61; 544/117; 544/230; 544/280

(58) Field of Search .................. 514/218, 228.5, 514/234.2, 252.16, 252.18, 252.19, 252.2, 258; 540/575; 544/61, 117, 230, 280

(56) References Cited

U.S. PATENT DOCUMENTS

| | | | |
|---|---|---|---|
| 4,140,851 A | 2/1979 | Townsend | 536/24 |
| 4,229,453 A | 10/1980 | Roth et al. | 424/251 |
| 4,892,865 A | 1/1990 | Townsend et al. | 514/43 |
| 4,927,830 A | 5/1990 | Townsend et al. | 514/258 |
| 4,968,686 A | 11/1990 | Townsend et al. | 514/258 |
| 4,996,206 A | 2/1991 | Taylor et al. | 514/258 |
| 5,028,608 A | 7/1991 | Taylor et al. | 514/258 |
| 5,248,775 A | 9/1993 | Taylor et al. | 544/280 |
| 5,254,687 A | 10/1993 | Taylor et al. | 544/280 |
| 5,344,932 A | 9/1994 | Taylor | 544/280 |
| 5,349,064 A | 9/1994 | Akimoto et al. | 544/280 |
| 5,416,211 A | 5/1995 | Barnett et al. | 544/280 |
| 5,593,997 A | 1/1997 | Dow et al. | 514/258 |
| 5,594,121 A | 1/1997 | Froehler et al. | 536/23.5 |
| 5,612,482 A | 3/1997 | Barnett et al. | 544/280 |
| 5,639,757 A | 6/1997 | Dow et al. | 514/261 |
| 5,644,057 A | 7/1997 | Yuan et al. | 544/280 |
| 5,644,058 A | 7/1997 | Barnett et al. | 544/280 |
| 5,686,457 A | 11/1997 | Traxler et al. | 514/258 |
| 5,721,356 A | 2/1998 | Ugarkar et al. | 536/27.2 |
| 5,726,302 A | 3/1998 | Ugarkar et al. | 536/27.13 |
| 5,763,596 A | 6/1998 | Boyer et al. | 536/27.13 |
| 5,763,597 A | 6/1998 | Ugarkar et al. | 536/27.13 |
| 5,834,469 A | 11/1998 | Elliott et al. | 514/249 |
| 6,001,839 A | * 12/1999 | Calderwood et al. | 514/258 |
| 6,051,577 A | * 4/2000 | Altman | 514/258 |

FOREIGN PATENT DOCUMENTS

| | | |
|---|---|---|
| DE | 30 36 390 A1 | 5/1982 |
| EP | 0 402 903 A1 | 12/1990 |
| EP | 0 496 617 A1 | 7/1992 |
| EP | 0 795 556 A1 | 9/1997 |
| WO | WO 94 17803 | 8/1994 |
| WO | WO 96 10028 | 4/1996 |

(List continued on next page.)

OTHER PUBLICATIONS

John D. Roberts and Marjorie C. Caserio, "Basic Principles of Organic Chemistry", Benjamin, New York, 1964, p 98.*

Hawley, Gessner, "The Condensed Chemical Dictonary", 1977, Van Nostrand, New York, p. 25.*

(List continued on next page.)

*Primary Examiner*—Mukund J. Shah
*Assistant Examiner*—Thomas McKenzie
(74) *Attorney, Agent, or Firm*—John D. Conway; Gayle B. O'Brien

(57) ABSTRACT

Chemical compounds having structural formula I

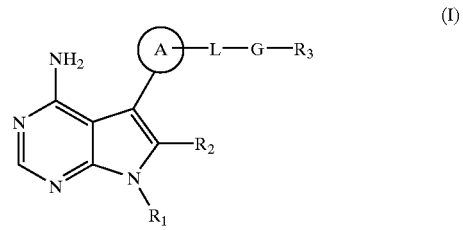

(I)

and physiologically acceptable salts and metabolites thereof, are inhibitors of serine/threonine and tyrosine kinase activity. Several of the kinases, whose activity is inhibited by these chemical compounds, are involved in immunologic, hyperproliferative, or angiogenic processes. Thus, these chemical compounds can ameliorate disease states where angiogenesis or endothelial cell hyperproliferation is a factor. These compounds can be used to treat cancer and hyper proliferative disorders, rheumatiod arthritis, disorders of the immune system, trasplant rejections and imflammatory disorders.

70 Claims, No Drawings

FOREIGN PATENT DOCUMENTS

| | | |
|---|---|---|
| WO | WO 96 40686 | 12/1996 |
| WO | WO 96/40705 | 12/1996 |
| WO | WO 96/40706 | 12/1996 |
| WO | WO 96/40707 | 12/1996 |
| WO | WO 97 02266 | 1/1997 |
| WO | WO 97/03069 | 1/1997 |
| WO | WO 97/13771 | 4/1997 |
| WO | WO 97 28161 | 8/1997 |
| WO | WO-97/28161 A1 * | 8/1997 |
| WO | WO-97/32879 A1 * | 9/1997 |
| WO | WO 97 32879 | 9/1997 |
| WO | WO 97 34895 | 9/1997 |
| WO | WO 97 49706 | 12/1997 |
| WO | WO 98 41525 | 9/1998 |
| WO | WO 00 17202 | 3/2000 |
| WO | WO 00 17203 | 3/2000 |

OTHER PUBLICATIONS

T.Y. Shen, "Non–Steroidal Anti–inflammatory Agents", in Burger's Medicinal Chemistry, 1981, John Wiley and Sons, New York, pp. 1205–1209.*

Salmon, S.E. et al "Principles of Cancer Therapy" in "Cecil Textbook of Medicine, 20th Edition", W.B. Saunders, Philadelphia, 1996, pp. 1036–1049.*

Balasubramanian, B.N. et al, "Recent Developments in Cancer Cytoxics" in "Annual Reports in Medicinal Chemistry, vol. 33", Academic Press, San Diego, 1998, pp. 151–159.*

Miller, D.M. "The Future of Oncology" in "Cecil Textbook of Medicine, 20th Edition", W.B. Saunders, Philadelphia, 1996, pp. 1071–1077.*

Murch, S.H. et al, Bailliere's, 8, 1994, 133–148.*

Polman, C.H. et al, BMJ 2000, 321, 490–4.*

Cohen, J.A. et al, J. Neuroimmun., 1999, 98 29–36.*

Khamashta, M.A. et al, Expert. Opin. Investig. Drugs, 2000, 9(7), 1581–93.*

Gittinger, J.W.. Eye Diseases in "Cecil Textbook of Medicine, 20th Edition", W.B. Saunders, Philadelphia, 1996, pp. 2174–2183.*

Hallegua, D. et al, Lupus, 2000, 9, 241–251.*

Hanke, J.H., et al., "Discovery of a Novel, Potent, and Src Family–selective Tyrosine Kinase Inhibitor; Study of Lck– and FynT–dependent T Cell Activation," *J Biol Chem.*, 271(2) :695–701, 1996.

Traxler, P.M., et al., "4– (Phenylamino) pyrrolopyrimidines: Potent and Selective, ATP Site Directed Inhibitors of the EGF–Receptor Protein Tyrosine Kinase," *J. Med. Chem.*, 39:2285–2292 (1996).

Showalter, H.D.H., et al., "Synthesis and SAR for a series of 4– substituted 1H–pyrimido [4,5–b] and 5H–pyrimido [5,4–b] indoles as EGF receptor tyrosine kinase inhibitors," Proceedings of the American Association for Cancer Research, vol. 37, Mar. 1996 (abstract).

Missbach, M., et al., "A Novel Inhibitor of the Tyrosine Kinase Src Suppresses Phosphorylation of Its Major Cellular Substrates and Reduces Bone Resorption In Vitro and in Rodent Models In Vivo," *Bone*, 24 (5) :437–449 (1999).

Dave, C.G., et al., "Synthesis & Biological Activity of Pyrrolo[2,3–d]pyrimidines," *Indian J. Chem.* 27B:778–780 (1988).

* cited by examiner

PYRROLOPYRIMIDINES AS THERAPEUTIC AGENTS

RELATED APPLICATIONS

This application is a Continuation-in-Part of International Application No.: PCT/US00/21560, filed Sep. 17, 1999, which claims the benefit of U.S. Provisional Application Nos. 60/100,832, filed Sep. 18, 1998; 60/100,833, filed Sep. 18, 1998; 60/100,834, filed Sep. 18, 1998, and 60/100,946, filed Sep. 18, 1998. The teachings of each of these referenced applications are expressly incorporated herein by reference in their entirety.

BACKGROUND OF THE INVENTION

There are at least 400 enzymes identified as protein kinases. These enzymes catalyze the phosphorylation of target protein substrates. The phosphorylation is usually a transfer reaction of a phosphate group from ATP to the protein substrate. The specific structure in the target substrate to which the phosphate is transferred is a tyrosine, serine or threonine residue. Since these amino acid residues are the target structures for the phosphoryl transfer, these protein kinase enzymmes are commonly referred to as tyrosine kinases or serine/threonine kinases.

The phosphorylation reactions, and counteracting phosphatase reactions, at the tyrosine, serine and threonine residues are involved in countless cellular processes that underlie responses to diverse intracellular signals (typically mediated through cellular receptors), regulation of cellular functions, and activation or deactivation of cellular processes. A cascade of protein kinases often participate in intracellular signal transduction and are necessary for the realization of these cellular processes. Because of their ubiquity in these processes, the protein kinases can be found as an integral part of the plasma membrane or as cytoplasmic enzymes or localized in the nucleus, often as components of enzyme complexes. In many instances, these protein kinases are an essential element of enzyme and structural protein complexes that determine where and when a cellular process occurs within a cell.

Protein Tyrosine Kinases. Protein tyrosine kinases (PTKs) are enzymes which catalyse the phosphorylation of specific tyrosine residues in cellular proteins. This post-translational modification of these substrate proteins, often enzymes themselves, acts as a molecular switch regulating cell proliferation, activation or differentiation (for review, see Schlessinger and Ullrich, 1992, *Neuron* 9:383–391). Aberrant or excessive PTK activity has been observed in many disease states including benign and malignant proliferative disorders as well as diseases resulting from inappropriate activation of the immune system (e.g., autoimmune disorders), allograft rejection, and graft vs. host disease. In addition, endothelial-cell specific receptor PTKs such as KDR and Tie-2 mediate the angiogenic process, and are thus involved in supporting the progression of cancers and other diseases involving inappropriate vascularization (e.g., diabetic retinopathy, choroidal neovascularization due to age-related macular degeneration, psoriasis, arthritis, retinopathy of prematurity, infantile hemangiomas).

Tyrosine kinases can be of the receptor-type (having extracellular, transmembrane and intracellular domains) or the non-receptor type (being wholly intracellular).

Receptor Tyrosine Kinases (RTKs). The RTKs comprise a large family of transmembrane receptors with diverse biological activities. At present, at least nineteen (19) distinct RTK subfamilies have been identified. The receptor tyrosine kinase (RTK) family includes receptors that are crucial for the growth and differentiation of a variety of cell types (Yarden and Ullrich, *Ann. Rev. Biochem.* 57:433–478, 1988; Ullrich and Schlessinger, *Cell* 61:243–254, 1990). The intrinsic function of RTKs is activated upon ligand binding, which results in phosphorylation of the receptor and multiple cellular substrates, and subsequently in a variety of cellular responses (Ullrich & Schlessinger, 1990, *Cell* 61:203–212). Thus, receptor tyrosine kinase mediated signal transduction is initiated by extracellular interaction with a specific growth factor (ligand), typically followed by receptor dimerization, stimulation of the intrinsic protein tyrosine kinase activity and receptor trans-phosphorylation. Binding sites are thereby created for intracellular signal transduction molecules and lead to the formation of complexes with a spectrum of cytoplasmic signaling molecules that facilitate the appropriate cellular response. (e.g., cell division, differentiation, metabolic effects, changes in the extracellular microenvironment) see Schlessinger and Ullrich, 1992, *Neuron* 9:1–20.

Proteins with SH2 (src homology-2) or phosphotyrosine binding (PTB) domains bind activated tyrosine kinase receptors and their substrates with high affinity to propagate signals into cell. Both of the domains recognize phosphotyrosine. (Fantl et al., 1992, *Cell* 69:413–423; Songyang et al., 1994, *Mol. Cell. Biol.* 14:2777–2785; Songyang et al., 1993, *Cell* 72:767–778; and Koch et al., 1991, *Science* 252:668–678; Shoelson, *Curr. Opin. Chem. Biol.* (1997), 1(2), 227–234; Cowburn, *Curr. Opin. Struct. Biol.* (1997), 7(6), 835–838). Several intracellular substrate proteins that associate with receptor tyrosine kinases (RTKs) have been identified. They may be divided into two principal groups: (1) substrates which have a catalytic domain; and (2) substrates which lack such a domain but serve as adapters and associate with catalytically active molecules (Songyang et al., 1993, *Cell* 72:767–778). The specificity of the interactions between receptors or proteins and SH2 or PTB domains of their substrates is determined by the amino acid residues immediately surrounding the phosphorylated tyrosine residue. For example, differences in the binding affinities between SH2 domains and the amino acid sequences surrounding the phosphotyrosine residues on particular receptors correlate with the observed differences in their substrate phosphorylation profiles (Songyang et al., 1993, *Cell* 72:767–778). Observations suggest that the function of each receptor tyrosine kinase is determined not only by its pattern of expression and ligand availability but also by the array of downstream signal transduction pathways that are activated by a particular receptor as well as the timing and duration of those stimuli. Thus, phosphorylation provides an important regulatory step which determines the selectivity of signaling pathways recruited by specific growth factor receptors, as well as differentiation factor receptors.

Several receptor tyrosine kinases such as FGFR-1, PDGFR, TIE-2 and c-Met, and growth factors that bind thereto, have been suggested to play a role in angiogenesis, although some may promote angiogenesis indirectly (Mustonen and Alitalo, *J. Cell Biol.* 129:895–898, 1995). One such receptor tyrosine kinase, known as "fetal liver kinase 1" (FLK-1), is a member of the type III subclass of RTKs. An alternative designation for human FLK-1 is "kinase insert domain-containing receptor" (KDR) (Terman et al., *Oncogene* 6:1677–83, 1991). Another alternative designation for FLK-1/KDR is "vascular endothelial cell growth factor receptor 2" (VEGFR-2) since it binds VEGF with high affinity. The murine version of FLK-1/VEGFR-2 has also been called NYK (Oelrichs et al, *Oncogene* 8(1): 11–15, 1993). DNAs encoding mouse, rat and human FLK-1 have been isolated, and the nucleotide and encoded amino acid sequences reported (Matthews et al., *Proc. Natl. Acad. Sci. USA*, 88:9026–30, 1991; Terman et al., 1991, supra; Terman et al., *Biochem. Biophys. Res. Comm.* 187:1579–86, 1992; Sarzani et al., supra; and Millauer et al., *Cell* 72:835–846, 1993). Numerous studies such as those reported in Millauer et al., supra, suggest that VEGF and FLK-1/KDR/VEGFR-2 are a ligand-receptor pair that play an important role in the proliferation of vascular endothelial cells, and formation and sprouting of blood vessels, termed vasculogenesis and angiogenesis, respectively.

Another type III subclass RTK designated "fms-like tyrosine kinase-1" (Flt-1) is related to FLK-1/KDR (DeVries et al. *Science* 255;989–991, 1992; Shibuya et al., *Oncogene* 5:519–524, 1990). An alternative designation for Flt-1 is "vascular endothelial cell growth factor receptor 1" (VEGFR-1). To date, members of the FLK-1/KDR/VEGFR-2 and Flt-1/VEGFR-1 subfamilies have been found expressed primarily on endothelial cells. These subclass members are specifically stimulated by members of the vascular endothelial cell growth factor (VEGF) family of ligands (Klagsburn and D'Amore, *Cytokine & Growth Factor Reviews* 7: 259–270, 1996). Vascular endothelial cell growth factor (VEGF) binds to Flt-1 with higher affinity than to FLK-1/KDR and is mitogenic toward vascular endothelial cells (Terman et al., 1992, supra; Mustonen et al. supra; DeVries et al., supra). Flt-1 is believed to be essential for endothelial organization during vascular development. Flt-1 expression is associated with early vascular development in mouse embryos, and with neovascularization during wound healing (Mustonen and Alitalo, supra). Expression of Flt-1 in monocytes, osteoclasts, and osteoblasts, as well as in adult tissues such as kidney glomeruli suggests an additional function for this receptor that is not related to cell growth (Mustonen and Alitalo, supra).

As previously stated, recent evidence suggests that VEGF plays a role in the stimulation of both normal and pathological angiogenesis (Jakeman et al., *Endocrinology* 133: 848–859, 1993; Kolch et al., *Breast Cancer Research and Treatment* 36: 139–155, 1995; Ferrara et al., *Endocrine Reviews* 18(1); 4–25, 1997; Ferrara et al., Regulation of Angiogenesis (ed. L. D. Goldberg and E. M. Rosen), 209–232, 1997). In addition, VEGF has been implicated in the control and enhancement of vascular permeability (Connolly, et al., *J. Biol. Chem.* 264: 20017–20024, 1989; Brown et al., Regulation of Angiogenesis (ed. L. D. Goldberg and E. M. Rosen), 233–269, 1997). Different forms of VEGF arising from alternative splicing of mRNA have been reported, including the four species described by Ferrara et al. (*J. Cell. Biochem.* 47:211–218, 1991). Both secreted and predominantly cell-associated species of VEGF have been identified by Ferrara et al. supra, and the protein is known to exist in the form of disulfide linked dimers.

Several related homologs of VEGF have recently been identified. However, their roles in normal physiological and disease processes have not yet been elucidated. In addition, the members of the VEGF family are often coexpressed with VEGF in a number of tissues and are, in general, capable of forming heterodimers with VEGF. This property likely alters the receptor specificity and biological effects of the heterodimers and further complicates the elucidation of their specific functions as illustrated below (Korpelainen and Alitalo, *Curr. Opin. Cell Biol.*, 159–164, 1998 and references cited therein).

Placenta growth factor (PlGF) has an amino acid sequence that exhibits significant homology to the VEGF sequence (Park et al., *J. Biol. Chem.* 269:25646–54, 1994; Maglione et al. *Oncogene* 8:925–31, 1993). As with VEGF, different species of PlGF arise from alternative splicing of mRNA, and the protein exists in dimeric form (Park et al., supra). PlGF-1 and PlGF-2 bind to Flt-1 with high affinity, and PlGF-2 also avidly binds to neuropilin-1 (Migdal et al, *J. Biol. Chem.* 273 (35): 22272–22278), but neither binds to FLK-1/KDR (Park et al., supra). PlGF has been reported to potentiate both the vascular permeability and mitogenic effect of VEGF on endothelial cells when VEGF is present at low concentrations (purportedly due to heterodimer formation) (Park et al., supra).

VEGF-B is produced as two isoforms (167 and 185 residues) that also appear to bind Flt-1/VEGFR-1. It may play a role in the regulation of extracellular matrix degradation, cell adhesion, and migration through modulation of the expression and activity of urokinase type plasminogen activator and plasminogen activator inhibitor 1 (Pepper et al, *Proc. Natl. Acad. Sci. U.S.A.* (1998), 95(20): 11709–11714).

VEGF-C was originally cloned as a ligand for VEGFR-3/Flt-4 which is primarily expressed by lymphatic endothelial cells. In its fully processed form, VEGF-C can also bind KDR/VEGFR-2 and stimulate proliferation and migration of endothelial cells in vitro and angiogenesis in in vivo models (Lymboussaki et al, *Am. J. Pathol.* (1998), 153(2): 395–403; Witzenbichler et al, *Am. J. Pathol.* (1998), 153(2), 381–394). The transgenic overexpression of VEGF-C causes proliferation and enlargement of only lymphatic vessels, while blood vessels are unaffected. Unlike VEGF, the expression of VEGF-C is not induced by hypoxia (Ristimaki et al, *J. Biol. Chem.* (1998), 273(14),8413–8418).

The most recently discovered VEGF-D is structurally very similar to VEGF-C. VEGF-D is reported to bind and activate at least two VEGFRs, VEGFR-3/Flt-4 and KDR/VEGFR-2. It was originally cloned as a c-fos inducible mitogen for fibroblasts and is most prominently expressed in the mesenchymal cells of the lung and skin (Achen et al, *Proc. Natl. Acad. Sci. U.S.A.* (1998), 95(2), 548–553 and references therein).

As for VEGF, VEGF-C and VEGF-D have been claimed to induce increases in vascular permeability in vivo in a Miles assay when injected into cutaneous tissue (PCT/US97/14696; WO98/07832, Witzenbichler et al., supra). The physiological role and significance of these ligands in modulating vascular hyperpermeability and endothelial responses in tissues where they are expressed remains uncertain.

There has been recently reported a virally encoded, novel type of vascular endothelial growth factor, VEGF-E (NZ-7 VEGF), which preferentially utilizes KDR/Flk-1 receptor and carries a potent mitotic activity without heparin-binding domain (Meyer et al, *EMBO J.* (1999), 18(2), 363–374; Ogawa et al, *J. Biol. Chem.* (1998), 273(47), 31273–31282.). VEGF-E sequences possess 25% homology to mammalian VEGF and are encoded by the parapoxvirus Orf virus (OV). This parapoxvirus that affects sheep and goats and occasionally, humans, to generate lesions with angiogenesis. VEGF-E is a dimer of about 20 kDa with no basic domain nor affinity for heparin, but has the characteristic cysteine knot motif present in all mammalian VEGFs, and was surprisingly found to possess potency and bioactivities similar to the heparin-binding VEGF165 isoform of VEGF-A, i.e. both factors stimulate the release of tissue factor (TF), the proliferation, chemotaxis and sprouting of cultured vascular endothelial cells in vitro and angiogenesis in vivo. Like VEGF165, VEGF-E was found to bind with high affinity to VEGF receptor-2 (KDR) resulting in receptor autophosphorylation and a biphasic rise in free intracellular Ca2+ concentrations, while in contrast to VEGF165, VEGF-E did not bind to VEGF receptor-1 (Flt-1).

Based upon emerging discoveries of other homologs of VEGF and VEGFRs and the precedents for ligand and receptor heterodimerization, the actions of such VEGF homologs may involve formation of VEGF ligand heterodimers, and/or heterodimerization of receptors, or binding to a yet undiscovered VEGFR (Witzenbichler et al., supra). Also, recent reports suggest neuropilin-1 (Migdal et al, supra) or VEGFR-3/Flt-4 (Witzenbichler et al., supra), or receptors other than KDR/VEGFR-2 may be involved in the induction of vascular permeability (Stacker, S. A., Vitali, A., Domagala, T., Nice, E., and Wilks, A. F., "Angiogenesis and Cancer" Conference, Amer. Assoc. Cancer Res., January 1998, Orlando, Fla.; Williams, *Diabetelogia* 40: S118–120 (1997)).

Tie-2 (TEK) is a member of a recently discovered family of endothelial cell specific receptor tyrosine kinases which is involved in critical angiogenic processes, such as vessel branching, sprouting, remodeling, maturation and stability. Tie-2 is the first mammalian receptor tyrosine kinase for which both agonist ligand(s) (e.g., Angiopoietin1 ("Ang1"), which stimulates receptor autophosphorylation and signal transduction), and antagonist ligand(s) (e.g., Angiopoietin2 ("Ang2")), have been identified. Knock-out and transgenic manipulation of the expression of Tie-2 and its ligands indicates tight spatial and temporal control of Tie-2 signaling is essential for the proper development of new vasculature. The current model suggests that stimulation of Tie-2 kinase by the Ang1 ligand is directly involved in the branching, sprouting and outgrowth of new vessels, and recruitment and interaction of periendothelial support cells important in maintaining vessel integrity and inducing quiescence. The absence of Ang1 stimulation of Tie-2 or the inhibition of Tie-2 autophosphorylation by Ang2, which is produced at high levels at sites of vascular regression, may cause a loss in vascular structure and matrix contacts resulting in endothelial cell death, especially in the absence of growth/survival stimuli. The situation is however more complex, since at least two additional Tie-2 ligands (Ang3 and Ang4) have recently been reported, and the capacity for heterooligomerization of the various agonistic and antagonistic angiopoietins, thereby modifying their activity, has been demonstrated. Targeting Tie-2 ligand-receptor interactions as an antiangiogenic therapeutic approach is thus less favored and a kinase inhibitory strategy preferred.

The soluble extracellular domain of Tie-2 ("ExTek") can act to disrupt the establishment of tumor vasculature in a breast tumor xenograft and lung metastasis models and in tumor-cell mediated ocular neovasculatization. By adenoviral infection, the in vivo production of mg/ml levels ExTek in rodents may be achieved for 7–10 days with no adverse side effects. These results suggest that disruption of Tie-2 signaling pathways in normal healthy animals may be well tolerated. These Tie-2 inhibitory responses to ExTek may be a consequence sequestration of ligand(s) and/or generation of a nonproductive heterodimer with full-length Tie-2.

Recently, significant upregulation of Tie-2 expression has been found within the vascular synovial pannus of arthritic joints of humans, consistent with a role in the inappropriate neovascularization. This finding suggests that Tie-2 plays a role in the progression of rheumatoid arthritis. Point mutations producing constitutively activated forms of Tie-2 have been identified in association with human venous malformation disorders. Tie-2 inhibitors are, thereful, useful in treating such disorders, and in other situations of inappropriate neovascularization.

The Non-Receptor Tyrosine Kinases. The non-receptor tyrosine kinases represent a collection of cellular enzymes which lack extracellular and transmembrane sequences. At present, over twenty-four individual non-receptor tyrosine kinases, comprising eleven (11) subfamilies (Src, Frk, Btk, Csk, Abl, Zap70, Fes/Fps, Fak, Jak, Ack and LIMK) have been identified. At present, the Src subfamily of non-receptor tyrosine kinases is comprised of the largest number of PTKs and include Src, Yes, Fyn, Lyn, Lck, Blk, Hck, Fgr and Yrk. The Src subfamily of enzymes has been linked to oncogenesis and immune responses. A more detailed discussion of non-receptor tyrosine kinases is provided in Bohlen, 1993, *Oncogene* 8:2025–2031, which is incorporated herein by reference.

Many of the tyrosine kinases, whether an RTK or non-receptor tyrosine kinase, have been found to be involved in cellular signaling pathways involved in numerous pathogenic conditions, including cancer, psoriasis, and other hyperproliferative disorders or hyper-immune responses.

Development of Compounds to Modulate the PTKs. In view of the surmised importance of PTKs to the control, regulation, and modulation of cell proliferation, the diseases and disorders associated with abnormal cell proliferation, many attempts have been made to identify receptor and non-receptor tyrosine kinase "inhibitors" using a variety of approaches, including the use of mutant ligands (U.S. Pat. No. 4,966,849), soluble receptors and antibodies (Application No. WO 94/10202; Kendall & Thomas, 1994, *Proc. Natl. Acad. Sci* 90:10705–09; Kim et al., 1993, *Nature* 362:841–844), RNA ligands (Jellinek, et al., *Biochemistry* 33:10450–56; Takano, et al., 1993, *Mol. Bio. Cell* 4:358A; Kinsella, et al. 1992, *Exp. Cell Res.* 199:56–62; Wright, et al., 1992, *J. Cellular Phys.* 152:448–57) and tyrosine kinase inhibitors (WO 94/03427; WO 92/21660; WO 91/15495; WO 94/14808; U.S. Pat. No. 5,330,992; Mariani, et al., 1994, *Proc. Am. Assoc. Cancer Res.* 35:2268).

More recently, attempts have been made to identify small molecules which act as tyrosine kinase inhibitors. For example, bis monocyclic, bicyclic or heterocyclic aryl compounds (PCT WO 92/20642) and vinylene-azaindole derivatives (PCT WO 94/14808) have been described generally as tyrosine kinase inhibitors. Styryl compounds (U.S. Pat. No. 5,217,999), styryl-substituted pyridyl compounds (U.S. Pat. No. 5,302,606), certain quinazoline derivatives (EP Application No. 0 566 266 A1; *Expert Opin. Ther. Pat.* (1998), 8(4): 475–478), selenoindoles and selenides (PCT WO 94/03427), tricyclic polyhydroxylic compounds (PCT WO 92/21660) and benzylphosphonic acid compounds (PCT WO 91/15495) have been described as compounds for use as tyrosine kinase inhibitors for use in the treatment of cancer. Anilinocinnolines (PCT WO97/34876) and quinazoline derivative compounds (PCT WO97/22596; PCT WO97/42187) have been described as inhibitors of angiogenesis and vascular permeability.

In addition, attempts have been made to identify small molecules which act as serine/threonine kinase inhibitors. For example, bis(indolylmaleimide) compounds have been described as inhibiting particular PKC serine/threonine kinase isoforms whose signal transducing function is associated with altered vascular permeability in VEGF-related diseases (PCT WO97/40830; PCT WO97/40831).

Plk-1 Kinase Inhibitors

Plk-1 is a serine/threonine kinase which is an important regulator of cell cycle progression. It plays critical roles in the assembly and the dynamic function of the mitotic spindle apparatus. Plk-1 and related kinases have also been shown to be closely involved in the activation and inactivation of other cell cycle regulators, such as cyclin-dependent kinases. High levels of Plk-1 expression are associated with cell proliferation activities. It is often found in malignant tumors of various origins. Inhibitors of Plk-1 are expected to block cancer cell proliferation by disrupting processes involving mitotic spindles and inappropriately activated cyclin-dependent kinases.

Cdc2/Cyclin B Kinase Inhibitors (Cdc2 is Also Known as cdk1)

Cdc2/cyclin B is another serine/threonine kinase enzyme which belongs to the cyclin-dependent kinase (cdks) family. These enzymes are involved in the critical transition between various phases of cell cycle progression. It is believed that uncontrolled cell proliferation, which is the hallmark of cancer is dependent upon elevated cdk activities in these cells. The inhibition of elevated cdk activities in cancer cells by cdc2/cyclin B kinase inhibitors could suppress proliferation and may restore the normal control of cell cycle progression.

The regulation of CDK activation is complex, but requires the association of the CDK with a member of the cyclin family of regulatory subunits (Draetta, *Trends in Cell Biology*, 3:287–289 (1993)); Murray and Kirschner, *Nature*, 339:275–280 (1989); Solomon et al., *Molecular Biology of the Cell*, 3:13–27 (1992)). A further level of regulation occurs through both activating and inactivating phosphorylations of the CDK subunit (Draetta, *Trends in Cell Biology*, 3:287–289 (1993)); Murray and Kirschner, *Nature*, 339:275–280 (1989); Solomon et al., *Molecular Biology of the Cell*, 3:13–27 (1992); Ducommun et al., *EMBO Journal*, 10:3311–3319 (1991); Gautier et al., *Nature* 339:626–629 (1989); Gould and Nurse, *Nature*, 342:39–45 (1989); Krek and Nigg, *EMBO Journal*, 10:3331–3341 (1991); Solomon et al., *Cell*, 63:1013–1024 (1990)). The coordinate activation and inactivation of different cyclin/CDK complexes is necessary for normal progression through the cell cycle (Pines, *Trends in Biochemical Sciences*, 18:195–197 (1993); Sherr, *Cell*, 73:1059–1065 (1993)). Both the critical G1-S and G2-M transitions are controlled by the activation of different cyclin/CDK activities. In G1, both cyclin D/CDK4 and cyclin E/CDK2 are thought to mediate the onset of S-phase (Matsushima et al., *Molecular & Cellular Biology*, 14:2066–2076 (1994); Ohtsubo and Roberts, *Science*, 259:1908–1912 (1993); Quelle et al., *Genes & Development*, 7:1559–1571 (1993); Resnitzky et al., *Molecular & Cellular Biology*, 14:1669–1679 (1994)). Progression through S-phase requires the activity of cyclin A/CDK2 (Girard et al., *Cell*, 67:1169–1179 (1991); Pagano et al., *EMBO Journal*, 11:961–971 (1992); Rosenblatt et al., *Proceedings of the National Academy of Science USA*, 89:2824–2828 (1992); Walker and Maller, *Nature*, 354:314–317 (1991); Zindy et al., *Biochemical & Biophysical Research Communications*, 182:1144–1154 (1992)) whereas the activation of cyclin A/cdc2 (CDK1) and cyclin B/cdc2 are required for the onset of metaphase (Draetta, *Trends in Cell Biology*, 3:287–289 (1993)); Murray and Kirschner, *Nature*, 339:275–280 (1989); Solomon et al., *Molecular Biology of the Cell*, 3:13–27 (1992); Girard et al., *Cell*, 67:1169–1179 (1991); Pagano et al., *EMBO Journal*, 11:961–971 (1992); Rosenblatt et al., *Proceedings of the National Academy of Science USA*, 89:2824–2828 (1992); Walker and Maller, *Nature*, 354:314–317 (1991); Zindy et al., *Biochemical & Biophysical Research Communications*, 182:1144–1154 (1992)). It is not surprising, therefore, that the loss of control of CDK regulation is a frequent event in hyperproliferative diseases and cancer. (Pines, *Current Opinion in Cell Biology*, 4:144–148 (1992); Lees, *Current Opinion in Cell Biology*, 7:773–780 (1995); Hunter and Pines, *Cell*, 79:573–582 (1994)).

Inhibitors of kinases involved in mediating or maintaining disease states represent novel therapies for these disorders. Examples of such kinases include, but are not limited to: (1) inhibition of c-Src (Brickell, *Critical Reviews in Oncogenesis*, 3:401–406 (1992); Courtneidge, *Seminars in Cancer Biology*, 5:236–246 (1994), raf (Powis, *Pharmacology & Therapeutics*, 62:57–95 (1994)) and the cyclin-dependent kinases (CDKs) 1, 2 and 4 in cancer (Pines, *Current Opinion in Cell Biology*, 4:144–148 (1992); Lees, *Current Opinion in Cell Biology*, 7:773–780 (1995); Hunter and Pines, *Cell*, 79:573–582 (1994)), (2) inhibition of CDK2 or PDGF-R kinase in restenosis (Buchdunger et al., *Proceedings of the National Academy of Science USA*, 92:2258–2262 (1995)), (3) inhibition of CDK5 and GSK3 kinases in Alzheimers (Hosoi et al., *Journal of Biochemistry (Tokyo)*, 117:741–749 (1995); Aplin et al., *Journal of Neurochemistry*, 67:699–707 (1996), (4) inhibition of c-Src kinase in osteoporosis (Tanaka et al., *Nature*, 383:528–531 (1996), (5) inhibition of GSK-3 kinase in type-2 diabetes (Borthwick et al., *Biochemical & Biophysical Research Communications*, 210:738–745 (1995), (6) inhibition of the p38 kinase in inflammation (Badger et al., *The Journal of Pharmacology and Experimental Therapeutics*, 279:1453–1461 (1996)), (7) inhibition of VEGF-R 1–3 and TIE-1 and -2 kinases in diseases which involve angiogenesis (Shawver et al., *Drug Discovery Today*, 2:50–63 (1997)), (8) inhibition of UL97 kinase in viral infections (He et al., *Journal of Virology*, 71:405–411 (1997)), (9) inhibition of CSF-1R kinase in bone and hematopoetic diseases (Myers et al., *Bioorganic & Medicinal Chemistry Letters*, 7:421–424 (1997), and (10) inhibition of Lck kinase in autoimmune diseases and transplant rejection (Myers et al., *Bioorganic & Medicinal Chemistry Letters*, 7:417–420 (1997)).

It is additionally possible that inhibitors of certain kinases may have utility in the treatment of diseases when the kinase is not misregulated, but it nonetheless essential for maintenance of the disease state. In this case, inhibition of the kinase activity would act either as a cure or palliative for these diseases. For example, many viruses, such as human papilloma virus, disrupt the cell cycle and drive cells into the S-phase of the cell cycle (Vousden, *FASEB Journal*, 7:8720879 (1993)). Preventing cells from entering DNA synthesis after viral infection by inhibition of essential S-phase initiating activities such as CDK2, may disrupt the virus life cycle by preventing virus replication. This same principle may be used to protect normal cells of the body from toxicity of cycle-specific chemotherapeutic agents (Stone et al., *Cancer Research*, 56:3199–3202 (1996); Kolin el al., *Journal of Cellular Biochemistry*, 54:44–452 (1994)). Inhibition of CDKs 2 or 4 will prevent progression into the cycle in normal cells and limit tile toxicity of cytotoxics which act in S-phase, G2 or mitosis. Furthermore, CDK2/cyclin E activity has also been shown to regulate NF-kB. Inhibition of CDK2 activity stimulates NF-kB-dependent gene expression, an event mediated through interactions with the p300 coactivator (Perkins et al., *Science*, 275:523–527 (1997)). NF-kB regulates genes involved in inflammatory responses (such as heniatopoetic growth factors, chemokines and leukocyte adhesion molecules) (Baeuerle and Henkel, *Annual Review of Immunology*, 12:141–179 (1994)) and may be involved in the suppression of apoptotic signals within the cell (Beg and Baltimore, *Science*, 274:782–784 (1996); Wang et al., *Science*, 274:784–787 (1996); Van Antwerp et al., *Science*, 274:787–789 (1996)). Thus, inhibition of CDK2 may suppress apoptosis induced by cytotoxic drugs via a mechanism which involves NF-kB. This therefore suggests that inhibition of CDK2 activity may also have utility in other cases where regulation of NF-kB plays a role in etiology of disease. A further example may be take from fungal infections: Aspergillosis is a common infection in immune-compromised patients (Armstrong, *Clinical Infectious Diseases*, 16:1–7 (1993)). Inhibition of the Aspergilus kinases Cdc2/CDC28 or Nim A (Osmani et al., *EMBO Journal*, 10:2669–2679 (1991); Osmani et al., *Cell*, 67:283–291 (1991)) may cause arrest or death in the fungi, improving the therapeutic outcome for patients with these infections.

The identification of effective small compounds which specifically inhibit signal transduction and cellular proliferation by modulating the activity of receptor and non-receptor tyrosine and serine/threonine kinases to regulate and modulate abnormal or inappropriate cell proliferation, differentiation, or metabolism is therefore desirable. In particular, the identification of methods and compounds that specifically inhibit the function of a tyrosine kinase which is essential for angiogenic processes or the formation of vascular hyperpermeability leading to edema, ascites, effusions, exudates, and macromolecular extravasation and matrix deposition as well as associated disorders would be beneficial.

SUMMARY OF THE INVENTION

The present invention provides compounds of Formula I,

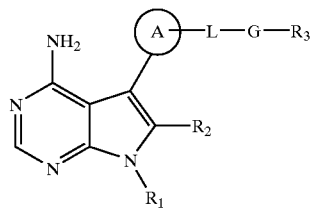

(I)

and pharmaceutically acceptable salts thereof.

In Formula I, Ring A is a six membered aromatic ring or a five or six membered heteroaromatic ring. Ring A is optionally substituted such as with one or more of the following substituents: a substituted or unsubstituted aliphatic group, a halogen, a substituted or unsubstituted aromatic group, substituted or unsubstituted heteroaromatic group, substituted or unsubstituted cycloalkyl, substituted or unsubstituted heterocycloalkyl, substituted or unsubstituted aralkyl, substituted or unsubstituted heteroaralkyl, cyano, nitro, —NR$_4$R$_5$, —C(O)$_2$H, —OH, a substituted or unsubstituted alkoxycarbonyl, —C(O)$_2$-haloalkyl, a substituted or unsubstituted alkylthio ether, a substituted or unsubstituted alkylsulfoxide, a substituted or unsubstituted alkylsulfone, a substituted or unsubstituted arylthio ether, a substituted or unsubstituted arylsulfoxide, a substituted or unsubstituted arylsulfone, a substituted or unsubstituted alkyl carbonyl, —C(O)-haloalkyl, a substituted or unsubstituted aliphatic ether, a substituted or unsubstituted aromatic ether, carboxamido, tetrazolyl, trifluoromethylsulphonamido, trifluoromethylcarbonylamino, a substituted or unsubstituted alkynyl, a substituted or unsubstituted alkyl amido, a substituted or unsubstituted aryl amido, a substituted or unsubstituted styryl and a substituted or unsubstituted aralkyl amido.

L is one of the following linkers: —O—; —S—; —S(O)—; —S(O)$_2$—; —N(R)—; —N(C(O)OR)—; —N(C(O)R)—; —N(SO$_2$R)—; —CH$_2$O—; —CH$_2$S—; —CH$_2$N(R)—; —CH(NR)—; —CH$_2$N(C(O)R))—; —CH$_2$N(C(O)OR)—; —CH$_2$N(SO$_2$R)—; —CH(NHR)—; —CH(NHC(O)R)—; —CH(NHSO$_2$R)—; —CH(NHC(O)OR)—; —CH(OC(O)R)—; —CH(OC(O)NHR)—; —CH=CH—; —C(=NOR)—; —C(O)—; —CH(OR)—; —C(O)N(R)—; —N(R)C(O)—; —N(R)S(O)—; —N(R)S(O)$_2$—; —OC(O)N(R)—; —N(R)C(O)N(R)—; —NRC(O)O—; —S(O)N(R)—; —S(O)$_2$N(R)—; N(C(O)R)S(O)—; N(C(O)R)S(O)$_2$—; —N(R)S(O)N(R)—; —N(R)S(O)$_2$N(R)—; —C(O)N(R)C(O)—; —S(O)N(R)C(O)—; —S(O)$_2$N(R)C(O)—; —OS(O)N(R)—; —OS(O)$_2$N(R)—; —N(R)S(O)O—; —N(R)S(O)$_2$O—; —N(R)S(O)C(O)—; —N(R)S(O)$_2$C(O)—; —SON(C(O)R)—; —SO$_2$N(C(O)R)—; —N(R)SON(R)—; —N(R)SO$_2$N(R)—; —C(O)O—; —N(R)P(OR')O—; —N(R)P(OR')—; —N(R)P(O)(OR')O—; —N(R)P(O)(OR')—; —N(C(O)R)P(OR')O—; —N(C(O)R)P(OR')—; —N(C(O)R)P(O)(OR')O—, —N(C(O)R)P(OR')—, CH(R)S(O)—; —CH(R)S(O)$_2$—; —CH(R)N(C(O)OR)—; —CH(R)N(C(O)R)—; —CH(R)N(SO$_2$R); —CH(R)O—; —CH(R)S—; —CH(R)N(R)—; —CH(R)N(C(O)R))—; —CH(R)N(C(O)OR)—; —CH(R)N(SO$_2$R)—; —CH(R)C(=NOR)—; —CH(R)C(O)—; —CH(R)CH(OR)—; —CH(R)C(O)N(R)—; —CH(R)N(R)C(O)—; —CH(R)N(R)S(O)—; —CH(R)N(R)S(O)$_2$—; —CH(R)OC(O)N(R)—; —CH(R)N(R)C(O)N(R)—; —CH(R)NRC(O)O—; —CH(R)S(O)N(R)—; —CH(R)S(O)$_2$N(R)—; —CH(R)N(C(O)R)S(O)—; —CH(R)N(C(O)R)S(O)$_2$—; —CH(R)N(R)S(O)N(R)—; —CH(R)N(R)S(O)$_2$N(R)—; —CH(R)C(O)N(R)C(O)—; —CH(R)S(O)N(R)C(O)—; —CH(R)S(O)$_2$N(R)C(O)—; —CH(R)OS(O)N(R)—; —CH(R)OS(O)$_2$N(R)—; —CH(R)N(R)S(O)O—; —CH(R)N(R)S(O)$_2$O—; —CH(R)N(R)S(O)C(O)—; —CH(R)N(R)S(O)$_2$C(O)—; —CH(R)SON(C(O)R)—; —CH(R)SO$_2$N(C(O)R)—; —CH(R)N(R)SON(R)—; —CH(R)N(R)SO$_2$N(R)—; —CH(R)C(O)O—; —CH(R)N(R)P(OR')O—; —CH(R)N(R)P(OR')—; —CH(R)N(R)P(O)(OR')O—; —CH(R)N(R)P(O)(OR')—; —CH(R)N(C(O)R)P(OR')O—; —CH(R)N(C(O)R)P(OR')—; —CH(R)N(C(O)R)P(O)(OR')O— or —CH(R)N(C(O)R)P(OR')—. R and R' are each, independently, —H, an acyl group, a substituted or unsubstituted aliphatic group, a substituted or unsubstituted aromatic group, a substituted or unsubstituted heteroaromatic group, or a substituted or unsubstituted cycloalkyl group.

Alternatively, L is —R$_b$N(R)S(O)$_2$—, —R$_b$N(R)P(O)—, or —RbN(R)P(O)O—. R$_b$ is an alkylene group which when taken together with the sulphonamide, phosphinamide, or phosphonamide group to which it is bound forms a five or six membered ring fused to ring A.

Alternatively, L is represented by one of the following structural formulas:

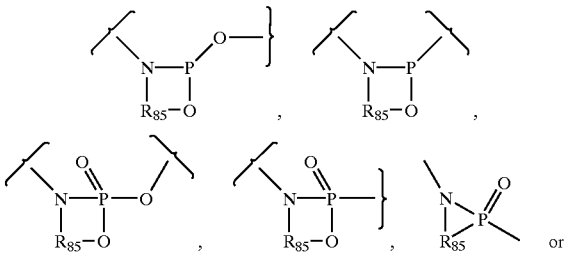

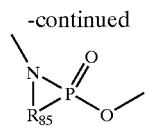

R$_{85}$ taken together with the phosphinamide, or phosphonamide is a 5-, 6-, or 7-membered, aromatic, heteroaromatic or heterocycloalkyl ring system.

In Formula I, R$_1$ is a substituted aliphatic group, a substituted cycloalkyl, a substituted bicycloalkyl, a substituted cycloalkenyl, an optionally substituted aromatic group, an optionally substituted heteroaromatic group, an optionally substituted heteroaralkyl, an optionally substituted heterocycloalkyl, an optionally substituted heterobicycloalkyl, an optionally substituted alkylarnindo, and optionally substituted arylamido, an optionally substituted —S(O)$_2$-alkyl or optionally substituted —S(O)$_2$-cycloalkyl, a —C(O)-alkyl or an optionally substituted —C(O)-alkyl.

R$_1$ can be substituted with one or more substituents. Preferably, R$_1$ is substituted with a substituted or unsubstituted aliphatic group, a substituted or unsubstituted aromatic group, a substituted or unsubstituted heteroaromatic, a substituted or unsubstituted aralkyl, a substituted or unsubstituted heteroaralkyl, a substituted or unsubstituted cycloalkyl, a substituted or unsubstituted heterocycloalkyl, a substituted or unsubstituted aromatic ether, a substituted or unsubstituted aliphatic ether, a substituted or unsubstituted alkoxycarbonyl, a substituted or unsubstituted alkylcarbonyl, a substituted or unsubstituted arylcarbonyl, a substituted or unsubstituted heteroarylcarbonyl, substituted or unsubstituted aryloxycarbonyl, —OH, a substituted or unsubstituted aminocarbonyl, an oxime, a substituted or unsubstituted azabicycloalkyl, heterocycloalkyl, oxo, aldehyde, a substituted or unsubstituted alkyl sulfonamido group, a substituted or unsubstituted aryl sulfonamido group, a substituted or unsubstituted bicycloalkyl, a substituted or unsubstituted heterobicycloalkyl, cyano, —NH$_2$, an alkylamino, ureido, thioureido and —B—E.

B is a substituted or unsubstituted cycloalkyl, a substituted or unsubstituted heterocycloalkyl, a substituted or unsubstituted aromatic, a substituted or unsubstituted heteroaromatic, an alkylene, an aminoalkyl, an alkylenecarbnonyl, or an aminoalkylcarbonyl.

E is a substituted or unsubstituted azacycloalkyl, a substituted or unsubstituted azacycloalkylcarbonyl, a substituted or unsubstituted azacycloalkylsulfonyl, a substituted or unsubstituted azacycloalkylalkyl, a substituted or unsubstituted heteroaryl, a substituted or unsubstituted heteroarylcarbonyl, a substituted or unsubstituted heteroarylsulfonyl, a substituted or unsubstituted heteroaralkyl, a substituted or unsubstituted alkyl sulfonamido, a substituted or unsubstituted aryl sulfonamido, a substituted or unsubstituted bicycloalkyl, a substituted or unsubstituted ureido, a substituted or unsubstituted thioureido or a substituted or unsubstituted aryl.

G is a direct bond; —(CH$_2$)$_j$—, wherein j is 1 to 6; a C$_2$–C$_6$-alkenylene group, a C$_3$–C$_8$-cycloalkylene group or a C$_1$–C$_6$-oxaalkylene group;

However, when R$_1$ is an aliphatic group or cycloalkyl group, R$_1$ is not exclusively substituted with one or more substitutent selected from the group consisting of hydroxyl and lower alkyl ethers. In addition, a heterocycloalkyl is not 2-phenyl-1,3-dioxan-5-yl, and an aliphatic group is not substituted exclusively with one or more aliphatic groups.

In Formula I, R$_2$ is —H, a substituted or unsubstituted aliphatic group, a substituted or unsubstituted cycloalkyl, a halogen, —OH, cyano, a substituted or unsubstituted aromatic group, a substituted or unsubstituted heteroaromatic group, a substituted or unsubstituted heterocycloalkyl, a substituted or unsubstituted aralkyl, a substituted or unsubstituted heteroaralkyl, —NR$_4$R$_5$, or —C(O)NR$_4$R$_5$.

In Formula I, R$_3$ is a substituted or unsubstituted cycloalkyl, a substituted or unsubstituted aromatic group, a substituted or unsubstituted heteroaromatic group, or a substituted or unsubstituted heterocycloalkyl.

In Formula I, R$_4$, R$_5$ and the nitrogen atom together form a 3, 4, 5, 6 or 7-membered, substituted or unsubstituted heterocycloalkyl, substituted or unsubstituted heterobicycloalkyl or a substituted or unsubstituted heteroaromatic.

Alternatively, R$_4$ and R$_5$ are each, independently, —H, azabicycloalkyl, heterocycloalkyl, a substituted or unsubstituted alkyl group or Y—Z.

Y is selected from the group consisting of —C(O)—, —(CH$_2$)$_p$—, —S(O)$_2$—, —C(O)O—, —SO$_2$NH—, —CONH—, (CH$_2$)$_p$O—, —(CH$_2$)$_p$NH—, —(CH$_2$)$_p$S—, —(CH$_2$)$_p$S(O)—, and —(CH$_2$)$_p$S(O)$_2$—.

p is an integer from 0 to about 6.

Z is a substituted or unsubstituted alkyl, substituted or unsubstituted amino, substituted or unsubstituted aryl, substituted or unsubstituted heteroaryl or substituted or unsubstituted heterocycloalkyl group.

j an integer from 0 to 6.

However, when L is —CH$_2$NR—, —C(O)NR— or —NRC(O)— and R$_3$ is azacycloalkyl or azaheteroaryl, j is 0. In addition, when L is —O— and R$_3$ is phenyl, j is 0.

In a preferred subset of the compounds of Formula I, R$_1$ is B—E, where E is a heterocyclyl group; L is —CH$_2$NHC(O)—; —CH$_2$NHC(O)NH—; —CH$_2$NHC(O)O—; —CH$_2$C(O)NH—; —CH$_2$NHS(O)$_2$—; —NHC(O)—; —NHC(O)NH—; —NHC(O)O—; —C(O)NH—; —NS(O)$_2$—; A is 1,4-phenylene or 1,4-phenylene substituted with one or more methoxy groups or fluorine atoms; R$_3$ is phenyl or phenyl substituted with one or more substituents selected from the group consisting of chloro, cyano, bromo, fluoro, trifluoromethoxy, methoxy, methylenedioxy, methyl, amino, dimethylamino and nitro; R$_2$ is hydrogen; and G is a direct bond or —(CH$_2$)$_j$—, wherein j is 0 to 4.

In another preferred subset of the compounds of Formula I, ring A is 1,4-phenylene, L is —O—, G is a direct bond and R$_3$ is phenyl.

The compounds of this invention are useful as inhibitors of serine/threonine and tyrosine kinases. In particular, compounds of this invention are useful as inhibitors of tyrosine kinases that are important in hyperproliferative diseases, especially in cancer and in the process of angiogenesis. For example, certain of these compounds are inhibitors of such receptor kinases as KDR, Flt-1, FGFR, PDGFR, c-Met, TIE-2 or IGF-1-R. Since certain of these compounds are anti-angiogenic, they are important substances for inhibiting the progression of disease states where angiogenesis is an important component. Certain compounds of the invention are effective as inhbitors of such serine/threonine kinases as PKCs, erk, MAP kinases, MAP kinase kinases, MAP kinase kinase kinases, cdks, Plk-1 or Raf-1. These compounds are useful in the treatment of cancer, and hyperproliferative disorders. In addition, certain compounds are effective inhibitors of non-receptor kinases such as those of the Src (for example, Ick, blk and lyn), Tec, Csk, Jak, Map, Nik and Syk families. These compounds are useful in the treatment of cancer, hyperproliferative disorders and immunologic diseases.

Certain compounds of this invention are selective TIE-2 kinase inhibitors which may be anti-angiogenic (especially in combination with one or more VEGFR inhibitors), or pro-angiogenic, when employed in the presence of, or in conjunction with, a VEGF-related stimulus. In this manner such inhibitors can be used in the promotion of therapeutic angiogenesis to treat, for example, ischemia, infarct or occlusion, or to promote wound healing.

The present invention provides a method of inhibiting the kinase activity of tyrosine kinases and serine/threonine kinases comprising the administration of a compound represented by formula I to said kinase in sufficient concentration to inhibit the enzyme activity of said kinase.

The present invention further includes the use of these compounds in pharmaceutical compositions with a pharmaceutically effective amount of the above-described compounds and a pharmaceutically acceptable carrier or excipient. These pharmaceutical compositions can be administered to individuals to slow or halt the process of angiogenesis in angiogenesis-aided diseases, or to treat edema, effusions, exudates or ascites and other conditions associated with vascular hyperpermeability. Certain pharmaceutical compositions can be administered to individuals to treat cancer and hyperproliferative disorders by inhibiting serine/threonine kinases such as cdk, Plk-1, erk, etc.

DETAILED DESCRIPTION OF THE INVENTION

The values of substituents in a first preferred group of compounds of formula I are given below.

Preferably, L is —N(R)C(O)N(R)—, —N(R)S(O)$_2$—, —S(O)$_2$N(R)—, —N(R)C(O)—, —C(O)N(R)—, or —O—.

Preferably, G is a direct bond; —(CH$_2$)$_j$—, wherein j is from 1 or 2; trans —CH=CH—; -cycloC$_3$H$_4$—; or —CH$_2$O—.

Preferably, $R_3$ is a substituted or unsubstituted phenyl, a substituted or unsubstituted naphthyl, a substituted or unsubstituted pyridyl, a substituted or unsubstituted thienyl, a substituted or unsubstituted benzotriazole, a substituted or unsubstituted tetrahydropyranyl, a substituted or unsubstituted tetrahydrofuranyl, a substituted or unsubstituted quinoline, a substituted or unsubstituted thiazol, a substituted or unsubstituted isoxazole, substituted or unsubstituted cyclopentanyl, a substituted or unsubstituted benzofuran, substituted or unsubstituted benzothiophene, substituted or unsubstituted benzisoxazole, substituted or unsubstituted benzisothiazole, substituted or unsubstituted benzisoxazole, substituted or unsubstituted benzoxazole, substituted or unsubstituted benzimidazole, substituted or unsubstituted benzoxadiazole, substituted or unsubstituted benzothiadiazole, substituted or unsubstituted isoquinoline, substituted or unsubstituted quinoxaline, substituted or unsubstituted indole or substituted or unsubstituted pyrazole. Alternatively, $R_3$ can be a substituted or unsubstituted aliphatic group or a substituted or unsubstituted alkenyl, provided that L is —SN(R)—, —S(O)N(R)—, —S(O)$_2$N (R)—, —N(R)S—, —N(R)S(O)—, —N(R)S(O)$_2$—, —N(R)C(O)N(R)—, —N(R)SN(R')—, —N(R)S(O)N (R')—, or —N(R)S(O)$_2$N(R')—;

In one embodiment, $R_3$ is a substituted or unsubstituted phenyl or phenyl fused to a five- or six-membered heterocyclic group. In this embodiment, suitable examples of $R_3$ include, but are not limited to, the groups shown below.

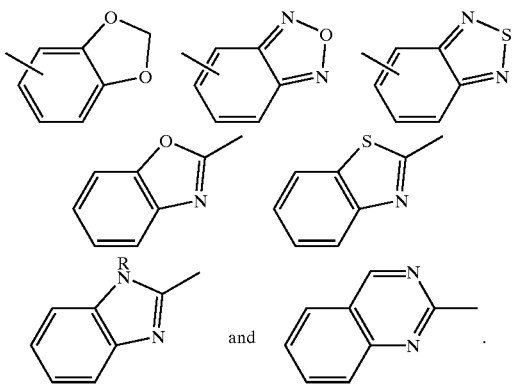

where R is hydrogen or alkyl.

$R_3$ can be substituted by one or more substituents. Preferable substituents for $R_3$ are F, Cl, Br, I, CH$_3$, NO$_2$, OCF$_3$, OCH$_3$, CN, CO$_2$CH$_3$, CF$_3$, t-butyl, pyridyl, substituted or unsubstituted oxazolyl, substituted or unsubstituted benzyl, substituted or unsubstituted benzenesulfonyl, substituted or unsubstituted phenoxy, substituted or unsubstituted phenyl, substituted or unsubstituted amino, carboxyl, substituted or unsubstituted tetrazolyl, styryl, —S-(substituted or unsubstituted aryl), —S-(substituted or unsubstituted heteroaryl), substituted or unsubstituted heteroaryl, substituted or unsubstituted heterocycloalkyl, alkynyl, —C(O)NR$_f$R$_g$, R$_c$, CH$_2$OR$_c$.

$R_f$, $R_g$ and the nitrogen atom together form a 3-, 4-, 5-, 6- or 7-membered, substituted or unsubstituted heterocycloalkyl, substituted or unsubstituted heterobicycloalkyl or a substituted or unsubstituted heteroaromatic.

Alternatively, $R_f$ and $R_g$ are each, independently, a substituted or unsubstituted aliphatic group or a substituted or unsubstituted aromatic group.

$R_c$ is hydrogen, or substituted or unsubstituted alkyl or substituted or unsubstituted aryl; —W—(CH$_2$)$_t$—NR$_d$R$_e$, —W—(CH$_2$)$_t$—O-alkyl, , —W—(CH$_2$)$_t$—S-alkyl, or —W—(CH$_2$)$_t$—OH.

t is an integer from 0 to about 6.

W is a bond or —O—, —S—, —S(O)—, —S(O)$_2$—, or —NR$_k$—.

$R_k$ is —H or alkyl.

$R_d$, $R_e$ and the nitrogen atom to which they are attached together form a 3, 4, 5, 6 or 7-membered substituted or unsubstituted heterocycloalkyl or substituted or unsubstituted heterobicyclic group.

Alternatively, $R_d$ and $R_e$ are each, independently, —H, alkyl, alkanoyl or —K—D.

K is —S(O)$_2$—, —C(O)—, —C(O)NH—, —C(O)$_2$—, or a direct bond.

D is a substituted or unsubstituted aryl, a substituted or unsubstituted heteroaryl, a substituted or unsubstituted aralkyl, a substituted or unsubstituted heteroaromatic group, a substituted or unsubstituted heteroaralkyl, a substituted or unsubstituted cycloalkyl, a substituted or unsubstituted heterocycloalkyl, a substituted or unsubstituted amino, a substituted or unsubstituted aminoalkyl, a substituted or unsubstituted aminocycloalkyl, COOR$_i$, or substituted or unsubstituted alkyl.

$R_i$ is a substituted or unsubstituted aliphatic group or a substituted or unsubstituted aromatic group.

More preferred substituents for $R_3$ are F, Cl, Br, I, cyano, nitro, OCF$_3$, CH$_3$, and CF$_3$.

Preferably, ring A is a substituted or unsubstituted phenyl, a substituted or unsubstituted naphthyl, a substituted or unsubstituted pyridyl, or a substituted or unsubstituted indole. In one embodiment, ring A is a substituted or unsubstituted phenyl. In one embodiment, ring A is a substituted or unsubstituted 1,4-phenylene group which is optionally substituted with one or more methoxy or fluoro groups.

Ring A can be substituted by one or more substituents. Preferable substituents for ring A are F, Cl, Br, I, $CH_3$, $NO_2$, $OCF_3$, $OCH_3$, CN, $CO_2CH_3$, $CF_3$, t-butyl, pyridyl, substituted or unsubstituted oxazolyl, substituted or unsubstituted benzyl, substituted or unsubstituted benzenesulfonyl, substituted or unsubstituted phenoxy, substituted or unsubstituted phenyl, substituted or unsubstituted amino, carboxyl, substituted or unsubstituted tetrazolyl, styryl, —S-(substituted or unsubstituted aryl), —S-(substituted or unsubstituted heteroaryl), substituted or unsubstituted heteroaryl, substituted or unsubstituted heterocycloalkyl, alkynyl, —C(O)$NR_fR_g$, $R_c$ and $CH_2OR_c$. $R_f$, $R_g$ and $R_c$ are defined as above.

Ring A is more preferably substituted with F, Cl, and nitro. $R_2$ is preferably hydrogen.

In one embodiment, $R_1$ is of the formula

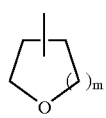

I(a)

m is an integer from 0 to about 3.

In another embodiment, $R_1$ is of the formula

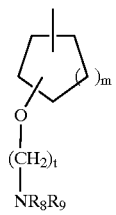

I(b)

m, t are defined as above. $R_8$, $R_9$ and the nitrogen atom together form a 3-, 4-, 5-, 6- or 7-membered, substituted or unsubstituted heterocycloalkyl, a substituted or unsubstituted heteroaromatic or substituted or unsubstituted heterobicyclicalkyl group. Alternatively, $R_8$ and $R_9$ are each, independently, —H, azabicycloalkyl, heterocycloalkyl, alkyl; hydroxyalkyl; dihydroxyalkyl or $Y_2$—$Z_2$. $Y_2$ is —C(O)—, —$(CH_2)_q$—, —$S(O)_2$—, —C(O)O—, —$SO_2NH$—, —CONH—, $(CH_2)_qO$—, —$(CH_2)_qNH$—, $(CH_2)_qS$—, $(CH_2)_qS(O)$—, or —$(CH_2)_qS(O)_2$—. q is an integer from 0 to 6. $Z_2$ is a substituted or unsubstituted alkyl, a substituted or unsubstituted amino, a substituted or unsubstituted aryl, a substituted or unsubstituted heteroaryl or a substituted or unsubstituted heterocycloalkyl group.

In another embodiment, $R_1$ is of the formula

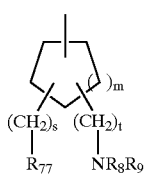

I(c)

m, t, $R_8$, and $R_9$ are defined as above. s is an integer from 0 to 6. q is an integer from 0 to about 6. $R_{77}$ is —$OR_{78}$, or —$NR_{79}R_{80}$. $R_{78}$ is —H or a substituted or unsubstituted aliphatic group. $R_{79}$, $R_{80}$ and the nitrogen atom together form a 3, 4, 5, 6 or 7-membered, substituted or unsubstituted heterocycloalkyl group, substituted or unsubstituted heteroaryl group, or a substituted heterobicyclicalkyl group. $R_{79}$ and $R_{80}$ are each, independently, —H, azabicycloalkyl, heterocycloalkyl or —$Y_3$—$Z_3$. $Y_3$ is selected from the group consisting of —C(O)—, —$(CH_2)_q$—, —$S(O)_2$—, —C(O)O—, —$SO_2NH$—, —CONH—, $(CH_2)_qO$—, —$(CH_2)_qNH$—, —$(CH_2)_qS$—, —$(CH_2)_qS(O)$— and —$(CH_2)_qS(O)_2$—. $Z_3$ is —H, a substituted or unsubstituted alkyl, a substituted or unsubstituted amino, a substituted or unsubstituted aryl, a substituted or unsubstituted heteroaryl or a substituted or unsubstituted heterocycloalkyl. In one embodiment, m is 2; s is 0; and $R_{77}$ is —OH. In one embodiment, $R_1$ is selected from the groups shown below.

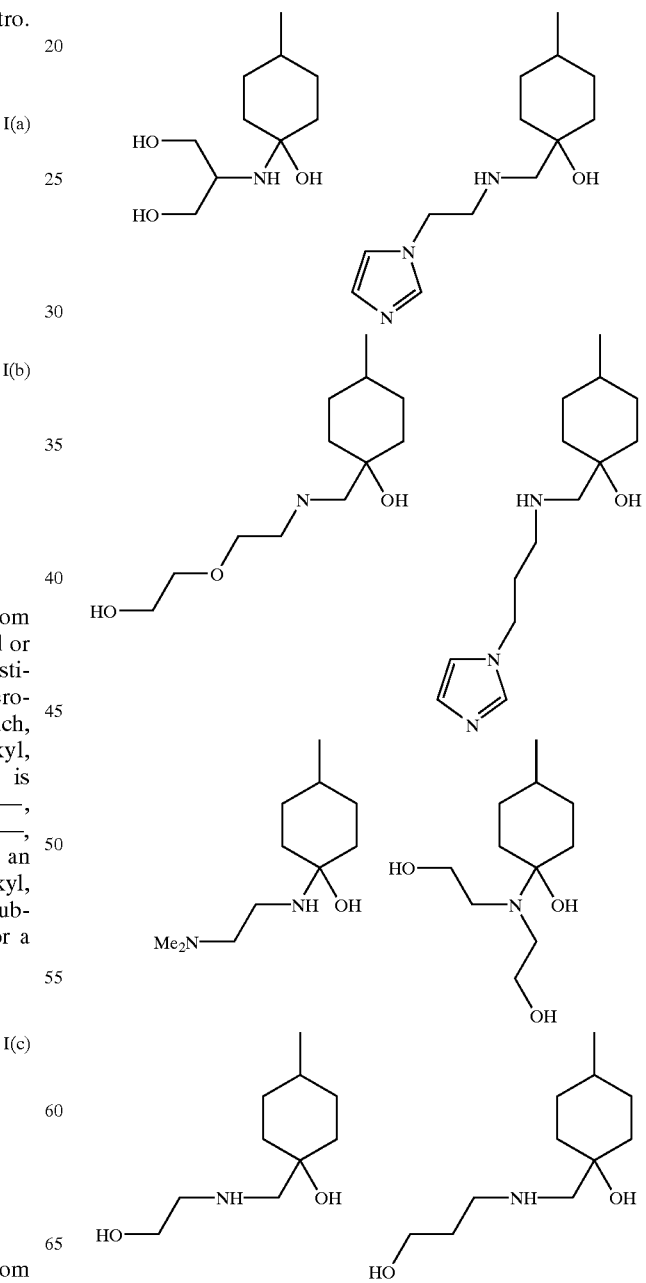

-continued
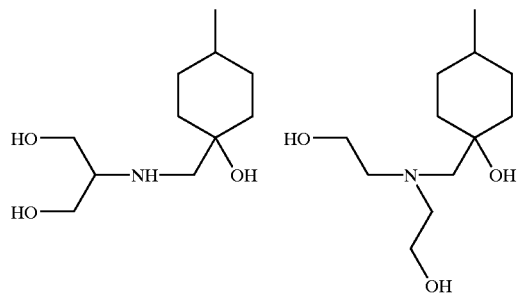
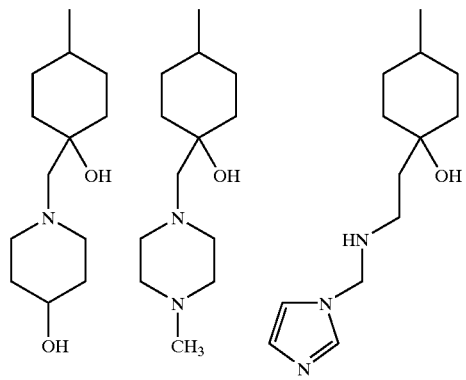
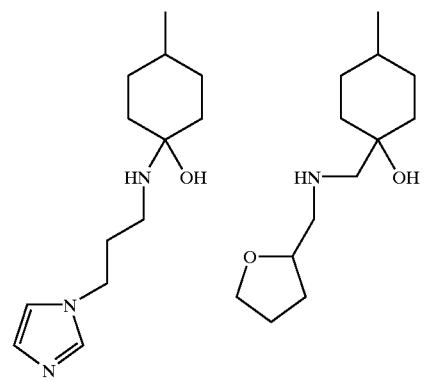
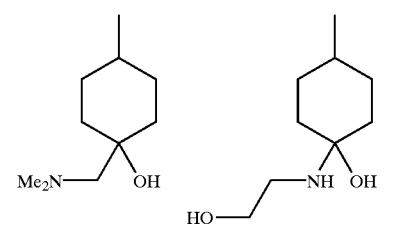
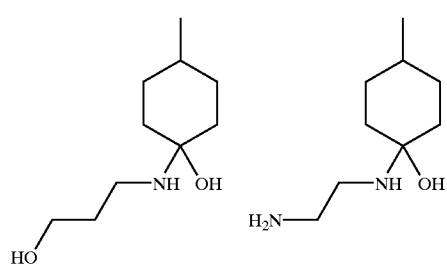
-continued
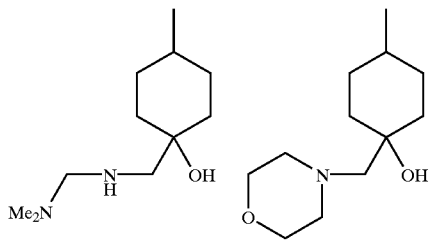
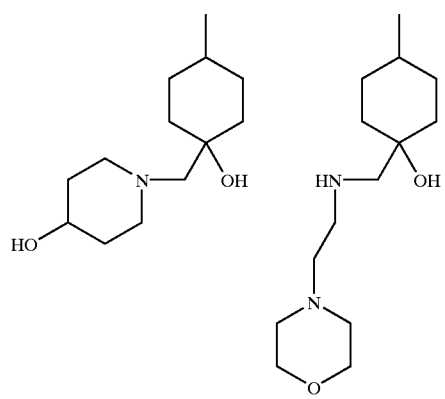
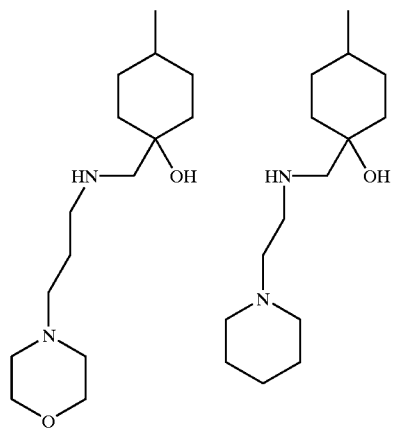
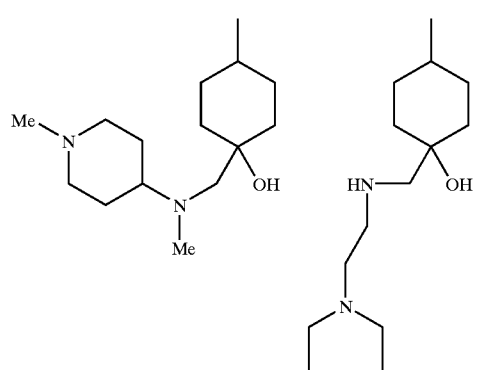

-continued

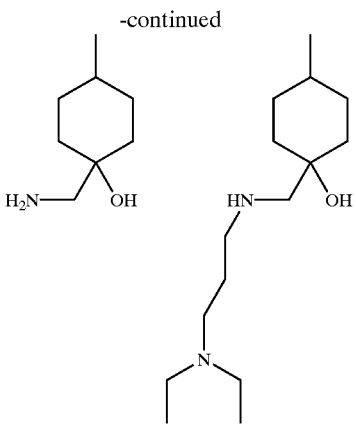

In another embodiment, $R_1$ is of the formula

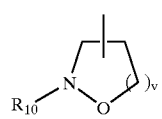

I(d)

v is an integer from 1 to about 3. $R_{10}$ is —H, azabicycloalkyl, heterocycloalkyl or $Y_2$—$Z_2$. $Y_2$ and $Z_2$ are as defined previously.

In another embodiment, $R_1$ is of the formula

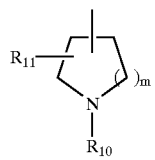

I(e)

m and $R_{10}$ are as previously defined. $R_{11}$ represents one or more substituents independently selected from the group consisting of hydrogen, hydroxy, oxo, a substituted or unsubstituted aliphatic group, a substituted or unsubstituted aromatic group, a substituted or unsubstituted heteroaromatic group, a substituted or unsubstituted alkoxycarbonyl, a substituted or unsubstituted alkoxyalkyl, a substituted or unsubstituted aminocarbonyl, a substituted or unsubstituted alkylcarbonyl, a substituted or unsubstituted arylcarbonyl, a substituted or unsubstituted heteroarylcarbonyl, a substituted or unsubstituted aminoalkyl and a substituted or unsubstituted aralkyl groups, provided that the carbon atoms adjacent to the nitrogen atom are not substituted by a hydroxy group.

In another embodiment, $R_1$ is of the formula

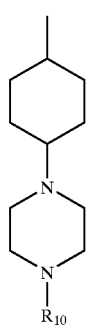

I(f)

$R_{10}$ is as previously defined. Preferably, $R_{10}$ is methyl, isopropyl or methoxyethyl.

In another embodiment, $R_1$ is of the formula

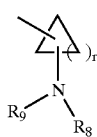

I(g)

r is an integer from 1 to about 6. $R_8$ and $R_9$ are as previously defined.

In another embodiment, $R_1$ is of the formula

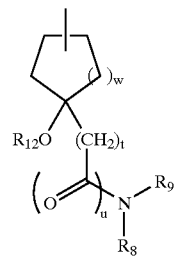

I(h)

$R_8$, $R_9$ and t are as previously defined. w is an integer from 0 to about 4. u is 0 or 1. $R_{12}$ is hydrogen or a substituted or unsubstituted alkyl group.

In another embodiment, $R_1$ is of the formula

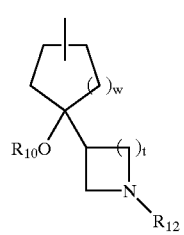

I(i)

w, t, $R_{10}$, $R_{12}$ are as previously defined.

In yet another embodiment, $R_1$ is of the formula

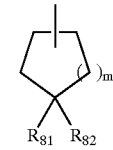

wherein m is 0, 1 or 2; $R_{81}$ and $R_{82}$ are each, independently, selected from the group consisting of hydrogen, hydroxyl, cyanomethyl, carboxymethyl, aminocarbonylmethyl,

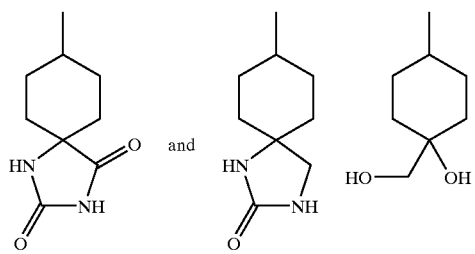

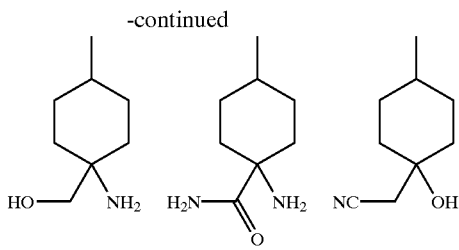

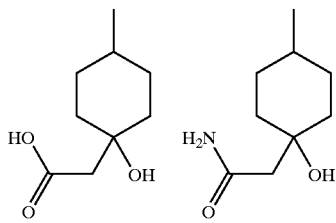

aminocarbonyl; aminomethyl, hydroxymethyl and amino, provided that no more than one of $R_{81}$ and $R_{82}$ is hydrogen. $R_{81}$ and $R_{82}$ can also together form oxo; —O—$(CH_2)_i$—O—, wherein i is 2 or 3; —NH—C(O)—NH—C(O)—; or —NH—C(O)—NH—$CH_2$—. For example, $R_1$ can be, but is not limited to, one of the groups shown below.

In another subset of the compounds of Formula I, $R_1$ is of the formula B—E, wherein B is cyclohexyl and E is substituted or unsubstituted heterocyclyl, heterocyclylalkylor heterocyclylazaalkyl. For example, E can be a substituted or unsubstituted pyrazolyl, diazepinyl, piperazyl, piperidyl or morpholyl group. Suitable examples of $R_1$ include, but are not limited to, the groups shown below.

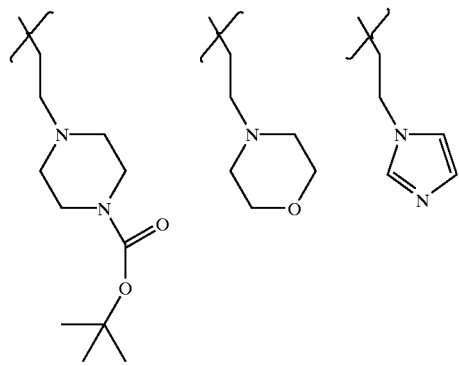

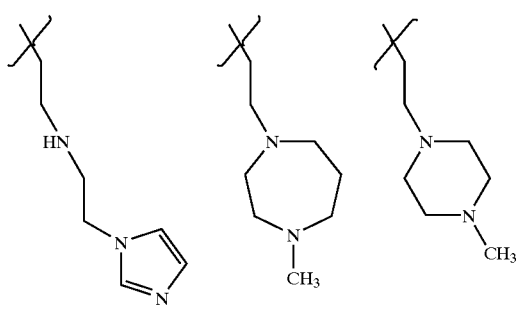

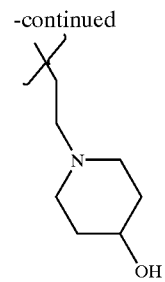

In another embodiment, when $R_1$ is I(g) or I(H), $R_8$, $R_9$ and the nitrogen atom together form a heterocycloalkyl group of the formula

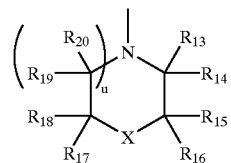

u is as previously defined. $R_{13}$, $R_{14}$, $R_{15}$, $R_{16}$, $R_{17}$, $R_{18}$, $R_{19}$ and $R_{20}$ are each, independently, lower alkyl or hydrogen. Alternatively, at least one pair of substituents $R_{13}$ and $R_{14}$; $R_{15}$ and $R_{16}$; $R_{17}$ and $R_{18}$; or $R_{19}$ and $R_{20}$ together are an oxygen atom. Alternatively, at least one of $R_{13}$ and $R_{15}$ is cyano, $CONHR_{21}$, $COOR_{21}$, $CH_2OR_{21}$ or $CH_2NR_{21}(R_{22})$. $R_{21}$, $R_{22}$ and the nitrogen atom together form a 3-, 4-, 5-, 6- or 7-membered, substituted or unsubstituted heterocycloalkyl group, substituted or unsubstituted heteroaryl group, or a substituted heterobicyclicalkyl group. Alternatively, $R_{21}$ and $R_{22}$ are each, independently, —H, azabicycloalkyl, heterocycloalkyl or $Y_3$—$Z_3$; $Y_3$ and $Z_3$ are as previously defined. X is —O—, —S—, —SO—, —$SO_2$—, —$CH_2$—, —$CH(OR_{23})$— or $NR_{23}$. $R_{23}$ is —H, substituted or unsubstituted alkyl, a substituted or unsubstituted aryl, a substituted or unsubstituted aralkyl, —C(NH)$NH_2$, —C(O)$R_{24}$, or —C(O)$OR_{24}$. $R_{24}$ is hydrogen, substituted or unsubstituted alkyl, a substituted or unsubstituted aryl or a substituted or unsubstituted aralkyl.

In another embodiment, $R_8$, $R_9$ and the nitrogen atom together form a heterocycloalkyl of the formula

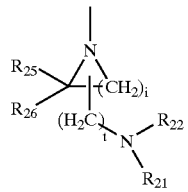

t, $R_{21}$ and $R_{22}$ are as previously defined. $R_{25}$ and $R_{26}$ are each, independently, hydrogen or lower alkyl. Alternatively, $R_{25}$ and $R_{26}$ together are an oxygen atom. i is an integer from 1 to about 6.

In another embodiment, $R_8$, $R_9$ and the nitrogen atom together form a heterocycloalkyl group; of the formula

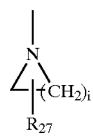

i is as previously defined. $R_{27}$ is $CH_2OH$, $C(O)NR_{24}R_{28}$ or $COOR_{24}$. $R_{24}$ and $R_{28}$ are as previously defined.

In another embodiment, $R_8$, $R_9$ and the nitrogen atom together form a heteroaromatic group of the formula

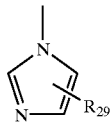

$R_{29}$ is a substituted or unsubstituted alkyl, a substituted or unsubstituted aryl or a substituted or unsubstituted aralkyl group, carboxylic acid, cyano, $C(O)OR_{30}$, $CH_2OR_{30}$, $CH_2NR_{21}R_{22}$ or $C(O)NR_{21}R_{22}$. $R_{30}$ is a substituted or unsubstituted alkyl, a substituted or unsubstituted aryl, a substituted or unsubstituted aralkyl, a substituted or unsubstituted heterocycloalkyl or heterocycloaryl group. $R_{21}$ and $R_{22}$ are as previously defined.

In another embodiment, at least one of $R_8$ and $R_9$ is of the formula $Y_3$—D, wherein D is of the formula

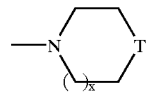

$Y_3$ is as previously defined. x is 0, 1 or 2. T is —O—, —C(O)—, —S—, —SO—, —SO$_2$—, —CH$_2$—, —CH(OR$_{24}$)— or —N(R$_{24}$)—. $R_{24}$ is as previously defined.

In another embodiment, at least one of $R_8$ and $R_9$ is of the formula $Y_3$—N($R_{31}$)$R_{32}$, $Y_3$ is as previously defined. $R_{31}$ and $R_{32}$ are each, independently, substituted or unsubstituted carboxyalkyl, a substituted or unsubstituted alkoxycarbonylalkyl, a substituted or unsubstituted hydroxyalkyl, a substituted or unsubstituted alkylsulfonyl, a substituted or unsubstituted alkylcarbonyl or a substituted or unsubstituted cyanoalkyl. Alternatively, $R_{31}$ and $R_{32}$, together with the nitrogen atom, form a five- or six-membered heterocycloalkyl group, a substituted or unsubstituted heteroaromatic or a substitutituted or unsubstituted heterobicycloalkyl.

In another embodiment, when $R_1$ is I(e), $Z_2$ is of the formula $N(R_{35})R_{36}$. $R_{35}$ and $R_{36}$ are each, independently, hydrogen, alkyl, alkoxycarbonyl, alkoxyalkyl, hydroxyalkyl, aminocarbonyl, cyano, alkylcarbonyl or aralkyl.

In another embodiment, when $R_1$ is I(e), $Z_2$ is of the formula

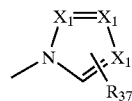

Each $X_1$ is, independently, CH or N. $R_{37}$ is hydrogen, cyano or a substituted or unsubstituted alkyl, a substituted or unsubstituted alkoxycarbonyl, a substituted or unsubstituted alkoxyalkyl, a substituted or unsubstituted hydroxyalkyl, a substituted or unsubstituted aminocarbonyl, a substituted or unsubstituted alkylcarbonyl or a substituted or unsubstituted aralkyl group.

In another embodiment, when $R_1$ is I(e), $Z_2$ is of the formula

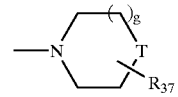

g is an integer from 0 to about 3. T is as previously defined. $R_{37}$ is hydrogen, cyano or a substituted or unsubstituted alkyl, a substituted or unsubstituted alkoxycarbonyl, a substituted or unsubstituted alkoxyalkyl, a substituted or unsubstituted hydroxyalkyl, a substituted or unsubstituted aminocarbonyl, a substituted or unsubstituted alkylcarbonyl or a substituted or unsubstituted aralkyl group.

In another embodiment, when $R_1$ is I(e), $Z_2$ is of the formula

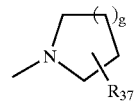

g and $R_{37}$ are as previously defined unsubstituted aralkyl group.

In another embodiment, when $R_1$ is I(e), $Z_2$ is of the formula

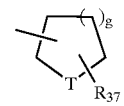

T, g and $R_{37}$ are as previously defined.

In another embodiment, when $R_1$ is I(e), $Z_2$ is of the formula

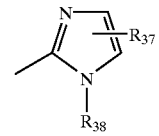

$R_{37}$ is as previously defined. $R_{38}$ is hydrogen, substituted or unsubstituted alkyl, a substituted or unsubstituted alkoxycarbonyl, a substituted or unsubstituted alkoxyalkyl, a substituted or unsubstituted aminocarbonyl, perhaloalkyl, a substituted or unsubstituted alkenyl, a substituted or unsubstituted alkylcarbonyl or a substituted or unsubstituted aralkyl.

In another embodiment, $R_1$ is of the formula

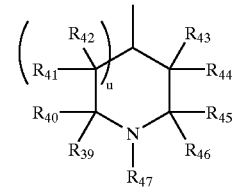

u is as previously defined. $R_{39}$, $R_{40}$, $R_{41}$, $R_{42}$, $R_{43}$, $R_{44}$, $R_{45}$ and $R_{46}$ are each, independently, methyl or hydrogen.

Alternatively, at least one pair of substituents $R_{39}$ and $R_{40}$; $R_{36}$ and $R_{37}$; $R_{38}$ and $R_{39}$. Alternatively, $R_{40}$ and $R_{41}$ together are an oxygen atom. $R_{47}$ is H, azabicycloalkyl, heterocycloalkyl or $Y_2$—$Z_2$. $Y_2$ and $Z_2$ are as previously defined. Alternatively, $R_{47}$ is of the formula

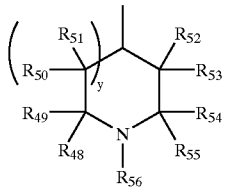

y is 0 or 1. $R_{48}$, $R_{49}$, $R_{50}$, $R_{51}$, $R_{52}$, $R_{53}$, $R_{54}$ and $R_{55}$ are each, independently, methyl or hydrogen. Alternatively, at least one pair of substituents $R_{48}$ and $R_{49}$; R50 and $R_{51}$; $R_{52}$ and $R_{53}$; or $R_{54}$ and $R_{55}$ together are an oxygen atom. $R_{56}$ is —H, azabicycloalkyl, heterocycloalkyl or $Y_3$—$Z_3$. $Y_3$ and $Z_3$ are defined as above.

In another embodiment, $R_1$ is of the formula

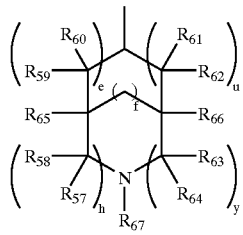

e, f, h, u and y are independently 0 or 1. $R_{57}$, $R_{58}$, $R_{59}$, $R_{60}$, $R_{61}$, $R_{62}$, $R_{63}$, $R_{64}$, $R_{65}$ and $R_{66}$ are each, independently, methyl or hydrogen. Alternatively, at least one pair of substituents $R_{57}$ and $R_{58}$; $R_{59}$ and $R_{60}$; $R_{61}$ and $R_{62}$; or $R_{63}$ and $R_{64}$ together are an oxygen atom. $R_{67}$ is H, azabicycloalkyl, heterocycloalkyl or $Y_2$—$Z_2$. $Y_2$ and $Z_2$ are defined as above. Alternatively, $R_{67}$ is of the formula

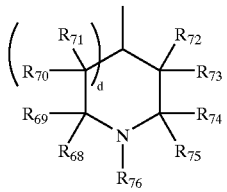

d is 0 or 1. $R_{68}$, $R_{69}$, $R_{70}$, $R_{71}$, $R_{72}$, $R_{73}$, $R_{74}$ and $R_{75}$ are each, independently, lower alkyl or hydrogen. Alternatively, at least one pair of substituents $R_{68}$ and $R_{69}$; $R_{70}$ and $R_{71}$; $R_{72}$ and $R_{73}$. $R_{74}$ and $R_{75}$ together are an oxygen atom. $R_{76}$ is —H, azabicycloalkyl, heterocycloalkyl or $Y_3$—$Z_3$. $Y_3$ and $Z_3$ are defined as above.

As used herein, aromatic groups include carbocyclic ring systems (e.g. benzyl and cinnamyl) and fused polycyclic aromatic ring systems (e.g. naphthyl and 1,2,3,4-tetrahydronaphthyl). Aromatic groups are also referred to as aryl groups herein.

Heteroaromatic groups, as used herein, include heteroaryl ring systems (e.g., thienyl, pyridyl, isoxazolyl, thiadiazolyl, oxadiazolyl, indazolyl, furanyls, pyrroles, imidazoles, pyrazoles, triazoles, pyrimidines, pyrazyls, thiazolyls, isoxazolyls, isothiazolyls, tetrazolyls, oxadiazolyls,) and heteroaryl ring systems in which a carbocyclic aromatic ring, carbocyclic non-aromatic ring or heteroaryl ring is fused to one or more other heteroaryl rings (e.g., benzo(b) thienyl, benzimidazole, indole, tetrahydroindole, azaindole, indazole, quinoline, imidazopyridine, purine, pyrrolo[2,3-d] pyrimidine, pyrazolo[3,4-d]pyrimidine, 2,1,3-benzoxadiazolyl, 2,1,3-benzothiadiazolyl, benzoxazolyl, 3,4-dihydro-2H-benzoxazyl, benzothiazolyl, quinazolyl, quinoxalyl, isoquinolyl, indolizyl) and their N-oxides.

An aralkyl group, as used herein, is an aromatic substituent that is linked to a compound by an aliphatic group having from one to about six carbon atoms.

An heteroaralkyl group, as used herein, is a heteroaromatic substituent that is linked to a compound by an aliphatic group having from one to about six carbon atoms.

A heterocycloalkyl group, as used herein, is a non-aromatic ring system that has 3 to 8 atoms and includes at least one heteroatom, such as nitrogen, oxygen, or sulfur.

An acyl group, as used herein, is an —C(O)NR$_x$R$_z$, —C(O)OR$_x$, —C(O)$_x$, in which R$_x$ and R$_z$ are each, independently, —H, a substituted or unsubstituted aliphatic group or a substituted or unsubstituted aromatic group.

As used herein, aliphatic groups include straight chained, branched or cyclic $C_1$-$C_8$ hydrocarbons which are completely saturated or which contain one or more units of unsaturation (e.g. one or more double or triple bonds). The term "alkyl" refers to a saturated hydrocarbyl group; "alkoxy" refers to an alkyl-O— group. A "lower alkyl group" is a saturated aliphatic group having form 1–6 carbon atoms; a "lower alkoxy group" is a lower-alkyl-O— group.

As used herein, the term "oxaalkylene" refers to an alkylene chain which is interrupted at one or more points by an oxygen atom. Examples of oxaalkylene groups include, but are not limited to, —OCH$_2$—, —CH$_2$O— and —CH$_2$OCH$_2$—.

For substituted groups described above, substituents can include, but are not to be construed as being limited to, one or more substituents independently selected from halo, hydroxy, oxo, nitro, amino, mono- or di-alkylamino, alkoxy, cyano, perfluoroalkyl (preferably CF$_3$), perfluoroalkoxy (preferably OCF$_3$), COOR (where R is H or alkyl), carboxamide, acetyl, cycloalkyl, aryloxy, heteroaryl, heteroaryloxy, heterocycloalkyl, amido, aminocarbonyl, alkylthio ether, alkylsulfonyl, alkylsulfonamido, aliphatic group (optionally substituted with one or more of the following: halo, hydroxy, oxo, nitro, amino, mono- or di-alkylamino, alkoxy, cyano, perfluoroalkyl, perfluoroalkoxy and COOR (where R is H or alkyl)), phenyl (optionally substituted with one or more of the following: halo, hydroxy, nitro, amino, alkylamino, mono- or di-alkylamino, mono- or di-alkylaminoalkyl, alkoxy, cyano, perfluoroalkyl, perfluoroalkoxy and COOR (where R is H or alkyl)).

Compounds of formula I may exist as salts with pharmaceutically acceptable acids. The present invention includes such salts. Examples of such salts include hydrochlorides, hydrobromides, sulfates, methanesulfonates, nitrates, maleates, acetates, citrates, fumarates, tartrates [eg (+)-tartrates, (–)-tartrates or mixtures thereof including racemic mixtures], succinates, benzoates and salts with amino acids such as glutamic acid. These salts may be prepared by methods known to those skilled in the art.

Certain compounds of formula I which have acidic substituents may exist as salts with pharmaceutically acceptable bases. The present invention includes such salts. Example of such salts include sodium salts, potassium salts, lysine salts and arginine salts. These salts may be prepared by methods known to those skilled in the art.

Certain compounds of formula I and their salts may exist in more than one crystal form and the present invention includes each crystal form and mixtures thereof.

Certain compounds of formula I and their salts may also exist in the form of solvates, for example hydrates, and the present invention includes each solvate and mixtures thereof.

Certain compounds of formula I may contain one or more chiral centres, and exist in different optically active forms. When compounds of formula I contain one chiral centre, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of formula I contains more than one chiral center it may exist in diastereoisomeric forms. The diastereoisomeric pairs may be separated by methods known to those skilled in the art, for example chromatography or crystallization and the individual enantiomers within each pair may be separated as described above. The present invention includes each diastereoisomer of compounds of formula I and mixtures thereof.

Certain compounds of formula I may exist in different tautomeric forms or as different geometric isomers, and the present invention includes each tautomer and/or geometric isomer of compounds of formula I and mixtures thereof.

Certain compounds of formula I may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of formula I and mixtures thereof.

Certain compounds of formula I may exist in zwitterionic form and the present invention includes each zwitterionic form of compounds of formula I and mixtures thereof.

A preferred group of compounds of the present invention are:

Cis-5-(4-phenoxyphenyl)-7-(4-pyrrolidinocyclohex-1-yl)-7H-pyrrolo[2,3-d]pyrimidin-4-ylamine Trans-5-(4-phenoxyphenyl)-7-(4-pyrrolidinocyclohex-1-yl)-7H-pyrrolo[2,3-d]pyrimidin-4-ylamine Cis-5-(4-phenoxyphenyl)-7-(4-piperidinocyclohex-1-yl)-7H-pyrrolo[2,3-d]pyrimidin-4-ylamine hydrochloride Trans-5-(4-phenoxyphenyl)-7-(4-piperidinocyclohex-1-yl)-7H-pyrrolo[2,3-d]pyrimidin-4-ylamine Trans-7-(4-dimethylaminocyclohexyl)-5-(4-phenoxyphenyl)-7H-pyrrolo[2,3-d]pyrimidin-4-ylamine Cis-7-(4-dimethylaminocyclohexyl)-5-(4-phenoxyphenyl)-7H-pyrrolo[2,3-d]pyrimidin-4-ylamine 5-(4-phenoxyphenyl)-7-(4-piperidyl)-7H-pyrrolo[2,3-d]pyrimidin-4-ylamine dihydrochloride 5-(4-phenoxyphenyl)-7-(3-pyrrolidinyl)-7H-pyrrolo[2,3-d]pyrimidin-4-ylamine dihydrochloride Cis-7-[4-(4-isopropylpiperazino)cyclohexyl]-5-(4-phenoxyphenyl)-7H-pyrrolo[2,3-d]pyrimidin-4-amine Trans-7-[4-(4-isopropylpiperazino)cyclohexyl]-5-(4-phenoxyphenyl)-7H-pyrrolo[2,3-d]pyrimidin-4-amine Cis-7-{4-[4-(2-methoxyethyl)piperazino]cyclohexyl}-5-(4-phenoxyphenyl)-7H-pyrrolo[2,3-d]pyrimidin-4-amine Trans-7-{4-[4-(2-methoxyethyl)piperazino]cyclohexyl}-5-(4-phenoxyphenyl)-7H-pyrrolo[2,3-d]pyrimidin-4-amine Cis-7-[-4-(4-ethylpiperazino)cyclohexyl]-5-(4-phenoxyphenyl)-7H-pyrrolo[2,3-d]pyrimidin-4-amine trans-7-[4-(4-ethylpiperazino)cyclohexyl]-5-(4-phenoxyphenyl)-7H-pyrrolo[2,3-d]pyrimidin-4-amine Cis-7-[4-(4-isopropylpiperazino)cyclohexyl]-5-(4-phenoxyphenyl)-7H-pyrrolo[2,3-d]pyrimidin-4-amine tris maleate Trans-7-[4-(4-isopropylpiperazino)cyclohexyl]-5-(4-phenoxyphenyl)-7H-pyrrolo[2,3-d]pyrimidin-4-amine tris maleate Cis-7-{4-[4-(2-methoxyethyl)piperazino]cyclohexyl}-5-(4-phenoxyphenyl)-7H-pyrrolo[2,3-d]pyrimidin-4-amine tris maleate Trans-7-{4-[4-(2-methoxyethyl)piperazino]cyclohexyl}-5-(4-phenoxyphenyl)-7H-pyrrolo[2,3-d]pyrimidin-4-amine tris maleate Cis-7-(4-{[3-(1H-1-imidazolyl)propyl]amino}cyclohexyl)-5-(4-phenoxyphenyl)-7H-pyrrolo[2,3-d]pyrimidin-4-amine trimaleate salt Trans-7-(4-{[3-(1H-1-imidazolyl)propyl]amino}cyclohexyl)-5-(4-phenoxyphenyl)-7H-pyrrolo[2,3-d]pyrimidin-4-amine dimaleate salt Cis-7-[4-(dimethylamino)cyclohexyl]-5-(4-phenoxyphenyl)-7H-pyrrolo[2,3-d]pyrimidin-4-amine dimaleate salt Trans-5-(4-phenoxyphenyl)-7-(4-piperidinocyclohexyl)-7H-pyrrolo[2,3-d]pyrimidin-4-amine dimaleate salt Trans-5-(4-phenoxyphenyl)-7-(4-tetrahydro-1H-1-pyrrolylcyclohexyl)-7H-pyrrolo[2,3-d]pyrimidin-4-amine dimaleate salt Cis-5-(4-phenoxyphenyl)-7-(4-piperazinocyclohexyl)-7H-pyrrolo[2,3-d]pyrimidin-4-amine trimaleate salt 7-[3-(4-methylpiperazino)cyclopentyl]-5-(4-phenoxyphenyl)-7H-pyrrolo[2,3-d]pyrimidin-4-amine tri-maleate Trans-7-[3-(4-methylpiperazino)cyclohextyl]-5-(4-phenoxyphenyl)-7H -pyrrolo[2,3-d]pyrimidin-4-amine trans-7-[3-(4-methylpiperazino)cyclohexyl]-5-(4-phenoxyphenyl)-7H-pyrrolo[2,3-d]pyrimidin-4-amine tri-hydrochloride cis-7-[3-(4-methylpiperazino)cyclohexyl]-5-(4-phenoxyphenyl)-7H-pyrrolo[2,3-d]pyrimidin-4-amine tri-maleate salt cis-7-[3-(4-methylpiperazino)cyclohexyl]-5-(4-phenoxyphenyl)-7H-pyrrolo[2,3-d]pyrimidin-4-amine tri-hydrochloride Trans-5-(2-methyl-4-phenoxyphenyl)-7-[4-(4-methylpiperazino)cyclohexyl]-7H-pyrrolo[2,3-d]pyrimidin-4-amine trimaleate Cis-benzyl N-(4-{4-amino-7-[4-(4-methylpiperazino) cyclohexyl]-7H-pyrrolo[2,3-d]pyrimidin-5-yl}2-methoxyphenyl)carbamate tri-maleate Trans-benzyl N-(4-{4-amino-7-[4-(4-methylpiperazino) cyclohexyl]-7H-pyrrolo[2,3-d]pyrimidin-5-yl}-2-methoxyphenyl)carbamate tri-maleate Trans-N1-(4-{4-amino-7-[4-(4-methylpiperazino) cyclohexyl]-7H-pyrrolo[2,3-d]pyrimidin-5-yl}-2-methoxyphenyl)benzamide Trans-N1-(4-{4-amino-7-[4-(4-methylpiperazino) cyclohexyl]-7H-pyrrolo[2,3-d]pyrimidin-5-yl}-2-methoxyphenyl)benzamide tri-maleate Cis-N1-(4-{4-amino-7-[4-(4-methylpiperazino) cyclohexyl]-7H-pyrrolo[2,3-d]pyrimidin-5-yl}-2-methoxyphenyl)-3-phenylpropanamide Trans-N1-(4-{4-amino-7-[4-(4-methylpiperazino) cyclohexyl]-7H-pyrrolo[2,3-d]pyrimidin-5-yl }-2-methoxyphenyl)-3-phenylpropanamide cis-N1-(4-4-amino-7-[4-(4-methylpiperazino) cyclohexyl]-7H-pyrrolo[2,3-d]pyrimidin-5-yl-2-methoxyphenyl)-3-phenylpropanamide trimaleate salt trans-N1-(4-4-amino-7-[4-(4-methylpiperazino) cyclohexyl]-7H-pyrrolo[2,3-d]pyrimidin-5-yl-2-methoxyphenyl)-3-phenylpropanamide tri-maleate cis-2-(4-b 4-amino-7-[4-(4-methylpiperazino) cyclohexyl]-7H-pyrrolo[2,3-d]pyrimidin-5-ylphenoxy)-6-[(3-methoxypropyl)amino]benzonitrile tri-maleate trans-2-(4-4-amino-7-[4-(4-methylpiperazino) cyclohexyl]-7H-pyrrolo[2,3-d]pyrimidin-5-ylphenoxy)-6-[(3-methoxypropyl)amino]benzonitrile tri-maleate cis-2-amino-6-(4-4-amino-7-[4-(4-methylpiperazino) cyclohexyl]-7H-pyrrolo[2,3-d]pyrimidin-5-ylphenoxy) benzonitrile tri-maleate trans-2-amino-6-(4-4-amino-7-[4-(4-methylpiperazino) cyclohexyl]-7H-pyrrolo[2,3-d]pyrimidin-5-ylphenoxy) benzonitrile tri-maleate cis-2-(4-4-amino-7-[4-(4-methylpiperazino)cyclohexyl]-7H-pyrrolo[2,3-d]pyrimidin-5-ylphenoxy)-6-[(4-methylphenyl)sulfanyl]benzonitrile tri-maleate trans-2-(4-4-amino-7-[4-(4-methylpiperazino) cyclohexyl]-7H-pyrrolo[2,3-d]pyrimidin-5-ylphenoxy)-6-[(4-methylphenyl)sulfanyl]benzonitrile tri-maleate cis-2-(4-4-amino-7-[4-(4-methylpiperazino)cyclohexyl]-7H-pyrrolo[2,3-d]pyrimidin-5-ylphenoxy)-6-(2-pyridylsulfanyl)benzonitrile tri-maleate trans-2-(4-4-amino-7-[4-(4-methylpiperazino) cyclohexyl]-7H-pyrrolo[2,3-d]pyrimidin-5-ylphenoxy)-6-(2-pyridylsulfanyl)benzonitrile tri-maleate cis-5-(2-methyl-4-phenoxyphenyl)-7-[4-(4-methylpiperazino)cyclohexyl]-7H-pyrrolo[2,3-d] pyrimidin-4-amine tri-maleate trans-5-(2-methyl-4-phenoxyphenyl)-7-[4-(4-methylpiperazino)cyclohexyl]-7H-pyrrolo[2,3-d] pyrimidin-4-amine tri-maleate cis-N1-(4-{4-amino-7-[4-(4-methylpiperazino) cyclohexyl]-7H-pyrrolo[2,3-d]pyrimidin-5-yl}-2-fluorophenyl)-4-fluoro-1-benzenesulfonamide tri-maleate trans-N1-(4-{4-amino-7-[4-(4-methylpiperazino) cyclohexyl]-7H-pyrrolo[2,3-d]pyrimidin-5-yl}-2-fluorophenyl)-4-fluoro-1-benzenesulfonamide tri-maleate N1-4-[4-amino-7-(1-benzyl-4-piperidyl)-7H-pyrrolo[2,3-d]pyrimidin-5-yl]-2-fluorophenyl-4-fluoro-1-benzenesulfonamide N1-4-[4-amino-7-(1-benzyl-4-piperidyl)-7H-pyrrolo[2,3-d]pyrimidin-5-yl]-2-fluorophenyl-2,3-dichloro-1-benzenesulfonamide N1-4-[4-amino-7-(4-piperidyl)-7H-pyrrolo[2,3-d]pyrimidin-5-yl]-2-fluorophenyl-4-fluoro-1-benzenesulfonamide N1-4-[4-amino-7-(1-formyl-4-piperidyl)-7H-pyrrolo[2,3-d]pyrimidin-5-yl]-2-fluorophenyl-4-fluoro-1-benzenesulfonamide N1-[4-(4-amino-7-1-[(1-methyl-1H-4-imidazolyl)sulfonyl]-4-piperidyl-7H-pyrrolo[2,3-d]pyrimidin-5-yl)-2-fluorophenyl]-4-fluoro-1-benzenesulfonamide dimaleate N1-[4-(4-amino-7-1-[(1,2-dimethyl-1H-4-imidazolyl)sulfonyl]-4-piperidyl-7H-pyrrolo[2,3-d]pyrimidin-5-yl)-2-fluorophenyl]-4-fluoro-1-benzenesulfonamide N1-[4-(4-amino-7-1-[(1,3-dimethyl-1H-5-pyrazolyl)carbonyl]-4-piperidyl-7H-pyrrolo[2,3-d]pyrimidin-5-yl)-2-fluorophenyl]-4-fluoro-1-benzenesulfonamide N1-(4-{4-amino-7-[1-(2-pyridylcarbonyl)-4-piperidyl]-7H-pyrrolo[2,3-d]pyrimidin-5-yl}-2-fluorophenyl)-4-fluoro-1-benzenesulfonamide N1-4-(4-amino-7-{4-[1-(1-methylpiperid-4-yl)piperidyl]-7H-pyrrolo[2,3-d]pyrimidin-5-yl})-2-fluorophenyl-4-fluoro-1-benzenesulfonamide tri-maleate trans-N-1-(4-{4-amino-7-[4-(4-methylpiperazino) cyclohexyl]-7H-pyrrolo[2,3-d]pyrimidin-5-yl}-2-fluorophenyl)-2-(trifluoromethoxy)-1-benzenesulfonamide trimaleate trans—N-1-(4-{4-amino-7-[4-(4-methylpiperazino) cyclohexyl]-7H-pyrrolo[2,3-d]pyrimidin-5-yl}-2-fluorophenyl)-5-chloro-2-thiophenesulfonamide benzenesulfonamide trimaleate trans-N-1-(4-{4-amino-7-[4-(4-methylpiperazino) cyclohexyl]-7H-pyrrolo[2,3-d]pyrimidin-5-yl}-2-fluorophenyl)-2-chloro-4-fluoro-1-benzenesulfonamide benzenesulfonamide trimaleate trans-N-1-(4-{4-amino-7-[4-(4-methylpiperazino) cyclohexyl]-7H-pyrrolo[2,3-d]pyrimidin-5-yl}-2-fluorophenyl)-2,3-dichloro-1-benzenesulfonamide tri-maleate cis-N-1-(4-4-amino-7-[4-(4-methylpiperazino) cyclohexyl]-7H-pyrrolo[2,3-d]pyrimidin-5-yl}-2-fluorophenyl)-2-chloro-4-fluoro-1-benzenesulfonamide trimaleate cis-N-1-(4-4-amino-7-[4-(4-methylpiperazino) cyclohexyl]-7H-pyrrolo[2,3-d]pyrimidin-5-yl-2-fluorophenyl)-2,5-difluoro-1-benzenesulfonamide tri-maleate trans—N-1-(4-{4-amino-7-[4-(4-methylpiperazino) cyclohexyl]-7H-pyrrolo[2,3-d]pyrimidin-5-yl}-2-fluorophenyl)-2,6-difluoro-1-benzenesulfonamide tri-maleate trans-N-4-(4-{4-amino-7-[4-(4-methylpiperazino) cyclohexyl]-7H-pyrrolo[2,3-d]pyrimidin-5-yl}-2-fluorophenyl)-2,1,3-benzothiadiazole-4-sulfonamide trimaleate trans-N-1-(4-{4-amino-7-[4-(4-methylpiperazino) cyclohexyl]-7H-pyrrolo[2,3-d]pyrimidin-5-yl}-2-fluorophenyl)-2,3,4-trifluoro-1-benzenesulfonamide trimaleate cis-N-1-(4-{4-amino-7-[4-(4-methylpiperazino)cyclohexyl]-7H-pyrrolo[2,3-d]pyrimidin-5-yl}-2-fluorophenyl)-2-nitro-1-benzenesulfonamide trimaleate cis-N-1-(4-{4-amino-7-[4-(4-methylpiperazino)cyclohexyl]-7H-pyrrolo[2,3-d]pyrimidin-5-yl}-2-fluorophenyl)-2-fluoro-1-benzenesulfonamide trimaleate cis-N-1-(4-{4-amino-7-[4-(4-methylpiperazino)cyclohexyl]-7H-pyrrolo[2,3-d]pyrimidin-5-yl}-2-fluorophenyl)-2,4,6-trichloro-1-benzenesulfonamide trimaleate cis-N-1-(4-4-amino-7-[4-(4-methylpiperazino)cyclohexyl]-7H-pyrrolo[2,3-d]pyrimidin-5-yl}-2-fluorophenyl)-2,6-dichloro-1-benzenesulfonamide trimaleate cis-N-1-(4-{4-amino-7-[4-(4-methylpiperazino)cyclohexyl]-7H-pyrrolo[2,3-d]pyrimidin-5-yl}-2-fluorophenyl)-2-chloro-1-benzenesulfonamide trimaleate cis-N-1-(4-{4-amino-7-[4-(4-methylpiperazino)cyclohexyl]-7H-pyrrolo[2,3-d]pyrimidin-5-yl}-2-fluorophenyl)-3-fluoro-1-benzenesulfonamide dimaleate cis-N-1-(4-{4-amino-7-[4-(4-methylpiperazino)cyclohexyl]-7H-pyrrolo[2,3-d]pyrimidin-5-yl}-2-fluorophenyl)-5-chloro-2-thiophenesulfonamide dimaleate cis-N-1-(4-{4-amino-7-[4-(4-methylpiperazino)cyclohexyl]-7H-pyrrolo[2,3-d]pyrimidin-5-yl}-2-fluorophenyl)-4-bromo-2,6-difluoro-1-benzenesulfonamide trimaleate cis-N-1-(4-{4-amino-7-[4-(4-methylpiperazino)cyclohexyl]-7H-pyrrolo[2,3-d]pyrimidin-5-yl}-2-fluorophenyl)-3-chloro-4-fluoro-1-benzenesulfonamide trimaleate cis-N-1-(4-{4-amino-7-[4-(4-methylpiperazino)cyclohexyl]-7H-pyrrolo[2,3-d]pyrimidin-5-yl}-2-fluorophenyl-2-iodo-1-benzenesulfonamide trimaleate cis-N-1-(4-4-amino-7-[4-(4-methylpiperazino)cyclohexyl]-7H-pyrrolo[2,3-d]pyrimidin-5-yl}-2-fluorophenyl)-2-(trifluoromethoxy)-1-benzenesulfonamide trimaleate cis-N-1-(4-{4-amino-7-[4-(4-methylpiperazino)cyclohexyl]-7H-pyrrolo[2,3-d]pyrimidin-5-yl}-2-fluorophenyl)-2,3-dichloro-1-benzenesulfonamide trimaleate cis-N-1-(4-{4-amino-7-[4-(4-methylpiperazino)cyclohexyl]-7H-pyrrolo[2,3-d]pyrimidin-5-yl}-2-fluorophenyl)-2-chloro-6-methyl-1-benzenesulfonamide trimaleate cis-N-1-(4-{4-amino-7-[4-(4-methylpiperazino)cyclohexyl]-7H-pyrrolo[2,3-d]pyrimidin-5-yl}-2-fluorophenyl)-2-chloro-4-cyano-1-benzenesulfonamide trimaleate cis-N-1-(4-{4-amino-7-[4-(4-methylpiperazino)cyclohexyl]-7H-pyrrolo[2,3-d]pyrimidin-5-yl}-2-fluorophenyl)-2,3,4-trifluoro-1-benzenesulfonamide trimaleate cis-N-1-(4-{4-amino-7-[4-(4-methylpiperazino)cyclohexyl]-7H-pyrrolo[2,3-d]pyrimidin-5-yl}-2-fluorophenyl)-3,4-difluoro-1-benzenesulfonamide trimaleate cis-N-1-(4-{4-amino-7-[4-(4-methylpiperazino)cyclohexyl]-7H-pyrrolo[2,3-d]pyrimidin-5-yl}-2-fluorophenyl)-4-bromo-2-fluoro-1-benzenesulfonamide trimaleate cis-N-1-(4-{4-amino-7-[4-(4-methylpiperazino)cyclohexyl]-7H-pyrrolo[2,3-d]pyrimidin-5-yl}-2-fluorophenyl)-5-bromo-2-thiophenesulfonamide trimaleate cis-N-1-(4-{4-amino-7-[4-(4-methylpiperazino)cyclohexyl]-7H-pyrrolo[2,3-d]pyrimidin-5-yl}-2-fluorophenyl)-2,4-dichloro-1-benzenesulfonamide trimaleate cis-N-1-(4-{4-amino-7-[4-(4-methylpiperazino)cyclohexyl]-7H-pyrrolo[2,3-d]pyrimidin-5-yl}-2-fluorophenyl)-2,3,4-trichloro-1-benzenesulfonamide trimaleate cis-N-1-(4-{4-amino-7-[4-(4-methylpiperazino)cyclohexyl]-7H-pyrrolo[2,3-d]pyrimidin-5-yl}-2-fluorophenyl)-3-bromo-5-chloro-2-thiophenesulfonamide trimaleate cis-N-4-(4-{4-amino-7-[4-(4-methylpiperazino)cyclohexyl]-7H-pyrrolo[2,3-d]pyrimidin-5-yl}-2-fluorophenyl)-2,1,3-benzothiadiazole-4-sulfonamide trimaleate cis-N-4-(4-{4-amino-7-[4-(4-methylpiperazino)cyclohexyl]-7H-pyrrolo[2,3-d]pyrimidin-5-yl}-2-fluorophenyl)-2,1,3-benzoxadiazole-4-sulfonamide trimaleate cis-N-1-(4-{4-amino-7-[4-(4-methylpiperazino)cyclohexyl]-7H-pyrrolo[2,3-d]pyrimidin-5-yl}-2-fluorophenyl)-2,5-dichloro-1-thiophenesulfonamide trimaleate cis-N-4-(4-{4-amino-7-[4-(4-methylpiperazino)cyclohexyl]-7H-pyrrolo[2,3-d]pyrimidin-5-yl}-2-fluorophenyl)-(7-chloro-2,1,3-benzoxadiazole)-4-sulfonamide trimaleate cis-N-4-(4-{4-amino-7-[4-(4-methylpiperazino)cyclohexyl]-7H-pyrrolo[2,3-d]pyrimidin-5-yl}-2-fluorophenyl)-(7-methyl-2,1,3-benzothiadiazole)-4-sulfonamide trimaleate cis-N-4-(4-{4-amino-7-[4-(4-methylpiperazino)cyclohexyl]-7H-pyrrolo[2,3-d]pyrimidin-5-yl}-2-fluorophenyl)-(5-methyl-2,1,3-benzothiadiazole)-4-sulfonamide trimaleate cis-N-4-(4-{4-amino-7-[4-(4-methylpiperazino)cyclohexyl]-7H-pyrrolo[2,3-d]pyrimidin-5-yl}-2-fluorophenyl)-(5-chloro-2,1,3-benzothiadiazole)-4-sulfonamide trimaleate cis-N-4-(4-{4-amino-7-[4-(4-methylpiperazino)cyclohexyl]-7H-pyrrolo[2,3-d]pyrimidin-5-yl}-2-fluorophenyl)-3-chloro-2-methyl-1-benzenesulfonamide trimaleate cis-N-1-(4-{4-amino-7-[4-(4-methylpiperazino)cyclohexyl]-7H-pyrrolo[2,3-d]pyrimidin-5-yl}-2-fluorophenyl)-2-bromo-1-benzenesulfonamide trimaleate cis-N-1-(4-{4-amino-7-[4-(4-methylpiperazino)cyclohexyl]-7H-pyrrolo[2,3-d]pyrimidin-5-yl}-2-fluorophenyl)-2,5-dibromo-3,6-difluoro-1-benzenesulfonamide trimaleate cis-N-1-(4-{4-amino-7-[4-(4-methylpiperazino)cyclohexyl]-7H-pyrrolo[2,3-d]pyrimidin-5-yl}-2-fluorophenyl)-2,3-dichloro-1-benzenesulfonamide trimaleate cis-N-1-(4-{4-amino-7-[4-(4-methylpiperazino)cyclohexyl]-7H-pyrrolo[2,3-d]pyrimidin-5-yl}-2-fluorophenyl)-(2-nitrophenyl)methanesulfonamide trimaleate trans-N-1-(4-{4-amino-7-[4-(4-methylpiperazino)cyclohexyl]-7H-pyrrolo[2,3-d]pyrimidin-5-yl}-2-fluorophenyl)-2-nitro-1-benzenesulfonamide trimaleate trans-N-1-(4-{4-amino-7-[4-(4-methylpiperazino)cyclohexyl]-7H-pyrrolo[2,3-d]pyrimidin-5-yl}-2-fluorophenyl)-2-fluoro-1-benzenesulfonamide trimaleate trans-N-1-(4-{4-amino-7-[4-(4-methylpiperazino)cyclohexyl]-7H -pyrrolo[2,3-d]pyrimidin-5-yl}-2-fluorophenyl)-2,4,6-trichloro-1-benzenesulfonamide trimaleate trans-N-1-(4-{4-amino-7-[4-(4-methylpiperazino)cyclohexyl]-7H-pyrrolo[2,3-d]pyrimidin-5-yl}-2-fluorophenyl)-2,6-dichloro-1-benzenesulfonamide trimaleate trans-N-1-(4-{4-amino-7-[4-(4-methylpiperazino)cyclohexyl]-7H-pyrrolo[2,3-d]pyrimidin-5-yl}-2-fluorophenyl)-2-chloro-1-benzenesulfonamide trimaleate trans-N-1-(4-{4-amino-7-[4-(4-methylpiperazino)cyclohexyl]-7H-pyrrolo[2,3-d]pyrimidin-5-yl}-2-fluorophenyl)-3-fluoro-1-benzenesulfonamide dimaleate trans-N-1-(4-{4-amino-7-[4-(4-methylpiperazino)cyclohexyl]-7H-pyrrolo[2,3-d]pyrimidin-5-yl}-2-fluorophenyl)-4-bromo-2,5-difluoro-1-benzenesulfonamide trimaleate trans-N-1-(4-{4-amino-7-[4-(4-methylpiperazino)cyclohexyl]-7H-pyrrolo[2,3-d]pyrimidin-5-yl}-2-fluorophenyl)-3-chloro-4-fluoro-1-benzenesulfonamide trimaleate trans-N-1-(4-{4-amino-7-[4-(4-methylpiperazino)cyclohexyl]-7H-pyrrolo[2,3-d]pyrimidin-5-yl}-2-fluorophenyl-2-iodo-1-benzenesulfonamide trimaleate trans-N-1-(4-{4-amino-7-[4-(4-methylpiperazino)cyclohexyl]-7H-pyrrolo[2,3-d]pyrimidin-5-yl}-2-fluorophenyl)-2,3-dichloro-1-benzenesulfonamide trimaleate trans-N-1-(4-{4-amino-7-[4-(4-methylpiperazino)cyclohexyl]-7H-pyrrolo[2,3-d]pyrimidin-5-yl}-2-fluorophenyl)-2-chloro-6-methyl-1-benzenesulfonamide trimaleate trans-N-1-(4-{4-amino-7-[4-(4-methylpiperazino)cyclohexyl]-7H-pyrrolo[2,3-d]pyrimidin-5-yl}-2-fluorophenyl)-2-chloro-4-cyano-1-benzenesulfonamide trimaleate trans-N-1-(4-{4-amino-7-[4-(4-methylpiperazino)cyclohexyl]-7H-pyrrolo[2,3-d]pyrimidin-5-yl}-2-fluorophenyl)-3,4-difluoro-1-benzenesulfonamide trimaleate trans-N-1-(4-{4-amino-7-[4-(4-methylpiperazino)cyclohexyl]-7H-pyrrolo[2,3-d]pyrimidin-5-yl}-2-fluorophenyl)-4-bromo-2-fluoro-1-benzenesulfonamide trimaleate trans-N-1-(4-{4-amino-7-[4-(4-methylpiperazino)cyclohexyl]-7H-pyrrolo[2,3-d]pyrimidin-5-yl}-2-fluorophenyl)-5-bromo-2-thiophenesulfonamide trimaleate trans-N-1-(4-{4-amino-7-[4-(4-methylpiperazino)cyclohexyl]-7H-pyrrolo[2,3-d]pyrimidin-5-yl}-2-fluorophenyl)-2,4-dichloro-1-benzenesulfonamide trimaleate trans-N-1-(4-{4-amino-7-[4-(4-methylpiperazino)cyclohexyl]-7H-pyrrolo[2,3-d]pyrimidin-5-yl}-2-fluorophenyl)-2,3,4-trichloro-1-benzenesulfonamide trimaleate trans-N-1-(4-{4-amino-7-[4-(4-methylpiperazino)cyclohexyl]-7H-pyrrolo[2,3-d]pyrimidin-5-yl}-2-fluorophenyl)-3-bromo-5-chloro-2-thiophenesulfonamide trimaleate trans-N-4-(4-{4-amino-7-[4-(4-methylpiperazino)cyclohexyl]-7H-pyrrolo[2,3-d]pyrimidin-5-yl}-2-fluorophenyl)-2,1,3-benzoxadiazole-4-sulfonamide trimaleate trans-N-1-(4-{4-amino-7-[4-(4-methylpiperazino)cyclohexyl]-7H-pyrrolo[2,3-d]pyrimidin-5-yl}-2-fluorophenyl)-2,5-dichloro-1-thiophenesulfonamide trimaleate trans-N-4-(4-{4-amino-7-[4-(4-methylpiperazino)cyclohexyl]-7H-pyrrolo[2,3-d]pyrimidin-5-yl}-2-fluorophenyl)-(7-chloro-2,1,3-benzoxadiazole)-4-sulfonamide trimaleate trans-N-4-(4-{4-amino-7-[4-(4-methylpiperazino)cyclohexyl]-7H-pyrrolo[2,3-d]pyrimidin-5-yl}-2-fluorophenyl)-(7-methyl-2,1,3-benzothiadiazole)-4-sulfonamide trimaleate trans-N-4-(4-{4-amino-7-[4-(4-methylpiperazino)cyclohexyl]-7H-pyrrolo[2,3-d]pyrimidin-5-yl}-2-fluorophenyl)-(5-methyl-2,1,3-benzothiadiazole)-4-sulfonamide trimaleate trans-N-4-(4-{4-amino-7-[4-(4-methylpiperazino)cyclohexyl]-7H-pyrrolo[2,3-d]pyrimidin-5-yl}-2-fluorophenyl)-(5-chloro-2,1,3-benzothiadiazole)-4-sulfonamide trimaleate trans-N-1-(4-{4-amino-7-[4-(4-methylpiperazino)cyclohexyl]-7H-pyrrolo[2,3-d]pyrimidin-5-yl}-2-fluorophenyl)-3-chloro-2-methyl-1-benzenesulfonamide trimaleate trans-N-1-(4-{4-amino-7-[4-(4-methylpiperazino)cyclohexyl]-7H-pyrrolo[2,3-d]pyrimidin-5-yl}-2-fluorophenyl)-2-bromo-1-benzenesulfonamide trimaleate trans-N-1-(4-{4-amino-7-[4-(4-methylpiperazino)cyclohexyl]-7H-pyrrolo[2,3-d]pyrimidin-5-yl}-2-fluorophenyl)-2,5-dibromo-3,6-difluoro-1-benzenesulfonamide trimaleate trans-N-1-(4-{4-amino-7-[4-(4-methylpiperazino)cyclohexyl]-7H-pyrrolo[2,3-d]pyrimidin-5-yl}-2-fluorophenyl)-(2-nitrophenyl)methanesulfonamide trimaleate The compounds of this invention have antiangiogenic properties. These antiangiogenic properties are due at least in part to the inhibition of protein tyrosine kinases essential for angiogenic processes. For this reason, these compounds can be used as active agents against such disease states as arthritis, atherosclerosis, restenosis, psoriasis, hemangiomas, myocardial angiogenesis, coronary and cerebral collaterals, ischemic limb angiogenesis, ischemia/reperfusion injury, wound healing, peptic ulcer Helicobacter related diseases, virally-induced angiogenic disorders, fractures, Crow-Fukase syndrome (POEMS), preeclampsia, menometrorrhagia, cat scratch fever, rubeosis, neovascular glaucoma and retinopathies such as those associated with diabetic retinopathy, retinopathy of prematurity, or age-related macular degeneration. In addition, some of these compounds can be used as active agents against solid tumors, malignant ascites, von Hippel Lindau disease, hematopoietic cancers and hyperproliferative disorders such as thyroid hyperplasia (especially Grave's disease), and cysts (such as hypervascularity of ovarian stroma characteristic of polycystic ovarian syndrome (Stein-Leventhal syndrome) and polycystic kidney disease since such diseases require a proliferation of blood vessel cells for growth and/or metastasis.

Further, some of these compounds can be used as active agents against burns, chronic lung disease, stroke, polyps, anaphylaxis, chronic and allergic inflammation, delayed-type hypersensitivity, ovarian hyperstimulation syndrome, brain tumor-associated cerebral edema, high-altitude, trauma or hypoxia induced cerebral or pulmonary edema, ocular and macular edema, ascites, glomerulonephritis and other diseases where vascular hyperpermeability, effusions, exudates, protein extravasation, or edema is a manifestation of the disease. The compounds will also be useful in treating disorders in which protein extravasation leads to the deposition of fibrin and extracellular matrix, promoting stromal proliferation (e.g. keloid, fibrosis, cirrhosis and carpal tunnel syndrome). Increased VEGF production potentiates inflammatory processes such as monocyte recruitment and activation. The compounds of this invention will also be useful in treating inflammatory disorders such as inflammatory bowel disease (IBD) and Crohn's disease.

VEGF's are unique in that they are the only angiogenic growth factors known to contribute to vascular hyperpermeability and the formation of edema. Indeed, vascular hyperpermeability and edema that is associated with the expression or administration of many other growth factors appears to be mediated via VEGF production. Inflammatory cytokines stimulate VEGF production. Hypoxia results in a marked upregulation of VEGF in numerous tissues, hence situations involving infarct, occlusion, ischemia, anemia, or circulatory impairment typically invoke VEGF/VPF mediated responses. Vascular hyperpermeability, associated edema, altered transendothelial exchange and macromolecular extravasation, which is often accompanied by diapedesis, can result in excessive matrix deposition, aberrant stromal proliferation, fibrosis, etc. Hence, VEGF-mediated hyperpermeability can significantly contribute to disorders with these etiologic features.

Because blastocyst implantation, placental development and embryogenesis are angiogenesis dependent, certain compounds of the invention areuseful as contraceptive agents and antifertility agents.

It is envisaged that the disorders listed above are mediated to a significant extent by protein tyrosine kinase activity involving the KDR/VEGFR-2 and/or the Flt-1/VEGFR-1 and/or TIE-2 tyrosine kinases. By inhibiting the activity of these tyrosine kinases, the progression of the listed disorders is inhibited because the angiogenic or vascular hyperpermeability component of the disease state is severely curtailed. The action of certain compounds of this invention, by their selectivity for specific tyrosine kinases, result in a minimization of side effects that would occur if less selective tyrosine kinase inhibitors were used. Certain compounds of the invention are also effective inhibitors of FGFR, PDGFR, c-Met and IGF-1-R. These receptor kinases can directly or indirectly potentiate angiogenic and hyperproliferative responses in various disorders, hence their inhibition can impede disease progression.

The compounds of this invention have inhibitory activity against protein kinases. That is, these compounds modulate signal transduction by protein kinases. Compounds of this invention inhibit protein kinases from serine/threonine and tyrosine kinase classes. In particular, these compounds selectively inhibit the activity of the KDR/FLK-1IVEGFR-2 tyrosine kinases. Certain compounds of this invention also inhibit the activity of additional tyrosine kinases such as Flt-1/VEGFR-1, Tie-2, FGFR, PDGFR, IGF-1R, c-Met, Src-subfamily kinases such as Lck, Src, fyn, yes, etc. Additionally, some compounds of this invention significantly inhibit serine/threonine kinases such as PKC, MAP kinases, erk, CDKs, Plk-1, or Raf-1 which play an essential role in cell proliferation and cell-cycle progression. The potency and specificity of the generic compounds of this invention towards a particular protein kinase can often be altered and optimized by variations in the nature, number and arrangement of the substituents (i.e., $R_1$, $R_2$, $R_3$, A and ring 1) and conformational restrictions. In addition the metabolites of certain compounds may also possess significant protein kinase inhibitory activity.

The compounds of this invention, when administered to individuals in need of such compounds, inhibit vascular hyperpermeability and the formation of edema in these individuals. These compounds act, it is believed, by inhibiting the activity of KDR tyrosine kinase which is involved in the process of vascular hyperpermeability and edema formation. The KDR tyrosine kinase may also be referred to as FLK-1 tyrosine kinase, NYK tyrosine kinase or VEGFR-2 tyrosine kinase. KDR tyrosine kinase is activated when vascular endothelial cell growth factor (VEGF) or another activating ligand (such as VEGF-C, VEGF-D, VEGF-E or HIV Tat protein) binds to a KDR tyrosine kinase receptor which lies on the surface of vascular endothelial cells. Following such KDR tyrosine kinase activation, hyperpermeability of the blood vessels occurs and fluid moves from the blood stream past the blood vessel walls into the interstitial spaces, thereby forming an area of edema. Diapedesis also often accompanies this response. Similarly, excessive vascular hyperpermeability can disrupt normal molecular exchange across the endothelium in critical tissues and organs (e.g., lung and kidney), thereby causing macromolecular extravasation and deposition. Following this acute response to KDR stimulation which is believed to facilitate the subsequent angiogenic process, prolonged KDR tyrosine kinase stimulation results in the proliferation and chemotaxis of vascular endothelial cells and formation of new vessels. By inhibiting KDR tyrosine kinase activity, either by blocking the production of the activating ligand, by blocking the activating ligand binding to the KDR tyrosine kinase receptor, by preventing receptor dimerization and transphosphorylation, by inhibiting the enzyme activity of the KDR tyrosine kinase (inhibiting the phosphorylation function of the enzyme) or by some other mechanism that interrupts its downstream signaling (D. Mukhopedhyay et al., *Cancer Res.* 58:1278–1284 (1998) and references therein), hyperpermeability, as well as associated extravasation, subsequent edema formation and matrix deposition, and angiogenic responses, may be inhibited and minimized.

One group of preferred compounds of this invention have the property of inhibiting KDR tyrosine kinase activity without significantly inhibiting Flt-1 tyrosine kinase activity (Flt-1 tyrosine kinase is also referred to as VEGFR-1 tyrosine kinase). Both KDR tyrosine kinase and Flt-1 tyrosine kinase are activated by VEGF binding to KDR tyrosine kinase receptors and to Flt-1 tyrosine kinase receptors, respectively. Certain preferred compounds of this invention are unique because they inhibit the activity of one VEGF-receptor tyrosine kinase (KDR) that is activated by activating ligands but do not inhibit other receptor tyrosine kinases, such as Flt-1, that are also activated by certain activating ligands. In this manner, certain preferred compounds of this invention are, therefore, selective in their tyrosine kinase inhibitory activity.

In one embodiment, the present invention provides a method of treating a protein kinase-mediated condition in a patient, comprising adiminstering to the patient a therapeutically or prophylactically effective amount of one or more compounds of Formula I.

A "protein kinase-mediated condition" is a medical condition, such as a disease or other undesirable physical condition, the genesis or progression of which depends, at least in part, on the activity of at least one protein kinase. The protein kinase can be, for example, a protein tyrosine kinase or a protein serine/threonine kinase.

The patient to be treated can be any animal, and is preferably a mammal, such as a domesticated animal or a livestock animal. More preferably, the patient is a human.

A "therapeutically effective amount" is an amount of a compound of Formula I or a combination of two or more such compounds, which inhibits, totally or partially, the progression of the condition or alleviates, at least partially, one or more symptoms of the condition. A therapeutically effective amount can also be an amount which is prophylactically effective. The amount which is therapeutically effective will depend upon the patient's size and gender, the condition to be treated, the severity of the condition and the result sought. For a given patient, a therapeutically effective amount can be determined by methods known to those of skill in the art.

The method of the present invention is useful in the treatment of protein kinase-mediated conditions, such as any of the conditions described above. In one embodiment, the protein kinase-mediated condition is characterized by undesired angiogenesis, edema, or stromal deposition. For example, the condition can be one or more more ulcers, such as ulcers caused by bacterial or fungal infections, Mooren ulcers and ulcerative colitis. The condition can also be due to a microbial infection, such as Lyme disease, sepsis, septic shock or infections by Herpes simplex, Herpes Zoster, human immunodeficincy virus, protozoa, toxoplasmosis or parapoxvirus; an angiogenic disorders, such as von Hippel Lindau disease, polycystic kidney disease, pemphigoid, Paget's disease and psoriasis; a reproductive condition, such as endometriosis, ovarian hyperstimulation syndrome, preeclampsia or menometrorrhagia; a fibrotic and edemic condition, such as sarcoidosis, fibrosis, cirrhosis, thyroiditis, hyperviscosity syndrome systemic, Osler-Weber-Rendu disease, chronic occlusive pulmonary disease, asthma, and edema following burns, trauma, radiation, stroke, hypoxia or ischemia; or an inflammatory/immunologic condition, such as systemic lupus, chronic inflammation, glomerulonephritis, synovitis, inflammatory bowel disease, Crohn's disease, rheumatoid arthritis, osteoarthritis, multiple sclerosis and graft rejection. Suitable protein kinase-mediated conditions also include sickle cell anaemia, osteoporosis, osteopetrosis, tumor-induced hypercalcemia and bone metastases. Additional protein kinase-mediated conditions which can be treated by the method of the present invention include ocular conditions such as ocular and macular edema, ocular neovascular disease, scleritis, radial keratotomy, uveitis, vitritis, myopia, optic pits, chronic retinal detachment, post-laser complications, conjunctivitis, Stargardt's disease and Eales disease, in addition to retinopathy and macular degeneration.

The compounds of the present invention are also useful in the treatment of cardiovascular conditions such as atherosclerosis, restenosis, vascular occlusion and carotid obstructive disease.

The compounds of the present invention are also useful in the treatment of cancer related indications such as solid tumors, sarcomas (especially Ewing's sarcoma and osteosarcoma), retinoblastoma, rhabdomyosarcomas, neuroblastoma, hematopoietic malignancies, including leukaemia and lymphoma, tumor-induced pleural or pericardial effusions, and malignant ascites.

The compounds of the present invention are also useful in the treatment of Crow-Fukase (POEMS) syndrome and diabetic conditions such as glaucoma, diabetic retinopathy and microangiopathy.

The Src, Tec, Jak, Map, Csk, NFκB and Syk families of kinases play pivotal roles in the regulation of immune function. The Src family currently includes Fyn, Lck, Fgr, Fes, Lyn, Src, Yrk, Fyk, Yes, Hck, and Blk. The Syk family is currently understood to include only Zap and Syk. The TEC family includes Tec, Btk, Rlk and Itk. The Janus family of kinases is involved in the transduction of growth factor and proinflammatory cytokine signals through a number of receptors. Although BTK and ITK, members of the Tec family of kinases, play a less well understood role in immunobiology, their modulation by an inhibitor may prove therapeutically beneficial. The Csk family is currently understood to include Csk and Chk. The kinases RIP, IRAK-1, IRAK-2, NIK, p38 MAP kinases, Jnk, IKK-1 and IKK-2 are involved in the signal transduction pathways for key pro-inflammatory cytokines, such as TNF and IL-1. By virtue of their ability to inhibit one or more of these kinases, compounds of formula I may function as immunomodulatory agents useful for the maintenance of allografts, the treatment of autoimmune disorders and treatment of sepsis and septic shock. Through their ability to regulate the migration or activation of T cells, B-cells, mast cells, monocytes and neutrophils, these compounds could be used to treat such autoimmune diseases and sepsis. Prevention of transplant rejection, either host versus graft for solid organs or graft versus host for bone marrow, are limited by the toxicity of currently available immunosuppressive agents and would benefit from an efficacious drug with improved therapeutic index. Gene targeting experiments have demonstrated the essential role of Src in the biology of osteoclasts, the cells responsible for bone resorption. Compounds of formula I, through their ability to regulate Src, may also be useful in the treatment of osteoporosis, osteopetrosis, Paget's disease, tumor-induced hypercalcemia and in the treatment of bone metastases.

A number of protein kinases have been demonstrated to be protooncogenes. Chromosome breakage (at the Itk kinase break point on chromosome 5), translocation as in the case of the Abl gene with BCR (Philadelphia chromosome), truncation in instances such as c-Kit or EGFR, or mutation (e.g., Met) result in the creation of dysregulated proteins converting them from protooncogene to oncogene products. In other tumors, oncogenesis is driven by an autocrine or paracrine ligand/growth factor receptor interactions. Members of the src-family kinases are typically involved in downstream signal transduction thereby potentiating the oncogenesis and themselves may become oncogenic by over-expression or mutation. By inhibiting the protein kinase activity of these proteins the disease process may be disrupted. Vascular restenosis may involve FGF and/or PDGF-promoted smooth muscle and endothelial cell proliferation. The ligand stimulation of FGFR, PDGFR, IGF1-R and c-Met in vivo is proangiogenic, and potentiates angiogenesis dependent disorders. Inhibition of FGFr, PDGFr, c-Met, or IGF1-R kinase activities individually or in combination may be an efficacious strategy for inhibiting these phenomena. Thus compounds of formula I which inhibit the kinase activity of normal or aberrant c-kit, c-met, c-fms, src-family members, EGFr, erbB2, erbB4, BCR-Abl, PDGFr, FGFr, IGF1-R and other receptor or cytosolic tyrosine kinases may be of value in the treatment of benign and neoplastic proliferative diseases.

In many pathological conditions (for example, solid primary tumors and metastases, Kaposi's sarcoma, rheumatoid arthritis, blindness due to inappropriate ocular neovascularization, psoriasis and atherosclerosis) disease progression is contingent upon persistent angiogenesis. Polypeptide growth factors often produced by the disease tissue or associated inflammatory cells, and their corresponding endothelial cell specific receptor tyrosine kinases (e.g., KDR/VEGFR-2, Flt-1/VEGFR-1, Tie-2/Tek and Tie) are essential for the stimulation of endothelial cell growth, migration, organization, differentiation and the establishment of the requisite new functional vasculature. As a result of the vascular permeability factor activity of VEGF in mediating vascular hyperpermeability, VEGF-stimulation of a VEGFR kinase is also believed to play an important role in the formation of tumor ascites, cerebral and pulmonary edema, pleural and pericardial effusions, delayed-type hypersensitivity reactions, tissue edema and organ dysfunction following trauma, burns, ischemia, diabetic complications, endometriosis, adult respiratory distress syndrome (ARDS), post-cardiopulmonary bypass-related hypotension and hyperpermeability, and ocular edema leading to glaucoma or blindness due to inappropriate neovascularization. In addition to VEGF, recently identified VEGF—C and VEGF-D, and virally-encoded VEGF-E or HIV-Tat protein can also cause a vascular hyperpermeability response through the stimulation of a VEGFR kinase. KDR/VEGFR-2 and/or Tie-2 are expressed also in a select population of hematopoietic stem cells. Certain members of this population are pluripotent in nature and can be stimulated with growth factors to differentiate into endothelial cells and participate in vasculogenetic angiogenic processes. For this reason these have been called Endothelial Progenitor Cells (EPCs) (*J. Clin. Investig.* 103: 1231–1236 (1999)). In some progenitors, Tie-2 may play a role in their recruitment, adhesion, regulation and differentiation (*Blood*, 4317–4326 (1997)). Certain agents according to formula I capable of blocking the kinase activity of endothelial cell specific kinases could therefore inhibit disease progression involving these situations.

Vascular destabilization of the antagonist ligand of Tie-2 (Ang2) is believed to induce an unstable "plastic" state in the endothelium. In the presence of high VEGF levels a robust angiogenic response may result; however, in the absence of VEGF or a VEGF-related stimulus, frank vessel regression and endothelial apoptosis can occur (Genes and Devel. 13: 1055–1066 (1999)). In an analogous manner a Tie-2 kinase inhibitor can be proangiogenic or antiangiogenic in the presence or absence of a VEGF-related stimulus, respectively. Hence, Tie-2 inhibitors can be employed with appropriate proangiogenic stimuli, such as VEGF, to promote therapeutic angiogenesis in situations such as wound healing, infarct and ischemia.

The compounds of formula I or a salt thereof or pharmaceutical compositions containing a therapeutically effective amount thereof may be used in the treatment of protein kinase-mediated conditions, such as benign and neoplastic proliferative diseases and disorders of the immune system, as described above. For example, such diseases include autoimmune diseases, such as rheumatoid arthritis, thyroiditis, type 1 diabetes, multiple sclerosis, sarcoidosis, inflammatory bowel disease, Crohn's disease, myasthenia gravis and systemic lupus erythematosus; psoriasis, organ transplant rejection (eg. kidney rejection, graft versus host disease), benign and neoplastic proliferative diseases, human cancers such as lung, breast, stomach, bladder, colon, pancreas, ovarian, prostate and rectal cancer and hematopoietic malignancies (leukemia and lymphoma), and diseases involving inappropriate vascularization for example diabetic retinopathy, retinopathy of prematurity, choroidal neovascularization due to age-related macular degeneration, and infantile hemangiomas in human beings. In addition, such inhibitors may be useful in the treatment of disorders involving VEGF mediated edema, ascites, effusions, and exudates, including for example macular edema, cerebral edema, acute lung injury and adult respiratory distress syndrome (ARDS).

The compounds of the present invention may also be useful in the prophylaxis of the above diseases.

It is envisaged that the disorders listed above are mediated to a significant extent by protein tyrosine kinase activity involving the VEGF receptors (e.g. KDR, Flt-1 and/or Tie-2). By inhibiting the activity of these receptor tyrosine kinases, the progression of the listed disorders is inhibited because the angiogenic component of the disease state is severely curtailed. The action of the compounds of this invention, by their selectivity for specific tyrosine kinases, result in a minimization of side effects that would occur if less selective tyrosine kinase inhibitors were used.

In another aspect the present invention provides compounds of formula I as defined initially above for use as medicaments, particularly as inhibitors of protein kinase activity for example tyrosine kinase activity, serine kinase activity and threonine kinase activity. In yet another aspect the present invention provides the use of compounds of formula I as defined initially above in the manufacture of a medicament for use in the inhibition of protein kinase activity.

Physiologically acceptable salts can refer to those salts which retain the biological effectiveness and properties of the free bases and which are obtained by reaction with inorganic acids such as hydrochloric acid, hydrobromic acid, sulfuric acid, nitric acid, phosphoric acid or organic acids such as sulfonic acid, carboxylic acid, organic phosphoric acid, methanesulfonic acid, ethanesulfonic acid, p-toluenesulfonic acid, salicylic acid, lactic acid, tartaric acid and the like.

"Alkyl" refers to a saturated aliphatic hydrocarbon, including straight-chain and branched-chain groups having 1 to 6 carbons or cyclic hydrocarbons having 3 to 6 carbons.

"Alkoxy" refers to an "O-alkyl" group, where "alkyl" is defined as described above.

Phamaceutical Formulations

The compounds of this invention can be administered to a human patient by themselves or in pharmaceutical compositions where they are mixed with suitable carriers or excipient(s) at doses to treat or ameliorate vascular hyperpermeability, edema and associated disorders. Mixtures of these compounds can also be administered to the patient as a simple mixture or in suitable formulated pharmaceutical compositions. A therapeutically effective dose further refers to that amount of the compound or compounds sufficient to result in the prevention or attenuation of inappropriate neovascularization, progression of hyperproliferative disorders, edema, VEGF-associated hyperpermeability and/or VEGF-related hypotension. Techniques for formulation and administration of the compounds of the instant application may be found in "Remington's Pharmaceutical Sciences," Mack Publishing Co., Easton, Pa., latest edition.

Routes of Administration

Suitable routes of administration may, for example, include oral, eyedrop, rectal, transmucosal, topical, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer the compound in a local rather than a systemic manner, for example, via injection of the compound directly into an edematous site, often in a depot or sustained release formulation.

Furthermore, one may administer the drug in a targeted drug delivery system, for example, in a liposome coated with endothelial cell-specific antibody.

Composition/Formulation

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds can be formulated for parenteral administration by injection, e.g. bolus injection or continuous infusion. Formulations for injection may be presented in unit dosage form, e.g.in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly or by intramuscular injection). Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

An example of a pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethysulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free-base forms.

Effective Dosage

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art.

For any compound used in the method of the invention, the therapeutically effective dose can be estimated initially from cellular assays. For example, a dose can be formulated in cellular and animal models to achieve a circulating concentration range that includes the $IC_{50}$ as determined in cellular assays (i.e., the concentration of the test compound which achieves a half-maximal inhibition of a given protein kinase activity). In some cases it is appropriate to determine the $IC_{50}$ in the presence of 3 to 5% serum albumin since such a determination approximates the binding effects of plasma protein on the compound. Such information can be used to more accurately determine useful doses in humans. Further, the most preferred compounds for systemic administration effectively inhibit protein kinase signaling in intact cells at levels that are safely achievable in plasma.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. Compounds which exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, in "The Pharmacological Basis of Therapeutics", Ch. 1 p1). In the treatment of crises, the administration of an acute bolus or an infusion approaching the MTD may be required to obtain a rapid response.

Dosage amount and interval may be adjusted individually to provide plasma levels of the active moiety which are sufficient to maintain the kinase modulating effects, or minimal effective concentration (MEC). The MEC will vary for each compound but can be estimated from in vitro data; e.g. the concentration necessary to achieve 50–90% inhibition of protein kinase using the assays described herein. Dosages necessary to achieve the MEC will depend on individual characteristics and route of administration. However, HPLC assays or bioassays can be used to determine plasma concentrations.

Dosage intervals can also be determined using the MEC value. Compounds should be administered using a regimen which maintains plasma levels above the MEC for 10–90% of the time, preferably between 30–90% and most preferably between 50–90% until the desired amelioration of symptoms is achieved. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

Packaging

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

In some formulations it may be beneficial to use the compounds of the present invention in the form of particles of very small size, for example as obtained by fluid energy milling.

The use of compounds of the present invention in the manufacture of pharmaceutical compositions is illustrated by the following description. In this description the term "active compound" denotes any compound of the invention but particularly any compound which is the final product of one of the preceding Examples.

a) Capsules

In the preparation of capsules, 10 parts by weight of active compound and 240 parts by weight of lactose can be de-aggregated and blended. The mixture can be filled into hard gelatin capsules, each capsule containing a unit dose or part of a unit dose of active compound.

b) Tablets

Tablets can be prepared from the following ingredients.

| Parts by weight | |
| --- | --- |
| Active compound | 10 |
| Lactose | 190 |
| Maize starch | 22 |
| Polyvinylpyrrolidone | 10 |
| Magnesium stearate | 3 |

The active compound, the lactose and some of the starch can be de-aggregated, blended and the resulting mixture can be granulated with a solution of the polyvinyl-pyrrolidone in ethanol. The dry granulate can be blended with the magnesium stearate and the rest of the starch. The mixture is then compressed in a tabletting machine to give tablets each containing a unit dose or a part of a unit dose of active compound.

c) Enteric coated tablets

Tablets can be prepared by the method described in (b) above. The tablets can be enteric coated in a conventional manner using a solution of 20% cellulose acetate phthalate and 3% diethyl phthalate in ethanol:dichloromethane (1:1).

d) Suppositories

In the preparation of suppositories, 100 parts by weight of active compound can be incorporated in 1300 parts by weight of triglyceride suppository base and the mixture formed into suppositories each containing a therapeutically effective amount of active ingredient.

In the compositions of the present invention the active compound may, if desired, be associated with other compatible pharmacologically active ingredients. For example, the compounds of this invention can be administered in combination with one or more additional pharmaceutical agents that inhibit or prevent the production of VEGF or angiopoietins, attenuate intracellular responses to VEGF or angiopoietins, block intracellular signal transduction, inhibit vascular hyperpermeability, reduce inflammation, or inhibit or prevent the formation of edema or neovascularization. The compounds of the invention can be administered prior to, subsequent to or simultaneously with the additional pharmaceutical agent, whichever course of administration is appropriate. The additional pharmaceutical agents include but are not limited to anti-edemic steroids, NSAIDS, ras inhibitors, anti-TNF agents, anti-IL1 agents, antihistamines, PAF-antagonists, COX-1 inhibitors, COX-2 inhibitors, NO synthase inhibitors, Akt/PTB inhibitors, IGF-1R inhibitors, PKC inhibitors and PI3 kinase inhibitors. The compounds of the invention and the additional pharmaceutical agents act either additively or synergistically. Thus, the administration of such a combination of substances that inhibit angiogenesis, vascular hyperpermeability and/or inhibit the formation of edema can provide greater relief from the deletrious effects of a hyperproliferative disorder, angiogenesis, vascular hyperpermeability or edema than the administration of either substance alone. In the treatment of malignant disorders combinations with antiproliferative or cytotoxic chemotherapies or radiation are anticipated.

The present invention also comprises the use of a compound of formula I as a medicament.

A further aspect of the present invention provides the use of a compound of formula I or a salt thereof in the manufacture of a medicament for treating vascular hyperpermeability, angiogenesis-dependent disorders, proliferative diseases and/or disorders of the immune system in mammals, particularly human beings.

The present invention also provides a method of treating vascular hyperpermeability, inappropriate neovascularization, proliferative diseases and/or disorders of the immune system which comprises the administration of a therapeutically effective amount of a compound of formula I to a mammal, particularly a human being, in need thereof.

The in vitro potency of compounds in inhibiting these protein kinases may be determined by the procedures detailed below.

The potency of compounds can be determined by the amount of inhibition of the phosphorylation of an exogenous substrate (e.g., synthetic peptide (Z. Songyang et al., *Nature*. 373:536–539)) by a test compound relative to control.

KDR Tyrosine Kinase Production Using Baculovirus System

The coding sequence for the human KDR intra-cellular domain (aa789–1354) was generated through PCR using cDNAs isolated from HUVEC cells. A poly-His6 sequence was introduced at the N-terminus of this protein as well. This fragment was cloned into transfection vector pVL1393 at the Xba 1 and Not 1 site. Recombinant baculovirus (BV) was generated through co-transfection using the BaculoGold Transfection reagent (PharMingen). Recombinant BV was plaque purified and verified through Western analysis. For protein production, SF-9 cells were grown in SF-900-II medium at 2×106/ml, and were infected at 0.5 plaque forming units per cell (MOI). Cells were harvested at 48 hours post infection.

Purification of KDR

SF-9 cells expressing $(His)_6KDR(aa789–1354)$ were lysed by adding 50 ml of Triton X-100 lysis buffer (20 mM Tris, pH 8.0, 137 mM NaCl, 10% glycerol, 1% Triton X-100, 1 mM PMSF, 10 $\mu$g/ml aprotinin, 1 $\mu$g/ml leupeptin) to the cell pellet from 1 L of cell culture. The lysate was centrifuged at 19,000 rpm in a Sorval SS-34 rotor for 30 min at 4° C. The cell lysate was applied to a 5 ml $NiCl_2$ chelating sepharose column, equilibrated with 50 mM HEPES, pH7.5, 0.3 M NaCl. KDR was eluted using the same buffer containing 0.25 M imidazole. Column fractions were analyzed using SDS-PAGE and an ELISA assay (below) which measures kinase activity. The purified KDR was exchanged into 25 mM HEPES, pH7.5, 25 mM NaCl, 5 mM DTT buffer and stored at −80° C.

Human Tie-2 Kinase Production and Purification

The coding sequence for the human Tie-2 intra-cellular domain (aa775–1124) was generated through PCR using cDNAs isolated from human placenta as a template. A poly—$His_6$ sequence was introduced at the N-terminus and this construct was cloned into transfection vector pVL 1939 at the Xba 1 and Not 1 site. Recombinant BV was generated through co-transfection using the BaculoGold Transfection reagent (PharMingen). Recombinant BV was plaque purified and verified through Western analysis. For protein production, SF-9 insect cells were grown in SF-900-II medium at 2×106/ml, and were infected at MOI of 0.5. Purification of the His-tagged kinase used in screening was analogous to that described for KDR.

Human Flt-1 Tyrosine Kinase Production and Purification

The baculoviral expression vector pVL1393 (Phar Mingen, Los Angeles, Calif.) was used. A nucleotide sequence encoding poly-His6 was placed 5' to the nucleotide region encoding the entire intracellular kinase domain of human Flt-1 (amino acids 786–1338). The nucleotide sequence encoding the kinase domain was generated through PCR using cDNA libraries isolated from HUVEC cells. The histidine residues enabled affinity purification of the protein as a manner analogous to that for KDR and ZAP70. SF-9 insect cells were infected at a 0.5 multiplicity and harvested 48 hours post infection.

EGFR Tyrosine Kinase Source

EGFR was purchased from Sigma (Cat #E-3641; 500 units/50 µl) and the EGF ligand was acquired from Oncogene Research Products/Calbiochem (Cat #PF011-100).

Expression of ZAP70

The baculoviral expression vector used was pVL1393. (Pharmingen, Los Angeles, Calif.) The nucleotide sequence encoding amino acids M(H)6 LVPR$_9$S was placed 5' to the region encoding the entirety of ZAP70 (amino acids 1–619). The nucleotide sequence encoding the ZAP70 coding region was generated through PCR using cDNA libraries isolated from Jurkat immortalized T-cells. The histidine residues enabled affinity purification of the protein (vide infra). The LVPR$_9$S bridge constitutes a recognition sequence for proteolytic cleavage by thrombin, enabling removal of the affinity tag from the enzyme. SF-9 insect cells were infected at a multiplicity of infection of 0.5 and harvested 48 hours post infection.

Extraction and Purification of ZAP70

SF-9 cells were lysed in a buffer consisting of 20 mM Tris, pH 8.0, 137 mM NaCl, 10% glycerol, 1% Triton X-100, 1 mM PMSF, 1 µg/ml leupeptin, 10 µg/ml aprotinin and 1 mM sodium orthovanadate. The soluble lysate was applied to a chelating sepharose HiTrap column (Pharmacia) equilibrated in 50 mM HEPES, pH 7.5, 0.3 M NaCl. Fusion protein was eluted with 250 mM imidazole. The enzyme was stored in buffer containing 50 mM HEPES, pH 7.5, 50 mM NaCl and 5 mM DTT.

Protein Kinase Source

Lck, Fyn, Src, Blk, Csk, and Lyn, and truncated forms thereof may be commercially obtained (e.g. from Upstate Biotechnology Inc. (Saranac Lake, N.Y.) and Santa Cruz Biotechnology Inc. (Santa Cruz, Calif.)) or purified from known natural or recombinant sources using conventional methods.

Enzyme Linked Immunosorbent Assay (ELISA) for PTKs

Enzyme linked immunosorbent assays (ELISA) were used to detect and measure the presence of tyrosine kinase activity. The ELISA were conducted according to known protocols which are described in, for example, Voller, et al., 1980, "Enzyme-Linked Immunosorbent Assay," In: *Manual of Clinical Immunology*, 2d ed., edited by Rose and Friedman, pp 359–371 Am. Soc. of Microbiology, Washington, D.C.

The disclosed protocol was adapted for determining activity with respect to a specific PTK. For example, preferred protocols for conducting the ELISA experiments is provided below. Adaptation of these protocols for determining a compound's activity for other members of the receptor PTK family, as well as non-receptor tyrosine kinases, are well within the abilities of those in the art. For purposes of determining inhibitor selectivity, a universal PTK substrate (e.g., random copolymer of poly(Glu$_4$ Tyr), 20,000–50,000 MW) was employed together with ATP (typically 5 µM) at concentrations approximately twice the apparent Km in the assay.

The following procedure was used to assay the inhibitory effect of compounds of this invention on KDR, Flt-1, Tie-2, EGFR, FGFR, PDGFR, IGF-1-R, c-Met, Lck, Blk, Csk, Src, Lyn, Fyn and ZAP70 tyrosine kinase activity:

Buffers and Solutions

PGTPoly (Glu,Tyr) 4:1
Store powder at −20° C. Dissolve powder in phosphate buffered saline (PBS) for 50 mg/ml solution. Store 1 ml aliquots at −20° C. When making plates dilute to 250 µg/ml in Gibco PBS.
Reaction Buffer: 100 mM Hepes, 20 mM MgCl$_2$, 4 mM MnCl$_2$, 5 mM DTT, 0.02% BSA, 200 µM NaVO$_4$, pH 7.10
ATP: Store aliquots of 100 mM at −20° C. Dilute to 20 µM in water
Washing Buffer: PBS with 0.1% Tween 20
Antibody Diluting Buffer: 0.1% bovine serum albumin (BSA) in PBS
TMB Substrate: mix TMB substrate and Peroxide solutions 9:1 just before use or use K-Blue Substrate from Neogen
Stop Solution: 1M Phosphoric Acid

Procedure

1. Plate Preparation:
   Dilute PGT stock (50 mg/ml, frozen) in PBS to a 250 µg/ml. Add 125 µl per well of Corning modified flat bottom high affinity ELISA plates (Corning #25805-96). Add 125 µl PBS to blank wells. Cover with sealing tape and incubate overnight 37° C. Wash 1× with 250 µl washing buffer and dry for about 2hrs in 37° C. dry incubator. Store coated plates in sealed bag at 4° C. until used.
2. Tyrosine Kinase Reaction:
   Prepare inhibitor solutions at a 4×concentration in 20% DMSO in water.
   Prepare reaction buffer
   Prepare enzyme solution so that desired units are in 50 µl, e.g. for KDR make to 1 ng/µl for a total of 50 ng per well in the reactions. Store on ice.
   Make 4×ATP solution to 20 µM from 100 mM stock in water. Store on ice
   Add 50 µl of the enzyme solution per well (typically 5–50 ng enzyme/well depending on the specific activity of the kinase)
   Add 25 µl 4×inhibitor
   Add 25 µl 4×ATP for inhibitor assay
   Incubate for 10 minutes at room temperature
   Stop reaction by adding 50 µl 0.05N HCl per well
   Wash plate

**Final Concentrations for Reaction: 5 μM ATP, 5% DMSO

3. Antibody Binding

Dilute 1 mg/ml aliquot of PY20-HRP (Pierce) antibody(a phosphotyrosine antibody) to 50 ng/ml in 0.1% BSA in PBS by a 2 step dilution (100×, then 200×)

Add 100 μl Ab per well. Incubate 1 hr at room temp. Incubate 1 hr at 4 C.

Wash 4×plate

4. Color Reaction

Prepare TMB substrate and add 100 μl per well

Monitor OD at 650 nm until 0.6 is reached

Stop with 1M Phosphoric acid. Shake on plate reader.

Read OD immediately at 450 nm

Optimal incubation times and enzyme reaction conditions vary slightly with enzyme preparations and are determined empirically for each lot.

For Lck, the Reaction Buffer utilized was 100 mM MOPSO, pH 6.5, 4 mM $MnCl_2$, 20 mM $MgCl_2$, 5 mM DTT, 0.2% BSA, 200 mM $NaVO_4$ under the analogous assay conditions.

Compounds of formula I may have therapeutic utility in the treatment of diseases involving both identified, including those not mentioned herein, and as yet unidentified protein tyrosine kinases which are inhibited by compounds of formula I. All compounds exemplified herein significantly inhibit either FGFR, PDGFR, KDR, Tie-2, Lck, Fyn, Blk, Lyn or Src at concentrations of 50 micromolar or below. Some compounds of this invention also significantly inhibit other tyrosine or serine/threonine kinases such as cdc2 (cdk1) at concentrations of 50 micromolar or below.

Cdc2 Source

The human recombinant enzyme and assay buffer may be obtained commercially (New England Biolabs, Beverly, Mass. USA) or purified from known natural or recombinant sources using conventional methods.

Cdc2 Assay

The protocol used was that provided with the purchased reagents with minor modifications. In brief, the reaction was carried out in a buffer consisting of 50 mM Tris pH 7.5, 100 mM NaCl, 1 mM EGTA, 2 mM DTT, 0.01% Brij, 5% DMSO and 10 mM $MgCl_2$ (commercial buffer) supplemented with fresh 300 μM ATP (31 μCl/ml) and 30 μg/ml histone type IIIss final concentrations. A reaction volume of 80 μL, containing units of enzyme, was run for 20 minutes at 25 degrees C. in the presence or absence of inhibitor. The reaction was terminated by the addition of 120 μL of 10% acetic acid. The substrate was separated from unincorporated label by spotting the mixture on phosphocellulose paper, followed by 3 washes of 5 minutes each with 75 mM phosphoric acid. Counts were measured by a betacounter in the presence of liquid scintillant.

Certain compounds of this invention significantly inhibit cdc2 at concentrations below 50 uM.

PKC Kinase Source

The catalytic subunit of PKC may be obtained commercially (Calbiochem).

PKC Kinase Assay

A radioactive kinase assay was employed following a published procedure (Yasuda, I., Kirshimoto, A., Tanaka, S., Tominaga, M., Sakurai, A., Nishizuka, Y. *Biochemical and Biophysical Research Communication* 3:166, 1220–1227 (1990)). Briefly, all reactions were performed in a kinase buffer consisting of 50 mM Tris-HCl pH7.5, 10 mM $MgCl_2$, 2 mM DTT, 1 mM EGTA, 100 μM ATP, 8 μM peptide, 5% DMSO and $^{33}P$ ATP (8 Ci/mM). Compound and enzyme were mixed in the reaction vessel and the reaction initiated by addition of the ATP and substrate mixture. Following termination of the reaction by the addition of 10 μL stop buffer (5 mM ATP in 75 mM phosphoric acid), a portion of the mixture was spotted on phosphocellulose filters. The spotted samples were washed 3 times in 75 mM phosphoric acid at room temperature for 5 to 15 minutes. Incorporation of radiolabel was quantified by liquid scintillation counting.

Erk2 Enzyme Source

The recombinant murine enzyme and assay buffer may be obtained commercially (New England Biolabs, Beverly Mass. USA) or purified from known natural or recombinant sources using conventional methods.

Erk2 Enzyme Assay

In brief, the reaction was carried out in a buffer consisting of 50 mM Tris pH 7.5, 1 mM EGTA, 2 mM DTT, 0.01% Brij, 5% DMSO and 10 mM $MgCl_2$ (commercial buffer) supplemented with fresh 100 μM ATP (31 μCi/ml) and 30 μM myelin basic protein under conditions recommended by the supplier. Reaction volumes and method of assaying incorporated radioactivity were as described for the PKC assay (vide supra).

In Vitro Models for T-cell Activation

Upon activation by mitogen or antigen, T-cells are induced to secrete IL-2, a growth factor that supports their subsequent proliferative phase. Therefore, one may measure either production of IL-2 from or cell proliferation of, primary T-cells or appropriate T-cell lines as a surrogate for T-cell activation. Both of these assays are well described in the literature and their parameters well documented (in Current Protocols in Immunology, Vol 2, 7.10.1–7.11.2).

In brief, T-cells may be activated by co-culture with allogenic stimulator cells, a process termed the one-way mixed lymphophocyte reaction. Responder and stimulator peripheral blood mononuclear cells are purified by Ficoll—Hypaque gradient (Pharmacia) per directions of the manufacturer. Stimulator cells are mitotically inactivated by treatment with mitomycin C (Sigma) or gamma irradiation. Responder and stimulator cells are co-cultured at a ratio of two to one in the presence or absence of the test compound. Typically $10^5$ responders are mixed with $5 \times 10^4$ stimulators and plated (200 μl volume) in a U bottom microtiter plate (Costar Scientific). The cells are cultured in RPMI 1640 supplemented with either heat inactivated fetal bovine serum (Hyclone Laboratories) or pooled human AB serum from male donors, $5 \times 10^{-5}$ M 2-mercaptoethanol and 0.5% DMSO, The cultures are pulsed with 0.5 μCi of $^3H$ thymidine (Amersham) one day prior to harvest (typically day three). The cultures are harvested (Betaplate harvester, Wallac) and isotope uptake assessed by liquid scintillation (Betaplate, Wallac).

The same culture system may be used for assessing T-cell activation by measurement of IL-2 production. Eighteen to twenty-four hours after culture initiation, the supernatants are removed and the IL-2 concentration is measured by ELISA (R and D Systems) following the directions of the manufacturer.

In-vivo Models of T-Cell Activation

The in vivo efficacy of compounds can be tested in animal models known to directly measure T-cell activation or for which T-cells have been proven the effectors. T-cells can be activated in vivo by ligation of the constant portion of the T-cell receptor with a monoclonal anti-CD3 antibody (Ab). In this model, BALB/c mice are given 10 μg of anti-CD3 Ab intraperitoneally two hours prior to exsanguination. Animals to receive a test drug are pre-treated with a single dose of the compound one hour prior to anti-CD3 Ab administration. Serum levels of the proinflammatory cytokines interferon-γ(IFN-γ) and tumor necrosis factor-α(TNF-α), indicators of T-cell activation, are measured by ELISA. A similar model employs in vivo T-cell priming with a specific antigen such as keyhole limpet hemocyanin (KLH) followed by a secondary in vitro challenge of draining lymph node cells with the same antigen. As previously, measurement of cytokine production is used to assess the activation state of the cultured cells. Briefly, C57BL/6 mice are immunized subcutaneously with 100 μg KLH emulsified in complete Freund's adjuvant (CFA) on day zero. Animals are pre-treated with the compound one day prior to immunization and subsequently on days one, two and three post immunization. Draining lymph nodes are harvested on day 4 and their cells cultured at $6 \times 10^6$ per ml in tissue culture medium (RPMI 1640 supplemented with heat inactivated fetal bovine serum (Hyclone Laboratories) $5 \times 10^{-5}$ M 2-mercaptoethanol and 0.5% DMSO) for both twenty-four and forty-eight hours. Culture supernatants are then assessed for the autocrine T-cell growth factor Interleukin-2 (IL-2) and/or IFN-γ levels by ELISA.

Lead compounds can also be tested in animal models of human disease. These are exemplified by experimental autoimmune encephalomyelitis (EAE) and collagen-induced arthritis (CIA). EAE models which mimic aspects of human multiple sclerosis have been described in both rats and mice (reviewed FASEB J. 5:2560–2566, 1991; murine model: Lab. Invest. 4(3):278, 1981; rodent model:J. Immunol 146 (4): 1163–8, 1991). Briefly, mice or rats are immunized with an emulsion of myelin basic protein (MBP), or neurogenic peptide derivatives thereof, and CFA. Acute disease can be induced with the addition of bacterial toxins such as bordetella pertussis. Relapsing/remitting disease is induced by adoptive transfer of T-cells from MBP/peptide immunized animals.

CIA may be induced in DBA/1 mice by immunization with type II collagen (J. Immunol: 142(7):2237–2243). Mice will develop signs of arthritis as early as ten days following antigen challenge and may be scored for as long as ninety days after immunization. In both the EAE and CIA models, a compound may be administered either prophylactically or at the time of disease onset. Efficacious drugs should reduce severity and/or incidence.

Certain compounds of this invention which inhibit one or more angiogenic receptor PTK, and/or a protein kinase such as lck involved in mediating inflammatory responses can reduce the severity and incidence of arthritis in these models.

Compounds can also be tested in mouse allograft models, either skin (reviewed in Ann. Rev. Immunol., 10:333–58, 1992; Transplantation: 57(12): 1701-17D6, 1994) or heart (Am.J.Anat.: 113:273, 1963). Briefly, full thickness skin grafts are transplanted from C57BL/6 mice to BALB/c mice. The grafts can be examined daily, beginning at day six, for evidence of rejection. In the mouse neonatal heart transplant model, neonatal hearts are ectopically transplanted from C57BL/6 mice into the ear pinnae of adult CBA/J mice. Hearts start to beat four to seven days post transplantation and rejection may be assessed visually using a dissecting microscope to look for cessation of beating.

Cellular Receptor PTK Assays

The following cellular assay was used to determine the level of activity and effect of the different compounds of the present invention on KDR/VEGFR2. Similar receptor PTK assays employing a specific ligand stimulus can be designed along the same lines for other tyrosine kinases using techniques well known in the art.

VEGF-Induced KDR Phosphorylation in Human Umbilical Vein Endothelial Cells (HUVEC) as Measured by Western Blots:

1. HUVEC cells (from pooled donors) were purchased from Clonetics (San Diego, Calif.) and cultured according to the manufacturer directions. Only early passages (3–8) were used for this assay. Cells were cultured in 100 mm dishes (Falcon for tissue culture; Becton Dickinson; Plymouth, England) using complete EBM media (Clonetics).

2. For evaluating a compound's inhibitory activity, cells were trypsinized and seeded at $0.5–1.0 \times 10^5$ cells/well in each well of 6-well cluster plates (Costar; Cambridge, Mass.).

3. 3–4 days after seeding, plates were 90–100% confluent. Medium was removed from all the wells, cells were rinsed with 5–10 ml of PBS and incubated 18–24 h with 5 ml of EBM base media with no supplements added (i.e., serum starvation).

4. Serial dilutions of inhibitors were added in 1 ml of EBM media (25 μM, 5 μM, or 1 μM final concentration to cells and incubated for one hour at 37 C. Human recombinant $VEGF_{165}$ (R & D Systems) was then added to all the wells in 2 ml of EBM medium at a final concentration of 50 ng/ml and incubated at 37 C for 10 minutes. Control cells untreated or treated with VEGF only were used to assess background phosphorylation and phosphorylation induction by VEGF.

All wells were then rinsed with 5–10 ml of cold PBS containing 1 mM Sodium Orthovanadate (Sigma) and cells were lysed and scraped in 200 μl of RIPA buffer (50 mM Tris-HCl) pH7, 150 mM NaCl, 1% NP-40, 0.25% sodium deoxycholate, 1 mM EDTA) containing protease inhibitors (PMSF 1 mM, aprotinin 1 μg/ml, pepstatin 1 μg/ml, leupeptin 1 μg/ml, Na vanadate 1 mM, Na fluoride 1 mM) and 1 μg/ml of Dnase (all chemicals from Sigma Chemical Company, St Louis, Mo.). The lysate was spun at 14,000 rpm for 30 min, to eliminate nuclei.

Equal amounts of proteins were then precipitated by addition of cold (−20 C) Ethanol (2 volumes) for a minimum of I hour or a maximum of overnight. Pellets were reconstituted in Laemli sample buffer containing 5% -mercaptoethanol (BioRad; Hercules, Calif.) and boiled for 5 min. The proteins were resolved by polyacrylamide gel electrophoresis (6%, 1.5 mm Novex, San Deigo, Calif.) and transferred onto a nitrocellulose membrane using the Novex system. After blocking with bovine serum albumin (3%), the proteins were probed overnight with anti-KDR polyclonal antibody (C20, Santa Cruz Biotechnology; Santa Cruz, Calif.) or with anti-phosphotyrosine monoclonal antibody (4G10, Upstate Biotechnology, Lake Placid, N.Y.) at 4 C. After washing and incubating for 1 hour with HRP-conjugated F(ab)₂ of goat anti-rabbit or goat-anti-mouse IgG the bands were visualized using the emission chemiluminescence (ECL) system (Amersham Life Sciences, Arlington Height, Ill.). Certain examples of the present invention significantly inhibit cellular VEGF-induced KDR tyrosine kinase phosphorylation at concentrations of less than 50 μM.

In vivo Uterine Edema Model

This assay measures the capacity of compounds to inhibit the acute increase in uterine weight in mice which occurs in the first few hours following estrogen stimulation. This early onset of uterine weight increase is known to be due to edema caused by increased permeability of uterine vasculature. Cullinan-Bove and Koss (*Endocrinology* (1993), 133:829–837) demonstrated a close temporal relationship of estrogen-stimulated uterine edema with increased expression of VEGF mRNA in the uterus. These results have been confirmed by the use of neutralizing monoclonal antibody to VEGF which significantly reduced the acute increase in uterine weight following estrogen stimulation (WO 97/42187). Hence, this system can serve as a model for in vivo inhibition of VEGF signalling and the associated hyperpermeability and edema.

Materials: All hormones were purchased from Sigma (St. Louis, Mo.) or Cal Biochem (La Jolla, Calif.) as lyophilized powders and prepared according to supplier instructions. Vehicle components (DMSO, Cremaphor EL) were purchased from Sigma (St. Louis, Mo.).

Mice (Balb/c, 8–12 weeks old) were purchased from Taconic (Germantown, N.Y.) and housed in a pathogen-free animal facility in accordance with institutional Animal Care and Use Committee Guidelines.

Method:

Day 1: Balb/c mice were given an intraperitoneal (i.p.) injection of 12.5 units of pregnant mare's serum gonadotropin (PMSG).

Day 3: Mice received 15 units of human chorionic gonadotropin (hCG) i.p.

Day 4: Mice were randomized and divided into groups of 5–10. Test compounds were administered by i.p., i.v. or p.o. routes depending on solubility and vehicle at doses ranging from 1–100 mg/kg. Vehicle control group received vehicle only and two groups were left untreated.

Thirty minutes later, experimental, vehicle and 1 of the untreated groups were given an i.p. injection of 17-estradiol (500 μg/kg). After 2–3 hours, the animals were sacrificed by $CO_2$ inhalation. Following a midline incision, each uterus was isolated and removed by cutting just below the cervix and at the junctions of the uterus and oviducts. Fat and connective tissue were removed with care not to disturb the integrity of the uterus prior to weighing (wet weight). Uteri were blotted to remove fluid by pressing between two sheets of filter paper with a one liter glass bottle filled with water.

Uteri were weighed following blotting (blotted weight). The difference between wet and blotted weights was taken as the fluid content of the uterus. Mean fluid content of treated groups was compared to untreated or vehicle treated groups. Significance was determined by Student's test. Non-stimulated control group was used to monitor estradiol response.

Results demonstrate that certain compounds of the present invention inhibit the formation of edema when administered systemically by various routes.

Certain compounds of this invention which are inhibitors of angiogenic receptor tyrosine kinases can also be shown active in a Matrigel implant model of neovascularization. The Matrigel neovascularization model involves the formation of new blood vessels within a clear "marble" of extracellular matrix implanted subcutaneously which is induced by the presence of proangiogenic factor producing tumor cells (for examples see: Passaniti, A., et al, Lab. Investig. (1992), 67(4), 519–528; Anat. Rec. (1997), 249(1), 63–73; Int. J. Cancer (1995), 63(5), 694–701; Vasc. B (1995), 15(11), 1857–6). The model preferably runs over 3–4 days and endpoints include macroscopic visual/image scoring of neovascularization, microscopic microvessel density determinations, and hemoglobin quantitation (Drabkin method) following removal of the implant versus controls from animals untreated with inhibitors. The model may alternatively employ bFGF or HGF as the stimulus.

Certain compounds of this invention which inhibit one or more oncogenic, protooncogenic, or proliferation-dependent protein kinases, or angiogenic receptor PTK also inhibit the growth of primary murine, rat or human xenograft tumors in mice, or inhibit metastasis in murine models.

EXAMPLES

Processes for the preparation of compounds of formula I will now be described. These processes form a further aspect of the present invention. The processes are preferably carried out at atmospheric pressure.

Compounds of formula I may be prepared by condensing a compound of formula

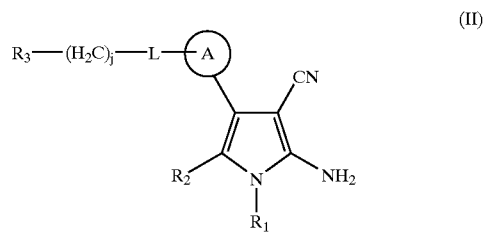

(II)

in which $R_1$, $R_2$, $R_3$, L and ring A are as previously defined with formamide at a temperature in the range of 50 to 250° C. optionally in the presence of a catalyst for example 4-dimethylaminopyridine.

Compounds of formula I may be prepared by reacting a compound of formula (III)

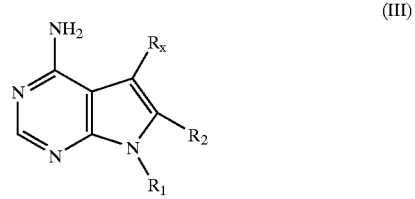

(III)

wherein $R_x$ is bromo or iodo bromo or iodo with one of the following compounds: $R_3B(OH)_2$, $R_3Sn(CH_3)_3$ or a compound represented by formula IV

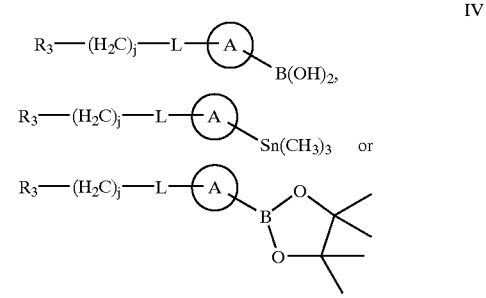

IV in which $R_3$ is as defined above, in the presence of a catalyst for example palladium (0) compounds eg. $Pd(PPh_3)_4$.

Compounds of formula I in which $R_1$ represents an alkyl group or an aralkyl group may be prepared by alkylating a compound of formula (V)

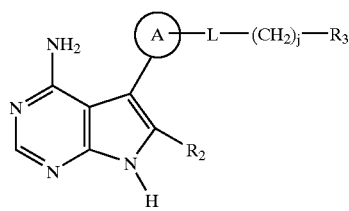

(V)

in which $R_2$ and $R_3$ are as previously defined with a compound of formula $R_1X'$ in which $R_1$ represents an alkyl group or an aralkyl group and $X'$ represents a leaving group, for example halo, mesyloxy or tosyloxy.

Compounds of formula I in which $R_1$ represents an optionally substituted cyclic ether, such as tetrahydrofuryl or tetrahydropyranyl, may be prepared by alkylating a compound of formula VI

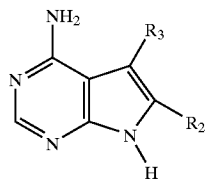

(VI)

in which $R_2$ and $R_3$ are as previously defined with a compound of formula $R_1X'$ in which $X'$ is as previously defined and $R_1$ is an optionally substituted cyclic ether.

Compounds of formula I in which $R_1$ represents cyclic ether, such as tetrahydrofuryl or tetrahydropyranyl, optionally substituted by formyl may be prepared by alkylating a compound of formula VI with a compound $R_1X$ in which $R_1$ represents a cyclic ether substituted by a formyl group which has been protected, by a method known to those skilled in the art, for example by means of an acetal, (See for example Tet. Letts. 30(46):6259–6262 (1989)) followed by deprotection. Compounds in which $R_1$ represents a cyclic ether, such as tetrahydrofuryl or tetrahydropyranyl, substituted by an (optionally substituted amino)methyl group may be prepared by reductive amination of a compound in which $R_1$ represents a cyclic ether substituted by formyl.

Compounds of formula I in which $R_1$ represents optionally substituted furyl, thienyl or pyrrolyl may be prepared by reacting 4-chloro-5-iodo-7H-pyrrolo[2,3-d]pyrimidine with the appropriate heteroarylboronic acid in the presence of a copper salt catalyst, for example copper (II) acetate in the presence of a solvent for the reactants, e.g. a halogenated solvent for example, dichloromethane, in the presence of a drying agent, for example 4 Å molecular sieves, in the presence of an organic base, e.g. triethylamine or pyridine, at a temperature in the range of 0–50° C., preferably at ambient temperature. (For conditions see Tet. Letts. (1998), 39:2942–2944 and references cited therein. This paper is incorporated herein by reference.) These compounds may be formulated by methods known to those skilled in the art to give compounds in which $R_1$ represents furyl, thienyl or pyrrolyl substituted by formyl. The formyl group in these compounds may be productively aminated by methods known to those skilled in the art to give compounds in which $R_1$ represents furyl, thienyl or pyrrolyl substituted by aminomethyl groups. Alternatively intermediates in which $R_1$ represents furyl, thienyl or pyrrolyl may be subjected to a Mannich reaction to give intermediates in which $R_1$ represents furyl, thienyl or pyrrolyl substituted by an aminomethyl group.

Compounds of formula I may be prepared by reacting a compound of formula VII

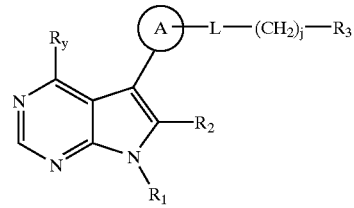

VII in which $R_1$, $R_2$, $R_3$, L and ring A are as previously defined and $R_y$ represents a leaving group, for example halo or phenoxy, with ammonia or an ammonium salt, for example ammonium acetate, at a temperature in the range of 15–250° C., preferably in a pressure vessel.

Compounds of formula I in which $R_2$ represents chloro, bromo or iodo may be prepared by reacting a compound of formula VIII

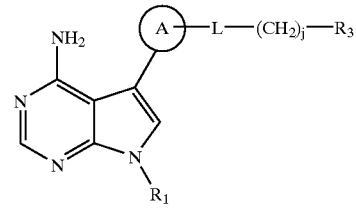

(VIII)

in which $R_1$, $R_3$, L and ring A are as previously defined with a halogenating agent for example an Iodinating agent, e.g. N-iodosuccinimide, or a brominating agent, e.g. N-bromosuccinimide, or a chlorinating agent, e.g. N-chlorosuccinimide.

Compounds of formula I in which —L—$R_3$ represents —NHC(O)$R_3$ may be prepared by reacting a compound of formula IX

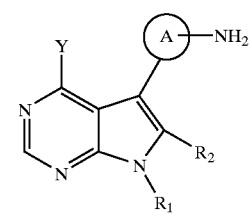

in which $R_1$, $R_2$ and ring A are as previously defined and Y represents a protected amine, with a compound of formula $R_3COR_x$ in which $R_x$ represents a leaving group, for example chloro. Alternatively compounds of formula IX in which Y represents halo, for example chloro, may be reacted with a compound of formula $R_3COR_x$ and the product reacted with ammonia to give a compound of formula I. Analogous methods may be used to prepare compounds of formula I in which —L—$R_3$ is —NRSO$_2R_3$. Analogous methods may be used to prepare compound of formula I in which —L—$R_3$ is —NRCO$_2$—$R_3$ or —NRCONR'. R and R' are as previously defined.

Compounds of formula I in which —L—$R_3$ is —OSO$_2$— may be prepared by reacting a compound of formula X

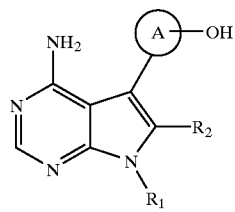

in which $R_1$, $R_2$ and ring A are as previously defined with a compound of formula $R_4SO_2R_x$.

Compounds of formula I may then be prepared from such intermediates following Scheme 2 or the alternative for Scheme 2, which is described later.

Compounds of formula II may be prepared as shown in Scheme 1 in which IPA represents propan-2-ol, Scheme I

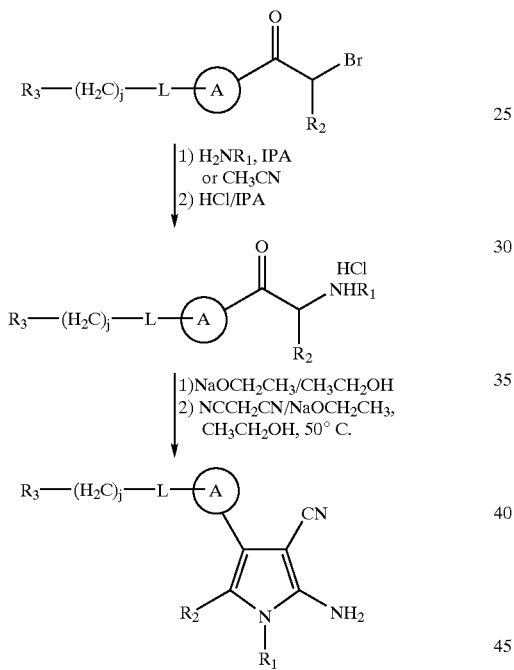

It will be appreciated by those skilled in the art that compounds of formula I may be converted into other compounds of formula I by known chemical reactions. For example, an alkoxy group may be cleaved to give hydroxy, nitro groups may be reduced to amines, amines may be acylated or sulfonylated and N-acyl compounds may be hydrolyzed to amines. Compounds of formula I in which —L— is S may be oxidized to give compounds of formula I in which —L— represents SO and $SO_2$, respectively, by methods known to those skilled in the art.

Compounds of formula III are commercially available or may be prepared by methods known to those skilled in the art.

Compounds of formula V in which $R_2$ represents hydrogen may be prepared as shown in Scheme 2. The amino group may be protected prior to the final step and then deprotected after the final step of scheme 2 by methods known to those skilled in the art. Compounds of formula V in which $R_2$ is other than hydrogen may be prepared by analogous methods. (see J. Med. Chem. (1990), 33, 1984.)

Scheme 2

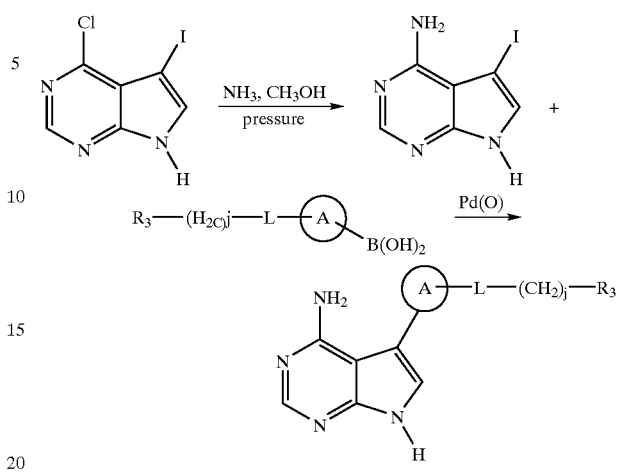

Alternatively in Scheme 2, (ring A)-L—$R_3$ may be coupled first, prior to amination. Alternatively a substituent $R_1$ as defined previously may be present prior to carrying out either process.

Compounds of formula VII, in which $R_y$ is a —Cl, may be prepared as shown in Scheme 3.

Scheme 3

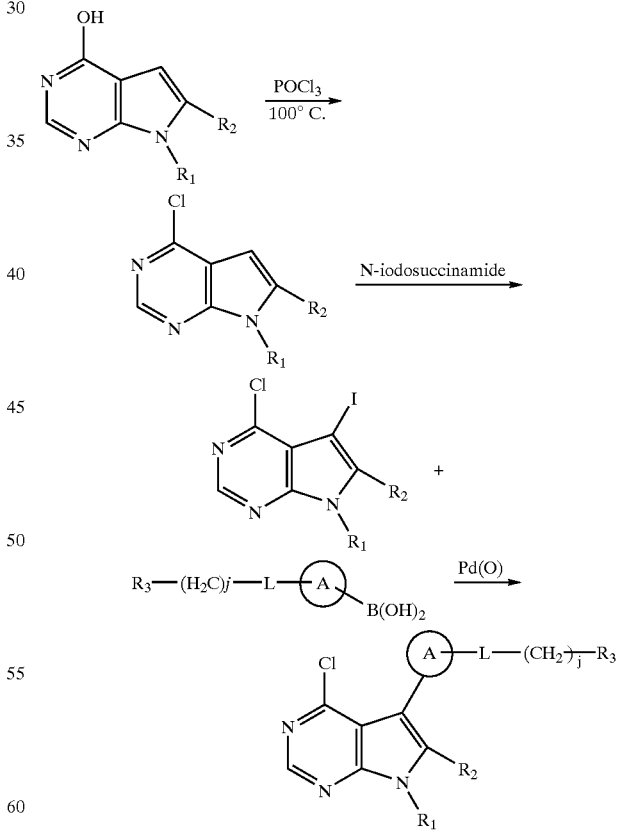

Compounds in which (ring A)-L—$R_3$ is absent may be prepared as in Scheme 4 and as described in J. Med. Chem., (1988), 31:390 and references cited therein. Compounds in which (ring A)-L—$R_3$ is other than hydrogen may be prepared by analogous methods.

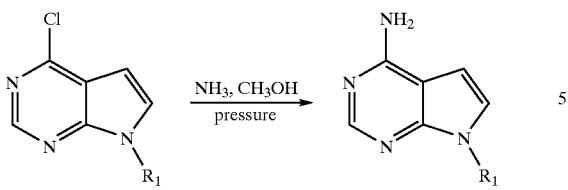

Compounds of formula VII may be prepared by coupling a 5-iodo compound in an analogous manner to that described for the preparation of compounds of formula V.

$R_1$ may be modified by the method depicted in Schemes 5 and 6. In Schemes 5 and 6 P represents a protecting group.

Scheme 5

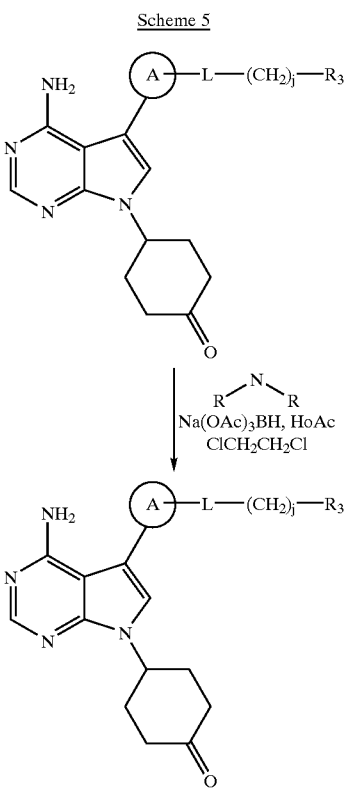

Scheme 6

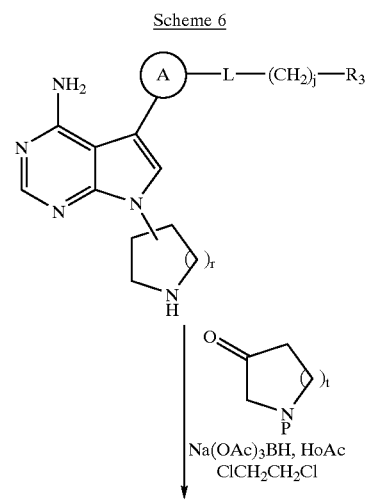

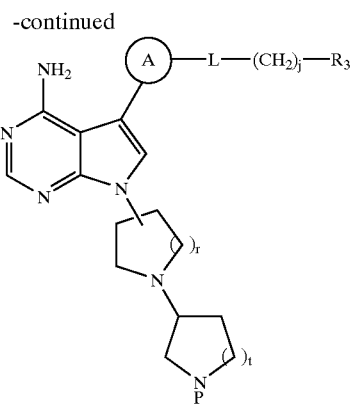

It will be appreciated by those skilled in the art that in cases where a substituent is identical with, or similar to, a functional group which has been modified in one of the above processes that these substituents will require protection before the process is undertaken, followed by deprotection after the process. Otherwise competing side-reactions will occur. Alternatively, another of the processes described above, in which the substituent does not interfere, may be used. Examples of suitable protecting groups and methods for their addition and removal may be found in the textbook "Protective Groups in Organic Synthesis" by T. W. Green, John Wiley and Sons, 1981. For example suitable protecting groups for amines are formyl or acetyl.

The following synthetic examples were prepared using the general preparative procedures described above:

Example 1

Benzyl N-(4-(4-Amino-7-tetrahydro-2H-4-pyranyl-7H-pyrrolo[2,3-d]pyrimidin-5-yl)-2-methoxyphenyl) carbamate a) Tetrahydro-2H-4-pyranyl trifluoromethanesulfonate. Pyridine (1.7 ml, 20.97 mmol) was added to a solution of tetrahydro-2H-4-pyranol (2 ml, 20.97 mmol) in dichloromethane (16 ml). The flask was immersed in an ice water bath and trifluoromethanesulfonic anhydride (3.6 ml, 20.97 mmol) in dichloromethane (7 ml) was added dropwise over 10 minutes. After 20 minutes, the reaction mixture was filtered and the solid was washed with minimum amount of dichloromethane. The combined filtrate was washed with water, 1.0 N HCl, water and brine. The organic layer was dried (MgSO$_4$) and filtered. The solvent was evaporated to give tetrahydro-2H-4-pyranyl trifluoromethanesulfonate. $^1$H NMR (CDCl$_3$) δ 1.99 (m, 2H), 2.11 (m, 2H), 3.58 (m, 2H), 3.96 (m, 2H), 5.17 (m, 1H).

b) 4-chloro-5-iodo-7-tetrahydro-2H-4-pyranyl-7H-pyrrolo [2,3-d]pyrimidine. 4-Chloro-5-iodo-7H-pyrrolo[2,3-d] pyrimidine (3.0 g, 10.73 mmol) was added in small portions to a solution of sodium hydride (0.891g 22.2 mmol) in N,N-dimethylformamide (40 ml) at 0° C. After completed the addition the ice water bath was removed and the resulting mixture was stirred for 30 minutes. Tetrahydro-2H-4-pyranyl trifluoromethanesulfonate was added dropwise and the reaction mixture was stirred at ambient temperature for 24 hours. The mixture was poured to ice water (100 ml) and the solid was collected by filtration and purified by re-crystallization to give 4-chloro-5-iodo-7-tetrahydro-2H-4-pyranyl-7H-pyrrolo [2,3-d]pyrimidine. $^1$H NMR (CDCl$_3$) δ 2.06 (m, 2H), 3.63 (m, 2H), 4.16 (m, 2H), 5.00 (m, 1H), 7.45 (s, 1H), 8.61 (s, 1H). LC/MS (MH$^+$=364).

c) tert-Butyl N-(4-(4-chloro-7-tetrahydro-2H-4-pyranyl-7H-pyrrolo[2,3-d]pyrimidin-5-yl)-2-methoxyphenyl)carbamate. tert-Butyl N-[2-methoxy-4-(4,4,5,5-tetramethyl-1,3,2-dioxaborolan-2-yl)phenyl]carbamate (1.66g, 4.75 mmol) in water was degassed by sonication under vacuum for 1 minute. 4—Chloro-5-iodo-7-tetrahydro-2H-4-pyranyl-7H-pyrrolo[2,3-d]pyrimidine (1.1 g, 3.17 mmol), tetrakis(triphenylphosphine)palladium(0) (0.22 g, 0.19 mmol), Sodium carbonate (0.8 g, 7.60 mmol) and 1,2-dimethoxyethane (30 ml) was added to the aqueous mixture. The resulting suspension was degassed again for 2 minutes and then headed to 85° C. for 24 hours. The reaction mixture was cooled to ambient temperature and solvent was evaporated. The residue was dissolved in ethyl acetate. The organic layer washed and dried (MgSO$_4$). The solid was purified by flash column chromatography on silica using heptane/ethyl acetate (7:3) as the mobile phase to give tert-butyl N-(4-(4-chloro-7-tetrahydro-2H-4-pyranyl-7H-pyrrolo[2,3-d]pyrimidin-5-yl)-2-methoxyphenyl) carbamate. $^1$H NMR (CDCl$_3$) δ 1.55 (s, 9H), 2.10 (m, 4H), 3.66 (m, 2H), 3.92 (s, 3H), 4.16 (m, 2H), 5.05 (m, 1H), 7.06 (m, 1H), 7.14 (s, 1H), 7.32 (s, 1H), 8.13 (br.d, J=8 Hz, 1H), 8.64(s, 1H). LC/MS (MH$^+$=459).

d) 4-(4-chloro-7-tetrahydro-2H-4-pyranyl-7H-pyrrolo[2,3-d]pyrimidin-5-yl)-2-methoxyaniline. A solution of ten percent trifluoroacetic acid in dichloromethane (50 ml) was added to tert-butyl N-(4-(4-chloro-7-tetrahydro-2H-4-pyranyl-7H-pyrrolo[2,3-d]pyrimidin-5-yl)-2-methoxyphenyl)carbamate at 0° C. After 20 minutes, the ice water bath was removed and the resulting solution was stirred at ambient temperature for 4 hours. The solvent was removed and the residue taken into dichloromethane. Saturated sodium bicarbonate was added and the layers separated. The aqueous layer was extracted with dichloromethane. The combined organic layer was washed with brine, dried (MgSO4), filtered and concentrated. The solid was purified by passing though a pat of silica gel using heptane/ethyl acetate (3:2) as the mobile phase to give 4-(4-chloro-7-tetrahydro-2H-4-pyranyl-7H-pyrrolo[2,3-d]pyrimidin-5-yl)-2-methoxyaniline. $^1$H NMR (CDCl$_3$) δ 2.09 (m, 4H), 2.51 (br. s, NH$_2$), 3.66 (m, 2H), 3.91 (s, 3H), 4.16 (m, 2H), 5.05 (m, 1H), 6.79 (d, J=8 Hz, 2H), 6.93 (d, J=8 Hz, 1H), 6.98 (s, 1H), 7.28 (s, 1H), 8.63 (s, 1H). LC/MS J=8 Hz, 2H), 6.93 (d, J=8 Hz, 1H), 6.98 (s, 1H), 7.28 (s, 1H), 8.63 (s, 1H). LC/MS (MH$^+$=359).

e) 5-(4-Amino-3-methoxyphenyl)-7-tetrahydro-2H-4-pyranyl-7H-pyrrolo[2,3-d]pyrimidin-4-amine. Ammonium hydroxide (25 ml) was added to a solution of 4-(4-chloro-7-tetrahydro-2H-4-pyranyl-7H-pyrrolo[2,3-d]pyrimidin-5-yl)-2-methoxyaniline (0.73 g, 2.03 mmol) in dioxane (25 ml) in a pressure tube. The pressure tube was sealed and heated to 122° C. for 2 days. The tube was cooled to ambient temperature and the solvent was evaporated. Ethyl acetate was added and the organic layer was washed, dried (MgSO$_4$), filtered and concentrated to give 5-(4-amino-3-methoxyphenyl)-7-tetrahydro-2H-4-pyranyl-7H-pyrrolo[2,3-d]pyrimidin-4-amine. $^1$H NMR (DMSO-d$_6$) δ 1.87 (m, 2H), 2.11 (m, 2H), 3.52 (m, 2H), 3.79 (s, 3H), 3.99 (m, 2H), 4.87 (m, 3H), 6.02 (br. s, NH$_2$), 6.73 (d, J=8 Hz, 2H), 6.77 (d, J=8 Hz, 1H), 6.88 (s, 1H), 7.33 (s, 1H), 8.10 (s, 1H). LC/MS (MH$^+$=340).

f) Benzyl N-(4-(4-amino-7-tetrahydro-2H-4-pyranyl-7H-pyrrolo[2,3-d]pyrimidin-5-yl)-2-methoxyphenyl)carbanate. Benzylchloroformate(16 uL, 0.110 mmol) was added dropwise to a stirring solution of 5-(4-amino-3-methoxyphenyl)-7-tetrahydro-2H-4-pyranyl-7H-pyrrolo[2,3-d]pyrimidin-4-amine (25 mg, 0.074 mmol) in pyridine (0.7 ml) and dichloromethane (0.7 ml) under nitrogen at 0° C. After 10 minutes, the ice water bath was removed and the resulting mixture was stirred for 4 hours. The solvent was evaporated and the residue was purified by preparative TLC using dichloromethane/methanol (95:5) as the mobile phase to give benzyl N-(4-(4-amino-7-tetrahydro-2H-4-pyranyl-7H-pyrrolo[2,3-d]pyrimidin-5-yl)-2-methoxyphenyl) carbamate. $^1$H NMR (CDCl$_3$) δ 2.07 (m, 4H), 3.65 (m, 2H), 3.9 (s, 3H), 4.13 (m, 2H), 4.97 (m, 1H), 5.23 (s, 2H), 6.96 (s, 1H), 7.03 (s, 1H), 7.08 (d, J=8 Hz, 1H), 7.42 (m, 6H), 8.20 (br. s, J=8 Hz, 1H). 8.32 (s, 1H). LC/MS (MH$^+$=474).

Example 2

Neopentyl N-(4-(4-Amino-7-tetrahydro-2H-4-pyranyl-7H-pyrrolo[2,3-d]pyrimidin-5-yl)-2-methoxyphenyl)carbamate Neopentylchloroformate(13 uL, 0.110 mmol) was added dropwise to a stirring solution of 5-(4-amino-3-methoxyphenyl)-7-tetrahydro-2H-4-pyranyl-7H-pyrrolo[2,3-d]pyrimidin-4-amine (25 mg, 0.074 mmol) in pyridine (0.7 ml) and dichloromethane (0.7 ml) under nitrogen at 0° C. After 10 minutes, the ice water bath was removed and the resulting mixture was stirred for 4 hours. The solvent was evaporated and the residue was purified by preparative TLC using dichloromethane/methanol (95:5) as the mobile phase to give neopentyl N-(4-(4-amino-7-tetrahydro-2H-4-pyranyl-7H-pyrrolo[2,3-d]pyrimidin-5-yl)-2-methoxyphenyl)carbamate. $^1$H NMR (CDCl$_3$) δ 1.00 (s, 3H), 2.07 (m, 4H), 3.65 (m, 2H), 3.91 (s, 2H), 3.94 (s, 3H), 4.13 (m, 2H), 4.97 (m, 1H), 5.18 (s, 2H), 6.97 (s, 1H), 7.03 (s, 1H), 7.07 (d, J=8 Hz, 1H), 7.25 (s, 1H), 8.19 (br. s, J=8 Hz, 1H). 8.33 (s, 1H). LC/MS (MH$^+$=454).

Example 3

Phenyl N-[4-(4-Amino-7-tetrahydro-2H-4-pyranyl-7H-pyrrolo[2,3-d]pyrimidin-5-yl)-2-methoxyphenyl] carbamate 5-(4-Amino-3-methoxyphenyl)-7-tetrahydro-2H-4-pyranyl-7H-pyrrolo[2,3-d]pyrimidin-4-amine (100 mg, 0.294 mmol) was dissolved in dichloromethane (2 mL). Pyridine (2mL) was added followed by phenylchloroformate (44 uL, 0.353 mmol). After stirring for 3 hours, another 44 uL of phenylmethanesulfonyl chloride was added and the reaction mixture was stirred overnight. The solvent was removed and the residue was purified by preparative LC/MS to give phenyl N-[4-(4-amino-7-tetrahydro-2H-4-pyranyl-7H-pyrrolo[2,3-d]pyrimidin-5-yl)-2-methoxyphenyl] carbamate (52 mg, 0.113 mmol). 1H NMR (CDCl$_3$-d) δ 2.09 (m, 4H), 3.66 (m, 2H), 3.98 (s, 3H), 4.16 (m, 2H), 4.98 (m, 1H), 5.24 (s, 2H), 7.09 (m ,3H), 7.23 (m, 4H), 7.41 (m, 2H), 7.62 (s, 1H), 8.20 (bd, J=7.80 Hz, 1H), 8.33 (s, 1H). LC/MS MH$^+$=460.

Example 4

Tetrahydro-2H-4-pyranyl N-[4-(4-Amino-7-tetrahydro-2H-4-pyranyl-7H-pyrrolo[2,3-d]pyrimidin-5-yl)-2-methoxyphenyl]carbamate 4-nitrophenyl tetrahydro-2H-4-pyranyl Carbonate Tetrahydro-2H-4-pyranol (1.0 ml, 10.5 mmol) was mixed with 4-methylmorpholine (2.0 ml) in dichloromethane (20 mL). 4-Nitrochlorofornate (1.98 g, 9.82 mmol) was added slowly to the reaction mixture. After stirring for 5 hours, the reaction mixture was diluted with dichloromethane. The organic layer was washed with water, 1.0 N HCl, saturated sodium bicarbonate, brine, dried over $MgSO_4$, filtered and evaporated. The crude product was purified by flash column chromatography chromatography using ethyl acetate/heptane (4:1) as the mobile phase to give 4-nitrophenyl tetrahydro-2H-4-pyranyl carbonate (1.5 g, 5.62 mmol). $^1H$ NMR ($CDCl_3$-d) δ 1.87 (m, 2H), 2.06 (m, 2H), 3.58 (m, 2H), 3.98 (m, 2H), 4.97 (m, 1H), 7.40 (d, J=9.0 Hz, 2H), 8.30 (d, J=9.0 Hz, 2H).

a) Tetrahydro-2H-4-pyranyl N-[4-(4-amino-7-tetrahydro-2H-4-pyranyl-7H-pyrrolo[2,3-d]pyrimidin-5-yl)-2-methoxyphenyl]carbamate. 5-(4-Amino-3-methoxyphenyl)-7-tetrahydro-2H-4-pyranyl-7H-pyrrolo[2,3-d]pyrimidin-4-amine (57 mg, 0.168 mmol) and 4-nitrophenyl tetrahydro-2H-4-pyranyl carbonate (90 mg, 0.336 mmol) was mixed in pyridine (1 mL). After stirring for 5 hours, another 90 mg of 4-nitrophenyl tetrahydro-2H-4-pyranyl carbonate was added and the reaction mixture was stirred for 2 days. The reaction mixture was heated at 70° C. for 2 hours. The solvent was removed and the residue was purified by preparative thin layer chromatography to give tetrahydro-2H-4-pyranyl N-[4-(4-amino-7-tetrahydro-2H-4-pyranyl-7H-pyrrolo[2,3-d]pyrimidin-5-yl)-2-methoxyphenyl]carbamate (30 mg, 0.064 mmol). 1H NMR ($CDCl_3$-d) δ 1.78 (m, 4H), 2.08 (m, 4H), 3.60 (m, 4H), 3.94 (s, 3H), 3.97 (m, 2H), 4.15 (m, 2H), 4.98 (m, 2H), 5.23 (s, 2H), 6.78 (s ,1H), 7.04 (s, 1H), 7.07 (d, J=8.3 Hz, 1H), 8.16(bd, J=7.90 Hz, 1H), 8.33 (s, 1H). LC/MS $MH^+$=468.

Example 5

3-Pyridylmethyl N-[4-(4-Amino-7-tetrahydro-2H-4-pyranyl-7H-pyrrolo[2,3-d]pyrimidin-5-yl)-2-methoxyphenyl]carbamate Hydrochloride a) 4-Nitrophenyl (3-pyridylmethyl) carbonate. 4- Nitrochloroformate (2.49 g, 12.3 mmol) in dichloromethane (20 mL) was cooled on an ice-water bath. 3-pyridylmethanol (1.0 mL, 10.3 mmol) and 4-methylmorpholine (2.0 mL, 18.5 mmol) was added slowly. After 20 minutes, the ice-water bath was removed and the reaction mixture was allowed to warm up to room temperature. 30 minues later, ethyl acetate was added and the reaction mixture was filtered. The filtrate was washed with water, saturated sodium bicarbonate, brine, dried over MgSO4, filtered and evaporated to give a dark brown solid which was re-crystallized with ethyl acetate/heptane to give 4-nitrophenyl (3-pyridylmethyl) carbonate (1.52 g, 5.54 mmol). 1H NMR (CDCl-d) δ 7.38 (m, 3H), 7.79 (m, 1H), 8.28 (d, J=9.09Hz, 2H), 8.65 (m, 1H), 8.72 (s, 1H).

b) 3-Pyridylmethyl N-[4-(4-amino-7-tetrahydro-2H-4-pyranyl-7H-pyrrolo[2,3-d]pyrimidin-5-yl)-2-methoxyphenyl]carbamate. 5-(4-Amino-3-methoxyphenyl)-7-tetrahydro-2H-4-pyranyl-7H-pyrrolo[2,3-d]pyrimidin-4-amine (25 mg, 0.074 mmol) was dissolved in dichloromethane (0.7 mL). Pyridine (0.7 mL) was added followed by 4-nitrophenyl (3-pyridylmethyl) carbonate (30 mg, 0.110 mmol). After heating at 100° C. overnight, the solvent was removed and the residue was purified by preparative LC/MS to give 3-pyridylmethyl N-[4-(4-amino-7-tetrahydro-2H-4-pyranyl-7H-pyrrolo[2,3-d]pyrimidin-5-yl)-2-methoxyphenyl]carbamate (12 mg, 0.025 mmol). 1H NMR ($CDCl_3$-d) δ 2.08 (m, 4H), 3.65 (m, 2H), 3.92 (s, 3H), 4.15 (m, 2H), 4.96 (m, 1H), 5.26 (s, 2H), 5.54 (bs, 2H), 6.97 (s, 1H), 7.04(s, 1H), 7.08 (d, J=8.2Hz, 1H), 7.35 (m, 2H), 7.79 (d, J=7.8Hz, 1H), 8.15 (m, 1H), 8.29 (s, 1H), 8.61 (s, 1H), 8.71 (s, 1H). LC/MS $MH^+$=475.

c) 3-Pyridylmethyl N-[4-(4-amino-7-tetrahydro-2H-4-pyranyl-7H-pyrrolo[2,3-d]pyrimidin-5-yl)-2-methoxyphenyl]carbamate hydrochloride. 3-Pyridylmethyl N-[4-(4-amino-7-tetrahydro-2H-4-pyranyl-7H-pyrrolo[2,3-d]pyrimidin-5-yl)-2-methoxyphenyl]carbamate (12 mg, 0.025 mmol) was dissolved in ethyl acetate (2.0 mL). 1.0N HCl in ether (1 mL) was added slowly. The precipatate was collected through filtration under nitrogen to give 3-pyridylmethyl N-[4-(4-amino-7-tetrahydro-2H-4-pyranyl-7H-pyrrolo[2,3-d]pyrimidin-5-yl)-2-methoxyphenyl]carbamate hydrochloride(13 mg, 0.25 mmol). 1H NMR (DMSO-$d_6$) δ 1.91 (m, 2H), 2.17(m, 2H), 3.54 (m, 2H), 3.87 (s, 3H), 4.03 (m, 2H), 4.97 (m, 1H), 5.23 (s, 2H), 7.05 (d, J=8.2 Hz, 1H), 7.13 (s, 1H), 7.51 (m, 1H), 7.81 (d, J=8.2 Hz, 1H), 7.84 (s, 1H), 7.95 (m, 1H), 8.42 (s, 1H), 8.60 (s, 1H), 8.71 (s, 1H), 8.82 (s, 1H). LC/MS $MH^+$=475.

Example 6

2-Morpholinoethyl N-[4-(4-Amino-7-tetrahydro-2H-4-pyranyl-7H-pyrrolo[2,3-d]pyrimidin-5-yl)-2-methoxyphenyl]carbamate Hydrochloride Phenyl N-[4-(4-amino-7-tetrahydro-2H-4-pyranyl-7H-pyrrolo[2,3-d]pyrimidin-5-yl)-2-methoxyphenyl]carbamate (25 mg, 0.054 mmol) was mixed with 2-morpholino-1-ethanol (0.1 mL) in pyridine (0.7 mL). The reaction mixture was heated at 100° C. overnight. The solvent was removed and the residue was purified by preparative reverse phase HPLC to give 2-morpholinoethyl N-[4-(4-amino-7-tetrahydro-2H-4-pyranyl-7H-pyrrolo[2,3-d]pyrimidin-5-yl)-2-methoxyphenyl] carbamate (24 mg, 0.048 mmol). The solid was dissolved in ethyl acetate (2 mL) and 1.0N HCl in ether (0.2 mL) was added slowly. The precipitate was collected through filtration under nitrogen to give 2-morpholinoethyl N-[4-(4-amino-7-tetrahydro-2H-4-pyranyl-7H-pyrrolo[2,3-d]pyrimidin-5-yl)-2-methoxyphenyl] carbamate hydrochloride (24 mg, 0.045 mmol). 1H NMR (DMSO-$d_6$) δ 1.88(m, 2H), 2.16(m, 2H), 3.55 (m, 8H), 3.90 (s, 3H), 4.03 (m, 4H), 4.49(m, 2H), 4.92 (m, 1H), 7.07 (m, 1H), 7.15 (s, 1H), 7.65 (bs, 2H), 7.84 (s, 1H), 8.45 (s, 1H), 8.75(s, 1H) 10.95 (bs, 1H). LC/MS $MH^+$=497.

Example 7

(4-Bromo-1,3-thiazol-5-yl)methyl N-[4-(4-amino-7-tetrahydro-2H-4-pyranyl-7H-pyrrolo[2,3-d]pyrimidin-5-yl)-2-methoxyphenyl]carbamate a) 2,4-Dibromo-1,3-thiazole-5-carbaldehyde. 1,3-Thiazolane-2,4-dione (3.52 g, 30 mmol) and phosphorus oxybromide (43 g, 150 mmol) were mixed with dimethyl formamide (2.56 mL, 34mmol). The mixture was then heated at 75° C. for 1 hours and at 100° C. for 5 hours. After cooled to room temperature, the mixture was added to ice-water (500 ml) and the aqueous layer was extracted with dichloromethane. The combined organic layer was washed with saturated sodium bicarbonate, dried over MgSO4, filtered and evaporated to give a brown solid which was washed with petroleum ether. Evaporation of solvent gave 2,4-dibromo-1,3-thiazole-5-carbaldehyde (1.74 g, 6.42 mmol). 1H NMR ($CDCl_3$-d) δ 9.90 (S, 1H).

b) (2,4-Dibromo-1,3-thiazol-5-yl)methanol. 2,4-Dibromo-1,3-thiazole-5-carbaldehyde (1.74 g, 6.42 mmol) was dissolved in methanol (70 ml) at 0° C. Sodium borohydride (0.244 g, 6.42 mmol) was added in small portions. The ice-water bath was removed 10 minutes later and the reaction mixture was stirred at room temperature overnight.

Solvent was removed and saturated ammonium chloride was added. 1.0N NaOH was added to adjust the pH to 10. The aqueous layer was extracted with ethyl acetate. The combined organic layer was washed with brine, dried over MgSO4, filtered and evaporated. The residue was purified by flash column chromatography to give (2,4-dibromo-1,3-thiazol-5-yl)methanol (0.946 g, 3.47 mmol). 1H NMR (CDCl$_3$-d) δ 2.11 (bs, 1H) δ 4.79 (S, 2H).

c) (4-Bromo-1,3-thiazol-5-yl)methanol. (2,4-Dibromo-1,3-thiazol-5-yl)methanol (0.94 g, 3.44 mmol), sodium carbonate tri-hydrade (1.34 g) and palladium on carbon g, 3.44 mmol), sodium carbonate tri-hydrade (1.34 g) and palladium on carbon (10%, 0.07 g) were mixed in methanol (33 mL). The resulting mixture was hydrogenated at 60 psi for 2 days. The solid was filtered off through a pat of celite. The solvent was evaporated and the residue was purified by frash column chromatography to give (4-bromo-1,3-thiazol-5-yl)methanol (0.32 g, 2.78 mmol). 1H NMR (CDCl$_3$-d) δ 2.29 (bs, 1H) δ 4.86 (s, 2H), 8.72 (s, 1H).

d) (4-Bromo-1,3-thiazol-5-yl)methyl N-[4-(4-amino-7-tetrahydro-2H-4-pyranyl-7H-pyrrolo[2,3-d]pyrimidin-5-yl)-2-methoxyphenyl]carbamate. Phenyl N-[4-(4-amino-7-tetrahydro-2H-4-pyranyl-7H-pyrrolo[2,3-d]pyrimidin-5-yl)-2-methoxyphenyl]carbamate (28 mg, 0.061 mmol) was mixed with (4-bromo-1,3-thiazol-5-yl)methanol (50 mg, 0.434 mmol) in pyridine (0.5 mL). The reaction mixture was heated at 100° C. overnight. The solvent was removed and the residue was purified by preparative reverse phase LC/MS to give (4-bromo-1,3-thiazol-5-yl)methyl N-[4-(4-amino-7-tetrahydro-2H-4-pyranyl-7H-pyrrolo[2,3-d]pyrimidin-5-yl)-2-methoxyphenyl] carbamate. 1H NMR (CDCl-d) δ 2.07 (m, 4H), 3.65 (m, 2H), 3.92 (s, 3H), 4.13 (m, 2H), 4.98 (m, 1H), 5.35 (s, 1H), 5.40(s, 2H), 6.97 (s, 1H), 7.04 (s, 1H), 7.09 (m, 1H), 7.35 (s, 1H), 8.17 (s, 1H), 8.32 (s, 1H), 8.78(s, 1H). LC/MS MH$^+$=481.

Example 8

Tetrahydro-3-furanyl N-[4-(4-Amino-7-tetrahydro-2H-4-pyranyl-7H-pyrrolo[2,3-d]pyrimidin-5-yl)-2-methoxyphenyl]carbamate Phenyl N-[4-(4-amino-7-tetrahydro-2H-4-pyranyl-7H-pyrrolo[2,3-d]pyrimidin-5-yl)-2-methoxyphenyl]carbamate (30 mg, 0.065 mmol) was mixed with tetrahydro-3-furanol (0.05 mL) in pyridine (0.5 mL). The reaction mixture was heated at 100° C. overnight. The solvent was removed and the residue was purified by preparative reverse phase PHLC to give tetrahydro-3-furanyl N-[4-(4-amino-7-tetrahydro-2H-4-pyranyl-7H-pyrrolo[2,3-d]pyrimidin-5-yl)-2-methoxyphenyl] carbamate (14 mg, 0.031 mmol). 1H NMR (CDCl-d) δ 2.07(m, 6H), 3.66 (m, 2H), 3.96 (m, 7H), 4.13 (m, 2H), 4.98 (m, 1H), 5.26 (s, 2H), 5.40(m, 1H), 6.97 (s, 1H), 7.04 (s, 1H), 7.08 (d, J=8.2Hz, 1H), 7.26 (s, 1H), 8.30 (s, 1H), 8.32 (s, 1H). LC/MS MH$^+$=455.

Examples 9 and 10

1,3-Dioxan-5-yl N-[4-(4-Amino-7-tetrahydro-2H-4-pyranyl-7H-pyrrolo[2,3-d]pyrimidin-5-yl)-2-methoxyphenyl]carbamate
1,3-Dioxolan-4-ylmethyl N-(4-(4-amino-7-tetrahydro-2H-4-pyranyl-7H-pyrrolo[2,3-d]pyrimidin-5-yl)-2-methoxyphenyl)carbamate
Phenyl N-[4-(4-amino-7-tetrahydro-2H-4-pyranyl-7H-pyrrolo[2,3-d]pyrimidin-5-yl)-2-methoxyphenyl]carbamate (30 mg, 0.065 mmol) was mixed glycerol formal (0.05 mL) in pyridine (0.5 mL). The reaction mixture was heated at 100° C. overnight. The solvent was removed and the residue was purified by preparative reverse phase PHLC to give tetrahydro-3-furanyl N-[4-(4-amino-7-tetrahydro-2H-4-pyranyl-7H-pyrrolo[2,3-d]pyrimidin-5-yl)-2-methoxyphenyl] carbamate (2 mg, 0.004 mmol). 1H NMR (CDCl-d) δ 2.06(m, 4H), 3.66 (m, 2H), 3.92 (m, 3H), 4.07 (m, 6H), 4.79 (m, 1H), 4.83 (d, J=6.3Hz, 1H), 4.96 (m, 1H), 5.04(d, J=6.3 Hz, 1H), 6.15 (vbs, 2H), 6.96 (s, 1H), 7.05 (m, 2H), 7.53 (s, 1H), 8.15 (d, J=8.2 Hz, 1H), 8.22 (s, 1H). LC/MS MH$^+$=471 and 1,3-dioxolan-4-ylmethyl N-(4-(4-amino-7-tetrahydro-2H-4-pyranyl-7H-pyrrolo[2,3-d]pyrimidin-5-yl)-2-methoxyphenyl) carbamate(6.0 mg, 0.013 mmol). 1H NMR (CDCl-d) δ 2.06 (m, 4H), 3.66 (m, 2H), 3.75 (m, 1H), 3.92 (m, 3H), 4.03 (m, 1H), 4.13 (m, 1H), 4.34 (m, 2H), 4.94 (s, 1H), 4.97 (m, 1H), 5.10(s, 1H), 5.32 (bs, 2H), 6.97 (s, 1H), 7.03 (m, 2H), 7.06 (d, J=8.2 Hz, 1H), 7.38(s, 1H), 8.15 (d, J=7.9 Hz, 1H), 8.31 (s, 1H). LC/MS MH$^+$=471.

Example 11

2-Pyridylmethyl N-[4-(4-Amino-7-tetrahydro-2H-4-pyranyl-7H-pyrrolo[2,3-d]pyrimidin-5-yl)-2-methoxyphenyl]carbamate Hydrochloride Phenyl N-[4-(4-amino-7-tetrahydro-2H-4-pyranyl-7H-pyrrolo[2,3-d]pyrimidin-5-yl)-2-methoxyphenyl]carbamate (30 mg, 0.065 mmol) was mixed 2-pyridylmethanol (0.05 mL) in pyridine (0.5 mL). The reaction mixture was heated at 100° C. overnight. The solvent was removed and the residue was purified by preparative reverse phase LC/MS to give 2-pyridylmethyl N-[4-(4-amino-7-tetrahydro-2H-4-pyranyl-7H-pyrrolo[2,3-d]pyrimidin-5-yl)-2-methoxyphenyl]carbamate (11 mg, 0.023 mmol). The solid was dissolved in ethyl acetate (2 mL) and 1.0N HCl in ether (0.1 mL) was added slowly. The precipitate was collected through filtration under nitrogen to give 2-pyridylmethyl N-[4-(4-amino-7-tetrahydro-2H-4-pyranyl-7H-pyrrolo[2,3-d]pyrimidin-5-yl)-2-methoxyphenyl] carbamate hydrochloride (12 mg, 0.023 mmol). 1H NMR (DMSO-d$_6$) δ 1.92(m, 2H), 2.16(m, 2H), 3.55 (m, 2H), 3.89 (s, 3H), 4.02 (m, 2H), 4.91 (m, 1H), 5.23 (s, 2H), 7.05 (d, J=8.2 Hz, 1H), 7.14 (s, 1H), 7.37 (m, 1H), 7. 53 (d, J=7.8 Hz, 1H), 7.87 (m, 3H), 8.42(s, 1H), 8.57 (d, J=4.2 Hz, 1H), 8.85 (s, 1H). LC/MS MH$^+$=475.

Example 12

4-Pyridylmethyl N-[4-(4-Amino-7-tetrahydro-2H-4-pyranyl-7H-pyrrolo[2,3-d]pyrimidin-5-yl)-2-methoxyphenyl]carbaniate Hydrochloride Phenyl N-[4-(4-amino-7-tetrahydro-2H-4-pyranyl-7H-pyrrolo[2,3-d]pyrimidin-5-yl)-2-methoxyphenyl]carbamate (30 mg, 0.065 mmol) was mixed 4-pyridylmethanol (0.05 mL) in pyridine (0.5 mL). The reaction mixture was heated at 100° C. overnight. The solvent was removed and the residue was purified by preparative reverse phase LC/MS to give 2-pyridylmethyl N-[4-(4-amino-7-tetrahydro-2H-4-pyranyl-7H-pyrrolo[2,3-d]pyrimidin-5-yl)-2-methoxyphenyl]carbamate (11 mg, 0.023 mmol). The solid was dissolved in ethyl acetate (2 mL) and 1.0N HCl in ether (0.1 mL) was added slowly. The precipatate was collected through filtration under nitrogen to give 4-pyridylmethyl N-[4-(4-amino-7-tetrahydro-2H-4-pyranyl-7H-pyrrolo[2,3-d]pyrimidin-5-yl)-2-methoxyphenyl]carbamate hydrochloride (12 mg, 0.023 mmol). 1H NMR (DMSO-d$_6$) δ 1.91(m, 2H), 2.16(m, 2H), 3.55 (m, 2H), 3.90 (s, 3H), 4.03 (m, 2H), 4.92 (m, 1H), 5.34 (s, 2H), 7.06 (d, J=8.2 Hz, 1H), 7.16 (s, 1H), 7.73 (m, 1H), 7. 81 (m, 1H), 7.87 (s, 1H), 8.46(s, 1H), 8.76 (d, J=5.6 Hz, 1H), 9.05 (s, 1H). LC/MS: MH$^+$=475.

Example 13

(5-Methyl-3-isoxazolyl)methyl N-[4-(4-Amino-7-tetrahydro-2H-4-pyranyl-7H-pyrrolo[2,3-d]pyrimidin-5-yl)-2-methoxyphenyl]carbamate Phenyl N-[4-(4-amino-7-tetrahydro-2H-4-pyranyl-7H-pyrrolo[2,3-d]pyrimidin-5-yl)-2-methoxyphenyl]carbamate (30 mg, 0.065 mmol) was mixed with (5-methyl-3-isoxazolyl)methanol (0.05 mL) in pyridine (0.5 mL). The reaction mixture was heated at 100° C. overnight. The solvent was removed and the residue was purified by preparative reverse phase LC/MS to give (5-methyl-3-isoxazolyl)methyl N-[4-(4-amino-7-tetrahydro-2H-4-pyranyl-7H-pyrrolo[2,3-d]pyrimidin-5-yl)-2-methoxyphenyl]carbamate (18 mg, 0.038 mmol). 1H NMR (CDCl-d) δ 2.06(m, 4H), 2.44 (s, 3H), 3.64 (m, 2H), 3.91 (s, 3H), 4.13 (m, 2H), 4.96 (m, 1H), 5.26 (s, 2H), 6.12(s, 1H), 6.95 (s, 1H), 7.06 (m, 2H), 7.39 (s, 1H), 8.17 (bs, 1H), 8.21(s, 1H). LC/MS: MH$^+$479.

Example 14

[(2S)-5-Oxotetrahydro-1H-2-pyrrolyl]methyl N-[4-(4-amino-7-tetrahydro-2H-4-pyranyl-7H-pyrrolo[2,3-d]pyrimidin-5-yl)-2-methoxyphenyl]carbamate Phenyl N-[4-(4-amino-7-tetrahydro-2H-4-pyranyl-7H-pyrrolo[2,3-d]pyrimidin-5-yl)-2-methoxyphenyl]carbamate (30 mg, 0.065 mmol) was mixed with (5S)-5-(hydroxymethyl)tetrahydro-1H-2-pyrrolone (0.05 mL) in pyridine (0.5 mL). The reaction mixture was heated at 100° C. overnight. The solvent was removed and the residue was purified by preparative reverse phase LC/MS to give [(2S)-5-oxotetrahydro-1H-2-pyrrolyl]methyl N-[4-(4-amino-7-tetrahydro-2H-4-pyranyl-7H-pyrrolo[2,3-d]pyrimidin-5-yl)-2-methoxyphenyl]carbamate (10 mg, 0.02 mmol). 1H NMR (CDCl-d) δ 1.90 (m, 1H), 2.06(m, 4H), 2.34 (m, 1H), 2.41 (m, 2H), 3.64 (m, 2H), 3.94 (s, 3H), 4.04(m, 2H), 4.14 (m, 2H), 4.98 (m, 1H), 5.33 (m, 3H), 6.10(s, 1H), 6.98 (s, 1H0, 7.04 (s, 1H), 7.09 (m, 1H), 7.31(s, 1H), 8.11 (bs, 1H), 8.32 (s, 1H). LC/MS: MH$^+$481.

Example 15

4-Aminobenzyl N-(4-(4-Amino-7-tetrahydro-2H-4-pyranyl-7H-pyrrolo[2,3-d]pyrimidin-5-yl)-2-methoxyphenyl)carbamate a) tert-Butyl N-(4-(hydroxymethyl)phenyl)carbamate. (4-Aminophenyl)methanol (1.23 g, 10 mmol) and diisopropylethylamine (2.6 mL, 15 mmol) was mixed with di-tert-butyl dicarbonate (2.62 g, 12 mmol) in dichloromethane (50 mL). The organic layer was washed with water, 1.0N HCl, saturated sodium carbonate, water, brine, dried over MgSO4, filtered and evaporated. The crude product was purified by flash column chromatography with Ethyl acetate/heptane (2:3) to give tert-butyl N-(4-(hydroxymethyl)phenyl) carbamate (2.16 g, 9.67 mmol). 1H NMR (CDCl-d) δ 1.52 (s, 9H), 4.63 (s, 2H), 6.47 (bs, 1H), 7.30 (d, 8.5 Hz, 2H), 7.36 (d, 8.5 Hz, 2H).

b) 4-Aminobenzyl N-(4-(4-amino-7-tetrahydro-2H-4-pyranyl-7H-pyrrolo[2,3-d]pyrimidin-5-yl)-2-methoxyphenyl)carbamate. Phenyl N-[4-(4-amino-7-tetrahydro-2H-4-pyranyl-7H-pyrrolo[2,3-d]pyrimidin-5-yl)-2-methoxyphenyl]carbamate (51 mg, 0.111 mmol) was mixed with tert-butyl N-(4-(hydroxymethyl)phenyl) carbamate (119 mg, 0.533) in pyridine (0.8 mL). The reaction mixture was heated at 100° C. overnight. The solvent was removed and the residue was purified by preparative reverse phase LC/MS to give 4-aminobenzyl N-(4-(4-amino-7-tetrahydro-2H-4-pyranyl-7H-pyrrolo[2,3-d]pyrimidin-5-yl)-2-methoxyphenyl)carbamate (9 mg, 0.015 mmol). 1H NMR (CDCl-d) δ 1.52(s, 1H), 2.08(m, 4H), 3.65 (m, 2H), 3.90 (s, 3H), 4.14(m, 2H), 4.97 (m, 1H), 5.17 (s, 2H), 5.37(bs, 1H), 6.55 (s, 1H), 6.95 (s, 1H), 7.03 (s, 1H), 7.06 (m, 1H), 7.31 (s, 1H), 7.38 (m, 3H), 8.16 (bs, 1H), 8.30 (s, 1H). LC/MS: MH$^+$589.

Example 16

N1-[4-(4-Amino-7-tetrahydro-2H-4-pyranyl-7H-pyrrolo[2,3-d]pyrimidin-5-yl)-2-methoxyphenyl] benzamide 5-(4-Amino-3-methoxyphenyl)-7-tetrahydro-2H-4-pyranyl-7H-pyrrolo[2,3-d]pyrimidin-4-amine (80 mg, 0.236 mmol) was dissolved in dichloromethane (2.0 mL). Pyridine (2.0 mL) was added followed by benzoyl chloride (41 uL, 0.353 mmol). After stirring at room temperature for 2 hours, the solvent was removed and the residue was dissolved in 1 ml DMSO, methanol (1 mL) was added and precipitate was formed. The solid was collected by filtration to give N1-[4-(4-amino-7-tetrahydro-2H-4-pyranyl-7H-pyrrolo[2,3-d]pyrimidin-5-yl)-2-methoxyphenyl]benzamide (64 mg, 0.144 mmol). 1H NMR (CDCl$_3$-d) δ 2.12 (m, 4H), 3.67 (m, 2H), 3.99 (s, 3H), 4.17(m, 2H), 4.99 (m, 1H), 7.03(s, 1H), 7.04 (s, 1H), 7.14 (d, J=8.2 Hz, 1H), 7.53 (m, 3H), 7.94(d, J=7.8 Hz, 1H), 8.33 (s, 1H), 8.58 (s, 1H), 8.63 (d, J=8.2 Hz, 1H). LC/MS: MH$^+$=444.

Example 17

N2-[4-(4-Amino-7-tetrahydro-2H-4-pyranyl-7H-pyrrolo[2,3-d]pyrimidin-5-yl)-2-methoxyphenyl]-2-pyridinecarboxamide 5-(4-Amino-3-methoxyphenyl)-7-tetrahydro-2H-4-pyranyl-7H-pyrrolo[2,3-d]pyrimidin-4-amine (80mg, 0.236 mmol) was dissolved in dichloromethane (2.0 mL). Pyridine (2.0 mL) was added followed by 2-pyridinecarbonyl chloride hydrochloride (63 mg, 0.353 mmol). After stirring at room temperature for 2 hours, the solvent was removed and the residue was dissolved in 1 ml DMSO, methanol (1 mL) was added and precipitate was formed. The solid was collected by filtration to give N1-[4-(4-amino-7-tetrahydro-2H-4-pyranyl-7H-pyrrolo[2,3-d]pyrimidin-5-yl)-2-methoxyphenyl]benzamide (84 mg, 0.189 mmol). 1H NMR (CDCl$_3$-d) δ 2.12 (m, 4H), 3.67 (m, 2H), 4.03 (s, 3H), 4.14(m, 2H), 5.00 (m, 1H), 5.37 (s, 1H), 7.04(s, 1H), 7.09 (s, 1H), 7.14 (d, J=8.2 Hz, 1H), 7.50 (m, 1H), 7.92 (m, 1H), 8.33 (s, 1H), 8.70(d, J=8.2 Hz, 1H), 10.62 (s, 1H). LC/MS: MH$^+$=445.

Example 18

N5-[4-(4-Amino-7-tetrahydro-2H-4-pyranyl-7H-pyrrolo[2,3-d]pyrimidin-5-yl)-2-methoxyphenyl]-1,3-dimethyl-1H-5-pyrazolecarboxamide 5-(4-Amino-3-methoxyphenyl)-7-tetrahydro-2H-4-pyranyl-7H-pyrrolo[2,3-d]pyrimidin-4-amine (80mg, 0.236 mmol) was dissolved in dichloromethane (2.0 mL). Pyridine (2.0 mL) was added followed by 2-pyridinecarbonyl chloride hydrochloride (63 mg, 0.353 mmol). After stirring at room temperature for 2 hours, the solvent was removed and the residue was dissolved in 1 ml DMSO, methanol (1 mL) was added and precipitate was formed. The solid was collected by filtration to give N5-[4-(4-amino-7-tetrahydro-2H-4-pyranyl-7H-pyrrolo[2,3-d]pyrimidin-5-yl)-2-methoxyphenyl]-1,3-dimethyl-1H-5-pyrazolecarboxamide (30 mg, 0.065 mmol). 1H NMR (CDCl$_3$-d) δ 2.11 (m, 4H), 2.32 (s, 3H), 3.66 (m, 2H), 3.99 (s, 3H), 4.13(m, 2H), 4.17 (s, 3H), 4.99 (m, 1H), 5.22 (bs, 2H), 6.46 (s, 1H), 7.03 (s, 1H), 7.07 (s, 1H), 7.12 (d, J=8.2 Hz, 1H), 8.33 (2, 2H), 8.49(d, J=8.2 Hz, 1H). LC/MS: MH$^+$=462.

Example 19

N1-[4-(4-Amino-7-tetrahydro-2H-4-pyranyl-7H-pyrrolo[2,3-d]pyrimidin-5-yl)-2-methoxyphenyl]-2,2-dimethylpropanamide 5-(4-Amino-3-methoxyphenyl)-7-tetrahydro-2H-4-pyranyl-7H-pyrrolo[2,3-d]pyrimidin-4-amine (50 mg, 0.147 mmol) was dissolved in dichloromethane (1.5 mL). Pyridine (1.5 mL) was added followed by 2,2-dimethylpropanoyl chloride (31 mg, 0.221 mmol). After stirring at room temperature for 2 hours, the solvent was removed and the residue was dissolved in 1 ml DMSO, methanol (1 mL) was added and precipitate was formed. The solid was collected by filtration to give N1-[4-(4-amino-7-tetrahydro-2H-4-pyranyl-7H-pyrrolo[2,3-d]pyrimidin-5-yl)-2-methoxyphenyl]-2,2-dimethylpropanamide (27 mg, 0.064 mmol). 1H NMR (CDCl$_3$-d) δ 1.35 (s, 9H), 2.09 (m, 4H), 3.66 (m, 2H), 3.96 (s, 3H), 4.13(m, 2H), 4.97 (m, 1H), 5.46(bs, 2H), 6.98 (s, 1H), 7.04 (s, 1H), 7.07 (d, J=8.2 Hz, 1H), 8.15 (s, 1H), 8.29 (s, 1H), 8.49 (d, J=8.2 Hz, 1H). LC/MS: MH$^+$=424.

Example 20

N1-[4-(4-Amino-7-tetrahydro-2H-4-pyranyl-7H-pyrrolo[2,3-d]pyrimidin-5-yl)-2-methoxyphenyl]-1-cyclopentanecarboxamide 5-(4-Amino-3-methoxyphenyl)-7-tetrahydro-2H-4-pyranyl-7H-pyrrolo[2,3-d]pyrimidin-4-amine (50mg, 0.147 mmol) was dissolved in dichloromethane (1.5 mL). Pyridine (1.5 mL) was added followed by 1-cyclopentanecarbonyl chloride (31 mg, 0.221 mmol). After stirring at room temperature for 2 hours, the solvent was removed and the residue was dissolved in 1 ml DMSO, methanol (1 mL) was added and precipitate was formed. The solid was collected by filtration to give N1-[4-(4-amino-7-tetrahydro-2H-4-pyranyl-7H-pyrrolo[2,3-d]pyrimidin-5-yl)-2-methoxyphenyl]-2,2-dimethylpropanamide (33 mg, 0.076 mmol). 1H NMR (CDCl$_3$-d) δ 1.66 (m, 2H), 1.81 (m, 2H), 1.95 (m, 4H), 2.06 (m, 4H), 2.77 (m, 1H), 3.65 (m, 2H), 3.94 (s, 3H), 4.15 9m, 4H), 4.96 (m, 1H), 5.37(bs, 2H), 6.98 (s, 1H), 7.03 (s, 1H), 7.07 (d, J=8.2 Hz, 1H), 7.84 (s, 1H), 8.30 (s, 1H), 8.49(d, J=8.2 Hz, 1H). LC/MS: MH$^+$=437.

Example 21

N1-[4-(4-Amino-7-tetrahydro-2H-4-pyranyl-7H-pyrrolo[2,3-d]pyrimidin-5-yl)-2-methoxyphenyl]-3-phenylpropanamide 5-(4-Amino-3-methoxyphenyl)-7-tetrahydro-2H-4-pyranyl-7H-pyrrolo[2,3-d]pyrimidin-4-amine (50 mg, 0.147 mmol) was dissolved in dichloromethane (1.5 mL). Pyridine (1.5 mL) was added followed by 3-phenylpropanoyl chloride (37 mg, 0.221 mmol). After stirring at room temperature for 2 hours, the solvent was removed and the residue was dissolved in 1 ml DMSO, methanol (1 mL) was added and precipitate was formed. The solid was collected by filtration to give N1-[4-(4-amino-7-tetrahydro-2H-4-pyranyl-7H-pyrrolo[2,3-d]pyrimidin-5-yl)-2-methoxyphenyl]-2,2-dimethylpropanamide (7 mg, 0.015 mmol). 1H NMR (CDCl$_3$-d) δ 2.07 (m, 4H), 2.75 (m, 2H), 3.09 (m,2H), 3.65 (m, 2H), 3.88 (s, 3H), 4.13(m, 2H), 4.96 (m, 1H), 5.97 (bs, 2H), 6.93 (s, 1H), 7.05 (m, 2H), 7.26 (m, 5H), 7.70 (s, 1H), 8.24 (s, 1H), 8.46 (d, J=8.2 Hz, 1H). LC/MS: MH$^+$=472.

Example 22

5-(4-Phenoxyphenyl)-7-(3-tetrahydrofuryl)-7H-pyrrolo[2,3-d]pyrimidin-4-ylamine.

a) Tosyl chloride (12.0 g) was added in portions to a mixture of hydroxytetrahydrofuran (5.0 g) in pyridine (100 ml) at 0 C under nitrogen with string. The mixture was stirred at 0° C. for 2 hours and then warmed to ambient temperature. The mixture was stirred at ambient temperature for 72 hours. The mixture was cooled to 0° C. and 5M hydrochloric acid (200 ml) was added. The mixture was extracted with ethyl acetate and the combined ethyl acetate extracts were washed with 2M hydrochloric acid and then with brine, then dried, filtered and evaporated to give 3-tosyloxytetrahydrofuran as an oil.

b) Sodium hydride (120 mg, of a 60% dispersion in mineral oil) was added to a solution of 4-amino-5-(4-phenoxyphenyl)-7H-pyrrolo[2,3-d]pyrimidine (906 mg) and dimethylformamide (30 ml) with stirring under nitrogen. The mixture was stirred for 30 minutes and then a solution of 3-(tosyloxy) tetrahydrofuran (750 mg) in dimethyl formamide (10 ml) was added with stirring. The mixture was stirred and heated at 95° C. for 18 hours and then evaporated under vacuum. The residue was partitioned between ethyl acetate and water. The ethyl acetate layer was separated, dried and evaporated to give a residual gummy solid which was triturated with ether and filtered to give 5-(4-phenoxyphenyl)-7-(3-tetrahydrofuryl)-7H-pyrrolo[2,3-d]pyrimidin-4-ylamine m.p. 196–196.5° C.

Example 23

5-(4-Phenoxyphenyl)-7-(4-tetrahydropyranyl)-7H-pyrrolo[2,3-d]pyrimidin-4-ylamine.

In a similar manner to Example 1, 4-amino-5-(4-phenoxyphenyl)-7H-pyrrolo[2,3-d]pyrimidine was reacted with 4-tosyloxytetrahydropyran to give after flash column chromatography 5-(4-phenoxyphenyl)-7-(4-tetrahydropyranyl)-7H-pyrrolo[2,3-d]pyrimidin-4-ylamine, m.p. 193–193.5° C.

Example 24

4-Amino-5-(4-phenoxyphenyl)-7-[4-(N-tert-butoxycarbonyl) tetrahydroisoxazolyl]-7H-pyrrolo[2,3-d]pyrimidin-4-ylamine a) Di-tert-butyl dicarbonate (4.56 g) was added to a solution of 4-hydroxytetrahydroisoxazole (2.4 g) and triethylamine (4.2 g) in tetrahydrofuran (100 ml) with stirring at 0° C. under nitrogen. The mixture was stirred at ambient temperature for 72 hours and then filtered. The filtrate was evaporated under reduced pressure to give N-(tert-butoxycarbonyl)-4-hydroxytetrahydroisoxazole as an oil which was used directly in the next part of this example.

b) The product from a) above (3.6 g) was stirred in pyridine (50 ml) at 0° C. under nitrogen and then tosyl chloride (3.62 g) was added in portions at 0° C. with stirring. The mixture was stirred at 0° C. for 1 hour and then allowed to warm to ambient temperature over 18 hours. The pyridine was removed under reduced pressure and ethyl acetate (50 ml) and citric acid (50 ml of a 1M solution in water) were added. The organic layer was separated and washed with 1M citric acid solution and then brine, then dried, filtered and evaporated to give an oil which was purified by flash column chromatography using petroleum ether, b.p 40–60° C. containing 20–30% of ethyl acetate as the mobile phase. Appropriate fractions were collected and combined to give N-(tert-butoxycarbonyl)-4-tosyloxy tetrahydroisoxazole, m.p. 63–65° C.

c) A solution of 4-amino-5-(4-phenoxyphenyl)-7H-pyrrolo[2,3-d]pyrimidine (1.0 g) in dimethylformamide (40 ml) was added dropwise with stirring to a suspension of sodium hydride (0.145 g, of a 60% dispersion in mineral oil) in dimethylformamide (60ml) with stirring under nitrogen at 0° C. The mixture was stirred at 0° C. for 1 hour and then the product from b) (1.25 g) was added. The mixture was heated at 100° C. for 3 hours and then cooled to ambient temperature, quenched with water and extracted with ethyl acetate to give an oil. The oil was triturated with ethyl acetate and the solid obtained was collected by filtration to give 4-amino-5-(4-phenoxyphenyl)-7-[4-(N-tert-butoxycarbonyl)tetrahydroisoxazolyl]-7H-pyrrolo[2,3-d]pyrimidin-4-ylamine, m.p. 162–163° C.

Example 25

5-(4-Phenoxyphenyl)-7-(4-tetrahydroisoxazolyl)-7H-pyrrolo[2,3-d]-pyrimidin-4-ylamine Dihydrochloride The product from Example 3 (0.29 g) was dissolved in dichloromethane (8 ml) and then stirred at 0° C. whilst trifluoroacetic acid (2.0 ml) was added. The mixture was allowed to warm to ambient temperature and stirred at ambient temperature for 2 hours. The mixture was basified with sodium bicarbonate solution and extracted with dichloromethane to give an oil which was purified by flash column chromatography using ethyl acetate and then ethyl acetate/methanol (9:1) as the mobile phase. The appropriate fractions were collected and combined, then evaporated to give a solid which was dissolved in ethyl acetate and then treated with ethereal hydrogen chloride (3.0 ml, of a 1M solution). The solid obtained was collected by filtration, washed with ether and dried under vacuum at 45° C. for 2 hours to give 5-(4-phenoxyphenyl)-7-(4-tetrahydroisoxazolyl)-7H-pyrrolo[2,3-d]-pyrimidin-4-ylamine dihydrochloride, m.p. 208° C. (with decomposition).

Example 26

4-Chloro-5-iodo-7-(3-tetrahydrofuryl)-7H-pyrrolo[2,3-d]pyrimidine a) 4-Chloro-5-iodo-7H-pyrrolo[2,3-d]pyrimidine (5.0 g) was added to a mixture of sodium hydride (0.79 g of a 60% dispersion in mineral oil) in dimethylformamide (100 ml) with stirring under nitrogen at 0° C. The mixture was stirred until hydrogen evolution ceased. 3-Tosyloxytetrahydrofuran (4.65 g) was added at 0° C. and then the mixture was warmed to 90° C. The mixture was stirred at this temperature for 2 hours and then overnight at ambient temperature. Water (100 ml) was added cautiously and the mixture was extracted with ethyl acetate to give 4-chloro-5-iodo-7-(3-tetrahydrofuryl)-7H-pyrrolo[2,3-d]pyrimidine, m.p. 184–186° C.

b) A mixture of 4-iodophenol (25.0 g), 2-fluorobenzaldehyde (14.14 g), potassium carbonate (31.5 g) and dimethylformamide (500 ml) was heated at 120° C. under nitrogen with stirring for 15 hours. The mixture was cooled to ambient temperature and filtered. Water (500 ml) was added to the filtrate and the mixture was extracted with ethyl acetate to give a solid which was triturated with hot hexane (500 ml). The supernatant liquid was decanted from a residual gum and cooled. The solid which precipitated was collected by filtration to give 2-(4-iodophenoxy)benzaldehyde, m.p. 84.5–86° C.

c) Toluene (250 ml) was deoxygenated and then nitrogenated for 30 minutes. 2-(4-Iodophenoxy)benzaldehyde (6.46 g), hexamethylditin (10.0 g) and tetrakis(triphenylphosphine) palladium(0) (1.4 g) were added to the toluene. The mixture was boiled under reflux under nitrogen with stirring for 7 hours. The mixture was cooled to ambient temperature then filtered. The filtrate was evaporated and the residue was purified by flash column chromatography on silica using 3% ethyl acetate in petroleum ether, b.p. 40–60° C. as the mobile phase to give 2-(4-trimethylstannylphenoxy)benzaldehyde as an oil.

d) A mixture of the product from c) (1.80 g), the product from b) (1.76 g), tris(dibenzylideneacetone)dipalladium (228 mg), triphenylarsine (383 mg) and dimethylformamide (75 ml) was heated at 65° C. under nitrogen with stirring for 70 hours. The mixture was cooled to ambient temperature and quenched with water. The mixture was extracted with ethyl acetate to give a residue which was purified by flash column chromatography on silica using increasing amounts of ethyl acetate from 30–50% in petroleum ether, b.p. 40–60° C. as the mobile phase to give a solid which was triturated with diethyl ether and filtered to give 2-[(4-(4-chloro-7-(3-tetrahydrofuryl)-7H-pyrrolo[2,3-d]pyrimidin-5-yl)phenoxy]benzaldehyde as a solid.

e) The product from d) (360 mg) was dissolved in methanol (5 ml) and sodium borohydride (65 mg) was added at 0° C. with stirring. The mixture was warmed to ambient temperature and stirred at this temperature for 1 hour. The mixture was quenched with dilute sodium hydroxide solution and then evaporated under reduced pressure to give a residue which was extracted with ethyl acetate to give 2-[(4-(4-chloro-7-(3-tetrahydrofuryl)-7H-pyrrolo[2,3-d]pyrimidin-5-yl)phenoxy]benzyl alcohol.

f) A mixture of the product from e) (280 mg), 1,4-dioxane (15 ml) and concentrated aqueous ammonia solution (15 ml, S.G. 0.88) was heated at 120° C. in a pressure vessel for 20 hours. The mixture was cooled to ambient temperature and the solvent removed under reduced pressure. The residue was taken up in ethyl acetate, washed with water, then dried, filtered and evaporated to give an oil which was purified by flash column chromatography on silica using ethyl acetate/methanol (9:1) as the mobile phase to give 2-[(4-(4-amino-7-(3-tetrahydrofuryl)-7H-pyrrolo[2,3-d]pyrimidin-5-yl)phenoxy]benzyl alcohol as a glassy solid, m.p. 92–96° C.

Example 27

2-[4-(4-Amino-7-(3-tetrahydrofuryl)-7H-pyrrolo[2,3-d]pyrimidin-5-yl)phenoxy]-N,N-diethylbenzylamine a) Sodium triacetoxyborohydride (264 mg) was added to a mixture of 2-[(4-(4-chloro-7-(3-tetrahydrofuryl)-7H- pyrrolo[2,3-d]pyrimidin-5-yl)phenoxy]benzaldehyde (330 mg) and diethylamine (121 mg) in 1,2-dichloroethane in a vial (5 ml) and the vial septum sealed. The mixture was stirred at ambient temperature for 20 hours then quenched with saturated aqueous sodium bicarbonate solution (5 ml). The mixture was extracted with ethyl acetate to give 2-[4-(4-chloro-7-(3-tetrahydrofuryl)-7H-pyrrolo[2,3-d)pyrimidin-5-yl) phenoxy]-N,N-diethylbenzylamine.

b) A mixture of the product from a) (280 mg), concentrated aqueous ammonia solution (10 ml, S.G. 0.88) and 1,4-dioxane (10 ml) was heated in a pressure vessel for 16 hours at 120° C. The mixture was cooled and the solvent removed under reduced pressure. The residue was taken up in ethyl acetate, washed with water, then dried, filtered and evaporated to give an oil which was purified by flash column chromatography using ethyl acetate/methanol as a mobile phase to give 2-[4-(4-amino-7-(3-tetrahydrofuryl)-7H-pyrrolo[2,3-d]pyrimidin-5-yl) phenoxy]-N,N-diethylbenzylamine, m.p. 107–110° C.

Example 28

2-[4-(4-Amino-7-(3-tetrahydrofuryl)-7H-pyrrolo[2, 3-d]pyrimidin-5-yl)phenoxy]-benzonitrile a) A mixture of 2-fluorobenzonitrile (28.8 g), 4-bromophenol (36.9 g), potassium carbonate (58.9 g) and dimethylformamide (30 ml) was heated with stirring under nitrogen at 120° C. for 5 hours. The mixture was allowed to stand overnight at ambient temperature and then partitioned between ethyl acetate and water. The organic layer was separated, washed, dried and evaporated to give an oil which solidified on standing. The solid was triturated with petroleum ether b.p. 40–60° C. and filtered to give 2-(4-bromophenoxy)benzonitrile.

b) A mixture from the product of part a) (5.57 g), hexamethylditin (10.0 g), tetrakis (triphenylphosphine) palladium (0) (1.4 g) and degassed toluene (250 ml) was heated at 110° C. with stirring under nitrogen for 4.5 hours. The mixture was allowed to stand for 18 hours at ambient temperature and then filtered through a silica pad. The pad was washed with ethyl acetate and the combined filtrate and washes evaporated to dryness. The residue was purified by flash column chromatography on silica using petroleum ether b.p. 40–60° C. and diethyl ether (2%) increasing to 5% as the mobile phase. Appropriate fractions were collected combined and evaporated to give 2-(4-trimethylstannylphenoxy)benzonitrile.

c) A mixture 4-chloro-5-iodo-7-(3-tetrahydroftiryl)pyrrolo [2,3-d]pyrimidine (1.8 g, prepared as described in Example 5) and the product from part b) (1.23 g) were reacted and then worked up in a similar manner to Example 5d) to give 2-[4-(4-chloro-7-(3-tetrahydrofuryl)-7H-pyrrolo[2,3-d]pyrimidin-5-yl)phenoxy]benzonitrile.

d) A mixture of the product from c) (470 mg), concentrated aqueous ammonia (33 ml, SG 0.880) and 1,4-dioxane (33 ml) were heated together in a pressure vessel at 120° C. for 18 hours and then worked up on a similar manner to Example 5 to give 2-[4-(4-amino-7-(3-tetrahydrofuryl)-7H-pyrrolo[2,3-d]pyrimidin-5-yl)phenoxy]-benzonitrile, m.p. 201–203° C.

Example 29

2-[4-(4-Amino-7-(3-tetrahydrofuryl)-7H-pyrrolo[2, 3-d)pyrimidin-5-yl)phenoxy]benzaldehyde a) In a similar manner to Example 2, 3-tosyloxytetrahydrofuran (1.84 g) was reacted with 5-(4-benzyloxyphenyl)-7H-pyrrolo[2,3-d]pyrimidin-4-ylamine (2.9 g) using sodium hydride (0.30 g, of a 60% dispersion in mineral oil) and dimethylformamide (40 ml) except that the mixture was heated for 4.5 hours at 90° C. to give 5-(4-benzyloxyphenyl)-7-(3-tetrahydrofuryl)-7H-pyrrolo[2,3-d]pyrimidin-4-ylamine as a solid.

b) A mixture of the product from part a) (6.0 g), 10% palladium on charcoal (3.0 g), ammonium formate (4.9 g) and ethanol (500 ml) was heated on a steam bath with stirring under nitrogen for 2 hours. The mixture was cooled and filtered and the solvent evaporated. The filtrate was concentrated to half volume and filtered to give a solid which was identified as 4-[4-amino-7-(3-tetrahydrofuryl)-7H-pyrrolo[2,3-d]pyrimidin-5-yl]phenol m.p. 257–259° C.

c) A mixture of 4-[4-amino-7-(3-tetrahydrofuryl-7H-pyrrolo [2,3-d]pyrimidin-5-yl]phenol (2.55 g), 2-fluorobenzaldehyde (1.07 g), potassium carbonate (2.13 g) and dimethylformamide (80 ml) was heated at 120° C. with stirring under nitrogen for 5 hours. The mixture was cooled to ambient temperature quenched with water and extracted with ethyl acetate to give 2-[4-(4-amino-7-(3-tetrahydrofuryl)-7H-pyrrolo[2,3-d]pyrimidin-5-yl) phenoxy]benzaldehyde, m.p. 185–187° C.

Example 30

4-[4-Amino-5-(4-phenoxyphenyl)-7H-pyrrolo-[2,3-d]pyrimidin-7-yl]tetrahydrofuran-3-ol Sodium hydride (120 mg of a 60% dispersion in mineral oil) was added to a solution of 4-amino-5-(4-phenoxyphenyl-7H-pyrrolo[2,3-d]pyrimidine (902 mg) and dimethylformamide (30 ml) with stirring under nitrogen. The mixture was stirred for 30 minutes and then 3,6-dioxabicyclo[3.1.0]hexane (300 mg) was added and the mixture was warmed to 80° C. The mixture was left for 64 hours and then evaporated under reduced pressure. The residue was triturated with water which left an oily gum. Ether was added and the mixture was stirred rapidly for 30 minutes which gave a solid which was collected by filtration and washed with methanol. The solid was discarded. The filtrate produced a second crop of solid which was recrystallised from ethanol to give 4-[4-amino-5-(4-phenoxyphenyl)-7H-pyrrolo-[2,3-d]pyrimidin-7-yl] tetrahydrofuran-3-ol, m.p. 234.5–235.5° C.

Example 31

5-[4-(2-Morpholinomethylphenoxy)phenyl]-7-(3-tetrahydrofuryl)-7H-pyrrolo[2,3-d]pyrimidin-4-ylamine A mixture of 2-[4-(4-amino-7-(3-tetrahydrofuryl)-7H-pyrrolo[2,3-d)pyrimidin-5-yl)phenoxy]benzaldehyde (0.15 g), morpholine (64 mg), sodium triacetoxyborohydride (117 mg) and 1,2 dichloroethane (5 ml) was stirred at ambient temperature for 18 hours. Saturated aqueous sodium bicarbonate solution was added and the mixture was filtered through an EMPORE® cartridge. The filtrate was evaporated and the residue was dissolved in dichloromethane (5 ml) and then tris(2-aminoethyl)amine-polymer bound (0.3 g) and 2 drops of glacial acetic acid were added and the mixture was stirred at ambient temperature overnight. The polymer was removed by filtration and washed with dichloromethane and then with methanol. The combined organic filtrate and washings were evaporated under reduced pressure to give an oil which was triturated with diethyl ether/ ethyl acetate with warming to dissolve the solid and then the solution was cooled in ice and filtered to give 5-[4-(2-morpholinomethylphenoxy)phenyl] -7-(3-tetrahydrofuryl)-7H-pyrrolo[2,3-d]pyrimidin-4-ylamine, m.p. 169–171° C.

Example 32

5-[4-(2-Piperidinomethylphenoxy)phenyl]-7-(3-tetrahydrofuryl)-7H-pyrrolo[2,3-d]pyrimidin-4-ylamine In a similar manner to Example 10, 2-[4-(4-amino-7-(3-tetrahydrofuryl)-7H-pyrrolo[2,3-d)pyrimidin-5-yl)phenoxy]benzaldehyde (0.15 g) was reacted with piperridine (63 mg) to give 5-[4-(2-piperidinomethylphenoxy)phenyl]-7-(3-tetrahydrofuryl)-7H-pyrrolo[2,3-d]pyrimidin-4-ylamine m.p. 76–78° C. (glassy foam).

Example 33

5-{4-[2-(2-Methoxyethyl)aminomethylphenoxy]phenyl}-7-(3-tetrahydrofuryl)-7H-pyrrolo[2,3-d]-pyrimidin-4-ylamine In a similar manner to Example 10, 2-[4-(4-amino-7-(3-tetrahydrofuryl)-7H-pyrrolo[2,3-d)pyrimidin-5-yl)phenoxy]benzaldehyde (0.15 g) and 2-methoxyethylamine (56 mg) were reacted together to give 5-{4-[2-(2-methoxyethyl)aminomethylphenoxy]phenyl}-7-(3-tetrahydrofuryl)-7H-pyrrolo[2,3-d]-pyrimidin-4-ylamine m.p. 66–68° C. (glassy foam).

Example 34

4-[(4-(4-Amino-7(3-tetrahydrofuryl-7H-pyrolo[2,3-d]-pyrimidin-5-yl)phenoxy]benzyl Alcohol a) In a similar manner to Example 9, 4-[4-amino-7-(3-tetrahydrofuryl)-7H-pyrrolo[2,3-d]pyrimidin-5-yl]phenol was reacted with 4-fluorobenzaldehyde to give 4-[4-(4-amino-7-(3-tetrahydrofuryl)-7H-pyrrolo[2,3-d]pyrimidin-5-yl)phenoxy]benzaldehyde.
b) The product from a) (0.35 g) was dissolved in methanol (10 ml) and to this solution was added sodium borohydride (32 mg) at 0° C. The mixture was warmed at ambient temperature and stirred at this temperature for 10 minutes. 1,2-Dichloroethane (4 ml) was added to aid solubility. The mixture was stirred to ambient temperature for 18 hours and then glacial acetic acid (1 ml) was added and the mixture evaporated under reduced pressure. The residue was partitioned between ethyl acetate and saturated aqueous sodium carbonate solution. The ethyl acetate was separated, dried, filtered and evaporated to give 4-[(4-(4-amino-7-(3-tetrahydrofuryl)-7H-pyrrolo[2,3-d]-pyrimidin-5-yl)phenoxy]benzyl alcohol, m.p. 92–95° C.

Example 35

5-[4-(4-Fluorophenoxy)phenyl]-7-(3-tetrahydrofuryl)-7H-pyrrolo[2,3-d]pyrimidin-4-ylamine A mixture of 4-[4-amino-7-(3-tetrahydrofuryl-7H-pyrrolo[2,3-d]pyrimidin-5-yl]phenol (0.59 g), 4-fluorophenylboronic acid (0.56 g), copper (II) acetate (0.36 g), triethylamine (1.01 g), dichloromethane (20 ml) and activated ground 4 molecular sieves (0.5 g) was stirred under nitrogen in a dry atmosphere for 64 hours. The reaction mixture was filtered through a small pre-flushed silica pad and eluted with dichloromethane (200 ml) then ethyl acetate (250 ml) and finally ethyl acetate/methanol 9:1 (250 ml). The dichlormethane and ethyl acetate fractions were combined and purified by flash column chromatography on silica using ethyl acetate/methanol as the mobile phase to give 5-[4-(4-fluorophenoxy)phenyl]-7-(3-tetrahydrofuryl)-7H-pyrrolo[2,3-d]pyrimidin-4-ylamine, m.p. 198–199° C.

Example 36

5-[4-(4-Morpholinomethylphenoxy)-phenyl]-7-(3-tetrahydrofuryl)-7H-pyrrolo[2,3-d]pyrimidin-4-ylamine In a similar manner to Example 10 a mixture of 4-[4-(4-amino-7-(3-tetrahydrofuryl)-7H-pyrrolo[2,3-d]pyrimidin-5-yl)phenoxy]benzaldehyde (336 mg), and morpholine (146 mg) were reacted to give 5-[4-(4-morpholinomethylphenoxy)-phenyl]-7-(3-tetrahydrofuryl)-7H-pyrrolo[2,3-d]pyrimidin-4-ylamine, m.p 142–144° C.

Example 37

5-[4-(3-Morpholinomethylphenoxy)phenyl]-7-(3-tetrahydrofuryl)-7H-pyrrolo[2,3-d]pyrimidin-4-ylamine a) A mixture of 4-[4-amino-7-(3-tetrahydrofuryl-7H-pyrrolo[2,3-d]pyrimidin-5-yl)phenol (0.297 g), was reacted with 3-formylphenylboronic acid in a similar manner to Example 14 to give 3-[4-(4-amino-7-(3-tetrahydrofuryl)-7-pyrrolo[2,3-d]pyrimidin-5-yl)phenoxy]benzaldehyde.
b) The product from part a) (100 mg) and morpholine (44 mg) were reacted together using similar reagents and conditions as described in Example 10 to give 5-[4-(3-morpholinomethylphenoxy)phenyl]-7-(3-tetrahydrofuryl)-7H-pyrrolo[2,3-d]pyrimidin-4-ylamine, m.p. 83–85° C.

Example 38

2-[4-(4-Amino-7-(3-tetrahydrofuryl)-7H-pyrrolo[2,3-d]pyrimidin-5-yl)phenoxy]-6-(2-(4-pyridyl)ethylamino)-benzonitrile A mixture of 4-[4-amino-7-(3-tetrahydrofuryl)-7H-pyrrolo[2,3-d]pyrimidin-5-yl]-phenol (0.517 g), 2-fluoro-6-(2-(4-pyridinyl)ethylamino)benzonitrile (0.42 g), potassium carbonate (0.48 g) and dimethylformamide (20 ml) were heated at 120° C. under nitrogen for 8 hours. The mixture was allowed to cool, diluted with water then extracted with ethyl acetate to give a solid which was recrystallised from ethyl acetate to give solid which was purified by flash column chromatography on silica using ethyl acetate and then ethyl acetate/methanol (9:1, 8:1, 4:1) to give 2-[4-(4-amino-7-(3-tetrahydrofuryl)-7H-pyrrolo[2,3-d]pyrimidin-5-yl)phenoxy]-6-(2-(4-pyridyl)ethylamino)-benzonitrile, m.p 212–213° C.

Example 39

2-[4-(4-Amino-7-(3-tetrahydrofuryl)-7H-pyrrolo[2,3-d]pyrimidin-5-yl)phenoxy]-6-(3-imidazol-1-yl)propylaminobenzonitrile 4-[4-Amino-7-(3-tetrahydrofuryl)-7H-pyrrolo[2,3-d]pyrimidin-5-ylphenol (0.49 g), 2-fluoro-6-(3-imidazol-1-yl)propylamino benzonitrile, potassium carbonate (0.45 g) and dimethylformamide were reacted in a similar manner to Example 17 to give 2-[4-(4-amino-7-(3-tetrahydrofuryl)-7H-pyrrolo[2,3-d]pyrimidin-5-yl)phenoxy]-6-(3-imidazol-1-yl)propylaminobenzonitrile, m.p.110° C. (glassy foam).

Example 40

4-Amino-6-bromo-5-(4-phenoxyphenyl)-7-(3-tetrahydrofuryl)-7H-pyrrolo[2,3-d]pyrimidine a) A mixture of 4-amino-5-(4-phenoxyphenyl)-7H-pyrrolo[2,3-d]pyrimidine (302 mg) was dissolved in dimethylacetamide (10 ml) and dichloromethane (50 ml) and then treated with N-bromosuccinimide (178 mg) in dichloromethane (10 ml). The mixture was left stirring ambient temperature for 16 hours. The mixture was evaporated under reduced pressure and the residue was triturated with water to give a solid which was collected by filtration and dried to give 4-amino-6-bromo-5-(4-phenoxyphenyl)-7H-pyrrolo[2,3-d]pyrimidine, m.p. 282–283° C.

b) A mixture of the product from a) (1.14 g) in dry dimethylformamide (30 ml) was stirred under nitrogen whilst sodium hydride (120 mg of a 60% dispersion in mineral oil) was added. This was followed by 3-tosyloxytetrahydrofuran (0.8 g) in dimethylformamide (10 ml). The mixture was heated at 90° C. overnight. The mixture was evaporated under reduced pressure and the residue was triturated with water to give a solid which was collected by filtration and dried to give a solid which was purified by dissolving in ethanol, adding water to cloud point and filtering. The filtrate was evaporated under reduced pressure to give a residue which was purified by flash column chromatography on silica to give 4-amino-6-bromo-5-(4-phenoxyphenyl)-7-(3-tetrahydrofuryl)-7H-pyrrolo[2,3-d]pyrimidine, m.p. 205–206° C.

Example 41

2-[4-(4-Amino-7-(3-tetrahydrofuryl)-7H-pyrrolo[2,3-d]pyrimidin-5-yl)phenoxy]-6-(3-methoxypropylamino)benzonitrile In a similar manner to Example 17, 4-amino-5-(4-phenoxyphenyl)-7H-pyrrolo[2,3-d]pyrimidine (0.65 g), 2-fluoro-6-(3-methoxypropylamino)benzonitrile (0.46 g), potassium carbonate (0.61 g) and dimethylformamide (40 ml) was heated under nitrogen at 120° C. for 8 hours to give, after workup, 2-[4-(4-amino-7-(3- tetrahydrofuryl)-7H-pyrrolo[2,3-d]pyrimidin-5-yl)phenoxy]-6-(3-methoxypropyl amino)benzonitrile, m.p. 183–184° C.

Example 42

2-[4-(4-Amino-7-(4-tetrahydropyranyl)-7H-pyrrolo[2,3-d]pyrimidin-5-yl)phenoxy]benzonitrile a) A mixture of 5-(4-benzyloxyphenyl)-7-(tetrahydropyran-4-yl)-7H-pyrrolo[2,3-d]pyrimidin-4-ylamine (2.83 g), 10% palladium on carbon (1.41 g), ammonium formate (2.31 g) and ethanol (250 ml) was boiled under reflux under nitrogen with stirring for 1.5 hours. The mixture was cooled to ambient temperature, filtered, then the filtrate cooled and filtered. The filtrate was evaporated to give a solid 4-[4-amino-7-(4-tetrahydropyranyl)-7H-pyrrolo[2,3-d]pyrimidin-5-yl]phenol.

b) A warm solution of 4-[4-amino-7-(4-tetrahydropyranyl)-7H-pyrrolo[2,3-d]pyrimidin-5-yl]phenol (0.082 g) in dimethylformamide (3.4 ml) was added to a The vial was flushed with nitrogen then sealed. The mixture was shaken at 120° C. for 6 hours and then left to cool to ambient temperature over 16 hours. The mixture was diluted with water (11 ml) and then extracted with ethyl acetate to give 2-[4-(4-amino-7-(4-tetrahydropyranyl)-7H-pyrrolo[2,3-d]pyrimidin-5-yl)phenoxy]benzonitrile, m.p. 125° C. (softens).

Examples 43–48 were prepared in a similar manner to the previous example by reacting 4-[4-amino-7-(4-tetrahydropyranyl)-7H-pyrrolo[2,3-d]pyrimidin-5-yl]phenol with the appropriate nitrile except that the mixtures were shaken together for periods up to 48 hours. The reactions were monitored for the disappearance of starting material and heated for the appropriate time.

Example 49

2-[4-(4-Amino-7-(4-tetrahydropyranyl)-7H-pyrrolo[2,3-d]pyrimidin-5-yl)phenoxy]-6-(3-imidazol-1-yl)propylaminobenzonitrile From 2-Fluoro-6-(3-(imidazol-1-yl)propylamino)-benzonitrile

Example 50

2-(4-(4-Amino-7-(4-tetrahydropyranyl)-7H-pyrrolo[2,3-d]pyrimidin-5-yl)phenoxy]-6-(2-morpholinoethoxy)benzonitrile, m.p. 110° C. (glass), from 2-fluorobenzonitrile.

Example 51

2-[4-(4-Amino-7-(4-tetrahydropyranyl)-7H-pyrrolo[2,3-d]pyrimidin-5-yl)phenoxy]-6-(2-(4-pyridyl)ethylamino)benzonitrile m.p. 120–123° C. (glass), from 2-fluoro-6-(2-(4-pyridyl)ethylamino)benzonitrile.

Example 52

2-[4-(4-Amino-7-(4-tetrahydropyranyl)-7H-pyrrolo[2,3-d]pyrimidin-5-yl)phenoxy]-6-(3-methoxypropylamino)benzonitrile m.p. 205–207° C., from 2-fluoro-6-(3-methoxypropylamino)benzonitrile.

Example 53

2-[4-(4-Amino-7-(4-tetrahydropyranyl)-7H-pyrrolo[2,3-d]pyrimidin-5-yl)phenoxy]-5-fluorobenzonitrile m.p. 216–217° C., from 2,5-difluorobenzonitrile.

Examples 54–101

General Method

Portions of the amines listed in Table 1 (9 molar equivalents with respect to the ester employed, weights ranging from 47.5 mg to 184.5 mg) were weighed into separate vials and methanol (1 ml) was added to each vial. A solution of ethyl 2-[4-amino-5-(4-phenoxyphenyl)-7H-pyrrolo[2,3-d]pyrimidin-7-yl acetate (1 molar equivalent) in a mixture of methanol and triethylamine (4 ml, ratio of methanol to triethylamine is 23.2:1 v/v. The reaction mixtures were shaken at 60–65° C. for 36 hours. The methanol and triethylamine were removed under reduced pressure at 50° C. for 3 hours and to each vial was added water (3 ml) followed by dichloromethane (3 ml). The vials were agitated for 15 seconds and then allowed to stand for 18 hours. The mixtures were poured into EMPORE® (10 mm/6 ml) extraction disk cartridges and the dichloromethane phases were collected and evaporated at 50° C. for 3 hours. During work-up it was observed that solid had separated out in the vials on standing for 18 hours. Consequently the aqueous layer in each cartridge was forced through with compressed air. Dichloromethane (4 ml) was added to each extraction cartridge. Each filtrate was evaporated under reduced pressure at 50° C. for 3 hours. The desired products were either found in the original dichloromethane extract, in which case they are indicated as being present in the liquid, or were found in the insoluble solid on reworking and are referred to as being found in the solid. Certain products were found in both phases. These phases are indicated in Table 1.

Each sample was analysed by LCMS and in each case the target ion was found. The retention time for each product is given in Table 1. The conditions used are given below.

| Column: | 5 μm hypersil BDS c18 (100 × 2.1 mm). |
|---|---|
| Mobile Phase: | 0.1M NH4OAc [pH 4.55]: MeCN (gradient - see below). |
| Conditions: (Gradient) | 10–100% MeCN in 8 minutes. 100% MeCN for 1 minute. 100–10% MeCN in 2 minutes. (Total analysis run time 11 minutes. |
| Flow Rate: | 1 ml/minute (no split in MS). |
| Wavelength Range: | 250–320 nm |
| Injection Volume: | 20 μl. |
| MS Method: | APCI11H. |
| Ionisation | APcI +ve/−ve. |
| Mass Range: | 100–700 m/z. |
| Cone voltage: | 20. |

In a similar manner to Examples 54–101, the amines listed in Table 2 were reacted, respectively, with ethyl 2-[4-amino-5-(4-phenoxyphenyl)-7H-pyrrolo[2,3-d]-pyrimidin-7-yl]propionate to give the products listed in Examples 102–146 respectively. The work-up and the analysis conditions were identical to those used for Examples 54–101. In each case the target ion was found by LCMS.

TABLE 1

| Amine Number | Name | Phase | RT/min Product |
|---|---|---|---|
| 54 | Ethanolamine | Solid | 3.44 |
| 55 | dl-2-Amino-1-propanol | Solid | 3.58 |
| 56 | 1-Amino-2-propanol | Solid | 3.56 |
| 57 | 2-Methoxyethylamine | Liquid | 3.78 |
| 58 | 3-Amino-1-propanol | Both | 3.50 |
| 59 | (S)-(+)-2-Amino-1-propanol | Both | 3.58 |
| 60 | (R)-(−)-1-Amino-2-propanol | Both | 3.56 |
| 61 | N,N-Dimethylethylenediamine | Both | 3.31 |
| 62 | (+/−)-2-Amino-1-butanol | Solid | 3.77 |
| 63 | 1-Amino-2-butanol | Both | 3.77 |
| 64 | 3-Amino-1,2-propanediol | Solid | 3.32 |
| 65 | (S)-3-Amino-1,2-propanediol | Solid | 3.32 |
| 66 | (R)-3-Amino-1,2-propanediol | Solid | 3.32 |
| 67 | 1-Methylpiperazine | Both | 3.28 |
| 68 | N,N-Dimethyl-1,3-propanediamine | Liquid | 3.29 |
| 69 | N2,N2-Dimethyl-1,2-propanediamine | Both | 3.37 |
| 70 | 1-Dimethylamino-2-propylamine | Liquid | 3.44 |
| 71 | dl-2-Amino-3-methyl-1-butanol | Solid | 3.98 |
| 72 | N-{2-[1-(N-Morpholine)-1-oxo]ethyl}piperazine | Liquid | 3.56 |

TABLE 1-continued

| Amine Number | Name | Phase | RT/min Product |
|---|---|---|---|
| 73 | 2-Amino-2-methyl-1-propanol | Both | 3.86 |
| 74 | 2-Amino-2-methyl-1,3-propanediol | Both | 3.49 |
| 45 | 2-(2-Aminoethoxy)ethanol | Both | 3.47 |
| 76 | 1-(2-Aminoethyl)-pyrrolidine | Liquid | 3.40 |
| 77 | N-Methylhomopiperazine | Liquid | 3.32 |
| 78 | 1-Amino-1-cyclopentane methanol | Both | 4.16 |
| 79 | 2-Aminocyclohexanol | Solid | 3.98 |
| 80 | N,N-Diethylethylenediamine | Liquid | 3.44 |
| 81 | N-(3-Hydroxypropyl)-ethylenediamine | Both | 3.24 |
| 82 | 2-((2-Aminoethyl)thio)-ethanol | Both | 3.69 |
| 83 | 2-(2-Aminoethyl)pyridine | Liquid | 3.89 |
| 84 | 3-(2-Aminoethyl)pyridine | Liquid | 3.79 |
| 85 | N-(3-Aminopropyl)-imidazole | Liquid | 3.37 |
| 86 | 1-[2-(N-Morpholine)ethyl]-piperazine | Liquid | 3.39 |
| 87 | 2-(Aminomethyl)-1-ethyl-pyrrolidine | Both | 3.48 |
| 88 | 1-(2-Aminoethyl)piperidine | Both | 3.49 |
| 89 | 1-Pyrrolidinepropanamine | Liquid | 3.37 |
| 90 | (R)-(+)-2-Aminomethyl-1-ethylpyrrolidine | Both | 3.48 |
| 91 | 4-(2-Aminoethyl)-morpholine | Both | 3.39 |
| 92 | 3-Diethylaminopropylamine | Both | 3.43 |
| 93 | N,N-Dimethylneopentane-diamine | Both | 3.47 |
| 94 | Ethyl 1-piperazine-carboxylate | Liquid | 4.34 |
| 95 | 2-(Aminomethyl)-2-ethyl-1,3-propanediol | Both | 3.69 |
| 96 | 1-(3-Aminopropyl)-2-pyrrolidinone | Both | 3.68 |
| 97 | 1-Piperidinepropylamine | Liquid | 3.46 |
| 98 | 4-(3-Aminopropyl)-morpholine | Liquid | 3.33 |
| 99 | N,N-Diisopropylethylene-diamine | Liquid | 3.59 |
| 100 | N,N-Bis(3-aminopropyl)-methylamine | Liquid | 3.03 |
| 101 | Tris(2-aminoethyl)amine | Liquid | 3.01 |

The compounds prepared are given below.

Example 54

4-Amino-5-(4-phenoxyphenyl)-7H-pyrrolo[2,3-d]pyrimidin-7-yl—N-(2-hydroxyethyl)acetamide Example 55

4-Amino-5-(4-phenoxyphenyl)-7H-pyrrolo[2,3-d]pyrimidin-7-yl-N-(1-hydroxyprop-2-yl)acetamide Example 56

4-Amino-5-(4-phenoxyphenyl)-7H-pyrrolo[2,3-d]pyrimidin-7-yl-N-(2-hydroxypropyl)acetamide Example 57

4-Amino-5-(4-phenoxyphenyl)-7H-pyrrolo[2,3-d]pyrimidin-7-yl-N-(2-methoxyethyl)acetamide Example 58

4-Amino-5-(4-phenoxyphenyl)-7H-pyrrolo[2,3-d]pyrimidin-7-yl-N-(3-hydroxypropyl)acetamide Example 59

(S)-4-Amino-5-(4-phenoxyphenyl)-7H-pyrrolo[2,3-d]pyrimidin-7-yl-N-(1-hydroxyprop-2-yl)acetamide

Example 60

(R)-4-Amino-5-(4-phenoxyphenyl)-7H-pyrrolo[2,3-d]pyrimidin-7-yl-N-(2-hydroxypropyl)acetamide

Example 61

4-Amino-5-(4-phenoxyphenyl)-7H-pyrrolo[2,3-d]pyrimidin-7-yl-N-[2-(N,N-dimethylamino)ethyl]acetamide

Example 62

4-Amino-5-(4-phenoxyphenyl)-7H-pyrrolo[2,3-d]pyrimidin-7-yl-N-(1-hydroxybut-2-yl)acetamide

Example 63

4-Amino-5-(4-phenoxyphenyl)-7H-pyrrolo[2,3-d]pyrimidin-7-yl-N-(2-hydroxybutyl)acetamide

Example 64

4-Amino-5-(4-phenoxyphenyl)-7H-pyrrolo[2,3-d]pyrimidin-7-yl-N-(2,3-dihydroxypropyl)acetamide

Example 65

(S)-4-Amino-5-(4-phenoxyphenyl)-7H-pyrrolo[2,3-d]pyrimidin-7-yl-N-(2,3-dihydroxypropyl)acetamide

Example 66

(R)-4-Amino-5-(4-phenoxyphenyl)-7H-pyrrolo[2,3-d]pyrimidin-7-yl-N-(2,3-dihydroxypropyl)acetamide

Example 67

4-Amino-5-(4-phenoxyphenyl)-7H-pyrrolo[2,3-d]pyrimidin-7-yl-N,N-(3-azapentamethylene)acetamide

Example 68

4-Amino-5-(4-phenoxyphenyl)-7H-pyrrolo[2,3-d]pyrimidin-7-yl-N-[3-(N,N-dimethylamino)propyl]acetamide

Example 69

4-Amino-5-(4-phenoxyphenyl)-7H-pyrrolo[2,3-d]pyrimidin-7-yl-N-[1-(N,N-dimethylamino)prop-2-yl]acetamide

Example 70

4-Amino-5-(4-phenoxyphenyl)-7H-pyrrolo[2,3-d]pyrimidin-7-yl-N-[2-(N,N-dimethylamino)propyl]acetamide

Example 71

4-Amino-5-(4-phenoxyphenyl)-7H-pyrrolo[2,3-d]pyrimidin-7-yl-N-(1-hydroxy-3-methylbut-2-yl)acetamide

Example 72

7-{2-[4-(2-Morpholino-2-oxoethyl)piperazin-1-yl]-2-oxo-ethyl}-5-phenoxyphenyl)-7H-pyrrolo[2,3-d]pyrimidin-4-ylamine

Example 73

4-Amino-5-(4-phenoxyphenyl)-7H-pyrrolo[2,3-d]pyrimidin-7-yl-N-(1-hydroxy-3-methylprop-2-yl)acetamide

Example 74

4-Amino-5-(4-phenoxyphenyl)-7H-pyrrolo[2,3-d]pyrimidin-7-yl-N-(1,3-dihydroxy-2-methylprop-2-yl)acetamide

Example 75

4-Amino-5-(4-phenoxyphenyl)-7H-pyrrolo[2,3-d]pyrimidin-7-yl-N-[2-(2-hydroxyethoxy)ethyl]acetamide

Example 76

4-Amino-5-(4-phenoxyphenyl)-7H-pyrrolo[2,3-d]pyrimidin-7-yl-N-[2-(pyrrolidin-1-yl)ethyl]acetamide

Example 77

4-Amino-5-(4-phenoxyphenyl)-7H-pyrrolo[2,3-d]pyrimidin-7-yl-N,N-(3-azahexamethylene)acetamide

Example 78

4-Amino-5-(4-phenoxyphenyl)-7H-pyrrolo[2,3-d]pyrimidin-7-yl-N-[1-(hydroxymethyl)cyclopentyl]acetamide

Example 79

4-Amino-5-(4-phenoxyphenyl)-7H-pyrrolo[2,3-d]pyrimidin-7-yl-N-(2-hydroxycyclohexyl)acetamide

Example 80

4-Amino-5-(4-phenoxyphenyl)-7H-pyrrolo[2,3-d]pyrimidin-7-yl-N-[2-(N,N-diethylamino)ethyl]acetamide

Example 81

4-Amino-5-(4-phenoxyphenyl)-7H-pyrrolo[2,3-d]pyrimidin-7-yl-N-[2-(3-hydroxypropylamino)ethyl]acetamide

Example 82

4-Amino-5-(4-phenoxyphenyl)-7H-pyrrolo[2,3-d]pyrimidin-7-yl-N-[2-(2-hydroxyethylthio)ethyl]acetamide

Example 83

4-Amino-5-(4-phenoxyphenyl)-7H-pyrrolo[2,3-d]pyrimidin-7-yl-N-[2-(pyrid-2-yl)ethyl]acetamide

Example 84

4-Amino-5-(4-phenoxyphenyl)-7H-pyrrolo[2,3-d]pyrimidin-7-yl-N-[2-(pyrid-3-yl)ethyl]acetamide

Example 85

4-Amino-5-(4-phenoxyphenyl)-7H-pyrrolo[2,3-d]pyrimidin-7-yl-N-[3-(imidazol-1-yl)propyl]acetamide

Example 86

7-{2-[4-(2-Morpholinoethyl)piperazin-1-yl]-2-oxoethyl}-5-(4-phenoxyphenyl)-7H-pyrrolo[2,3-d]pyrimidin-4-ylamine

Example 87

4-Amino-5-(4-phenoxyphenyl)-7H-pyrrolo[2,3-d]pyrimidin-7-yl-N-(N-ethylpyrrolidin-2-yl)methylacetamide

Example 88

4-Amino-5-(4-phenoxyphenyl)-7H-pyrrolo[2,3-d]pyrimidin-7-yl-N-(2-piperidinoethyl)acetamide

Example 89

4-Amino-5-(4-phenoxyphenyl)-7H-pyrrolo[2,3-d]pyrimidin-7-yl-N-[3-(pyrrolidin-1-yl)propyl]acetamide

Example 90

(R)-4-Amino-5-(4-phenoxyphenyl)-7H-pyrrolo[2,3-d]pyrimidin-7-yl-N-(N-ethylpyrrolidin-2-yl)methylacetamide

Example 91

4-Amino-5-(4-phenoxyphenyl)-7H-pyrrolo[2,3-d]pyrimidin-7-yl-N-(2-morpholinoethyl)acetamide

Example 92

4-Amino-5-(4-phenoxyphenyl)-7H-pyrrolo[2,3-d]pyrimidin-7-yl-N-[3-(N,N-diethylamino)propyl]acetamide

Example 93

4-Amino-5-(4-phenoxyphenyl)-7H-pyrrolo[2,3-d]pyrimidin-7-yl-N-[3-(N,N-dimethylamino)-2,2-dimethylpropyl]acetamide

Example 94

7-[2-(4-Ethoxycarbonylpiperazin-1-yl)-2-oxoethyl]-5-(4-phenoxyphenyl)-7H-pyrrolo[2,3-d]pyrimidin-4-ylamine

Example 95

4-Amino-S—(4-phenoxyphenyl)-7H-pyrrolo[2,3-d]pyrimidin-7-yl-N-[2,2-bis(hydroxymethyl)butyl]acetamide

Example 96

4-Amino-5-(4-phenoxyphenyl)-7H-pyrrolo[2,3-d]pyrimidin-7-yl-N-[3-(2-pyrrolidinon-1-yl)propyl]acetamide

Example 97

4-Amino-5-(4-phenoxyphenyl)-7H-pyrrolo[2,3-d]pyrimidin-7-yl-N-(3-piperidinopropyl)acetamide

Example 98

4-Amino-5-(4-phenoxyphenyl)-7H-pyrrolo[2,3-d]pyrimidin-7-yl-N-(3-morpholinopropyl)acetamide

Example 99

4-Amino-5-(4-phenoxyphenyl)-7H-pyrrolo[2,3-d]pyrimidin-7-yl-N-(3-hydroxy-1-methylprop-2-yl)acetamide

Example 100

4-Amino-5-(4-phenoxyphenyl)-7H-pyrrolo[2,3-d]pyrimidin-7-yl-N-[3-(N-3-aminopropyl,N-methyl)aminopropyl]acetamide

Example 101

4-Amino-5-(4-phenoxyphenyl)-7H-pyrrolo[2,3-d]pyrimidin-7-yl-N-[N-bis(2-aminoethyl)aminoethyl]acetamide

TABLE 2

| Amine Number | Name | Phase | RT/min Product |
|---|---|---|---|
| 102 | Ethanolamine | Both | 3.68 |
| 103 | dl-2-Amino-1-propanol | Both | 3.78 |
| 104 | 1-Amino-2-propanol | Both | 3.81 |
| 105 | 2-Methoxyethylamine | Both | 4.08 |
| 106 | 3-Amino-1-propanol | Both | 3.73 |
| 107 | (S)-(+)-2-Amino-1-propanol | Both | 3.78 |
| 108 | (R)-(−)-1-Amino-2-propanol | Liquid | 3.81 |
| 109 | N,N-Dimethylethylenediamine | Liquid | 3.50 |
| 110 | (+/−)-2-Amino-1-butanol | Both | 3.96 |
| 111 | 1-Amino-2-butanol | Both | 4.06 |
| 112 | 3-Amino-1,2-propanediol | Both | 3.52 |
| 113 | (S)-3-Amino-1,2-propanediol | Both | 3.53 |
| 114 | (R)-3-Amino-1,2-propanediol | Both | 3.53 |
| 115 | N,N-Dimethyl-1,3-propanediamine | Liquid | 3.47 |
| 116 | N2,N2-Dimethyl-1,2-propanediamine | Liquid | 3.57 |
| 117 | 1-Dimethylamino-2-propylamine | Liquid | 3.67 |
| 118 | Dl-2-Amino-3-methyl-1-butanol | Both | 4.15 |
| 119 | 2-(2-Aminoethylamino)ethanol | Liquid | 3.40 |
| 120 | 2-Amino-2-methyl-1-propanol | Both | 4.17 |
| 121 | 2-Amino-2-methyl-1,3-propanediol | Both | 3.76 |
| 122 | 2-(2-Aminoethoxy)ethanol | Liquid | 3.71 |
| 123 | 1-(2-Aminoethyl)-pyrrolidine | Both | 3.61 |
| 124 | 1-Amino-1-cyclopentane methanol | Both | 4.48 |
| 125 | 2-Aminocyclohexanol | Both | 4.19 |
| 126 | N,N-Diethylethylenediamine | Both | 3.68 |
| 127 | N-(3-Hydroxypropyl)-ethylenediamine | Both | 3.42 |
| 128 | 2-((2-Aminoethyl)thio)ethanol | Liquid | 3.94 |
| 129 | 2-(2-Aminoethyl)pyridine | Liquid | 4.13 |
| 130 | 3-(2-Aminoethyl)pyridine | Both | 4.05 |
| 131 | N-(3-Aminopropyl)-imidazole | Liquid | 3.58 |
| 132 | 2-(2-Aminoethylamino)-1-methylpyrrolidine | Both | 3.56 |
| 133 | 2-(Aminomethyl)-1-ethyl-pyrrolidine | Both | 3.70 |
| 134 | 1-(2-Aminoethyl)piperidine | Both | 3.70 |
| 135 | 1-Pyrrolidinepropanamine | Both | 3.60 |
| 136 | (R)-(+)-2-Aminomethyl-1-ethylpyrrolidine | Both | 3.70 |
| 137 | 4-(2-Aminoethyl)-morpholine | Both | 3.63 |
| 138 | 3-Diethylaminopropylamine | Both | 3.64 |
| 139 | N,N-Dimethylneopentanediamine | Both | 3.68 |

TABLE 2-continued

| Amine Number | Name | Phase | RT/min Product |
|---|---|---|---|
| 140 | 2-(Aminomethyl)-2-ethyl-1,3-propanediol | Both | 3.94 |
| 141 | 1-(3-Aminopropyl)-2-pyrrolidinone | Liquid | 3.91 |
| 142 | 1-Piperidinepropylamine | Both | 3.70 |
| 143 | 4-(3-Aminopropyl)-morpholine | Liquid | 3.53 |
| 144 | N,N-Diisopropylethylenediamine | Liquid | 3.86 |
| 145 | N,N-Bis(3-aminopropyl)-methylamine | Solid | 3.21 |
| 146 | Tris(2-aminoethyl)amine | Both | 3.17 |

Example 102

1-[4-Amino-5-(4-phenoxyphenyl)-7H-pyrrolo[2,3-d]pyrimidin-7-yl]-N-hydroxyethyl)propanamide

Example 103

1-[4-Amino-5-(4-phenoxyphenyl)-7H-pyrrolo[2,3-d]pyrimidin-7-yl]-N-(1-hydroxyprop-2-yl)propanamide

Example 104

1-[4-Amino-5-(4-phenoxyphenyl)-7H-pyrrolo[2,3-d]pyrimidin-7-yl]-N-(2-hydroxypropyl)propanamide

Example 105

1-[4-Amino-5-(4-phenoxyphenyl)-7H-pyrrolo[2,3-d]pyrimidin-7-yl]-N-(2-methoxyethyl)propanamide

Example 106

1-[4-Amino-5-(4-phenoxyphenyl)-7H-pyrrolo[2,3-d]pyrimidin-7-yl]-N-(3-hydroxypropyl)propanamide

Example 107

(S)-1-[4-Amino-5-(4-phenoxyphenyl)-7H-pyrrolo[2,3-d]pyrimidin-7-yl]-N-(1-hydroxyprop-2-yl)propanamide

Example 108

(R)-1-[4-Amino-5-(4-phenoxyphenyl)-7H-pyrrolo[2,3-d]pyrimidin-7-yl]-N-(2-hydroxypropyl)propanamide

Example 109

1-[4-Amino-5-(4-phenoxyphenyl)-7H-pyrrolo[2,3-d]
pyrimidin-7-yl]-N-[2-(N,N-dimethylamino)ethyl]
propanamide

Example 110

1-[4-Amino-5-(4-phenoxyphenyl)-7H-pyrrolo[2,3-d]
pyrimidin-7-yl]-N-(1-hydroxybut-2-yl)propanamide

Example 111

1-[4-Amino-5-(4-phenoxyphenyl)-7H-pyrrolo[2,3-d]
pyrimidin-7-yl]-N-(2-hydroxybutyl)propanamide

Example 112

1-[4-Amino-5-(4-phenoxyphenyl)-7H-pyrrolo[2,3-d]
pyrimidin-7-yl]-N-(2,3-dihydroxypropyl)
propanamide

Example 113

(S)-1-[4-Amino-5-(4-phenoxyphenyl)-7H-pyrrolo[2,
3-d]pyrimidin-7-yl]-N-(2,3-dihydroxypropyl)
propanamide

Example 114

(R)-1-[4-Amino-5-(4-phenoxyphenyl)-7H-pyrrolo[2,
3-d]pyrimidin-7-yl]-N-(2,3-dihydroxypropyl)
propanamide

Example 115

1-[4-Amino-5-(4-phenoxyphenyl)-7H-pyrrolo[2,3-d]
pyrimidin-7-yl]-N-[3-(N,N-dimethylamino)propyl]
propanamide

Example 116

1-[4-Amino-5-(4-phenoxyphenyl)-7H-pyrrolo[2,3-d]
pyrimidin-7-yl]-N-[2-(N,N-dimethylamino)propyl]
propanamide

Example 117

1-[4-Amino-5-(4-phenoxyphenyl)-7H-pyrrolo[2,3-d]
pyrimidin-7-yl]-N-[1-(N,N-dimethylamino)prop-2-
yl]propanamide

Example 118

1-[4-Amino-5-(4-phenoxyphenyl)-7H-pyrrolo[2,3-d]
pyrimidin-7-yl]-N-(1-hydroxy-3-methylbut-2-yl)
propanamide

Example 119

1-[4-Amino-5-(4-phenoxyphenyl)-7H-pyrrolo[2,3-d]
pyrimidin-7-yl]-N-[2-(2-hydroxyethylamino)ethyl]
propanamide

Example 120

1-[4-Amino-5-(4-phenoxyphenyl)-7H-pyrrolo[2,3-d]
pyrimidin-7-yl]-N-(1-hydroxy-2-methylprop-2-yl)
propanamide

Example 121

1-[4-Amino-5-(4-phenoxyphenyl)-7H-pyrrolo[2,3-d]
pyrimidin-7-yl]-N-(1,3-dihydroxy-2-methylprop-2-
yl)propanamide

Example 122

1-[4-Amino-5-(4-phenoxyphenyl)-7H-pyrrolo[2,3-d]
pyrimidin-7-yl]-N-[2-(2-hydroxyethoxy)ethyl]
propanamide

Example 123

1-[4-Amino-5-(4-phenoxyphenyl)-7H-pyrrolo[2,3-d]
pyrimidin-7-yl]-N-[2-(pyrrolidin-1-yl)ethyl]
propanamide

Example 124

1-[4-Amino-5-(4-phenoxyphenyl)-7H-pyrrolo[2,3-d]
pyrimidin-7-yl]-N-[1-(hydroxymethyl)cyclopentyl]
propanamide

Example 125

1-[4-Amino-5-(4-phenoxyphenyl)-7H-pyrrolo[2,3-d]
pyrimidin-7-yl]-N-(2-hydroxycyclohexyl)
propanamide

Example 126

1-[4-Amino-5-(4-phenoxyphenyl)-7H-pyrrolo[2,3-d]
pyrimidin-7-yl]-N-[2-(N,N-diethylamino)ethyl]
propanamide

Example 127

1-[4-Amino-5-(4-phenoxyphenyl)-7H-pyrrolo[2,3-d]
pyrimidin-7-yl]-N-[2-(3-hydroxypropylamino)ethyl]
propanamide

Example 128

1-[4-Amino-5-(4-phenoxyphenyl)-7H-pyrrolo[2,3-d]
pyrimidin-7-yl]-N-[2-(2-hydroxyethylthio)ethyl]
propanamide

Example 129

1-[4-Amino-5-(4-phenoxyphenyl)-7H-pyrrolo[2,3-d]
pyrimidin-7-yl]-N-[2-(pyrid-2-yl)ethyl]propanamide

Example 130

1-[4-Amino-5-(4-phenoxyphenyl)-7H-pyrrolo[2,3-d]
pyrimidin-7-yl]-N-[2-(pyrid-3-yl)ethyl]propanamide

Example 131

1-[4-Amino-5-(4-phenoxyphenyl)-7H-pyrrolo[2,3-d]
pyrimidin-7-yl]-N-[3-(imidazol-1-yl)propyl]
propanamide

Example 132

1-[4-Amino-5-(4-phenoxyphenyl)-7H-pyrrolo[2,3-d]
pyrimidin-7-yl]-N-[2-(N-methylpyrrolidin-2-yl)
ethyl]propanamide

Example 133

1-[4-Amino-5-(4-phenoxyphenyl)-7H-pyrrolo[2,3-d]
pyrimidin-7-yl]-N-[(N-ethylpyrrolidin-2-yl)methyl]
propanamide

Example 134

1-[4-Amino-5-(4-phenoxyphenyl)-7H-pyrrolo[2,3-d]
pyrimidin-7-yl]-N-(2-piperidinoethyl)propanamide

Example 135

1-[4-Amino-5-(4-phenoxyphenyl)-7H-pyrrolo[2,3-d]
pyrimidin-7-yl]-N-[3-(pyrrolidin-1-yl)propyl]
propanamide

Example 136

(R)-1-[4-Amino-5-(4-phenoxyphenyl)-7H-pyrrolo[2,
3-d]pyrimidin-7-yl]-N-[(N-ethylpyrrolidin-2-yl)
methyl]propanamide

Example 137

1-[4-Amino-5-(4-phenoxyphenyl)-7H-pyrrolo[2,3-d]
pyrimidin-7-yl]-N-(2-morpholinoethyl)propanamide

Example 138

1-[4-Amino-5-(4-phenoxyphenyl)-7H-pyrrolo[2,3-d]
pyrimidin-7-yl]-N-[3-(N,N-diethylamino)propyl]
propanamide

Example 139

1-[4-Amino-5-(4-phenoxyphenyl)-7H-pyrrolo[2,3-d]
pyrimidin-7-yl]-N-[3-(N,N-dimethylamino)-2,2-
dimethylpropyl]propanamide

Example 140

1-[4-Amino-5-(4-phenoxyphenyl)-7H-pyrrolo[2,3-d]
pyrimidin-7-yl]-N-[2,2-bis(hydroxymethyl)butyl]
propanamide

Example 141

1-[4-Amino-5-(4-phenoxyphenyl)-7H-pyrrolo[2,3-d]
pyrimidin-7-yl]-N-[3-(2-pyrrolidinon-1-yl)propyl]
propanamide

Example 142

1-[4-Amino-5-(4-phenoxyphenyl)-7H-pyrrolo[2,3-d]
pyrimidin-7-yl]-N-(3-piperidinopropyl)propanamide

Example 143

1-[4-Amino-5-(4-phenoxyphenyl)-7H-pyrrolo[2,3-d]
pyrimidin-7-yl]-N-(3-morpholinopropyl)
propanamide

Example 144

1-[4-Amino-5-(4-phenoxyphenyl)-7H-pyrrolo[2,3-d]
pyrimidin-7-yl]-N-[2-(N,N-di-isopropylamino)ethyl]
propanamide

Example 145

1-[Amino-5-(4-phenoxyphenyl)-7H-pyrrolo[2,3-d]
pyrimidin-7-yl]-N-[3-(N-3-aminopropyl,N-methyl)
aminopropyl]propanamide

Example 146

1-[4-Amino-5-(4-phenoxyphenyl)-7H-pyrrolo[2,3-d]
pyrimidin-7-yl]-N-[N-bis(2-aminoethyl)aminoethyl]
propanamide

Example 147

2-[4-amino-5-(4-phenoxyphenyl)-7H-pyrrolo[2,3-d]
pyrimidin-7-yl]-butyrolactone a) 4-Amino-5-(4-phenoxyphenyl)-7H-pyrrolo[2,3-d]
pyrimidine (1.0 g) was added to a mixture of sodium
hydride (0.158 g of a 60% dispersion in mineral oil) in
dimethyl formamide (70 ml) with stirring under nitrogen
at 0° C. The mixture was stirred at 0° C. for 1 hour and then α-bromo-γ-butyrolactone (0.60 g) in dimethylformamide (6 ml) was added dropwise with stirring at 0° C. The mixture was stirred at ambient temperature for 18 hours and then quenched with water (100 ml). The mixture was extracted with ethyl acetate. The combined extracts were dried and evaporated to give 2-[4-amino-5-(4-phenoxyphenyl)-7H-pyrrolo[2,3-d]pyrimidin-7-yl]-butyrolactone as an oil which was used directly in b).

b) N,N-Dimethylethylenediamine (5.0 ml) was added to a mixture of the product from a) (1.2 g) and pyridin-2-one (50 mg) in toluene (100 ml). The mixture was heated to 100° C. for 2 hours and then evaporated to dryness under reduced pressure. The residue was suspended in ethyl acetate and washed with water. The organic extracts were then extracted with 5M hydrochloric acid (3×50 ml) and the acidic extracts were washed with ethyl acetate then basified with 6M sodium hydroxide solution at 0° C. and then back extracted with ethyl acetate and then dichloromethane. The combined organic extracts were dried, filtered and evaporated to give an oil which was crystallised from ethyl acetate/ether to give 2-[4-amino-5-(4-phenoxyphenyl)-7H-pyrrolo[2,3-d]pyrimidin-7-yl]-4-hydroxy—N-[2-dimethylamino)ethyl]utyramide, m.p. 178–179° C.

Example 148

Ethyl 2-[4-Amino-5-(4-phenoxyphenyl)-7H-pyrrolo[2,3-d]pyrimidin-7-yl]propionate

Sodium hydride (120 mg, of a 60% dispersion in mineral oil) was added to a mixture of 4-amino-5-(4-phenoxyphenyl)-7H-pyrrolo[2,3-d]pyrimidine (906 mg) in dry dimethyformamide (30 ml) and the mixture was stirred under nitrogen for 30 minutes at ambient temperature. A solution of ethyl 2-bromopropionate (543 mg) in dry DMF (10 ml) was added dropwise via a syringe over 10 minutes. The mixture was stirred at ambient temperature for 2 hours and then left for 18 hours. The mixture was evaporated under vacuum and the residue was washed with water to give a solid which was triturated with ether and filtered to give ethyl 2-[4-amino-5-(4-phenoxyphenyl)-7H-pyrrolo[2,3-d]pyrimidin-7-yl]propionate, m.p. 139–140° C.

Example 149

N-(2-Dimethylaminoethyl)-2-[4-amino-5-(4-phenoxyphenyl)-7H-pyrrolo[2,3-d]pyrimidin-7-yl)propionamide A mixture of ethyl 2-[4-amino-5-(4-phenoxyphenyl)-7H-pyrrolo[2,3-d]pyrimidin-7-yl]propionate (425 mg), N,N-dimethylethylenediamine (2 ml) and methanol (20 ml) was boiled under reflux for 18 hours with the exclusion of carbon dioxide. The mixture was cooled and filtered, the filtrate was diluted with water (50 ml) and stirred with ether. The mixture was left standing for 18 hours and the solid which precipitated was collected by filtration, washed with water and then ether and dried to give N-(2-dimethylaminoethyl)-2-[4-amino-5-(4-phenoxyphenyl)-7H-pyrrolo[2,3-d]pyrimidin-7-yl)propionamide, m.p. 163–164° C.

Example 150

Ethyl 2-[4-Amino-5-(4-phenoxyphenyl)-7H-pyrrolo[2,3-d]pyrimidin-7-yl]acetate

A mixture of 4-amino-5-(4-phenoxyphenyl)-7H-pyrrolo[2,3-d]pyrimidine (906 mg), sodium hydride (120 mg, of a 60% dispersion in mineral oil) and dry dimethylformamide (30 ml) was stirred at ambient temperature under nitrogen for 30 minutes. Ethyl bromoacetate (0.5 g) in dimethylformamide (10 ml) was added over 5 minutes at 0–5° C. with stirring. The mixture was stirred for 30 minutes at ambient temperature and then allowed to stand for 18 hours. The mixture was evaporated under vacuum and the residue was triturated with water and ether. The solid obtained was collected by filtration, washed with water and then with ether to give ethyl 2-[4-amino-5-(4-phenoxyphenyl)-7H-pyrrolo[2,3-d]pyrimidin-7-yl]acetate, m.p. 161–161.3° C.

Examples 151–156

General Method

Ethyl 2-[4-amino-5-(4-phenoxyphenyl)-7H-pyrrolo[2,3-d]pyrimidin-7-yl]acetate (194 mg) was heated at 62° C. and stirred with 10 molar equivalents of the appropriate amine as listed below in methanol (12 ml) for 18 hours to give after work up the following compounds:

Example 151

N-[2-Hydroxyethyl-1,1-di(hydroxymethyl)]-2-[4-amino-5-(4-phenoxyphenyl)-7H-pyrrolo[2,3-d]pyrimidin-7-yl]acetamide m.p. 222–223° C. with decomposition, from 2-hydroxyethyl-1,1-di(hydroxymethyl)ethylamine.

Example 152

N-[2-(Piperazin-1-yl)ethyl]-2-[4-amino-5-[4-phenoxyphenyl)-7H-pyrrolo[2,3-d]-pyrimidin-7-yl]acetamide, m.p. 138–140° C., from 2-(piperazin-1-yl)ethylamine.

Example 153

N-(2-Morpholinoethyl)-2-[4-amino-5-(4-phenoxyphenyl)-7H-pyrrolo[2,3-d]pyrimidin-7-yl]acetamide m.p. 164–165° C., from 2-morpholinoethylamine.

Example 154

N-[3-(1-imidazol)propyl]-2-[4-amino-5-(4-phenoxyphenyl)-7H-pyrrolo[2,3-d]pyrimidin-7-yl]acetamide m.p. 170–171° C., from 3-(1-imidazolyl)propylamine.

Example 155

N-(N-Ethylpyrrolidin-2-ylmethyl)-2-[4-amino-5-(4-phenoxyphenyl)-7H-pyrrolo[2,3-d]-pyrimidin-7-yl]acetamide m.p. 122–122.5° C., from 1-(N-ethylpyrrolodin-2-yl)methyl-amine.

Example 156

N-[-2(2-hydroxyethoxy)ethyl]-2-[4-amino-5-(4-phenoxyphenyl)-7H-pyrrolo[2,3-d]-pyrimidin-7-yl]acetamide m.p. 145–147° C., from 2-(2-hydroxyethoxy)ethylamine.

Example 157

2-[4-Amino-5-(4-phenoxyphenyl)-7H-pyrrolo[2,3-d]pyrimidin-7-yl]propionic Acid

A mixture of ethyl 2-[4-amino-5-(4-phenoxyphenyl)-7H-pyrrolo[2,3-d]pyrimidin-7-yl]propionate (201 mg), aqueous potassium hydroxide solution (4 ml of 2M solution) and methanol (20 ml) was boiled under reflux for 1 hour. The mixture was concentrated under reduced pressure to around 5 ml and then diluted with water (30 ml). The mixture was hot filtered and filtrate was cooled and then acidified with dilute acetic acid until no further precipitation occurred. The mixture was heated on a hot plate until the gel which had been obtained became a finely divided solid. The solid was collected by filtration to give 2-[4-amino-5-(4-phenoxyphenyl)-7H-pyrrolo[2,3-d]pyrimidin-7-yl] propionic acid, m.p. 239.5–241° C.

Example 158

Ethyl 4-[4-Amido-5-(4-phenoxyphenyl)-7H-pyrrolo[2,3-d]pyrimidin-7-yl]butyrate

A mixture of 5-(4-phenoxyphenyl)-7H-pyrrolo[2,3-d]pyrimidin-4-ylamine (1.5 g) was dissolved in DMF (30 ml) and treated with sodium hydride (0.22 g of a 60% dispersion in mineral oil) and then with ethyl 4-bromobutyrate (1.08 g) in DMF (15 ml) in a similar manner to Example 95 to give ethyl 4-[4-amido-5-(4-phenoxyphenyl)-7H-pyrrolo[2,3-d]pyrimidin-7-yl]butyrate, m.p. 104–104.5° C.

Example 159

Ethyl 2-[4-Amino-5-(4-phenoxyphenyl)-7H-pyrrolo[2,3-d]pyrimidin-7-yl]carbox-amide In a similar manner to Example 97, 5-(4-phenoxyphenyl)-7H-pyrrolo[2,3-d]-pyrimidin-4-yl amine (1.0 g), sodium hydride (1.032 g of a 60% dispersion in mineral oil), 2-bromoacetamide (0.55 g) and dimethylformamide (50 ml) were reacted together to give after work-up a solid which was recrystallised from isopropanol to give ethyl 2-[4-amino-5-(4-phenoxyphenyl)-7H-pyrrolo[2,3-d]pyrimidin-7-yl]carbox-amide, m.p. 232–233° C.

Example 160

2-[4-Amino-5-(4-phenoxyphenyl)pyrrolo[2,3-d]pyrimidin-7-yl]-2-methylpropionamide 4-Amino-5-(4-phenoxyphenyl)-7H-pyrrolo[2,3-d]pyrimidine (200 mg) was dissolved in 1,3-dimethyl-3,4,5,6-tetrahydro-2-(1H)-pyrimidinone (1.5 ml) with stirring and sodium hydroxide (0.158 g) was added at ambient temperature and the mixture stirred for 15 minutes. 2-Bromo-2-methylpropanamide (0.5 g) was added and the mixture was stirred vigorously for 18 hours at ambient temperature under a water-free atmosphere, then further 2-bromo-2-methylpropanamide (0.15 g) was added and stirred for a further 24 hours. Water (3 ml) was added to the reaction mixture together with dilute hydrochloric acid (5M) to adjust the pH to 0. The suspension was added to water (60 ml) and the mixture left to stand for 18 hours at ambient temperature. The solid was collected by filtration, washed well with water and dried under high vacuum at 50° C. The solid was purified by preparative HPLC (reverse phase). Appropriate fractions were collected and combined and extracted with dichloromethane. Evaporation of the dichloromethane gave 2-[4-amino-5-(4-phenoxyphenyl)pyrrolo[2,3-d]pyrimidin-7-yl]-2-methylpropionamide, m.p. 227–228° C.

Example 161

4-[4-Amino-5-(4-phenoxyphenyl)-7H-pyrrolo[2,3-d]pyrimin-7-yl]-N-(2-dimethylaminoethyl)butyramide A mixture of ethyl 4-[4-amino-5-(4-phenoxyphenyl)-7H-pyrrolo[2,3-d]pyrimin-7-yl]butyrate (100 mg) in 30 ml methanol was heated under reflux with 0.6 ml 2-dimethylaminoethylamine for 18 hours. The mixture was evaporated under reduced pressure and the residue was heated with 2-dimethylaminoethylamine (10 ml) on a steam bath for 18 hours. Excess amine was removed under reduced pressure. Water was added to the residue and the mixture filtered to give 4-[4-amino-5-(4-phenoxyphenyl)-7H-pyrrolo[2,3-d]pyrimin-7-yl]-N-(2-dimethylaminoethyl)butyramide.

Examples 162, 163 and 164 were prepared in a similar manner to Example 108 by reacting the same ester with the appropriate amine listed.

Example 165

4-[4-Amino-5-(4-phenoxyphenyl)-7H-pyrrolo[2,3-d]pyrimin-7-yl]-N-[3-(1-imidazolyl)propyl]butyramide
From 3-(1-Imidazolyl)propylamine

Example 166

4-[4-Amino-5-(4-phenoxyphenyl)-7H-pyrrolo[2,3-d]pyrimin-7-yl]-N-(2-morpholinoethyl)butyramide
From 2-morpholinoethylamine

Example 167

4-[4-Amino-5-(4-phenoxyphenyl)-7H-pyrrolo[2,3-d]pyrimin-7-yl]-N-(3-morpholinopropyl)butyramide
From 3-morpholinopropylamine.

Preparation of Starting Materials a) Tert-butylamine (15 ml) was added with stirring to a solution of 2-bromo-4'-phenoxyacetophenone (12.7 g, prepared by bromination of 4'-phenoxyacetophenone according to Tetrahedron Letters, 1993, 34, 3177) in propan-2-ol and the mixture heated at 80° C. for 3 hours. The mixture was cooled to 0C and concentrated hydrochloric acid (10 ml) added. The suspension was stirred at ambient temperature for 18 hours and the solid collected by filtration to give 4'-phenoxy-2-(tert-butylamino)acetophenone hydrochloride (3.75 g), m.p. 210–212° C.

1) 4'-Phenoxy-2-(tert-butylamino)acetophenone hydrochloride (3.75 g) was added in one portion to sodium ethoxide (prepared by dissolving sodium (93 mg) in ethanol (50 ml)) and the mixture was stirred at 40° C. for 30 minutes under nitrogen.

2) In a separate flask sodium (331 mg) was dissolved in ethanol (50 ml) and malononitrile (858 mg) was added. The solution was stirred at ambient temperature for 5 minutes and then to this solution was added the solution of 4'-phenoxy-2-(tert-butylamino)acetophenone obtained in part (1) in one portion excluding the precipitated sodium chloride. The resultant mixture was heated at 50° C. for 3 hours and then at 80° C. for 2 hours. The solvent was removed under reduced pressure and the resultant oil was partitioned between water and ethyl acetate. The organic phase was separated, dried and evaporated to give a black solid. This solid was dissolved in hot ethanol and triturated with water, filtered and dried to give 2-amino-3-cyano-4-(4-phenoxyphenyl)-1-(tert-butyl)pyrrole.

b) A mixture of 2-amino-3-cyano-4-(4-phenoxyphenyl)-1-(tert-butyl)pyrrole (1.9 g), formamide (30 ml) and 4-dimethylaminopyridine (10 mg) was heated at 180° C. for 6 hours. The mixture was cooled to ambient temperature and water was added to precipitate a dark solid. The solid was collected by filtration, washed with water, then boiled up in ethanol and the insoluble material collected by hot filtration and dried. The solid was purified by preparative HPLC on a silica column using dichloromethane/propan-2-ol/ethanol, 98:1:1 as the mobile phase to give 7-tert-butyl-5-(4-phenoxyphenyl)-7H-pyrrolo[2,3-d]pyrimidin-4-ylamine (4-amino-5-(4-phenoxyphenyl)-7-(tert-butyl)pyrrolo[2,3-d]pyrimidine), m.p. 157–158° C. 1H NMR (d6 DMSO) δ 8.15 (1H, s), 7.50–7.35 (4H, m), 7.30 (1H, s), 7.15 (1H, t), 7.10 (4H, m), 6.05 (2H, brs), 1.75 (9H, s).

c) A mixture of 4-amino-5-(4-phenoxyphenyl)-7-(tert-butyl) pyrrolo[2,3-d]-pyrimidine (5.8 g), glacial acetic acid (55 ml) and hydrobromic acid (55 ml of a 48% solution) (5.8 g), glacial acetic acid (55 ml) and hydrobromic acid (55 ml of a 48% solution) cool and a solid was collected by filtration. This solid was washed with methanol and then with ether to give 4-amino-5-(4-phenoxyphenyl)-7H-pyrrolo[2,3-d]-pyrimidine hydrobromide, m.p. 288–292° C. The hydrobromide salt was converted into the free base by warming with dilute sodium hydroxide solution (100 ml of 5% w/v solution) and ethanol (60 ml) with stirring and removing the ethanol by distillation. The mixture was cooled and the solid was collected by filtration and washed well with water to give 5-(4-phenoxyphenyl)-7H-pyrrolo[2,3-d]pyrimidin-4-ylamine, m.p. 272° C.

Example 168

7-Cyclopentanesulphonyl-5-(4-phenoxyphenyl)-7H-pyrrolo[2,3-d]pyrimidin-4-ylamine Sodium hydride (0.132 g of a 60% dispersion in mineral oil) was added to a solution of 5-(4-phenoxyphenyl)-7H-pyrrolo[2,3-d]pyrimidin-4-ylamine (1.0 g) in dry dimethylformamide (30 ml) with stirring under nitrogen. The mixture was stirred for 30 minutes and then cyclopentanesulphonyl chloride (0.558 g, prepared as described in J.O.C.1952, 17, 1529–1533) in dry dimethylformamide (5 ml) was added dropwise. The mixture was allowed to stand for 72 hours and then evaporated under vacuum. The residue was triturated with water and filtered to give a solid which was washed well with water, then stirred with ethyl acetate then filtered. The filtrate was purified by flash column chromatography on silica using ethyl acetate as the mobile phase. Appropriate fractions were collected and evaporated to give 7-cyclopentanesulphonyl-5-(4-phenoxyphenyl)-7H-pyrrolo[2,3-d]pyrimidin-4-ylamine, m.p. 188–188.5° C.

Example 169

5-(4-Phenoxyphenyl)-7-(8-phthalimidooctyl)-7H-pyrrolo[2,3-d]pyrimidin-4-ylamine

Sodium hydride (120 mg of a 60% dispersion in mineral oil) was added to a solution of 5-(4-phenoxyphenyl)-7H-pyrrolo[2,3-d]pyrimidin-4-ylamine (906 mg) in dry dimethylformamide (30 ml) with stirring under nitrogen. The mixture was stirred for 30 minutes under nitrogen and then N-(8-bromooctyl)phthalimide (1.4 g) in dimethylformamide (5 ml) was added. The mixture was stirred at ambient temperature for 18 hours under nitrogen and then partitioned between water and ethyl acetate. The ethyl acetate layer was separated and purified by flash column chromatography using ethyl acetate as the mobile phase to give 5-(4-phenoxyphenyl)-7-(8-phthalimidooctyl)-7H-pyrrolo[2,3-d]pyrimidin-4-ylamine, m.p. 85–86° C.

Example 170

7-(8-Aminooctyl)-5-(4-phenoxyphenyl)-7H-pyrrolo[2,3-d]pyrimidin-4-ylamine Dihydrochloride Dihydrate A mixture of 5-(4-phenoxyphenyl)-7-(8-phthalimidooctyl)-7H-pyrrolo[2,3-d]pyrimidin-4-ylamine (1.0 g), hydrazine hydrate (1.0 ml) and ethanol (40 ml) was boiled under reflux for 2 hours with the exclusion of carbon dioxide. The mixture was cooled for 18 hours and a solid which precipitated was collected by filtration and discarded. The filtrate was evaporated under reduced pressure and the residue was dissolved in ethyl acetate, dried and then treated with a solution of concentrated hydrochloric acid in isopropanol dropwise until no further precipitation occurred. The mixture was left to stand overnight, then supernatent liquid was decanted off and the semi-solid residue was triturated with ethyl acetate to give 7-(8-aminooctyl)-5-(4-phenoxyphenyl)-7H-pyrrolo[2,3-d]pyrimidin-4-ylamine dihydrochloride dihydrate, m.p 120° C.

Example 171

N-{2-[4-Amino-5-(4-phenoxyphenyl)-7H-pyrrolo[2,3-d]pyrimidin-7-yl]ethyl}phthalimide In a similar manner to Example 468, but with additional heating at 90° C. for 3 hours, 5-(4-phenoxyphenyl)-7H-pyrrolo[2,3-d]pyrimidin-4-ylamine was reacted with 2-bromoethylphthalimide to give N-{2-[4-amino-5-(4-phenoxyphenyl)-7H-pyrrolo[2,3-d]pyrimidin-7-yl]ethyl}phthalimide, m.p. 111–112° C.

Example 172

7-(2-Aminoethyl)-5-(4-phenoxyphenyl)-7H-pyrrolo[2,3-d]pyrimidin-4-ylamine Hydrochloride In a similar manner to Example 469, the product from the previous example was treated with hydrazine hydrate to give 7-(2-aminoethyl)-5-(4-phenoxyphenyl)-7H-pyrrolo[2,3-d]pyrimidin-4-ylamine hydrochloride, m.p. 284–285° C.

Example 173

7-Isobutyryl-5-(4-phenoxyphenyl)-7H-pyrrolo[2,3-d]pyrimidin-4-ylamine

Isobutyryl chloride (1.8 g) was added dropwise to a mixture of 5-(4-phenoxyphenyl)-7H-pyrrolo[2,3-d]pyrimidin-4-ylamine (4.32 g), dry dimethyl-formamide (200 ml) and dry pyridine (2 ml) with stirring under nitrogen at 20° C. The mixture was stirred at ambient temperature for 1 hour and evaporated under vacuum. The residue was partitioned between water and ethyl acetate. The ethyl acetate was separated, dried and evaporated and the residue obtained was recrystallised from toluene to give 7-isobutyryl-5-(4-phenoxyphenyl)-7H-pyrrolo[2,3-d]pyrimidin-4-ylamine, m.p. 160.5–161° C.

Example 174

5-(4-Phenoxyphenyl)-7-(1,4-dioxaspiro[4,5]decan-8-yl)-7H-pyrrolo[2,3-d]pyrimidin-4-ylamine Sodium hydride (0.26 g of a 60% dispersion in mineral oil) was added to a mixture of 5-(4-phenoxyphenyl)-7H-pyrrolo[2,3-d]pyrimidin-4-ylamine (1.94 g) in dimethylformamide 950 ml) at ambient temperature with stirring. The mixture was stirred until the evolution of hydrogen ceased and then 8-tosyloxy-1,4-dioxaspiro[4,5]decane (2.0 g, prepared as described in U.S. Pat. No. 4,360,531 from 1,4-dioxaspiro[4,5]decan-8-one, (which was prepared according to J. Med. Chem. 1992, 22460) was added. The mixture was heated at 120° C. for 5 hours under nitrogen, cooled to ambient temperature, quenched with water and extracted with ethyl acetate to give a residue which was purified by flash column chromatography on silica using ethyl acetate followed by ethyl acetate containing increasing amounts of methanol up to 6% to give 5-(4-phenoxyphenyl)-7-(1,4-dioxaspiro[4,5]decan-8-yl)-7H-pyrrolo[2,3-d]pyrimidin-4-ylamine, m.p. 193–194° C.

Example 175

4-[4-Amino-5-(4-phenoxyphenyl)-7H-pyrrolo[2,3-d]pyrimidin-7-yl]cyclohexanone

The product from the previous example (500 mg), acetone (20 ml) and 3M hydrochloric acid (10 ml) was stirred under nitrogen at ambient temperature for 20 minutes. The mixture was then heated at 60° C. for 1 hour and then the acetone was removed under reduced pressure. The residue was basified with aqueous 5M sodium hydroxide solution and then extracted with ethyl acetate to give a solid which was triturated with diethyl ether and filtered to give 4-[4-amino-5-(4-phenoxyphenyl)-7H-pyrrolo[2,3-d]pyrimidin-7-yl]cyclohexanone, m.p. 252–254° C.

Example 176 and 177 cis-5-(4-Phenoxyphenyl)-7-(4-morpholinocyclohex-1-yl)-7H-pyrrolo[2,3-d]pyrimidin-4-ylamine, and trans-5-(4-Phenoxyphenyl)-7-(4-morpholinocyclohex-1-yl)-7H-pyrrolo[2,3-d]pyrimidin-4-ylamine Sodium triacetoxyborohydride (42 mg) and glacial acetic acid (18 mg) were added to the product from the previous example (120 mg) and morpholine (31 mg) in 1,2-dichloroethane. The mixture was stirred at 40° C. for 2 hours and then a further portion of morpholine (0.15 g) and sodium triacetoxyborohydride (0.21 g) were added. The mixture was stirred at ambient temperature for 20 hours then quenched with saturated aqueous bicarbonate solution. The mixture was filtered through an EMPORE® cartridge and the filtrate was extracted with 3M hydrochloric acid. The acidic extracts were basified with 5M sodium hydroxide solution and extracted with dichloromethane to give a residue which was purified by chromatography on silica to give cis-5-(4-phenoxyphenyl)-7-(4-morpholinocyclohex-1-yl)-7H-pyrrolo[2,3-d]pyrimidin-4-ylamine, and trans-5-(4-phenoxyphenyl)-7-(4-morpholinocyclohex-1-yl)-7H-pyrrolo[2,3-d]pyrimidin-4-ylamine.

Examples 178 and 179 cis-7-(4-N-Ethoxycarbonyl)piperazin-1-ylcyclohexyl)-5-(4-phenoxy-phenyl)-7H-pyrrolo[2,3-d]pyrimidin-4-ylamine and trans-7-(4-N-ethoxycarbonyl)-piperazin-1-ylcyclohexyl)-5-(4-phenoxyphenyl)-7H-pyrrolo[2,3-d]pyrimidin-4-ylamine In a similar manner to the previous Example, 4-[4-amino-5-(4-phenoxyphenyl)-7H-pyrrolo[2,3-d]pyrimidin-7-yl] cyclohexanone (0.4 g from 1.0 g of 40% pure material) and 1-ethoxycarbonyl-piperidine (158 mg) were reacted together in the presence of sodium triacetoxyborohydride (296 mg) in dichloromethane (15 ml) containing glacial acetic acid (60 mg) to give after workup and chromatography cis-7-(4-N-ethoxycarbonyl)piperazin-1-ylcyclohexyl)-5-(4-phenoxyphenyl)-7H-pyrrolo[2,3-d]pyrimidin-4-ylamine and trans-7-(4-N-ethoxycarbonyl)-piperazin-1-ylcyclohexyl)-5-(4-phenoxyphenyl)-7H-pyrrolo[2,3-d]pyrimidin-4-ylamine.

Example 180

2-[4-Amino-5-(4-phenoxyphenyl)-7H-pyrrolo[2,3-d]pyrimidin-7-yl]pyridine-3-carbonitrile 5-(4-Phenoxyphenyl)-7H-pyrrolo[2,3-d]-pyrimidin-4-ylamine (906 mg) was reacted with 2-chloronicotinonitrile (510 mg) in the presence of sodium hydride (150 mg) in dimethylformamide (30 ml) at 100° C. for 5 hours to give 2-[4-amino-5-(4-phenoxyphenyl)-7H-pyrrolo[2,3-d]pyrimidin-7-yl]pyridine-3-carbonitrile, m.p. 242–242.5° C., after workup.

Example 181

7-[3-(Aminomethyl)pyrid-2-yl]-5-(4-phenoxyphenyl)-7H-pyrrolo[2,3-d]-pyrimidin-4-ylamine dimaleate The product from the previous example (468 mg), ethanol saturated with ammonia (200 ml) and Raney® nickel (2 ml) was shaken under hydrogen at a pressure of 26 bar at 80° C. for 6 hours and then left standing at ambient temperature for 68 hours. The mixture was filtered and the residue was washed well with ethanol. The filtrate was evaporated under reduced pressure and the residue was taken up in ethyl acetate and filtered. Maleic acid (135 mg) dissolved in ethyl acetate (20 ml) was added in portions to the filtrate until no further precipitation occurred. The mixture was warmed and decanted from a small residual amount of gum. The gum was further heated with ethyl acetate and decanted. The combined ethyl acetate extracts were cooled and the solid which precipitated was collected by filtration to give 7-[3-(aminomethyl)pyrid-2-yl]-5-(4-phenoxyphenyl)-7H-pyrrolo[2,3-d]-pyrimidin-4-ylamine dimaleate, m.p. 131–134° C.

Example 182

3-[4-Amino-5-(4-phenoxyphenyl)-7H-pyrrolo[2,3-d]pyrimidin-7-yl]-8-methyl-8-azabicyclo[3.2]octane Sodium hydride (168 mg, of a 60% dispersion in mineral oil) was added to a mixture of 5-(4-phenoxyphenyl)-7H-pyrrolo[2,3-d]pyrimidin-4-ylamine (770 mg, in dimethylformamide (30 ml). 3-Mesyloxy-8-methyl-8-azabicyclo[3.2.1]octane (900 mg, prepared as described in J.A.C.S. 1958, 80, 4679) in dimethylformamide (10 ml) was added under nitrogen with stirring. The mixture was warmed at 75° C. for 5 hours (and left standing at ambient temperature for 7 days). The solvent was removed under reduced pressure. Water was added to the residue and the mixture was extracted with ethyl acetate to give a residue which was purified by flash column chromatography on silica using ethyl acetate/methanol (50:50) as the mobile phase to remove starting material and then a mixture of ethyl acetate/methanol/triethylamine (5:5:1) as the mobile phase to elute the product. Appropriate fractions were combined and evaporated to give a solid which was triturated with ether and filtered to give 3-[4-amino-5-(4-phenoxyphenyl)-7H-pyrrolo[2,3-d]pyrimidin-7-yl]-8-methyl-8-azabicyclo[3.2.1] octane, m.p. 238–250° C.

Examples 183 and 184 cis-7-(N-Methylhomopiperazin-1-ylcyclohexyl)-5-(4-phenoxyphenyl)-7H-pyrrolo[2,3-d]prymidin-4-ylamine and trans 7-(N-Methylhomopiperazin-1-ylcyclohexyl)-5-(4-phenoxyphenyl)-7H-pyrrolo[2,3-d]prymidin-4-ylamine In a similar manner to Examples 176 and 177, 4-[4-amino-5-(4-phenoxyphenyl)-7H-pyrrolo[2,3-d]pyrimidin-7-yl]cyclohexanone (0.4 g from 1.0 g of a 40% pure material), N-methylhomopiperazine (114 mg), sodium triacetoxyborohydride (296 mg), glacial acetic acid (60 mg) and 1,2-dichloroethane (15 ml) were reacted together. After filtration, the filtrate was evaporated and the residue was purified by chromatography on silica to give cis-7-(N-methylhomopiperazin-1-ylcyclohexyl)-5-(4-phenoxyphenyl)-7H-pyrrolo[2,3-d]prymidin-4-ylamine and trans 7-(N-methylhomo-piperazin-1-ylcyclohexyl)-5-(4-phenoxyphenyl)-7H-pyrrolo[2,3-d]prymidin-4-ylamine.

Examples 185 and 186 cis 7-(N-Methylpiperazin-1-ylcyclohexyl)-5-(4-phenoxyphenyl)-7-pyrrolo[2,3-d]prymidin-4-ylamine and trans 7-(N-Methylpiperazin-1-ylcyclohexyl)-5-(4-phenoxy-phenyl)-7-pyrrolo[2,3-d]prymidin-4-ylamine In a similar manner to the previous Example, N-methylpiperazine (100 mg) was reacted with the same amounts of cyclohexanone derivative and other reagents to give cis 7-(N-methylpiperazin-1-ylcyclohexyl)-5-(4-phenoxyphenyl)-7-pyrrolo[2,3-d]prymidin-4-ylamine and trans 7-(N-methylpiperazin-1-ylcyclohexyl)-5-(4-phenoxyphenyl)-7-pyrrolo[2,3-d]prymidin-4-ylamine.

Example 187

3-[4-Amino-5-(4-phenoxyphenyl)-7H-pyrrolo[2,3-d]pyrimidin-7-yl]-cyclopentan-1-one A mixture of 3-[4-amino-5-(4-phenoxyphenyl)-7H-pyrrolo[2,3-d]pyrimidin-7-yl]-cyclopentan-1-ol (100 mg), activated manganese dioxide (500 mg) and dichloromethane (100 ml) was stirred at ambient temperature for 18 hours to give, after filtration, a solution of 3-[4-amino-5-(4-phenoxyphenyl)-7H-pyrrolo[2,3-d]pyrimidin-7-yl]-cyclopentan-1-one in dichloromethane which was used in the next Example.

Example 188 cis-7-(3-Morpholinocyclopent-1-yl)-5-(4-phenoxyphenyl)-7H-pyrrolo[2,3-d]pyrimidin-4-ylamine and trans-7-(3-Morpholinocyclopent-1-yl)-5-(4-phenoxyphenyl)-7H-pyrrolo[2,3-d]-pyrimidin-4-ylamine Morpholine (45 mg) was added to the solution obtained in the previous Example followed by sodium triacetoxyborohydride (151 mg) and glacial acetic acid (47 mg). The mixture was stirred at ambient temperature under nitrogen for 18 hours during which time the dichloromethane evaporated. Tetrahydrofuran (100 ml) was added and the mixture was stirred for a further 8 hours. The mixture was worked up to give cis-7-(3-morpholinocyclopent-1-yl)-5-(4-phenoxyphenyl)-7H-pyrrolo[2,3-d]pyrimidin-4-ylamine and trans-7-(3-morpholinocyclopent-1-yl)-5-(4-phenoxyphenyl)-7H-pyrrolo[2,3-d]-pyrimidin-4-ylamine.

Example 189

3-(4-Amino-5-(4-phenoxyphenyl)-7H-pyrrolo[2,3-d]pyrimidin-7-yl)cyclopentyl N-(2-morpholinoethyl)-carbamate Hydrochloride a) To a solution of 3-(4-Amino-5-(4-phenoxyphenyl)-7H-pyrrolo[2,3-d]pyrimidin-7-yl)cyclopentanol (20 mg) in dichloromethane (1 ml) at 0° C. was added N-methylmorpholine (7 ml) and the mixture stirred for 20 minutes. The cooling bath was removed and 4-nitrophenylchloroformate (12.5 mg) was added and the resulting mixture stirred overnight at ambient temperature. The mixture was diluted with dichloromethane, washed with water, saturated aqueous sodium bicarbonate solution and brine. The organic solution was dried over magnesium sulphate and evaporated to give crude product.

b) The crude product from a) in dichloromethane (2 ml) was added to 2-morpholinoethylamine (0.2 ml) and the mixture stirred overnight at ambient temperature. The mixture was diluted with ethyl acetate and washed with water and brine. The organics were dried, filtered and evaporated to give a crude product which was purified by preparative HPLC to give 3-(4-amino-5-(4-phenoxyphenyl)-7H-pyrrolo[2,3-d]pyrimidin-7-yl)cyclopentyl N-(2-morpholinoethyl)carbamate.

c) The product from b) was dissolved in ethyl acetate (2 ml) and hydrogen chloride gas was bubbled through the solution for 2 minutes. A precipitate formed and stirring was continued for a further 10 minutes. The solvent was evaporated and water added to dissolve the solid. Lyophilisation gave 3-(4-amino-5-(4-phenoxyphenyl)-7H-pyrrolo[2,3-d]pyrimidin-7-yl)cyclopentyl N-(2-morpholinoethyl)-carbamate hydrochloride as a solid.

Example 190

3-[4-Amino-5-(4-phenoxyphenyl)-7H-pyrrolo[2,3-d]pyrimidin-7-yl]cyclopentyl 2-aminoacetate Hydrochloride a) 3-[4-Amino-5-(4-phenoxyphenyl)-7H-pyrrolo[2,3-d]pyrimidin-7-yl]cyclopentanol (50 mg, 0.129 mmol) and N-tert-butoxycarbonyl glycine (34 mg, 0.194 mmol) was mixed in N,N-dimethylformamide (1 ml). 1-(3-Dimethylaminopropyl)-3-ethylcarbodiimide hydrochloride (31 mg, 0.155 mmol) and 4-dimethylamino pyridine (16 mg, 0.129 mmol) was added. The resulting mixture was stirred under nitrogen at ambient temperature for 24 hours. The reaction mixture was poured into ice water and extracted with ethyl acetate. The organic extracts were washed with brine, dried (MgSO4), filtered and evaporated. The solid was purified by flash column chromatography on silica using ethyl acetate as the mobile phase to give 3-[4-amino-5-(4-phenoxyphenyl)-7H-pyrrolo[2,3-d]pyrimidin-7-yl]cyclopentyl 2-[(tert-butoxycarbonyl)amino]acetate. The structure was confirmed by $^1$H NMR.

b) 3-[4-Amino-5-(4-phenoxyphenyl)-7H-pyrrolo[2,3-d]pyrimidin-7-yl]cyclopentyl 2-[(tert-butoxycarbonyl)amino]acetate (39 mg, 0.072 mmol) was dissolved in ethyl acetate (2.5 ml). Hydrogen chloride gas was passed through for 1 minute. The flask was capped and the solution stirred for additional 30 minutes. Diethyl ether was added and precipitate formed. The solid was collected by filtration to give 3-[4-amino-5-(4-phenoxyphenyl)-7H-pyrrolo[2,3-d]pyrimidin-7-yl]cyclopentyl 2-aminoacetate hydrochloride. The structure was confirmed by $^1$H NMR and LC/MS (MH$^+$=444).

Example 191

3-[4-Amino-5-(4-phenoxyphenyl)-7H-pyrrolo[2,3-d]pyrimidin-7-yl]cyclopentyl (2S)-2-amino-3-methylbutanoate Hydrochloride a) (2S)-1-[(tert-Butoxycarbonyl)amino]-2-methylbutanoic 2,5-dioxo-2,5-dihydro-1H-1-pyrrolecarboxylic anhydride (114 mg, 0.362 mmol) was added to a solution of 3-[4-amino-5-(4-phenoxyphenyl)-7H-pyrrolo[2,3-d]pyrimidin-7-yl]cyclopentanol (66 mg, 0.171 mmol) in dichloromethane (1 ml). The resulting mixture was stirred under nitrogen at ambient temperature for 24 hours. The reaction mixture was diluted with ethyl acetate and washed, dried ($MgSO_4$), filtered and evaporated. The solid was purified by flash column chromatography on silica using ethyl acetate as the mobile phase to give 3-[4-amino-5-(4-phenoxyphenyl)-7H-pyrrolo[2,3-d]pyrimidin-7-yl]cyclopentyl (2S)-2-[(tert-butoxycarbonyl)amino]-3-methylbutanoate. The structure was confirmed by $^1$H NMR and LC/MS ($MH^+$=586).

b) 3-[4-Amino-5-(4-phenoxyphenyl)-7H-pyrrolo[2,3-d]pyrimidin-7-yl]cyclopentyl (2S)-2-[(tert-butoxycarbonyl)amino]-3-methylbutanoate (35 mg, 0.060 mmol) was dissolved in ethyl acetate (2.5 ml). Hydrogen chloride gas was passed through for 5 minutes. The flask was capped and the solution stirred for additional 30 minutes. Diethyl ether was added and precipitate formed. The solid was collected by filtration to give 3-[4-amino-5-(4-phenoxyphenyl)-7H-pyrrolo[2,3-d]pyrimidin-7-yl]cyclopentyl (2S)-2-amino-3-methylbutanoate hydrochloride. The structure was confirmed by $^1$H NMR and LC/MS ($MH^+$=486).

Example 192

3-(4-Amino-5-(4-phenoxyphenyl)-7H-pyrrolo[2,3-d]pyrimidin-7-yl)cyclopentyl N-(2-morpholinoethyl)carbamate Hydrochloride a) N-Methylmorpholine (0.007 ml, 0.062 mmol) was added dropwise to solution of 4-nitrophenyl chloroformate (12.5 mg, 0.062 mmol) in dichloromethane (1 ml) with stirring under nitrogen at 0° C. After 20 minutes, the ice-water bath was removed and the mixture was allowed to warm up to ambient temperature. 3-[4-amino-5-(4-phenoxyphenyl)-7H-pyrrolo[2,3-d]pyrimidin-7-yl]cyclopentanol (20 mg, 0.052 mmol) was added to the mixture and the resulting solution was stirred for 24 hours. The reaction mixture was diluted with dichloromethane and washed with water, saturated sodium bicarbonate, and brine. The organic layer was dried ($MgSO_4$), filtered and evaporated to give 3-[4-amino-5-(4-phenoxyphenyl)-7H-pyrrolo[2,3-d]pyrimidin-7-yl]cyclopentyl (4-nitrophenyl) carbonate. The structure was confirmed by $^1$H NMR.

b) 3-[4-Amino-5-(4-phenoxyphenyl)-7H-pyrrolo[2,3-d]pyrimidin-7-yl]cyclopentyl (4-nitrophenyl) carbonate (0.052 mmol) in dichloromethane (1 ml) was added to 2-morpholinoethylamine (0.2 ml). The resulting mixture was stirred under nitrogen at ambient temperature for 24 hours. The reaction mixture was diluted with ethyl acetate and washed, dried ($MgSO_4$), filtered and evaporated. The solid was purified by preparative HPLC to give 3-[4-amino-5-(4-phenoxyphenyl)-7H-pyrrolo[2,3-d]pyrimidin-7-yl]cyclopentyl N-(2-morpholinoethyl)carbamate. The structure was confirmed by $^1$H NMR and LC/MS ($MH^+$=543).

c) 3-[4-Amino-5-(4-phenoxyphenyl)-7H-pyrrolo[2,3-d]pyrimidin-7-yl]cyclopentyl N-(2-morpholinoethyl)carbamate (10 mg, 0.018 mmol) was dissolved in ethyl acetate (2.5 ml). Hydrogen chloride gas was passed through for 2 minutes, and a precipitate formed. The flask was capped and the solution stirred for additional 10 minutes.

The solid was collected by filtration to give 3-(4-amino-5-(4-phenoxyphenyl)-7H-pyrrolo[2,3-d]pyrimidin-7-yl)cyclopentyl N-(2-morpholinoethyl)carbamate hydrochloride. The structure was confirmed by $^1$H NMR and LC/MS ($MH^+$=543).

Preparation of Starting Materials a) Tert-butylamine (15 ml) was added with stirring to a solution of 2-bromo-4'-phenoxyacetophenone (12.7 g, prepared by bromination of 4'-phenoxyacetophenone according to Tetrahedron Letters, 1993, 34, 3177) in propan-2-ol and the mixture heated at 80° C. for 3 hours. The mixture was cooled to 0° C. and concentrated hydrochloric acid (10 ml) added. The suspension was stirred at ambient temperature for 18 hours and the solid collected by filtration to give 4'-phenoxy-2-(tert-butylamino)acetophenone hydrochloride (3.75 g), m.p. 210–212° C. butylamino)acetophenone hydrochloride (3.75 g), m.p. 210–212° C.

b) (1) 4'-Phenoxy-2-(tert-butylamino)acetophenone hydrochloride (3.75 g) was added ethanol (50 ml)) and the mixture was stirred at 40° C. for 30 minutes under nitrogen.

(2) In a separate flask sodium (331 mg) was dissolved in ethanol (50 ml) and malononitrile (858 mg) was added. The solution was stirred at ambient temperature for 5 minutes and then to this solution was added the solution of 4'-phenoxy-2-(tert-butylamino)acetophenone obtained in part (1) in one portion excluding the precipitated sodium chloride. The resultant mixture was heated at 50° C. for 3 hours and then at 80° C. for 2 hours. The solvent was removed under reduced pressure and the resultant oil was partitioned between water and ethyl acetate. The organic phase was separated, dried and evaporated to give a black solid. This solid was dissolved in hot ethanol and triturated with water, filtered and dried to give 2-amino-3-cyano-4-(4-phenoxyphenyl)-1-(tert-butyl)pyrrole.

c) A mixture of 2-amino-3-cyano-4-(4-phenoxyphenyl)-1-(tert-butyl)pyrrole (1.9 g), formamide (30 ml) and 4-dimethylaminopyridine (10 mg) was heated at 180° C. for 6 hours. The mixture was cooled to ambient temperature and water was added to precipitate a dark solid. The solid was collected by filtration, washed with water, then boiled up in ethanol and the insoluble material collected by hot filtration and dried. The solid was purified by preparative HPLC on a silica column using dichloromethane/propan-2-ol/ethanol, 98:1:1 as the mobile phase to give 7-tert-butyl-5-(4-phenoxyphenyl)-7H-pyrrolo[2,3-d]pyrimidin-4-ylamine (4-amino-5-(4-phenoxyphenyl)-7-(tert-butyl)pyrrolo[2,3-d]pyrimidine), m.p. 157–158° C. 1H NMR (d6 DMSO) δ 8.15 (1H, s), 7.50–7.35 (4H, m), 7.30 (1H, s), 7.15 (1H, t), 7.10 (4H, m), 6.05 (2H, brs), 1.75 (9H, s).

d) A mixture of 4-amino-5-(4-phenoxyphenyl)-7-(tert-butyl)pyrrolo[2,3-d]-pyrimidine (5.8 g), glacial acetic acid (55 ml) and hydrobromic acid (55 ml of a 48% solution) was boiled under reflux for 18 hours under nitrogen. The mixture was allowed to cool and a solid was collected by filtration. This solid was washed with methanol and then with ether to give 4-amino-5-(4-phenoxyphenyl)-7H-pyrrolo[2,3-d]-pyrimidine hydrobromide, m.p. 288–292° C. The hydrobromide salt was converted into the free base by warming with dilute sodium hydroxide solution (100 ml of 5% w/v solution) and ethanol (60 ml) with stirring and removing the ethanol by distillation. The mixture was cooled and the solid was collected by filtration and washed well with water to give 5-(4-phenoxyphenyl)-7H-pyrrolo[2,3-d]pyrimidin-4-ylamine.

e) A mixture of 5-(4-phenoxyphenyl)-7H-pyrrolo[2,3-d] pyrimidin-4-ylamine (600 mg) and tetrakis (triphenylphosphine) palladium (40 ml) and dry dimethyl sulphoxide (30 ml) was stirred under nitrogen in an ice/water bath and then a solution of cyclopentadiene monoepoxide (200 mg) in tetrahydrofuran (10 ml) was added via syringe under nitrogen at 0° C. The mixture was stirred at ambient temperature (with exclusion of light) for 66 hours and then the tetrahydrofuran was removed under reduced pressure and water was added to the residue. The mixture was allowed to stand for 18 hours and then extracted with ethyl acetate to give a residue which was purified by flash column chromatography on silica using ethyl acetate/industrial methylated spirit (9:1) as the mobile phase to give 4-[4-amino-5-(4-phenoxyphenyl)-7H-pyrrolo[2,3-d]pyrimidin-7-yl]-cyclopent-2-enol, as an oil. The structure was confirmed by $^1$Hnmr and mass spectra.

f) 4-[4-Amino-5-(4-phenoxyphenyl)-7H-pyrrolo[2,3-d] pyrimidin-7-yl]cyclopent-2-enol (110 mg) was hydrogenated in ethanol (20 ml) with gaseous hydrogen at atmospheric pressure using 10% palladium on charcoal (50 mg) as the catalyst. The catalyst was removed by filtration and the filtrate was evaporated to give 3-[4-amino-5-(4-phenoxyphenyl)-7H-pyrrolo[2,3-d]pyrimidin-7-yl] cyclopentanol, as an oil. The structure was confirmed by 1H nmr and mass spectra.

Example 193 cis-5-(4-Phenoxyphenyl)-7-(4-pyrrolidinocyclohex-1-yl)-7H-pyrrolo[2,3-d]pyrimidin-4-ylamine
trans-5-(4-Phenoxyphenyl)-7-(4-pyrrolidinocyclohex-1-yl)-7H-pyrrolo[2,3-d]pyrimidin-4-ylamine To a stirred suspension of 4-[4-amino-5-(4-phenoxyphenyl)-7H-pyrrolo[2,3-d]pyrimidinyl-7-yl] cyclohexanone (2.34 g, 5.9 mmol) in 1,2 dichloroethane (250 mL) was added, under an atmosphere of nitrogen, pyrrolidine (1.25 g, 17.6 mmol) and glacial acetic acid (1.00 mL, 17.6 mmol), and the resultant mixture stirred for 70 hours. The mixture was temperature for 30 minutes. Sodium triacetoxyborohydride (1.87 g, 8.8 mmol) was added in one portion, and the resultant mixture stirred for 70 hours. The mixture was extracted with 2M aqueous hydrochloric acid (2×200 mL). The combined extracts were washed with dichloromethane (300 mL), made basic with 12.5M aqueous sodium hydroxide solution, and extracted with dichloromethane (3×200 mL). The combined extracts were dried over sodium sulphate, and purified by chromatography with a Biotage 40S column using ethyl acetate/triethylamine (95:5) and ethyl acetate/triethylamine/methanol (85:10:5) as a mobile phase to yield Cis-5-(4-phenoxyphenyl)-7-(4-pyrrolidinocyclohex-1-yl)-7H-pyrrolo[2,3-d]pyrimidin-4-ylamine as an off-white solid (0.65 g, 1.4 mmol), melting point 101–104 deg. C., LC/MS Hypersil BDS c18 (10×2.1 mm) 0.1M ammoniumacetate/acetonitrile, 10–1005 acetonitrile in 8 min.): MH$^+$454 t$_r$=3.56 minutes and Trans-5-(4-phenoxyphenyl)-7-(4-pyrrolidinocyclohex-1-yl)-7H-pyrrolo[2,3-d]pyrimidin-4-ylamine as an off-white solid (0.93 g, 2.1 mmol), melting point 183–185 deg. C., LC/MS (Hypersil BDS c18 (100×2.1 mm) 0.1M ammoniumacetate/ acetonitrile, 10–100% acetonitrile in 8 min.): MH$^+$454, t$_r$=3.68 minutes Example 194 cis-5-(4-Phenoxyphenyl)-7-(4-piperidinocyclohex-1-yl)-7H-pyrrolo[2,3-d]pyrimidin-4-ylamine Hydrochloride
trans-5-(4-Phenoxyphenyl)-7-(4-piperidinocyclohex-1-yl)-7H-pyrrolo[2,3-d]pyrimidin-4-ylamine To a stirred suspension of 4-[4-amino-5-(4-phenoxyphenyl)-7H-pyrrolo[2,3-d]pyrimin-7-yl] cyclohexanone (2.34 g, 5.9 mmol) in 1,2 dichloroethane (250 mL) was d]pyrimin-7-yl]cyclohexanone (2.34 g, 5.9 mmol) in 1,2 dichloroethane (250 mL) was added, under an atmosphere of nitrogen, piperidine (1.50 g, 17.6 mmol) and glacial acetic acid (1.00 mL, 17.6 mmol), and the resultant mixture stirred at room temperature for 30 minutes. Sodium triacetoxyborohydride (1.87 g, 8.8 mmol) was added in one portion, and the resultant mixture stirred for 70 hours. The mixture was extracted with 2M aqueous hydrochloric acid (2×200 mL). The combined extracts were washed with dichloromethane (300 mL), made basic with 12.5M aqueous sodium hydroxide solution, and extracted with dichloromethane (3×200 mL). The combined extracts were dried over sodium sulphate, and purified by chromatography with a Biotage 40S column using ethyl acetate/triethylamine (95:5) as a mobile phase to yield Cis-5-(4-phenoxyphenyl)-7-(4-piperidinocyclohex-1-yl)-7H-pyrrolo[2,3-d]pyrimidin-4-ylamine (0.23 g) as a clear oil., LC/MS:ypersil BDS c18 (100×2.1 mm) 0.1M ammoniumacetate/acetonitrile, 10–100% acetonitrile in 8 min.) MH+468 t$_r$=3.67 minutes and Trans-5-(4-phenoxyphenyl)-7-(4-piperidinocyclohex-1-yl)-7H-pyrrolo[2,3-d]pyrimidin-4-ylamine as an off-white solid (193 mg, 0.4 mmol), melting point 192–195 deg. C., LC/MS: Hypersil BDS c18 (100×2.1 mm) 0.1M ammoniumacetate/acetonitrile, 10–100% acetonitrile in 8 min.) MH$^+$468 t$_r$=3.71 minutes.

Example 195

Cis-5-(4-phenoxyphenyl)-7-(4-piperidinocyclohex-1-yl)-7H-pyrrolo[2,3-d]pyrimidin-4-ylamine was dissolved in ethyl acetate (50 mL), diluted with diethyl ether (50 mL) and treated with a 1 M solution of hydrogen chloride in diethyl ether until no further precipitation occurred. The resultant solid was collected and re-crystallised from absolute ethanol to give Cis-5-(4-phenoxyphenyl)-7-(4-piperidinocyclohex-1-yl)-7H-pyrrolo[2,3-d]pyrimidin-4-ylamine hydrochloride as a colourless solid (75 mg, 0.2 mmol) melting point 185–189 deg. C.

Example 196

Trans-7-(4-Dimethylaminocyclohexyl)-5-(4-phenoxyphenyl)-7H-pyrrolo[2,3-d]pyrimidin-4-ylamine
cis-7-(4-Dimethylaminocyclohexyl)-5-(4-phenoxyphenyl)-7H-pyrrolo[2,3-d]pyrimidin-4-ylamine To a stirred solution of 4-[4-amino-5-(4-phenoxyphenyl)-7H-pyrrolo[2,3-d]pyrimin-7-yl]cyclohexanone (3.24 g, 8.1 mmol) in dichloromethane (1000 mL) was d]pyrimin-7-yl] cyclohexanone (3.24 g, 8.1 mmol) in dichloromethane (1000 mL) was added, under an atmosphere of nitrogen, N-methylpiperazine (1.20 g, 12.0 mmol) and glacial acetic acid (0.69 mL, 12.0 mmol), and the resultant solution stirred at room temperature for 10 minutes. Sodium triacetoxyborohydride (1.70 g, 8.0 mmol) was added in one portion, and the resultant solution stirred for 70 hours. The solution repeated on the same scale and the resultant solution stirred for 70 hours. The solution was extracted with 2M aqueous hydrochloric acid (2×300 mL). The combined extracts were washed with dichloromethane (300 mL), made basic with 880 aqueous ammonia solution, and extracted with ethyl acetate (3×250 mL). The combined extracts were washed with saturated aqueous sodium chloride solution, dried over sodium sulphate, and purified by chromatography with a Biotage 40M column using ethyl acetate/methanol/triethylamine (8:1:1) as a mobile phase to yield Cis-7-(4-dimethylaminocyclohexyl)-5-(4-phenoxyphenyl)-7H-pyrrolo[2,3-d]pyrimidin-4-ylamine as an off-white solid (220 mg, 0.5 mmol.) melting point 180–182 deg. C., LC/MS: Hypersil BDS c18 (100×2.1 mm) 0.1M ammoniumacetate/acetonitrile, 10–100% acetonitrile in 8 min.) MH$^+$428 t$_r$=3.43 minutes.

The column was flushed with ethyl acetate/methanol/triethylamine (4:1:1, 500 mL), and the solvent removed under reduced pressure. The residue was dissolved in dichloromethane (200 mL)and purified by chromatography with a Biotage 40M column using dichloromethane/methanol (9:1 to 7:3) to yield Trans-7-(4-dimethylaminocyclohexyl)-5-(4-phenoxyphenyl)-7H-pyrrolo[2,3-d]pyrimidin-4-ylamine as an off-white solid (320 mg, 0.75 mmol) melting point 207.5–210 deg. C., LC/MS: Hypersil BDS c18 (100×2.1 mm) 0.1M ammoniumacetate/acetonitrile, 10–100% acetonitrile in 8 min.) MH$^+$428 t$_r$=3.48 minutes.

R-(+)-4-[4-amino-5-(4-phenoxyphenyl)-7-(3-tetrahydrofuryl)-7H-pyrrolo[2,3-d]pyrimidine.

Example 197

4-{(S)-tetrahydrofuran-3-yl}toluenesulphonate

To a solution of (S)-3-hydroxytetrahydrofuran (2.0 g, 23 mmol) in pyridine (40 ml) at 0° C. was added tosylchloride portionwise (4.8 g, 25 mmol). The solution was stirred at 0° C. for 1 hr and then at room temperature overnight. The pyridine was evaporated in vacuo and the residue was partioned between EtOAc and saturated aqueous citric acid (200 ml each). The aqueous layer was extracted with EtOAc (2×200 ml) and the combined organics were dried (sodium sulphate), filtered and evaporated to leave an oil (4.5 g, 85%). $^1$H NMR (CDCl$_3$, 250 MHz): 7.78 (2H, d), 7.35 (2H, d), 5.12 (1H, m), 3.76–3.93 (4H, m), 2.45 (3H, s,), 2.01–2.20 (2H, m).

To a stirred suspension of 4-amino-5-(4-phenoxyphenyl)-7H-pyrrolo[2,3-d]pyrimidine (4.83 g, 16 mmol) in N,N-dimethylformamide (80 mL), under an d]pyrimidine (4.83 g, 16 mmol) in N,N-dimethylformamide (80 mL), under an atmosphere of nitrogen, was added 60% sodium hydride in mineral oil (0.75 g, 19 mmol), and the mixture stirred at room temperature for 30 minutes. The resultant dark solution was treated with a solution of 4-{(S)-tetrahydrofuran-3-yl}toluenesulphonate (4.20 g, 18 mmol) in N,N-dimethylformamide (20 mL) in 2 mL aliquots. The resultant solution was stirred at room temperature for 30 minutes, then at 95 deg. C. for 18 hours. The solution was allowed to cool to ambient temperature, then poured onto ice/water (200 mL). The aqueous was extracted with ethyl acetate (3×200 mL). The combined organic extracts were washed with water (4×150 mL), dried over sodium sulphate, and the solvent was removed under reduced pressure. The residue was warmed with dichloromethane (1000 mL) until a solution was obtained, cooled to ambient temperature, and purified by chromatography with a Biotage 40M column using ethyl acetate/triethylamine (95:5), then ethyl acetate/triethylamine/methanol (90:5:5) as a mobile phase, to yield R-(+)-4-[4-amino-5-(4-phenoxyphenyl)-7-(3-tetrahydrofuryl)-7H-pyrrolo[2,3-d]pyrimidine as an off-white solid (4.35 g, 12 mmol) melting point 165–166 deg. C., LC/MS: Hypersil BDS c18 (100×2.1 mm) 0.1M ammoniumacetate/acetonitrile, 10–100% acetonitrile in 8 min.) MH$^+$373 t$_r$=4.44 minutes. [ ]$_D$+20.5±0.6 (dichloromethane, 22.6 deg. C.)

Example 198

5-(4-Phenoxyphenyl)-7-(4-piperidyl)-7H-pyrrolo[2,3-d]pyrimidin-4-ylamine

N-tert-Butoxycarbonylpiperidinol

To a solution of N-tert-butoxycarbonylpiperidone (10.0 g, 50 mmol) in MeOH (100 ml) at 0° C. was added sodium borohydride (1.9 g, 50 mmol) portionwise. Stir at 0° C. for 1 hr and then at room temperature for 20 hr. Quench with 2N NaOH (20 ml), evaporate solvent and partition residue between ethylacetate and water (100 ml each). Extract the aqueous layer with ethylacetate (3×100 ml) and wash the combined organic layers with brine and water (1×100 ml each). Dry (Na$_2$SO$_4$), filter and concentrate to leave N-tert-butoxycarbonylpiperidinol as a colourless oil (10.5 g, 100%). R$_f$ in 20% EtOAc/hexane=0.05 (KMnO$_4$ dip). IR (thin film): 3428, 2939, 1693 cm$^{-1}$ Example 199 tert-Butyl 4-[(4-Methylphenyl)sulfonyl]oxy-1-piperidinecarboxylate

To a solution of N-tert-butoxycarbonylpiperidinol (10.5 g, 0.052 mol) in pyridine (150 ml) at 0° C. under nitrogen was added tosylchloride (9.94 g, 0.052 mol) portionwise. Stir at 0° C. for 2 hr. Warm to room temperature and stir at room temperature overnight. Evaporate the solvent and partition between citric acid solution (1M, 100 ml) and ethylacetate (200 ml). Extract acidic layer with ethylacetate (1×100 ml) and wash combined organics with citric acid solution (1M, 2×100 ml), brine (100 ml) and water (100 ml). Dry (Na$_2$SO$_4$), filter and evaporate to leave an oil which was purifed by flash column chromatography using 10% EtOAc/cyclohexane then 15% EtOAc/cyclohexane to give in F 30–68 tert-butyl 4-[(4-methylphenyl)sulfonyl]oxy-1-piperidinecarboxylate as a white solid (11.0 g, 60%) Rf in 20% EtOAc/cyclohexane=0.17 $^1$H NMR (CDCl$_3$, 250 MHz): δ 7.79 (2H, d), 7.34 (2H, d), 4.67 (1H, m), 3.58 (2H, m), 3.27 (2H, m), 2.45 (3H, s), 1.59–1.83 (4H, m), 1.43 (9H, s).

Example 200 tert-Butyl 4-[4-Amino-5-(4-phenoxyphenyl)-7H-pyrrolo[2,3-d]pyrimidin-7-yl]-1-piperidinecarboxylate To a solution of 4-amino-5-(4-phenoxyphenyl)-7H-pyrrolo[2,3-d]pyrimidine (2.0 g, 6.6 mmol) in dry DMF (100 ml) under nitrogen at 0° C. was added NaH (0.264 g, 60% dispersion, 6.6 mmol) and the reaction mixture warmed to room temperature and stirred for 1 hr. Tert-butyl 4-[(4-methylphenyl)sulfonyl]oxy-1-piperidinecarboxylate (2.34 g, 6.6 mmol) was added and the resulting solution heated at 95° C. for 72 hr. The reaction was quenched by careful addition of water (150 ml). Extract with EtOAc (3×100 ml) and wash with water (4×100 ml) and brine (2×100 ml). The organic solution was dried ($Na_2SO_4$), filtered and evaporated to leave a solid which was adsorbed onto silica and purified by flash silica gel column chromatography using EtOAc then 5% MeOH/EtOAc as eluent to give in F 13–22 tert-butyl4-[4-amino-5-(4-phenoxyphenyl)-7H-pyrrolo[2,3-d]pyrimidin-7-yl]-1-piperidinecarboxylate (1.0 g, 31%) as a white solid, m.pt. 168.5–169.5° C. $R_f$ in 10% EtOAc/MeOH=0.4. $^1$H NMR ($d_6$ DMSO, 250 MHz): δ 8.14 (1H, s), 7.38–7.49 (5H, m), 7.07–7.23 (5H, m), 6.14 (2H, bs), 4.76 (1H, m), 4.11 (2H, m), 2.93 (2H, m), 1.92–2.02 (4H, m), 1.43 (9H, s). Mass spec. $C_{28}H_{31}O_3N_5$ (485.2430). IR (KBr disc): 3059, 1695, 1588, 1235 $cm^{-1}$.

Example 201

5-(4-Phenoxyphenyl)-7-(4-piperidyl)-7H-pyrrolo[2,3-d]pyrimidin-4-ylamine

To a solution of tert-butyl 4-[4-amino-5-(4-phenoxyphenyl)-7H-pyrrolo[2,3-d]pyrimidin-7-yl]-1-piperidinecarboxylate (0.69 g, 1.4 mmol) in dry $CH_2Cl_2$ (25 ml) at 0° C. was added TFA (5 ml). The solution was stirred at room temperature for 20 hr and the solvent evaporated. NaOH solution (5N, 10 ml) was added and the resulting slurry was extracted with EtOAc (3×50 ml). Wash with brine (1×50 ml). Dry, filter and concentrate to leave a solid which was triturated with diethylether and filtered to leave 5-(4-phenoxyphenyl)-7-(4-piperidyl)-7H-pyrrolo[2,3-d]pyrimidin-4-ylamine (433258) as a white solid (500 mg, 91%). M.pt 209–211° C. $R_f$ in 1:1 EtOAc : MeOH=0.1. $^1$H NMR ($d_6$ DMSO, 250 MHz) 8.13 (1H, s), 7.36–7.48 (4H, m), 7.29 (1H, s), 7.04–7.16 (5H, m), 5.80 (2H, bs), 4.64 (1H, m), 3.10 (2H, m), 2.80 (1H, bs), 2.67 (2H, m), 1.94 (4H, m). Mass spec. $C_{23}H_{23}ON_5$ (385.1902). IR (KBr disc): 3278, 1620, 1585, 1490, 1245 $cm^{-1}$.

Example 202

5-(4-Phenoxyphenyl)-7-(4-piperidyl)-7H-pyrrolo[2,3-d]pyrimidin-4-ylamine Dihydrochloride To 5-(4-phenoxyphenyl)-7-(4-piperidyl)-7H-pyrrolo[2,3-d]pyrimidin-4-ylamine (433258) (200 mg) in EtOAc/MeOH (15 ml, 1:1) was added ether.HCl solution (1.0 M, 3 ml). The resulting white precipitate was filtered under a stream of nitrogen and dried in vacuo for 6 hr to leave 5-(4-phenoxyphenyl)-7-(4-piperidyl)-7H-pyrrolo[2,3-d]pyrimidin-4-ylamine dihydrochloride (1.4 hydrate) as a white solid (120 mg), m.pt. 304° C (dec.). $^1$H NMR ($D_2O$, 250 MHz) 8.48(1H, s), 7.69 (1H, s), 7.50–7.58 (4H, m), 7.18–7.34 (5H, m), 5.16 (1H, m), 3.81 (2H, d), 3.46 (2H, m), 2.49 (4H, m).). IR (KBr disc): 3937, 1657, 1231 $cm^{-1}$.

Example 203 tert-Butyl 3-[4-Amino-5-(4-phenoxyphenyl)-7H-pyrrolo[2,3-d]pyrimidin-7-yl]-1-pyrrolidinecarboxylate
N-tert-Butoxycarbonylpyrrolidin-3-ol To a solution of pyrrolidin-3-ol (10.0 g, 0.11 mol) in dichloromethane (200 mL) was added triethylamine (22.2 g, 30.5 ml, 0.22 mol) followed by di-tert-butyldicarbonate (28.8 g, 0.13 mol) at 0° C. Warm to room temperature and stir at room temperature overnight. Quench with saturated aqueous citric acid (150 ml) and wash the organic layer with water, brine and water again (1×100 ml each). The organic layer was dried (sodium sulphate), filtered and evaporated to leave N-tert-butoxycarbonylpyrrolidin-3-ol (20.0g, 93% crude) as a golden oil.

Example 204 tert-Butyl 3-[(4-Methylphenyl)sulfonyl]oxy-1-pyrrolidinecarboxylate

To a solution of N-tert-butoxycarbonylpyrrolidin-3-ol (19.8 g, 0.106 mol) in pyridine (200 ml) at 0° C. under nitrogen was added tosyl chloride (22.3 g, 0.117 mol) portionwise. Stir at 0° C. for 2 hr, warm to room temperature and stir at room temperature overnight. The pyridine was evaporated in vacuo and the residue was partioned between EtOAc and saturated aqueous citric acid (200 ml each). The aqueous layer was extracted with EtOAc (2×200 ml) and the combined organics were dried (sodium sulphate), filtered and evaporated to leave an oil which was purified by flash silica gel column chromatography using 10% EtOAc/cyclohexane as eluent to give in F40–85 an oil. The oil was dissolved in a small volume of cyclohexane/diethylether (5:1, 50 ml), cooled and scratched with a spatula to induce crystallisation. The resulting solid was filtered to give tert-butyl 3-[(4-methylphenyl)sulfonyl]oxy-1-pyrrolidinecarboxylate (10.5 g, 29%) as a white solid. $R_f$ in EtOAc/cyclohexane=0.13. $^1$H NMR ($CDCl_3$, 250 MHz): 7.79 (2H, d), 7.35 (2H, d), 5.04 (1H, m), 3.43 (4H, m), 2.46 (3H, s), 2.03–2.20 (2H, bm), 1.43 (9H, s).

To a solution of 4-amino-5-(4-phenoxyphenyl)-7H-pyrrolo[2,3-d]pyrimidine (2.0 g, 6.6 mmol) in dry DMF (120 ml) under nitrogen at 0° C. was added NaH (0.264 g, 60% dispeersion, 6.6 mmol) and then reaction mixture warmed to room temperature and stirred for 1 hr. tert-butyl 3-[(4-methylphenyl)sulfonyl]oxy-1-pyrrolidinecarboxylate (2.25 g, 6.6 mmol) was added portionwise and the mixture heated at 95° C. for 72 hr. Quench with water and extract with EtOAc (4×100 ml). Wash the combined organic solutions with water (4×100 ml) and brine (2×100 ml). The organics were dried (sodium sulphate), filtered and evaporated to leave a solid which was dissolved in EtOAc/MeOH and adsorbed onto silica. Purification using flash silica gel column chromatography with 5% MeOH/EtOAc as eluent gave in F 17–25 tert-butyl 3-[4-amino-5-(4-phenoxyphenyl)-7H-pyrrolo[2,3-d]pyrimidin-7-yl]-1-pyrrolidinecarboxylate (1.0 g, 32%) as a white solid m.pt. 168–170° C. $R_f$ in 9:1 EtOAc: MeOH=0.46. $^1$H NMR ($d_6$ DMSO, 250 MHz): 8.17 (1H, s), 7.38–7.50 (5H, m), 6.19 (2H, bs), 5.31 (1H, m), 3.77 (1H, m), 3.42–3.60 (3H, m), 2.38 (2H, m), 1.40 (9H, s). Mass spec. 471.2250 ($C_{27}H_{29}O_3N_5$) IR (KBr disc): 3130, 1683, 1585, 1404, 1245 $cm^{-1}$.

Example 205

5-(4-Phenoxyphenyl)-7-(3-pyrrolidinyl) -7H-pyrrolo[2,3-d]pyrimidin-4-ylamine

To a solution of tert-butyl 3-[4-amino-5-(4-phenoxyphenyl)-7H-pyrrolo[2,3-d]pyrimidin-7-yl]-1-pyrrolidinecarboxylate (0.8 g, 1.7 mmol) in dichloromethane (25 ml) at 0° C. was added trifluoroacetic acid (5 ml). The reaction mixture was warmed to room temperature and stirred at room temperature for 20 hr. The solvent was evaporated and dilute NaOH added (5N, 10 ml). The resulting residue solution was extracted with EtOAc (3×50 ml) and the combined organics were washed with brine (1×75 ml). The organic solution was dried (sodium sulphate), filtered and evaporated in vacuo to leave 5-(4-phenoxyphenyl)-7-(3-pyrrolidinyl) -7H-pyrrolo[2,3-d]pyrimidin-4-ylamine as a white solid (0.5 g, 79%) m.pt. 182–184° C. $R_f$ in 1:1 EtOAc : MeOH=0.15. $^1$H NMR ($d_6$ DMSO, 250 MHz): 8.14 (1H, s), 7.37–7.50 (5H, m), 7.05–7.18 (5H, m), 6.14 (2H, bs), 5.23 (1H, m), 3.09–3.27 (2H, m), 2.83–2.98 (2H, m), 2.19–2.33 (1H, m), 1.88–2.01 (1H, m). Mass spec. 371.1758 ($C_{22}H_2ON_5$). IR (KBr disc): 3106, 1585, 1489, 1232 cm$^{-1}$.

Example 206

5-(4-Phenoxyphenyl)-7-(3-pyrrolidinyl)-7H-pyrrolo[2,3-d]pyrimidin-4-ylamine Dihydrochloride To a solution of 5-(4-phenoxyphenyl)-7-(3-pyrrolidinyl)-7H-pyrrolo[2,3-d]pyrimidin-4-ylamine (200 mg) in EtOAc/MeOH (2:1, 20 ml) was added ether.HCl (1.0 M, 3 ml) and the resulting precipitate was filtered under nitrogen to give 5-(4-phenoxyphenyl)-7-(3-pyrrolidinyl)-7H-pyrrolo[2,3-d]pyrimidin-4-ylamine dihydrochloride (0.4 hydrate) as a white solid (190 mg) m.pt. 298° C. (dec.). IR (KBr disc): 2909, 1658, 1249 cm$^{-1}$.

Example 207

7-Perhydro-1-pyrrolizinyl-5-(4-phenoxyphenyl)-7H-pyrrolo[2,3,d]pyrimidin-4-amine dihydrochloride Salt a) Perhydro-1-pyrrolizinol Prepared as described by Schnekenburger J, Briet E, Arch. Pharm. (Wienheim) 310, 152–160 (1977).

b) Perhydro-1-pyrrolizinyl Methanesulfonate

A mixture of perhydro-1-pyrrolizinol (0.5 g, 3.94 mmol) and triethylamine (0.60 g, 5.91 mmol) in dichloromethane (10 ml) was stirred at 0° C. under an atmosphere of nitrogen. Methanesulfonyl chloride (0.68 g, 5.91 mmol) was added, then the mixture was allowed to warm to ambient temperature and stirred for 8 hours. Saturated aqueous ammonium chloride (10 ml), dichloromethane (25 ml) and saturated aqueous sodium bicarboante (10 ml) were added. The organic layer was dried over magnesium sulfate filtered and the filtrate evaporated under reduced pressure to give a residue. Purification of the material by flash chromatography on silica gel using heptane/ethyl acetate (1:3) as an eluent yielded perhydro-l-pyrrolizinyl methanesulfonate (0.54 g): $^1$H NMR (DMSO-$d_6$, 400 MHz) δ 4.96 (m, 1H), 3.61 (m, 1H), 2.9–3.3 (m, 6H), 2.35 (m, 1H), 1.55–2.25 (m, 6H).

c) 7-Perhydro-1-pyrrolizinyl-5-(4-phenoxyphenyl)-7H-pyrrolo[2,3,d]pyrimidin-4-amine Dihydrochloride Salt A mixture of 5-(4-phenoxyphenyl)-7H-pyrrolo[2,3-d]pyrimidin-4-amine (0.49 g, 1.62 mmol) and 60% sodium hydride in oil (100 mg, 2.43 mmol) in DMF was stirred at ambient temperature for 15 minutes under an atmosphere of nitrogen. The mixture was heated at 100° C. for 18 hours then cooled to ambient temperature. Additional 60% sodium hydride in oil (100 mg, 2.43 mmol) was added and heating continued for another 2 hours. The mixture was cooled to ambient temperature and the solvents removed under reduced pressure. The residue was partitioned between water (10 ml) and dichloromethane (30 ml). The organic layer was dried over magnesium sulfate, filtered and the solvent was removed from the filtrate under reduced pressure. The resulting residue was purified by preparative C-18 RP HPLC to give 150 mg of white solid which was dissolved in ethyl acetate (10 ml) and treated with 1 N hydrogen chloride in diethyl ether to give 7-perhydro-1-pyrrolizinyl-5-(4-phenoxyphenyl)-7H-pyrrolo[2,3,d]pyrimidin-4-amine dihydrochloride salt as a white solid: $^1$H NMR (DMSO-$d_6$, 400 MHz) δ 8.52 (s, 1H), 7.95 (s, 1H), 7.02–7.58 (m, 1H), 5.38 (m, 1H0, 4.40 (m, 1H), 1.9–3.9 (m, 10H); (Hypersil HS C18, 5 µm, 100 A, 250×4.6 mm; 25–100% acetonitrile-0.1 M ammonium acetate over 10 min, 1 ml/min) t$_r$=7.62 min; MS: MH$^+$412.

Example 208

7-(2-Methylperhydrocyclopenta[c]pyrrol-5-yl)-5-(4-phenoxyphenyl)-7H-25 pyrrolo[2,3-d]pyrimidin-4-amine Dihydrochloride Salt a) 2-Methylperhydrocyclopenta[c]pyrrol-5-ol Prepared as described by Bohme H, Setiz G, Arch. Pharm. (Wienheim) 301, 341 (1968).

b) 4-Chloro-5-iodo-7-(2-methylperhydrocyclopenta[c]pyrrol-5-yl)-7H-pyrrolo[2,3-d]pyrimidine A mixture of 4-chloro-5-iodo-7H-pyrrolo[2,3-d]pyrimidine (0.38 g, 1.36 mmol), 2-methylperhydrocyclopenta[c]pyrrol-5-ol (0.23 g, 1.63 mmol) and triphenylphosphine (0.71 g, 2.72 mmol) in tetrahydrofuran (20 mL) was treated with diethylazodicarboxylate (0.474 g, 2.72 mmol) and stirred for 2 hours at ambient temperature. The solvent was removed under reduced pressure and the residue was partitioned between dichloromethane (30 ml) and water (10 ml). The organic layer was washed with saturated aqueous sodium chloride (10 ml) then dried over magnesium sulfate then filtered and the filtrate evaporated under reduced pressure to give a residue. The residue was purified by flash chromatography on silica using dichloromethane/methanol (8:2) as mobile phase to yield 4-chloro-5-iodo-7-(2-methylperhydrocyclopenta[c]pyrrol-5-yl)-7H-pyrrolo[2,3-d]pyrimidine (0.25 g): $^1$H NMR (DMSO-$d_6$, 400 MHz) δ 8.62 (s, 1H), 7.44 (s, 1H), 7.26 (s, 2H), 5.36 (m, 1H), 2.88 (m, 2H), 2.68 (m, 2H), 2.43 (m, 2H), 2.36 (s, 3H), 2.06–2.02 (m, 4H); TLC (dichloromethane/methanol 8:2) R$_f$ =0.29; RP-HPLC (Hypersil HS C18, 5 µm, 100 A, 250×4.6 mm; 25–100% acetonitrile-0.1 M ammonium acetate over 10 min, 1 ml/min) t$_r$=6.50 min; MS: MH$^+$403.

c) 7-(2-Methylperhydrocyclopenta[c]pyrrol-5-yl)-5-(4-phenoxyphenyl)-7H-pyrrolo[2,3-d]pyrimidin-4-amine Dihydrochloride Salt A mixture of 4-chloro-5-iodo-7-(2-methylperhydrocyclopenta[c]pyrrol-5-yl)-7H-pyrrolo[2,3-d]pyrimidine (0.25 g, 0.622 mmol), 4-phenoxyphenyl boronic acid (0.16 g, 0.746 mmol), tetrakis(triphenylphosphine)palladium (0.043 g, 0.037 mmol) and sodium carbonate (0.172 g, 1.62 mmol) was heated in a mixture of ethylene glycol dimethyl ether (8 mL) and water (4 mL) at 90° C. for 18 hours under an atmosphere of nitrogen. The mixture was allowed to cool to ambient temperature and solvents were removed under reduced pressure. The residue was partitioned between water (10 mL) and dichloromethane (30 ml) The layers were separated and the organic solution was dried over magnesium sulfate, filtered and the filtrate concentrated to a residue under reduced pressure (0.354 g). The material was dissolved in 1,4-dioxane (10 ml) and concentrated (28%) ammonium hydroxide (10 ml). The mixture was heated in a sealed tube at 120° C. for 20 hours then cooled to ambient temperature. The solvents were evaporated under reduced pressure then purified by flash column chromatography on silica using dichloromethane/methanol 7:3) as an eluent to give 7-(2-methylperhydrocyclopenta [c]pyrrol-5-yl)-5-(4-phenoxyphenyl)-7H-pyrrolo[2,3-d]pyrimidin-4-amine (0.05 g): $^1$H NMR (DMSO-$d_6$, 400 MHz) shows two sets of peaks due to the cis and trans isomers of the desired compound δ 10.6–10.8 (bs, 1H), 8.49 (s, 1H), 6.99–7.98 (m, 1H), 5.39 and 5.48 (m, 1H), 2–3.8 (m, 10H); PH 454098: RP-HPLC (Hypersil HS C18, 5 µm, 100 A, 250×4.6 mm; 25–1 00% acetonitrile-0.1 M ammonium acetate over 10 min, 1 ml/min) t$_r$=7.53 min; MS: MH$^+$426. The dihydrochloride salt of 7-(2-methylperhydrocyclopenta[c]pyrrol-5-yl)-5-(4-phenoxyphenyl)-7H-pyrrolo[2,3-d]pyrimidin-4-amine was prepared by dissolving the free base in 10 ml 1 N hydrochloric acid and lyophilizing.

Example 209 cis and trans-7-[4-(N-tert-Butoxycarbonyl-1S, 4S-2, 5-diaza[2.2.1]heptanyl)cyclohexyl]-5-(4-phenoxyphenyl)-7H-pyrrolo[2,3-d]pyrimidin-4-amine A suspension of 4-[4-amino-5-(4-phenoxyphenyl)-7H-pyrrolo[2,3-d]pyrimidin-7-yl]-1-cyclohexanone (0.67 g, 1.68 mmol) in dichloroethane (40 ml) was treated with tert-Butyl (1S, 4S)-(−) 2,5-diazabicyclo[2.2.1]heptane-2-carboxylate (1.0 g, 5.04 mmol) and glacial acetic acid (0.30 g, 5.04 mmol) at room temperature for 1 h. Subsequently, Na(OAc)$_3$BH (0.46 g, 2.17 mmol) was added and stirred for 8 days at 80° C. To the cooled reaction solution, a solution of NaHCO$_3$ (0.377 g, 10.08 mmol) in water (15 ml) washed with water and brine (3×100 ml each ). The aqueous layer was extracted with washed with water and brine (3×100 ml each ). The aqueous layer was extracted with CH$_2$Cl$_2$, the organic layers combined, dried (MgSO$_4$), filtered and concentrated. The solid was purified by flash silica gel column chromatography, (2 L, 6% MeOH in CH$_2$Cl$_2$, then 2 L 10% MeOH/5% NH$_4$OH in CH$_2$Cl$_2$) to give:

Example 210 cis-7-[4-(N-tert-Butoxycarbonyl-1S, 4S-2,5-Diaza [2.2.1]heptanyl)cyclohexyl]-5-(4-phenoxyphenyl)-7H-pyrrolo[2,3-d]pyrimidin-4-amine (605 mg, 64%)

$^1$H NMR (d$_6$ DMSO, 400 MHz): δ 8.13 (1H, s), 7.39–7.49 (4H, m), 7.32 (1H, m), 7.07–7.17 (5H, m), 6.09 (2H, bs), 4.63 (1H, m), 4.15 (1H, m), 3.30–3.70 (2H, m), 3.03–3.08 (2H, m), 2.80–2.90 (1H, m), 2.70–2.75 (1H, m), 2.29–2.35, (1H, m), 2.09–2.21 (1H, m), 1.81–1.93 (4H, m), 1.60–1.80 (4H, m), 1.39 (9H, m). HPLC/MS: Perkin Elmer Pecosphere C18, 3μM, 33×4.6, 3.5 ml/min 100—100% 50 mM ammonium acetate to acetonitrile in 4.5 minutes, C$_{36}$H$_{44}$N$_6$O$_3$ (581.2), 95%.

Example 211 trans-7-[4-(N-tert-Butoxycarbonyl-1S, 4S-2,5-Diaza [2.2.1]heptanyl)cyclohexyl]-5-(4-phenoxyphenyl)-7H-pyrrolo[2,3-d]pyrimidin-4-amine (183 mg, 20%)

$^1$H NMR (d$_6$ DMSO, 400 MHz): δ 8.13 (1H, s), 7.39–7.47 (5H, m), 7.15–7.17 (1H, m), 7.07–7.11 (4H, m), 6.10 (2H, bs), 4.62 (1H, m), 4.1–4.2 (1H, m), 3.71 (1H, bs), 3.03 (2H, m), 2.35 (2H, m), 1.93–2.01 (6H, m), 1.60–1.68 (2H, m), 1.40 (9H, s). HPLC/MS Perkin Elmer Pecosphere C18, 3 μM, 33×4.6, 3.5 ml/min 100—100% 50 mM ammonium acetate to acetonitrile in 4.5 minutes, C$_{30}$H$_{36}$N$_6$O (581.2), 99%

Example 212 cis-N1-{4-[4-Amino-5-(4-phenoxyphenyl)-7H-pyrrolo[2,3-d]pyrimidin-7-yl]cyclohexyl}-N1,N2, N2-trimethyl-1,2-ethanaediamine Trimaleate Salt trans-N1-{4-[4-Amino-5-(4-phenoxyphenyl)-7H-pyrrolo[2, 3-d]pyrimidin-7-yl]cyclohexyl}—N1,N2,N2-trimethyl-1,2-ethanaediamine Trimaleate Salt A mixture of 4-[4-amino-5-(4-phenoxyphenyl)-7H-pyrrolo[2,3-d]pyrimidine-7-yl]-1-cyclohexanone (1.0 g, 2.51 mmol), N,N,N'-trimethylethylenediamine (0.77 g, 7.54 mmol) and acetic acid (0.45 g, 7.54 mmol) in 1,2-dichloroethane (50 ml) was stirred at ambient temperature under an atmosphere of nitrogen for 30 minutes. Sodium triacetoxyborohydride (0.69 g, 3.26 mmol) was added and the mixture stirred at ambient temperature for 18 hours. Water (20 ml) and sodium bicarbonate (1.26 g, 15.1 mmol) were added, the mixture was stirred for one hour, filtered through a pad of celite and the pad was washed with dichloromethane (75 ml). The filtrate was transferred to a separatory funnel and the layers were separated. The organic layer was dried over magnesium sulfate, filtered and the filtrate evaporated under reduced pressure. The cis and trans isomers were purified by flash chromatography on silica gel using dichloromethane/methanol (7:3) as an eluent to give cis-N1-{4-[4-amino-5-(4-phenoxyphenyl)-7H-pyrrolo[2,3-d]pyrimidin-7-yl]cyclohexyl}—N1,N2,N2-trimethyl-1,2-ethanaediamine (0.442 g) and trans-N1-{4-[4-amino-5-(4-phenoxyphenyl)-7H-pyrrolo[2,3-d]pyrimidin-7-yl] cyclohexyl}-N1,N2,N2-trimethyl-1,2-ethanaediamine (0.336 g). The cis-N1-{4-[4-amino-5-(4-phenoxyphenyl)-7H-pyrrolo[2,3-d]pyrimidin-7-yl]cyclohexyl}-N1,N2,N2-trimethyl-1,2-ethanaediamine (0.44 g, 0.909 mmol) was dissolved in warm ethyl acetate (100 ml) then maleic acid (0.32 g, 2.73 mmol) in ethyl acetate (30 ml) was added. The resulting salt formed an oily residue on the bottom and sides of the flask. The supernatant was poured off and the residue was dissolved in water and lyophilized to give cis-N1-{4-[4-amino-5-(4-phenoxyphenyl)-7H-pyrrolo[2,3-d] pyrimidin-7-yl]cyclohexyl}-N1,N2,N2-trimethyl-1,2-ethanaediamine trimaleate salt (0.55 g): $^1$H NMR (DMSO-d$_6$, 400 MHz) δ 8.22 (s, 1H), 7.41–7.50 (m, 5H), 7.08–7.19 (m, 5H), 6.5 (bs, 2H), 6.15 (s, 6H), 4.78 (m, 1H), 3.28 (m, 2H), 3.00 (m, 2H), 2.80 (m, 1H), 2.79 (s, 6H), 2.50 (s, 3H), 2.19 (m, 2H), 1.99 (m, 2H), 1.78 (m, 4H); RP-HPLC (Hypersil CPS, 5 μm, 100 A, 250×4.6 mm; 25–100% acetonitrile-0.1 M ammonium acetate over 10 min, 1 ml/min) t$_r$=9.27 min; MS: MH$^+$485.

trans-N1-{4-[4-Amino-5-(4-phenoxyphenyl)-7H-pyrrolo[2,3-d]pyrimidin-7-yl]cyclohexyl}-N1,N2, N2-trimethyl-1,2-ethanaediamine Trimaleate Salt was Prepared From the Free Base in the Same Manner $^1$H NMR (DMSO-d$_6$, 400 MHz) δ 8.20 (s, 1H), 7.41–7.48 (m, 5H), 7.08–7.19 (m, 5H), 6.45 (bs, 2H), 6.15 (s, 6H), 4.62 (m, 1H), 2.9–3.3 (m, 5H), 2.74 (s, 6H), 2.56 (s, 3H), 1.9–2.2 (m, 6H), 1.73 (m, 2H); RP-HPLC (Hypersil CPS, 5 μm, 100 A, 250×4.6 mm; 25–100% acetonitrile-0.1 M ammonium acetate over 10 min, 1 ml/min) t$_r$=8.17 min; MS: MH$^+$485.

The following compounds were made in a similar manner to cis-N1-{4-[4-amino-5-(4-phenoxyphenyl)-7H-pyrrolo[2, 3-d]pyrimidin-7-yl]cyclohexyl}-N1,N2,N2-trimethyl-1,2-ethanaediamine

Example 214 cis-7-[4-(4-Isopropylpiperazino)cyclohexyl]-5-(4-phenoxyphenyl)-7H-pyrrolo[2,3-d]pyrimidin-4-amine $^1$H NMR (d$_6$ DMSO, 400 MHz): δ 8.13 (1H, s), 7.39–7.50 (4H, m), 7.28 (1H, s), 7.07–7.16 (5H, m), 6.08 (2H, bs), 4.67 (1H, m), 2.49–2.67 (9H, m), 2.06–2.16 (5H, m), 1.70–1.72 (2H, m), 1.53–1.59 (2H, m), 0.97 (d, J=6.5 Hz, 6H). Mass spec. C$_3$H$_{38}$N$_6$O (511.2). HPLC: (Hypersil HS C18, 5μm, 254 nm, 250×4.6 mm; 25–100% acetonitrile-0.1N ammonium acetate over 10 min, 1 ml/min) t$_r$=7.817 min., 99% TLC: R$_f$ in 90% CH$_2$Cl$_2$/MeOH=0.30 (UV visible).

Example 215 trans-7-[4-(4-Isopropylpiperazino)cyclohexyl]-5-(4-phenoxyphenyl)-7H-pyrrolo[2,3-d]pyrimidin-4-amine $^1$H NMR (d$_6$ DMSO, 400 MHz): δ 8.13 (1H, s), 7.40–7.47 (5H, m), 7.08–7.18 (5H, m), 6.08 (2H, bs), 4.53 (1H, m), 2.45–2.55 (9H, m), 2.17–2.20 (1H, m), 1.86–1.96 (6H, m), 1.44–1.49 (2H, m), 0.97 (d, J=5.5 Hz, 6H). Mass spec. $C_{31}H_{38}N_6O$ (511.2). HPLC: (Hypersil HS C18, 5 μm, 254 nm, 250×4.6 mm; 25–100% acetonitrile-0.1N ammonium acetate over 10 min, 1 ml/min) $t_r$=7.367 min., 91% TLC: $R_f$ in 90% $CH_2Cl_2$/MeOH=0.21 (UV visible).

Example 216 cis-7-{4-[4-(2-Methoxyethyl)piperazino] cyclohexyl}-5-(4-phenoxyphenyl)-7H-pyrrolo[2,3-d] pyrimidin-4-amine $^1$H NMR (d$_6$ DMSO, 400 MHz): δ 8.13 (1H, s), 7.39–7.50 (4H, m), 7.27 (1H, s), 7.07–7.11 (5H, m), 6.09 (2H, bs), 4.68 (1H, m), 3.42 (2H, t, J=5.9 Hz), 3.22 (3H, s), 2.43–2.55 (9H, m), 2.03–2.16 (6H, m), 1.60–1.71 (2H, m), 1.52–1.59 (2H, m). Mass spec. $C_{31}H_{38}N_6O_2$ (527.2). HPLC: (Hypersil HS C18, 5 μm, 254 nm, 250×4.6 mm; 25–100% acetonitrile-0.1N ammonium acetate over 10 min, 1 ml/min) $t_r$=7.317 min, 95% TLC: $R_f$ in 90% $CH_2Cl_2$/MeOH=0.22 (UV visible).

Example 217 trans-7-{4-[4-(2-Methoxyethyl)piperazino] cyclohexyl}-5-(4-phenoxyphenyl)-7H-pyrrolo[2,3-d] pyrimidin-4-amine $^1$H NMR (d$_6$ DMSO, 400 MHz): δ 8.13 (1H, s), 7.39–7.47 (5H, m), 7.07–7.16 (5H, m), 6.09 (2H, bs), 4.55 (1H, m), 3.36–3.42 (2H, m), 3.23 (3H, s), 2.33–2.55 (11H, m), 1.90–1.96 (6H, m), 1.44–1.47 (2H, m). Mass spec. $C_{31}H_{38}N_6O_2$ (527.2). HPLC: (Hypersil HS C18, 5 μm, 254 nm, 250×4.6 mm; 25–100% acetonitrile-0.1N ammonium acetate over 10 min, 1 ml/min) $t_r$=7.200 min, 99% TLC: $R_f$ in 90% $CH_2Cl_2$/MeOH=0.31 (UV visible).

Example 218 cis-7-[-4-(4-Ethylpiperazino)cyclohexyl]-5-(4-phenoxyphenyl)-7H-pyrrolo[2,3-d]pyrimidin-4-amine $^1$H NMR (d$_6$ DMSO, 400 MHz): δ 8.23 (1H, s), 7.41–7.49 (4H, m), 7.07–7.17 (6H, m), 6.57 (2H, bs), 6.20 (5H, s), 4.77 (1H, m), 2.04–2.13 (8H, m), 1.62–1.77 (5H, m), 1.21 (3H, t). HPLC (Waters delta pack C 18, 150×3.9 mm; 5–95% acetonitrile-0.1 M ammonium acetate over 30 min, 1 ml/min) $t_r$=13.851, 100%.

trans-7-[4-(4-Ethylpiperazino)cyclohexyl]-5-(4-phenoxyphenyl)-7H-pyrrolo[2,3-d]pyrimidin-4-amine $^1$H NMR (d$_6$ DMSO, 400 MHz): δ 8.19 (1H,s), 7.40–7.47 (4H, m), 7.19 (1H, m), 7.08–7.19 (5H, m), 6.40 (2H, bs), 6.18 (6H, s), 4.95 (1H, m), 3.17 (2H, bs), 2.98 (2H, bs), 2.69 (2H, bs), 1.94–2.01 (8H, m), 1.54–1.57 (2H, d, J=7.5 Hz), 1.17 (3H, t). HPLC (Waters delta pack C 18, 150×3.9 mm; 5–95% acetonitrile-0. 1 M ammonium acetate over 30 min, 1 ml/min) $t_r$=13.701, 96%.

The following compounds were prepared as salts in a similar manner to that of trans-N1-{4-[4-amino-5-(4-phenoxyphenyl)-7H-pyrrolo[2,3-d]pyrimidin-7-yl] cyclohexyl}—N 1,N2,N2-trimethyl-1 ,2-ethanaediamine trimaleate salt:

Example 219 cis-7-[4-(4-Isopropylpiperazino)cyclohexyl]-5-(4-phenoxyphenyl)-7H-pyrrolo[2,3-d]pyrimidin-4-amine tris maleate $^1$H NMR (d$_6$ DMSO, 400 MHz): δ 8.23 (1H, s), 7.40–7.49 (5H, m), 7.07–7.19 (5H, m), 6.55 (2H, bs), 6.16 (6H, s), 4.74 (1H, m), 3.26 (6H, bs), 2.04–2.49 (13H, m), 1.63–1.75 (5H, m), 1.25 (d, J=6.6 Hz, 6H). Mass spec. $C_{31}H_{38}N_6O$ (511.1). HPLC: (Hypersil HS C18, 5 μm, 254 nm, 250×4.6 mm; 25–100% acetonitrile-0.1N ammonium acetate over 10 min, 1 ml/min) $t_r$=7.967 min, 99%.

Example 220 trans-7-[4-(4-Isopropylpiperazino)cyclohexyl]-5-(4-phenoxyphenyl)-7H-pyrrolo[2,3-d]pyrimidin-4-amine tris maleate $^1$H NMR (d$_6$ DMSO, 400 MHz): δ 8.20 (1H, s), 7.40–7.65 (5H, m), 7.08–7.19 (5H, m), 6.46 (2H, bs), 6.14 (6H, s), 4.60 (1H, m), 2.50–3.45 (17H, m), 1.95–2.02 (5H, m), 1.56–1.59 (2H, m), 1.20 (d, J=6.5 Hz, 6H). Mass spec. $C_{31}H_{38}N_6O$ (511.2). HPLC: (Hypersil HS C18, 5 μm, 254 nm, 250×4.6 mm; 25–100% acetonitrile-0.1N ammonium acetate over 10 min, 1 ml/min) $t_r$=7.733 min, 90%.

Example 221 cis-7-{4-[4-(2-Methoxyethyl)piperazino] cyclohexyl}-5-(4-phenoxyphenyl)-7H-pyrrolo[2,3-d] pyrimidin-4-amine tris maleate $^1$H NMR (d$_6$ DMSO, 400 MHz): δ 8.23 (1H, s), 7.41–7.49 (5H, m), 7.07–7.19 (5H, m), 6.55 (2H, bs), 6.16 (6H, s), 4.75 (1H, m), 3.62 (2H, m), 3.30 (3H, s), 3.17 (6H, bs), 2.50 (9H, m), 2.02–2.16 (5H, m), 1.74 (5H, m). Mass spec. $C_{31}H_{38}N_6O_2$ (527.2). HPLC: (Hypersil HS C18, 51 μm, 254 nm, 250×4.6 mm; 25–100% acetonitrile-0.1N ammonium acetate over 10 min, 1 ml/min) $t_r$=7.750 min, 99%.

Example 222 trans-7-{4-[4-(2-Methoxyethyl)piperazino] cyclohexyl}-5-(4-phenoxyphenyl)-7H-pyrrolo[2,3-d] pyrimidin-4-amine tris maleate $^1$H NMR (d$_6$ DMSO, 400 MHz): δ 8.21 (1H, s), 7.41–7.48 (5H, m), 7.08–7.17 (5H, m), 6.53 (2H, bs), 6.17 (6H, s), 4.61 (1H, m), 3.45 (3H, s), 2.50–3.56 (19H, m), 1.99–2.08 (6H, m), 1.64 (2H, m). Mass spec. $C_{31}H_{38}N_6O_2$ (527.2). HPLC: (Hypersil HS C18, 5 μm, 254 nm, 250×4.6 mm; 25–100% acetonitrile-0.1N ammonium acetate over 10 min, 1 ml/min) $t_r$=7.383 min, 99%.

Example 223 cis-N1-{4-[4-Amino-5-(4-phenoxyphenyl)-7H-pyrrolo[2,3-d]pyrimidin-7-yl]cyclohexyl}-N2,N2-dimethyl-1,2-ethanaediamine Trimaleate Salt trans-N1-{4-[4-Amino-5-(4-phenoxyphenyl)-7H-pyrrolo[2,3-d]pyrimidin-7-yl]cyclohexyl}-N2,N2-dimethyl-1,2-ethanaediamine Monomaleate Salt cis-N1-{4-[4-amino-5-(4-phenoxyphenyl)-7H-pyrrolo[2,3-d]pyrimidin-7-yl]cyclohexyl}-N2,N2-dimethyl-1,2-ethanaediamine Trimaleate Salt $^1$H NMR (DMSO-d$_6$, 400MHz) δ 8.19 (s, 1H), 7.40–7.49 (m, 5H), 7.08–7.19 (m, 5H), 6.35 (bs, 2H), 6.13 (s, 6H), 4.78 (m, 1H), 3.15–3.45 (m, 5H), 2.74 (s, 6H), 1.8–2.25 (m, 8H); RP-HPLC (Hypersil CPS, 5 μm, 100 A, 250×4.6 mm; 25–100% acetonitrile-0.1 M ammonium acetate over 10 min, 1 ml/min) $t_r$=8.90 min; MS: MH$^+$471.

Example 224 trans-N1-{4-[4-Amino-5-(4-phenoxyphenyl)-7H-pyrrolo[2,3-d]pyrimidin-7-yl]cyclohexyl}-N2,N2-dimethyl-1,2-ethanaediamine Monomaleate Salt $^1$H NMR (DMSO-d$_6$, 400 MHz) δ 9.5 (bs, 1H), 8.26 (s, 1H), 7.41–7.55 (m, 5H), 7.08–7.19 (m, 5H), 6.7 (bs, 2H), 6.16 (s, 2H), 4.63 (m, 1H), 3.12–3.55 (m, 5H), 2.85 (s, 3H), 2.27 (m, 2H), 1.99–2.05 (m, 4H), 1.67–1.75 (m, 2H); RP-HPLC (Hypersil CPS, 5 μm, 100 A, 250×4.6 mm; 25–100% acetonitrile-0.1 M ammonium acetate over 10 min, 1 ml/min) $t_r$=8.6 min, MS: MH$^+$471.

Example 225 cis-7-(4-{[3-(1H-1-Imidazolyl)propyl]amino}cyclohexyl)-5-(4-phenoxyphenyl)-7H-pyrrolo[2,3-d]pyrimidin-4-amine Trimaleate Salt Trans-7-(4-{[3-(1H-1-imidazolyl)propyl]amino}cyclohexyl)-5-(4-phenoxyphenyl)-7H-pyrrolo[2,3-d]pyrimidin-4-amine Dimaleate Salt Example 227 cis-7-(4-{[3-(1H-1-Imidazolyl)propyl]amino}cyclohexyl)-5-(4-phenoxyphenyl)-7H-pyrrolo[2,3-d]pyrimidin-4-amine Trimaleate Salt $^1$H NMR (DMSO-d$_6$, 400 MHz) δ 8.78 (bs, 1H), 8.48 (bs, 2H), 8.18 (s, 1H), 7.66 (s, 1H), 7.55 (s, 1H), 7.41–7.49 (m, 5H), 7.08–7.19 (m, 5H), 6.33 (bs, 2H), 6.12 (s, 6H), 4.78 (m, 1H), 4.27 (t, 2H), 2.99 (m, 3H), 1.8–2.25 (m, 10H); RP-HPLC (Hypersil CPS, 5 μm, 100 A, 250×4.6 mm; 25–100% acetonitrile-0.1 M ammonium acetate over 10 min, 1 ml/min ) $t_r$=9.07 min; MS: MH$^+$508.

Example 228 trans-7-(4-{[3-(1H-1-Imidazolyl)propyl]amino}cyclohexyl)-5-(4-phenoxyphenyl)-7H-pyrrolo[2,3-d]pyrimidin-4-amine Dimaleate Salt $^1$H NMR (DMSO-d$_6$, 400 MHz) δ 8.76 (bs, 1H), 8.51 (bs, 2H), 8.18 (s, 1H), 7.66 (s, 1H), 7.55 (s, 1H), 7.40–7.47 (m, 5H), 7.08–7.21 (m, 5H), 6.3 (bs, 2H), 6.11 (s, 4H), 4.60 (m, 1H), 4.26 (t, 2H), 3.14 (m, 1H), 2.97 (m, 2H), 1.9–2.25 (m, 8H), 1.53–1.61 (m, 2H); RP-HPLC (Hypersil CPS, 5 μm, 100 A, 250×4.6 mm; 25–100% acetonitrile-0.1 M ammonium acetate over 10 min, 1 ml/min) $t_r$=8.72 min; MS: MH$^+$508.

Example 229 cis-7-[4-(Dimethylamino)cyclohexyl]-5-(4-phenoxyphenyl)-7H-pyrrolo[2,3-d]pyrimidin-4-amine Dimaleate Salt $^1$H NMR (DMSO-d$_6$, 400 MHz) δ 9.06 (bs, 1H), 8.2 (s, 1H), 7.41–7.50 (m, 5H), 7.08–7.19 (m, 5H), 6.4 (bs, 2H), 6.13 (s, 4H), 4.83 (m, 1H), 3.34 (m, 1H), 2.88 (s, 6H), 2.10–2.17 (m, 4H), 1.88–1.99 (m, 4H); RP-HPLC (Hypersil HS C-18, 5 μm, 100 A, 250×4.6 mm; 25–100% acetonitrile-0.1 M ammonium acetate over 10 min, 1 ml/min) $t_r$=7.38 min; MS: MH$^+$428.

Example 230 trans-5-(4-Phenoxyphenyl)-7-(4-piperidinocyclohexyl)-7H-pyrrolo[2,3-d]pyrimidin-4-amine Dimaleate Salt $^1$H NMR (DMSO-d$_6$, 400 MHz) δ 8.92 (bs, 1H), 8.18 (s, 1H), 7.4–7.5 (m, 5H), 7.08–7.19 (m, 5H), 6.3 (bs, 2H), 6.13 (s, 4H), 4.63 (m, 1H), 3.15–3.5 (m, 3H), 2.9–3.1 (m, 2H), 1.16–2.18 (m, 14H); RP-HPLC (Hypersil HS C-18, 5 μm, 100 A, 250×4.6 mm; 25–100% acetonitrile-0.1 M ammonium acetate over 10 min, 1 ml/min) $t_r$=7.98 min; MS: MH$^+$468. Trans-5-(4-phenoxyphenyl)-7-(4-tetrahydro-1H-1-pyrrolylcyclohexyl)-7H-pyrrolo[2,3-d]pyrimidin-4-amine dimaleate salt.

$^1$H NMR (DMSO-d$_6$, 400 MHz) δ 9.54 (bs, 1H), 8.18 (s, 1H), 7.40–7.47 (m, 5H), 7.08–7.18 (m, 5H), 6.3 (bs, 1H), 6.12 (s, 4H), 4.63 (m, 1H), 3.1–3.55 (m, 5H), 2.24 (m, 2H), 2.00 (m, 6H), 1.86 (m, 2H), 1.67 (m, 2H); RP-HPLC (Hypersil HS C-1 8, 5 μm, 100 A, 250×4.6 mm; 25–100% acetonitrile-0.1 M ammonium acetate over 10 min, 1 ml/min) $t_r$=7.82 min; MS: MH$^+$454.

Example 231 cis-7-[4-(4-Methyl-1,4-diazepan-1-yl)cyclohexyl]-5-(4-phenoxyphenyl)-7H-pyrrolo[2,3-d]pyrimidin-4-amine Dihydrochloride Salt trans-7-[4-(4-Methyl-1,4-diazepan-1-yl)cyclohexyl]-5-(4-phenoxyphenyl)-7H-pyrrolo[2,3-d]pyrimidin-4-amine Dihydrochloride Salt cis-7-[4-(4-Methyl-1,4-diazepan-1-yl)cyclohexyl]-5-(4-phenoxyphenyl)-7H-pyrrolo[2,3-d]pyrimidin-4-amine Dihydrochloride Salt $^1$H NMR (DMSO-d$_6$, 400 MHz) δ 11.7 (d, 1H), 11.38 (d, 1H), 8.57 (s, 1H), 8.34 (d, 1H), 7.42–7.51 (m, 4H), 7.03–7.20 (m, 5H), 4.93 (m, 1H), 4.7 (bs, 2H), 3.4–3.99 (m, 9H), 2.8 (s, 3H), 1.86–2.57 (10H); RP-HPLC (Hypersil HS C-18, 5 μm, 100 A, 250×4.6 mm; 25–100% acetonitrile-0.1 M ammonium acetate over 10 min, 1ml/min) $t_r$32 7.67 min; MS: MH$^+$497. trans-7-[4-(4-methyl-1,4-diazepan-1-yl)cyclohexyl]-5-(4-phenoxyphenyl)-7H-pyrrolo[2,3-d]pyrimidin-4-amine Dihydrochloride Salt $^1$H NMR (DMSO-d$_6$, 400 MHz) δ 11.94 (d, 1H), 11.52 (d, 1H), 8.56 (s, 1H), 7.8 (s, 1H), 7.42–7.51 (m, 4H), 7.10–7.20 (m, 5H), 4.76 (1H, m)<3.2–4.0 (m, 9H), 2.80 (s, 3H), 1.78–2.4 (m, 10H); RP-HPLC (Hypersil HS C-18, 5 μm, 100 A, 250×4.6 mm; 25–100% acetonitrile-0.1 M ammonium acetate over 10 min, 1 ml/min) $t_r$=7.42 min; MS: MH$^+$492.

Example 232 cis-5-(4-Phenoxyphenyl)-7-(4-piperazinocyclohexyl)-7H-pyrrolo[2,3-d]pyrimidin-4-amine Trimaleate Salt trans-5-(4-Phenoxyphenyl)-7-(4-piperazinocyclohexyl)-7H-pyrrolo[2,3-d]pyrimidin-4-amine Trimaleate Salt a) cis and trans-tert-Butyl 4-{4-[4-amino-5-(4-phenoxyphenyl)-7H-pyrrolo[2,3-d]pyrimidin-7-yl]cyclohexyl}-1-piperazinecarboxylate Example 233 cis-tert-Butyl 4-{4-[4-amino-5-(4-phenoxyphenyl)-7H-pyrrolo[2,3-d]pyrimidin-7-yl]cyclohexyl}-1-piperazinecarboxylate $^1$H NMR (DMSO-d$_6$, 400 MHz) δ 8.14 (s, 1H), 7.3–7.5 (m, 6H), 7.07–7.16 (m, 5H), 6.1 (bs, 2H), 4.69 (m, 1H), 3.2–3.4 (4H, m), 2.38 (m, 4H), 2.0–2.25 (m, 5H), 1.5–1.8 (m, 4H), 1.41 (s, 9H); RP-HPLC (Hypersil HS C-18, 5 μm, 100 A, 250×4.6 mm; 25–100% acetonitrile-0.1 M ammonium acetate over 10 min, 1 min/ml) $t_r$=13.60 min.

trans-tert-Butyl 4-{4-[4-Amino-5-(4-phenoxyphenyl)-7H-pyrrolo[2,3-d]pyrimidin-7-yl]cyclohexyl}-1-piperazinecarboxylate $^1$H NMR (DMSO-d$_6$, 400 MHz) δ 8.13 (s, 1H), 7.40–7.47 (m, 6H), 7.08–7.16 (m, 5H), 6.1 (bs, 2H), 4.55 (m, 1H), 3.34 (m, 4H), 2.35–2.51 (m, 3H), 1.89–1.99 (m, 6H), 1.38–1.49

(m, 4H), 1.39 (s, 9H); RP-HPLC (Hypersil HS C-18, 5 μm, 100 A, 250×4.6 mm; 25–100% acetonitrile-0.1 M ammonium acetate over 10 min, 1 ml/min) $t_r$=10.40 min.

b) cis-5-(4-Phenoxyphenyl)-7-(4-piperazinocyclohexyl)-7H-pyrrolo[2,3-d]pyrimidin-4-amine Trimaleate Salt The cis-tert-butyl 4-{4-[4-amino-5-(4-phenoxyphenyl)-7H-pyrrolo[2,3-d]pyrimidin-7-yl]cyclohexyl}-1-piperazinecarboxylate (1.85 g, 3.27 mmol) was treated with a 20% trifluoroacetic acid/dichloromethane solution (60 ml) and stirred for 30 minutes at ambient temperature. The solvents were removed under reduced pressure then the residue was partitioned between dichloromethane (200 ml) and aqueous saturated sodium bicarbonate solution (30 ml). The organic solution was dried over magnesium sulfate, filtered and the filtrate evaporated to a residue (1.55 g). A portion of this material (1.0 g, 2.15 mmol) was dissolved in warm ethyl acetate (220 ml) then treated with maleic acid (0.75 g, 0.44 mmol) in warm ethyl acetate (75 ml). The mixture was cooled to ambient temperature then the solid was collected by filtration and dried to give Cis-5-(4-phenoxyphenyl)-7-(4-piperazinocyclohexyl)-7H-pyrrolo[2,3-d]pyrimidin-4-amine trimaleate salt (1.15 g) as a white solid: $^1$H NMR (DMSO-$d_6$, 400 MHz) δ 8.5 (bs, 1H), 8.23 (s, 1H), 7.41–7.51 (m, 5H), 7.08–7.19 (m, 5H), 6.65 (bs, 2H), 6.16 (s, 6H), 4.74 (m, 1H), 1.16–3.2 (m, 17H); RP—HPLC (Hypersil CPS, 5 μm, 100 A, 250×4.6 mm; 25–100% acetonitrile-0.1 M ammonium acetate over 10 min, 1 ml/min) $t_r$=8.63 min; MS: MH$^+$469.

c) trans-5-(4-Phenoxyphenyl)-7-(4-piperazinocyclohexyl)-7H-pyrrolo[2,3-d]pyrimidin-4-amine Trimaleate Salt $^1$H NMR (DMSO-$d_6$, 400 MHz) δ 8.22 (s, 1H), 7.41–7.51 (m, 5H), 7.08–7.19 (m, 5H), 6.6 (bs, 2H), 6.16 (s, 6H), 4.58 (m, 1H), 1.4–3.2 (m, 17H); RP-HPLC (Hypersil HS C-18, 5 μm, 100 A, 250×4.6 mm; 25–100% acetonitrile-0.1 M ammonium acetate over 10 min, 1 ml/min) $t_r$=8.08 min; MS: MH$^+$469.

Example 234

7-[3-(4-Methylpiperazino)cyclopentyl]-5-(4-phenoxyphenyl)-7H-pyrrolo[2,3-d]pyrimidin-4-amine tri-Maleate 3-[4-amino-5-(4-phenoxyphenyl)-7H-pyrrolo[2,3-d]pyrimidin-7-yl]cyclopentan-1-ol (2.14 g, 0.0055 mol) in 11 dichloromethane was stirred with 12 g active manganese dioxide for 5 hours, filtered and fresh manganese dioxide (8 g) added to the filtrate. After stirring for a further 17 hours, the mixture was filtered and used directly. HPLC/MS showed starting material and 3-[4-amino-5-(4-phenoxyphenyl)-7H-pyrrolo[2,3-d]pyrimidin-7-yl]-1-cyclopentanone 62.7% $t_r$ 4.38 minutes. The dichloromethane solution was stirred with 1.0 g N-methylpiperazine (0.01 mol) and acetic acid (0.6 g, 0.01 mol) for 15 minutes then sodium triacetoxyborohydride (0.89 g, 0.0042 mol) was added. After 2 hours 1.0 g N-methylpiperazine, 0.6 g acetic acid and 0.89 g sodium triacetoxyborohydride was added and the mixture stirred for 17 hours. Further addition of 2.0 g N-methylpiperazine, 1.2 g acetic acid and 1.2 g sodium triacetoxyborohydride and stirring for 3 days gave a mixture which was evaporated under reduced pressure. The residue was treated with water (200 ml) and 6M -hydrochloric acid (50 ml) then washed with ethyl acetate (discarded) and basified with excess aqueous ammonia. The mixture was extracted with ethyl acetate and the extract dried (sodium sulphate) then purified by flash chromatography in 9:1 ethyl acetate: ethanol to remove impurities followed by 8:1:1 ethyl acetate:ethanol-:triethylamine to elute the product. Solvent was removed under reduced pressure, the residue dissolved in ethyl acetate and treated with a solution of maleic acid in ethyl acetate giving 7-[3-(4-methylpiperazino) cyclopentyl]-5-(4-phenoxyphenyl)-7H-pyrrolo[2,3-d]pyrimidin-4-amine tri-maleate (444395) as a 1.4 solvate with ethyl acetate after drying at 80° C. under reduced pressure (0.95 g, 0.001 mol) m.pt. 168–170° C. (decomposes).

Example 235

[4-(4-amino-7-cyclopentyl-7H-pyrrolo[2,3-d]pyrimidin-5-yl)phenyl](phenyl)-methanol, Sodium borohydride (0.052 g, 0.0013 mol) was added to a solution of [4-(4-amino-7-cyclopentyl-7H-pyrrolo[2,3-d]pyrimidin-5-yl)phenyl](phenyl)methanone (0.1 g, 0.00026 mol) in tetrahydrofuran (4 mL) followed by the addition of Amberlyst-15H$^+$. The mixture was stirred at ambient temperature under an atmosphere of nitrogen for 15 min, filtered through a celite pad and the solvent removed under reduced pressure. The residue was purified by preparative RP-HPLC (Rainin, Hypersil C18, 8 μm, 100 A, 25 cm; 5%–85% acetonitrile—0.1% ammonium acetate over 20 min, 21 mL/min) to yield [4-(4-amino-7-cyclopentyl-7H-pyrrolo[2,3-d]pyrimidin-5-yl)phenyl](phenyl)methanol (0.005 g, 0.000013 mol):

$^1$H NMR (DMSO-$d_6$ 400 MHz) δ 8.12 (s, 1H), 7.31 (m, 10H), 6.01 (br, 2H), 5.91 (d, 1H), 5.75 (d, 1H), 5.06 (m, 1H), 2.10(br, 2H), 1.88 (br, 4H), 1.67 (br, 2H) RP-HPLC(Delta Pak C18, 5 μm, 300 A, 15 cm; 5%–85% acetonitrile—0.1M ammonium acetate over 20 min, 1 mL/min) $R_t$ 16.74 min. MH$^+$385.

Example 236

Trans-7-[3-(4-Methylpiperazino)cyclohexyl]-5-(4-phenoxyphenyl)-7H-pyrrolo[2,3-d]pyrimidin-4-amine tri-Maleate trans-7-[3-(4-methylpiperazino)cyclohexyl]-5-(4-phenoxyphenyl)-7H-pyrrolo[2,3-d]pyrimidin-4-amine (1.30 g, 0.0027 mol) in 300 ml warm ethyl acetate was treated with a solution of maleic acid (0.94 g, 0.0081 mol) in 100 ml ethyl acetate and allowed to cool. The colourless solid was collected, washed with ethyl acetate and dried to constant weight at 90° C./3 mbar giving 1.85 g (0.0022 mol) of trans-7-[3-(4-methylpiperazino)cyclohexyl]-5-(4-phenoxyphenyl)-7H-pyrrolo[2,3-d]pyrimidin-4-20 amine tri-maleate solvated with 0.18 mol ethyl acetate m.p. 189° C. (decomposes).

Example 237 trans-7-[3-(4-Methylpiperazino)cyclohexyl]-5-(4-phenoxyphenyl)-7H-pyrrolo[2,3-d]pyrimidin-4-amine tri-Hydrochloride trans-7-[3-(4-methylpiperazino)cyclohexyl]-5-(4-phenoxyphenyl)-7H-pyrrolo[2,3-d]pyrimidin-4-amine (0.36 g, 0.00075 mol) in 25 ml warm isopropanol was treated with a solution of 0.225 ml 12M hydrochloric acid (0.0027 mol) in 2 ml isopropanol and the suspension heated briefly to boiling then volatile material was removed under reduced pressure. The resulting colourless solid was dried to constant weight at 84° C./5 mbar giving the trans-7-[3-(4-methylpiperazino)cyclohexyl]-5-(4-phenoxyphenyl)-7H-pyrrolo[2,3-d]pyrimidin-4-amine tri-hydrochloride (444626) solvated with 1 mol water and 0.25 mol isopropanol (0.25 g, 0.0004 mol) m.p. 304–306° C.(dec).

Example 238 cis-7-[3-(4-Methylpiperazino)cyclohexyl]-5-(4-phenoxyphenyl)-7H-pyrrolo[2,3-d]pyrimidin-4-amine tri-Maleate Salt cis-7-[3-(4-methylpiperazino)cyclohexyl]-5-(4-phenoxyphenyl)-7H-pyrrolo[2,3-d]pyrimidin-4-amine (1.45 g, 0.0030 mol) in ethyl acetate with 1.05 g (0.0091 mol) maleic acid giving colourless solid after drying to constant weight at 90° C./3 mbar. 2.15 g cis-7-[3-(4-methylpiperazino)cyclohexyl]-5-(4-phenoxyphenyl)-7H-pyrrolo[2,3-d]pyrimidin-4-amine tri-maleate salt solvated with 0.14 mol ethyl acetate and 0.5 mol water (0.0025 mol) obtained m.p. 186 (dec).

Example 239 cis-7-[3-(4-Methylpiperazino)cyclohexyl]-5-(4-phenoxyphenyl)-7H-pyrrolo[2,3-d]pyrimidin-4-amine tri-Hydrochloride cis-7-[3-(4-methylpiperazino)cyclohexyl]-5-(4-phenoxyphenyl)-7H-pyrrolo[2,3-d]pyrimidin-4-amine 0.80 g (0.0017 mol) in isopropanol was treated with 0.5 ml 12M hydrochloric acid (0.006 mol). The resulting solid was filtered to give cis-7-[3-(4-methylpiperazino)cyclohexyl]-5-(4-phenoxyphenyl)-7H-pyrrolo[2,3-d]pyrimidin-4-amine tri-hydrochloride as a hygroscopic solid until dried at 80° C./3 mbar to constant weight. (0.75 g, 0.0011 mol) m.p. 224.5–226.5 (dec).

Example 240 trans-5-(2-Methyl-4-phenoxyphenyl)-7-[4-(4-methylpiperazino)cyclohexyl]-7H-pyrrolo[2,3-d]pyrimidin-4-amine Trimaleate A mixture of 3-phenoxytoluene (2.5 g, 0.0136 mol) and N-bromosuccinimide (2.54 g, 0.0142 mol) was stirred in acetonitrile (20 mL) for 2.5 hours under an atmosphere of nitrogen. The solvent was removed under reduced pressure. Carbon tetrachloride was added to the residue and the resulting solid was removed by filtration. The filtrate was concentrated to yield 4-bromo-3-methylphenyl phenyl ether as yellow oil (3.5 g, 0.0133 mol):

$^1$H NMR (Chloroform-d, 400 MHz) δ 7.45 (d, 1H), 7.33 (m, 2H), 7.12 (t, 1H), 7.00 (d, 2H), 6.89 (s, 1H), 6.71 (d, 1H), 2.34 (s, 3H) RP-HPLC (Hypersil C18, 5 µm, 250×4.6 mm; 25%–100% over 23 min with 0.1 M ammonium acetate, 1 mL/min) $R_t$ 14.72 min.

A mixture of 4-bromo-3-methylphenyl phenyl ether (1.7 g, 0.00646 mol), diboron pinacol ester (2.0 g, 0.00775 mol), [1,1'-bis(diphenylphosphino)ferrocene]dichloropalladium (II) complex with dichloromethane (1:1) (0.16 g, 0.00019 mol) and potassium acetate (1.9 g, 0.01938 mol) in N,N-dimethylformamide (65 mL) was heated at 80° C. under an atmosphere of nitrogen for 22 hours. The mixture was allowed to cool to ambient temperature and the solvent was removed under reduced pressure. Dichloromethane was added to the residue and the resulting solid was removed by filtration through a pad of celite. The filtrate was concentrated into black mixture, which was purified by flash chromatography on silica using ethyl acetate/n-heptane (3:97) as mobile phase to yield 3-methyl-4-(4,4,5,5-tetramethyl-1,3,2-dioxaborolan-2-yl)phenyl phenyl ether (1.05 g, 0.00338 mol):

$^1$H NMR (Chloroform-d, 400 MHz) δ 7.73 (d, 1H), 7.33 (m, 2H), 7.08 (t, 1H), 7.01 (d, 2H), 6.79 (d, 2H), 2.51 (s, 3H), 1.34 (s, 12H) TLC (ethyl acetate/n-heptane=3:97) $R_f$ 0.28.

A mixture of 4-chloro-7-(1,4-dioxaspiro[4.5]dec-8-yl)-5-iodo-7H-pyrrolo[2,3-d]pyrimidine (20 g, 47.7 mmol) and 6 N HCl(aq) (60 mL, 360 mmol) in tetrahydrofuran (120 mL) and acetone (600 mL) was stirred at ambient temperature under an atmosphere of nitrogen for 17 hours. The solvent was removed under reduced pressure and 6NHCl(aq) (20 mL), tetrahydrofuran (60 mL), and acetone (300 mL) were added to the mixture. The mixture was stirred at ambient temperature under an atmosphere of nitrogen for 4.5 hour. The solvent was removed under reduced pressure and the yellow colored residue was washed with water to yield 4-(4-chloro-5-iodo-7H-pyrrolo[2,3-d]pyrimidin-7-yl)-1-cyclohexanone (12.3 g, 32.7 mmol). RP-HPLC (Hypersil C18, 5 µm, 250×4.6 mm; 25%–100% over 15 min with 0.05 M ammonium acetate, 1 mL/min) $R_t$ 10.20 min.

A mixture of 4-(4-chloro-5-iodo-7H-pyrrolo[2,3-d]pyrimidin-7-yl)-1-cyclohexanone (5.6 g, 14.9 mmol), N-methylpiperazine (3.3 mL, 29.8 mmol), acetic acid (2.6 mL, 44.7 mmol), and trimethylorthoformate (9.9 mL, 89.4 mmol) in dichloroethane (100 mL) was stirred at ambient temperature under an atmosphere of nitrogen for 1 hr. Sodium triacetoxyborohydride (14.2 g, 67.05 mmol) was added into the mixture and stirred at ambient temperature under an atmosphere of nitrogen for 18 hours. The solvent was removed under reduced pressure. The residue was partitioned between saturated aqueous sodium bicarbonate solution and ethyl acetate. The water phase was further extracted with ethyl acetate and the combined organic extracts were dried over sodium sulfate. The solvent was removed under reduced pressure and the residue was purified by flash chromatography on silica gel using triethylamine/dichloromethane (2:98) followed by methanol/triethylamine/dichloromethane (2:3:95) as mobile phase to yield trans-4-chloro-5-iodo-7-[4-(4-methylpiperazino)cyclohexyl]-7H-pyrrolo[2,3-d]pyrimidine (1.7 g, 3.7 mmol). $^1$H NMR (DMSO-d$_6$, 400 MHz) 8.63 (s, 1H), 8.12 (s, 1H), 4.63 (br, 1H), 2.15 (s, 3H), 1.94 (br, 6H), 1.45 (br, 2H) RP-20 HPLC (Hypersil C18, 5 µm, 250×4.6 mm; 25%–100% over 15 min with 0.05 M ammonium acetate, 1 mL/min) $R_t$ 6.17 min.

Trans-4-chloro-5-iodo-7-[4-(4-methylpiperazino)cyclohexyl]-7H-pyrrolo[2,3-d]pyrimidine (0.89 g, 1.9 nmol) in concentrated ammonium hydroxide (40 mL) and dioxane (40 mL) was heated at 120° C. in a pressure vessel for 18 hours. The mixture was allowed to cool to ambient temperature and the solvent was removed under reduced pressure. The residue was partitioned between saturated aqueous sodium bicarbonate solution and ethyl acetate. The water phase was further extracted with ethyl acetate and the combined organic extracts were washed with brine and dried over sodium sulfate. The solvent was removed under reduced pressure to yield trans-5-iodo-7-[4-(4-methylpiperazino)cyclohexyl]-7H-pyrrolo[2,3-d]pyrimidin-4-amine (0.35 g, 0.8 mmol). RP-HPLC (Hypersil C18, 5 µm, 250×4.6 mm; 25%–100% over 15 min with 0.1 M ammnonium acetate, 1 mL/min) $R_t$ 4.01 min. MS: MH$^+$441.

A mixture of trans-5-iodo-7-[4-(4-methylpiperazino)cyclohexyl]-7H-pyrrolo[2,3-d]pyrimidin-4-amine (0.347 g, 0.000788 mol), 3-methyl-4-(4,4,5,5-tetramethyl-1,3,2-dioxaborolan-2-yl)phenyl phenyl ether (0.27 g, 0.000867 mol), tetrakis(triphenyl-phosphine)palladium(0) (0.054 g, 0.000047 mmol), and sodium carbonate (0.209 g, 0.00197 mol) in N,N-dimethylformamide (15 mL) and water (10 mL) was heated at 80° C. under an atmosphere of nitrogen for 16 hours. The mixture was allowed to cool to ambient temperature and the solvent removed under reduced pressure. The residue was partitioned between saturated aqueous sodium bicarbonate solution and ethyl acetate. The water phase was further extracted with ethyl acetate and the combined organic extracts were dried over sodium sulfate. The solvent was removed under reduced pressure and the residue was purified by flash chromatography on silica gel using triethylamine/dichloromethane (5:95) followed by methanol/triethylamine/ dichloromethane (3:5:92) as mobile phase to yield trans-5-(2-methyl-4-phenoxyphenyl)-7-[4-(4-methylpiperazino)cyclohexyl]-7H-pyrrolo[2,3-d]pyrimidin-4-amine (0.376 g, 0.000757 mol). Trans-5-(2-methyl-4-phenoxyphenyl)-7-[4-(4-methylpiperazino)-cyclohexyl]-7H-pyrrolo[2,3-d]pyrimidin-4-amine (0.376 g, 0.000757 mol) was dissolved in refluxing ethanol (10 mL) and a preheated solution of maleic acid (0.264 g, 0.00227 mol) in ethanol (5 mL) was added. The mixture was refluxed for 15 minutes, cooled to ambient temperature and the precipitate collected by filtration, washed with cool ethanol and dried to give trans-5-(2-methyl-4-phenoxyphenyl)-7-[4-(4-methylpiperazino)-cyclohexyl]-7H-pyrrolo[2,3-d]pyrimidin-4-amine trimaleate (0.153 g, 0.000181 mol): $^1$H NMR (DMSO-$d_6$, 400 MHz) 8.22 (s, 1H), 7.42 (m, 3H), 7.25 (d, 1H), 7.17 (t, 1H), 7.09 (d, 2H), 7.02 (s, 1H), 6.89 (d, 1H), 6.16 (s, 6H), 4.58 (m, 1H), 3.3 (br, 9H), 2.68 (s, 3H), 2.22 (s, 3H), 2.01 (br, 6H), 1.57 (br, 2H) RP-HPLC (Hypersil C18, 5 μm, 250×4.6 mm; 25%–100% over 23 min with 0.1 M ammonium acetate, 1 mL/min) $R_t$ 7.30 min. MS: $MH^+$497.

Example 241

3-[4-Amino-5-(4-phenoxyphenyl)-7H-pyrrolo[2,3-d]pyrimidin-7-yl]cyclopentyl 2-Aminoacetate Hydrochloride A mixture of 3-[4-amino-5-(4-phenoxyphenyl)-7H-pyrrolo[2,3-d]pyrimidin-7-yl]-1-cyclopentanol (50 mg, 0.129 mmol), 2-[(tert-butoxycarbonyl)amino]acetic acid (34 mg, 0.194 mmol), 1-[3-(dimethylamino)propyl]-3-ethylcarbodiimide hydrochloride (31 mg, 0.155 mmol) and 4-(dimethylamino)pyridine (16 mg, 0.129 mmol) in DMF (1 mL) was stirred under nitrogen for 24 hours. The mixture was pour onto ice-water. The aqueous layer was extracted with ethyl acetate three times. The combined organic layer was washed with brine, dried over $MgSO_4$, filtered and evaporated. The residue was purified by flash column chromatography using ethyl acetate as mobile phase to give 3-[4-amino-5-(4-phenoxyphenyl)-7H-pyrrolo[2,3-d]pyrimidin-7-yl]cyclopentyl 2-[(tert-butoxycarbonyl)amino] acetate (39 mg, 0.072 mmol). HPLC: $t_r$=19.22 min. (Delta-Pack, C-18, 5 μm, 300 A, 3.9×150 mm; 5–85% acetonitrile—0.1 M ammonium acetate over 20 min, 1 ml/min).

3-[4-Amino-5-(4-phenoxyphenyl)-7H-pyrrolo[2,3-d]pyrimidin-7-yl]cyclopentyl 2-[(tert-butoxycarbonyl)amino] acetate (39 mg, 0.072 mmol) was dissolved in ethyl acetate (2.5 mL). Hydrochloride gas was bubbled through the solution for 3 minutes. The reaction mixture was stirred for additional 30 minutes. Ether was added and the precipatate was collected through filtration under nitrogen to give 3-[4-amino-5-(4-phenoxyphenyl)-7H-pyrrolo[2,3-d]pyrimidin-7-yl]cyclopentyl 2-amino acetate hydrochloride (39 mg) as white solid. 1H NMR (DMSO-$d_6$) δ 2.20 (m, 5H), 2.67 (m, 1H), 3.83 (s, 2H), 5.25 (m, 1H), 5.31 (m, 1H), 7.14 (m, 2H), 7.43, (m, 1H), 7.50 (m, 1H), 7.68 (m, 1H), 8.26 (bs, 2H), 8.40 (s, 1H). LC/MS: $MH^+$=444, $t_r$=2.25 min. (Pecospher, 3C-18, 3 um, 4.6×33 mm; 0–100% acetonitrile—0.1 M ammonium acetate over 5 min, 3.5 ml/min).

Example 242

3-[4-Amino-5-(4-phenoxyphenyl)-7H-pyrrolo[2,3-d]pyrimidin-7-yl]cyclopentyl N-(2-morpholinoethyl) carbamate Hydrochloride 4- Nitrochloroformate (12.5 mg, 0.062 mmol) in dichloromethane (1 mL) was cooled on an ice-water bath. 4-Methylmorpholine (7 uL, 0.062 mmol) was added slowly. After 20 minutes, the ice-water bath was removed and the reaction mixture was allowed to warm up to room temperature. 3-(4-Amino-5-(4-phenoxyphenyl)-7H-pyrrolo[2,3-d]pyrimidin-7-yl)-1-cyclopentanol (20 mg, 0.052 mmol) was added and the reaction mixture was stirred for 4days. The reaction mixture was diluted with dichloromethane. The organic layer was washed with water, saturated sodium bicarbonate, brine, dried over $MgSO4$, filtered and evaporated to give a yellow solid. A solution of the yellow solid in dichloromethane (1 mL) was added to 2-morpholino-1-ethanamine (0.2 mL). After stirring at room temperature overnight, the reaction mixture was diluted with ethyl acetate. The organic layer was washed with water (3 times), brine, dried over $MgSO4$, filtered and evaporated. The crude product was purified by HPLC to give 3-[4-amino-5-(4-phenoxyphenyl)-7H-pyrrolo[2,3-d]pyrimidin-7-yl] cyclopentyl N-(2-morpholinoethyl)carbamate (17 mg, 0.031 mmol). 1H NMR ($CDCl_3$-d) δ 2.08 (m, 4H), 2.43 (m, 7H), 2.73 (m, 1H), 3.29 (m, 2H), 3.67, (m, 4H), 5.28 (m, 5H), 7.09 (m, 6H), 7.40 (m, 4H), 8.30 (s, 1H). LC/MS: $MH^+$=543, $t_r$=2.13 min. (Pecospher, 3C-18, 3 um, 4.6×33 mm; 0–100% acetonitrile—0.1 M ammonium acetate over 5 min, 3.5 ml/min).

3-[4-Amino-5-(4-phenoxyphenyl)-7H-pyrrolo[2,3-d]pyrimidin-7-yl]cyclopentyl N-(2-morpholinoethyl) carbamate (10 mg, 0.0184 mmol) was dissolved in ethyl acetate (2.5 mL). Hydrochloride gas was bubbled through the solution for 3 minutes. The reaction mixture was stirred for additional 10 minutes. The precipitate was collected through filtration under nitrogen to give 3-[4-amino-5-(4-phenoxyphenyl)-7H-pyrrolo[2,3-d]pyrimidin-7-yl] cyclopentyl N-(2-morpholinoethyl)carbamate hydrochloride as white solid. 1H NMR (DMSO-$d_6$) δ 1.99 (m, 4H), 2.55 (m, 2H), 3.32 (m, 12H), 5.08 (m, 1/2H), 5.19 (m, 1/2H), 7.16 (m, 5H), 7.45, (m, 5H), 8.26 (s, 1H). LC/MS: $MH^+$=543, $t_r$=2.16 min. (Pecospher, 3C-18, 3 um, 4.6×33 mm; 0–100% acetonitrile—0.1 M ammonium acetate over 5 min, 3.5 ml/min).

Example 243

4-[4-Amino-5-(4-phenoxyphenyl)-7H-pyrrolo[2,3-d]pyrimidin-7-yl]cyclohexanol

Sodium borohydride (500mg, 13 mmol) was added in one portion to a stirred solution of 4-[4-amino-5-(4-phenoxyphenyl)-7H-pyrrolo[2,3-d]pyrimin-7-yl] cyclohexan-1-one (780mg, 2.0 mmol) in methanol (500 mL), and the mixture stirred under an atmosphere of nitrogen for 1 hour, then left to stand overnight. The solvent was removed under reduced pressure, and the residue partitioned between 2M aqueous sodium hydroxide solution (100 mL) and dichloromethane (100 mL). The organic layer was separated and the aqueous layer further extracted with dichloromethane (2×100 mL). The combined organic extracts were washed with water (150 mL), dried over potassium carbonate, and purified by chromatography with a Biotage 40S column using ethyl acetate/triethylamine (98:2 to 95:5) and ethyl acetate/ethanol (95:5) as a mobile phase to yield 4-[4-amino-5-(4-phenoxyphenyl)-7H-pyrrolo [2,3-d]pyrimidin-7-yl]cyclohexanol as a white solid (750mg, 1.9 mmol), melting point: 199–200 deg. C.LC/MS: Hypersil BDS c18 (100×2.1 mm) 0.1M ammoniumacetate/acetonitrile, 10–100% acetonitrile in 8 min.)$MH^+$401 , $t_r$=4.12 minutes.

Example 244

Phenyl N-[4-(4-Amino-7-tetrahydro-2H-4-pyranyl-7H-pyrrolo[2,3-d]pyrimidin-5-yl)-2-methoxyphenyl] carbamate (4-Amino-3-methoxyphenyl)-7-tetrahydro-2H-4-pyranyl-7H-pyrrolo[2,3-d]pyrimidin-4-amine (100 mg, 0.294 mmol) was dissolved in dichloromethane (2 mL). Pyridine (2mL) was added followed by phenylchloroformate (44 uL, 0.353 mmol). After stirring for 3 hours, another 44 uL of phenylmethanesulfonyl chloride was added and the reaction mixture was stirred overnight. The solvent was removed and the residue was purified by preparative LC/MS to give phenyl N-[4-(4-amino-7-tetrahydro-2H-4-pyranyl-7H-pyrrolo[2,3-d]pyrimidin-5-yl)-2-methoxyphenyl]carbamate (52 mg, 0.113 mmol). 1H NMR (CDCl$_3$-d) δ 2.09 (m, 4H), 3.66 (m, 2H), 3.98 (s, 3H), 4.16 (m, 2H), 4.98 (m, 1H), 5.24 (s, 2H), 7.09 (m, 3H), 7.23 (m, 4H), 7.41 (m, 2H), 7.62 (s, 1H), 8.20 (bd, J=7.80 Hz, 1H), 8.33 (s, 1H). LC/MS MH$^+$=460.

Example 245

Tetrahydro-2H-4-pyranyl N-[4-(4-Amino-7-tetrahydro-2H-4-pyranyl-7H-pyrrolo[2,3-d]pyrimidin-5-yl)-2-methoxyphenyl]carbamate 4-nitrophenyl Tetrahydro-2H-4-pyranyl Carbonate Tetrahydro-2H-4-pyranol (1.0 ml, 10.5 mmol) was mixed with 4-methylmorpholine (2.0 ml) in dichloromethane (20 mL). 4- Nitrochloroformate (1.98 g, 9.82 mmol) was added slowly to the reaction mixture. After stirring for 5 hours, the reaction mixture was diluted with dichloromethane. The organic layer was washed with water, 1.0 N HCl, saturated sodium bicarbonate, brine, dried over MgSO4, filtered and evaporated. The crude product was purified by flash column chromatography chromatography using ethyl acetate/heptane (4:1) as the mobile phase to give 4-nitrophenyl tetrahydro-2H-4-pyranyl carbonate (1.5 g, 5.62 mmol). 1H NMR (CDCl$_3$-d) δ 1.87 (m, 2H), 2.06 (m, 2H), 3.58 (m, 2H), 3.98 (m, 2H), 4.97 (m, 1H), 7.40 (d, J=9.0 Hz, 2H), 8.30 (d, J=9.0 Hz, 2H).

a) Tetrahydro-2H-4-pyranyl N-[4-(4-amino-7-tetrahydro-2H-4-pyranyl-7H-pyrrolo[2,3-d]pyrimidin-5-yl)-2-methoxyphenyl]carbamate 5-(4-Amino-3-methoxyphenyl)-7-tetrahydro-2H-4-pyranyl-7H-pyrrolo[2,3-d]pyrimidin-4-amine (57 mg, 0.168 mmol) and 4-nitrophenyl tetrahydro-2H-4-pyranyl carbonate (90 mg, 0.336 mmol) was mixed in pyridine (1 mL). After stirring for 5 hours, another 90 mg of 4-nitrophenyl tetrahydro-2H-4-pyranyl carbonate was added and the reaction mixture was stirred for 2 days. The reaction mixture was heated at 70° C. for 2 hours. The solvent was removed and the residue was purified by preparative thin layer chromatography to give tetrahydro-2H-4-pyranyl N-[4-(4-amino-7-tetrahydro-2H-4-pyranyl-7H-pyrrolo[2,3-d]pyrimidin-5-yl)-2-methoxyphenyl]carbamate (30 mg, 0.064 mmol). 1H NMR (CDCl$_3$-d) δ 1.78 (m, 4H), 2.08 (m, 4H), 3.60 (m, 4H), 3.94 (s, 3H), 3.97 (m, 2H), 4.15 (m, 2H), 4.98 (m, 2H), 5.23 (s, 2H), 6.78 (s, 1H), 7.04 (s, 1H), 7.07 (d, J=8.3 Hz, 1H), 8.16 (bd, J=7.90 Hz, 1H), 8.33 (s, 1H). LC/MS MH$^+$=468.

Example 246

3-Pyridylmethyl N-[4-(4-Amino-7-tetrahydro-2H-4-pyranyl-7H-pyrrolo[2,3-d]pyrimidin-5-yl)-2-methoxyphenyl]carbamate Hydrochloride a) 4-Nitrophenyl (3-Pyridylmethyl)carbonate 4- Nitrochloroformate (2.49 g, 12.3 mmol) in dichloromethane (20 mL) was cooled on an ice-water bath. 3-pyridylmethanol (1.0 mL, 10.3 mmol) and 4-methylmorpholine (2.0 mL, 18.5 mmol) was added slowly. After 20 minutes, the ice-water bath was removed and the reaction mixture was allowed to warm up to room temperature. 30 minues later, ethyl acetate was added and the reaction mixture was filtered. The filtrate was washed with water, saturated sodium bicarbonate, brine, dried over MgSO4, filtered and evaporated to give a dark brown solid which was re-crystallized with ethyl acetate/heptane to give 4-nitrophenyl (3-pyridylmethyl) carbonate (1.52 g, 5.54 mmol). 1H NMR (CDCl-d) δ 7.38 (m, 3H), 7.79 (m, 1H), 8.28 (d, J=9.09 Hz, 2H), 8.65 (m, 1H), 8.72 (s, 1H).

b) 3-Pyridylmethyl N-[4-(4-Amino-7-tetrahydro-2H-4-pyranyl-7H-pyrrolo[2,3-d]pyrimidin-5-yl)-2-methoxyphenyl]carbamate 5-(4-Amino-3-methoxyphenyl)-7-tetrahydro-2H-4-pyranyl-7H-pyrrolo[2,3-d]pyrimidin-4-amine (25 mg, 0.074 mmol) was dissolved in dichloromethane (0.7 mL). Pyridine (0.7 mL) was added followed by 4-nitrophenyl (3-pyridylmethyl) carbonate (30 mg, 0.110 mmol). After heating at 100° C. overnight, the solvent was removed and the residue was purified by preparative LC/MS to give 3-pyridylmethyl N-[4-(4-amino-7-tetrahydro-2H-4-pyranyl-7H-pyrrolo[2,3-d]pyrimidin-5-yl)-2-methoxyphenyl] carbamate (12 mg, 0.025 mmol). 1H NMR (CDCl$_3$-d) δ 2.08 (m, 4H), 3.65 (m, 2H), 3.92 (s, 3H), 4.15 (m, 2H), 4.96 (m, 1H), 5.26 (s, 2H), 5.54 (bs, 2H), 6.97 (s, 1H), 7.04 (s, 1H), 7.08 (d, J=8.2 Hz, 1H), 7.35 (m, 2H), 7.79 (d, J=7.8 Hz, 1H), 8.15 (m, 1H), 8.29 (s, 1H), 8.61 (s, 1H), 8.71 (s, 1H). LC/MS MH$^+$=475.

b) 3-Pyridylmethyl N-[4-(4-Amino-7-tetrahydro-2H-4-pyranyl-7H-pyrrolo[2,3-d]pyrimidin-5-yl)-2-methoxyphenyl]carbamate Hydrochloride 3-Pyridylmethyl N-[4-(4-amino-7-tetrahydro-2H-4-pyranyl-7H-pyrrolo[2,3-d]pyrimidin-5-yl)-2-methoxyphenyl]carbamate (12 mg, 0.025 mmol) was dissolved in ethyl acetate (2.0 mL). 1.0N HCl in ether (1 mL) was added slowly. The precipatate was collected through filtration under nitrogen to give 3-pyridylmethyl N-[4-(4-amino-7-tetrahydro-2H-4-pyranyl-7H-pyrrolo[2,3-d]pyrimidin-5-yl)-2-methoxyphenyl]carbamate hydrochloride (13 mg, 0.25 mmol). 1H NMR (DMSO-d$_6$) δ 1.91 (m, 2H), 2.17 (m, 2H), 3.54 (m, 2H), 3.87 (s, 3H), 4.03 (m, 2H), 4.97 (m, 1H), 5.23 (s, 2H), 7.05 (d, J=8.2 Hz, 1H), 7.13 (s, 1H), 7.51 (m, 1H), 7.81 (d, J=8.2 Hz, 1H), 7.84 (s, 1H), 7.95 (m, 1H), 8.42 (s, 1H), 8.60 (s, 1H), 8.71 (s, 1H), 8.82 (s, 1H). LC/MS MH$^+$=475.

Example 247

2-Morpholinoethyl N-[4-(4-Amino-7-tetrahydro-2H-4-pyranyl-7H-pyrrolo[2,3-d]pyrimidin-5-yl)-2-methoxyphenyl]carbamate Hydrochloride Phenyl N-[4-(4-amino-7-tetrahydro-2H-4-pyranyl-7H-pyrrolo[2,3-d]pyrimidin-5-yl)-2-methoxyphenyl]carbamate (25 mg, 0.054 mmol) was mixed with 2-morpholino-1-ethanol (0.1 mL) in pyridine (0.7 mL). The reaction mixture was heated at 100° C. overnight. The solvent was removed and the residue was purified by preparative reverse phase HPLC to give 2-morpholinoethyl N-[4-(4-amino-7-tetrahydro-2H-4-pyranyl-7H-pyrrolo[2,3-d]pyrimidin-5-yl)-2-methoxyphenyl]carbamate (24 mg, 0.048 mmol). The solid was dissolved in ethyl acetate (2 mL) and 1.0N HCl in ether (0.2 mL) was added slowly. The precipitate was collected through filtration under nitrogen to give 2-morpholinoethyl N-[4-(4-amino-7-tetrahydro-2H-4-pyranyl-7H-pyrrolo[2,3-d]pyrimidin-5-yl)-2-methoxyphenyl]carbamate hydrochloride (24 mg, 0.045 mmol). 1H NMR (DMSO-d$_6$) δ 1.88(m, 2H), 2.16(m, 2H), 3.55(m, 8H), 3.90(s, 3H), 4.03 (m, 4H), 4.49(m, 2H), 4.92(m, 1H), 7.07(m, 1H), 7.15(s, 1H), 7.65(bs, 2H), 7.84(s, 1H), 8.45(s, 1H), 8.75(s, 1H) 10.95(bs, 1H). LC/MS MH$^+$=497.

Example 248

(4-Bromo-1,3-thiazol-5-yl)methyl N-[4-(4-Amino-7-tetrahydro-2H-4-pyranyl-7H-pyrrolo[2,3-d]pyrimidin-5-yl)-2-methoxyphenyl]carbamate a) 2,4-Dibromo-1,3-thiazole-5-carbaldehyde 1,3-Thiazolane-2,4-dione (3.52 g, 30 mmol) and phosphorus oxybromide (43 g, 150 mmol) were mixed with dimethyl formamide (2.56 mL, 34 mmol). The mixture was then heated at 75° C. for 1 hours and at 100° C. for 5 hours. After cooled to room temperature, the mixture was added to ice-water (500 ml) and the aqueous layer was extracted with dichloromethane. The combined organic layer was washed with saturated sodium bicarbonate, dried over MgSO4, filtered and evaporated to give a brown solid which was washed with petroleum ether. Evaporation of solvent gave 2,4-dibromo-1,3-thiazole-5-carbaldehyde (1.74 g, 6.42 mmol). IH NMR (CDCl$_3$-d) δ 9.90(S, 1H).

b) (2,4-Dibromo-1,3-thiazol-5-yl)methanol 2,4-Dibromo-1,3-thiazole-5-carbaldehyde (1.74 g, 6.42 mmol) was dissolved in methanol (70 ml) at 0° C. Sodium borohydride (0.244 g, 6.42 mmol) was added in small portions. The ice-water bath was removed 10 minutes later and the reaction mixture was stirred at room temperature overnight. Solvent was removed and saturated ammonium chloride was added. 1.0N NaOH was added to adjust the pH to 10. The aqueous layer was extracted with ethyl acetate. The combined organic layer was washed with brine, dried over MgSO4, filtered and evaporated. The residue was purified by flash column chromatogrphy to give (2,4-dibromo-1,3-thiazol-5-yl)methanol (0.946 g, 3.47 mmol). 1H NMR (CDCl$_3$-d) δ 2.11 (bs, 1H), 4.79(S, 2H).

c) (4-Bromo-1,3-thiazol-5-yl)methanol (2,4-Dibromo-1,3-thiazol-5-yl)methanol (0.94 g, 3.44 mmol), sodium carbonate tri-hydrade (1.34 g) and palladium on carbon (10%, 0.07g) were mixed in methanol (33 mL). The resulting mixture was hydrogenated at 60 psi for 2 days. The solid was filtered off through a pat of celite. The solvent was evaporated and the residue was purified by frash column chromatography to give (4-bromo-1,3-thiazol-5-yl)methanol (0.32 g, 2.78 mmol). 1H NMR (CDCl$_3$-d) δ 2.29 (bs, 1H), 4.86(s, 2H), 8.72(s, 1H).

d) (4-Bromo-1,3-thiazol-5-yl)methyl N-[4-(4-Amino-7-tetrahydro-2H-4-pyranyl-7H-pyrrolo[2,3-d]pyrimidin-5-yl)-2-methoxyphenyl]carbamate Phenyl N-[4-(4-amino-7-tetrahydro-2H-4-pyranyl-7H-pyrrolo[2,3-d]pyrimidin-5-yl)-2-methoxyphenyl]carbamate (28 mg, 0.061 mmol) was mixed with (4-bromo-1,3-thiazol-5-yl)methanol (50 mg, 0.434 mmol) in pyridine (0.5 mL). The reaction mixture was heated at 100° C. overnight. The solvent was removed and the residue was purified by preparative reverse phase LC/MS to give (4-bromo-1,3-thiazol-5-yl)methyl N-[4-(4-amino-7-tetrahydro-2H-4-pyranyl-7H-pyrrolo[2,3-d]pyrimidin-5-yl)-2-methoxyphenyl]carbamate. 1H NMR (CDCl-d) δ 2.07(m, 4H), 3.65(m, 2H), 3.92(s, 3H), 4.13(m, 2H), 4.98(m, 1H), 5.35(s, 1H), 5.40(s, 2H), 6.97(s, 1H), 7.04(s, 1H), 7.09(m, 1H), 7.35(s, 1H), 8.17(s, 1H), 8.32(s, 1H), 8.78(s, 1H). LC/MS MH$^+$=481.

Example 249

Tetrahydro-3-furanyl N-[4-(4-amino-7-tetrahydro-2H-4-pyranyl-7H-pyrrolo[2,3-d]pyrimidin-5-yl)-2-methoxyphenyl]carbamate Phenyl N-[4-(4-amino-7-tetrahydro-2H-4-pyranyl-7H-pyrrolo[2,3-d]pyrimidin-5-yl)-2-methoxyphenyl]carbamate (30 mg, 0.065 mmol) was mixed with tetrahydro-3-furanol (0.05 mL) in pyridine (0.5 mL). The reaction mixture was heated at 100° C. overnight. The solvent was removed and the residue was purified by preparative reverse phase PHLC to give tetrahydro-3-furanyl N-[4-(4-amino-7-tetrahydro-2H-4-pyranyl-7H-pyrrolo[2,3-d]pyrimidin-5-yl)-2-methoxyphenyl]carbamate (14 mg, 0.031 mmol). 1H NMR (CDCl-d) δ 2.07(m, 6H), 3.66(m, 2H), 3.96(m, 7H), 4.13(m, 2H), 4.98(m, 1H), 5.26(s, 2H), 5.40(m, 1H), 6.97(s, 1H), 7.04(s, 1H), 7.08(d, J=8.2 Hz, 1H), 7.26(s, 1H), 8.30(s, 1H), 8.32(s, 1H). LC/MS MH$^{30}$ =455.

Examples 250

1,3-Dioxan-5-yl N-[4-(4-amino-7-tetrahydro-2H-4-pyranyl-7H-pyrrolo[2,3-d]pyrimidin-5-yl)-2-methoxyphenyl]carbamate 1,3-Dioxolan-4-ylmethyl N-(4-(4-amino-7-tetrahydro-2H-4-pyranyl-7H-pyrrolo[2,3-d]pyrimidin-5-yl)-2-methoxyphenyl)carbamate Phenyl N-[4-(4-amino-7-tetrahydro-2H-4-pyranyl-7H-pyrrolo[2,3-d]pyrimidin-5-yl)-2-methoxyphenyl]carbamate (30 mg, 0.065 mmol) was mixed glycerol formal (0.05 mL) in pyridine (0.5 mL). The reaction mixture was heated at 100° C. overnight. The solvent was removed and the residue was purified by preparative reverse phase PHLC to give tetrahydro-3-furanyl N-[4-(4-amino-7-tetrahydro-2H-4-pyranyl-7H-pyrrolo[2,3-d]pyrimidin-5-yl)-2-methoxyphenyl]carbamate (2 mg, 0.004 mmol). 1H NMR (CDCl-d) δ 2.06(m, 4H), 3.66(m, 2H), 3.92(m, 3H), 4.07(m, 6H), 4.79(m, 1H), 4.83(d, J=6.3 Hz, 1H), 4.96(m, 1H), 5.04(d, J=6.3 Hz, 1H), 6.15(vbs, 2H), 6.96 (s, 1H), 7.05(m, 2H), 7.53(s, 1H), 8.15(d, J=8.2 Hz, 1H), 8.22(s, 1H). LC/MS MH$^{30}$ =471 and 1,3-dioxolan-4-ylmethyl N-(4-(4-amino-7-tetrahydro-2H-4-pyranyl-7H-pyrrolo[2,3-d]pyrimidin-5-yl)-2-methoxyphenyl)carbamate(6.0 mg, 0.013 mmol). 1H NMR (CDCl-d) δ 2.06(m, 4H), 3.66(m, 2H), 3.75(m, 1H), 3.92(m, 3H), 4.03(m, 1H), 4.13(m, 1H), 4.34(m, 2H), 4.94(s, 1H), 4.97(m, 1H), 5.10(s, 1H), 5.32(bs, 2H), 6.97(s, 1H), 7.03 (m, 2H), 7.06(d, J=8.2 Hz, 1H), 7.38(s, 1H), 8.15(d, J=7.9 Hz, 1H), 8.31(s, 1H). LC/MS MH$^{30}$ =471.

Example 251

2-Pyridylmethyl N-[4-(4-Amino-7-tetrahydro-2H-4-pyranyl-7H-pyrrolo[2,3-d]pyrimidin-5-yl)-2-methoxyphenyl]carbamate Hydrochloride Phenyl N-[4-(4-amino-7-tetrahydro-2H-4-pyranyl-7H-pyrrolo[2,3-d]pyrimidin-5-yl)-2-methoxyphenyl]carbamate (30 mg, 0.065 mmol) was mixed 2-pyridylmethanol (0.05 mL) in pyridine (0.5 mL). The reaction mixture was heated at 100° C. overnight. The solvent was removed and the residue was purified by preparative reverse phase LC/MS to give 2-pyridylmethyl N-[4-(4-amino-7-tetrahydro-2H-4-pyranyl-7H-pyrrolo[2,3-d]pyrimidin-5-yl)-2-methoxyphenyl]carbamate (11 mg, 0.023 mmol). The solid was dissolved in ethyl acetate (2 mL) and 1.0N HCl in ether (0.1 mL) was added slowly. The precipitate was collected through filtration under nitrogen to give 2-pyridylmethyl N-[4-(4-amino-7-tetrahydro-2H-4-pyranyl-7H-pyrrolo[2,3-d]pyrimidin-5-yl)-2-methoxyphenyl]carbamate hydrochloride (12 mg, 0.023 mmol). 1H NMR (DMSO-d$_6$) δ 1.92(m, 2H), 2.16(m, 2H), 3.55(m, 2H), 3.89(s, 3H), 4.02(m, 2H), 4.91 (m, 1H), 5.23(s, 2H), 7.05(d, J=8.2 Hz, 1H), 7.14 (s, 1H), 7.37(m, 1H), 7.53(d, J=7.8 Hz, 1H), 7.87(m, 3H), 8.42(s, 1H), 8.57(d, J=4.2 Hz, 1H), 8.85(s, 1H). LC/MS MH$^{30}$ =475.

Example 252

4-Pyridylmethyl N-[4-(4-Amino-7-tetrahydro-2H-4-pyranyl-7H-pyrrolo[2,3-d]pyrimidin-5-yl)-2-methoxyphenyl]carbamate Hydrochloride Phenyl N-[4-(4-amino-7-tetrahydro-2H-4-pyranyl-7H-pyrrolo[2,3-d]pyrimidin-5-yl)-2-methoxyphenyl]carbamate (30 mg, 0.065 mmol) was mixed 4-pyridylmethanol (0.05 mL) in pyridine (0.5 mL). The reaction mixture was heated at 100° C. overnight. The solvent was removed and the residue was purified by preparative reverse phase LC/MS to give 2-pyridylmethyl N-[4-(4-amino-7-tetrahydro-2H-4-pyranyl-7H-pyrrolo[2,3-d]pyrimidin-5-yl)-2-methoxyphenyl]carbamate (11 mg, 0.023 mmol). The solid was dissolved in ethyl acetate (2 mL) and 1.0N HCl in ether (0.1 mL) was added slowly. The precipatate was collected through filtration under nitrogen to give 4-pyridylmethyl N-[4-(4-amino-7-tetrahydro-2H-4-pyranyl-7H-pyrrolo[2,3-d]pyrimidin-5-yl)-2-methoxyphenyl]carbamate hydrochloride (12 mg, 0.023 mmol). 1H NMR (DMSO-$d_6$) δ 1.91(m, 2H), 2.16(m, 2H), 3.55(m, 2H), 3.90(s, 3H), 4.03 (m, 2H), 4.92(m, 1H), 5.34(s, 2H), 7.06(d, J=8.2 Hz, 1H), 7.16(s, 1H), 7.73(m, 1H), 7.81(m, 1H), 7.87(s, 1H), 8.46(s, 1H), 8.76(d, J=5.6 Hz, 1H), 9.05(s, 1H). LC/MS: MH$^{30}$ =475.

Example 253

(5-Methyl-3-isoxazolyl)methyl N-[4-(4-Amino-7-tetrahydro-2H-4-pyranyl-7H-pyrrolo[2,3-d]pyrimidin-5-yl)-2-methoxyphenyl]carbamate Phenyl N-[4-(4-amino-7-tetrahydro-2H-4-pyranyl-7H-pyrrolo[2,3-d]pyrimidin-5-yl)-2-methoxyphenyl]carbamate (30 mg, 0.065 mmol) was mixed with (5-methyl-3-isoxazolyl)methanol (0.05 mL) in pyridine (0.5 mL). The reaction mixture was heated at 100° C. overnight. The solvent was removed and the residue was purified by preparative reverse phase LC/MS to give (5-methyl-3-isoxazolyl)methyl N-[4-(4-amino-7-tetrahydro-2H-4-pyranyl-7H-pyrrolo[2,3-d]pyrimidin-5-yl)-2-methoxyphenyl]carbamate (18 mg, 0.038 mmol). 1H NMR (CDCl-d) δ 2.06(m, 4H), 2.44(s, 3H), 3.64(m, 2H), 3.91(s, 3H), 4.13(m, 2H), 4.96(m, 1H), 5.26 (s, 2H), 6.12(s, 1H), 6.95(s, 1H), 7.06(m, 2H), 7.39(s, 1H), 8.17(bs, 1H), 8.21(s, 1H). LC/MS: MH$^+$479.

Example 254

[(2S)-5-Oxotetrahydro-1H-2-pyrrolyl]methyl N-[4-(4-Amino-7-tetrahydro-2H-4-pyranyl-7H-pyrrolo[2,3-d]pyrimidin-5-yl)-2-methoxyphenyl]carbamate Phenyl N-[4-(4-amino-7-tetrahydro-2H-4-pyranyl-7H-pyrrolo[2,3-d]pyrimidin-5-yl)-2-methoxyphenyl]carbamate (30 mg, 0.065 mmol) was mixed with (5S)-5-(hydroxymethyl)tetrahydro-1H-2-pyrrolone (0.05 mL) in pyridine (0.5 mL). The reaction mixture was heated at 100° C. overnight. The solvent was removed and the residue was purified by preparative reverse phase LC/MS to give [(2S)-5-oxotetrahydro-1H-2-pyrrolyl]methyl N-[4-(4-amino-7-tetrahydro-2H-4-pyranyl-7H-pyrrolo[2,3-d]pyrimidin-5-yl)-2-methoxyphenyl]carbamate (10 mg, 0.02lmmol). 1H NMR (CDCl-d) δ 1.90(m, 1H), 2.06(m, 4H), 2.34(m, 1H), 2.41(m, 2H), 3.64(m, 2H), 3.94 (s, 3H), 4.04(m, 2H), 4.14(m, 2H), 4.98(m, 1H), 5.33(m, 3H), 6.10(s, 1H), 6.98(s, 1H), 7.04 (s, 1H), 7.09(m, 1H), 7.31(s, 1H), 8.11(bs, 1H), 8.32(s, 1H). LC/MS: MH$^+$481.

Example 255

4-Aminobenzyl N-(4-(4-Amino-7-tetrahydro-2H-4-pyranyl-7H-pyrrolo[2,3-d]pyrimidin-5-yl)-2-methoxyphenyl)carbamate a) tert-Butyl N-(4-(Hydroxymethyl)phenyl)carbamate (4-Aminophenyl)methanol (1.23 g, 10 mmol) and diisopropylethylamine (2.6 mL, 15 mmol) was mixed with di-tert-butyl dicarbonate (2.62 g, 12 mmol) in dichloromethane (50 mL). The mixture was stirred at room temperature overnight. Ethyl acetate was added and the organic layer was washed with water, 1.0N HCl, saturated sodium carbonate, water, brine, dried over MgSO4, filtered and evaporated. The crude product was purified by flash column chromatography with Ethyl acetate/heptane (2:3) to give tert-butyl N-(4-(hydroxymethyl)phenyl)carbamate (2.16 g, 9.67 mmol). 1H NMR (CDCl-d) δ 1.52(s, 9H), 4.63(s, 2H), 6.47(bs, 1H), 7.30(d, 8.5 Hz, 2H), 7.36(d, 8.5 Hz,2H).

b) 4-Aminobenzyl N-(4-(4-Amino-7-tetrahydro-2H-4-pyranyl-7H-pyrrolo[2,3-d]pyrimidin-5-yl)-2-methoxyphenyl)carbamate Phenyl N-[4-(4-amino-7-tetrahydro-2H-4-pyranyl-7H-pyrrolo[2,3-d]pyrimidin-5-yl)-2-methoxyphenyl]carbamate (51 mg, 0.111 mmol) was mixed with tert-butyl N-(4-(hydroxymethyl)phenyl)carbamate (119 mg, 0.533) in pyridine (0.8 mL). The reaction mixture was heated at 100° C. overnight. The solvent was removed and the residue was purified by preparative reverse phase LC/MS to give 4-aminobenzyl N-(4-(4-amino-7-tetrahydro-2H-4-pyranyl-7H-pyrrolo[2,3-d]pyrimidin-5-yl)-2-methoxyphenyl) carbamate (9 mg, 0.015 mmol). 1H NMR (CDCl-d) δ 1.52(s, 1H), 2.08(m, 4H), 3.65(m, 2H), 3.90(s, 3H), 4.14(m, 2H), 4.97(m, 1H), 5.17(s, 2H), 5.37(bs, 1H), 6.55(s, 1H), 6.95(s, 1H), 7.03(s, 1H), 7.06(m, 1H), 7.31(s, 1H), 7.38(m, 3H), 8.16(bs, 1H), 8.30(s, 1H). LC/MS: MH$^+$589.

Example 256

N1-[4-(4-Amino-7-tetrahydro-2H-4-pyranyl-7H-pyrrolo[2,3-d]pyrimidin-5-yl)-2-methoxyphenyl]benzamide 5-(4-Amino-3-methoxyphenyl)-7-tetrahydro-2H-4-pyranyl-7H-pyrrolo[2,3-d]pyrimidin-4-amine (80 mg, 0.236 mmol) was dissolved in dichloromethane (2.0 mL). Pyridine (2.0 mL) was added followed by benzoyl chloride (41 uL, 0.353 mmol). After stirring at room temperature for 2 hours, the solvent was removed and the residue was dissolved in 1 ml DMSO, methanol (1 mL) was added and precipitate was formed. The solid was collected by filtration to give N1-[4-(4-amino-7-tetrahydro-2H-4-pyranyl-7H-pyrrolo[2,3-d]pyrimidin-5-yl)-2-methoxyphenyl]benzamide (64 mg, 0.144 mmol). 1H NMR (CDCl$_3$-d) δ 2.12(m, 4H), 3.67(m, 2H), 3.99(s, 3H), 4.17(m, 2H), 4.99(m, 1H), 7.03(s, 1H), 7.04(s, 1H), 7.14(d, J=8.2 Hz, 1H), 7.53(m, 3H), 7.94(d, J=7.8 Hz, 1H), 8.33(s, 1H), 8.58(s, 1H), 8.63(d, J=8.2 Hz, 1H). LC/MS: MH$^+$=444.

Example 257

N2-[4-(4-Amino-7-tetrahydro-2H-4-pyranyl-7H-pyrrolo[2,3-d]pyrimidin-5-yl)-2-methoxyphenyl]-2-pyridinecarboxamide 5-(4-Amino-3-methoxyphenyl)-7-tetrahydro-2H-4-pyranyl-7H-pyrrolo[2,3-d]pyrimidin-4-amine (80 mg, 0.236 mmol) was dissolved in dichloromethane (2.0 mL). Pyridine (2.0 mL) was added followed by 2-pyridinecarbonyl chloride hydrochloride (63 mg, 0.353 mmol). After stirring at room temperature for 2 hours, the solvent was removed and the residue was dissolved in 1 ml DMSO, methanol (1 mL) was added and precipitate was formed. The solid was collected by filtration to give N1-[4-(4-amino-7-tetrahydro-2H-4-pyranyl-7H-pyrrolo[2,3-d]pyrimidin-5-yl)-2-methoxyphenyl]benzamide (84 mg, 0.189 mmol). 1H NMR (CDCl$_3$-d) δ 2.12(m, 4H), 3.67(m, 2H), 4.03(s, 3H), 4.14(m, 2H), 5.00(m, 1H), 5.37(s, 1H), 7.04(s, 1H), 7.09(s, 1H), 7.14(d, J=8.2 Hz, 1H), 7.50(m, 1H), 7.92(m, 1H), 8.33(s, 1H), 8.70(d, J=8.2 Hz, 1H), 10.62(s, 1H). LC/MS: MH$^+$=445.

Example 258

N5-[4-(4-Amino-7-tetrahydro-2H-4-pyranyl-7H-pyrrolo[2,3-d]pyrimidin-5-yl)-2-methoxyphenyl]-1,3-dimethyl-1H-5-pyrazolecarboxamide 5-(4-Amino-3-methoxyphenyl)-7-tetrahydro-2H-4-pyranyl-7H-pyrrolo[2,3-d]pyrimidin-4-amine (80 mg, 0.236 mmol) was dissolved in dichloromethane (2.0 mL). Pyridine (2.0 mL) was added followed by 2-pyridinecarbonyl chloride hydrochloride (63 mg, 0.353 mmol). After stirring at room temperature for 2 hours, the solvent was removed and the residue was dissolved in I ml DMSO, methanol (1 mL) was added and precipitate was formed. The solid was collected by filtration to give N5-[4-(4-amino-7-tetrahydro-2H-4-pyranyl-7H-pyrrolo[2,3-d]pyrimidin-5-yl)-2-methoxyphenyl]-1,3-dimethyl-1H-5-pyrazolecarboxamide (30 mg, 0.065 mmol). 1H NMR (CDCl$_3$-d) δ 2.11 (m, 4H), 2.32(s, 3H), 3.66(m, 2H), 3.99(s, 3H), 4.13(m, 2H), 4.17(s, 3H), 4.99(m, 1H), 5.22(bs, 2H), 6.46(s, 1H), 7.03 (s, 1H), 7.07(s, 1H), 7.12(d, J=8.2 Hz, 1H), 8.33 (2, 2H), 8.49(d, J=8.2 Hz, 1H). LC/MS: MH$^+$=462.

Example 259

N1-[4-(4-Amino-7-tetrahydro-2H-4-pyranyl-7H-pyrrolo[2,3-d]pyrimidin-5-yl)-2-methoxyphenyl]-2,2-dimethylpropanamide 5-(4-Amino-3-methoxyphenyl)-7-tetrahydro-2H-4-pyranyl-7H-pyrrolo[2,3-d]pyrimidin-4-amine (50 mg, 0.147 mmol) was dissolved in dichloromethane (1.5 mL). Pyridine (1.5 mL) was added followed by 2,2-dimethylpropanoyl chloride (31 mg, 0.221 mmol). After stirring at room temperature for 2 hours, the solvent was removed and the residue was dissolved in 1 ml DMSO, methanol (1 mL) was added and precipitate was formed. The solid was collected by filtration to give N1-[4-(4-amino-7-tetrahydro-2H-4-pyranyl-7H-pyrrolo[2,3-d]pyrimidin-5-yl)-2-methoxyphenyl]-2,2-dimethylpropanamide (27 mg, 0.064 mmol). 1H NMR (CDCl$_3$-d) δ 1.35(s, 9H), 2.09 (m, 4H), 3.66(m, 2H), 3.96(s, 3H), 4.13(m, 2H), 4.97(m, 1H), 5.46 (bs, 2H), 6.98(s, 1H), 7.04(s, 1H), 7.07(d, J=8.2 Hz, 1H), 8.15(s, 1H), 8.29(s, 1H), 8.49(d, J=8.2 Hz, 1H). LC/MS: MH$^{30}$=424.

Example 260

N1-[4-(4-Amino-7-tetrahydro-2H-4-pyranyl-7H-pyrrolo[2,3-d]pyrimidin-5-yl)-2-methoxyphenyl]-1-cyclopentanecarboxamide 5-(4-Amino-3-methoxyphenyl)-7-tetrahydro-2H-4-pyranyl-7H-pyrrolo[2,3-d]pyrimidin-4-amine (50 mg, 0.147 mmol) was dissolved in dichloromethane (1.5 mL). Pyridine (1.5 mL) was added followed by 1-cyclopentanecarbonyl chloride (31 mg, 0.221 mmol). After stirring at room temperature for 2 hours, the solvent was removed and the residue was dissolved in 1 ml DMSO, methanol (1 mL) was added and precipitate was formed. The solid was collected by filtration to give N1-[4-(4-amino-7-tetrahydro-2H-4-pyranyl-7H-pyrrolo[2,3-d]pyrimidin-5-yl)-2-methoxyphenyl]-2,2-dimethylpropanamide (33 mg, 0.076 mmol). 1H NMR (CDCl$_3$-d) δ 1.66(m, 2H), 1.81 (m, 2H), 1.95(m, 4H), 2.06(m, 4H), 2.77(m, 1H), 3.65(m, 2H), 3.94(s, 3H), 4.15(m, 2H), 4.96(m, 1H), 5.37(bs, 2H), 6.98(s, 1H), 7.03(s, 1H), 7.07(d, J=8.2 Hz, 1H), 7.84 (s, 1H), 8.30(s, 1H), 8.49(d, J=8.2 Hz, 1H). LC/MS: MH$^{30}$=437.

Example 261

N1-[4-(4-Amino-7-tetrahydro-2H-4-pyranyl-7H-pyrrolo[2,3-d]pyrimidin-5-yl)-2-methoxyphenyl]-3-phenylpropanamide 5-(4-Amino-3-methoxyphenyl)-7-tetrahydro-2H-4-pyranyl-7H-pyrrolo[2,3-d]pyrimidin-4-amine (50 mg, 0.147 mmol) was dissolved in dichloromethane (1.5 mL). Pyridine (1.5 mL) was added followed by 3-phenylpropanoyl chloride (37 mg, 0.221 mmol). After stirring at room temperature for 2 hours, the solvent was removed and the residue was dissolved in 1 ml DMSO, methanol (1 mL) was added and precipitate was formed. The solid was collected by filtration to give Nl-[4-(4-amino-7-tetrahydro-2H-4-pyranyl-7H-pyrrolo[2,3-d]pyrimidin-5-yl)-2-methoxyphenyl]-2,2-dimethylpropanamide (7 mg, 0.015 mmol). 1H NMR (CDCl$_3$-d) δ 2.07(m, 4H), 2.75 (m, 2H), 3.09(m, 2H), 3.65(m, 2H), 3.88(s, 3H), 4.13(m, 2H), 4.96(m, 1H), 5.97 (bs, 2H), 6.93(s, 1H), 7.05(m, 2H), 7.26(m, 5H), 7.70(s, 1H), 8.24(s, 1H), 8.46(d, J=8.2 Hz, 1H). LC/MS: MH$^+$=472.

Examples 262-267 were synthesized using the following procedure:

a)

A mixture of cis-5-(4-amino-3-methoxyphenyl0-7-[4-(4-methylpiperazino)cyclohexyl]-7H-pyrrolo[2,3-d]pyrimidin-4-amine (0.25 g, 0.575 mmol), pyridine (2.5 ml) and dichloromethane (2.5 ml) was treated with the appropriate acid chloride (0.862 mmol) and then stirred at ambient temperature under an atmosphere of nitrogen for 1 hour. The solvents were removed under reduced pressure and the residue was purified by preparative reverse phase chromatography. The compound (280 mg, 0.460 mmol) was dissolved in hot ethyl acetate (25 ml) then treated with maleic acid (160 mg, 1.38 mmol) dissolved in ethyl acetate (10 ml) the mixture was allowed to cool to ambient temperature then stirred for 1 hour. The solid was collected by filtration and dried to give the compound as the trimaleate salt. (370 mg).

Analytical RP-HPLC RT listed in the table were obtained on a Hypersil HS C18 column ((5 um, 100 A) 250×4.6 mm) using a linear gradient of 25–100% acetonitrile/0.1 M ammonium acetate over 10 min at 1 ml/min. Retention time is indicated by "RT" Mass spectrum molecular weights are indicated by "MH+".

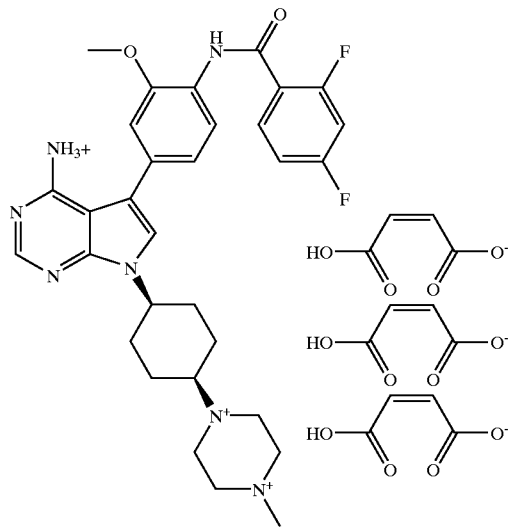

Example 262

RT 6.62
MH+576.3
Gradient a

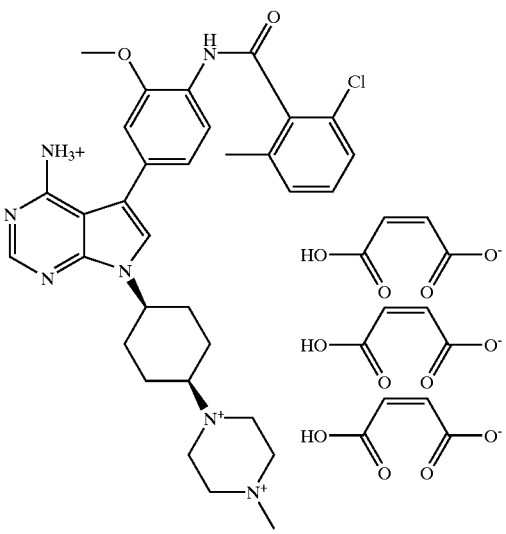

Example 264

RT 14.23
MH+588.3
Gradient b

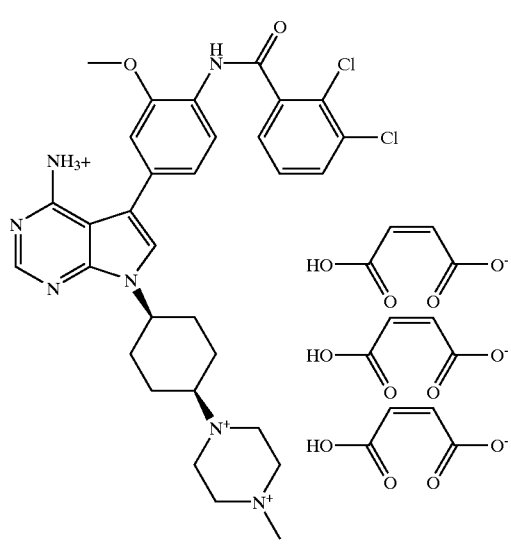

Example 263

RT 7.7
MH+608.2
Gradient a

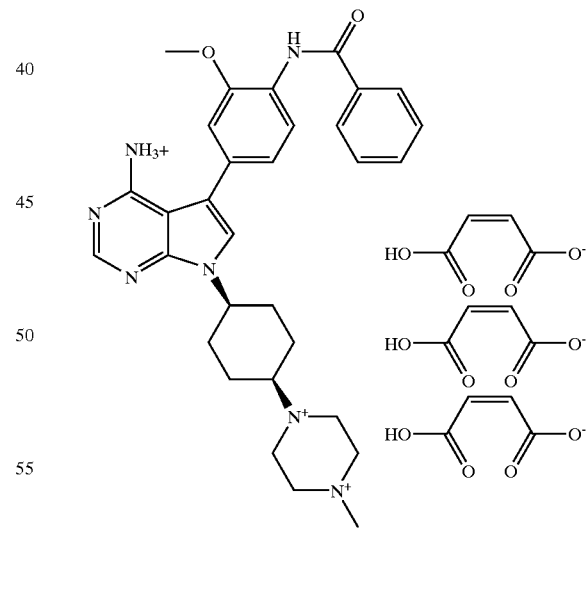

Example 265

RT 6.85
MH+540.2
Gradient a

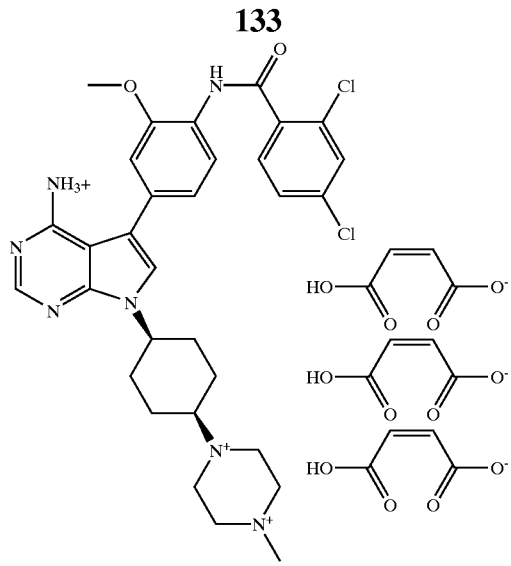

Example 266

RT 8.15
MH+608.2
Gradient a

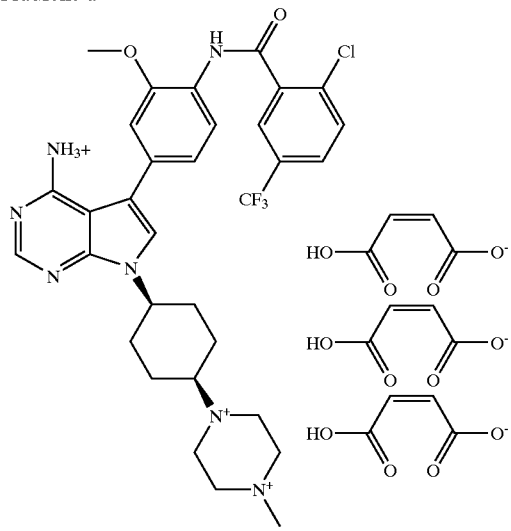

Example 267

RT 8.15
MH+642.3

General Salt Formation Procedure

Trans-benzyl N-(4-{4-amino-7-[4-(4-methylpiperazino)cyclohexyl]-7H-pyrrolo[2,3-d]pyrimidin-5-yl}-2-methoxyphenyl)carbamate was dissolved in ethylacetate and treated with maleic acid (280 mg) in ethylacetate. The resulting solid was filtered under a stream of nitrogen and dried in vacuo for 4 hr to give Cis-benzyl N-(4-{4-amino-7-[4-(4-methylpiperazino)cyclohexyl]-7H-pyrrolo[2,3-d]pyrimidin-5-yl}-2-methoxyphenyl)carbamate tri-maleate salt (580 mg) as a cream solid. M.pt. 158° C. (dec.)

$^1$H NMR (d$_6$ DMSO, 400 MHz):8.74(1H, s), 8.27 (1H, s), 7.78(1H, d), 7.35–7.77(5H, m), 7.10(1H, s), 7.04(1H, s), 6.16(6H, s), 5.17(2H, s), 4.74(1H, m), 3.82(3H, s), 3.23 (5H, m), 2.78(3H, s), 2.51(3H, m), 2.41(1H, s), 2.09(4H, m), 1.70(4H, m). HPLC: (5 to 95% CH$_3$CN in 0.1 N aqueous ammonium acetate over 20 min.) t$_r$=13.30 min, 94%.

In a similar manner were prepared the following salts. The LCMS conditions are described below.

LSMS data: Perkin Elmer Pecosphere C18, 3mM, 33 x 4.6, 3.5 ml/min 100 - 100% 50 mM ammonium acetate to acetonitrile in 4.5 minutes

| Structure | Ret. Time | MH+ |
|---|---|---|
| 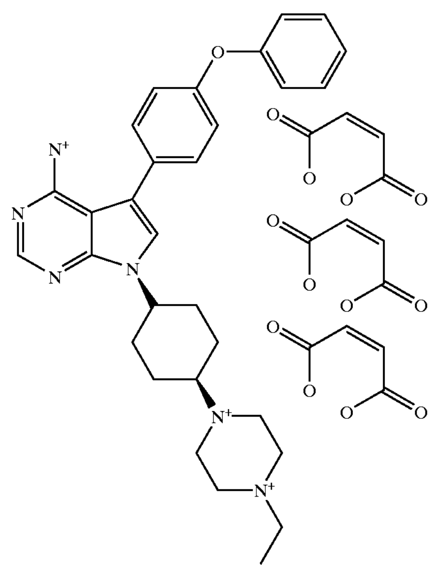 | 2.92 | 497.1 |
| 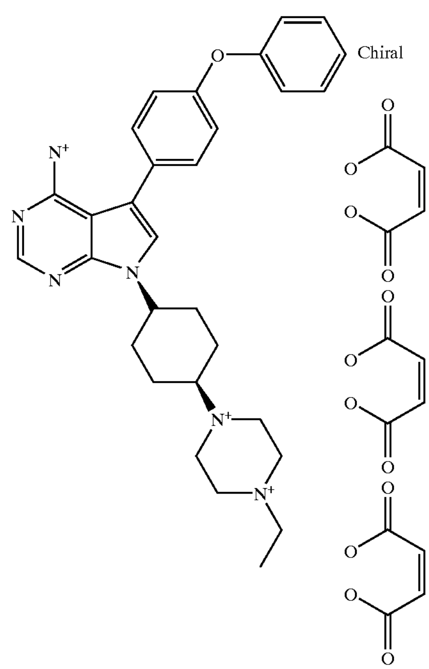 | 3.02 | 497.2 |

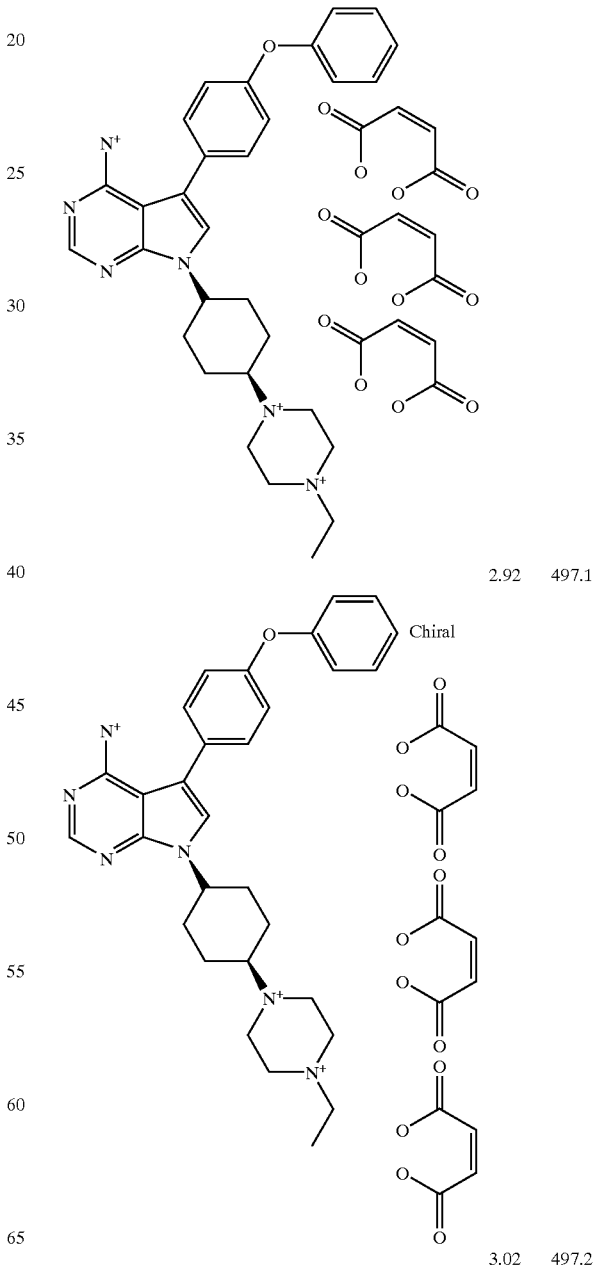

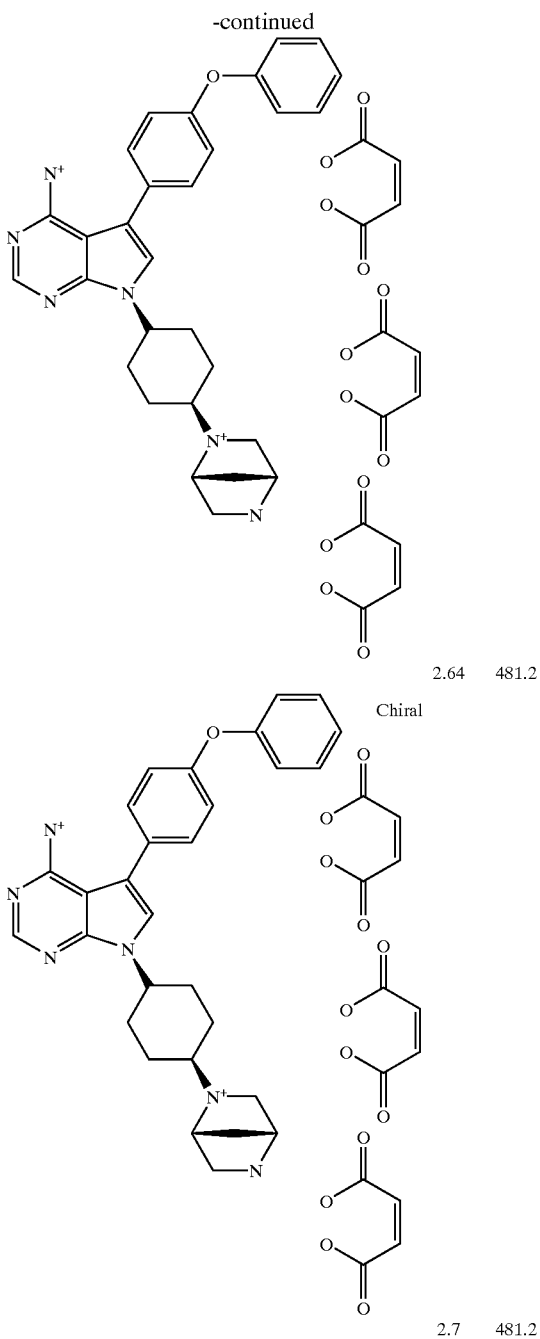

2.64  481.2

Chiral 2.7  481.2

Example 268 cis and trans-N1-(4-4-Amino-7-[4-(4-methylpiperazino)cyclohexyl]-7H-pyrrolo[2,3-d]pyrimidin-5-yl-2-methoxyphenyl)-3-phenylpropanamide To 4-[4-amino-5-(4-amino-3-methoxyphenyl)-7H-pyrrolo[2,3-d]pyrimidin-7-yl]-1-cyclohexanone (0.8 g, 2.3 mmol) in pyridine/dichloromethane (1:2.5, 45 ml) was added hydrocinnamylchloride (0.57 g, 3.4 mmol) in dichloromethane (2 ml) at 0° C. under a flow of nitrogen. The solution was stirred at 0° C. for 2 hr. The solution was quenched with saturated aquoeus citric acid solution (50 ml) and the organic layer was washed with saturated aquoeus citric acid solution (2×50 ml). Dry, filter and concentrate to leave a brown foam (1.0 g). This was dissolved in dichloroethane (100 ml) and N-methylpiperazine (0.63 g, 6.3 mmol) and acetic acid (0.38 g, 6.3 mmol) was added. Sodium triacetoxyborohydride (0.67 g, 3.15 mmol) was added portionwise under nitrogen and the mixture stirred overnight at room temperature. Quench with saturated aq. NaHCO3 solution (50 ml) and extract with dichloromethane (3×100 ml). The combined organics were dried (sodium sulphate), filtered and evaporated to leave a sludge which was purified by flash silica gel column chromatography using dichloromethane/methanol (100/0 to 50/50 in 5% increments). The fractions corresponding to the faster running material were combined to give cis- N1-(4-4-amino-7-[4-(4-methylpiperazino)cyclohexyl]-7H-pyrrolo[2,3-d] pyrimidin-5-yl-2-methoxyphenyl)-3-phenylpropanamide (0.26 g) as a glass. This was dissolved in ethylacetate (5 ml) and maleic acid (160 mg) in ethylacetate (2 ml) added. The resulting solid was filtered to give cis-N1-(4-4-amino-7-[4-(4-methylpiperazino)cyclohexyl]-7H-pyrrolo[2,3-d] pyrimidin-5-yl-2-methoxyphenyl)-3-phenylpropanamide trimaleate salt (260 mg) as a white solid. Analytical LC/MS conditions: Column: Pecosphere, C18, 3 um, 33×4.6 mm. Eluent: 0% B/A to 100% B/A in 4.5 min.(B: acetonitrile, A: 50 mM ammonia acetate buffer, PH 4.5), 3.5 mL/min. ($r_t$=2.86 mins, 568.4).

The fractions corresponding to the slower running material were combined to give trans-N1-(4-4-amino-7-[4-(4-methylpiperazino)cyclohexyl]-7H-pyrrolo[2,3-d]pyrimidin-5-yl-2-methoxyphenyl)-3-phenylpropanamide (0.11 g) as a glass. This was dissolved in ethylacetate (5 ml) and treated with a solution of maleic acid (68 mg) in ethylacetate (2 ml). The resulting solid was filtered to give trans-N1-(4-4-amino-7-[4-(4-methylpiperazino)cyclohexyl]-7H-pyrrolo[2,3-d] pyrimidin-5-yl-2-methoxyphenyl)-3-phenylpropanamide tri-maleate (94 mg) as a white solid. Analytical LC/MS conditions: Column: Pecosphere, C18, 3 um, 33×4.6 mm. Eluent: 0% B/A to 100% B/A in 4.5 min.(B: acetonitrile, A: 50 mM ammonia acetate buffer, PH 4.5), 3.5 mL/min. ($r_t$=2.68 mins, 568.2).

4-[4-amino-5-(4-amino-3-methoxyphenyl)-7H-pyrrolo[2,3-d]pyrimidin-7-yl]-1-cyclohexanone (2.25 g, 6.5 mmol), acetic acid (1.17 g, 19.5 mmol) and N-methylpiperazine (1.95 g, 19.5 mmol) were dissolved in dichloroethane (200 ml). Sodium triacetoxyborohydride (2.07 g, 9.75 mmol) was added portionwise and the mixture stirred at room temperature overnight. Saturated sodium bicarbonate solution (150 ml) was added and the aqueous layer extracted with dichloromethane (3×100 ml). The combined organics were washed with water, dried (sodium sulphate), filtered and evaporated to leave a semi-solid whaich was purified by flash silica gel column chromatography using CH$_2$Cl$_2$/methanol (0% MeOH to 50% MeOH in 5% increments). The fractions corresponding to the faster running material were combined and evaporated to give cis-5-(4-amino-3-methoxyphenyl)-7-[4-(4-methylpiperazino)cyclohexyl]-7H-pyrrolo[2,3-d]pyrimidin-4-amine (1.2 g, 43%) as a cream solid. $^1$H NMR (d$_6$-DMSO): δ 8.1(1H, s), 7.11 (1H, s), 6.87(1H, s), 6.79(1H, d), 6.05(2H, bs), 4.80(2H, bs), 4.64(1H, m), 4.08(1H, m), 3.82(3H, s), 3.17(2H, m), 2.37(6H, m), 2.21(3H, s), 2.08 (4H, m), 1.70(2H, m), 1.53(2H, m). HPLC (r$_t$=11.24 min, 97.6%).

The fractions corresponding to the slower running material were combined and evaporated to give trans-5-(4-amino-3-methoxyphenyl)-7-[4-(4-methylpiperazino)cyclohexyl]-7H-pyrrolo[2,3-d]pyrimidin-4-amine (0.4 g, 14%) as a white solid. $^1$H NMR (d$_6$-DMSO): δ 8.10(1H, s), 7.26(1H, s), 6.87(1H, s), 6.77(1H, d), 6.71(1H, d), 6.05(2H, bs), 4.79(2H, s), 4.52(1H, m), 3.81(3H, s), 3.35(1H, m), 2.50(5H, m), 2.31(5H, m), 2.14(1H, m), 1.97(6H, m), 1.45 (2H, m). HPLC (r$_t$=10.13 min, 97.9%).

To a solution of cis-5-(4-amino-3-methoxyphenyl)-7-[4-(4-methylpiperazino)cyclohexyl]-7H-pyrrolo[2,3-d]pyrimidin-4-amine (30 mg, 0.069 mmol) in pyridine (0.5 ml) was added the appropriate acid chloride (2 eq., 0.138 mmol).

The vials were capped and shaken overnight on an orbital shaker. Another two equivalent of acid chlorides (0.138 mmol) was added in two portions (1 equivalent each) and the resulting mixtures were shaken overnight again. LCMS (Micromass-Column: Pecosphere, C18, 3 um, 33×4.6 mm. Eluents: 0% B/A to 100% B/A in 4.5 min.(B: acetonitrile, A: 50 mM ammonia acetate buffer, PH 4.5), 3.5 mL/min.) of the resulting mixtures showed presence of product in all cases. The solutions were evaporated to dryness and the resulting residues were re-dissolved in a small volume of DMF and purified by reverse phase prep. HPLC. The structures are detailed below alongwith the appropriate LCMS data.

Examples 269 to 293 were made by methods analogous to Example 268.

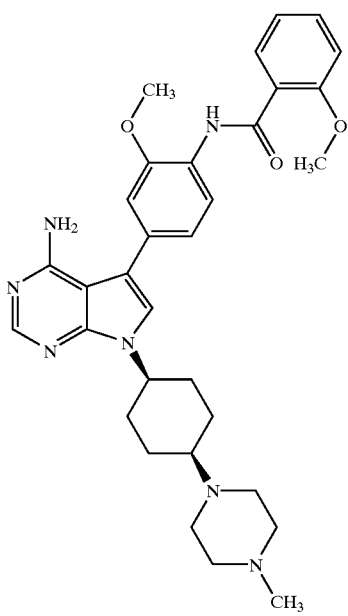

Example 270

RT 3.02
MH+570.3

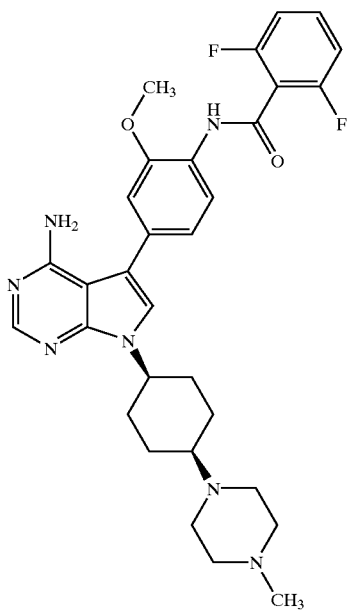

Example 269

RT 2.61
MH+576.3

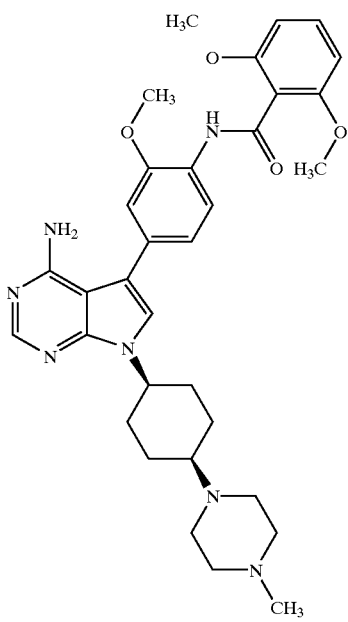

Example 271

RT 2.61
MH+600.3

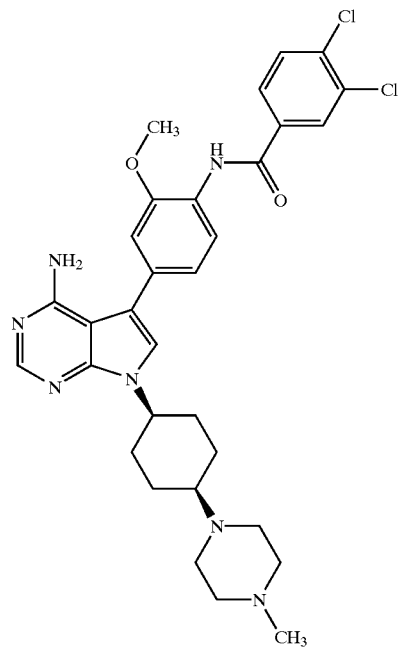
Example 272
RT 3.26
MH+608.3
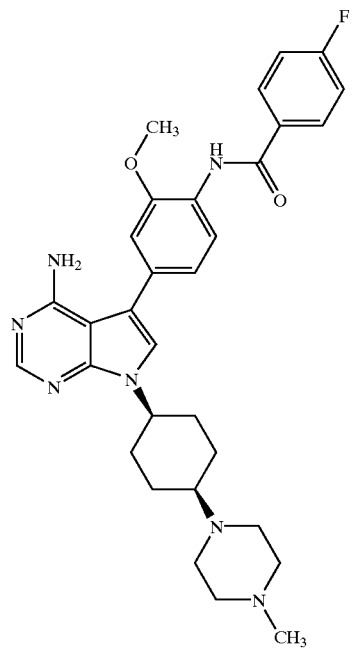
Example 274
RT 2.78
MH+558.4
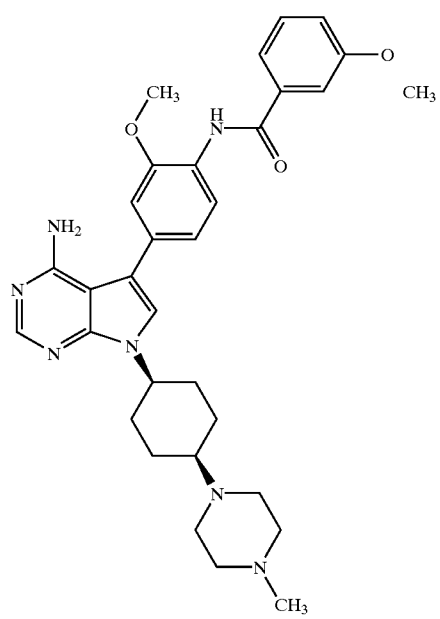
Example 273
RT 2.74
MH+570.3
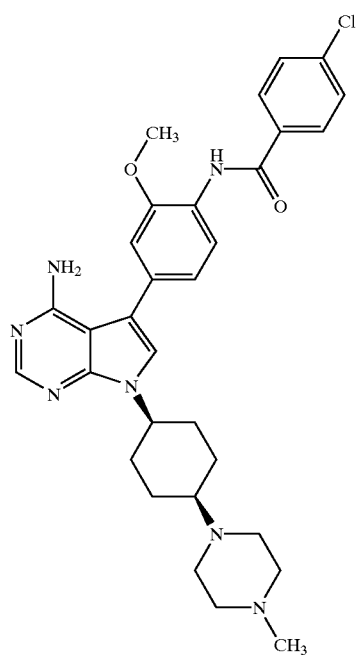
Example 275
RT 3.00
MH+574.3

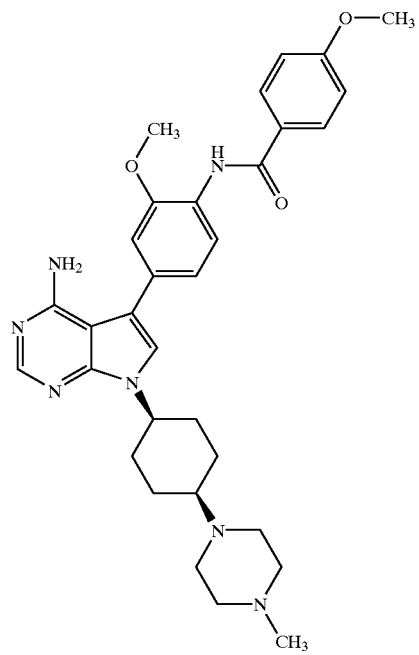
Example 276
RT 2.76
570.3
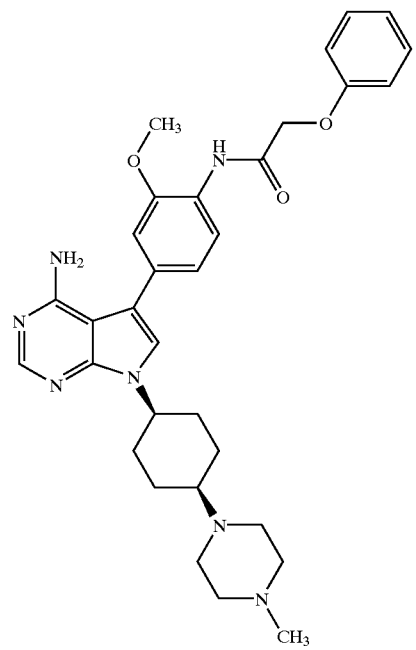
Example 278
RT 2.94
MH+570.3
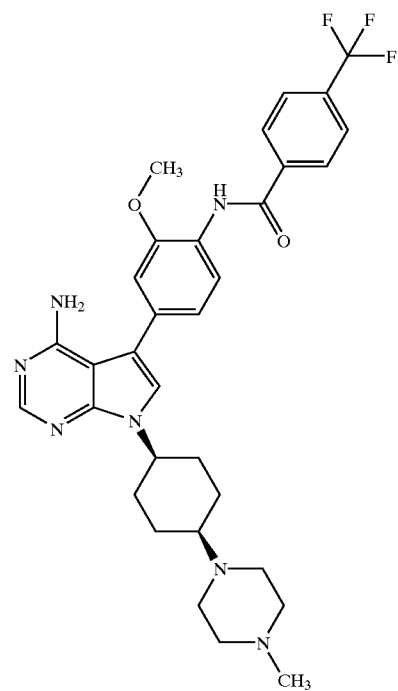
Example 277
RT 3.26
MH+608.3
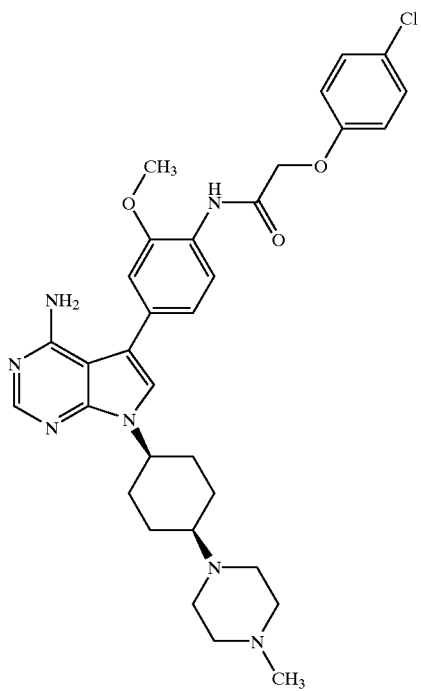
Example 279
RT 3.13
MH+604.3

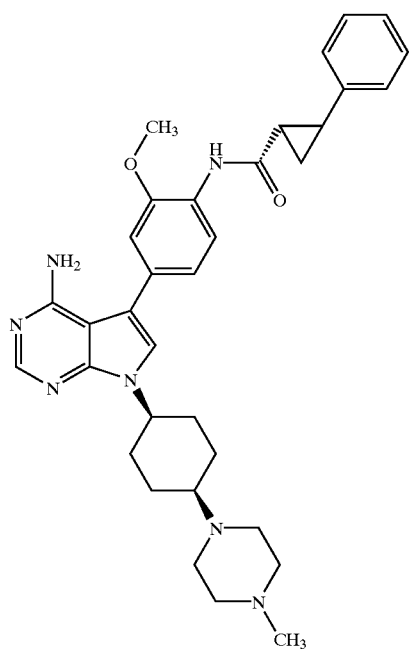
Example 280
RT 3.16
580.3
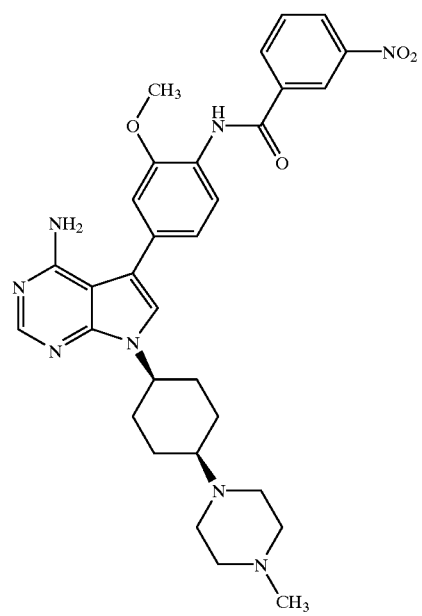
Example 282
RT 2.90
MH+585.3
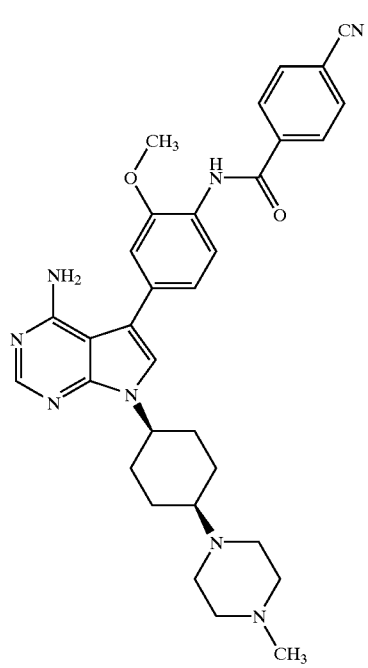
Example 281
RT 2.68
MH+565.3
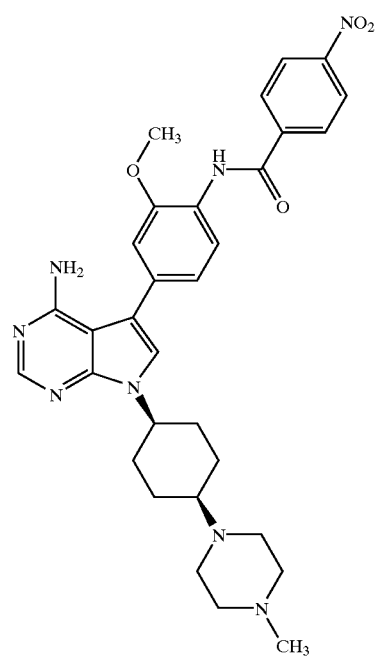
Example 283
RT 2.84
MH+585.3

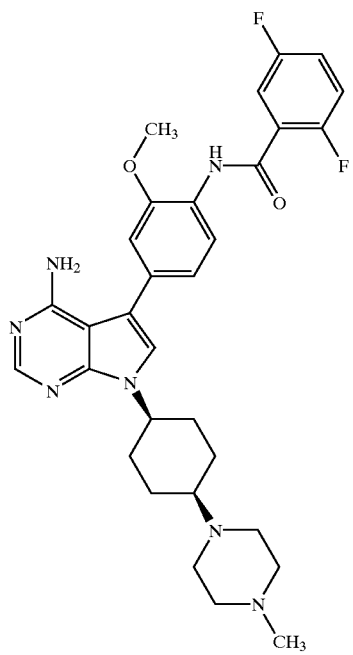
Example 284
RT 2.90
Example 284
RT 2.90
MH+576.3
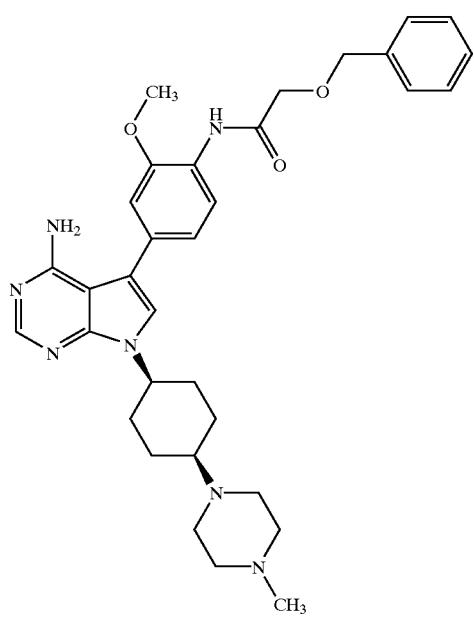
Example 285
RT 2.90
MH+584.4
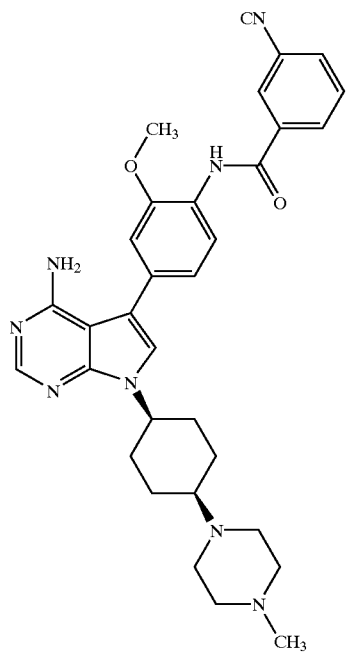
Example 286
RT 2.74
MH+565.6
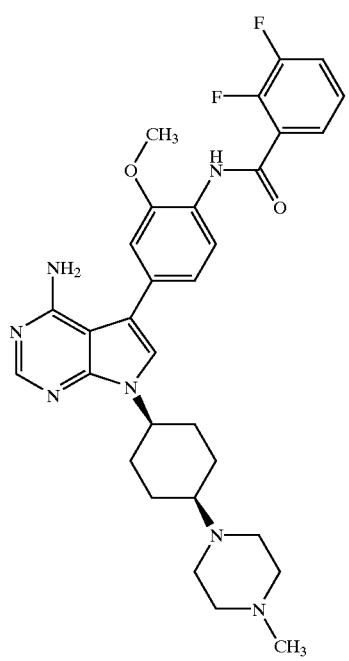
Example 287
RT 3.06
MH+576.3

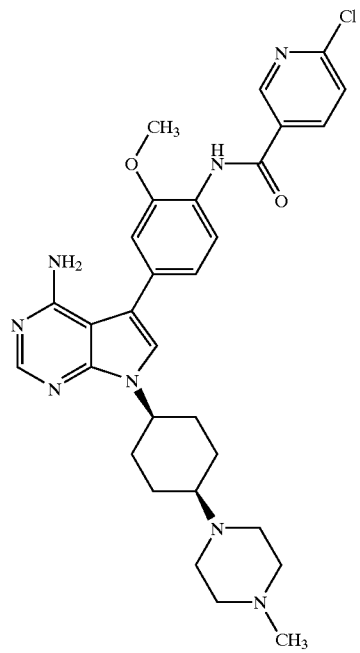
Example 288
RT 2.53
MH+575.3
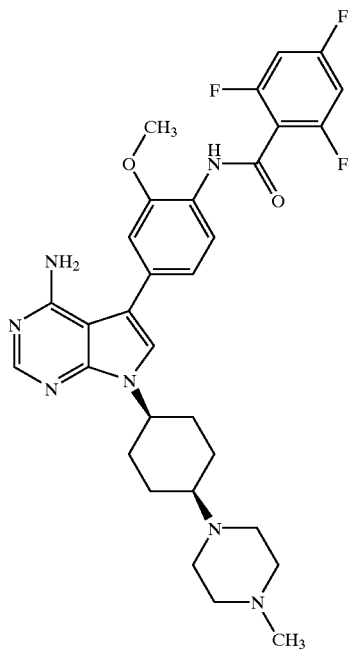
Example 290
RT 2.85
MH+594.4
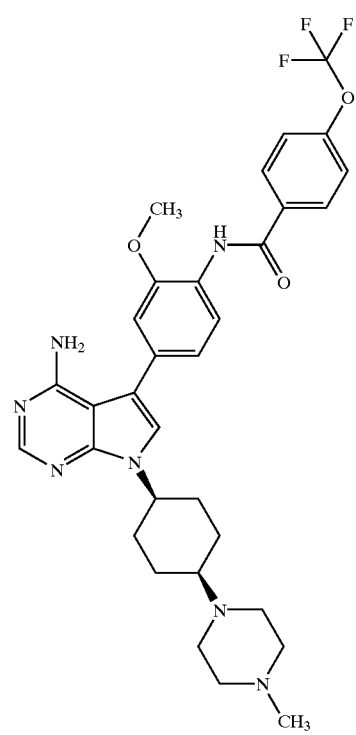
Example 289
RT 3.32
MH+624.3
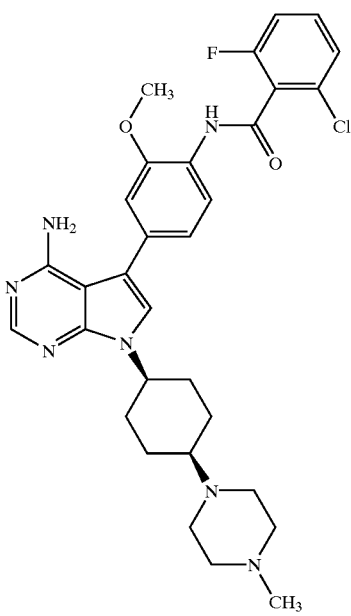
Example 291
RT 2.76
MH+592.3

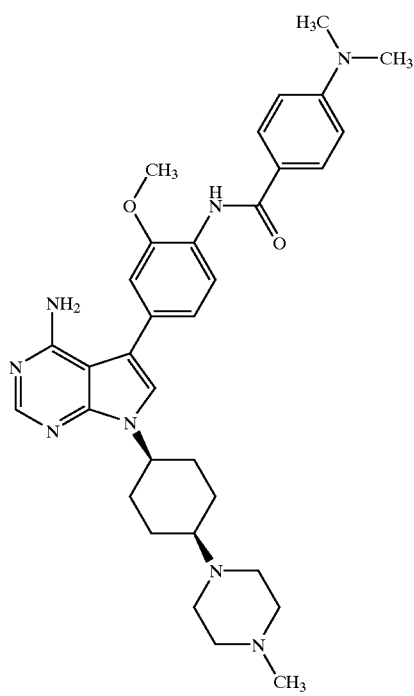

Example 292

RT 2.86
MH+583.3

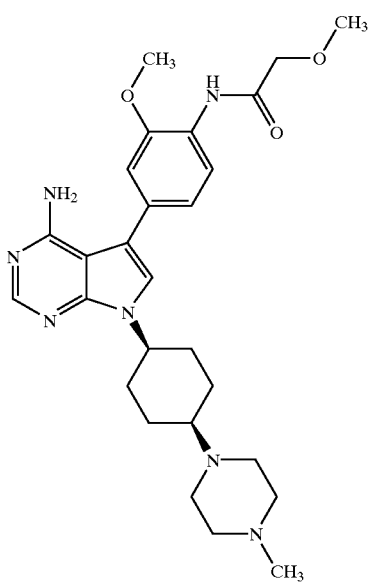

Example 293

RT 2.29
MH+508.3

General Synthesis for Examples 294–301
Method A
A mixture of the appropriate piperazine (7.60 mmol), 4-[4-amino-5-(4-phenoxyphenyl)-7H-pyrrolo[2,3-d]pyrimidin-7-yl]-1-cyclohexanone (2.53 mmol), and glacial acetic acid (7.60 mmol) in 50 mL of dichloroethane was stirred at room temperature for 1.5 hours. Sodium triacetoxyborohydride (3.28 mmol) was added and the mixture was stirred at room temperature for 16 hours. A solution of 1.35 g of sodium bicarbonate in 50 mL of water was added and the reaction mixture was stirred for 1 hour. The organic portion was separated, dried over magnesium sulfate, filtered, and the filtrate concentrated to afford a brown oil. Purification by flash chromatography on silica gel afforded the cis- and trans-7-[(4-piperazino)cyclohexyl]-5-(4-phenoxyphenyl)-7H-pyrrolo[2,3-d]pyrimidin-4-amines.

Method B

A mixture of the appropriate pyrrolidine (7.53 mmol), 4-[4-amino-5-(4-phenoxyphenyl)-15 7H-pyrrolo[2,3-d] pyrimidin-7-yl]-1-cyclohexanone (2.51 mmol), and glacial acetic acid (7.35 mmol) in 45 mL of dichloroethane was stirred at room temperature for 30 minutes. Sodium triacetoxyborohydride (3.26 mmol) was added and the mixture was stirred at room temperature for 22 hours. A solution of 1.35 g of sodium bicarbonate in 50 mL of water was added and the reaction mixture was stirred for 1 hour. The organic portion was separated, dried over magnesium sulfate, filtered, and the filtrate concentrated to afford a brown oil. Purification by flash chromatography on silica gel afforded the cis- and trans-7-(4-pyrrolidino)cyclohexyl]-5-(4-phenoxyphenyl)-7H-pyrrolo[2,3-dlpyrimidin-4-amines.

Salt Formation

To a warm solution of pyrrolopyrimidine (2.48 mmol; from methods A or B, above) in ethanol was added a solution of maleic acid (7.28 mmol) in ethanol. A white precipitate formed as the solution was cooled to ambient temperature. The resulting solid was isolated by filtration and dried under vacuum to yield the desired tris maleate salt.

Analytical RP-HPLC RT listed in the table were obtained on a Hypersil HyPurity Elite C18 column ((5 uM, 200 A) 250×4.6 mm) using a linear gradient of 25–100% acetonitrile/0.1 M ammonium acetate over 10 min. (gradient a) or 25 min. (gradient b) at 1 mL/min.

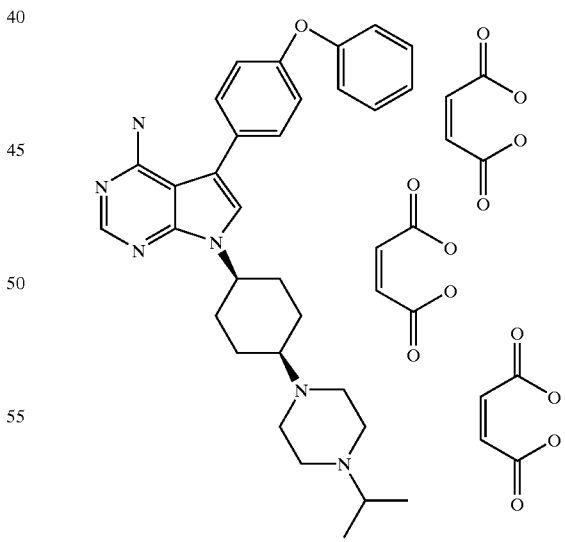

Example 294

RT 7.967
MH+511.1
Gradient a

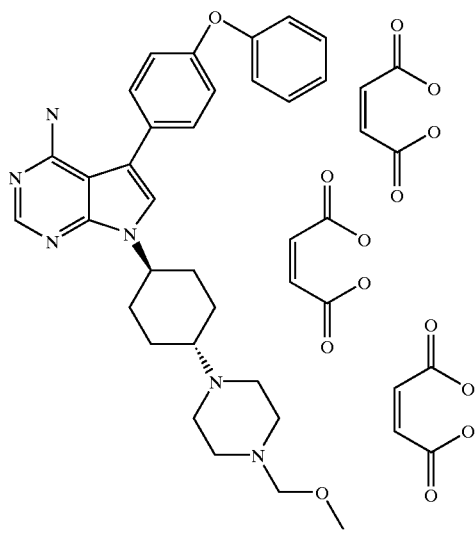
Example 295
RT 7.383
MH+527.2
Gradient a
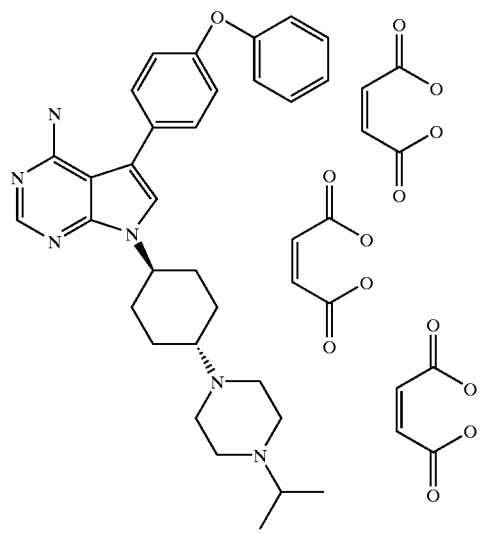
Example 297
RT 7.733
MH+511.2
Gradient a
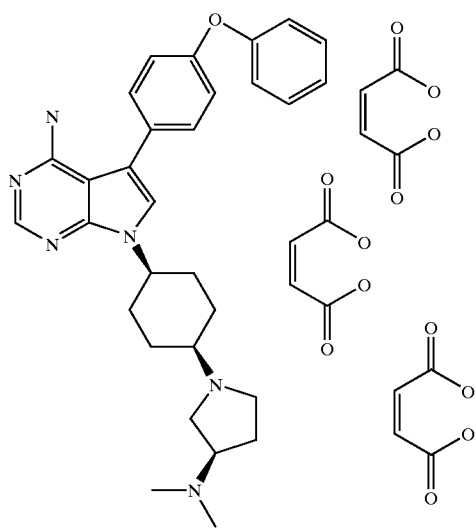
Example 296
RT 13.941
MH+497.1
Gradient b
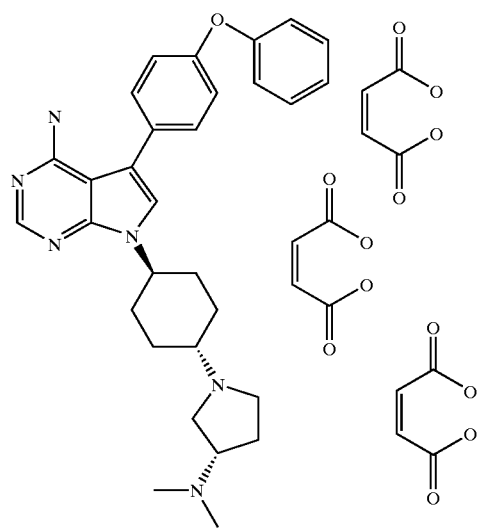
Example 298
RT 14.067
MH+497.1
Gradient b

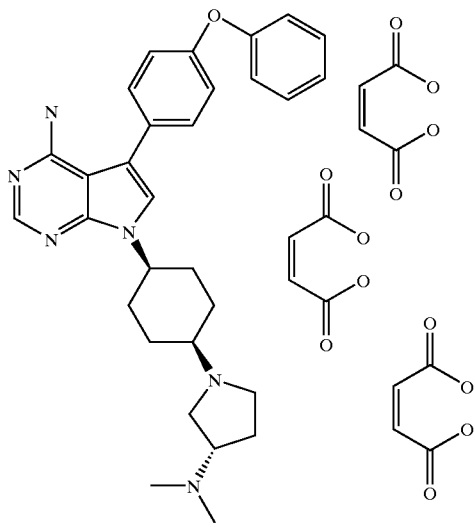

Example 299

RT 13.891
MH+497.1
Gradient b

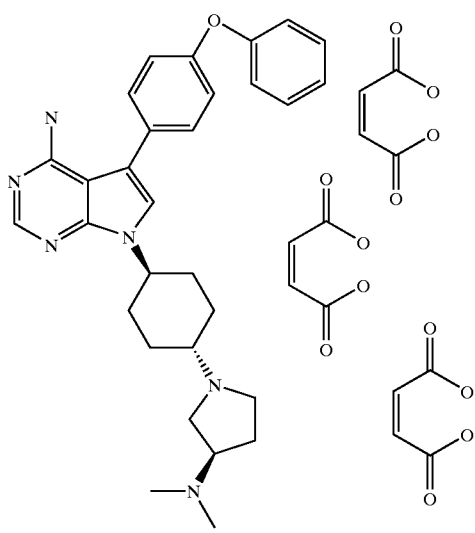

Example 300

RT 14.076
MH+497.1
Gradient b

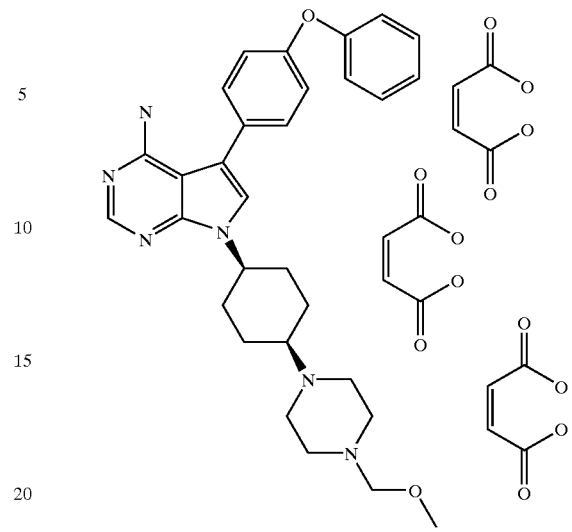

Example 301

RT 7.750
MH+527.2
Gradient a

Example 302 cis and trans 4-[4-Amino-5-(4-phenoxyphenyl)-7H-pyrrolo[2,3-d]pyrimidin-7-yl]-1-hydroxycyclohexylmethyl Cyanide A solution of diisopropylamine (0.649 g, 0.0050 mol) in tetrahydrofuran (10 mL) was cooled to 0° C. A solution of 1.6 M n-butyl lithium (3.14 mL, 0.0050 mol) in hexanes was added dropwise, keeping the temperature less than 5° C. After the addition was complete, the mixture was stirred for 20 minutes at 0° C. The mixture was cooled to −78° C., and dry acetonitrile (0.175 g, 0.0043 mol) was added, keeping the temperature less than −70° C. After the addition was complete, the mixture was stirred for 20 minutes at −78° C., and a mixture of 4-[4-amino-5-(4-phenoxyphenyl)-7H-pyrrolo[2,3-d]pyrimidin-7-yl]-1-cyclohexanone (1.000 g, 0.0025 mmol) in tetrahydrofuran (10 mL) and hexamethylphosphoramide (10 mL) was added, keeping the temperature less than −70° C. After the addition was complete, the mixture was stirred for 30 minutes at −78° C., then stirred at ambient temperature for 18 hours. The mixture was partitioned between dichloromethane and saturated ammonium chloride (aq). The organic phase was washed with water and saturated sodium bicarbonate (aq), and dried over magnesium sulfate. The solvent was removed in vacuo and the cis and trans isomers were separated by flash column chromatography on silica using dichloromethane/methanol (95:5) as an eluent to give less polar 4-[4-amino-5-(4-phenoxyphenyl)-7H-pyrrolo[2,3-d]pyrimidin-7-yl]-1-hydroxycyclohexylmethyl cyanide (0.120 g, 0.00027 mol) and more polar 4-[4-amino-5-(4-phenoxyphenyl)-7H-pyrrolo[2,3-d]pyrimidin-7-yl]-1-hydroxycyclohexylmethyl cyanide (0.170 g, 0.00038 mol):

Less polar:

$^1$H NMR (DMSO-$d_6$,400 MHz) δ 8.13(s, 1H), 7.48(d, 2H), 7.41(t, 2H), 7.37(s, 1H), 7.15(t, 1H), 7.093(d, 2H), 7.088(d, 2H), 6.11(b, 2H) 5.05(s, 1H), 4.53–4.61(m, 1H), 2.66(s, 2H), 2.18(q, 2H), 1.80(t, 4H) 1.66(t, 2H); RP-HPLC (Delta Pak C18, 5 μm, 300 A, 15 cm; 5%–85% acetonitrile—0.1M ammonium acetate over 20 min, 1 mL/min) $R_t$ 15.90. MH$^+$440.

More Polar: (Probably Trans, Aryl-axial, OH-axial)

$^1$H NMR (DMSO-d$_6$, 400 MHz) δ 8.13(s, 1H), 7.63(s, 1H), 7.48(d, 2H), 7.41(t, 2H), 7.15(t, 1H), 7.11(d, 2H), 7.08(d, 2H), 6.11(b, 2H) 5.22(s, 1H), 4.62–4.67(m, 1H), 2.98(s, 2H), 1.82–1.99(m, 6H), 1.65–1.73(m, 2H); RP-HPLC (Delta Pak C18, 5 μm, 300 A, 15 cm; 5%–85% acetonitrile—0.1M ammonium acetate over 20 min, 1 mL/min) $R_t$ 15.88. MH$^+$440.

Example 303 cis- and trans-5-(4-Amino-3-fluorophenyl)-7-[4-(4-methylpiperazino)cyclohexyl]-7H-pyrrolo[2, 3-d]pyrimidin-4-amine a) tert-Butyl N-(4-Bromo-2-fluorophenyl)carbamate Sodium bis(trimethylsilyl)amide solution (1.0Msoln. in THF, 2.05 equiv., 270 mL, 270 mmol) was added dropwise to a solution of 4-bromo-2-fluoroaniline (24.78 g, 130.4 mmol) in THF (250 mL) over 15 min. under nitrogen. After a further 15 min., di-tert-butyl dicarbonate (1.2 equiv., 34.12 g, 156.3 mmol) was added portionwise (note: a slight exotherm was observed). The reaction became very viscous and after 4 h. reached completion (t.l.c. analysis using 1:9 EtOAc:heptane as the eluent). The reaction was concentrated in vacuo and the residue was partitioned between EtOAc (300 mL) and saturated aq. NaHCO$_3$(150 mL). The aqueous layer was further extracted EtOAc (2×200 mL) and the combined organic layers were dried (NaSO4) and concentrated under reduced pressure. Purification by column chromatography using a 10% to 15% EtOAc: heptane gradient afforded tert-butyl N-(4-bromo-2-fluorophenyl) carbamate a light yellow waxy solid (30.0 g, 79%), $^1$H NMR (400 MHz, CDCl$_3$) 1.51(9H, s), 7.22(1H, m), and 7.24(2H, m).

b) tert-Butyl N-[2-Fluoro-4-(4,4,5,5-tetramethyl-1,3,2-dioxaborolan-2-yl)phenyl]carbamate A solution of the tert-butyl N-(4-bromo-2-fluorophenyl) carbamate (54.0 g, 0.186 mmol), bis-pinacolatodiborane (1.2 equiv, 56.8 g, 223.3 mmol), potassium acetate (3.0 equiv, 54.7 g, 558 mmol) and PdCl$_2$(dppf) (0.03 equiv, 4.65 g, 5.58 mmol) in degassed DMF (1l) was heated at 80° C. under nitrogen for 16 h. The DMF was removed under reduced pressure and the resulting dark solid residue was dissolved in CH$_2$Cl$_2$(500 mL). The inorganic residues were removed by filtration through a silica gel pad and the filtrate was purified by column chromatography using a 10% to 15% EtOAc: heptane gradient to afford the product as a yellow viscous oil which crystallized on standing to give tert-butyl N-[2-fluoro-4-(4,4,5,5-tetramethyl-1,3,2-dioxaborolan-2-yl)phenyl]carbamate (56.5 g, 92%), $^1$H NMR (400 MHz, CDCl$_3$) 1.33(12H, s), 1.53(9, H, s), 6.82(1H, brs), 7.46(1H, d, J11 Hz), 7.55 (1H, brd), and 8.12(1H, brt), m/z 337.2, and RP-HPLC (5 to 100% CH$_3$CN in 0.1 N aqueous ammonium acetate over 15 min at 1 mL/min using a Hypersil HyPurity Elite C18, 5 m, 200 Å, 250×4.6 mm column) $t_r$=10.16 min, 90%.

c) tert-Butyl N-4-[4-Chloro-7-(1,4-dioxaspiro[4.5]dec-8-yl)-7H-pyrrolo[2,3-d]pyrimidin-5-yl]-2-fluorophenylcarbamate A suspension of the 4-chloro-7-(1,4-dioxaspiro[4.5]dec-8-yl)-5-iodo-7H-pyrrolo[2,3-d]pyrimidine (31.18 g, 74.41 mmol), tert-butyl N-[2-fluoro-4-(4,4,5,5-tetramethyl-1,3,2-dioxaborolan-2-yl)phenyl]carbamate (1.5 equiv, 37.6 g, 111.6 mmol), sodium carbonate (2.5 equiv, 19.72 g, 186 mmol) and Pd(PPh$_3$)$_4$(4 mol%, 3.44 g, 2.98 mmol)in DME (1.2 l) and degassed H$_2$0(230 mL) was heated at 80° C. under nitrogen for 17 h. Additional Pd catalyst (I mol%, .86 g, 0.74 mmol) was added and the reaction was continued heating at 80° C. for a further 24 h. at which point the reaction had proceeded to completion (t.l.c. analysis using 3:7 EtOAc:heptane as the eluent, Rf=0.7). The solvent was removed under reduced pressure and the residue dissolved in EtOAc (500 mL) and the inorganics were removed by filtration through a celite pad. The filtrate was washed with 10% aq. Na$_2$CO$_3$(200 mL) and brine (200 mL), dried (MgSO$_4$) and concentrated in vacuo. Column chromatography purification over silica gel using 1:2 EtOAc:heptane afforded tert-butyl N-4-[4-chloro-7-(1,4-dioxaspiro[4.5]dec-8-yl)-7H-pyrrolo[2,3-d]pyrimidin-5-yl]-2-fluorophenylcarbamate as an off-white solid (21.0 g, 56%), $^1$H NMR (400 MHz, CDCl$_3$) 1.55(9H, s), 1.89(4H, m), 2.07(4H, m), 4.01 (4H, s), 4.89(1H, m), 6.75(1H, br s), 7.23 (1H, br s), 7.25(1H, br s), 7.34(1H, br s), 8.14(1H, br t), and 8.64(1H, s) and RP-HPLC (5 to 100% CH$_3$CN in 0.1 N aqueous ammonium acetate over 15 min at 1 mL/min using a Hypersil HyPurity Elite C18, 5 μm, 200 Å, 250×4.6 mm column) $t_r$=10.48 min., 100%.

d) 5-(4-Amino-3-fluorophenyl)-7-(1,4-dioxaspiro[4.5]dec-8-yl)-7H-pyrrolo[2,3-d]pyrimidin-4-amine A cloudy mixture of tert-butyl N-4-[4-chloro-7-(1,4-dioxaspiro[4.5]dec-8-yl)-7H-pyrrolo[2,3-d]pyrimidin-5-yl]-2-fluorophenylcarbamate (10.5 g, 20.92 mmol), aq. ammonium hydroxide (28–30%, 100 mL) and dioxane (100 mL) was placed in a sealed vessel at ambient temperature then heated to 120° C. with stirring for 24 h. (t.l.c. analysis using 9:1 EtOAc:heptane as the eluent). The reaction was concentrated in vacuo, diluted with EtOAc (300 mL), washed with brine (2×150 mL), dried (Na$_2$SO$_4$) and concentrated under reduced pressure and scrupulously dried to afford 5-(4-Amino-3-fluorophenyl)-7-(1,4-dioxaspiro[4.5]dec-8-yl)-7H-pyrrolo[2, 3-d]pyrimidin-4-amine as a yellow solid (7.93 g, 99%), $^1$H NMR (400 MHz, d$_6$-DMSO) 1.74(4H, m), 1.90(2H, m), 2.06(2H, m), 3.90(4H, m), 4.64(1H, m), 5.18 (2H, brs), 6.02(2H, brs), 6.84(1H, t), 6.97(1H, d), 7.08(1H, d), 7.26 (1H, s) and 8.10(1H, s) and m/z 384.2(MH$^+$).

e) 4-[4-Amino-5-(4-amino-3-fluorophenyl)-7H-pyrrolo[2,3-d]pyrimidin-7-yl]-1-cyclohexanone 5M HCl (300 mL) was added slowly to a solution of 5-(4-amino-3-fluorophenyl)-7-(1,4-dioxaspiro[4.5]dec-8-yl)-7H-pyrrolo[2,3-d]pyrimidin-4-amine (18.49 g, 48.28 nmol) in acetone (800 mL) at 0° C. the resulting dark orange-brown solution was heated at 60° C. for 4 h. (t.l.c. analysis using 10% MeOH in CH$_2$Cl$_2$). The acetone was removed under reduced pressure and the acidic layer was basified to approx. pH 8 using sat. aq. Na$_2$CO$_3$. The resulting precipitate was collect by filtration and scrupulously dried to afford 4-[4-amino-5-(4-amino-3-fluorophenyl)-7H-pyrrolo[2,3-d]pyrimidin-7-yl]-1-cyclohexanone as a light brown solid (12.67 g, 77%). A second crop was also obtained from the mother liquor on standing (2.01 g, 12%), $^1$H NMR (400 MHz, d$_6$-DMSO) 2.27(2H, m), 2.30 (4H, br d), 2.73(2H, m), 5.14(1H, m), 5.20(2H, brs), 6.05(2H, brs), 6.85 (1H, t), 6.97(1H, dd), 7.06(1H, dd), 7.35(1H, s) and 8.12(1H, s) and m/z 340.1(MH$^+$).

cis- and trans-5-(4-Amino-3-fluorophenyl)-7-[4-(4-methylpiperazino)cyclohexyl]-7H-pyrrolo[2,3-d]pyrimidin-4

Example 304 cis-N1-(4-{4-Amino-7-[4-(4-methylpiperazino) cyclohexyl]-7H-pyrrolo[2,3-d]pyrimidin-5-yl}-2-fluorophenyl)-4-fluoro-1-benzenesulfonamide tri-Maleate To a solution of 4-[4-amino-5-(4-amino-3-fluorophenyl)-7H-pyrrolo[2,3-d]pyrimidin-7-yl]-1-cyclohexanone (1.0 g, 2.95 mmol), N-methylpiperazine (3 equiv, 0.885 g, 8.85 mmol, 0.98 mL) and glacial acetic acid (3 equiv., 0.51 mL, 8.85 mmol) in dichloroethane (50 mL) under nitrogen was added sodium triacetoxyborohydride (1.3 equiv., 0.81 g, 3.84 mmol). The solution was stirred for 18 hr then additional sodium triacetoxyborohydride (0.40 g, 1.9 mmol) was added and the reaction continued for a further 48 hr. The reaction was concentrated in vacuo, partitioned between dichloromethane (100 mL) and sat. aq. NaHCO$_3$(100 mL). The aqueous layer was further extracted with dichloromethane (4×100 mL) and the combined organic layers were dried over magnesium sulfate and evaporated to dryness to give a yellow foam (0.95 g). Purification by column chromatography over silica gel using a dichloromethane:methanol (9:1 to 5:1) gradient afforded cis-5-(4-amino-3-fluorophenyl)-7-[4-(4-methylpiperazino) cyclohexyl]-7H-pyrrolo[2,3-d]pyrimidin-4-amine, the higher running component, as a cream solid (400 mg, 32%) $^1$H NMR (d$_6$ DMSO, 400 MHz) 1.56(3H, br t), 1.68(2H, br d), 1.99(5H, m), 2.20(3H, s), 2.43(7H, br m), 4.65(1H, m), 5.20(1H, s), 6.01(2H, br s), 6.85(1H, t, J=9.6 Hz), 6.98(1H, dd, J=8.0 and 1.6 Hz), 7.10(1H, dd, J=12.4 and 1.6 Hz), 7.12(1H, s), and 8.10(1H, s) and RP-HPLC (10 to 90% CH$_3$CN in 0.1 N aqueous ammonium acetate over 12 min at 2 mL/min using a Waters Symmetry C18, 250×4.6 nun column) tr=8.619 min., 96% A mixed fraction was obtained which contained both cis- and trans-isomers (440 mg, 50:50 mixture), and in addition the lower running fraction contained trans-5-(4-amino-3-fluorophenyl)-7-[4-(4-methylpiperazino)cyclohexyl]-7H-pyrrolo[2,3-d]pyrimidin-4-amine, as a yellow solid (110 mg, 9%), $^1$H NMR (d$_6$ DMSO, 400 MHz) 1.94(6H, m), 2.17(3H, s), 2.33(7H, br m), 2.51(3H, m), 3.28(1H, m), 4.51(1H, m), 5.18(2H, s), 6.01(2H, br s), 6.84(1H, t), 6.96(1H, dd), 7.04(1H, dd), 7.30(1H, s), and 8.08(1H, s) and RP-HPLC (10 to 40% CH$_3$CN in 0.1 N aqueous ammonium acetate over 12 min at 2 mL/min using a Waters Symmetry C18, 250×4.6 mm column) t$_r$=7.595 min, 97%

Example 305 trans-N1-(4-{4-Amino-7-[4-(4-methylpiperazino) cyclohexyl]-7H-pyrrolo[2,3-d]pyrimidin-5-yl}-2-fluorophenyl)-4-fluoro-1-benzenesulfonamide tri-Maleate 4-Fluorobenzenesulfonyl chloride (45.9 mg, 0.236 mmol) was added to a solution of trans-5-(4-amino-3-fluorophenyl)-7-[4-(4-methylpiperazino)cyclohexyl]-7H-pyrrolo[2,3-d]pyrimidin-4-amine (100 mg, 0.236 mmol) in pyridine (2 mL) at 40° C. After 27 hr at 40° C. the reaction had reached completion and was concentrated in vacuo. Purification by column chromatography over silica gel using 10% to 50% MeOH in dichloromethane as the gradient afforded as a colurless oil (0.78 mmol). The product was dissolved in ethanol and maleic acid (3 equiv., 27 mg, 0.233 mmol) added. The mixture was heated until homogeneous and trans-N1-(4-{4-amino-7-[4-(4-methylpiperazino) cyclohexyl-7H-pyrrolo[2,3-d]pyrimidin-5-yl}-2-fluorophenyl)-4-fluoro-1-benzenesulfonamide trimaleate crystallised on cooling as a fawn solid (37 mg, 17%), RP-HPLC (10 to 40% CH$_3$CN in 0.1 N aqueous ammonium acetate over 12 min at 2 mL/min using a Waters Symmetry C18, 250×4.6 mm column) t$_r$=14.528 min., 96% and m/z 582.0(MH$^+$).

Example 306 cis-N1-(4-{4-Amino-7-[4-(4-methylpiperazino) cyclohexyl]-7H-pyrrolo[2,3-d]pyrimidin-5-yl}-2-fluorophenyl)-4-fluoro-1-benzenesulfonamide cis-N1-(4{-4-amino-7-[4-(4-methylpiperazino) cyclohexyl]-7H-pyrrolo[2,3-d]pyrimidin-5-yl}-2-fluorophenyl)-4-fluoro-1-benzenesulfonamide was prepared using the same procedure as detailedfor the free base of trans-N1-(4{-4-amino-7-[4-(4-methylpiperazino) cyclohexyl]-7H-pyrrolo[2,3-d]pyrimidin-5-yl}-2-fluorophenyl)-4-fluoro-1-benzenesulfonamide except on a 3.36 mmol scale.

(400 mg, 32%), RP-HPLC (10 to 40% CH$_3$CN in 0.1 N aqueous ammonium acetate over 12 min at 2 mL/min using a Waters Symmetry C18, 250×4.6 mm column) t$_r$=15.232, 94% min. and m/z =582.1(MH$^+$).

Example 307

5-(4-Amino-3-fluorophenyl)-7-(1-benzyl-4-piperidyl)-7H-pyrrolo[2,3-d]pyrimidin-4-amine a) 7-(1-benzyl-4-piperidyl)-4-Chloro-5-iodo-7H-pyrrolo[2,3-d]pyrimidine Diethyl diazodicarboxylate (2.0 equiv., 18.19 g, 41.2 mL, 104.8 mmol) was added dropwise over approx. 1 h to a solution of 4-chloro-3-iodopyrrolo[2,3-d]pyrimidine (14.55 g, 52.4 mmol), 1-benzyl-4-hydroxypiperidine (3.0 equiv., 30.06 g, 157.16 mmol) and triphenylphosphine (2.0 equiv., 27.51 g, 104.8 mmol) in THF (730 mL) at room temperature under nitrogen. The reaction reached completion after 72 h (t.l.c. analysis using 1:1 EtOAc:heptane as the eluent, Rf=0.2). The reaction was concentrated in vacuo and 1:4 ethyl acetate:heptane was added until a precipitate in a clear solution was observed. The precipitate was collected by filtration (Ph3PO) and the filtrate was concentrated, dissolved in ethyl acetate (500 mL) and extracted with aq. HCl (1M, 3×200 mL). The combined acidic layers were basified with aq NaOH (4 N) to pH 12 then extracted into ethyl acetate(3×300 mL), dried (MgSO4) and concentrated in vacuo. Purification by column chromatography using 5:4 light petroleum (30–60° C.):ethyl acetate over silica gel gave 2 main fractions of which the first fraction contained the product as a pale yellow crystalline solid which was recrystallised from ethyl acetate to give 7-(1-benzyl-4-piperidyl)-4-chloro-5-iodo-7H-pyrrolo[2,3-d]pyrimidine as a cream crystalline solid (5.7 g, 24%); $^1$H NMR (400 MHz, CDCl$_3$) 2.02(4H, m), 2.24(2H, m), 3.06(2H, br d), 3.58(2H, s), 4.76(1H, m), 7.27(2H, m), 7.32(3H, m), 7.49(1H, s) and 8.60(1H, s) and m/z =452.8(MH$^+$).

b) tert-Butyl N-4-[7-(1-Benzyl-4-piperidyl)-4-chloro-7H-pyrrolo[2,3-d]pyrimidin-5-yl]-2-fluorophenylcarbamate A suspension of 7-(1-benzyl-4-piperidyl)-4-chloro-5-iodo-7H-pyrrolo[2,3-d]pyrimidine (5.7 g, 12.6 mmol), tert-butyl N-[2-fluoro-4-(4,4,5,5-tetramethyl-1,3,2-dioxaborolan-2-yl)phenyl]carbamate (1.5 equiv, 18.9 g, 6.38 mmol), sodium carbonate (2.5 equiv, 3.34 g, 31.5 mmol) and Pd(PPh$_3$)$_4$(4 mol%, 0.58 g, 0.5 mmol) in DME (210 mL) and degassed water (37 mL) was heated at 80° C. under nitrogen for 17 h (t.l.c. analysis using 1:1 EtOAc:heptane as the eluent). The reaction mixture was concentrated in vacuo, dissolved in ethyl acetate (400 mL) and washed with 10% aq. Na$_2$CO$_3$(3×200 mL). The organic layer was dried (MgSO$_4$), concentrated and purified by column chromatography using 1:1 ethyl acetate:heptane as the eluent to afford tert-butyl N-4-[7-(1-benzyl-4-piperidyl)-4-chloro-7H-pyrrolo[2,3-d]pyrimidin-5-yl]-2-fluorophenylcarbamate as a white crystalline solid (5.2 g, 9.7 mmol, 77%), $^1$H NMR (400 MHz, CDCl$_3$) 1.55(9H, s), 2.05(4H, m), 2.24(2H, m), 3.06(2H, br d), 3.60(2H, s), 4.83(1H, m), 7.25(2H, m), 7.29 (1H, m), 7.33(6H, m), 8.12(1H, br t) and 8.64 (1H, s).

c) 5-(4-Amino-3-fluorophenyl)-7-(1-benzyl-4-piperidyl)-7H-pyrrolo[2,3-d]pyrimidin-4-amine A mixture of the tert-butyl N-4-[7-(1-benzyl-4-piperidyl)-4-chloro-7H-pyrrolo[2,3-d]pyrimidin-5-yl]-2- fluorophenylcarbamate (5.2 g, 9.7 mmol), aq. ammonium hydroxide (28–30%, 100 mL) and 1,4-dioxane (100 mL) was placed in a sealed vessel at ambient temperature then heated to 120° C. with stirring for 16 h. (t.l.c. analysis using EtOAc as the eluent). The reaction was concentrated in vacuo, diluted with EtOAc (300 mL), washed with brine (2×200 mL), dried ($Na_2SO4$) and concentrated under reduced pressure to afford a brown solid which was triurated with ether (approx. 50 mL) to give 5-(4-amino-3-fluorophenyl)-7-(1-benzyl-4-piperidyl)-7H-pyrrolo[2,3-d]pyrimidin-4-amine as a cream solid (3.0 g, 74%), $^1$H NMR (400 MHz, $CDCl_3$) 2.06(4H, m), 2.27(2H, m), 3.06(2H, m), 3.59(2H, br s), 3.70(2H, br s), 4.73(1H, m), 5.12(2H, s), 6.85(1H, t), 7.01(1H, s), 7.06(1H, dd), 7.10(1H, dd), 7.28 (2H, m), 7.34(3H, m) and 8.31 (1H, s) and m.p. 141–142° C.

Example 308

N1-4-[4-Amino-7-(1-benzyl-4-piperidyl)-7H-pyrrolo[2,3-d]pyrimidin-5-yl]-2-fluorophenyl-4-fluoro-1-benzenesulfonamide N1-4-[4-amino-7-(1-benzyl-4-piperidyl)-7H-pyrrolo[2,3-d]pyrimidin-5-yl]-2-fluorophenyl-4-fluoro-1-benzenesulfonamide (470981) was prepared using the same procedure as detailed for trans-N1-(4-{4-amino-7-[4-(4-methylpiperazino)cyclohexyl]-7H-pyrrolo[2,3-d]pyrimidin-5-yl}-2-fluorophenyl)-4-fluoro-1-benzenesulfonamide trimaleate except on a 6.96 mmol scale. N1-4-[4-amino-7-(1-benzyl-4-piperidyl)-7H-pyrrolo[2,3-d]pyrimidin-5-yl]-2-fluorophenyl-4-fluoro-1-benzenesulfonamide was obtained as a cream solid (3.2 g, 80%), m/z 575 ($MH^+$) and m.p. 265–6° C.

Example 309

N1-4-[4-Amino-7-(1-benzyl-4-piperidyl)-7H-pyrrolo[2,3-d]pyrimidin-5-yl]-2-fluorophenyl-2,3-dichloro-1-benzenesulfonamide N1-4-[4-amino-7-(1-benzyl-4-piperidyl)-7H-pyrrolo[2,3-d]pyrimidin-5-yl]-2-fluorophenyl-2,3-dichloro-1-benzenesulfonamide was prepared in the same manner as detailed above on a 5.04 mmol scale. The resulting N1-4-[4-amino-7-(1-benzyl-4-piperidyl)-7H-pyrrolo[2,3-d]pyrimidin-5-yl]-2-fluorophenyl-4-fluoro-1-benzenesulfonamide was obtained as a brown solid (1.0 g, 32%), m/z 625 ($MH^+$) and RP-HPLC (5 to 85% $CH_3CN$ in 0.1 N aqueous ammonium acetate over 20 min at 1 mL/min using a Waters Delta pack Sm C18, 300 Å, 150×3.9 mm column) tr=14.963 min., 95%.

Example 310

N1-4-[4-Amino-7-(4-piperidyl)-7H-pyrrolo[2,3-d]pyrimidin-5-yl]-2-fluorophenyl-4-fluoro-1-benzenesulfonamide A mixture containing N1-4-[4-amino-7-(1-benzyl-4-piperidyl)-7H-pyrrolo[2,3-d]pyrimidin-5-yl]-2-fluorophenyl-4-fluoro-1-benzenesulfonamide (2.40 g, 4.18 mmol), ammonium formate (10 equiv., 41.8 mmol, 2.62 g), palladium on carbon (10%, 1.2 g) and ethanol (100 mL) was heated at reflux with vigorous stirring for 6 h., filtered and concentrated in vacuo. The solid was partitioned between dichloromethane (50 mL) and water (50 mL). The brown solid which formed at the phase boundary was collected and analysed for N1-4-[4-amino-7-(4-piperidyl)-7H-pyrrolo[2,3-d]pyrimidin-5-yl]-2-fluorophenyl-4-fluoro-1-benzenesulfonamide (0.33 g), m/z 485($MH^+$) and m.p. 238–9° C. (dec.).

Example 311

N1-4-[4-Amino-7-(1-formyl-4-piperidyl)-7H-pyrrolo[2,3-d]pyrimidin-5-yl]-2-fluorophenyl-4-fluoro-1-benzenesulfonamide The procedure detailed for the preparation of N1-4-[4-amino-7-(4-piperidyl)-7H-pyrrolo[2,3-d]pyrimidin-5-yl]-2-fluorophenyl-4-fluoro-1-benzenesulfonamide was performed on a smaller scale (0.35 mmol) where the combined organic layers from the work up were isolated, dried ($NaSO_4$) and the solvent removed under reduced pressure to afford a white oil which was purified by preparative HPLC (100% pH 4.5 50 mM ammonium acetate to 100% $CH_3CN$ in 8.5 minutes with a 1.5 minute hold at 25 mL/min using a Hypersil Sm BDS C18, 100×21.2 mm column) to yield N1-4-[4-amino-7-(1-formyl-4-piperidyl)-7H-pyrrolo[2,3-d]pyrimidin-5-yl]-2-fluorophenyl-4-fluoro-benzenesulfonamide as a white solid (50 mg, 27%), m/z= 512.9($MH^+$) and RP-HPLC (5 to 85% $CH_3CN$ in 0.1 N aqueous ammonium acetate over 20 min at 1 mL/min using a Waters Delta pack 5 m C18, 300 Å, 150×3.9 mm column) $t_r$=13.091 min., 95%.

Example 312

N1-[4-(4-Amino-7-1-[(1-methyl-1H-4-imidazolyl)sulfonyl]-4-piperidyl-7H-pyrrolo[2,3-d]pyrimidin-5-yl)-2-fluorophenyl]-4-fluoro-1-benzenesulfonamide Dimaleate 1-Methylimidazol-4-yl sulphonyl chloride (1.1 equiv., 0.068 mmol, 12.3 mg) was added to a suspension of 5-(4-amino-3-fluorophenyl)-7-(1-benzyl-4-piperidyl)-7H-pyrrolo[2,3-d]pyrimidin-4-amine (30 mg, 0.062 mmol) and triethylamine (3 equiv., 0.186 mmol, 26 1) in dichloromethane (1 mL) and stirred at ambient temperature for 24 h. The reaction was concentrated in vacuo, partitioned between dichloromethane (100 mL) and water (50 mL) and the aqueous layer was further extracted with dichloromethane (3×100 mL). The combined organic layers were dried over magnesium sulfate and concentrated in vacuo. Purification by column chromatography over silica gel using 10% methanol in dichloromethane yielded a waxy white solid (10 mg). Maleic acid (2 equiv., 4 mg) was added to the product in hot ethanol and N1-[4-(4-amino-7-1-[(1-methyl-]H-4-imidazolyl)sulfonyl]-4-piperidyl-7H-pyrrolo[2,3-d]pyrimidin-5-yl)-2-fluorophenyl]-4-fluoro-1-benzenesulfonamide dimaleatesalt crystallized on cooling (10 mg), RP-HPLC (5 to 85% $CH_3CN$ in 0.1 N aqueous ammonium acetate over 20 min at 1 mL/min using a Waters Delta pack 5 m C18, 300 Å, 150×3.9 mm column) $t_r$=14.186, 100% min. and m/z =629($MH^+$).

Example 313

N1-[4-(4-Amino-7-1-[(1,2-dimethyl-1H-4-imidazolyl)sulfonyl]-4-piperidyl-7H-pyrrolo[2,3-d]pyrimidin-5-yl)-2-fluorophenyl]-4-fluoro-1-benzenesulfonamide Using the procedure detailed for the synthesis of the free base of N1-[4-(4-amino-7-1-[(1-methyl-1H-4-imidazolyl)sulfonyl]-4-piperidyl-7H-pyrrolo[2,3-d]pyrimidin-5-yl)-2-fluorophenyl]-4-fluoro-1-benzenesulfonamide dimaleate, N1-[4-(4-amino-7-1-[(1,2-dimethyl-]H-4-imidazolyl)

sulfonyl]-4-piperidyl-7H-pyrrolo[2,3-d]pyrimidin-5-yl)-2-fluorophenyl]-4-fluoro-1-benzenesulfonamide was prepared as a cream solid (9 mg), m.p. 217–8° C. and m/z=643.2 (MH+).

Example 314

N1-[4-(4-amino-7-1-[(1,3-dimethyl-1H-5-pyrazolyl) carbonyl]-4-piperidyl-7H-pyrrolo[2,3-d]pyrimidin-5-yl)-2-fluorophenyl]-4-fluoro-1-benzenesulfonamide 1,3-Dimethylpyrazole-5-carbonyl chloride (1.5 equiv., 14.8 mg, 0.093 mmol) was added to a stirred suspension of 5-(4-amino-3-fluorophenyl)-7-(1-benzyl-4-piperidyl)-7H-pyrrolo[2,3-d]pyrimidin-4-amine (30 mg, 0.062 mmol) and potassium carbonate (2 equiv., 17.1 mg, 0.124 mmol) in N-methylpyrrolidinone (2 mL) and the resulting mixture was stirred at ambient temperature under nitrogen for 16 h. The solvent was removed in vacuo and the mixture purified by column chromatography over silica gel using 5% methanol in dichloromethane as the eluent to give N1-[4-(4-amino-7-1-[(1,3-dimethyl-1H-5-pyrazolyl)carbonyl]-4-piperidyl-7H-pyrrolo[2,3-d]pyrimidin-5-yl)-2-fluorophenyl]-4-fluoro-1-benzenesulfonamide as a colourless glass (10 mg), RP-HPLC HPLC (100% pH 4.5 50 mM ammonium acetate to 100% CH$_3$CN in 4.5 minutes with a 0.5 minute hold at 3.5 mL/min using a Perkin Elmer Pecosphere 3 m C18(33×4.6 mm) column) t$_r$=2.98 min., 96% and m/z=629(MH+).

Example 315

N1-(4-{4-Amino-7-[1-(2-pyridylcarbonyl)-4-piperidyl]-7H-pyrrolo[2,3-d]pyrimidin-5-yl}-2-fluorophenyl)-4-fluoro-1-benzenesulfonamide N1-(4-{4-amino-7-[1-(2-pyridylcarbonyl)-4-piperidyl]-7H-pyrrolo[2,3-d]pyrimidin-5-yl}-2-fluorophenyl)-4-fluoro-1-benzenesulfonamide was prepared using the same procedure as detailed for N1-[4-(4-amino-7-1-[(1,3-dimethyl-1H-5-pyrazolyl)carbonyl]-4-piperidyl-7H-pyrrolo[2,3-d]pyrimidin-5-yl)-2-fluorophenyl]-4-fluoro-1-benzenesulfonamide, (12 mg), RP-HPLC HPLC (100% pH 4.5 50 mM ammonium acetate to 100% CH$_3$CN in 4.5 minutes with a 0.5 minute hold at 3.5 mL/min using a Perkin Elmer Pecosphere 3 m C18(33×4.6 mm) column) t$_r$=2.73 min., 98% and m/z =590.2(MH+).

Example 316

N1-4-(4-Amino-7-{4-[1-(1-methylpiperid-4-yl) piperidyl]-7H-pyrrolo[2,3-d]pyrimidin-5-yl})-2-fluorophenyl-4-fluoro-1-benzenesulfonamide tri-Maleate Sodium triacetoxyborohydride (28.1 mg, 0.134 mmol) was added to a solution of N1-4-[4-amino-7-(4-piperidyl)-7H-pyrrolo[2,3-d]pyrimidin-5-yl]-2-fluorophenyl-4-fluoro-1-benzenesulfonamide (50 mg, 0.103 mmol) and 1-methylpiperid-4-one (0.92 ml, 0.155 mmol) in glacial acetic acid (0.025 mL) and NMP (3 mL). The reaction was stirred for 20 h at room temperature then additional sodium triacetoxyborohydride (1.3 equiv.) was added. After a further 24 h the reaction had proceeded to completion and was concentrated in vacuo, partitioned between dichloromethane (100 mL) and sat. aq. NaHCO$_3$(100 mL). The aqueous layer was further extracted with dichloromethane (4×100 mL) and the combined organic layers were dried over magnesium sulfate and evaporated to dryness. Purification by column chromatography over silica gel using dichloromethane:methanol:ammonium hydroxide (78:19:3) as the eluent to afford a brown solid. The tri maleate salt was then formed by standard methods to give N1-4-(4-amino-7-{4-[-(1-methylpiperid-4-yl)piperidyl]-7H-pyrrolo[2,3-d]pyrimidin-5-yl})-2-fluorophenyl-4-fluoro-1-benzenesulfonamide tri-maleate as a brown solid (45 mg, 75%), m/z 582(MH+) and RP-HPLC (5 to 85% CH$_3$CN in 0.1 N aqueous ammonium acetate over 20 min at 1 mL/min using a Waters Delta pack 5 m C18, 300 Å, 150×3.9 mm column) t$_r$=10.658 min., 95%.

Example 317

N1-4-[4-Amino-7-(4-oxocyclohexyl)-7H-pyrrolo[2,3-d]pyrimidin-5-yl]-2-methoxyphenylbenzamide a) To a solution of 4-chloro-5-iodo-7H-pyrrolo[2,3-d]pyrimidine (25.0 g, 0.09 mol), 1,4-dioxaspiro[4.5]decan-8-ol (35.8 g, 0.0267 mol) and triphenylphosphine (46.7 g, 0.178 mol) in THF (1.2 L) was added diethylazodicarboxylate (30.9 g, 0.178 mol) under nitrogen. The solution was stirred for 20 hr and the majority of solvent was then evaporated (250 mL remaining). EtOAc (450 mL) was then added and the resulting solid was filtered, washed with EtOAc (2×50 mL) and dried in vacuo to give 4-chloro-7-(1,4-dioxaspiro[4.5]dec-8-yl)-5-iodo-7H-pyrrolo[2,3-d]pyrimidine (22.5 g, 60%) as a cream solid. $^1$H NMR (d$_6$ DMSO, 400 MHz) 8.64(1H, s), 8.10(1H, s), 4.74(1H, m), 3.90(4H, m), 2.12(2H, m), 1.91(2H, m), 1,71–1.83(4H, m). R$_f$ in 1:4 EtOAc:heptane=0.12.

b) A solution of tert-butyl N-[2-methoxy-4-(4,4,5,5-tetramethyl-1,3,2-dioxaborolan-2-yl)phenyl]carbamate (8.2 g, 23.5 mmol), 4-chloro-7-(1,4-dioxaspiro[4.5]dec-8-yl)-5-iodo-7H-pyrrolo[2,3-d]pyrimidine (6.57 g, 15.7 mmol), tetrakistriphenylphosphinepalladium (1.1 g, 0.93 mmol), sodium carbonate (4.16 g, 39.2 mmol) in dimethoxyethane (200 mL) and water (100 mL) was heated at 80° C. for 20 hr under nitrogen. The resulting solution was cooled to room temperature and partitioned between EtOAc (300 mL) and water (100 mL). The aqueous layer was extracted with EtOAc (3×150 mL) and the combined organics were washed with water (1×150 mL). The organics were dried (sodium sulphate), filtered and evaporated to leave a solid. On attempting to dissolve in EtOAc/heptane (1:4), a cream solid (2.5 g) crashed out. The filtrate was adsorbed onto silica and purified by flash silica gel column chromatography using 10:1 heptane:EtOAc, 4:1 heptane: EtOAc, 1:1 heptane:EtOAc and 4:1 EtOAc:heptane. The appropriate fractions were combined to give a white solid which was triturated with heptane/EtOAc (5:1) to give tert-butyl N-4-[4-chloro-7-(1,4-dioxaspiro[4.5]dec-8-yl)-7H-pyrrolo[2,3-d] pyrimidin-5-yl]-2-methoxyphenylcarbamate as a solid (3.2 g), combined yield is 71%. $^1$H NMR (d$_6$ DMSO, 400 MHz): 8.66(1H, s), 7.93 (2H, m), 7.74(1H, m), 7.19(1H, s), 7.07(1H, d), 4.81(1H, m), 3.93(4H, m), 3.91(3H, s), 2.18(2H, m), 1.99(2H, m), 1.79(4H, m), 1. 48(9H, s). HPLC (conditions: 5 to 95% CH$_3$CN in 0.1 N aqueous ammonium acetate over 20 min.) t$_r$=21.24 min, 100%.

c) tert-Butyl N-4-[4-chloro-7-(1,4-dioxaspiro[4.5]dec-8-yl)-7H-pyrrolo[2,3-d]pyrimidin-5-yl]-2-methoxyphenylcarbamate (5.7 g, 0.011 mol), conc. ammonia solution (100 mL) and dioxan (100 mL) were heated in a pressure vessel for 20 hr at 120° C. The solvent was evaporated and the residue reconstituted in EtOAc/water (250 mL/100 mL). The organic layer was separated, dried (sodium sulphate), filtered and evaporated to give a solid which by HPLC (conditions: 5 to 95% CH₃CN in 0.1 N aqueous ammonium acetate over 20 min.) was observed to be a 2:1 mixture of tert-butyl N-4-[4-amino-7-(1,4-dioxaspiro[4.5]dec-8-yl)-7H-pyrrolo[2,3-d]pyrimidin-5-yl]-2-methoxyphenylcarbamate and 5-(4-amino-3-methoxyphenyl)-7-(1,4-dioxaspiro[4.5]dec-8-yl)-7H-pyrrolo[2,3-d]pyrimidin-4-amine. The mixture was dissolved in acetone (200 mL) and HCl (5N, 100 mL) was added dropwise over 0.5 hr. The resulting solution was stirred at room temperature overnight and the solvent was then evaporated. The acidic solution was basified with 2N NaOH (ice-cooling) and extracted with EtOAc (3×150 mL). The combined organics were washed with water (2×100 mL). During the extraction process a solid precipitated. This solid was filtered and triturated in hot EtOAc/MeOH. The insolubles were filtered, the filtrate evaporated and then resulting solid triturated with diethylether/ethyl acetate to give a yellow solid. The organic layers from the original extraction were dried (sodium sulphate), filtered and evaporated. The resulting solid was triturated with diethyl ether/ethyl acetate (5:1) and filtered to give 4-[4-amino-5-(4-amino-3-methoxyphenyl)-7H-pyrrolo[2,3-d]pyrimidin-7-yl]-1-cyclohexanone as a yellow solid. (2.3 g, combined yield=78%). $^1$H NMR (d₆ DMSO, 400 MHz): 8.17(1H, s), 7.32(1H, s), 6.88(1H, s), 6.77(1H, m), 6.73(1H, m), 6.71(1H, m), 6.07(2H, bs), 5.14(1H, m), 3.81 (3H, s), 2.72(2H, m), 2.35(4H, m), 2.18 (2H, m). HPLC: (5 to 95% CH₃CN in 0.1 N aqueous ammonium acetate over 20 min.) $t_r$=11.24 min, 95% d) To a solution of 4-[4-amino-5-(4-amino-3-methoxyphenyl)-7H-pyrrolo[2,3-d]pyrimidin-7-yl]-1-cyclohexanone (0.105 g, 0.3 mmol) in pyridine (2 mL) and dichloromethane (5 mL) was added benzoyl chloride (63 mg, 0.45 mmol) in dichloromethane (1 mL) at 0° C. under nitrogen. The solution was stirred at 0° C. for 2 hr and then quenched with water (5 mL). HCl (1N, 40 mL) was added and the aqueous layer extracted with dichloromethane (3×25 mL). The combined organic layers were washed with water (1×30 mL). The organic layer was dried (sodium sulphate), filtered and evaporated to leave an oil which was purified by flash silica gel column 5 chromatography using 2%–10% MeOH/EtOAc as eluent to give N1-4-[4-amino-7-(4-oxocyclohexyl)-7H-pyrrolo[2,3-d]pyrimidin-5-yl]-2-methoxyphenylbenzamide as a white solid (0.130 g, 96%). M.pt 234–237° C. Rf in 9:1 EtOAc: MeOH=0.30. HPLC: (5 to 95% CH₃CN in 0.1 N aqueous ammonium acetate over 20 min.) $t_r$=14.82 min, 96%. $^1$H NMR (d₆ DMSO, 400 MHz): 9.43(1H, s), 8.19(1H, s), 7.94(3H, m), 7.59 (4H, m), 7.18(1H, s), 7.06(1H, d, J=8 Hz), 6.18(2H, bs), 5.20(1H, m), 3.92(3H, s), 2.76(2H, m), 2.35(4H, m), 2.22(2H, m).

Example 318

Benzyl N-4-[4-Amino-7-(4-oxocyclohexyl)-7H-pyrrolo[2,3-d]pyrimidin-5-yl]-2-methoxyphenylcarbamate To a solution of give 4-[4-amino-5-(4-amino-3-methoxyphenyl)-7H-pyrrolo[2,3-d]pyrimidin-7-yl]-1-cyclohexanone (0.40 g, 1.15 mmol) in pyridine (5 mL) and dichloromethane (10 mL) was added benzylchloroformate (0.29 g, 1.73 mmol) at −5° C. under nitrogen. The solution was warmed to 0° C. and stirred for 1 hr. The reaction was quenched with water (5 mL) and the solvent evaporated. The residue was partitioned between EtOAc and water (100 mL each) and the aqueous layer was extracted with EtOAc (3×50 mL). The combined organics were dried (sodium sulphate), filtered and evaporated to leave a solid which was triturated with EtOAc/Et₂O to give benzyl N-4-[4-amino-7-(4-oxocyclohexyl)-7H-pyrrolo[2,3-d]pyrimidin-5-yl]-2-methoxyphenylcarbamate (0.28 g) as a yellow solid. M.pt 175–176° C. Rf in 9:1 EtOAc:MeOH=0.24. HPLC: (5 to 95% CH₃CN in 0.1 N aqueous ammonium acetate over 20 min.) $t_r$=16.69 min, 98%. $^1$H NMR (d₆ DMSO, 400 MHz): 8.64(1H, s), 8.17(1H, s), 7.75(1H, d, J=8.4 Hz), 7.50(1H, s), 7.36(5H, m), 7.10(1H, s), 7.02(1H, d, J=8 Hz), 6.15(2H, bs), 5.19(3H, m), 3.81 (3H, s), 2.72(2H, m), 2.35(4H, m), 2.22(2H, m).

Example 319 cis-Benzyl N-(4-{4-Amino-7-[4-(4-methylpiperazino)cyclohexyl]-7H-pyrrolo[2,3-d]pyrimidin-5-yl}2-methoxyphenyl)carbamate tri-Maleate and trans-Benzyl N-(4-{4-amino-7-[4-(4-methylpiperazino)cyclohexyl]-7H-pyrrolo[2,3-d]pyrimidin-5-yl}-2-methoxyphenyl)carbamate tri-Maleate To a solution of benzyl N-4-[4-amino-7-(4-oxocyclohexyl)-7H-pyrrolo[2,3-d]pyrimidin-5-yl]-2-methoxyphenylcarbamate (0.83 g, 1.74 mmol), N-methylpiperazine (0.52 g, 5.22 mmol) and glacial acetic acid (0.31 g, 5.22 mmol) in dichloroethane (100 mL) under nitrogen was added sodium triacetoxyborohydride (0.55 g, 2.61 mmol) portionwise. The solution was stirred for 6 hr and then quenched by the addition of sodium hydroxide (2N, 20 mL). The organic layer was separated and the aqueous layer was extracted with dichloromethane (2×50 mL). The combined organics were washed with brine (1×50 mL), dried (sodium sulphate), filtered and evaporated to leave an oil which was purified by flash silica gel column chromatography using EtOAc, 9:1 EtOAc:MeOH, CH₂Cl₂ and 9:1 CH₂Cl₂:MeOH to give in F20–25 an oil (480 mg). This oil was dissolved in ethyl acetate and treated with maleic acid (280 mg) in ethyl acetate. The resulting solid was filtered under a stream of nitrogen and dried in vacuo for 4 hr to give Cis-benzyl N-(4-{4-amino-7-[4-(4-methylpiperazino)cyclohexyl]-7H-pyrrolo[2,3-d]pyrimidin-5-yl}-2-methoxyphenyl)carbamate tri-maleate salt (580 mg) as a cream solid. M.pt. 158° C. (dec.) $^1$H NMR (d₆ DMSO, 400 MHz):8.74(1H, s), 8.27(1H, s), 7.78 (1H, d), 7.35–7.77(5H, m), 7.10(1H, s), 7.04(1H, s), 6.16(6H, s), 5.17(2H, s), 4.74 (1H, m), 3.82(3H, s), 3.23(5H, m), 2.78 (3H, s), 2.51(3H, m), 2.41(1H, s), 2.09 (4H, m), 1.70(4H, m). HPLC: (5 to 95% CH₃CN in 0.1 N aqueous ammonium acetate over 20 min.) $t_r$=13.30 min, 94%.

F28–45 gave a glassy foam (186 mg) which was dissolved in in ethyl acetate (10 mL) and treated with maleic acid (114 mg) in ethyl acetate (3 mL). The resulting solid was filtered under nitrogen and dried in vacuo for 4 hr to give trans-benzyl N-(4-{4-amino-7-[4-(4-methylpiperazino)cyclohexyl]-7H-pyrrolo[2,3-d]pyrimidin-5-yl}-2-methoxyphenyl)carbamate tri-maleate salt (250 mg) as a cream solid. M.pt 146–148° C. HPLC: (5 to 95% CH₃CN in 0.1 N aqueous ammonium acetate over 20 min.) $t_r$=13.54 min, 94.6%. $^1$H NMR (d₆ DMSO, 400 MHz): 8.72 (1H, s), 8.25(1H, s), 7.77(1H, d), 7.51(1H, s), 7.35(5H, m), 7.10(1H, s), 7.04(1H, d), 6.16(6H, s), 5.17(2H, s), 4.59 (1H, m), 3.86(3H, s), 2.70–3.10(11H, m), 2.50(3H, s), 1.97(6H, m), 1.56(2H, m).

Example 320 trans-N1-(4-{4-Amino-7-[4-(4-methylpiperazino)cyclohexyl]-7H-pyrrolo[2,3-d]pyrimidin-5-yl}-2-methoxyphenyl)benzamide To a solution of N1-4-[4-amino-7-(4-oxocyclohexyl)-7H-pyrrolo[2,3-d]pyrimidin-5-yl]-2-methoxyphenylbenzamide (1.2 g, 2.66 mmol), N-methylpiperazine (0.80 g, 7.98 mmol) and glacial acetic acid (0.48 g, 7.98 mmol) in dichloroethane (150 mL) under nitrogen was added sodium triacetoxyborohydride (0.85 g, 3.99 mmol) portionwise. The solution was stirred at room temperature overnight and then quenched by the addition of sodium hydroxide (2 N, 20 mL). The aqueous layer was extracted with dichloromethane (3×50 mL) and the combined organics were dried (sodium sulphate), filtered and evaporated to leave a solid which was purified by flash silica gel column chromatography using dichloromethane then 5% MeOH/dichloromethane to 20% MeOH/ dichloromethane in 5% increments. F23–36 were combined and evaporated to give a cream solid (0.11 g) which was dissolved in EtOAc (10 mL) and treated with a solution of maleic acid ( ) in EtOAc (5 mL). The resulting fine solid was filtered under a stream of nitrogen to give trans-N1-(4-{4-amino-7-[4-(4-methylpiperazino)cyclohexyl]-7H-pyrrolo[2,3-d]pyrimidin-5-yl}-2-methoxyphenyl)benzamide (0.108 g) as a cream solid. $^1$H NMR (d$_6$ DMSO, 400 MHz): 9.48(1H, s), 8.28(1H, s), 7.97(3H, m), 7.53–25 7.63(4H, m), 7.18(1H, s), 7.08(1H, d), 6.85(1H, bs), 6.16(6H, s), 4.61 (1H, m), 3,92 (3H, s), 2.70–3.11(11H, m), 2.01(7H, m), 1.58(2H, m). HPLC/MS (Column=Pecosphere 3 C$_{18}$ 3 micron, conditions=100% 100 mM ammonium acetate to 100% acetonitrile over 5 min), t$_r$=1.83 min, MH$^{30}$ =540.8

Example 321 cis-N1-(4-{4-Amino-7-[4-(4-methylpiperazino) cyclohexyl]-7H-pyrrolo[2,3-d]pyrimidin-5-yl}-2-methoxyphenyl)-3-phenylpropanamide and trans-N1-(4-{4-Amino-7-[4-(4-methylpiperazino) cyclohexyl]-7H-pyrrolo[2,3-d]pyrimidin-5-yl}-2-methoxyphenyl)-3-phenylpropanamide a) To a solution of 4-[4-amino-5-(4-amino-3-methoxyphenyl)-7H-pyrrolo[2,3-d]pyrimidin-7-yl]-1-cyclohexanone (0.8 g, 2.3 mmol) in pyridine (13 mL) and dichloromethane (32 mL) at 0° C. was added hydrocinnamoylchloride (0.57 g, 3.4 mmol) in dichloromethane (5 mL) under nitrogen. The solution was stirred at 0° C. for 2 hr, warmed to room temperature and quenched by addition of saturated aqueous citric acid solution (50 mL). The organic layer was washed with saturated aqueous citric acid solution (2×50 mL), dried (sodium sulphate), filtered and evaporated to leave N1-{4-[4-amino-7-(4-oxocyclohexyl)-7H-pyrrolo[2,3-d]pyrimidin-5-yl]-2-methoxyphenyl}-3-phenylpropanamide (1.0 g, 92% crude) as a brown foam. $^1$H NMR (d$_6$ DMSO, 400 MHz):9.17(1H, s), 8.18(1H, s), 8.06(1H, d), 7.51(1H, s), 7.18–7.29(6H, m), 7.09(1H, m), 6.99(1H, d), 6.21(2H, bs), 5.18 (1H, m), 3.88(3H, s), 1.99–2.93(12H, m). HPLC: (5 to 95% CH$_3$CN in 0.1 N aqueous ammonium acetate over 20 min.) t$_r$=14.48 min, 92.2%.

c) To a solution of 92% pure N1-{4-[4-amino-7-(4-oxocyclohexyl)-7H-pyrrolo[2,3-d]pyrimidin-5-yl]-2-methoxyphenyl}-3-phenylpropanamide (1.0 g, 2.1 mmol), N-methylpiperazine (0.63 g, 6.3 mmol), acetic acid (0.38 g, 6.3 mmol) in dichloroethane (100 mL) was added sodium triacetoxyborohydride (0.67 g, 3.15 mmol) portionwise under nitrogen. The solution was stirred for 20 hr and then quenched by the addition of saturated aqueous sodium bicarbonate solution (50 mL). The aqueous layer was extracted with dichloromethane (3×50 mL), dried (sodium sulphate), filtered and evaporated to leave a sludge which was purified by flash silica gel column chromatography using dichloromethane to 50% MeOH/ dichloromethane in 10% increments. F84–96 were combined and evaporated to leave cis-N1-(4-{4-amino-7-[4-(4-methylpiperazino)cyclohexyl]-7H-pyrrolo[2,3-d] pyrimidin-5-yl}-2-methoxyphenyl)-3-phenylpropanamide (0.26 g) as a cream foamy glass. HPLC: (5 to 95% CH$_3$CN in 0.1 N aqueous ammonium acetate over 20 min.) t$_r$=12.65 min, 95.2%.$^1$H NMR (d$_6$ DMSO, 400 MHz): 9.17(1H, s), 8.14(1H, s), 8.05(1H, d), 7.28(5H, m), 7.18(1H, m), 7.10(1H, s), 6.99(1H, d), 6.11(2H, bs), 4.67(1H, m), 3.88(3H, s), 2.90(2H, m), 2.73(2H, m), 2.50(7H, m), 2.28(3H, s), 2.06(3H, m), 1.71(2H, m), 1.55(2H, m). F121–138 were combined and evaporated to leave trans-N1-(4-{4-amino-7-[4-(4-methylpiperazino)cyclohexyl]-7H-pyrrolo[2,3-d] pyrimidin-5-yl}-2-methoxyphenyl)-3-phenylpropanamide (0.11 g) as a white solid. HPLC: (5 to 95% CH$_3$CN in 0.1 N aqueous ammonium acetate over 20 min.) t$_r$=12.61 min, 96.2%. $^1$H NMR (d$_6$ DMSO, 400 MHz): 9.16(1H, s), 8.13 (1H, s), 8.04(1H, d), 7.44(1H, s), 7.29 (4H, m), 7.18(1H, m), 7.09(1H, s), 6.97 (1H, d), 6.11(2H bs), 4.53(1H, m), 3.88 (3H, s), 2.93(2H, m), 2.71(2H, m), 2.50 (4H, m), 2.30(5H, m), 2.14(3H, s), 1.89(6H, m), 1.46(2H, m).

General Procedure for Substituted Pyrrolopyrimidine Aryl Sulfonamides are as Follows A 0.19 M solution of 5-(4-amino-3-fluorophenyl)-7-[4-(4-methylpiperazino)cyclohexyl]-7H-pyrrolo[2,3-d] pyrimidin-4-amine in pyridine was added one equivalent of substituted aryl sulfonyl chloride. The mixture was heated to 45° C. while being shaken in an Incubator Shaker for 24 h. The reaction mixture was purified by using mass actuated preparative RP-HPLC (Micromass/Gilson, Hypersil BDS C18, 5 u, 100×21.2 mm; 100–100% ammonium acetate (0.05 M, pH 4.5)-acetonitrile over 12.5 min, 25 mL/min).

Compounds synthesized by the above procedure include:

| Name | HPLC rt min | m/z |
|---|---|---|
| Example 322: Trans-N-1-(4-{4-amino-7-[4-(4-methylpiperazino)cyclohexyl]-7H-pyrrolo[2,3-d]-pyrimidin-5-yl}-2-fluorophenyl)-2-(trifluoromethoxy)-1-benzenesulfonamide trimaleate | 3.18 | 648.39 |
| Example 323: Trans-N-1-(4-{4-amino-7-[4-(4-methylpiperazino)cyclohexyl]-7H-pyrrolo[2,3-d]-pyrimidin-5-yl}-2-fluorophenyl)-5-chloro-2-thiophenesulfonamide benzenesulfonamide trimaleate | 3.14 | 604.03 |
| Example 324: Trans-N-1-(4-{4-amino-7-[4-(4-methylpiperazino)cyclohexyl]-7H-pyrrolo[2,3-d]-pyrimidin-5-yl}-2-fluorophenyl)-2-chloro-4-fluoro-1-benzenesulfonamide benzenesulfonamide trimaleate | 3.07 | 616.1 |
| Example 325: Trans-N-1-(4-{4-amino-7-[4-(4-methylpiperazino)cyclohexyl]-7H-pyrrolo[2,3-d]-pyrimidin-5-yl}-2-fluorophenyl)-2,3-dichloro-1-benzenesulfonamide trimaleate | 3.39 | 632.12 |
| Example 326: cis-N-1-(4-{4-amino-7-[4-(4-methylpiperazino)cyclohexyl]-7H-pyrrolo[2,3-d]-pyrimidin-5-yl}-2-fluorophenyl)-2-chloro-4-fluoro-1-benzenesulfonamide trimaleate | 2.82 | 616.2 |
| Example 327: cis-N-1-(4-4-amino-7-[4-(4-methylpiperazino)cyclohexyl]-7H-pyrrolo[2,3-d]-pyrimidin-5-yl-2-fluorophenyl)-2,6-difluoro-1-benzenesulfonamide trimaleate | 2.66 | 600.3 |
| Example 328: Trans-N-1-(4-{4-amino-7-[4-(4-methylpiperazino)cyclohexyl]-7H-pyrrolo[2,3-d]-pyrimidin-5-yl}-2-fluorophenyl)-2,6-difluoro-1-benzenesulfonamide trimaleate | 2.53 | 600.3 |
| Example 329: Trans-N-4-(4-{4-amino-7-[4-(4-methylpiperazino)cyclohexyl]-7H-pyrrolo[2,3-d]-pyrimidin-5-yl}-2-fluorophenyl)-2,1,3-benzothiadiazole-4-sulfonamide trimaleate | 2.63 | 622.1 |

| Name | HPLC rt min | m/z |
|---|---|---|
| Example 330: Trans-N-1-(4-{4-amino-7-[4-(4-methylpiperazino)cyclohexyl]-7H-pyrrolo[2,3-d]-pyrimidin-5-yl}-2-fluorophenyl)-2,3,4-trifluoro-1-benzenesulfonamide trimaleate | 2.87 | 618.1 |
| Example 331: Cis-N-1-(4-{4-amino-7-[4-(4-methylpiperazino)cyclohexyl]-7H-pyrrolo[2,3-d]-pyrimidin-5-yl}-2-fluorophenyl)-2-nitro-1-benzenesulfonamide trimaleate | 3.13 | 609.1 |
| Example 332: Cis-N-1-(4-{4-amino-7-[4-(4-methylpiperazino)cyclohexyl]-7H-pyrrolo[2,3-d]-pyrimidin-5-yl}-2-fluorophenyl)-2-fluoro-1-benzenesulfonamide trimaleate | 2.89 | 582.1 |
| Example 333: Cis-N-1-(4-{4-amino-7-[4-(4-methylpiperazino)cyclohexyl]-7H-pyrrolo[2,3-d]-pyrimidin-5-yl}-2-fluorophenyl)-2,4,6-trichloro-1-benzenesulfonamide trimaleate | 3.4 | 668 |
| Example 334: Cis-N-1-(4-{4-amino-7-[4-(4-methylpiperazino)cyclohexyl]-7H-pyrrolo[2,3-d]-pyrimidin-5-yl}-2-fluorophenyl)-2,6-dichloro-1-benzenesulfonamide trimaleate | 3.04 | 632.1 |
| Example 335: Cis-N-1-(4-{4-amino-7-[4-(4-methylpiperazino)cyclohexyl]-7H-pyrrolo[2,3-d]-pyrimidin-5-yl}-2-fluorophenyl)-2-chloro-1-benzenesulfonamide trimaleate | 2.94 | 598.1 |
| Example 336: Cis-N-1-(4-{4-amino-7-[4-(4-methylpiperazino)cyclohexyl]-7H-pyrrolo[2,3-d]-pyrimidin-5-yl}-2-fluorophenyl)-3-fluoro-1-benzenesulfonamide dimaleate | 2.76 | 582.1 |
| Example 337: cis-N-1-(4-{4-amino-7-[4-(4-methylpiperazino)cyclohexyl]-7H-pyrrolo[2,3-d]-pyrimidin-5-yl}-2-fluorophenyl)-5-chloro-2-thiophene-sulfonamide dimaleate | 3.01 | 604.3 |
| Example 338: Cis-N-1-(4-{4-amino-7-[4-(4-methylpiperazino)cyclohexyl]-7H-pyrrolo[2,3-d]-pyrimidin-5-yl}-2-fluorophenyl)-4-bromo-2,5-difluoro-1-benzenesulfonamide trimaleate | 3.38 | 718.3 |
| Example 339: Cis-N-1-(4-{4-amino-7-[4-(4-methylpiperazino)cyclohexyl]-7H-pyrrolo[2,3-d]-pyrimidin-5-yl}-2-fluorophenyl)-3-chloro-4-fluoro-1-benzenesulfonamide trimaleate | 2.98 | 616.3 |
| Example 340: Cis-N-1-(4-{4-amino-7-[4-(4-methylpiperazino)cyclohexyl]-7H-pyrrolo[2,3-d]-pyrimidin-5-yl}-2-fluorophenyl-2-iodo-1-benzenesulfonamide trimaleate | 3.02 | 690.3 |
| Example 341: cis-N-1-(4-{4-amino-7-[4-(4-methylpiperazino)cyclohexyl]-7H-pyrrolo[2,3-d]-pyrimidin-5-yl}-2-fluorophenyl)-2-(trifluoromethoxy)-1-benzenesulfonamide trimaleate | 3.22 | 648.3 |
| Example 342: Cis-N-1-(4-{4-amino-7-[4-(4-methylpiperazino)cyclohexyl]-7H-pyrrolo[2,3-d]-pyrimidin-5-yl}-2-fluorophenyl)-2,3-dichloro-1-benzenesulfonamide trimaleate | 2.97 | 600.3 |
| Example 343: Cis-N-1-(4-{4-amino-7-[4-(4-methylpiperazino)cyclohexyl]-7H-pyrrolo[2,3-d]-pyrimidin-5-yl}-2-fluorophenyl)-2-chloro-6-methyl-1-benzenesulfonamide trimaleate | 3.12 | 612.3 |
| Example 344: Cis-N-1-(4-{4-amino-7-[4-(4-methylpiperazino)cyclohexyl]-7H-pyrrolo[2,3-d]-pyrimidin-5-yl}-2-fluorophenyl)-2-chloro-4-cyano-1-benzenesulfonamide trimaleate | 3.02 | 623.2 |
| Example 345: Cis-N-1-(4-{4-amino-7-[4-(4-methylpiperazino)cyclohexyl]-7H-pyrrolo[2,3-d]-pyrimidin-5-yl}-2-fluorophenyl)-2,3,4-trifluoro-1-benzenesulfonamide trimaleate | 3.08 | 618.3 |
| Example 346: Cis-N-1-(4-{4-amino-7-[4-(4-methylpiperazino)cyclohexyl]-7H-pyrrolo[2,3-d]-pyrimidin-5-yl}-2-fluorophenyl)-3,4-difluoro-1-benzenesulfonamide trimaleate | 2.98 | 600.3 |
| Example 347: Cis-N-1-(4-{4-amino-7-[4-(4-methylpiperazino)cyclohexyl]-7H-pyrrolo[2,3-d]-pyrimidin-5-yl}-2-fluorophenyl)-4-bromo-2-fluoro-1-benzenesulfonamide trimaleate | 3.13 | 660.2 |
| Example 348: Cis-N-1-(4-{4-amino-7-[4-(4-methylpiperazino)cyclohexyl]-7H-pyrrolo[2,3-d]-pyrimidin-5-yl}-2-fluorophenyl)-5-bromo-2-thiophene-sulfonamide trimaleate | 3.16 | 648.1 |
| Example 349: Cis-N-1-(4-{4-amino-7-[4-(4-methylpiperazino)cyclohexyl]-7H-pyrrolo[2,3-d]-pyrimidin-5-yl}-2-fluorophenyl)-2,4-dichloro-1-benzenesulfonamide trimaleate | 3.09 | 632.1 |
| Example 350: Cis-N-1-(4-{4-amino-7-[4-(4-methylpiperazino)cyclohexyl]-7H-pyrrolo[2,3-d]-pyrimidin-5-yl}-2-fluorophenyl)-2,3,4-trichloro-1-benzenesulfonamide trimaleate | 3.41 | 668.1 |
| Example 351: Cis-N-1-(4-{4-amino-7-[4-(4-methylpiperazino)cyclohexyl]-7H-pyrrolo[2,3-d]-pyrimidin-5-yl}-2-fluorophenyl)-3-bromo-5-chloro-2-thiophenesulfonamide trimaleate | 3.29 | 683.9 |
| Example 352: Cis-N-4-(4-{4-amino-7-[4-(4-methylpiperazino)cyclohexyl]-7H-pyrrolo[2,3-d]-pyrimidin-5-yl}-2-fluorophenyl)-2,1,3-benzo-thiadiazole-4-sulfonamide trimaleate | 2.73 | 622.1 |
| Example 353: cis-N-4-(4-{4-amino-7-[4-(4-methylpiperazino)cyclohexyl]-7H-pyrrolo[2,3-d]-pyrimidin-5-yl}-2-fluorophenyl)-2,1,3-benzoxadiazole-4-sulfonamide trimaleate | 2.8 | 606.1 |
| Example 354: Cis-N-1-(4-{4-amino-7-[4-(4-methylpiperazino)cyclohexyl]-7H-pyrrolo[2,3-d]-pyrimidin-5-yl}-2-fluorophenyl)-2,5-dichloro-1-thiophenesulfonamide trimaleate | 3.18 | 638 |
| Example 355: cis-N-4-(4-{4-amino-7-[4-(4-methylpiperazino)cyclohexyl]-7H-pyrrolo[2,3-d]-pyrimidin-5-yl}-2-fluorophenyl)-(7-chloro-2,1,3-benzoxadiazole)-4-sulfonamide trimaleate | 2.84 | 640.2 |
| Example 356: Cis-N-4-(4-{4-amino-7-[4-(4-methylpiperazino)cyclohexyl]-7H-pyrrolo[2,3-d]-pyrimidin-5-yl}-2-fluorophenyl)-(7-methyl-2,1,3-benzothiadiazole)-4-sulfonamide trimaleate | 2.89 | 636.2 |
| Example 357: Cis-N-4-(4-{4-amino-7-[4-(4-methylpiperazino)cyclohexyl]-7H-pyrrolo[2,3-d]-pyrimidin-5-yl}-2-fluorophenyl)-(5-methyl-2,1,3-benzothiadiazole)-4-sulfonamide trimaleate | 2.82 | 636.2 |
| Example 358: Cis-N-4-(4-{4-amino-7-[4-(4-methylpiperazino)cyclohexyl]-7H-pyrrolo[2,3-d]-pyrimidin-5-yl}-2-fluorophenyl)-(5-chloro-2,1,3-benzothiadiazole)-4-sulfonamide trimaleate | 2.82 | 656.2 |
| Example 359: Cis-N-1-(4-{4-amino-7-[4-(4-methylpiperazino)cyclohexyl]-7H-pyrrolo[2,3-d]-pyrimidin-5-yl}-2-fluorophenyl)-3-chloro-2-methyl-1-benzenesulfonamide trimaleate | 3.01 | 612 |
| Example 360: Cis-N-1-(4-{4-amino-7-[4-(4-methylpiperazino)cyclohexyl]-7H-pyrrolo[2,3-d]-pyrimidin-5-yl}-2-fluorophenyl)-2-bromo-1-benzenesulfonamide trimaleate | 2.81 | 644.2 |
| Example 361: Cis-N-1-(4-{4-amino-7-[4-(4-methylpiperazino)cyclohexyl]-7H-pyrrolo[2,3-d]-pyrimidin-5-yl}-2-fluorophenyl)-2,5-dibromo-3,6-difluoro-1-benzenesulfonamide trimaleate | 3.29 | 758.1 |
| Example 362: Cis-N-1-(4-{4-amino-7-[4-(4-methylpiperazino)cyclohexyl]-7H-pyrrolo[2,3-d]-pyrimidin-5-yl}-2-fluorophenyl)-2,3-dichloro-1-benzenesulfonamide trimaleate | 2.77 | 632 |
| Example 363: Cis-N-1-(4-{4-amino-7-[4-(4-methylpiperazino)cyclohexyl]-7H-pyrrolo[2,3-d]-pyrimidin-5-yl}-2-fluorophenyl)-(2-nitrophenyl)-methanesulfonamide trimaleate | 2.73 | 623.2 |

General Synthesis

Method (a)

A mixture of 4-[4-amino-5-(4-phenoxyphenyl)-7H-pyrrolo[2,3-d]pyrimidine-7-yl]-1-cyclohexanone (1.0 g, 2.51 mmol), the appropriate amine (7.54 mmol) and acetic acid (0.45 g, 7.54 mmol) in 1,2-dichloroethane (50 mL) was stirred at ambient temperature under an atmosphere of nitrogen for 30 minutes. Sodium triacetoxyborohydride (0.69 g, 3.26 mmol) was added and the mixture stirred at ambient temperature for 18 hours. Water (20 mL) and sodium bicarbonate (1.26 g, 15.1 mmol) were added to the mixture and stirred for one hour. The mixture was then filtered through a pad of celite and the pad was washed with dichloromethane (75 mL). The organic layer was extracted from the filtrate, dried over magnesium sulfate, filtered and evaporated to dryness under reduced pressure. The cis and trans isomers were purified by flash chromatography on silica gel using a methanol:dichloromethane gradient.

Method (b)

Where appropriate the salts were made as follows. The above amine (0.909 mmol) was dissolved in warm ethyl acetate (100 mL) then maleic acid (0.32 g, 2.73 mmol) in ethyl acetate (30 mL) was added. The resulting salt formed an oily residue on the bottom and sides of the flask. The supernatant was poured off and the residue was dissolved in water and lyophilized to give the salt Method (c)

Guanidines were made as follows. The amine (0.536 mmol) was dissolved in DMF (5 and cooled to −5° C. and then 1-H pyrazole-1-carbonamide (95 mg, 0.644 mmol) followed by diisopropylethylamine (208 mg, 1.6 mmol) were added. The reaction mixture was allowed to warm to rt over 16 h and then concentrated in vacuo. The reaction was partititoned between water (10 mL) and ethyl acetate (10 mL). The aqueous phase was lyophilized and purified by RP-HPLC. HPLC protocols:

1. RP-HPLC—Hypersil HyPurity Elite C18, 5 mm, 200 Å, 250×4.6 mm; 25–100% acetonitrile—0.1 M ammonium acetate over 15 min, ml/min.
2. RP-HPLC—Hypersil HyPurity Elite C18, 5 mm, 200 Å, 250×4.6 mm; 5–100% acetonitrile—0.1 M ammonium acetate over 15 min, 1 ml/min.

It should be appreciated that protecting group chemistry is used where approriate.

The following examples were prepared using the methods described above:

| Name | Synthetic method | HPLC-RT (Min) (Protocol) | m/z (MH+) | Additional chemistry |
|---|---|---|---|---|
| Example 364: Cis-4-{4-[4-amino-5-(4-phenoxy-phenyl)-7H-pyrrolo[2,3-d]-pyrimidin-7-yl]cyclo-hexyl}-1-piperazine-carboximidamide | c | 14.56 (2) | 511.7 | |
| Example 365: Trans-4-{4-[4-amino-5-(4-phenoxy-phenyl)-7H-pyrrolo[2,3-d]-pyrimidin-7-yl]cyclo-hexyl}-1-piperazine-carboximidamide | c | 14.25 (2) | 511.7 | |
| Example 366: Trans-7-(4-{methyl[2-(2-pyridyl)-ethyl]amino}cyclohexyl)-5-(4-phenoxyphenyl)-7H-pyrrolo[2,3-d]pyrimidin-4-amine trimaleate | a, b | 8.55 (2) | 519.6 | |
| Example 367: Cis-3-({4-[4-amino-5-(4-phenoxy phenyl)-7H-pyrrolo[2,3-d]-pyrimidin-7-yl]cyclo-hexyl}amino)propanoic acid | a | 10.21 (2) | 472.6 | Made by hydrolysis of the ester |
| Example 368: 3-({4-[4-amino-5-(4-phenoxy-phenyl)-7H-pyrrolo[2,3-d]-pyrimidin-7-yl]cyclo-hexyl}amino)propanoic acid | a | 6.33 (1) | 472.6 | Made by hydrolysis of the ester |
| Example 369: Ethyl cis-3-({4-[4-amino-5-(4-phenoxyphenyl)-7H-pyrrolo[2,3-d]pyrimidin-7-yl]cyclohexyl}amino)-propanoate dimaleate | a, b | 10.42 (1) | 500.6 | |

General Synthesis

Method (d)

To a solution of sodium hydride (22 mg, 0.553 mmol) in THF (2 mL) was added the appropriate phosphonate (0.553 mmol) at 0° C. and the resultant mixture was stirred at this temperature for 20 min and then at ambient temperature for 10 min. The reaction mixture was cooled to 0° C. and 4-[4-amino-5-(4-phenoxyphenyl)-7H-pyrrolo[2,3-d] pyrimin-7-yl]cyclohexanone (200 mg, 0.503 mmol) added in THF (10 mL) and the resultant mixture allowed to warm to ambient temperature and stirred for 16 h. The solvents were removed in vacuo and the residue partitioned between ethyl acetate (10 mL) and water (10 mL). The aqueous layer was further extracted into ethyl acetate (3×5 mL) and the combined organics were washed with water (3×5 mL), dried (MgSO4) and concentrated in vacuo. Purification by flash column chromatography on silica gel (for intermediates) or RP-HPLC (for final compounds) gave the desired compound.

Method (e)

Hydrogenations were carried out as follows. A mixture of the alkene, (0.068 mmol) and 10% Pd/C (12 mg) in ethanol (18 mL) was stirred under hydrogen (4 atm) for 14 h. The solids were removed by filtration and the filtrate concentrated in vacuo. Purification by RP-HPLC gave the final compound.

Method (f)

Lithium aluminum hydride reuctions were carried out as follows. A mixture of the substrate (0.19 mmol), lithium aluminum hydride (40 mg, 1.07 mmol) in THF (5 mL) was stirred at room temperature for 16 h. Fieser work up followed by purification by RP-HPLC gave the desired compound. HPLC conditions: RP-HPLC Pecosphere3 C18, 33×4.6 mm, 3m column; 0–100% acetonitrile—0.1 M ammonium acetate over 5 min, flow 4 ml/min. It should be appreciated that protecting group chemistry is used where approriate.

| Name | Synthetic Method | HPLC-RT (Min) | m/z (MH+) | Additional Chemistry |
|---|---|---|---|---|
| Example 370: {4-[4-Amino-5-(4-phenoxy-phenyl)-7H-pyrrolo[2,3-d]pyrimidin-7-yl]cyclo-hexyliden}methyl cyanide | d | 3.1 | 422.5 | |
| Example 371: tert-Butyl 2-[4-[4-amino-5-(4-phenoxyphenyl)-7H-pyrrolo[2,3-d]-pyrimidin-7-yl]cyclo-hexyliden}acetate | d | 3.97 | 497.1 | |

| Name | Synthetic Method | HPLC-RT (Min) | m/z (MH+) | Additional Chemistry |
|---|---|---|---|---|
| Example 372: Ethyl 2-[4-[4-amino-5-(4-phenoxyphenyl)-7H-pyrrolo[2,3-d]-pyrimidin-7-yl]cyclohexyliden}acetate | d | 3.56 | 469.0 | |
| Example 373: 2-[4-[4-Amino-5-(4-phenoxy-phenyl)-7H-pyrrolo[2,3-d]pyrimidin-7-yl]cyclohexyliden}acetate | d | 2.69 | 441.5 | Made by hydrolysis of the ethyl ester |
| Example 374: 7-[4-(2-aminoethyl)cyclohexyl]-5-(4-phenoxyphenyl)-7H-pyrrolo[2,3-d]pyrimidin-4-amine | f | 2.11 | 428.5 | Made by lithium aluminum hydride reduction of the unsaturated cyanide |
| Example 375: 2-{4-[4-amino-5-(4-phenoxy-phenyl)-7H-pyrrolo[2,3-d]pyrimidin-7-yl]cyclohexyl}acetic acid | e | 2.64 | 443.5 | Made by hydrogenation of the unsaturated acid |

Example 376 trans-5-{4-Amino-7-[4-(4-methylpiperazino)cyclohexyl]-7H-5 pyrrolo[2,3-d]pyrimidin-5-yl}-2-phenoxybenzonitrile Bisacetate a) 5-Bromo-phenoxybenzonitrile A mixture of 4-bromo-2-fluorobenzonitrile (5.0 g, 25 mmol), phenol (4.7 g, 50 mmol) and potassium carbonate (6.9 g, 50 mmol) in dimethylsulfoxide (30 mL) was heated at 100° C. for 18 hours. The mixture was cooled and water (200 mL) was added. The mixture was extracted with dichloromethane (2×50 mL). The combined organic solutions were washed with 15% aqueous sodium hydroxide (50 mL), saturated aqueous sodium bicarbonate (50 mL), dried over magnesium sulfate and filtered. The filtrate was concentrated under reduced pressure to give 5-bromo-phenoxybenzonitrile (7.25 g, quant.): $^1$H NMR (DMSO-d$_6$, 400 MHz) δ 8.20(d, 1H), 7.84(dd, 1H), 7.47(t, 2H), 7.30 (t, 1H), 7.20(dd, 2H), 6.87(d, 1H); RP-HPLC (Hypersil HS, 5 μm, 100 A, 4.6×250 mm; 25%–100% acetonitrile—0.05 M ammonium acetate over 10 min, 1 ml/min) t$_r$ 12.50 min.

b) 2-Phenxoy-5-(4,4,5,5-tetramethyl-1,3,2-dioxaborolane-2-yl)benzonitrile

A mixture of 5-bromo-phenoxybenzonitrile (2.0 g, 7.22 mmol), diboron pinacol ester (2.2 g, 8.66 mmol), potassium acetate (2.12 g, 21.7 mmol) and [1,1'-bis(diphenylphosphino)ferrocene]dichloropalladium (II) complex with dichloromethane (1:1) (0.35 g, 0.49 mmol) in N,N-dimethylformamide (40 mL) was heated at 85° C. for 20 hours then cooled and the solvents evaporated under reduced pressure. The residue was triturated with dichloromethane (40 mL), then filtered through a pad of celite and the filtrate concentrated to give an oil which was purified by flash chromatography on silica gel using heptane/ethyl acetate (9:1) as an eluent to give 2-phenoxy-5-(4,4,5,5-tetramethyl-1,3,2-dioxaborolane-2-yl)benzonitrile (1.56 g, 67%): $^1$H NMR (DMSO-d$_6$, 400 MHz) δ 8.01(s, 1H), 7.88(d, 1H), 7.49 (t, 2H), 7.32(t, 1H), 7.22(d, 2H), 6.90(d, 1H), 1.29(s, 12H); RP-HPLC (Hypersil HS, 5 μm, 100 A, 4.6×250 mm; 25%–100% acetonitrile—0.05 M ammonium acetate over 10 min, 1 ml/min) t$_r$ 13.85 min.

c) trans-5-(4-Chloro-7-(4-(4-methylpiperazino)cyclohexyl)-7H-pyrrolo[2,3-d]pyrimidin-5-yl)-2-phenoxybenzonitrile A mixture of trans-4-chloro-5-iodo-7-[4-(4-methylpiperazino)cyclohexyl]-7H-pyrrolo[2,3-d]pyrimidine (500 mg, 1.09 mmol), 2-phenxoy-5-(4,4,5,5-tetramethyl-1,3,2-dioxaborolane-2-yl)benzonitrile (425 mg, 1.31 mmol), sodium carbonate monohydrate (325 mg, 2,62 mmol) and tetrakis(triphenylphosphine)palladium(0) (75 mg, 0.065 mmol) in ethylene glycol dimethyl ether (8 mL) and water (4 mL) was heated at 85° C. for 18 hours. The mixture was cooled and evaporated under reduced pressure then partitioned between water (10 mL) and dichloromethane (25 mL). The combined organic solutions were dried over magnesium sulfate and then filtered. The filtrate was concentrated to give a material which was then purified by flash chromatography on silica gel using dichloromethane/methanol (9:1) as an eluent to give trans-5-(4-chloro-7-(4-(4-methylpiperazino)cyclohexyl)-7H-pyrrolo[2,3-d]pyrimidin-5-yl)-2-phenoxybenzonitrile: $^1$H NMR (DMSO-d$_6$, 400 MHz) δ 8.11(s, 1H), 8.07(d, 1H), 7.5–7.55(m, 3H), 7.01(d, 1H), 4.71(m, 1H), 2.2–2.6(m, 9H), 2.17(s, 3H), 1.8–2.1(m, 6H), 1.4–1.6(m, 2H); RP-HPLC (Hypersil HS, 5 μm, 100 A, 4.6×250 mm; 25%–100% acetonitrile—0.05 M ammonium acetate over 10 min, 1 ml/min) t$_r$ 9.20 min.

d) trans-5-{4-Amino-7-[4-(4-methylpiperazino)cyclohexyl]-7H-pyrrolo[2,3-d]pyrimidin-5-yl}-2-phenoxybenzonitrile Bisacetate A mixture of trans-5-(4-chloro-7-(4-(4-methylpiperazino)cyclohexyl)-7H-pyrrolo[2,3-d]pyrimidin-5-yl)-2-phenoxybenzonitrile (150 mg) in 1,4-dioxane (25 mL) and 30% aqueous ammonium hydroxide (25 mL) was heated at 120° C. in a sealed tube for 18 hours then cooled and evaporated under reduced pressure. The residue was purified by preparative RP-HPLC to give 5-{4-amino-7-[4-(4-methylpiperazino)cyclohexyl]-7H-pyrrolo[2,3-d]pyrimidin-5-yl}-2-phenoxybenzonitrile bisacetate: $^1$H NMR (DMSO-d$_6$, 400 MHz) δ 8.14(s, 1H), 7.91(s, 1H), 7.70(d, 1H), 7.55(s, 1H), 7.48(t, 2H), 7.27(t, 1H), 7.20(d, 2H), 7.06(d, 1H), 6.27(bs, 2H), 4.55 (m, 1H), 2.53 m, 4H), 2.36(m, 5H), 2.17 (s, 3H), 2.0(m, 6H), 1.96(s, 6H); MS MH$^+$508.3; RP-HPLC (Hypersil HS, 5 μm, 100 A, 4.6×250 mm; 25%–100% acetonitrile—0.05 M ammonium acetate over 10 min, 1 ml/min) t$_r$ 7.27 min.

Example 377 trans-5-{4-Amino-7-[4-(4-methylpiperazino)cyclohexyl]-7H-pyrrolo[2,3-d]pyrimidin-5-yl}-2-phenoxybenzamide A mixture of (50 mg, 0.1 mmol) was dissolved in dimethylsulfoxide (1.6 mL) then treated with 30% aqueous hydrogen peroxide (1.25 mL) and 15% aqueous sodium hydroxide (1 mL). The mixture was stirred at ambient temperature for 18 hours then evaporated and the residue purified by preparative RP-HPLC then lyophilized. The material was dissolved in methanol (8 mL) and acetic acid (2 mL) then hydrogenated for 4 hours at atmospheric pressure and ambient temperature in the presence of 10% Pd-C (15 mg). The mixture was filtered through a pad of celite, evaporated under reduced pressure and then lyophilized to give trans-5-{4-amino-7-[4-(4-methylpiperazino)cyclohexyl]-7H-pyrrolo[2,3-d]pyrimidin-5-yl}-2-phenoxybenzamide (10 mg, 20%): $^1$H NMR (DMSO-d$_6$, 400 MHz) δ 8.14(s, 1H), 7.78(d, 1H), 7.65(s, 1H), 7.58(s, 1H), 7.39–7.50(m, 4H), 7.16(t, 1H), 7.10(d, 2H), 6.98(d, 1H), 6.15(bs, 2H), 4.55(m, 1H), 2.2–2.6(m, 9H), 2.14(s, 3H), 1.8–2.0(m, 6H), 1.41–1.48(m, 2H); MS MH$^+$526.4; RP-HPLC (Hypersil HS, 5 μm, 100 A, 4.6×250 mm; 25%–100% acetonitrile—0.05 M ammonium acetate over 10 min, 1 ml/min) t$_r$ 5.83 min

Example 378 trans-5-(3-Methoxy-4-phenoxyphenyl)-7-[4-(4-methylpiperazino)cyclohexyl]-7H-pyrrolo[2,3-d]pyrimidin-4-amine Acetate a) 4-Bromo-2-methoxy-1-phenoxybenzene A mixture of 4-bromoguaiacol (2.23 g, 11 mmol), phenyl boronic acid (4.03 g, 33 mmol), copper(II) acetate (2.18 g, 12 mmol) and 4A powdered molecular sieves (20 g) in dichloromethane (100 mL) was treated with triethylamine (5.5 g, 55 mmol) then stirred at ambient temperature for 20 hours. The mixture was filtered, concentrated under reduced pressure and purified by flash chromatography on silica gel using heptane/ethyl acetate (75:25) as an eluent to give 4-bromo-2-methoxy-1-phenoxybenzene (350 mg, 12%): $^1$H NMR (DMSO-d$_6$, 400 MHz) δ 7.3–7.4(m, 3H), 7.15(d, 1H), 7.05(t, 1H), 6.98(d, 1H), 6.85 (d, 2H), 3.77(s, 3H); RP-HPLC (Hypersil HS, 5 μm, 100 A, 4.6×250 mm; 25%–100% acetonitrile—0.05 M ammonium acetate over 10 min, 1 ml/min) t$_r$ 13.12 min.

b) 2-(3-Methoxy-4-phenoxyphenyl)-4,4,5,5-tetramethyl-1,3,2-dioxaborolane

The title compound was prepared from 4-bromo-2-methoxy-1-phenoxybenzene and pinacol diboron ester in the same manner as described for 2-phenoxy-5-(4,4,5,5-tetramethyl-1,3,2-dioxaborolane-2-yl)benzonitrile (58% yield) $^1$H NMR (DMSO-d$_6$, 400 MHz) δ 7.34(m, 4H), 7.07(t, 1H), 7.06(d, 1H), 6.87(d, 2H), 3.77(s, 3H), 1.31(s, 12H); TLC (heptane/ethyl acetate 9:1) R$_f$ 0.23.

c) trans-4-Chloro-5-(3-methoxy-4-phenoxyphenyl)-7-[4-(methylpiperazino)cyclohexyl]-7H-pyrrolo[2,3-d]pyrimidine The title compound (223 mg, 64%) was prepared from trans-4-chloro-5-iodo-7-[4-(4-methylpiperazino)cyclohexyl]-7H-pyrrolo[2,3-d]pyrimidine (300 mg, 0.655 mmol) and 2-(3-methoxy-4-phenoxyphenyl)-4,4,5,5-tetramethyl-1,3,2-dioxaborolane (235 mg, 0.727 mmol) in a similar manner to that described for the preparation of trans-5-(4-chloro-7-(4-(4-methylpiperazino)cyclohexyl)-7H-pyrrolo[2,3-d ]pyrimidin-5-yl)-2-phenoxybenzonitrile: $^1$H NMR (DMSO-d$_6$, 400 MHz) δ 8.67(s, 1H), 8.04(s, 1H), 7.32(m, 4H), 7.12(d, 1H), 7.08(d, 1H), 6.88(d, 2H), 4.71(m, 1H), 3.80(s, 3H), 2.2–2.6(m, 9H), 2.15(s, 3H), 1.9–2.1 (m, 6H), 1.49(m, 2H); MS MH$^+$532.4; RP-HPLC (Hypersil HS, 5 μm, 100 Å 4.6×250 mm; 25%–100% acetonitrile—0.05 M ammonium acetate over 10 min, 1 ml/min) t$_r$ 9.58 min.

d) trans-5-(3-Methoxy-4-phenoxyphenyl)-7-[4-(4-methylpiperazino)cyclohexyl]-7H-pyrrolo[2,3-d]pyrimidin-4-amine Acetate A mixture of trans-4-chloro-5-(3-methoxy-4-phenoxyphenyl)-7-[4-(methylpiperazino)cyclohexyl]-7H-pyrrolo[2,3-d]pyrimidine (220 mg, 0.414 mmol) in 1,4-dioxane (20 mL) and 30% aqueous ammonium hydroxide (20 mL) was heated at 120° C. in a sealed tube for 18 hours then cooled, concentrated under reduced pressure and purified by preparative RP-HPLC to give trans-5-(3-methoxy-4-phenoxyphenyl)-7-[4-(4-methylpiperazino)cyclohexyl]-7H-pyrrolo[2,3-d]pyrimidin-4-amine acetate (122 mg, 58%): $^1$H NMR (DMSO-d$_6$, 400 MHz) δ 8.14(s, 1H), 7.49(s, 1H), 7.32(t, 2H), 7.22(s, 1H), 7.10(d, 1H), 7.05(m, 2H), 6.92(d, 2H), 6.2(bs, 2H), 4.56(m, 1H), 3.79 (s, 3H), 2.2–2.6 (m, 9H), 2.15(s, 3H), 1.8–2.05(m, 6H), 1.90(s, 6H), 1.45(m, 2H); MS MH-513.4; RP-HPLC (Hypersil HS, 5 μm, 100 A 4.6×250 mm; 25%–100% acetonitrile—0.05 M ammonium acetate over 10 min, 1 ml/min) t$_r$ 14.77 min.

Example 379 trans-5-{4-Amino-7-[4-(4-methylpiperazino)cyclohexyl]-7H-pyrrolo[2,3-d]pyrimidin-5-yl}-2-phenoxyphenol A mixture of trans-5-(3-methoxy-4-phenoxyphenyl)-7-[4-(4-methylpiperazino)cyclohexyl]-7H-pyrrolo[2,3-d]pyrimidin-4-amine acetate (50 mg, 0.098 mmol) in 48% aqueous hydrobromic acid (1 mL) was heated at 120° C. for 2 hours. The solution was cooled and concentrated under reduced pressure then purified by preparative RP-HPLC to give trans-5-{4-amino-7-[4-(4-methylpiperazino)cyclohexyl]-7H-pyrrolo[2,3-d]pyrimidin-5-yl}-2-phenoxyphenol (32 mg, 66%): $^1$H NMR (DMSO-d$_6$, 400 MHz) δ 9.8(bs, 1H), 8.13(s, 1H), 7.39(s, 1H), 7.31(t, 2H), 7.03(m, 3H), 6.89(m, 3H), 6.17(bs, 2H), 4.55(m, 1H), 2.2–2.6(m, 9H), 2.15(s, 3H), 1.8–2.2(m, 6H), 1.44 (m, 2H); MS MH$^+$499.4; RP-HPLC (Hypersil HS, 5 μm, 100 A 4.6×250 mm; 25%–100% acetonitrile—0.05 M ammonium acetate over 10 min, 1 ml/min) tr 13.47 min.

Example 380 trans-5-(3-Chloro-4-phenoxyphenyl)-7-[4-(4-methylpiperazino)cyclohexyl]-7H-pyrrolo[2,3-d]pyrimidin-4-amine a) 4-Bromo-2-chloro-1-phenoxybenzene A mixture of 4-bromo-2-chlorophenol (2.07 g, 10 mmol), phenyl boronic acid (3.66 g, 30 mmol), copper(II) acetate (2.0 g, 1.1 mmol) and 4A powdered molecular sieves (20 g) in dichloromethane (100 mL) was treated with triethylamine (5.0 g, 50 mmol) then stirred at ambient temperature for 5 days. The mixture was diluted with heptane (100 mL), then filtered through a bed of celite. The filtrate was concentrated under reduced pressure to remove dichloromethane. The mixture was extracted with IN hydrochloric acid, 15 wt % aqueous sodium hydroxide, brine and then dried over magnesium sulfate. The mixture was filtered and the filtrate concentrated under reduced pressure to provide (1.27 g, 45%): $^1$H NMR (DMSO-d$_6$, 400 MHz) δ 7.87(s, 1H), 7.55(d, 1H), 7.40(t, 2H), 7.17(t, 1H), 6.99(m, 3H); MS MH$^+$283; RP-HPLC (Hypersil HS, 5 μm, 100 A 4.6×250 mm; 25%–100% acetonitrile—0.05 M ammonium acetate over 10 min, 1 m/min) t$_r$ 14.42min.

b) 2-(3-Chloro-4-phenoxyphenyl)-4,4,5,5-tetrametyl-1,3,2-dioxaborolane

The title compound (472 mg, 81%) was prepared from 4-bromo-2-chloro-1-phenoxybenzene (500 mg, 1.77 mmol) in a similar manner to that described for the preparation 2-phenoxy-5-(4,4,5,5-tetramethyl-1,3,2-dioxaborolane-2-yl)benzonitrile: $^1$H NMR (DMSO-d$_6$, 400 MHz) δ 7.75(s, 1H), 7.60 (d, 1H), 7.42(t, 2H), 7.21(t, 1H), 7.02 (m, 3H), 1.30(s, 12H); RP-HPLC (Hypersil HS, 5 μm, 100 A 4.6×250 mm; 25%–100% acetonitrile—0.05 M ammonium acetate over 10 min, 1 ml/min) tr 15.53 min.

c) trans-5-(3-Chloro-4-phenoxyphenyl)-7-[4-(4-methylpiperazino)cyclohexyl]-7H-pyrrolo[2,3-d]pyrimidin-4-amine The title compound was prepared from 2-(3-chloro-4-phenoxyphenyl)-4,4,5,5-tetramethyl-1,3,2-dioxaborolane and trans-4-chloro-5-iodo-7-[4-(4-methylpiperazino)cyclohexyl]-7H-pyrrolo[2,3-d]pyrimidine in a similar manner to that described for the preparation of trans-5-{4-amino-7-[4-(4-methylpiperazino)cyclohexyl]-7H-pyrrolo[2, 3-d]pyrimidin-5-yl}-2-phenoxybenzonitrile: $^1$H NMR (DMSO-d$_6$, 400 MHz) δ 8.14 (s, 1H), 7.79(s, 1H), 7.65 (s, 1H), 7.38(m, 3H), 7.16(t, 2H), 7.04 (d, 2H), 6.24(bs, 2H), 4.55(m, 1H), 2.2–2.6(m, 9H), 2.16(s, 3H), 1.89(m, 6H), 1.48 (m, 2H); MS MH$^+$517.3; RP-HPLC (Hypersil HS, 5 μm, 100 A 4.6×250 mm; 25%–100% acetonitrile—0.05 M ammonium acetate over 10 min, 1 ml/min) t$_r$ 15.75 min.

Example 381 trans-5-(3-Fluoro-4-phenoxyphenyl)-7-[4-(4-methylpiperazino)cyclohexyl]-7H-pyrrolo[2,3-d]pyrimidin-4-amine Bisacetate a) 4-Bromo-2-fluoro-1-phenoxybenzene The title compound was prepared in a 33% yield from 4-bromo-2-fluorophenol and phenyl boronic acid in a manner similar to that described for the preparation of 4-bromo-2-chloro-1-phenoxybenzene: $^1$H NMR (DMSO-d$_6$, 400 MHz) δ 7.75(dd, 1H), 7.40(m, 3H), 7.15(m, 2H), 7.01(dd, 2H); MS MH+267.2; RP-HPLC (Hypersil HS, 5 μm, 100 A 4.6×250 mm; 25%–100% acetonitrile—0.05 M ammonium acetate over 10 min, 1 ml/min) tr 13.57 min.

b) 2-(3-Fluoro-4-phenoxyphenyl)-4,4,5,5-tetramethyl-1,3,2-dioxaborolane

The title compound was prepared in a 65% from 4-bromo-2-fluoro-1-phenoxybenzene in a similar manner to that described for the preparation 2-phenoxy-5-(4,4,5,5-tetramethyl-1,3,2-dioxaborolane-2-yl)benzonitrile: $^1$H NMR (DMSO-d$_6$, 400 MHz) δ 7.49(dd, 2H), 7.41(m, 2H), 7.18 (t, 1H), 7.08(d, 1H), 7.05(d, 2H), 1.30(s, 12H); RP-HPLC (Hypersil HS, 5 μm, 100 A 4.6×250 mm; 25%–100% acetonitrile—0.05 M ammonium acetate over 10 min, I mmin) t$_r$ 14.63 min.

c) trans-4-{4-Chloro-7-[4-(4-methylpiperazino)cyclohexyl]-7H-pyrrolo[2,3-d]pyrimidin-5-yl}-2-fluorophenyl Phenyl Ether The title compound was prepared in an 85% yield from trans-4-chloro-5-iodo-7-[4-(4-methylpiperazino)cyclohexyl]-7H-pyrrolo[2,3-d]pyrimidine and 2-(3-fluoro-4-phenoxyphenyl)-4,4,5,5-tetrametyl-1,3,2-dioxaborolane in a similar manner to that described for the preparation of trans-5-(4-chloro-7-(4-(4-methylpiperazino)cyclohexyl)-7H-pyrrolo[2,3-d]pyrimidin-5-yl)-2-phenoxybenzonitrile: $^1$H NMR (DMSO-d$_6$, 400 MHz) δ 8.67 (s, 1H), 8.07(s, 1H), 7.58 (d, 1H), 7.41(m, 3H), 7.22(m, 1H), 7.16(m, 1H), 7.04(d, 2H), 4.70(m, 1H), 2.2–2.6 (m, 9H), 2.16(s, 3H), 1.94–2.03(m, 6H), 1.48(m, 2H); MS MH$^+$520.3; RP-HPLC (Hypersil HS, 5 μm, 100 A 4.6×250 mm; 25%–100% acetonitrile—0.05 M ammonium acetate over 10 min, 1 ml/min) tr 9.45 min.

d) trans-5-(3-Fluoro-4-phenoxyphenyl)-7-[4-(4-methylpiperazino)cyclohexyl]-7H-pyrrolo[2,3-d]pyrimidin-4-amine Bisacetate The title compound was prepared in a 75% yield from trans-4-{4-chloro-7-[4-(4-methylpiperazino)cyclohexyl]-7H-pyrrolo[2,3-d]pyrimidin-5-yl}-2-fluorophenyl phenyl ether in a similar manner to that described for the preparation of trans-5-(3-methoxy-4-phenoxyphenyl)-7-[4-(4-methylpiperazino)cyclohexyl]-7H-pyrrolo[2,3-d]pyrimidin-4-amine acetate: $^1$H NMR (DMSO-d$_6$, 400 MHz) δ 8.14(s, 1H), 7.52(s, 1H), 7.40(m, 3H), 7.27(m, 2H), 7.13 (t, 1H), 7.06(d, 2H), 6.25(bs, 2H), 4.55(m, 1H), 2.2–2.6(m, 9H), 2.14(s, 3H), 1.8–2.0(m, 6H), 1.92(s, 6H), 1.44(m, 2H); MS MH$^+$501; RP-HPLC (Hypersil HS, 5 μm, 100 A 4.6×250 mm; 25%–100% acetonitrile—0.05 M ammonium acetate over 10 min, 1 ml/min) tr 7.52 min.

Example 382 trans-5-(3-Methyl-4-phenoxyphenyl)-7-[4-(4-methylpiperazino)cyclohexyl]-7H-pyrrolo[2,3-d]pyrimidin-4-amine a) 4-Bromo-2-methyl-1-phenoxybenzene The title compound was prepared in a 35% yield from 4-bromo-2-methylphenol and phenyl boronic acid in a manner similar to that described for the preparation of 4-bromo-2-chloro-1-phenoxybenzene: $^1$H NMR (DMSO-d$_6$, 400 MHz) δ 7.54(s, 1H), 7.35(m, 3H), 7.12(t, 1H), 6.93(d, 2H), 6.82(d, 2H), 2.18(s, 3H); RP-HPLC (Hypersil HS, 5 μm, 100 A, 4.6×250 mm; 25%–100% acetonitrile—0.05 M ammonium acetate over 10 min, 1 mmin) tr 14.25min.

b) 2-Methyl-4-(4,4,5,5-tetrametyl-1,3,2-dioxaborolan-2-yl) phenyl Phenyl Ether

The title compound was prepared in a 77% from 4-bromo-2-methyl-1-phenoxybenzene in a similar manner to that described for the preparation 2-phenoxy-5-(4,4,5,5-tetramethyl-1,3,2-dioxaborolane-2-yl)benzonitrile: $^1$H NMR (DMSO-d$_6$, 400 MHz) δ 7.67(s, 1H), 7.50(d, 1H), 7.38(t, 2H), 7.14(t, 1H), 6.94(d, 2H), 6.80(d, 1H), 2.21(t, 3H); TLC (heptane/ethyl acetate 9:1) R$_f$0.6.

c) trans-4-{4-Chloro-7-[4-(4-methylpiperazino)cyclohexyl]-7H-pyrrolo[2,3-d]pyrimidin-5-yl}-2-methylphenyl Phenyl Ether The title compound was prepared in an 82% yield from from trans-4-chloro-5-iodo-7-[4-(4-methylpiperazino)cyclohexyl]-7H-pyrrolo[2,3-d]pyrimidine and 2-methyl-4-(4,4,5,5-tetrametyl-1,3,2-dioxaborolan-2-yl)phenyl phenyl ether in similar manner to that described for the preparation of trans-5-(4-chloro-7-(4-(4-methylpiperazino)cyclohexyl)-7H-pyrrolo[2,3-d]pyrimidin-5-yl)-2-phenoxybenzonitrile: $^1$H NMR (DMSO-d$_6$, 400 MHz) δ 8.65 (s, 1H), 7.98(s, 1H), 7.49 (s, 1H), 7.37(m, 3H), 7.10(t, 1H), 6.95(m, 3H), 4.72(m, 1H), 2.2–2.6(m, 9H), 2.23(s, 3H), 2.17(s, 3H), 2.01(m, 6H), 1.48 (m, 2H); MS MH$^+$516.4; RP-HPLC (Hypersil HS, 5 μm, 100 A 4.6×250 mm; 25%–100% acetonitrile—0.05 M ammonium acetate over 10 min, 1 ml/min) tr 10.53 min.

d) trans-5-(3-Methyl-4-phenoxyphenyl)-7-[4-(4-methylpiperazino)cyclohexyl]-7H-pyrrolo[2,3-d]pyrimidin-4-amine The title compound was prepared in a 75% yield from trans-4-{4-chloro-7-[4-(4-methylpiperazino)cyclohexyl]-7H-pyrrolo[2,3-d]pyrimidin-5-yl}-2-methylphenyl phenyl ether in a similar manner to that described for the preparation of trans-5-(3-methoxy-4-phenoxyphenyl)-7-[4-(4-methylpiperazino)cyclohexyl]-7H-pyrrolo[2,3-d]pyrimidin-4-amine acetate: $^1$H NMR (DMSO-d$_6$, 400 MHz) δ 8.13(s, 1H), 7.42(m, 4H), 7.37(t, 2H), 7.27(m, 1H), 7.10 (t, 1H), 6.97(m, 3H), 6.11(bs, 2H), 4.55(m, 1H), 2.2–2.6(m, 9H), 2.22(s, 3H), 2.14 (s, 3H), 1.7–2.0(m, 6H), 1.45(m, 2H); MS MH$^+$497.4; RP-HPLC (Hypersil HS, 5 μm, 100 A 4.6×250 mm; 5%–100% acetonitrile—0.05 M ammonium acetate over 25 min, 1 ml/min) tr 15.93 min.

Example 383 trans-7-[4-(4-methylpiperazino)cyclohexyl]-5-(3-nitro-4-phenoxyphenyl)-7H-pyrrolo[2,3-d]pyrimidin-4-amine Acetate a) 4-Bromo-2-nitro-1-phenoxybenzene The title compound was prepared in a quantitative yield from 5-bromo-2-fluoro-nitrobenzene and phenol in a manner similar to that described for the preparation of 5-bromo-phenoxybenzonitrile: $^1$H NMR (DMSO-d$_6$, 400 MHz) δ 8.31 9d, 1H), 7.86(dd, 1H), 7.45(t, 2H), 7.25(t, 1H), 7.13(d, 1H), 7.08(d, 2H); RP-HPLC (Hypersil HS, 5 μm, 100 A 4.6×250 mm; 25%–100% acetonitrile—0.05 M ammonium acetate over 10 min, 1 ml/min) tr 12.70 min.

b) 2-Nitro-4-(4,4,5,5-tetramethyl-1,3,2-dioxaborolan-2-yl) phenyl Phenyl Ether

The title compound was prepared in a 56% from 4-bromo-2-nitro-1-phenoxybenzene in a similar manner to that described for the preparation 2-phenoxy-5-(4,4,5,5-tetramethyl-1,3,2-dioxaborolane-2-yl)benzonitrile: $^1$H NMR (DMSO-d$_6$, 400 MHz) δ 8.19(d, 1H), 7.91(d, 1H), 7.46(t, 2H), 7.27(t, 1H), 7.14(d, 2H), 7.06(d, 1H), 1.31(s, 12H); RP-HPLC (Hypersil HS, 5 μm, 100 A 4.6×250 mm; 25%–100% acetonitrile—0.05 M ammonium acetate over 10 min, 1 ml/min) t$_r$ 14.02 min.

c) trans-7-[4-(4-Methylpiperazino)cyclohexyl]-5-(3-nitro-4-phenoxyphenyl)-7H-pyrrolo[2,3-d]pyrimidin-4-amine Acetate The title compound was prepared from trans-4-chloro-5-iodo-7-[4-(4-methylpiperazino)cyclohexyl]-7H-pyrrolo[2,3-d]pyrimidine and 2-nitro-4-(4,4,5,5-tetramethyl-1,3,2-dioxaborolan-2-yl)phenyl phenyl ether in a similar manner to that described for the preparation of trans-5-(4-chloro-7-(4-(4-methylpiperazino)cyclohexyl)-7H-pyrrolo[2,3-d]pyrimidin-5-yl)-2-phenoxybenzonitrile: $^1$H NMR (DMSO-d$_6$, 400 MHz) δ 8.15(s, 1H), 8.08(d, 1H), 7.74 (d, 1H), 7.46(s, 1H), 7.42(t, 2H), 7.23(m, 2H), 7.12(d, 2H), 6.36(bs, 2H), 4.56(m, 1H), 2.2–2.6(m, 9H), 2.16(s, 3H), 1.8–2.0(m, 6H), 1.92(s, 3H), 1.45 (m, 2H); MS MH$^+$528.4; RP-HPLC (Hypersil HS, 5 μm, 100 A 4.6×250 mm; 5%–100% acetonitrile—0.05 M ammonium acetate over 25 min, 1 ml/min) tr 14.88 min.

Example 384 trans-5-(3-amino-4-phenoxyphenyl)-7-[4-(4-methylpiperazino)cyclohexyl]-7H-pyrrolo[2,3-d]pyrimidin-4-amine A mixture of(135 mg, 0.256 mmol) in ethanol (5 mL) and water (2 mL) was heated at 80° C. then treated with sodium dithionite (270 mg, 1.54 mmol) in three portions over approximately 15 minutes. Heating was continued for 15 minutes then more sodium dithionite (135 mg, 0.75 mmol) was added and heating was continued for 10 minutes. The mixture was treated with 15 wt % sodium hydroxide in water (1 mL) and then cooled to ambient temperature after 10 minutes. Acidification with acetic acid and preparative RP-HPLC followed by lyophilization gave a residue which was dissolved in ethanol (20 mL) and acetic acid (1 mL) then hydrogenated for 1 hour at ambient temperature and atmospheric pressure in the presence of 10% Pd-C (30 mg). Filtration and purification by RP-HPLC gave trans-5-(3-amino-4-phenoxyphenyl)-7-[4-(4-methylpiperazino)cyclohexyl]-7H-pyrrolo[2,3-d]pyrimidin-4-amine (26 mg, 20%): $^1$H NMR (DMSO-d$_6$, 400 MHz) δ 8.13(s, 1H), 7.35(m, 3H), 7.06(t, 1H), 6.97(d, 2H), 6.89(m, 2H), 6.60(m, 1H), 6.2(bs, 2H), 5.08(bs, 2H), 4.54(m, 1H), 2.2–2.6(m, 9H), 2.15(s, 3H), 1.8–2.1(m, 6H), 1.45 (m, 2H); MS MH+498.4; RP-HPLC (Hypersil HS, 5 μm, 100 A 4.6×250 mm; 25%–100% acetonitrile—0.05 M ammonium acetate over 10 min, 1 m/min) tr 6.90 min Example 385 trans-5-(3-(Dimethylamino)-4-phenoxyphenyl)-7-[4-(4-methylpiperazino)cyclohexyl]-7H-pyrrolo[2,3-d]pyrimidin-4-amine A mixture of Trans-5-(3-amino-4-phenoxyphenyl)-7-[4-(4-methylpiperazino)cyclohexyl]-7H-pyrrolo[2,3-d]pyrimidin-4-amine (120 mg, 0.241 mmol), 37% aqueous formaldehyde (80 mg, 0.966 mmol) and acetic acid (45 mg, 0.724) in 1,2-dichloroethane (5 mL) was stirred at ambient temperature for 30 minutes then sodium triacetoxyborohydride (154 mg, 0.72 mmol) was added. The mixture was stirred at ambient temperature for an additional 18 hours then the mixture was concentrated under reduced pressure and the residue was purified by preparative RP-HPLC to give trans-5-(3-(dimethylamino)-4-phenoxyphenyl)-7-[4-(4-methylpiperazino)cyclohexyl]-7H-pyrrolo[2,3-d]pyrimidin-4-amine (10 mg, 12%): $^1$H NMR (DMSO-d$_6$, 400 MHz) δ 8.13(s, 1H), 7.45 (s, 1H), 7.34(t, 2H), 7.05(m, 2H), 6.9–7.0(m, 4H), 6.16(bs, 2H), 4.55 (m, 2H), 2.78(s, 6H), 2.2–2.6(m, 9H), 2.23(s, 3H), 1.8–2.0(m, 6H), 1.45(m, 2H); MS MH$^+$526.4; RP-HPLC (Hypersil HS, 5 μm, 100 A 4.6×250 mm; 5%–50% acetonitrile—0.05 M ammonium acetate over 25 min, 1 ml/min) t$_r$ 25.6 min.

Example 386 trans-N1-(5-{4-Amino-7-[4-(4-methylpiperazino)cyclohexyl]-7H-pyrrolo[2,3-d]pyrimidin-5-yl}-2-phenoxyphenyl)acetamide Acetate A mixture of trans-5-(3-amino-4-phenoxyphenyl)-7-[4-(4-methylpiperazino)cyclohexyl]-7H-pyrrolo[2,3-d]pyrimidin-4-amine (120 mg, 0.241 mmol) in pyridine (2 mL) and dichloromethane (2 mL) was cooled to 0° C. then treatd with acetyl chloride (25 mg, 0.3 mmol). The mixture was warmed to ambient temperature for one hour then the solvents were removed under reduced pressure and the residue purified by preparative RP-HPLC to give trans-N1-(5-{4-amino-7-[4-(4-methylpiperazino)cyclohexyl]-7H-pyrrolo[2,3-d]pyrimidin-5-yl}-2-phenoxyphenyl)acetamide acetate (45 mg, 35%): $^1$H NMR (DMSO-d$_6$, 400 MHz) δ 9.67 (bs, 1H), 8.11(s, 1H), 8.00(s, 1H), 7.40(t, 3H), 7.17(m, 2H), 7.05(d, 2H), 6.95(d, 1H), 6.30(bs, 2H), 4.55(m, 1H), 2.2–2.6(m, 9H), 2.14(s, 3H), 2.04(s, 3H), 1.8–2.0(m, 6H), 1.89(s, 3H), 1.44(m, 2H); MS MH$^+$540.5; RP-HPLC (Hypersil HS, 5 μm, 1000 A, 4.6×250 mm; 5%–50% acetonitrile—0.05 M ammonium acetate over 25 min, 1 ml/min) tr 20.37 min.

Example 387 trans-5-{4-Amino-7-[4-(4-methylpiperazino)cyclohexyl]-7H-pyrrolo[2,3-d]pyrimidin-5-yl}-2-phenoxybenzaldehyde Trismaleate a) 4-Bromo-2-phenoxybenzaldehyde The title compound was prepared in a 46% yield from 5-bromo-2-fluoro-benzaldehyde and phenol in a manner similar to that described for the preparation of 5-bromo-phenoxybenzonitrile: $^1$H NMR (DMSO-d$_6$, 400 MHz) δ 10.32(s, 1H), 7.92(s, 1H), 7.81(d, 1H), 7.46(t, 2H), 7.27(t, 1H), 7.18(d, 2H), 6.90(d, 1H) RP-HPLC (Hypersil HS, 5 μm, 100 A 4.6×250 mm; 25%–100% acetonitrile—0.05 M ammonium acetate over 10 min, 1 ml/min) tr 13.08 min.

b) 2-Phenoxy-5-(4,4,5,5-tetramethyl-1,3,2-dioxaborolan-2-yl)benzaldehyde

The title compound was prepared in a 62% from 4-bromo-2-phenoxybenzaldehyde in a similar manner to that described for the preparation 2-phenoxy-5-(4,4,5,5-tetramethyl-1,3,2-dioxaborolane-2-yl)benzonitrile: $^1$H NMR (DMSO-d$_6$, 400 MHz) δ 10.43(s, 1H), 8.14(s, 1H), 7.89(d, 1H), 7.48(t, 2H), 7.27(t, 1H), 7.20(d, 2H), 6.88(d, 1H), 1.30(s, 12H); RP-HPLC (Hypersil HS, 5 μm, 100 A, 4.6×250 mm; 25%–100% acetonitrile—0.05 M ammonium acetate over 10 min, 1 ml/min) t$_r$ 14.02min.

c) trans-5-iodo-7-[4-(4-Methylpiperazino)cyclohexyl]-7H-pyrrolo[2,3-d]pyrimidin-4-amine Hydrochloride A mixture of trans-4-chloro-5-iodo-7-[4-(4-methylpiperazino)cyclohexyl]-7H-pyrrolo[2,3-d]pyrimidine (750 mg, 1.63 mmol) and 1,4-dioxane (10 mL) and 30% aqueous ammonium hydroxide (10 mL) was heated at 120° C. in a sealed tube for 18 hours. The mixture is cooled and lyophilized to give trans-5-iodo-7-[4-(4-methylpiperazino)cyclohexyl]-7H-pyrrolo[2,3-d]pyrimidin-4-amine hydrochloride (750 mg, quantitative): $^1$H NMR (DMSO-$d_6$, 400 MHz) δ 10.2 (bs, 1H), 8.08(s, 1H), 7.53(s, 1H), 6.59(bs, 2H), 4.50(m, 1H), 2.5–3.2 (m, 9H), 2.51(s, 3H), 1.8–2.0(m, 6H), 1.46 (m, 2H); MS MH$^+$441.2; RP-HPLC (Hypersil HS, 5 μm, 100 A 4.6×250 mm; 25%–100% acetonitrile—0.05 M ammonium acetate over 10 min, 1 ml/min) tr 3.85 min.

d) trans-5-{4-Amino-7-[4-(4-methylpiperazino)cyclohexyl]-7H-pyrrolo[2,3-d]pyrimidin-5-yl}-2-phenoxybenzaldehyde Trismaleate A mixture of trans-5-iodo-7-[4-(4-methylpiperazino)cyclohexyl]-7H-pyrrolo[2,3-d]pyrimidin-4-amine hydrochloride (750 mg, 1.63 mmol), 2-phenoxy-5-(4,4,5,5-tetramethyl-1,3,2-dioxaborolan-2-yl)benzaldehyde (635 mg, 1.96 mmol), sodium carbonate monohydrate (490 mg, 3.92 mmol) and tetrakis(triphenylphosphine)palladium(0) (115 mg, 0.1 mmol) in ethylene glycol dimethyl ether (40 mL) and water (20 mL) was heated at 85° C. for 18 hours. The mixture was cooled, concentrated under reduced pressure then purified by preparative RP-HPLC then lyophilized to give trans-5-{4-amino-7-[4-(4-methylpiperazino)cyclohexyl]-7H-pyrrolo[2,3-d]pyrimidin-5-yl}-2-phenoxybenzaldehyde bisacetate (636 mg, 68%). A portion of this compound (75 mg, 0.132 mmol) was dissolved in ethanol (2 mL) and the treated with maleic acid (61 mg, 0.526 mmol) in ethanol (1 mL). The precipitate was collected by filtration and dried under reduced pressure: $^1$H NMR (DMSO-$d_6$, 400 MHz) δ 10.41(s, 1H), 8.22(s, 1H), 7.88(s, 1H), 7.72(d, 1H), 7.60(s, 1H), 7.47(t, 2H), 7.24(m, 3H), 7.08(d, 1H), 6.62 (bs, 2H), 6.16(s, 6H), 4.61(m, 1H), 2.5–3.4(m, 9H), 2.69(s, 3H), 1.8–2.1 (m, 6H), 1.56 (m, 2H); MS MH$^+$511.4; RP-HPLC (Hypersil HS, 5 μm, 100 A 4.6×250 mm; 5%–100% acetonitrile—0.05 M ammonium acetate over 25 min, 1 ml/min) $t_r$ 14.55 min.

Example 388 trans 2-4-[4-Amino-5-(4-phenoxyphenyl)-7H-pyrrolo[2,3-d]pyrimidin-7-yl]-1-hydroxycyclohexylacetamide A mixture of trans 4-[4-amino-5-(4-phenoxyphenyl)-7H-pyrrolo[2,3-d]pyrimidin-7-yl]-1-hydroxycyclohexylmethyl cyanide (0.300 g, 0.68 mmol) and potassium carbonate (0.377 g, 2.73 mmol) in dimethylsulfoxide (3 ml) was stirred rapidly and 30% hydrogen peroxide (0.5 mL) was added dropwise, keeping the temperature at 20° C. The mixture was stirred for seven hours at ambient temperature. Water (20 mL) was added, and a precipitate formed the mixture was extracted with ethyl acetate (3×10 mL), dried over magnesium sulfate, and concentrated. The residue was purified by preparative RP-HPLC (Rainin C18, 8 μm, 300 A, 25 cm; 30% isocratic for five minutes, then 30%–60% acetonitrile—0.1 M ammonium acetate over 30 min, 21 ml/min). The acetonitrile was removed in vacuo and the aqueous mixture was lyopholyzed to give trans 2-4-[4-amino-5-(4-phenoxyphenyl)-7H-pyrrolo[2,3-d]pyrimidin-7-yl]-1-hydroxycyclohexylacetamide as a white solid (0.055 g, 0.12 mmol): $^1$H NMR (DMSO-$d_6$, 4000 MHz) δ 8.14(s, 1H), 7.48 (d, 2H), 7.47(s, 1H), 7.42(t, 2H), 7.17(t, 1H), 7.06–7.13(m, 4H), 6.11(b, 2H), 5.18(s, 1H) 4.61–4.67(m, 1H), 1.91–2.00 (m, 2H), 1.82–1.86(m, 4H), 1.57–1.65 (m, 2H); RP-HPLC (Delta Pak C18, 5 μm, 300 A, 15 cm; 5%–85% acetonitrile—0.1 M ammonium acetate over 20 min, 1 mL/min) $R_t$ 14.46 min.; MS: M$^+$458.

Example 389 trans 4-[4-Amino-5-(4-phenoxyphenyl)-7H-pyrrolo[2,3-d]pyrimidin-7-yl]-1-(hydroxymethyl)-1-cyclohexanol A trans/cis (4:1) mixture of 7-(1-oxaspiro[2.5]oct-6-yl)-5-(4-phenoxyphenyl)-7H-pyrrolo[2,3-d]pyrimidin-4-amine (0.300 g, 0.42 mmol) in 1,2-dimethoxyethane (15 mL) was reacted with 2.5 M aqueous potassium hydroxide (15 mL). The mixture was stirred at reflux for eighteen hours. The mixture was cooled to room temperature and water (25 mL) was added. The precipitate which formed was filtered, washing with water (20 mL). The precipitate was purified by preparative RP-HPLC (Rainin C18, 8 μm, 300 A, 25 cm; 30% isocratic for five minutes, then 30%–60% acetonitrile—0.1M ammonium acetate over 30 min, 21 ml/min). The acetonitrile was removed in vacuo and the aqueous mixture was lyopholyzed to give to give a trans/cis (4:1) mixture of 4-[4-amino-5-(4-phenoxyphenyl)-7H-pyrrolo[2,3-d]pyrimidin-7-yl]-1-(hydroxymethyl)-1-cyclohexanol. The isomers were separated by NP-MPLC (ISCO RediSep™ (10 g), 2% isocratic for five minutes, then 2–10% methanol-dichloromethane over 25 minutes, 20 mL/min). The solvent was removed in vacuo to give trans 4-[4-amino-5-(4-phenoxyphenyl)-7H-pyrrolo[2,3-d]pyrimidin-7-yl]-1-(hydroxymethyl)-1-cyclohexanol as a white solid (0.026 g, 0.60 mmol): $^1$H NMR (DMSO-$d_6$, 400 MHz) δ 8.13(s, 1H), 7.53 (s, 1H), 7.47(d, 2H), 7.41(t, 2H), 7.16(t, 1H), 7.05–7.12(m, 4H), 6.08(b, 1H), 4.56–4.66(m, 1H), 4.39(t, 1H), 4.25(s, 1H), 3.55(d, 2H), 1.85–2.00(m, 4H), 1.76–1.84(m, 2H), 1.43–1.54(m, 2H); RP-HPLC (Delta Pak C18, 5 μm, 300 A, 15 cm; 5%–85% acetonitrile—0.1M ammonium acetate over 20 min, 1 mL/min) $R_t$ 14.45 min.; MS: M$^+$431.

Example 390

7-[1-(1H-2-Imidazolylmethyl)-4-piperidyl]-5-(4-phenoxyphenyl)-7H-pyrrolo[2,3-d]pyrimidin-4-amine A mixture of 5-(4-phenoxyphenyl)-7-(4-piperidyl)-7H-pyrrolo[2,3-d]pyrimidin-4-amine (0.096 g, 0.249 mmol) in dichloroethane (5 mL) was treated with 2-imidazolcarboxaldehyde (0.026 g, 0.274 mmol) and glacial acetic acid (0.030 g, 0.498 mmol). The reaction mixture stirred for one hour at 0° C. under nitrogen atmosphere. Sodium triacetoxyborohydride (0.132 g, 0.623 mmol) was added to the reaction mixture and stirred at 0° C. for 20 minutes. The ice bath was then removed, and the reaction mixture stirred for 18 hours at ambient temperature under a nitrogen atmosphere. Additional 2-imidazolcarboxaldehyde (0.096 g, 0.996 mmol) was added to the reaction mixture, and stirred for an additional 24 hours. Acetonitrile (2 mL) was added to the reaction mixture, and then was allowed to stir for an additional 72 hours. Sodium bicarbonate (0.126 g, 1.49 mmol) in water (5 mL) was added to the reaction mixture and stirred for 2 hours. The layers were partitioned, and the aqueous layer was extracted with dichloromethane (150 mL). The combined organic layers were washed with water and brine (250 mL each), dried over magnesium sulfate, filtered and evaporated under reduced pressure. The front-running impurity (by TLC analysis) was removed by recrystallization using ethyl acetate: heptane. The filtrate from the recrystallization was evaporated under reduced pressure, and purified using a Flashtube chromatography column using 20% methanol in dichloromethane was the eluent. Some impure product was isolated and this was purified by preparative HPLC. 7-[1-(1H-2-imidazolylmethyl)-4-piperidyl]-5-(4-phenoxyphenyl)-7H-pyrrolo[2,3-d]pyrimidin-4-amine was isolated and was dried on the lyophilizer. Dichloromethane (3 mL) and 1 N sodium hydroxide (1 mL) was added to the product. The layers were separated using an Empore extraction cartridge. The dichloromethane layer was collected and evaporated under reduced pressure to give 7-[1-(1H-2-imidazolylmethyl)-4-piperidyl]-5-(4-phenoxyphenyl)-7H-pyrrolo[2,3-d] pyrimidin-4-amine as a free base (0.011 g, 10%). $^1$H NMR (CDCl$_3$, 400 MHz) δ 8.31(s, 1H), 7.43–7.35(m, 4H), 7.2–7.1 (m, 1H), 7.09–7.00 (m, 7H), 5.18(s, 2H), 4.75–4.69(m, 1H), 3.73(s, 2H), 3.03–2.96(m, 2H), 2.43–2.37(m, 2H), 2.15–2.08(m, 4H); Waters 2690 Alliance HPLC (Symmetry Shield RP$_{18}$ 3.5 μm, 2.1×50 mm; 5%–95% acetonitrile—0.1 M ammonium acetate over 15 min, 0.5 mL/min) R$_t$ 5.363 min.

Example 391 cis-N2-(4-{4-Amino- 7-[4-(4-methylpiperazino) cyclohexyl]-7H-pyrrolo[2,3-d]pyrimidin-5-yl}-2-fluorophenyl)-1,3-benzoxazol-2-amine N2-(4-Bromo-2-fluorophenyl)-1,3-benzoxazol-2-amine To a solution of 4-bromo-2-fluoroaniline 1.00 g, 5.26 mmol) in toluence (25 mL) was added 2-chlorobenzoxazole (0.66 mL, 5.79 mmol, 1.1 equiv). The purple solution was heated at reflux for 30 min. and then at 100° C. for 17 hours. The resulting white suspension/purple solution was cooled to room temperature and the precipitate was filtered. The filter cake was washed with five 2-mL portion of heptane to afford N2-(4-bromo-2-fluorophenyl)-1,3-benzoxazol-2-amine (1.480 g, 92%) as a light purple powder. RP-HPLC (25 to 100% CH$_3$CN in 0.1 N aqueous ammonium acetate over 10 minutes at 1 mL/min using a Hypersil HS C18, 250×4.6 mm column) tr=12.87 min., 97%; and m/z 306.7 (MH$^+$).

N2-[2-Fluoro-4-(4,4,5,5-tetramethyl-1,3,2-dioxaborolan-2-yl)phenyl]-1,3-benzoxazol-2-amine To a solution of N2-(4-bromo-2-fluorophenyl)-1,3-benzoxazol-2-amine (1.480 g, 4.819 mmol) in dimethylformamide (15 mL) under nitrogen was added bis(pinacolato) diboron (1.468 g, 5.781 mmol, 1.2 equiv), potassium acetate (1.419 g, 14.45 mmol, 3.0 equiv), and [1,1'-bis (diphenylphosphino)ferrocene]dichloropalladium (II) complexed with dichloromethane (1:1) (0.119 g, 0.146 mmol, 0.03 equiv). The violet solution was stirred at 80° C. for 20 hours and then cooled to room temperature. The resulting dark brown mixture was concentrated in vacuo to give a dark brown liquid which was purified via flash chromatography on silica gel (eluting with 30% ethyl acetate/heptane) to afford 2.28 g of a yellow solid. This material was triturated with heptane and the solid was collected to afford N2-[2-fluoro-4-(4,4,5,5-tetramethyl-1,3,2-dioxaborolan-2-yl) phenyl]-1,3-benzoxazol-2-amine (0.961 g, 56%) as a white powder. RP-HPLC (25 to 100% CH$_3$CN in 0.1 N aqueous ammonium acetate over 10 minutes at 1 mL/min using a Hypersil HS C18, 250×4.6 mm column) tr=13.80 min., 88%; and m/z 354.9(MH$^{30}$).

cis-N2-(4-{4-Amino-7-[4-(4-methylpiperazino) cyclohexyl]-7H-pyrrolo[2,3-d]pyrimidin-5-yl}-2-fluorophynyl)-1,3-benzoxazol-2-amine To a solution of cis-5-iodo-7-[4-(4-methylpiperazino) cyclohexyl]-7H-pyrrolo[2,3-d]pyrimidin-4-amine (0.100 g, 0.227 mmol) in ethylene glycol dimethyl ether (3 mL) and water (1.5 mL) under nitrogen was added N2-[2-fluoro-4-(4,4,5,5-tetramethyl-1,3,2-dioxaborolan-2-yl)phenyl]-1,3-benzoxazol-2-amine (0.100 g, 0.283 mmol, 1.25 equiv.), tetrakis(triphenylphosphine) palladium (0) (0.013 mg, 0.011 mmol, 0.05 equiv), and sodium carbonate monohydrate (0.070 mg, 0.568 mmol, 2.5 equiv). The solution was stirred at 80° C. for 21 hours. The resulting yellow mixture was concentrated in vacuo to give a yellow oil. Purification by preparative HPLC (25 to 100% CH$_3$CN in 0.1 N aqueous ammonium acetate over 20 minutes at 21 mL/min. using a 8μ Hypersil HS C18, 250×21 mm column, tr=6.4–8.5 min.) afforded cis-N2-(4-{4-amino-7-[4-(4-methylpiperazino) cyclohexyl]-7H-pyrrolo[2,3-d]pyrimidin-5-yl}-2-fluorophenyl)-1,3-benzoxazol-2-amine as a cream solid (34 mg, 28%). RP-HPLC (25 to 100% CH$_3$CN in 0.1 N aqueous ammonium acetate over 10 min at 1 mL/min using a Hypersil HS C18, 250×4.6 mm column) tr=7.167 min., 98%; and m/z 540.8(MH$^+$).

Example 392

N1-4-{4-Amino-7-{4-[4-(1-methylpiperidyl) piperidyl]-7H-pyrrolo[2,3-d]pyrimidin-5-yl})-2-fluorophenyl-2,3-dichloro-1-benzenesulfonamide Using N1–4-[4-amino-7-(4-piperidyl)-7H-pyrrolo[2,3-d] pyrimidin-5-yl]-2-fluorophenyl-2,3-dichloro-1-benzenesulfonamide (0.075 mmol scale), the above methodology was followed to afford N1-4-(4-amino-7-{4-[4-(1-methylpiperidyl)piperidyl]-7H-pyrrolo[2,3-d]pyrimidin-5-yl])-2-fluorophenyl-2,3-dichloro-1-benzenesulfonamide (32 mg), RP-HPLC RT=2.46 min and m/z 632.1.

Example 393

7-{4-[2-(4-Methylpiperazino)ethyl]cyclohexyl}-5-(4-phenoxyphenyl)-7H-pyrrolo[2,3-d]pyrimidin-4-amine a) 2-{4-[4-Amino-5-(4-phenoxyphenyl)-7H-pyrrolo[2,3-d] pyrimidin-7-yl]cyclohexyliden}acetic Acid A solution of diisopropylamine (1.40 g, 13.82 mmol) in tetrahydrofuran (60 mL) was added into a solution of 2.2 M n-BuLi (6.29 mL, 13.82 mmol) in tetrahydrofuran (20 mL) at −78° C. A solution of diethylphosphonoacetic acid (1.29 g, 6.59 mmol) in tetrahydrofuran (60 mL) was added at −78° C. under the atmosphere of nitrogen. The mixture was kept at −78° C. for 20 minutes and allowed to warm up to ambient temperature. The mixture was then transferred into a suspension of 4-[4-amino-5-(4-phenoxyphenyl)-7H-pyrrolo[2, 3-d]pyrimidin-7-yl]cyclohexanone (2.50 g, 6.28 mmol) in tetrahydrofuran (150 mL) at −78° C. quickly. The resulting mixture was allowed to warm up to ambient temperature overnight and the solvent was removed under reduced pressure. The residue was taken in water and adjusted PH to be 3–4 with 1M aqueous acetic acid followed by extraction with ethyl acetate three times. The combined organic extracts were washed with saturated aqueous sodium chloride solution, dried over magnesium sulfate, filtered and evaporated under reduced pressure to give 2-{4-[4-amino-5-(4-phenoxyphenyl)-7H-pyrrolo[2,3-d]pyrimidin-7-yl] cyclohexyliden}acetic acid (1.96 g, 4.44 mmol) as a white solid: $^1$H NMR (DMSO-d$_6$, 400 MHz) δ 11.98(br, 1H), 7.45(d, 2H), 7.41(s, 1H), 7.40(d, 2H), 7.16(t, 1H), 7.08(m, 4H), 6.10(br, 2H), 5.70(s, 1H), 4.80(m, 1H), 2.50–1.90(m, 8H); RP-HPLC (Hypersil C18, 5 μm, 100 A, 250×4.6 mm; 25%–100% acetonitrile-0.05M ammonium acetate over 10 min, 1 mL/min) R$_t$ 9.70 min. MS: MH$^+$ 441.

b) 2-{4-[4-Amino-5-(4-phenoxyphenyl)-7H-pyrrolo[2,3-d]pyrimidin-7-yl]cyclohexyl}acetic Acid A mixture of 2-{4-[4-amino-5-(4-phenoxyphenyl)-7H-pyrrolo[2,3-d]pyrimidin-7-yl]cyclohexyliden}acetic acid (0.60 g, 1.36 mmol), 10% palladium on activated carbon (0.18 g), 1M aqueous sodium hydroxide (9 mL) and ethanol (60 mL) was hydrogenated under an atmosphere of hydrogen (60 psi) for 20 hours and filtered through a pad of celite. The filtrate was evaporated under reduced pressure to yield a white solid which was taken into water (20 mL) followed by addition of 1M acetic acid (20 mL) to precipitate the product. The suspension was then filtered and the solid was lyophilized to yield 2-{4-[4-amino-5-(4-phenoxyphenyl)-7H-pyrrolo[2,3-d]pyrimidin-7-yl]cyclohexyl}acetic acid (0.51 g, 1.15 mmol) as a white solid: $^1$H NMR (DMSO-$d_6$, 400 MHz) δ 11.99(br, 1H), 8.13(s, 1H), 7.60 (s, 1H), 7.49(d, 2H), 7.41(t, 2H), 7.15(t, 1H), 7.09(m, 4H), 6.09(br, 2H), 4.60 (m, 1H), 2.20–1.24(m, 11H); RP-HPLC (Hypersil C18, 5 μm, 100 A, 250×4.6 mm; 25%–100% acetonitrile-0.05M ammonium acetate over 10 min, 1 mL/min) $R_t$ 9.62 min. MS: MH$^+$ 443.

c) 2-{4-[4-Amino-5-(4-phenoxyphenyl)-7H-pyrrolo[2,3-d]pyrimidin-7-yl]cyclohexyl}-1-ethanol A mixture of 2-{4-[4-amino-5-(4-phenoxyphenyl)-7H-pyrrolo[2,3-d]pyrimidin-7-yl]cyclohexyl}acetic acid (0.23 g, 0.51 mmol) and lithium aluminum hydride (0.30 g, 7.89 mmol) in tetrahydrofuran (25 mL) was stirred at ambient temperature overnight. Water (3 mL) was added followed by 15% aqueous sodium hydroxide (3.5 mL) and water (10.5 mL). Tetrahydrofuran (25 mL) was added and the mixture was stirred for 1 hour. The mixture was filtered through a pad of celite. The filtrate was concentrated and lyophilized to yield 2-{4-[4-amino-5-(4-phenoxyphenyl)-7H-pyrrolo[2,3-d]pyrimidin-7-yl]cyclohexyl}-1-ethanol (0.18 g, 0.42 mmol) as a white solid: $^1$H NMR (DMSO-$d_6$, 400 MHz) δ 8.13(s, 1H), 7.51(s, 1H), 7.48 (d, 2H), 7.42(t, 2H), 7.16(t, 1H), 7.09(m, 4H), 6.10(br, 2H), 4.57(m, 1H), 4.36 (t, 1H), 3.47(q, 2H), 2.70–1.65(m, 10H); RP-HPLC (Hypersil C18, 5 μm, 100 A, 250×4.6 mm; 25%–100% over 10 min then 100%–25% over 2 min acetonitrile-0.05M ammonium acetate, 1 mL/min) $R_t$ 10.28 min. MS: MH$^+$ 429.

d) 2-{4-[4-Amino-5-(4-phenoxyphenyl)-7H-pyrrolo[2,3-d]pyrimidin-7-yl]cyclohexyl}acetaldehyde Dimethylsulfoxide (0.040 g, 0.51 mmol) was added into a solution of oxalyl chloride (0.033 g, 0.26 mmol) in dichloromethane (3 mL) at −78° C. The mixture was allowed to warm up to −40° C. and stirred for 15 minutes followed by cooling down to −78° C. again. 2-{4-[4-amino-5-(4-phenoxyphenyl)-7H-pyrrolo[2,3-d]pyrimidin-7-yl]cyclohexyl}-1-ethanol (0.10 g, 0.23 mmol) was added followed by triethylamine (0.12 mg, 1.165 mmol). The mixture was allowed to warm up to 0° C. and saturated aqueous sodium bicarbonate solution (10 mL) was added to quench the reaction. The organic layer was separated from the aqueous layer and washed with 10% aqueous sodium hydorgensulfate solution (4 mL), saturated aqueous sodium bicarbonate solution (4 mL) and saturated aqueous sodium chloride (4 mL). The organic layer was dried over magnesium sulfate and the solvent was removed under reduced pressure. The residue was purified by flash chromatography on silica gel using methanol/dichloromethane(5:95) as a mobile phase to yield 2-{4-[4-amino-5-(4-phenoxyphenyl)-7H-pyrrolo[2,3-d]pyrimidin-7-yl]cyclohexyl}acetaldehyde (0.053 g, 0.12 mmol) as a white solid: $^1$H NMR (CDCl$_3$, 400 MHz) δ 9.81(s, 1H), 8.33(s, 1H), 7.68(m, 1H), 7.43(d, 2H), 7.38(t, 2H), 7.15(t, 1H), 7.07(m, 4H), 5.14 (br, 2H), 4.72(m, 1H), 2.63–1.72(m, 11H); TLC (methanol/dichloromethane=5:95) $R_f$ 0.41. MS: MH$^+$ 427.

e) 7-{4-[2-(4-Methylpiperazino)ethyl]cyclohexyl}-5-(4-phenoxyphenyl)-7H-pyrrolo[2,3-d]pyrimidin-4-amine A mixture of 2-{4-[4-amino-5-(4-phenoxyphenyl)-7H-pyrrolo[2,3-d]pyrimidin-7-yl]cyclohexyl}acetaldehyde (0.025 g, 0.059 mmol), N-methylpiperazine (0.0083 g, 0.083 mmol) and acetic acid (0.0035 g, 0.059 mmol) in 1,2-dichloroethane (0.4 mL) was stirred for 10 min at ambient temperature and sodium triacetoxyborohydride (0.019 g, 0.089 mmol) was added. The mixture was stirred at ambient temperature under an atmosphere of nitrogen for 6 hours and the solvent removed under reduced to yield a yellow oil. The compound was purified by preparative RP-HPLC to yield 7-{4-[2-(4-methylpiperazino)ethyl]cyclohexyl}-5-(4-phenoxyphenyl)-7H-pyrrolo[2,3-d]pyrimidin-4-amine (0.016 g, 0.031 mmol) as a white solid: $^1$H NMR (CDCl$_3$, 400 MHz) δ 8.27(s, 1H), 7.45(d, 2H), 7.37(t, 2H), 7.16(t, 1H), 7.09(m, 5H), 5.57(br, 2H), 4.73(m, 1H), 2.33(s, 3H), 2.49–1.65(m, 19H); RP-HPLC (Hypersil C18, 5 μm, 100 A, 250×4.6 mm; 25%–100% acetonitrile-0.05M ammonium acetate over 10 min, 1 mL/min) $R_t$ 8.15 min. MS: MH$^+$ 511.

Example 394

7-[4-(2-Morpholinoethyl)cyclohexyl]-5-(4-phenoxyphenyl)-7H-pyrrolo[2,3-d]pyrimidin-4-amine A similar procedure to the preparation 7-{4-[2-(4-methylpiperazino)ethyl]cyclohexyl}-5-(4-phenoxyphenyl)-7H-pyrrolo[2,3-d]pyrimidin-4-amine yielded 7-[4-(2-Morpholinoethyl)cyclohexyl]-5-(4-phenoxyphenyl)-7H-pyrrolo[2,3-d]pyrimidin-4-amine (0.015 g, 0.030 mmol) as a white solid: $^1$H NMR (CDCl$_3$, 400 MHz) δ 8.32(br, 1H), 7.44(d, 2H), 7.38(t, 2H), 7.15(t, 1H), 7.08(m, 5H), 5.26(br, 2H), 4.73(m, 1H), 3.74(m, 4H), 2.80–1.64(m, 15H); RP-HPLC (Hypersil C18, 5 μm, 100 A, 250×4.6 mm; 25%–100% acetonitrile-0.05M ammonium acetate over 10 min, 1 mL/min) $R_t$ 8.50 min. MS: MH$^+$ 498.

Example 395

N1-Methyl-2-{4-[4-amino-5-(4-phenoxyphenyl)-7H-pyrrolo[2,3-d]pyrimidin-7-yl]cyclohexyl}acetamide A mixture of 2-{4-[4-amino-5-(4-phenoxyphenyl)-7H-pyrrolo[2,3-d]pyrimidin-7-yl]cyclohexyl}acetic acid (0.094 g, 0.21 mmol), 1-hydroxy-7-azabenzotriazole (0.044 g, 0.32 mmol), 1-(3-dimethylaminopropyl)-3-ethylcarbodiimide hydrochloride (0.082 g, 0.43 mmol), 2M methylamine in tetrahydrofuran (2.13 mL, 4.26 mmol) and N,N-dimethylformamide (1.50 mL) was heated at 60° C. overnight. The mixture was allowed to cool to ambient temperature and purified by preparative RP-HPLC to yield N1-methyl-2-{4-[4-amino-5-(4-phenoxyphenyl)-7H-pyrrolo[2,3-d]pyrimidin-7-yl]cyclohexyl}acetamide (0.025 g, 0.055 mmol) as a white solid: $^1$H NMR (CDCl$_3$, 400 MHz) δ 8.24(s, 1H), 7.42(d, 2H), 7.38 (t, 2H), 7.16(t, 1H), 7.07(m, 5H), 5.82(br, 2H), 5.62(br, 1H), 4.70(m, 1H), 2.83 (d, 3H), 2.36–1.70(m, 11H); MS: MH$^+$ 456; TLC (ethyl acetate) $R_f$ 0.34; RP-HPLC (Hypersil C18, 5 μm, 100 A, 250×4.6 mm; 25%–100% acetonitrile-0.05M ammonium acetate over 10 min, 1 mL/min) $R_t$ 9.32 min.

Example 396

7-{4-[2-(Dimethylamino)ethyl]cyclohexyl}-5-(4-phenoxyphenyl)-7H-pyrrolo[2,3-d]pyrimidin-4-amine A similar procedure to the preparation 7-{4-[2-(4-methylpiperazino)ethyl]cyclohexyl}-5-(4-phenoxyphenyl)-

7H-pyrrolo[2,3-d]pyrimidin-4-amine yielded 7-{4-[2-(dimethylamino)ethyl]cyclohexyl}-5-(4-phenoxyphenyl)-7H-pyrrolo[2,3-d]pyrimidin-4-amine (0.001 g, 0.002 mmol) as a white solid: $^1$H NMR (CDCl$_3$, 400 MHz) δ 8.19(s, 1H), 7.63(br, 2H), 7.44(d, 2H), 7.38(t, 2H), 7.17(s, 1H), 7.15(t, 1H), 7.07(t, 4H), 4.72(m, 1H), 2.76(m, 2H), 2.58(s, 6H), 2.03–1.75 (m, 9H); RP-HPLC (Hypersil C18, 5 μm, 100 A, 250×4.6 mm; 25%–100% acetonitrile-0.05M ammonium acetate over 10 min, 1 mL/min) R$_t$ 8.17 min. MS: MH$^+$ 456.

Example 397

N1-(2-{4-[4-Amino-5-(4-phenoxyphenyl)-7H-pyrrolo[2,3-d]pyrimidin-7-yl]cyclohexyl}ethyl)-N1,N2,N2-trimethyl-1,2-ethanediamine A similar procedure to the preparation 7-{4-[2-(4-methylpiperazino)ethyl]cyclohexyl}-5-(4-phenoxyphenyl)-7H-pyrrolo[2,3-d]pyrimidin-4-amine yielded N1-(2-{4-[4-amino-5-(4-phenoxyphenyl)-7H-pyrrolo[2,3-d]pyrimidin-7-yl]cyclohexyl}ethyl)-N1,N2,N2-trimethyl-1,2-ethanediamine (0.0015 g, 0.003 mmol) as a white solid: $^1$H NMR (CDCl$_3$, 400 MHz) δ 8.20(s, 1H), 8.11(br, 2H), 7.43(d, 2H), 7.38(t, 2H), 7.15(m, 2H), 7.06(t, 4H), 4.70(m, 1H), 2.44(s, 3H), 2.04 (s, 6H), 2.80–1.71(m, 17H); RP-HPLC (Hypersil C18, 5 μm, 100 A, 250×4.6 mm; 25%–100% acetonitrile-0.05M ammonium acetate over 10 min 1 mL/min) R$_t$ 8.70 min. MS: MH$^+$ 513.

Example 398

Ethyl 3-[(2-{4-[4-amino-5-(4-phenoxyphenyl)-7H-pyrrolo[2,3-d]pyrimidin-7-yl]cyclohexyl}ethyl)amino]propanoate A similar procedure to the preparation 7-{4-[2-(4-methylpiperazino)ethyl]cyclohexyl}-5-(4-phenoxyphenyl)-7H-pyrrolo[2,3-d]pyrimidin-4-amine yielded ethyl 3-[(2-{4-[4-amino-5-(4-phenoxyphenyl)-7H-pyrrolo[2,3-d]pyrimidin-7-yl]cyclohexyl}ethyl)amino]propanoate (0.004 g, 0.008 mmol) as a white solid: $^1$H NMR (CDCl$_3$, 400 MHz) δ 8.18(s, 1H), 7.58(br, 2H), 7.39(m, 4H), 7.08(m, 6H), 4.72(m, 1H), 4.17(q, 2H), 3.13 (m, 2H), 2.83(m, 2H), 2.74(m, 2H), 2.03–1.76(m, 11H), 1.25(t, 3H); RP-HPLC (Hypersil C18, 5 μm, 100 A, 250×4.6 mm; 25%–100% acetonitrile-0.05M ammonium acetate over 10 min, 1 mL/min) R$_t$ 8.98 min. MS: MH$^+$ 528.

Example 399 tert-Butyl 4-(2-{4-[4-Amino-5-(4-phenoxyphenyl)-7H-pyrrolo[2,3d]pyrimidin-7-yl]cyclohexyl}ethyl)-1-piperazinecarboxylate A similar procedure to the preparation 7-{4-[2-(4-methylpiperazino)ethyl]cyclohexyl}-5-(4-phenoxyphenyl)-7H-pyrrolo[2,3-d]pyrimidin-4-amine yielded tert-butyl 4-(2-{4-[4-amino-5-(4-phenoxyphenyl)-7H-pyrrolo[2,3-d]pyrimidin-7-yl]cyclohexyl}ethyl)-1-piperazinecarboxylate (0.002 g, 0.003 mmol) as a white solid: $^1$H NMR (CDCl$_3$, 400 MHz) δ 8.27(s, 1H), 7.44(d, 2H), 7.40(t, 2H), 7.15 (t, 1H), 7.08(m, 5H), 5.62(br, 2H), 4.73(m, 1H), 3.45(m, 4H), 2.43–1.23(m, 17H), 1.46(s, 9H); RP-HPLC (Hypersil C18, 5 μm, 100 A, 250×4.6 mm; 25%–100% over 10 min then 100%–25% over 2 min and stayed at 25% for 3 min acetonitrile-0.05M ammonium acetate, 1 mL/min) R$_t$ 12.22 min. MS: MH$^+$ 597.

Example 400

7-[4-(2-{[3-(1H-1-Imidazolyl)propyl]amino}ethyl)cyclohexyl]-5-(4-phenoxyphenyl)-7H-pyrrolo[2,3-d]pyrimidin-4-amine A similar procedure to the preparation 7-{4-[2-(4-methylpiperazino)ethyl]cyclohexyl}-5-(4-phenoxyphenyl)-7H-pyrrolo[2,3-d]pyrimidin-4-amine yielded 7-[4-(2-{[3-(1H-1-imidazolyl)propyl]amino}ethyl)cyclohexyl]-5-(4-phenoxyphenyl)-7H-pyrrolo[2,3-d]pyrimidin-4-amine (0.003 g, 0.006 mmol) as a white solid: $^1$H NMR (CDCl$_3$, 400 MHz) δ 8.23(s, 1H), 7.57(s, 1H), 7.43(d, 2H), 7.38(t, 2H), 7.16(t, 1H), 7.08(m, 6H), 6.94 (br, 1H), 5.98(br, 1H), 4.69(m, 1H), 4.58(br, 2H), 4.07(t, 2H), 2.69(m, 4H), 2.06–1.71(m, 13H); RP-HPLC (Hypersil C18, 5 μm, 100 A, 250×4.6 mm; 25%–100% acetonitrile-0.05M ammonium acetate over 10 min, 1 mL/min) R$_t$ 7.00 min. MS: MH$^+$ 536.

Example 401

1-(2-{4-[4-Amino-5-(4-phenoxyphenyl)-7H-pyrrolo[2,3-d]pyrimidin-7-yl]cyclohexyl}ethyl)-4-piperidinol A similar procedure to the preparation 7-{4-[2-(4-methylpiperazino)ethyl]cyclohexyl}-5-(4-phenoxyphenyl)-7H-pyrrolo[2,3-d]pyrimidin-4-amine yielded 1-(2-{4-[4-amino-5-(4-phenoxyphenyl)-7H-pyrrolo[2,3-d]pyrimidin-7-yl]cyclohexyl}ethyl)-4-piperidinol (0.007 g, 0.014 mmol) as a white solid: $^1$H NMR (CDCl$_3$, 400 MHz) δ 8.24(s, 1H), 7.44(d, 2H), 7.38(t, 2H), 7.15(t, 1H), 7.07(m, 5H), 5.82(br, 2H), 4.73(m, 1H), 3.85(m, 1H), 3.36(br, 1H), 2.94(m, 2H), 2.53(m, 4H), 2.05–1.75(m, 15H); RP-HPLC (Hypersil C18, 5 μm, 100 A, 250×4.6 mm; 25%–100% acetonitrile-0.05M ammonium acetate over 10 min, 1 mL/min) R$_t$ 7.75 min. MS: MH$^+$ 512.

Example 402

7-{4-[2-(4-Methyl-1,4-diazepan-1-yl)ethyl]cyclohexyl}-5-(4-phenoxyphenyl)-7H-pyrrolo[2,3-d]pyrimidin-4-amine A similar procedure to the preparation 7-{4-[2-(4-methylpiperazino)ethyl]cyclohexyl}-5-(4-phenoxyphenyl)-7H-pyrrolo[2,3-d]pyrimidin-4-amine yielded 7-{4-[2-(4-methyl-1,4-diazepan-1-yl)ethyl]cyclohexyl}-5-(4-phenoxyphenyl)-7H-pyrrolo[2,3-d]pyrimidin-4-amine (0.003 g, 0.006 mmol) as a white solid: $^1$H NMR (CDCl$_3$, 400 MHz) δ 8.26(s, 1H), 7.44(d, 2H), 7.38(t, 2H), 7.15(t, 1H), 7.08(m, 5H), 5.71(br, 2H), 4.71(m, 1H), 2.88(m, 8H), 2.62(t, 2H), 2.49 (s, 3H), 1.98–1.70(m, 13H); RP-HPLC (Hypersil C18, 5 μm, 100 A, 250×4.6 mm; 25%–100% acetonitrile-0.05M ammonium acetate over 10 min, 1 mL/min) R$_t$ 7.90 min. MS: MH$^+$ 525.

Example 403

7-{4-[2-(1H-1-Imidazolyl)ethyl]cyclohexyl}-5-(4-phenoxyphenyl)-7H-pyrrolo[2,3-d]pyrimidin-4-amine a) 2-{4-[4-Amino-5-(4-phenoxyphenyl)-7H-pyrrolo[2,3-d]pyrimidin-7-yl]cyclohexyl}ethyl Methanesulfonate Methanesulfonyl chloride (0.036 g, 0.31 mmol) was added into a solution of 2-{4-[4-amino-5-(4-phenoxyphenyl)-7H-pyrrolo[2,3-d]pyrimidin-7-yl]cyclohexyl}-1-ethanol (0.11 g, 0.26 mmol) and triethylamine (2.5 mL) in dichloromethane (2.5 mL) at 0° C. The mixture was allowed to warm up to ambient temperature and stirred overnight. Methanesulfonyl chloride (0.036 g, 0.31 mmol) and dichloromethane (2.5 mL) was added. The mixture was stirred at ambient temperature for 17 hours. Methanesulfonyl chloride (0.036 g, 0.31 mmol) and dichloromethane (2.5 mL) was added. The mixture was stirred at ambient temperature for 4 hours. The solvent was removed under reduced pressure and the residue was purified by flash chromatography on silica gel using methanol/dichloromethane (5:95) as a mobile phase to yield 2-{4-[4-amino-5-(4-phenoxyphenyl)-7H-pyrrolo[2,3-d]pyrimidin-7-yl]cyclohexyl}ethyl methanesulfonate (0.10 g, 0.21 mmol) as a white solid: $^1$H NMR (CDCl$_3$, 400 MHz) δ 8.31(s, 1H), 7.44 (d, 2H), 7.38(t, 2H), 7.15(t, 1H), 7.08 (m, 5H), 5.31(br, 2H), 4.73(m, 1H), 4.32(t, 2H), 3.03(s, 3H), 1.99–1.61(m, 11H); TLC (methanol/dichloromethane=5:95) R$_f$ 0.37; RP-HPLC (Hypersil C18, 5 μm, 100 A, 250×4.6mm; 25%–100% over 10 min then 100%–25% over 2 min acetonitrile-0.05M ammonium acetate, 1 mL/min) R$_t$ 11.45 min; MS: MH$^+$ 507.

b) 7-Δ4-[2-(1H-1Imidazolyl)ethyl]cyclohexyl}-5-(4-phenoxyphenyl)-7H-pyrrolo[2,3-d]pyrimidin-4-amine Imidazole (0.070 g, 1.03 mmol) was added into a solution of 2-{4-[4-amino-5-(4-phenoxyphenyl)-7H-pyrrolo[2,3-d]pyrimidin-7-yl]cyclohexyl}ethyl methanesulfonate (0.052 g, 0.10 mmol) in N,N-dimethylformamide (2 mL). The mixture was stirred at 40° C. for 5 hours. 60% Sodium hydride in mineral oil (0.021 g, 052 mmol) was added and the mixture was stirred at ambient temperature overnight. The solvent was removed under reduced pressure and the residue was purified by preparative RP-HPLC to yield 7-{4-[2-(1H-1-imidazolyl)ethyl]cyclohexyl}-5-(4-phenoxyphenyl)-7H-pyrrolo[2,3-d]pyrimidin-4-amine (0.030 g, 0.063 mmol) as a white solid: $^1$H NMR (CDCl$_3$, 400 MHz) δ 8.30(s, 1H), 7.55(br, 1H), 7.44(d, 2H), 7.42(t, 2H), 7.16(t, 1H), 7.08(m, 6H), 6.95(br, 1H), 5.49(br, 2H), 4.72(m, 1H), 4.01(t, 2H), 1.99–1.71 (m, 11H); RP-HPLC (Hypersil C18, 5 μm, 100 A, 250×4.6 mm; 25%–100% over 10 min acetonitrile-0.05M ammonium acetate, 1 mL/min) R$_t$ 9.18 min; MS: MH$^+$ 479.

EXAMPLES 404 and 405 cis and trans-N1-(4-4-Amino-7-[4-(4-methylpiperazino)cyclohexyl]-7H-pyrrolo[2,3-d]pyrimidin-5-yl-2-methoxyphenyl)-3-phenylpropanamide To 4-[4-amino-5-(4-amino-3-methoxyphenyl)-7H-pyrrolo[2,3-d]pyrimidin-7-yl]-1-cyclohexanone (0.8 g, 2.3 mmol) in pyridine/dichloromethane (1:2.5, 45 ml) was added hydrocinnamylchloride (0.57 g, 3.4 mmol) in dichloromethane (2 ml) at 0° C. under a flow of nitrogen. The solution was stirred at 0° C. for 2 hr. The solution was quenched with saturated aquoeus citric acid solution (50 ml) and the organic layer was washed with saturated aquoeus citric acid solution (2×50 ml). Dry, filter and concentrate to leave a brown foam (1.0 g). This was dissolved in dichloroethane (100 ml) and N-methylpiperazine (0.63 g, 6.3 mmol) and acetic acid (0.38 g, 6.3 mmol) was added. Sodium triacetoxyborohydride (0.67 g, 3.15 mmol) was added portionwise under nitrogen and the mixture stirred overnight at room temperature. The mixture was quenched with saturated aq. NaHCO3 solution (50 ml) and extracted with dichloromethane (3×100 ml). The combined organics were dried (sodium sulphate), filtered and evaporated to leave a sludge which was purified by flash silica gel column chromatography using dichloromethane/methanol (100/0 to 50/50 in 5% increments). The fractions corresponding to the less polar material were combined to give cis-N1-(4-4-amino-7-[4-(4-methylpiperazino)cyclohexyl]-7H-pyrrolo[2,3-d]pyrimidin-5-yl-2-methoxyphenyl)-3-phenylpropanamide (0.26 g) as a glass. This was dissolved in ethylacetate (5 ml) and maleic acid (160 mg) in ethylacetate (2 ml) added. The resulting solid was filtered to give cis-N1-(4-4-amino-7-[4-(4-methylpiperazino)cyclohexyl]-7H-pyrrolo[2,3-d]pyrimidin-5-yl-2-methoxyphenyl)-3-phenylpropanamide trimaleate salt (260 mg) as a white solid. Analytical LC/MS conditions: Column: Pecosphere, C18, 3 um, 33×4.6 mm. Eluent: 0% B/A to 100% B/A in 4.5 min.(B: acetonitrile, A: 50 mM ammonia acetate buffer, PH 4.5), 3.5 mL/min. (r$_t$=2.86 mins, 568.4).

The fractions corresponding to the more polar material were combined to give trans-N1-(4-4-amino-7-[4-(4-methylpiperazino)cyclohexyl]-7H-pyrrolo[2,3-d]pyrimidin-5-yl-2-methoxyphenyl)-3-phenylpropanamide (0.11 g ) as a glass. This was dissolved in ethylacetate (5 ml) and treated with a solution of maleic acid (68 mg) in ethylacetate (2 ml). The resulting solid was filtered to give trans-N1-(4-4-amino-7-[4-(4-methylpiperazino)cyclohexyl]-7H-pyrrolo[2,3-d]pyrimidin-5-yl-2-methoxyphenyl)-3-phenylpropanamide tri-maleate (94 mg) as a white solid. Analytical LC/MS conditions:

Column: Pecosphere, C18, 3 um, 33×4.6 mm. Eluent: 0% B/A to 100% B/A in 4.5 min.(B: acetonitrile, A: 50 mM ammonia acetate buffer, PH 4.5), 3.5 mL/min. (r$_t$=2.68 mins, 568.2).

EXAMPLES 406 and 407 cis and trans -5-(4-Amino-3-methoxyphenyl)-7-[4-(4-methylpiperazino)cyclohexyl]-7H-pyrrolo[2,3-d]pyrimidin-4-amine 4-[4-amino-5-(4-amino-3-methoxyphenyl)-7H-pyrrolo[2,3-d]pyrimidin-7-yl]-1-cyclohexanone (2.25 g, 6.5 mmol), acetic acid (1.17 g, 19.5 mmol) and N-methylpiperazine (1.95 g, 19.5 mmol) were dissolved in dichloroethane (200 ml). Sodium triacetoxyborohydride (2.07 g, 9.75 mmol) was added portionwise and the mixture stirred at room temperature overnight. Saturated sodium bicarbonate solution (150 ml) was added and the aqueous layer extracted with dichloromethane (3×100 ml). The combined organics were washed with water, dried (sodium sulphate), filtered and evaporated to leave a semi-solid whaich was purified by flash silica gel column chromatography using CH$_2$Cl$_2$/methanol (0% MeOH to 50% MeOH in 5% increments). The fractions corresponding to the faster running material were combined and evaporated to give cis-5-(4-amino-3-methoxyphenyl)-7-[4-(4-methylpiperazino)cyclohexyl]-7H-pyrrolo[2,3-d]pyrimidin-4-amine (1.2 g, 43%) as a cream solid. $^1$H NMR (d$_6$-DMSO): δ 8.1(1H, s), 7.11(1H, s), 6.87(1H, s), 6.79(1H, d), 6.05(2H, bs), 4.80(2H, bs), 4.64(1H, m), 4.08(1H, m), 3.82(3H, s), 3.17(2H, m), 2.37(6H, m), 2.21(3H, s), 2.08 (4H, m), 1.70(2H, m), 1.53(2H, m). HPLC (r$_t$=11.24 min, 97.6%).

The fractions corresponding to the slower running material were combined and evaporated to give trans-5-(4-amino-3-methoxyphenyl)-7-[4-(4-methylpiperazino)cyclohexyl]-7H-pyrrolo[2,3-d]pyrimidin-4-amine (0.4 g, 14%) as a white solid. $^1$H NMR (d$_6$-DMSO): δ 8.10(1H, s), 7.26 (1H, s), 6.87(1H, s), 6.77(1H, d), 6.71(1H, d), 6.05(2H, bs), 4.79(2H, s), 4.52(1H, m), 3.81(3H, s), 3.35(1H, m), 2.50(5H, m), 2.31(5H, m), 2.14(1H, m), 1.97(6H, m), 1.45 (2H, m). HPLC (r$_t$=10.13 min, 97.9%).

To a solution of trans-5-(4-amino-3-methoxyphenyl)-7-[4-(4-methylpiperazino)cyclohexyl]-7H-pyrrolo[2,3-d]pyrimidin-4-amine (30 mg, 0.069 mmol) in pyridine (0.5 ml) was added the appropriate acid chloride (2 eq., 0.138 mmol). The vials were capped and shaken overnight on an orbital shaker. LCMS (Micromass-Column: Pecosphere, C18, 3 um, 33×4.6 mm. Eluents: 0% B/A to 100% B/A in 4.5 min.(B: acetonitrile, A: 50 mM ammonia acetate buffer, PH 4.5), 3.5 mL/min.) of the resulting mixtures showed presence of product in all cases. The solutions were evaporated to dryness and the resulting residues were re-dissolved in DMF (1 ml) and purified by reverse phase prep. HPLC (Hypersil BSD C18, 5 um, 100×21 mm, 0%–100% acetonitrile/0.05M ammonium acetate over 10 min, 25.0 mL/min). The resulting products were further purified by dissolving in dichloromethane (4 ml) and washed with 1.0 N sodium hydroxide (2 ml) to give the corresponding products. The compounds are detailed below alongwith the appropriate $^1$H NMR and LCMS data

Example 408 trans-N1-(4-4-Amino-7-[4-(4-methylpiperazino) cyclohexyl]-7H-20 pyrrolo[2,3-d]pyrimidin-5-yl-2-methoxyphenyl)-2-phenylcyclopropane-1-carboxamide $^1$H NMR (d$_6$-DMSO): δ 9.54(1H, s), 8.13(1H, s), 8.08 (2H, d, J=11.2 Hz), 7.44(1H, s), 7.32(2H, m), 7.20(3H, m), 6.99(1H, m), 6.11(2H, bs), 4.55(1H, s), 3.88(3H, s), 2.50 (6H, m), 2.38(6H, m), 2.14(3H, s), 1.93(6H, m), 1.47(3H, m) LC/MS (Pecosphere C18, 3 um, 33×4.6 mm; 0%–100% acetonitrile/0.05M ammonium acetate over 5 min, 3.0 mL/min): R$_t$ 2.69 min. MH$^+$ 580.4.

Example 409 trans-N1-(4-4-Amino-7-[4-(4-methylpiperazino) cyclohexyl]-7H-pyrrolo[2,3-d]pyrimidin-5-yl-2-methoxyphenyl)-4-dimethylaminobenzamide $^1$H NMR (CDCl$_3$): δ 8.61(1H, d, J=8 Hz), 8.48(1H, s), 8.33(1H, s), 7.83(2H, d, J=8 Hz), 7.11(1H, d, J=8 Hz), 7.02 (2H, d, J=8 Hz), 6.74(2H, d, J=8 Hz), 5.15 (2H, bs), 4.69(1H, m), 3.98(3H, s), 3.06 (6H, s), 2.43–2.65(8H, m), 2.30(3H, s), 2.22(2H, m), 2.08(2H, m), 1.85(3H, m), 1.60 (2H, m) LC/MS (Pecosphere C18, 3 um, 33×4.6 mm; 0%–100% acetonitrile/0.05M ammonium acetate over 5 min, 3.0 mL/min): R$_t$ 2.59 min. MH$^{30}$ 582.9.

Example 410 trans-N1-(4-4-Amino-7-[4-(4-methylpiperazino) cyclohexyl]-7H-pyrrolo[2,3-d]pyrimidin-5-yl-2-methoxyphenyl)-4-trifluoromethoxybenzamide $^1$H NMR (d$_6$-DMSO): δ 9.63(1H, s), 8.15(1H, s), 8.09 (2H, d, J=11.6 Hz), 7.85(1H, d, J=8 Hz), 7.52(3H, m), 7.17(1H, s), 7.06(1H, d, J=8 Hz), 6.15(2H, bs), 4.56(1H, m), 3.89(3H, s), 2.50(4, m), 2.35 (5H, m), 2.15(3H, s), 1.92(6H, m), 1.47 (2H, m). LC/MS (Pecosphere C18, 3 um, 33×4.6 mm; 0%–100% acetonitrile/0.05M ammonium acetate over 5 min, 3.0 mL/min): R$_t$ 2.86 min. MH$^+$ 624.1.

Example 411 trans-N1-(4-4-Amino-7-[4-(4-methylpiperazino) cyclohexyl]-7H-pyrrolo[2,3-d]pyrimidin-5-yl-2-methoxyphenyl)-4-trifluoromethylbenzamide $^1$H NMR (d$_6$-DMSO): δ 9.76(1H, s), 8.15(3H, m), 7.91 (2H, d, J=8.4 Hz), 7.86(1H, d, J=8.4 Hz), 7.51(1H, s), 7.19 (1H, s), 7.08(1H, d, J=8 Hz), 6.15(2H, bs), 4.56(1H, m), 3.91(3H, s), 2.50(4H, m), 2.35(5H, m), 2.32(3H, s), 1.94 (6H, m), 1.46(2, m); LC/MS (Pecosphere C18, 3 um, 33×4.6 mm; 0%–100% acetonitrile/0.05M ammonium acetate over 5 min, 3.0 mL/min): R$_t$ 2.69 min. MH$^+$ 608.4.

Example 412 cis-N-(4-4-Amino-7-[4-(4-methylpiperazino) cyclohexyl]-7H-pyrrolo[2,3-d]pyrimidin-5-yl-2-methoxyphenyl)-N'-benzylurea To a solution of cis-5-(4-amino-3-methoxyphenyl)-7-[4-(4-methylpiperazino)cyclohexyl]-7H-pyrrolo[2,3-d] pyrimidin-4-amine (50 mg, 0.116 mmol) in pyridine (1 ml) at room temperature was added benzylisocyanate (15.4 mg, 0.116 mmol). The resulting solution was shaken overnight at room temperature on an orbital shaker and then submitted directly to preparative HPLC. The resulting product was further purified by dissolving in dichloromethane (4 ml) and washed with 1.0 N sodium hydroxide (2 ml) to furnish, after evaporation of the solvent, cis-N-(4-4-amino-7-[4-(4-methylpiperazino)cyclohexyl]-7H-pyrrolo[2,3-dupyrimidin-5-yl-2-methoxyphenyl)-N'-benzylurea as a white powder.

$^1$H NMR (CDCl$_3$): δ 8.32(1H, s), 8.18(1H, d), 7.34(4H, m), 7.26(1H, m), 7.08 2H, m), 6.95(2H, m), 5.25(1H, m), 5.10(2H, bs), 4.82(1H, m), 4.48(2H, m), 3.85(3H, s), 2.47 (3H, m), 2.29(4H, m), 2.12(4H, m), 1.82(3H, m), 1.62(2H, m), 1.31(4H, m), 0.89(2H, m). LC/MS (Pecosphere C18, 3 um, 33×4.6 mm; 0%–100% acetonitrile/0.05M ammonium acetate over 5 min, 3.0 mL/min): R$_t$ 2.57 min. MH$^{30}$ 569.3.

Example 413 cis-N1-(4-4-Amino-7-[4-(4-methylpiperazino) cyclohexyl]-7H-pyrrolo[2,3-d]pyrimidin-5-yl-2-methoxyphenyl)-(E)-3-phenyl-2-propenamide To a solution of cis-5-(4-amino-3-methoxyphenyl)-7-[4-(4-methylpiperazino)cyclohexyl]-7H-pyrrolo[2,3-d] pyrimidin-4-amine (50 mg, 0.116 mmol) in pyridine (1 ml) at room temperature was added cinnamoylchloride (39 mg, 0.232 mmol) and the solution shaken overnight at room temperature. The resulting solution was submitted directly to prep HPLC. The resulting product was further purified by dissolving in dichloromethane (4 ml) and washed with 1.0 N sodium hydroxide (2 ml) to furnish, after evaporation of the solvent, cis-N1-(4-4-amino-7-[4-(4-methylpiperazino) cyclohexyl]-7H-pyrrolo[2,3-d]pyrimidin-5-yl-2-methoxyphenyl)-(E)-3-phenyl-2-propenamide as an off-white powder (42 mg).

$^1$H NMR (CDCl$_3$): δ 8.62(1H, d, J=8.4 Hz), 8.34(1H, s), 7.99(1H, s), 7.77(1H, d, J=8 Hz), 7.57(2H, m), 7.40(3H, m), 7.15(2H, m), 7.04(1H, s), 6.63(1H, d, J=15.2 Hz),5.16(2H, bs), 4.83(1H, m), 3.99(3H, s), 2.61(6H, m), 2.29(4H, m), 2.12 (4H, m), 1.86(4H, m), 1.65(2H, m); LC/MS (Pecosphere C18, 3 um, 33×4.6 mm; 0%–100% acetonitrile/ 0.05M ammonium acetate over 5 min, 3.0 mL/min): R$_t$ 2.82 min. MH$^{30}$ 566.3.

Example 414 cis-N1-(4-4-Amino-7-[4-(4-methylpiperazino) cyclohexyl]-7H-pyrrolo[2,3-d]pyrimidin-5-yl-2-methoxyphenyl)-2-phenylacetamide To a solution of cis-5-(4-amino-3-methoxyphenyl)-7-[4-(4-methylpiperazino)cyclohexyl]-7H-pyrrolo[2,3-d] pyrimidin-4-amine (50 mg, 0.116 mmol) in pyridine (1 ml) at room temperature was added phenacetyl chloride (36 mg, 0.232 mmol). The resulting solution was shaken overnight and then submitted directly for prep. HPLC. The resulting product was further purified by dissolving in dichloromethane (4 ml) and washed with 1.0 N sodium hydroxide (2 ml) to furnish, after evaporation of the solvent, cis-N1-(4-4-amino-7-[4-(4-methylpiperazino)cyclohexyl]-7H-pyrrolo[2,3-d]pyrimidin-5-yl-2-methoxyphenyl)-2-phenylacetamide as a white powder (15 mg).

$^1$H NMR (CDCl$_3$): δ 8.44(1H, d, J=8.4 Hz), 8.42(1H, s), 7.83(1H, s), 7.37(4H, m), 7.06(2H, m), 6.93(1H, s), 5.12 (2H, s), 4.80(1H, m), 3.80(3H, s), 2.61(6H, m), 2.29(4H, m), 2.13(4H, m), 1.98(2H, m), 1.83(2H, m), 1.62(2H, m). LC/MS (Pecosphere C18, 3 um, 33×4.6 mm; 0%–100% acetonitrile/0.05M ammonium acetate over 5 min, 3.0 mL/min): $R_t$ 2.58 min. $MH^{30}$ 554.3.

All the following compounds were made by parallel synthesis according to the following procedure:

To cis-5-(4-amino-3-methoxyphenyl)-7-[4-(4-methylpiperazino)cyclohexyl]-7H-pyrrolo[2,3-d]pyrimidin-4-amine (30 mg, 0.069 mmol) in pyridine (0.5 mL) was added the appropriated acid chloride (0.138 mmol) slowly while vortexing. The reaction mixtures were shaken for 5–20 hr. The reactions were monitored by analytical HPLC. For the reactions that still had starting material left after 5 hours, another two equivalents of acid chloride were added while vortexing. The crude reaction mixtures were purified by reverse phase preparative LC/MS (Hypersil BSD C18, 5 um, 100×21 mm, 0%–100% acetonitrile/0.05M ammonium acetate over 10 min, 25.0 mL/min). The resulting products were further purified by dissolving in dichloromethane (4 ml) and washed with 1.0 N sodium hydroxide (2 ml) to give the corresponding products. Product yields are from 38% to 88% and purities are from 94% to 100%.

Example 415 cis N1-(4-4-Amino-7-[4-(4-methylpiperazino) cyclohexyl]-7H-pyrrolo[2,3-d]pyrimidin-5-yl-2-methoxyphenyl)-2-methoxyacetamide LC/MS (Pecosphere C18, 3 um, 33×4.6 mm; 0%–100% acetonitrile/0.05M ammonium acetate over 5 min, 3.0 mL/min): Rt 2.32 min. MH+ 508.3.

Example 416 cis N1-(4-4-Amino-7-[4-(4-methylpiperazino) cyclohexyl]-7H-pyrrolo[2,3-d]pyrimidin-5-yl-2-methoxyphenyl)-2,6-difluorobenzamide LC/MS (Pecosphere C18, 3 um, 33×4.6 mm; 0%–100% acetonitrile/0.05M ammonium acetate over 5 min, 3.0 mL/min): $R_t$ 2.61 min. $MH^+$ 576.3.

Example 417 cis N1-(4-4-Amino-7-[4-(4-methylpiperazino) cyclohexyl]-7H-pyrrolo[2,3-d]pyrimidin-5-yl-2-methoxyphenyl)-2-methoxybenzamide LC/MS (Pecosphere C18, 3 um, 33×4.6 mm; 0%–100% acetonitrile/0.05M ammonium acetate over 5 min, 3.0 mL/min): $R_t$ 3.02 min. $MH^+$ 570.3.

Example 418 cis N1-(4-4-Amino-7-[4-(4-methylpiperazino) cyclohexyl]-7H-pyrrolo[2,3-d]pyrimidin-5-yl-2-methoxyphenyl)-2,6-dimethoxybenzamide LC/MS (Pecosphere C18, 3 um, 33×4.6 mm; 0%–100% acetonitrile/0.05M ammonium acetate over 5 min, 3.0 mL/min): $R_t$ 2.61 min. $MH^+$ 600.3.

Example 419 cis N1-(4-4-Amino-7-[4-(4-methylpiperazino) cyclohexyl]-7H-pyrrolo[2,3-d]pyrimidin-5-yl-2-methoxyphenyl)-3,4-dichlorobenzamide LC/MS (Pecosphere C18, 3 um, 33×4.6 mm; 0%–100% acetonitrile/0.05M ammonium acetate over 5 min, 3.0 mL/min): $R_t$ 3.26 min. $MH^+$ 608.3.

Example 420 cis N1-(4-4-Amino-7-[4-(4-methylpiperazino) cyclohexyl]-7H-pyrrolo[2,3-d]pyrimidin-5-yl-2-methoxyphenyl)-3-methoxybenzamide LC/MS (Pecosphere C18, 3 um, 33×4.6 mm; 0%—100% acetonitrile/0.05M ammonium acetate over 5 min, 3.0 mL/min): $R_t$ 2.74 min. $MH^+$ 570.3.

Example 421 cis N1-(4-4-Amino-7-[4-(4-methylpiperazino) cyclohexyl]-7H-pyrrolo[2,3-d]pyrimidin-5-yl-2-methoxyphenyl)-4-fluorobenzamide LC/MS (Pecosphere C18, 3 um, 33×4.6 mm; 0%–100% acetonitrile/0.05M ammonium acetate over 5 min, 3.0 mL/min): $R_t$ 2.78 min. $MH^+$ 558.34.

Example 422 cis N1-(4-4-amino-7-[4-(4-methylpiperazino) cyclohexyl]-7H-pyrrolo[2,3-d]pyrimidin-5-yl-2-methoxyphenyl)-4-chlorobenzamide LC/MS (Pecosphere C18, 3 um, 33×4.6 mm; 0%–100% acetonitrile/0.05M ammonium acetate over 5 min, 3.0 mL/min): $R_t$ 3.00 min. $MH^+$ 574.3.

Example 423 cis N1-(4-4-Amino-7-[4-(4-methylpiperazino) cyclohexyl]-7H-pyrrolo[2,3-d]pyrimidin-5-yl-2-methoxyphenyl)-4-methoxybenzamide LC/MS (Pecosphere C18, 3 um, 33×4.6 mm; 0%–100% acetonitrile/0.05M ammonium acetate over 5 min, 3.0 mL/min): $R_t$ 2.76 min. $MH^+$ 570.3.

Example 424 cis N1-(4-4-Amino-7-[4-(4-methylpiperazino) cyclohexyl]-7H-pyrrolo[2,3-d]pyrimidin-5-yl-2-methoxyphenyl)-4-(trifluoromethyl)benzamide LC/MS (Pecosphere C18, 3 um, 33×4.6 mm; 0%–100% acetonitrile/0.05M ammonium acetate over 5 min, 3.0 mL/min): $R_t$ 3.26 min. $MH^+$ 608.3.

Example 425 cis N1-(4-4-Amino-7-[4-(4-methylpiperazino) cyclohexyl]-7H-pyrrolo[2,3-d]pyrimidin-5-yl-2-methoxyphenyl)-2-phenoxyacetamide LC/MS (Pecosphere C18, 3 um, 33×4.6 mm; 0%–100% acetonitrile/0.05M ammonium acetate over 5 min, 3.0 mL/min): $R_t$ 2.94 min. $MH^+$ 570.3.

Example 426 cis N1-(4-4-Amino-7-[4-(4-methylpiperazino) cyclohexyl]-7H-pyrrolo[2,3-d]pyrimidin-5-yl-2-methoxyphenyl)-2-(4-chlorophenoxy)acetamide LC/MS (Pecosphere C18, 3 um, 33×4.6 mm; 0%–100% acetonitrile/0.05M ammonium acetate over 5 min, 3.0 mL/min): $R_t$ 3.13 min. $MH^+$ 604.3.

Example 427 cis N1-(4-4-Amino-7-[4-(4-methylpiperazino) cyclohexyl]-7H-pyrrolo[2,3-d]pyrimidin-5-yl-2-methoxyphenyl-cis-2-phenylcyclopropane-1-carboxamide LC/MS (Pecosphere C18, 3 um, 33×4.6 mm; 0%–100% acetonitrile/0.05M ammonium acetate over 5 min, 3.0 mL/min): $R_t$ 3.16 min. $MH^+$ 580.3.

Example 428 cis N1-(4-4-Amino-7-[4-(4-methylpiperazino) cyclohexyl]-7H-pyrrolo[2,3-d]pyrimidin-5-yl-2-methoxyphenyl)-3-nitrobenzamide LC/MS (Pecosphere C18, 3 um, 33×4.6 mm; 0%–100% acetonitrile/0.05M ammonium acetate over 5 min, 3.0 mL/min): $R_t$ 2.90 min. $MH^+$ 585.3.

Example 429 cis N1-(4-4-Amino-7-[4-(4-methylpiperazino) cyclohexyl]-7H-pyrrolo[2,3-d]pyrimidin-5-yl-2-methoxyphenyl)-2,5-difluorobenzamide LC/MS (Pecosphere C18, 3 um, 33×4.6 mm; 0%–100% acetonitrile/0.05M ammonium acetate over 5 min, 3.0 mL/min): $R_t$ 2.90 min. $MH^+$ 576.3.

Example 430 cis N1-(4-4-Amino-7-[4-(4-methylpiperazino) cyclohexyl]-7H-pyrrolo[2,3-d]pyrimidin-5-yl-2-methoxyphenyl)-2-(benzyloxy)acetamide LC/MS (Pecosphere C18, 3 um, 33×4.6 mm; 0%–100% acetonitrile/0.05M ammonium acetate over 5 min, 3.0 mL/min): $R_t$ 2.90 min. $MH^+$ 584.3.

Example 431 cis N1-(4-4-Amino-7-[4-(4-methylpiperazino) cyclohexyl]-7H-pyrrolo[2,3-d]pyrimidin-5-yl-2-methoxyphenyl)-3-cyanobenzamide LC/MS (Pecosphere C18, 3 um, 33×4.6 mm; 0%–100% acetonitrile/0.05M ammonium acetate over 5 min, 3.0 mL/min): $R_t$ 2.74 min. $MH^+$ 565.6.

Example 432 cis N1-(4-4-Amino-7-[4-(4-methylpiperazino) cyclohexyl]-7H-pyrrolo[2,3-d]pyrimidin-5-yl-2-methoxyphenyl)-2,3-difluorobenzamide LC/MS (Pecosphere C18, 3 um, 33×4.6 mm; 0%–100% acetonitrile/0.05M ammonium acetate over 5 min, 3.0 mL/min): $R_t$ 3.06 min. $MH^+$ 576.3.

Example 433 cis N3-(4-4-Amino-7-[4-(4-methylpiperazino) cyclohexyl]-7H-pyrrolo[2,3-d]pyrimidin-5-yl-2-methoxyphenyl)-6-chloronicotinamide LC/MS (Pecosphere C18, 3 um, 33×4.6 mm; 0%–100% acetonitrile/0.05M ammonium acetate over 5 min, 3.0 mL/min): $R_t$ 2.53 min. $MH^+$ 575.3.

Example 434

N1-(4-4-Amino-7-[4-(4-methylpiperazino) cyclohexyl]-7H-pyrrolo[2,3-d]pyrimidin-5-yl-2-methoxyphenyl)-4-(tert-butoxy)benzamide LC/MS (Pecosphere C18, 3 um, 33×4.6 mm; 0%–100% acetonitrile/0.05M ammonium acetate over 5 min, 3.0 mL/min): $R_t$ 3.32 min. $MH^+$ 624.3.

Example 435 cis N1-(4-4-Amino-7-[4-(4-methylpiperazino) cyclohexyl]-7H-pyrrolo[2,3-d]pyrimidin-5-yl-2-methoxyphenyl)-2,4,6-trifluorobenzamide LC/MS (Pecosphere C18, 3 um, 33×4.6 mm; 0%–100% acetonitrile/0.05M ammonium acetate over 5 min, 3.0 mL/min): $R_t$ 2.85 min. $MH^+$ 594.4.

Example 436 cis N1-(4-4-Amino-7-[4-(4-methylpiperazino) cyclohexyl]-7H-pyrrolo[2,3-d]pyrimidin-5-yl-2-methoxyphenyl)-2-chloro-6-fluorobenzamide LC/MS (Pecosphere C18, 3 um, 33×4.6 mm; 0%–100% acetonitrile/0.05M ammonium acetate over 5 min, 3.0 mL/min): $R_t$ 2.76 min. $MH^+$ 592.3.

Example 437 cis N1-(4-4-Amino-7-[4-(4-methylpiperazino) cyclohexyl]-7H-pyrrolo[2,3-d]pyrimidin-5-yl-2-methoxyphenyl)-4-(dimethylamino)benzamide LC/MS (Pecosphere C18, 3 um, 33×4.6 mm; 0%–100% acetonitrile/0.05M ammonium acetate over 5 min, 3.0 mL/min): $R_t$ 2.86 min. $MH^+$ 583.3.

Example 438 cis N1-(4-4-Amino-7-[4-(4-methylpiperazino) cyclohexyl]-7H-pyrrolo[2,3-d]pyrimidin-5-yl-2-methoxyphenyl)-4-cyanobenzamide LC/MS (Pecosphere C18, 3 um, 33×4.6 mm; 0%–100% acetonitrile/0.05M ammonium acetate over 5 min, 3.0 mL/min): $R_t$ 2.68 min. $MH^+$ 565.3.

Example 439 cis N1-(4-4-Amino-7-[4-(4-methylpiperazino) cyclohexyl]-7H-pyrrolo[2,3-d]pyrimidin-5-yl-2-methoxyphenyl)-4-nitrobenzamide LC/MS (Pecosphere C18, 3 um, 33×4.6 mm; 0%–100% acetonitrile/0.05M ammonium acetate over 5 min, 3.0 mL/min): $R_t$ 2.84 min. $MH^+$ 585.3.

Example 440 cis N1-(4-4-Amino-7-[4-(4-methylpiperazino) cyclohexyl]-7H-pyrrolo[2,3-d]pyrimidin-5-yl-2-methoxyphenyl)-3-fluorobenzamide LC/MS (Pecosphere C18, 3 um, 33×4.6 mm; 0%–100% acetonitrile/0.05M ammonium acetate over 5 min, 3.0 mL/min): $R_t$ 2.73 min. $MH^+$ 558.1.

Example 441 cis N1-(4-4-Amino-7-[4-(4-methylpiperazino) cyclohexyl]-7H-pyrrolo[2,3-d]pyrimidin-5-yl-2-methoxyphenyl)-2,5-dimethoxybenzamide LC/MS (Pecosphere C18, 3 um, 33×4.6 mm; 0%–100% acetonitrile/0.05M ammonium acetate over 5 min, 3.0 mL/min): $R_t$ 2.93 min. $MH^+$ 600.2.

Example 442 cis N5-(4-4-Amino-7-[4-(4-methylpiperazino) cyclohexyl]-7H-pyrrolo[2,3-d]pyrimidin-5-yl-2-methoxyphenyl)-1,3-benzodioxole-5-carboxamide LC/MS (Pecosphere C18, 3 um, 33×4.6 mm; 0%–100% acetonitrile/0.05M ammonium acetate over 5 min, 3.0 mL/min): $R_t$ 2.73 min. $MH^+$ 584.3.

Example 443 cis N1-(4-4-Amino-7-[4-(4-methylpiperazino) cyclohexyl]-7H-pyrrolo[2,3-d]pyrimidin-5-yl-2-methoxyphenyl)-2,6-dimethylbenzamide LC/MS (Pecosphere C18, 3 um, 33×4.6 mm; 0%–100% acetonitrile/0.05M ammonium acetate over 5 min, 3.0 mL/min): $R_t$ 2.84 min. $MH^+$ 568.2.

Example 444 cis N1-(4-4-Amino-7-[4-(4-methylpiperazino) cyclohexyl]-7H-pyrrolo[2,3-d]pyrimidin-5-yl-2-methoxyphenyl)-2-chloro-4-fluorobenzamide LC/MS (Pecosphere C18, 3 um, 33×4.6 mm; 0%–100% acetonitrile/0.05M ammonium acetate over 5 min, 3.0 mL/min): $R_t$ 2.86 min. MH+ 592.1.

Example 445 cis N5-(4-4-Amino-7-[4-(4-methylpiperazino) cyclohexyl]-7H-pyrrolo[2,3-d]pyrimidin-5-yl-2-methoxyphenyl)-2,1,3-benzoxadiazole-5-carboxamide LC/MS (Pecosphere C18, 3 um, 33×4.6 mm; 0%–100% acetonitrile/0.05M ammonium acetate over 5 min, 3.0 mL/min): $R_t$ 2.74 min. MH+ 582.1.

Example 446 cis N1-(4-4-Amino-7-[4-(4-methylpiperazino) cyclohexyl]-7H-pyrrolo[2,3-d]pyrimidin-5-yl-2-methoxyphenyl)-4-phenylbutanamide LC/MS (Pecosphere C18, 3 um, 33×4.6 mm; 0%–100% acetonitrile/0.05M ammonium acetate over 5 min, 3.0 mL/min): $R_t$ 2.92 min. MH+ 582.1.

Example 447 cis N4-(4-4-Amino-7-[4-(4-methylpiperazino) cyclohexyl]-7H-pyrrolo[2,3-d]pyrimidin-5-yl-2-methoxyphenyl)-1-methyl-5-propyl-1H-4-pyrazolecarboxamide LC/MS (Pecosphere C18, 3 um, 33×4.6 mm; 0%–100% acetonitrile/0.05M ammonium acetate over 5 min, 3.0 mL/min): $R_t$ 2.57 min. MH+ 586.4.

Example 448 cis N1-(4-4-Amino-7-[4-(4-methylpiperazino) cyclohexyl]-7H-pyrrolo[2,3-d]pyrimidin-5-yl-2-methoxyphenyl)-2-methoxybenzamide LC/MS (Pecosphere C18, 3 um, 33×4.6 mm; 0%–100% acetonitrile/0.05M ammonium acetate over 5 min, 3.0 mL/min): Rt 2.32 min. MH+ 508.3.

Example 449 cis-5-(4-Phenoxyphenyl)-7-{4-[(3R)tetrahydro-1H-3-pyrrolylamino]cyclohexyl}-pyrrolo[2,3-d] pyrimidin-4-amine A mixture of 4-[4-amino-5-(4-phenoxyphenyl)-7H-pyrrolo[2,3-d]pyrimidin-7-yl]cyclohexanone (1.00 g, 2.51 mmol), (3R)-(+)-3-aminopyrrolidine (0.65 g, 7.5 mmol), and acetic acid (0.43 mL, 7.5 mmol) in 1,2-dichloroethane (50 mL) was stirred at ambient temperature under an atmosphere of nitrogen for 45 minutes. Sodium triacetoxyborohydride (0.691 g, 3.26 mmol) was added and the mixture stirred at ambient temperature for 15 hours. Water (50 mL) and sodium bicarbonate (1.35 g, 16.1 mmol) were added and the mixture was stirred for 45 minutes. The reaction mixture was transferred to a separatory funnel and the organic layer was separated. The organic portion was dried over magnesium sulfate, filtered, and the solvent removed under reduced pressure to yield an oily brown solid. The compound was purified by flash chromatography on silica gel (1 L 10% MeOH in $CH_2Cl_2$, then 1 L 20% MeOH in $CH_2Cl_2$, followed by 500 mL 30% MeOH in $CH_2Cl_2$) to yield cis-5-(4-phenoxyphenyl)-7-{4-[(3R)tetrahydro-1H-3-pyrrolylamino]cyclohexyl}-7H-pyrrolo[2,3-d]pyrimidin-4-amine as a beige solid (0.285 g, 0.608 mmol): $^1$H NMR ($d_6$ DMSO, 400 MHz): δ H 8.13(1H, s), 7.39–7.49(5H, m), 7.07–7.17(5H, m), 6.09(2H, bs), 4.65 (1H, m), 3.29–3.35 (3H, m), 2.63–2.67(2H, m), 1.94–2.51(8H, m), 1.46–1.80 (4H, m); RP-HPLC (Delta Pak C18, 5 μm, 300 A, 15 cm; 5%–85% acetonitrile-0.1M ammonium acetate over 20 min, 1 mL/min) $R_t$ 12.59 min.

The following compound was made in a similar manner to cis-5-(4-phenoxyphenyl)-7-{4-[(3R)tetrahydro-1H-3-pyrrolylamino]cyclohexyl}-7H-pyrrolo[2,3-d]pyrimidin-4-amine.

Example 450 cis-5-(4-Phenoxyphenyl)-7-{4-[(3S)tetrahydro-1H-3-pyrrolylamino]cyclohexyl}-7H-pyrrolo[2,3-d] pyrimidin-4-amine $^1$H NMR ($d_6$ DMSO, 400 MHz): δ H 8.13(1H, s), 7.37–7.49(5H, m), 7.07–7.17(5H, m), 6.11(2H, bs), 4.64 (1H, m), 3.17–3.33 (3H, m), 2.49–2.56(2H, m), 1.90–2.36 (8H, m), 1.58–1.89(4H, m); RP-HPLC (Delta Pak C18, 5 82 m, 300 A, 15 cm; 5%–85% acetonitrile-0.1M ammonium acetate over 20 min, 1 mL/min) $R_t$ 12.75 min.

Examples 451 and 452 cis-1-{4-[4-Amino-5-(4-phenoxyphenyl)-7H-pyrrolo [2,3-d]pyrimidin-7-yl]cyclohexyl}-4-piperidinol Dimaleate Salt and trans-1-{4-[4-Amino-5-(4-phenoxyphenyl)-7H-pyrrolo[2,3-d]pyrimidin-7-yl] cyclohexyl}-4-piperidinol Dimaleate Salt A mixture of 4-[4-amino-5-(4-phenoxyphenyl)-7H-pyrrolo[2,3-d]pyrimidin-7-yl]cyclohexanone (0.997 g, 2.50 mmol), 4-hydroxypiperidine (0.760 g, 7.5 mmol), sodium triacetoxyborohydride (0.689 g, 3.25 mmol), and acetic acid (0.43 mL, 7.5 mmol) in 1,2-dichloroethane (50 mL) was stirred at 80° C. under an atmosphere of nitrogen for 58 hours. The reaction mixture was cooled and water (50 mL) and sodium bicarbonate (1.35 g, 16.1 mmol) were added and the mixture was stirred for 2 hours. The organic layer was separated, dried over magnesium sulfate, filtered, and the solvent removed under reduced pressure to yield a brown solid. The cis and trans isomers were purified by flash chromatography on silica gel (1 L 5% MeOH in $CH_2Cl_2$, then 500 mL 10% MeOH in $CH_2Cl_2$, 500 mL 50:45:5 $CH_2Cl_2$:MeOH:$Et_3N$, and 500 mL 45:45:10 $CH_2Cl_2$:MeOH:$Et_3N$). In order to remove residual $Et_3N$, each of the products was taken up in $CH_2Cl_2$, washed with 40 mL water, the organic portion separated, dried over magnesium sulfate, filtered, and concentrated to yield cis-1-{4-[4-amino-5-(4-phenoxyphenyl)-7H-pyrrolo[2,3-d] pyrimidin-7-yl]cyclohexyl}-4-piperidinol as a brown solid (0.185 g, 0.382 mmol) and trans-1-{4-[4-amino-5-(4-phenoxyphenyl)-7H-pyrrolo[2,3-d]pyrimidin-7-yl] cyclohexyl}-4-piperidinol as a brown solid (0.115 g, 0.237 mmol). The cis-1-{4-[4-amino-5-(4-phenoxyphenyl)-7H-pyrrolo[2,3-d]pyrimidin-7-yl]cyclohexyl}-4-piperidinol (0.185 g, 0.383 mmol) was dissolved in warm ethyl acetate (5 mL) then added to a solution of maleic acid (0.089 g, 0.765 mmol) in ethanol (5 mL). The mixture was cooled to ambient temperature and the solid was collected by filtration and dried to give cis-1-{4-[4-amino-5-(4-phenoxyphenyl)-7H-pyrrolo[2,3-d]pyrimidin-7-yl]cyclohexyl}-4-piperidinol dimaleate salt (0.202 g) as a yellow solid: $^1$H NMR (d$_6$ DMSO, 400 MHz): δ H 8.61(1H, bs), 8.25(1H, s), 7.40–7.56 (5H, m), 7.08–7.19(5H, m), 6.40 (2H, bs), 6.13(4H, s), 5.00–5.20(1H, m), 4.80 (1H, m), 3.03–3.95(9H, m), 2.30–2.32(2H, m), 1.63–1.99(6H, m); RP-HPLC (Delta Pak C18, 5 μm, 300 A, 15 cm; 5%–85% acetonitrile-0.1M ammonium acetate over 20 min, 1 mL/min) R$_t$ 13.33 min. MS: MH$^+$ 484.

Trans-1-{4-[4-amino-5-(4-phenoxyphenyl)-7H-pyrrolo[2,3-d]pyrimidin-7-yl]cyclohexyl}-4-piperidinol dimaleate salt was prepared from the free base in the same manner: $^1$H NMR (d$_6$ DMSO, 400 MHz): δ 1H 8.90 (1H, bs), 8.20(1H, s), 7.40–7.48 (5H, m), 7.08–7.19(5H, m), 6.45(2H, bs), 6.14(4H, s), 5.00–5.15(1H, m), 4.75(1H, m), 4.00(1H, m), 3.05–3.90(8H, m), 1.50–2.17(8H, m); RP-HPLC (Delta Pak C18, 5 μm, 300 A, 15 cm; 5%–85% acetonitrile-0.1M ammonium acetate over 20 min, 1 mL/min) R$_t$ 13.49 min. MS: MH$^+$ 484.

Examples 453 and 454

Cis-7-{4-[(3R)-3-(Dimethylamino)tetrahydro-1H-1-pyrrolyl]cyclohexyl}-5-(4-phenoxyphenyl)-7H-pyrrolo[2,3-d]pyrimidin-4-amine Trimaleate Salt and trans-7-{4-[(3R)-3-(Dimethylamino)tetrahydro-1H-1-pyrrolyl]cyclohexyl}-5-(4-phenoxyphenyl)-7H-pyrrolo[2,3-d]pyrimidin-4-amine Trimaleate Salt A mixture of 4-[4-amino-5-(4-phenoxyphenyl)-7H-pyrrolo[2,3-d]pyrimidin-7-yl]cyclohexanone (100 g, 2.51 mmol), (3R)-(+)-3-(dimethylamino)pyrrolidine (0.86 g, 7.5 mmol), and acetic acid (0.43 mL, 7.5 mmol) in 1,2-dichloroethane (45 mL) was stirred at ambient temperature under an atmosphere of nitrogen for 30 minutes. Sodium triacetoxyborohydride (0.689 g, 3.26 mmol) was added and the mixture stirred at ambient temperature for 22 hours. Water (50 mL) and sodium bicarbonate (1.35 g, 16.1 mmol) were added and the mixture was stirred for 3 hours. The reaction mixture was transferred to a separatory funnel and the organic layer was separated. The aqueous layer was extracted with CH$_2$Cl$_2$(20 mL), and the combined organic extracts were dried over magnesium sulfate, filtered, and the solvent removed under reduced pressure to yield a red oil. The cis and trans isomers were purified by flash chromatography on silica gel (1 L 5% MeOH in CH$_2$Cl$_2$, then 1 L 10% MeOH in CH$_2$Cl$_2$, 1 L 20% MeOH in CH$_2$Cl$_2$, 1 L 30% MeOH in CH$_2$Cl$_2$, 1 L 40% MeOH in CH$_2$Cl$_2$, and 1 L 50% MeOH in CH$_2$Cl$_2$) to yield cis-7-{4-[(3R)-3-(dimethylamino)tetrahydro-1H-1-pyrrolyl]cyclohexyl}-5-(4-phenoxyphenyl)-7H-pyrrolo[2,3-d]pyrimidin-4-amine as a pink solid (0.558 g, 1.12 mmol) and trans-7-{4-[(3R)-3-(dimethylamino)tetrahydro-1H-1-pyrrolyl]cyclohexyl}-5-(4-phenoxyphenyl)-7H-pyrrolo[2,3-d]pyrimidin-4-amine as a pink solid (0.210 g, 0.422 mmol). The cis-7-{4-[(3R)-3-(dimethylamino)tetrahydro-1H-1-pyrrolyl]cyclohexyl}-5-(4-phenoxyphenyl)-7H-pyrrolo[2,3-d]pyrimidin-4-amine (0.330 g, 0.670 mmol) was dissolved in warm ethanol (5 mL) then maleic acid (0.233 g, 2.01 mmol) in ethanol (5 mL) was added. The mixture was cooled to ambient temperature and the solid was collected by filtration and dried to give cis-7-{4-[(3R)-3-(dimethylamino)tetrahydro-1H-1-pyrrolyl]cyclohexyl}-5-(4-phenoxyphenyl)-7H-pyrrolo[2,3-d]pyrimidin-4-amine trimaleate salt (0.622 g) as a beige solid: $^1$H NMR (d$_6$ DMSO, 400 MHz): δ H 8.20(1H, s), 7.41–7.48(4H, m), 7.35(1H, s), 7.08–7.19 (5H, m), 6.45(2H, bs), 6.16(6H, s), 4.70(1H, m), 4.30(2H, bs), 3.80(1H, bs), 3.08(3H, m), 2.76(6H, s), 2.00–2.21(6H, m), 1.74–1.72(4H, m); RP-HPLC (Delta Pak C18, 5 μm, 300 A, 15 cm; 5%–85% acetonitrile-0.1M ammonium acetate over 20 min, 1 mL/min) R$_t$ 13.94 min. MS: MH$^+$ 497.

Trans-7-{4-[(3R)-3-(dimethylamino)tetrahydro-1H-1-pyrrolyl]cyclohexyl}-5-(4-phenoxyphenyl)-7H-pyrrolo[2,3-d]pyrimidin-4-amine trimaleate salt was prepared from the free base in the same manner: $^1$H NMR (d$_6$ DMSO, 400 MHz): δ H 8.18(1H, s), 7.40–7.47(5H, m), 7.08–7.19(5H, m), 6.33(2H, bs), 6.12(6H, s), 4.61(1H, m), 3.07–3.60(6H, m), 2.64(6H, s), 2.18–2.20 (3H, m), 1.98–2.03(5H, m), 1.55–1.58(2H, m); RP-HPLC (Delta Pak C18, 5 μm, 300 A, 15 cm; 5%–85% acetonitrile-0.1M ammonium acetate over 20 min, 1 mL/min) R$_t$ 14.08 min. MS: MH$^+$ 497.

The following compounds were made in a similar manner to cis- and trans-7-{4-[(3R)-3-(dimethylamino)tetrahydro-1H-1-pyrrolyl]cyclohexyl }-5-(4-phenoxyphenyl)-7H-pyrrolo[2,3-d]pyrimidin-4-amine trimaleate salt.

Examples 455 and 456 cis-7-{4-[(3S)-3-(Dimethylamino)tetrahydro-1H-1-pyrrolyl]cyclohexyl}-5-(4-phenoxyphenyl)-7H-pyrrolo[2,3-d]pyrimidin-4-amine Trimaleate Salt $^1$H NMR (d$_6$ DMSO, 400 MHz): δ H 8.20(1H, s), 7.42–7.48 (4H, m), 7.41(1H, s), 7.08–7.17(5H, m), 6.45(2H, bs), 6.15(6H, s), 4.67(1H, m), 3.08–3.79(6H, m), 2.76(6H, s), 1.91–2.23(6H, m), 1.74–1.77(4H, m); RP-HPLC (Delta Pak C18, 5 μm, 300 A, 15 cm; 5%–85% acetonitrile-0.1M ammonium acetate over 20 min, 1 mL/min) R$_t$ 13.89 min. MS: MH$^+$ 497.

trans-7-{4-1(3S)-3-(Dimethylamino)tetrahydro-1H-1-pyrrolyl]cyclohexyl}-5-(4-phenoxyphenyl)-7H-pyrrolo[2,3-d]pyrimidin-4-amine Trimaleate Salt $^1$H NMR (d$_6$ DMSO, 400 MHz): δ H 8.18(1H, s), 7.40–7.48 (5H, m), 7.08–7.19(5H, m), 6.34(2H, bs), 6.12 (6H, s), 4.62(1H, m), 3.24–3.91(6H, m), 2.66(6H, s), 2.18–2.21(3H, m), 1.94–2.03(5H, m), 1.55–1.58(2H, m); RP-HPLC (Delta Pak C18, 5 μm, 300 A, 15 cm;

5%–85% acetonitrile-0.1M ammonium acetate over 20 min, 1 mL/min) R$_t$ 14.07 min. MS: MH$^+$ 497.

Example 457 cis-(3R)-{4-[4-Amino-5-(4-phenoxyphenyl)-7H-pyrrolo[2,3-d]pyrimidin-7-yl]cyclohexyl}tetrahydro-1H-3-pyrrolol Dimaleate Salt A mixture of 4-[4-amino-5-(4-phenoxyphenyl)-7H-pyrrolo[2,3-d]pyrimidin-7-yl]cyclohexanone (1.00 g, 2.51 mmol) and (R)-(+)-3-pyrrolidinol (0.62 mL, 7.5 mmol) in 1,2-dichloroethane (50 mL) was stirred at ambient temperature under an atmosphere of nitrogen for 1.5 hours. Sodium triacetoxyborohydride (0.691 g, 3.26 mmol) was added and the mixture stirred at ambient temperature for 22 hours. Water (50 mL) and sodium bicarbonate (1.34 g, 16.1 mmol) were added and the mixture was stirred for 2 hours. The reaction mixture was transferred to a separatory funnel and the organic layer was separated, dried over magnesium sulfate, filtered, and the solvent removed under reduced pressure to yield a yellow-brown solid. The cis isomer was purified by flash chromatography on silica gel (1 L 5% MeOH in CH$_2$Cl$_2$, then 2 L 10% MeOH in CH$_2$Cl$_2$, 1 L 20% MeOH in CH$_2$Cl$_2$, and 1 L 40% MeOH in CH$_2$Cl$_2$) to yield cis-(3R)-1-{4-[4-amino-5-(4-phenoxyphenyl)-7H-pyrrolo

[2,3-d]pyrimidin-7-yl]cyclohexyl}tetrahydro-1H-3-pyrrolol as a pale yellow oil (0.529 g, 1.12 mmol). The cis-(3R)-1-{4-[4-Amino-5-(4-phenoxyphenyl)-7H-pyrrolo[2,3-d]pyrimidin-7-yl]cyclohexyl}tetrahydro-1H-3-pyrrolol (0.464 g, 0.988 mmol) was dissolved in warm ethanol (5 mL) and added to a solution of maleic acid (0.344 g, 2.96 mmol) in ethanol (5 mL). The mixture was cooled to ambient temperature then the solid was collected by filtration and dried to give cis-(3R)-1-{4-[4-amino-5-(4-phenoxyphenyl)-7H-pyrrolo[2,3-d]pyrimidin-7-yl]cyclohexyl}tetrahydro-1H-3-pyrrolol dimaleate salt (0.549 g) as a pale yellow solid: $^1$H NMR ($d_6$ DMSO, 400 MHz): δ H 8.22(1H, s), 7.41–7.50 (5H, m), 7.08–7.19(5H, m), 6.49(2H, bs), 6.13(4H, s), 4.85(1H, bs), 4.49(1H, bs), 3.37–3.68(5H, m), 1.92–2.18 (11H, m); HPLC: (Hypersil HS C18, 5 μm, 254 nm, 250×4.6 mm; 25–100% acetonitrile-0.1N ammonium acetate over 10 min, 1 ml/min) $t_r$=7.167 min.

Examples 458 trans-((2S)-1-{4-[4-Amino-5-(4-phenoxyphenyl)-7H-pyrrolo[2,3-d]pyrimidin-7-yl]cyclohexyl}tetrahydro-1H-2-pyrrolyl)methanol Dimaleate Salt A mixture of 4-[4-amino-5-(4-phenoxyphenyl)-7H-pyrrolo[2,3-d]pyrimidin-7-yl]cyclohexanone (0.200 g, 0.502 mmol) and (S)-(+)-2-pyrrolidinemethanol (0.152 g, 1.51 mmol) in ethanol (2 mL) was stirred at ambient temperature under an atmosphere of nitrogen for 20 hours. The reaction mixture was filtered and concentrated to afford a yellow oil. The crude product was combined with sodium borohydride (0.019 g, 0.502 mmol) in methanol (10 mL) and stirred at ambient temperature under an atmosphere of nitrogen for 2 hours. Water (10 mL) was added, the organic portion was separated, and the aqueous portion was extracted with ethyl acetate (25 mL). The organic portions were combined, dried over magnesium sulfate, filtered, and concentrated to afford an oily yellow solid. Purification by flash chromatography on silica gel afforded trans-((2S)-1-{4-[4-amino-5-(4-phenoxyphenyl)-7H-pyrrolo[2,3-d]pyrimidin-7-25 yl]cyclohexyl}tetrahydro-1H-2-pyrrolyl) methanol (0.064 g, 0.132 mmol) as a white solid. The trans-((2S)-1-{4-[4-amino-5-(4-phenoxyphenyl)-7H-pyrrolo[2,3-d]pyrimidin-7-yl]cyclohexyl}tetrahydro-1H-2-pyrrolyl)methanol (0.064 g, 0.132 mmol) was dissolved in warm ethyl acetate (2 mL) and a solution of maleic acid (0.031 g, 0.265 mmol) in ethanol (2 mL) was added. The mixture was cooled to ambient temperature and the solid was collected by filtration and dried to give trans-((2S)-1-{4-[4-amino-5-(4-phenoxyphenyl)-7H-pyrrolo[2,3-d]pyrimidin-7-yl]cyclohexyl}tetrahydro-1H-2-pyrrolyl)methanol dimaleate salt (0.062 g) as a pale yellow solid: $^1$H NMR ($d_6$ DMSO, 400 MHz): δ H 8.18 (1H, s), 7.40–7.47 (5H, m), 7.08–7.19(5H, m), 6.32(2H, bs), 6.13(4H, s), 5.50(1H, s), 4.65(1H, m), 3.34–3.81(6H, m), 1.77–2.09 (12H, m); RP-HPLC (Delta Pak C18, 5 μm, 300 A, 15 cm; 5%–85% acetonitrile-0.1M ammonium acetate over 20 min, 1 mL/min) $R_t$ 13.78 min. MS: MH$^{30}$ 484.

The following compound was made in a similar manner to trans-((2S)-1-{4-[4-amino-5-(4-phenoxyphenyl)-7H-pyrrolo[2,3-d]pyrimidin-7-yl]cyclohexyl}tetrahydro-1H-2-pyrrolyl)methanol dimaleate salt:

Examples 459 trans-((2R)-1-{4-[4-Amino-5-(4-phenoxyphenyl)-7H-pyrrolo[2,3-d]pyrimidin-7-yl]cyclohexyl}tetrahydro-1H-2-pyrrolyl)methanol Dimaleate Salt $^1$H NMR ($d_6$ DMSO, 400 MHz): δ H 8.18(1H, s), 7.40–7.47 (5H, m), 7.08–7.19(5H, m), 6.31 (2H, bs), 6.13 (4H, s), 5.50(1H, s), 4.65 (1H, m), 3.33–3.81(6H, m), 1.78–2.06 (12H, m); RP-HPLC (Delta Pak C18, 5 μm, 300 A, 15 cm; 5%–85% acetonitrile-0.1M ammonium acetate over 20 min, 1 mL/min) $R_t$ 13.83 min. MS: MH$^+$ 484.

cis-7-(1-Oxaspiro[2.5]oct-6-yl)-5-(4-phenoxyphenyl)-7H-pyrrolo[2,3-d]pyrimidin-4-amine (Intermediate 1)

In a heat dried flask, trimethylsulfoxonium iodide (1.33 g, 6 mmol) in dimethyl-sulfoxide (10 mL) was reacted with 60% sodium hydride dispersion in mineral oil (0.22 g, 5.5 mmol). The mixture was stirred at room temperature for 30 minutes and then cooled to 10° C. A solution of 4-[4-amino-5-(4-phenoxyphenyl)-7H-pyrrolo[2,3-d]pyrimidin-7-yl]-1-cyclohexanone (2 g, 5 mmol) in dimethylsulfoxide (10 mL) was added, and the mixture was stirred at ambient temperature for 2 hours. Water (10 mL) was added and the mixture was extracted with ethyl acetate (2×20 mL). The organic phase was separated and dried over magnesium sulfate. The solvent was removed in vacuo to give cis-7-(1-oxaspiro[2.5] oct-6-yl)-5-(4-phenoxyphenyl)-7H-pyrrolo[2,3-d]pyrimidin-4-amine as a white solid (1.98 g, 4.8 mmol).

$^1$H NMR (DMSO-$d_6$, 400 MHz) δ 8.15(s, 1H), 7.49 (d, 2H), 7.48(s, 1H), 7.42(t, 2H), 7.16(t, 1H), 7.09(d, 2H), 6.11(bs, 2H), 4.72–4.78(m, 1H), 2.70(s, 2H), 2.47–2.52(m, 2H), 2.03–2.26(m, 4H), 1.26–1.35(m, 2H); MS: M$^+$ 413.

trans-7-(1-Oxaspiro[2.5]oct-6-yl)-5-(4-phenoxyphenyl)-7H-pyrrolo[2,3-d]pyrimidin-4-amine (Intermediate 2)

To a mixture of 4-[4-amino-5-(4-phenoxyphenyl)-7H-pyrrolo[2,3-d]pyrimidin-7-yl]-1-cyclohexanone (2 g, 5 mmol) in tetrahydrofuran (17.5 mL) were added trimethylsulfonium iodide (1.53 g, 7.5 mmol) in dimethyl sulfoxide (25 mL) and potassium-t-butoxide (7.5 mL, 7.5 mmol, 1 M in tetrahydrofuran) under an atmosphere of nitrogen at −5° C. The mixture was stirred at −5° C. for 1 hour. The mixture was poured into ice water (50 mL). The water phase was extracted with ethyl acetate (3×30 mL). The combined organic extracts were washed with saturated ammonium chloride solution (2×30 mL), water (1×30 mL), and brine (2×30 mL) and dried over sodium sulfate. The solvent was removed under reduced pressure to yield 7-(1-oxaspiro[2.5] oct-6-yl)-5-(4-phenoxyphenyl)-7H-pyrrolo[2,3-d] pyrimidin-4-amine (1.9 g, 4.6 mmol, 2:1-mixture of trans and cis). The suspension was suspended in dichloromethane (3 mL). The solid was filtered and was washed with dichloromethane (1 mL) to yield 7-(1-oxaspiro[2.5]oct-6-yl)-5-(4-phenoxyphenyl)-7H-pyrrolo[2,3-d]pyrimidin-4-amine (0.994 g, 2.4 mmol, 4:1-mixture of trans and cis).

$^1$H NMR for trans isomer (DMSO-$d_6$, 400 MHz) δ 8.15 (s, 1H), 7.45(m, 5H), 7.16(t, 1H), 7.09(m, 4H), 6.1 I(br, 2H), 4.73 (br, 1H), 2.65(s, 2H), 2.16(br, 6H), 1.38(br, 2H); RP-HPLC (Hypersil C18, 5 μm, 250×4.6 mm; 25%–100% over 23 min with 0.1 M ammonium acetate, 1 mL/min) $R_t$ 10.53 min. MS: MH$^+$ 413.

Example 460 cis-4-[4-Amino-5-(4-phenoxyphenyl)-7H-pyrrolo[2,3-d]pyrimidin-7-yl]-1-hydroxycyclohexylmethyl Cyanide A mixture of cis-7-(1-oxaspiro[2.5]oct-6-yl)-5-(4-phenoxyphenyl)-7H-pyrrolo[2,3-d]pyrimidin-4-amine (0.750 g, 1.8 mmol), lithium perchlorate (0.290 g, 2.7 mmol) and potassium cyanide (0.177 g, 2.7 mmol) in acetonitrile (100 mL) was heated at 80° C. for three days. Cooled to ambient temperature, diluted with water (50 mL) and extracted with diethyl ether (3×50 mL). The combined organic phases were dried over magnesium sulfate. The solvent was removed in vacuo and the crude product was purified by flash column chromatography on silica using dichloromethane/methanol (95:5). The solvent was removed in vacuo to give cis-4-[4-amino-5-(4-phenoxyphenyl)-7H-pyrrolo[2,3-d]pyrimidin-7-yl]-1-hydroxycyclohexylmethyl cyanide as a white solid (0.380 g, 0.9 mmol, 50% yield):

$^1$H NMR (DMSO-d$_6$, 400 MHz) δ 8.14(s, 1H), 7.49 (d, 2H), 7.42(t, 2H), 7.37(s, 1H), 7.16(t, 1H), 7.09(d, 2H), 6.11(bs, 2H), 4.51–4.62(m, 1H), 2.66(s, 2H), 2.10–2.29(m, 2H), 1.72–1.87(m, 4H), 1.60–1.72(m, 2H); RP-HPLC (Delta Pak C18, 5 μm, 300 A, 15 cm; 5%–85% acetonitrile-0.1M ammonium acetate over 20 min, 1 mL/min) R$_t$ 15.90 min.; MS: M$^+$ 440.

Example 461 trans-4-[4-Amino-5-(4-phenoxyphenyl)-7H-pyrrolo [2,3-d]pyrimidin-7-yl]-1-hydroxycyclohexylmethyl Cyanide Ring opening of trans-7-(1-oxaspiro[2.5]oct-6-yl)-5-(4-phenoxyphenyl)-7H-pyrrolo[2,3-d]pyrimidin-4-amine (1 g, 2.4 mmol) with cyanide as described above led to trans-4-[4-amino-5-(4-phenoxyphenyl)-7H-pyrrolo[2,3-d]pyrimidin-7-yl]-1-hydroxycyclohexyl-methyl cyanide as a white solid (0.435 g, 1.03 mmol, 43% yield):

$^1$H NMR (DMSO-d$_6$, 400 MHz) δ 8.14(s, 1H), 7.63 (s, 1H), 7.47(d, 2H), 7.43(t, 2H), 7.15–7.07(m, 5H), 6.20(br, 2H), 4.65 (m, 1H), 2.98(s, 2H), 1.92–1.86(m, 6H), 1.80–1.65(m, 2H), RP-HPLC (Delta Pak C18, 5 μm, 300 A, 15 cm; 5%–85% acetonitrile-0.1M ammonium acetate over 20 min, 1 mL/min) R$_t$ 15.88. MS: M$^+$ 440.

Example 462 cis-1-(2-Aminoethyl)-4-[4-amino-5-(4-phenoxyphenyl)-7H-pyrrolo[2,3-d]pyrimidin-7-yl]-1-cyclohexanol To cis-4-[4-amino-5-(4-phenoxyphenyl)-7H-pyrrolo[2,3-d]pyrimidin-7-yl]-1-hydroxy-cyclohexylmethyl cyanide (0.340 g, 0.77 mmol) in methanol (30 ml) and ammonium hydroxide (2 mL) was added Raney nickel (0.5 mL). The mixture was stirred 18 hours under hydrogen (1 atm). The reaction mixture was filtered through celite and the solvent was removed in vacuo to give cis-1-(2-aminoethyl)-4-[4-amino-5-(4-phenoxyphenyl)-7H-pyrrolo[2,3-d]pyrimidin-7-yl]-1-cyclohexanol as a white solid (0.230 g, 0.52 mmol):

$^1$H NMR (DMSO-d$_6$, 400 MHz) δ 8.13(s, 1H), 7.48 (d, 2H), 7.42(t, 2H), 7.36(s, 1H), 7.16(t, 1H), 7.09(d, 2H), 6.09(bs, 2H), 4.50–4.63(m, 1H), 2.77–2.87(m, 2H), 2.09–2.24(m, 2H), 166–1.78(m, 4H), 1.42–1.62(m, 2H); RP-HPLC (Delta Pak C18, 5 μm, 300 A, 15 cm; 5%–85% acetonitrile-0.1 M ammonium acetate over 20 min, 1 mL/min) R$_t$ 13.07 min.; MS: M$^+$ 444.

Example 463 trans-1-(2-Aminoethyl)-4-[4-amino-5-(4-phenoxyphenyl)-7H-pyrrolo[2,3-d]pyrimidin-7-yl]-1-cyclohexanol Reduction of trans-4-[4-amino-5-(4-phenoxyphenyl)-7H-pyrrolo[2,3-d]pyrimidin-7-yl]1-hydroxy-cyclohexylmethyl cyanide (0.448 g, 1.0 mmol) as described above for the cis-isomer yielded trans-1-(2-aminoethyl)-4-[4-amino-5-(4-phenoxyphenyl)-7H-pyrrolo[2,3-d]pyrimidin-7-yl]-1-cyclohexanol (0.015 g, 0.034 mmol)

$^1$H NMR (Chloroform-d, 400 MHz) δ 8.32(s, 1H), 7.44 (m, 4H), 7.15(t, 1H), 7.09(m, 4H), 6.99(s, 1H), 5.13(br, 2H), 4.77 (br, 1H), 3.09(br, 2H), 2.10(br, 2H), 2.00(br, 2H), 1.84(br, 6H). RP-HPLC (Hypersil C18, 5 μm, 250×4.6 mm; 25%–100% over 10 min with 0.1 M ammonium acetate, 1 mL/min) R$_t$ 6.75 min. MS: MH$^+$ 444.

Example 464 cis-4-[4-Amino-5-(4-phenoxyphenyl)-7H-pyrrolo[2, 3-d]pyrimidin-7-yl]-1-2-[(1H-2-imidazolylmethyl) amino]ethyl-1-cyclohexanol Diacetate A mixture of cis-1-(2-aminoethyl)-4-[4-amino-5-(4-phenoxyphenyl)-7H-pyrrolo[2,3-d]pyrimidin-7-yl]-1-cyclohexanol (0.192 g, 0.43 mmol), 1H-2-imidazolecarbaldehyde (0.042 g, 0.43 mmol), sodium triacetoxyborohydride (0.119 g, 0.56 mmol) and acetic acid (0.052 g, 0.87 mmol) in 1,2-dichloroethane (25 ml) was heated at 40° C. for one hour, after which time additional sodium triacetoxyborohydride (0.119 g, 0.56 mmol) was added. The mixture was stirred at 40° C. for two days. The solvent was removed in vacuo and the residue was partitioned between saturated aqueous sodium bicarbonate (50 mL) and dichloromethane (25 mL). The layers were separated, and the aqueous layer was extracted with dichloromethane (3×25 mL). The combined organic layers were dried over magnesium sulfate and the solvent was removed in vacuo. The residue was purified by preparative RP-HPLC (Rainin C18, 8 μm, 300 A, 25 cm; 30% isocratic for five minutes, then 30%–60% acetonitrile-0.1 M ammonium acetate over 30 min, 21 ml/min). The solvent was removed and the residue was subjected to a second purification by preparative RP-HPLC using identical conditions. The organics were removed and the aqueous mixture was lyopholyzed to give cis-4-[4-amino-5-(4-phenoxyphenyl)-7H-pyrrolo[2, 3-d]pyrimidin-7-yl]-1-2-[(1H-2-imidazolylmethyl)amino] ethyl-1-cyclohexanol diacetate as a white solid (0.020 g, 0.03 mmol):

$^1$H NMR (DMSO-d$_6$, 400 MHz) δ 8.12(s, 1H), 7.48 (d, 2H), 7.42(t, 2H), 7.34(s, 1H), 7.16(t, 1H), 7.08–1.10(m, 4H), 6.90 (bs, 2H), 6.09(bs, 1H), 4.52–4.58(m, 1H), 3.69(s, 2H), 2.67–2.70(m, 2H), 2.11–2.17 (m, 2H), 1.90(s, 6H), 1.69–1.71(m, 4H), 1.53–1.62(m, 2H), 1.42–1.51(m, 2H); RP-HPLC (Delta Pak C18, 5 μm, 300 A, 15 cm; 5%–85% acetonitrile-0.1 M ammonium acetate over 20 min, 1 mL/min) R$_t$ 13.55 min.; MS: M$^+$ 524.

Example 465 cis-2-{4-[4-Amino-5-(4-phenoxyphenyl)-7H-pyrrolo [2,3-d]pyrimidin-7-yl]-1-hydroxycyclohexyl}-acetic Acid A mixture of cis-4-[4-amino-5-(4-phenoxyphenyl)-7H-pyrrolo[2,3-d]pyrimidin-7-yl]-1-hydroxycyclohexylmethyl cyanide (0.172 g, 0.39 mmol) in dioxane (2 ml) was reacted with 2 M aqueous sodium hydroxide (2 mL) and 30% hydrogen peroxide (3 drops) at reflux for ten days. The mixture was cooled to ambient temperature and adjusted to pH7 with 5% aqueous citric acid. The solvent was removed in vacuo and the residue was purified by preparative RP-LC/ MS (Gilson-Micromass C18, 5 μm, 130 A, 21 cm, 0%–100% acetonitrile-0.1 M ammonium acetate over 9 min, 25 mL/min). The solvent was removed and the residue was subjected to a second purification by preparative RP-HPLC (Rainin C18, 8 μm, 300 A, 25 cm; 35%–80% acetonitrile-0.1 M ammonium acetate over 20 min, 21 ml/min). The acetonitrile was removed in vacuo and the aqueous mixture was lyopholyzed to give to give cis-{2-4-[4-amino-5-(4-phenoxyphenyl)-7H-pyrrolo[2,3-d]pyrimidin-7-yl]-1-hydroxycyclohexylacetic acid as a white solid (0.008 g, 0.02 mmol):

$^1$H NMR (DMSO-$d_6$, 400 MHz) δ 11.94(b, 1H), 8.13 (s, 1H), 7.48(d, 2H), 7.41(t, 2H), 7.35(s, 1H), 7.16(t, 1H), 7.08–7.10(m, 4H), 6.09(b, 2H), 4.51–4.57(m, 2H), 2.39(s, 2H), 2.10–2.28(m, 2H), 1.79–1.90 (m, 2H), 1.62–1.78(m, 4H); RP-HPLC (Delta Pak C18, 5 μm, 300 A, 15 cm; 5%–85% acetonitrile-0.1 M ammonium acetate over 20 min, 1 mL/min) $R_t$ 14.25 min.; MS: M$^+$ 459.

Example 466 cis-2-{4-[4-Amino-5-(4-phenoxyphenyl)-7H-pyrrolo [2,3-d]pyrimidin-7-yl]-1-hydroxycyclohexyl}-acetamide A mixture of cis-4-[4-amino-5-(4-phenoxyphenyl)-7H-pyrrolo[2,3-d]pyrimidin-7-yl]-1-hydroxycyclohexylmethyl cyanide (0.150 g, 0.34 mmol) and potassium carbonate (0.200 g, 1.45 mmol) in dimethylsulfoxide (3 ml) was stirred rapidly and 30% hydrogen peroxide (0.5 mL) was added dropwise, keeping the temperature at 20° C. The mixture was stirred for seven hours at ambient temperature. Water (9 mL) was added, and the precipitate which formed was filtered, washing with water. The precipitate was purified by preparative RP-HPLC (Rainin C18, 8 μm, 300 A, 25 cm; 30% isocratic for five minutes, then 30%–60% acetonitrile-0.1M ammonium acetate over 30 min, 21 ml/min). The acetonitrile was removed in vacuo and the aqueous mixture was lyopholyzed to give cis-2-{4-[4-amino-5-(4-phenoxyphenyl)-7H-pyrrolo[2,3-d]pyrimidin-7-yl]-1-hydroxy-cyclohexyl}-acetamide as a white solid (0.040 g, 0.09 mmol):

$^1$H NMR (DMSO-$d_6$, 400 MHz) δ 8.13(s, 1H), 7.48 (d, 2H), 7.42(t, 2H), 7.36(s, 1H), 7.16(t, 1H), 7.05–7.12(m, 4H), 6.09 (b, 2H), 4.98(s, 1H) 4.51–4.59(m, 1H), 2.24(s,2H), 2.13–2.23(m, 2H), 1.91(s, 1H), 1.72–1.77(m, 4H), 1.57–1.65(m, 2H); RP-HPLC (Delta Pak C18, 5 μm, 300 A, 15 cm; 5%–85% acetonitrile-0.1M ammonium acetate over 20 min, 1 mL/min) $R_t$ 14.34 min.; MS: M$^+$ 458.

Example 467 cis-4-[4-Amino-5-(4-phenoxyphenyl)-7H-pyrrolo[2, 3-d]pyrimidin-7-yl]-1-(hydroxy-methyl)-1-cyclohexanol A mixture of cis-7-(1-oxaspiro[2.5]oct-6-yl)-5-(4-phenoxyphenyl)-7H-pyrrolo[2,3-d]pyrimidin-4-amine (0.100 g, 0.24 mol) in 1,2-dimethoxyethane (3 mL) was reacted with 2.5 M aqueous potassium hydroxide (3 mL). The mixture was stirred at reflux for eighteen hours. The mixture was cooled to room temperature and water (10 mL) was added. The precipitate which formed was filtered, washing with water (20 mL). The precipitate was purified by preparative RP-HPLC (Rainin C18, 8 μm, 300 A, 25 cm; 30% isocratic for five minutes, then 30%–60% acetonitrile-0.1M ammonium acetate over 30 min, 21 ml/min). The acetonitrile was removed in vacuo and the aqueous mixture was lyopholyzed to give to give cis-4-[4-amino-5-(4-phenoxyphenyl)-7H-pyrrolo[2,3-d]pyrimidin-7-yl]-1-(hydroxymethyl)-1-cyclohexanol as a white solid (0.012 g, 0.03 mol):

$^1$H NMR (DMSO-$d_6$, 400 MHz) δ 8.13(s, 1H), 7.49 (d, 2H), 7.42(t, 2H), 7.36(s, 1H), 7.16(t, 1H), 7.05–7.12(m, 4H), 6.08(b, 1H), 4.48–4.61(m, 2H), 4.12(s, 1H), 3.22(d, 2H), 2.10–2.25(m, 2H), 1.72–1.76 (m, 2H), 1.55–1.70(m, 4H); RP-HPLC (Delta Pak C18, 5 μm, 300 A, 15 cm; 5%–85% acetonitrile-0.1 M ammonium acetate over 20 min, 1 mL/min) $R_t$ 14.31 min.; MS: M$^+$ 431.

General Procedure for Epoxide Opening by Amines

A mixture of 7-(1-oxaspiro[2.5]oct-6-yl)-5-(4-phenoxyphenyl)-7H-pyrrolo[2,3-d]pyrimidin-4-amine (0.075 g, 0.18 mmol) and amine (0.54 mmol) in 25% dimethylformamide/iso-propanol (2.5 mL) was heated at 80° C. for 8 hours. The mixture was allowed to cool to ambient temperature and the solvent was removed under reduced pressure. The residue was purified by preparative HPLC-MS (Hypersil 100×21.2 mm; 5μ BDS $C_{18}$, 25 mL/min; 0–70% over 8 min; 0.05 M ammonium acetate/acetonitrile; Micromass Mass spec). The solvent of the collected fractions was removed under the reduced pressure. The residue was dissolved in $H_2O$ and lyophilized for 24 hours.

Compounds prepared from cis-7-(1-oxaspiro[2.5]oct-6-yl)-5-(4-phenoxyphenyl)-7H-pyrrolo[2,3-d]pyrimidin-4-amine and the corresponding amine:

Example 468 cis-1-(Aminomethyl)-4-[4-amino-5-(4-phenoxyphenyl)-7H-pyrrolo[2,3-d]pyrimidin-7-yl]-1-cyclohexanol $^1$H NMR (Chloroform-d, 400 MHz) δ 8.19(s, 1H), 7.34 (m, 4H), 7.10(t, 1H), 7.03(m, 5H), 5.74(br, 2H), 4.65(br, 1H), 2.85(s, 2H), 2.17(br, 2H), 1.93(br, 4H), 1.56(br, 2H). RP-HPLC (Delta Pak C18, 5 μm, 300 A, 15 cm; 5%–85% acetonitrile-0.1 M ammonium acetate over 20 min, 1 mL/min) $R_t$ 13.0 min. MS: MH$^+$ 430.

Example 469 cis-4-[4-Amino-5-(4-phenoxyphenyl)-7H-pyrrolo[2, 3-d]pyrimidin-7-yl]-1-[(dimethylamino)methyl]-1-cyclohexanol $^1$H NMR (Chloroform-d, 400 MHz) δ 8.32(s, 1H), 7.40 (m, 4H), 7.16(t, 1H), 7.10(m, 4H), 7.00(s, 1H), 5.30(br, 2H), 4.77 (br, 1H), 2.58(s, 2H), 2.41(s, 6H), 2.09(br, 2H), 1.93(br, 4H), 1.83(br, 2H). RP-HPLC (Hypersil C18, 5 μm, 250×4.6 mm; 25%–100% over 10 min with 0.1 M ammonium acetate, 1 mL/min) $R_t$ 7.28 min. MS: MH$^+$ 458.

Example 470 cis-2-[(4-[4-Amino-5-(4-phenoxyphenyl)-7H-pyrrolo[2,3-d]pyrimidin-7-yl]-1-hydroxycyclohexylmethyl)amino]-1,3-propanediol $^1$H NMR (Chloroform-d, 400 MHz) δ 8.27(s, 1H), 7.40 (m, 4H), 7.15(t, 1H), 7.10(m, 5H), 5.24(br, 2H), 4.65(br, 1H), 3.70(m, 4H), 2.75(m, 1H), 2.65(s, 2H), 2.20(m, 2H), 2.12(m, 4H), 1.55(m, 2H). RP-HPLC (Hypersil C18, 5 μm, 250×4.6 mm; 25%–100% over 10 min with 0.1 M ammonium acetate, 1 mL/min) $R_t$ 6.87 min. MS: MH$^+$ 504.

Example 471 cis-4-[4-Amino-5-(4-phenoxyphenyl)-7H-pyrrolo[2, 3-d]pyrimidin-7-yl]-1-1(2-morpholinoethyl)amino] methyl-1-cyclohexanol $^1$H NMR (Chloroform-d, 400 MHz) δ 8.31(s, 1H), 7.42 (m, 4H), 7.10(m, 6H), 5.11 (br, 2H), 4.70(br, 1H), 3.73(br, 4H), 2.85(m, 2H), 2.65(s, 2H), 2.54(m, 2H), 2.49(br, 4H), 2.21(br, 2H), 1.96(br, 2H), 1.85(br, 2H), 1.58(br, 2H). RP-HPLC (Delta Pak C18, 5 µm, 300 A, 15 cm; 5%–85% acetonitrile-0.1 M ammonium acetate over 20 min, 1 mL/min) $R_t$ 13.6 min. MS: MH$^+$ 543.

Compounds preprared from trans-7-(1-oxaspiro[2.5]oct-6-yl)-5-(4-phenoxyphenyl)-7H-pyrrolo[2,3-d]pyrimidin-4-amine.

Example 472 trans-1-(Aminomethyl)-4-[4-amino-5-(4-phenoxyphenyl)-7H-pyrrolo[2,3-d]pyrimidin-7-yl]-1-cyclohexanol Diacetate $^1$H NMR (Chloroform-d, 400 MHz) δ 8.19(s, 1H), 7.40 (m, 4H), 7.14(t, 1H), 7.07(m, 5H), 5.91(br, 2H), 4.70(br, 1H), 3.14(s, 2H), 2.00(br, 6H), 1.92(br, 2H). RP-HPLC (Delta Pak C18, 5 µm, 300 A, 15 cm; 5%–85% acetonitrile-0.1 M ammonium acetate over 20 min, 1 mL/min) $R_t$ 12.7 min. MS: MH$^-$ 430.

Example 473 trans-4-[4-Amino-5-(4-phenoxyphenyl)-7H-pyrrolo[2,3-d]pyrimidin-7-yl]-1-f(dimethylamino)methyl]-1-cyclohexanol $^1$H NMR (Chloroform-d, 400 MHz) δ 8.26(s, 1H), 7.40 (m, 4H), 7.15(t, 1H), 7.10(m, 5H), 5.31(br, 2H), 4.70(br, 1H), 3.11(s, 2H), 2.76(s, 6H), 2.10(br, 6H), 1.87(br, 2H). RP-HPLC (Delta Pak C18, 5 µm, 300 A, 15 cm; 5%–85% acetonitrile-0.1 M ammonium acetate over 20 min, 1 mL/min) $R_t$ 13.3 min. MS: MH$^+$ 458.

Example 474 trans-2-[(4-[4-Amino-5-(4-phenoxyphenyl)-7H1-pyrrolo[2,3-d]pyrimidin-7-yl]-1-hydroxycyclohexylmethyl)amino]-1,3-propanediol $^1$H NMR (Chloroform-d, 400 MHz) δ 8.17(s, 1H), 7.35 (m, 4H), 7.15(t, 1H), 7.06(m, 5H), 6.20(br, 2H), 4.70(br, 1H), 3.89(m, 4H), 3.34(s, 2H), 3.27(br, 1H), 2.10(br, 6H), 1.90(br, 2H). RP-HPLC (Delta Pak C18, 5 µm, 300 A, 15 cm; 5%–85% acetonitrile-0.1 M ammonium acetate over 20 min, 1 mL/min) $R_t$ 12.8 min. MS: MH$^+$ 504.

Example 475 trans-4-[4-Amino-5-(4-phenoxyphenyl)-7H-pyrrolo[2,3-d]pyrimidin-7-y-1-[(2-morpholinoethyl]amino]methyl-1-cyclohexanol $^1$H NMR (Chloroform-d, 400 MHz) δ 8.30(s, 1H), 7.42 (m, 4H), 7.10(m, 5H), 6.99(s, 1H), 5.46(br, 2H), 4.70(br, 1H), 3.71(br, 4H), 2.91(s, 2H), 2.86(m, 2H), 2.55(m, 2H), 2.44(br, 4H), 2.10(br, 2H), 1.90(br, 4H), 1.80(br, 2H). RP-HPLC (Delta Pak C18, 5 µm, 300 A, 15 cm; 5%–85% acetonitrile-0.1 M ammonium acetate over 20 min, 1 mL/min) $R_t$ 13.6 min. MS: MH$^-$ 543.

Compounds prepared from a mixture of cis-and trans-7-(1-oxaspiro[2.5]oct-6-yl)-5-(4-phenoxyphenyl)-7H-pyrrolo[2,3-d]pyrimidin-4-amine (ratio cis/trans 2:1) and the corresponding amine (RP-HPLC (Delta Pak C18, 5 µm, 300 A, 15 cm; 5%–85% acetonitrile-0.1 M ammonium acetate over 20 min, 1 mL/min)).

Example 476

4-[4-Amino-5-(4-phenoxyphenyl)-7H-pyrrolo[2,3-d]pyrimidin-7-yl]-1-[(2-hydroxyethyl)amino]methyl-1-cyclohexanol HPLC: Rt 12.9 min, 13.1 min; MS: M$^+$=474.

Example 477

4-[4-Amino-5-(4-phenoxyphenyl)-7H-pyrrolo[2,3-d]pyrimidin-7-yl-1l-1(3-hydroxypropyl)amino]methyl-1-cyclohexanol HPLC:Rt 13.1 min; MS: M$^+$=488.

Example 478

4-[4-Amino-5-(4-phenoxyphenyl)-7H-pyrrolo[2,3-d]pyrimidin-7-yl]-1-([3-(1H-1-imidazolyl)propyl]aminomethyl)-1-cyclohexanol HPLC: Rt 12.4 min, 12.8 min MS: M$^+$=538.

Example 479

4-[4-Amino-5-(4-phenoxyphenyl)-7H-pyrrolo[2,3-d]pyrimidin-7-yl]-1-(1H-1-imidazolylmethyl)-1-cyclohexanol HPLC: Rt 13.9 MS: M$^+$=481.

Example 480

4-[4-Amino-5-(4-phenoxyphenyl)-7H-pyrrolo[2,3-d]pyrimidin-7-yl]-1-([2-(2-hydroxyethoxy)ethyl]aminomethyl)-1-cyclohexanol HPLC:Rt 13.1 min MS: M$^+$=518.

Example 481

4-[4-Amino-5-(4-phenoxyphenyl)-7H-pyrrolo[2,3-d]pyrimidin-7-yl]-1-[di(2-hydroxyethyl)amino]methyl-1-cyclohexanol HPLC:Rt 13.1 min, 13.3 min MS: M$^+$=518.

Example 482

4-[4-Amino-5-(4-phenoxyphenyl)-7H-pyrrolo[2,3-d]pyrimidin-7-yl]-1-([2-(dimethylamino)ethyl]aminomethyl)-1-cyclohexanol HPLC: Rt 12.9 min, 13. min MS: M$^+$=501.

Example 483

4-[4-Amino-5-(4-phenoxyphenyl)-7H-pyrrolo[2,3-d]pyrimidin-7-yl]-1-[(4-methylpiperazino)methyl]-1-cyclohexanol HPLC: Rt 13.7 min, 14.0 min MS: M$^+$=513.

Example 484

4-[4-Amino-5-(4-phenoxyphenyl)-7H-pyrrolo[2,3-d]pyrimidin-7-yl]-1-(morpholinomethyl)-1-cyclohexanol HPLC: Rt 13.9 min, 14.0 min MS: M$^+$=500.

Example 485

1-(4-[4-Amino-5-(4-phenoxyphenyl)-7H-pyrrolo[2,3-d]pyrimidin-7-yl]-1-hydroxycyclohexylmethyl)-4-piperidinol HPLC: Rt 13.2 min, 13.4 min MS: M$^+$=514.

Example 486

4-[4-Amino-5-(4-phenoxyphenyl)-7H-pyrrolo[2,3-d]pyrimidin-7-yl]-1-[methyl(1-methyl-4-piperidyl)amino]methyl-1-cyclohexanol HPLC: Rt 12.5 min, 13.0 min MS: M$^+$=541.

Example 487

4-[4-Amino-5-(4-phenoxyphenyl)-7H-pyrrolo[2,3-d] pyrimidin-7-yl]-1-[(3-morpholinopropyl)amino] methyl-1-cyclohexanol HPLC: Rt 12.8 min, 13.1 min MS: M$^+$=557.

Example 488

4-[4-Amino-5-(4-phenoxyphenyl)-7H-pyrrolo[2,3-d] pyrimidin-7-yl]-1-[(2-piperidinoethyl)amino]methyl-1-cyclohexanol HPLC: Rt 13.4 min, 13.6 min MS: M$^+$=541.

Example 489 4-[4-amino-5-(4-phenoxyphenyl)-7H-pyrrolo[2,3-d]pyrimidin-7-yl]-1-([3-(diethylamino) propyl]aminomethyl)-1-cyclohexanol HPLC: Rt 12.5 min, 13.0 min MS: M$^+$=543.

Example 490

4-[4-Amino-5-(4-phenoxyphenyl)-7H-pyrrolo[2,3-d] pyrimidin-7-yl]-1-[(tetrahydro-2-furanylmethyl) amino]methyl-1-cyclohexanol HPLC: Rt 14.2 min MS: M$^+$=514.

Example 491 cis-8–14-Amino-5-(4-phenoxyphenyl)-7H-pyrrolo[2, 3-d]pyrimidin-7-yl]-1,3-diazaspiro[4.5]decane-2,4-dione A mixture of 4-[4-amino-5-(4-phenoxyphenyl)-7H-pyrrolo[2,3-d]pyrimidin-7-yl]-1-cyclohexanone (0.500 g, 0.00125 mol), ammonium carbonate (0.602 g, 6.27 mmol), and potassium cyanide (0.163 g, 2.51 mmol) in ethyl alcohol (5 mL) and water (5 mL) was stirred 18 hours at 60° C., after which time all material had gone into solution. The solvents were removed in vacuo and the residue was partitioned between ethyl acetate (80 mL) and water (20 mL). The phases were separated and the organic phase was washed with brine (20 mL). The organic phase was dried over magnesium sulfate, and the solvent was removed in vacuo. The crude material had a cis:trans ratio of 7:1. The product was purified by flash column chromatography on silica using dichloromethane/methanol (90:10). The solvent was removed in vacuo to give cis-8-[4-amino-5-(4-phenoxyphenyl)-7H-pyrrolo[2,3-d]pyrimidin-7-yl]-1,3-diazaspiro[4.5]decane-2,4-dione as a white solid (0.183 g, 0.39 mmol):

$^1$H NMR (DMSO-d$_6$, 400 MHz) δ 10.71(s, 1H), 8.64 (s, 1H), 8.15(s, 1H), 7.48(d, 2H), 7.42(t, 2H), 7.16(t, 1H), 7.12(d, 2H), 7.09(d, 2H), 6.13(b, 2H), 4.73–4.79(m, 1H), 2.00–2.10(m, 2H), 1.88–1.94(m, 4H), 1.71–1.74(m, 2H); RP-HPLC (Delta Pak C18, 5 μm, 300 A, 15 cm; 5%–85% acetonitrile-0.1M ammonium acetate over 20 min, 1 mL/min) R$_t$ 15.04 min. MS: M$^+$ 469.

Example 492 cis-8-[4-Amino-5-(4-phenoxyphenyl)-7H-pyrrolo[2, 3-d]pyrimidin-7-yl]-1,3-diazaspiro[4.5]decan-2-one A mixture of cis-8-[4-amino-5-(4-phenoxyphenyl)-7H-pyrrolo[2,3-d]pyrimidin-7-yl]-1,3-diazaspiro[4.5]decane-2,4-dione (0.350 g, 0.75 mmol) in tetrahydrofuran (20 mL) was stirred at room temperature and lithium aluminum hydride (0.057 g, 1.49 mmol) was added over a 10 minute time period at ambient temperature. Gas evolution was observed, and the mixture was stirred for 18 hours at 50° C. Additional lithium aluminum hydride (0.057 g, 1.49 mmol) was added and the mixture was heated at reflux for 24 hours. Water (10 mL) was added, followed by 15% aqueous sodium hydroxide (10 mL). The mixture was stirred 30 minutes and additional water (15 mL) was added. The mixture was filtered through a pad of Celite® 521. The filtrate was extracted with ethyl acetate (3×25 mL). The combined organic layers were dried over magnesium sulfate and the solvent was removed in vacuo. The residue was purified by by flash column chromatography on silica using dichloromethane/methanol (95:5) as an eluent. The solvent was removed in vacuo to give cis-8-[4-amino-5-(4-phenoxyphenyl)-7H-pyrrolo[2,3-d]pyrimidin-7-yl]-1,3-diazaspiro[4.5]decan-2-one as a white solid (0.045 g, 0.10 mmol):

$^1$H NMR (DMSO-d$_6$, 400 MHz) δ 8.12(s, 1H), 7.64(s, 1H), 7.47(d, 2H), 7.42(t, 2H), 7.14(t, 1H), 7.11(d, 2H), 7.09(d, 2H), 6.18(s, 1H), 6.08(b, 2H), 4.66–4.71(m, 1H), 3.09(s, 2H), 2.06–2.11(m, 2H), 1.76–1.81(m, 4H), 1.63–1.69(m, 2H); RP-HPLC (Delta Pak C18, 5 μm, 300 A, 15 cm; 5%–85% acetonitrile-0.1M ammonium acetate over 20 min, 1 mL/min) R$_t$ 15.11 min.; MS: M$^+$ 455.

Example 493 cis-4-[4-Amino-5-(4-phenoxyphenyl)-7H-pyrrolo[2, 3-d]pyrimidin-7-yl]-1-ammoniocyclohexylmethanol Acetate a) 1-Amino-4-[4-amino-5-(4-phenoxyphenyl)-7H-pyrrolo [2,3-d]pyrimidin-7-yl]-1-cyclohexanecarboxylic Acid A mixture of cis-and trans-8-[4-amino-5-(4-phenoxyphenyl)-7H-pyrrolo[2,3-d]pyrimidin-7-yl]-1,3-diazaspiro[4.5]decane-2,4-dione (0.600 g, 1.3 mmol, ratio cis/trans 7:1) in 2 M aqueous sodium hydroxide (25 mL) was heated at reflux for seven days. The mixture was cooled to room temperature and brought to pH 8 by drop-wise addition of concentrated hydrochloric acid. The precipitate which formed was collected by filtration and washed with water. The precipitate was triturated with methanol (50 mL) for 18 hours. The mixture was filtered, and the solvent was removed from the filtrate in vacuo to give 1-amino-4-[4-amino-5-(4-phenoxyphenyl)-7H-pyrrolo[2,3-d]pyrimidin-7-yl]-1-cyclohexanecarboxylic acid (0.194 g, 0.43 mol) which was used without further purification.:

$^1$H NMR (DMSO-d$_6$, 400 MHz) δ 8.12–8.14(m, 1H), 7.37–7.55(m, 5H), 7.05–7.11(m, 5H), 6.08(b, 2H), 4.47–4.53(m, 1H), 4.10(b, 3H), 1.35–1.2.22(m, 8H); RP-HPLC (Hypercil C18, 5 μm, 100 A, 15 cm; 5%–100% acetonitrile-0.1M ammonium acetate over 15 min, 1 mL/min) R$_t$ 10.12 min.; MS: M$^+$ 444.

b.) Methyl 1-Amino-4-[4-amino-5-(4-phenoxyphenyl)-7H-pyrrolo[2,3-d]pyrimidin-7-yl]-1-cyclohexanecarboxylate A mixture of cis-and trans-1-amino-4-[4-amino-5-(4-phenoxyphenyl)-7H-pyrrolo[2,3-d]pyrimidin-7-yl]-1-cyclohexanecarboxylic acid (0.696 g, 1.6 mmol, ratio cis/trans 7:1) was suspended in methanol (50 mL). The mixture was cooled to 0° C. and thionyl chloride (0.211 g, 0.1.77 mmol) was added dropwise. After the addition was complete, the mixture was heated at reflux for three days, with addition of an additional equivalent of thionyl chloride each day. The solvent was removed in vacuo to give crude methyl 1-amino-4-[4-amino-5-(4-phenoxyphenyl)-7H-pyrrolo[2,3-d]pyrimidin-7-yl]-1-cyclohexanecarboxylate (1.171 g) which was carried forward without further purification.:

$^1$H NMR (DMSO-d$_6$, 400 MHz) δ 9.08(b, 2H), 8.53(s, 1H), 8.30(s, 1H), 7.51(d, 2H), 7.43(t, 2H), 7.18(t, 1H), 7.10–7.15 (m, 4H), 4.82–4.98(m, 1H), 3.17(s, 3H), 2.05–2.28(m, 4H), 1.86–1.98(m, 2H); RP-HPLC (Perkin-Elmer Pecosphere C18, 3 μm, 100 A, 33×4.6 mm; 0%–100% acetonitrile-0.1 M ammonium acetate; 3–3.5 mL/min over 4.5 min, then 100% acetonitrile at 3 mL/min over 0.5 min) R$_t$ 2.81 min.; MS:M$^+$ 458.

c.)

cis-4-[4-Amino-5-(4-phenoxyphenyl)-7H-pyrrolo[2,3-d]pyrimidin-7-yl]-1-ammoniocyclohexylmethanol Acetate A crude mixture of cis-and trans-ethyl 1-amino-4-[4-amino-5-(4-phenoxyphenyl)-7H-pyrrolo[2,3-d]pyrimidin-7-yl]-1-cyclohexanecarboxylate (1.17 g,) in tetrahydrofuran (75 mL) was stirred at room temperature and lithium aluminum hydride (0.18 g, 4.7 mmol) was added over a 10 minute time period at ambient temperature. Gas evolution was observed, and the mixture was stirred for 18 hours at 40° C. Water (5 mL) was added, followed by 15% aqueous sodium hydroxide (15 mL) and additional water (15 mL). The mixture was filtered through a pad of Celite® 521. The filtrate was extracted with ethyl acetate (3×25 mL). The combined organic layers were dried over magnesium sulfate and the solvent was removed in vacuo. The residue was purified by preparative RP-HPLC (Rainin C18, 8 μm, 300 A, 25 cm; 35%–80% acetonitrile-0.1 M ammonium acetate over 10 min, 21 ml/min). The acetonitrile was removed in vacuo and the aqueous mixture was lyopholyzed to give cis-4-[4-amino-5-(4-phenoxyphenyl)-7H-pyrrolo[2,3-d]pyrimidin-7-yl]-1-ammoniocyclohexylmethanol acetate as a white solid (0.577 g, 1.16 mmol):

$^1$H NMR (DMSO-d$_6$ 400 MHz) δ 8.13(s, 1H), 7.55 (s, 1H), 7.48(d, 2H), 7.42(t, 2H), 7.14(t, 1H), 7.11(d, 2H), 7.09(d, 2H), 6.08(b, 1H), 4.56–4.65(m, 1H), 3.29 (s, 2H), 2.13–2.26(m, 2H), 1.80(s, 3H), 1.50–1.79(m, 8H); RP-HPLC (Delta Pak C18, 5 μm, 300 A, 15 cm; 5%–85% acetonitrile-0.1 M ammonium acetate over 20 min, 1 mL/min) R$_t$ 12.92 min.; MS: M$^+$ 430.

Example 494 and 495 cis- and trans-7-[4-Amino-4-(ammoniomethyl)cyclohexyl]-5-(4-phenoxyphenyl)-7H-pyrrolo[2,3-d]pyrimidin-4-amine Acetate a.) cis- and trans-1-Amino-4-[4-amino-5-(4-phenoxyphenyl)-7H-pyrrolo[2,3-d]pyrimidin-7-yl]-1-cyclohexanecarbonitrile.

A mixture of 4-[4-amino-5-(4-phenoxyphenyl)-7H-pyrrolo[2,3-d]pyrimidin-7-yl]-1-cyclohexanone (3.24 g, 8.1 mmol), potassium cyanide (1.06 g, 0.0162 mol), and ammonium chloride (0.869 g, 16.2 mmol) in ammonium hydroxide (32 ml) and ethyl alcohol (26 mL) was heated at 50° C. for eighteen hours. Water (150 mL) was added and the mixture was extracted with dichloromethane (3×60 mL). The combined organic layers were dried over magnesium sulfate and the solvent was removed in vacuo to give a mixture of cis and trans-1-amino-4-[4-amino-5-(4-phenoxyphenyl)-7H-pyrrolo[2,3-d]pyrimidin-7-yl]-1-cyclohexanecarbonitrile as an amorphous white solid (3.17 g, 7.5 mmol):

$^1$H NMR (DMSO-d$_6$, 400 MHz) δ 8.14(s, 0.7H), 8.13(s, 0.3H), 7.45–7.51(m, 2H), 7.38–7.44(m, 3H), 7.13–7.18(m, 1H), 7.06–7.12(m, 4H), 6.11(b, 1H), 4.60–4.68(m, 1H), 2.19–2.28(m, 2H), 1.97–2.10(m, 4H), 1.72–1.76(m, 2H); RP-HPLC (Delta Pak C18, 5 μm, 300 A, 15 cm; 5%–85% acetonitrile-0.1M ammonium acetate over 20 min, 1 mL/min) R$_t$ 15.98, 16.38 min.; MS: M$^+$ 425.

b.)

cis-7-14-Amino-4-(ammoniomethyl)cyclohexyl]-5-(4-phenoxyphenyl)-7H-pyrrolo[2,3-d]pyrimidin-4-amine Acetate A mixture of cis and trans-1-amino-4-[4-amino-5-(4-phenoxyphenyl)-7H-pyrrolo[2,3-d]pyrimidin-7-yl]-1-cyclohexanecarbonitrile (1.00 g, 2.4 mmol) in tetrahydrofuran (75 mL) was stirred at room temperature and lithium aluminum hydride (0.16 g, 4.2 mmol) was added over a 10 minute time period at ambient temperature. Gas evolution was observed, and the mixture was stirred for 18 hours. Water (5 mL) was added, followed by 15% aqueous sodium hydroxide (15 mL) and additional water (15 mL). The mixture was filtered through a pad of Celite® 521. The filtrate was extracted with ethyl acetate (3×15 mL). The combined organic layers were dried over magnesium sulfate and the solvent was removed in vacuo. The isomers were separated by preparative RP-HPLC (Rainin C18, 8 μm, 300 A, 25 cm; 30% isocratic for five minutes, then 30%–60% acetonitrile-0.1M ammonium acetate over 30 min, 21 ml/min). The acetonitrile was removed from the less polar fraction and this fraction was lyopholyzed to give cis-7-[4-amino-4-(ammoniomethyl)cyclohexyl]-5-(4-phenoxyphenyl)-7H-pyrrolo[2,3-d]pyrimidin-4-amine acetate as a white solid (0.137 g, 0.28 mmol):

$^1$H NMR (DMSO-d$_6$, 400 MHz) δ 8.13(s, 1H), 7.48 (d, 2H), 7.41(t, 2H), 7.41(s, 1H), 7.16(t, 1H), 7.10(d, 2H), 7.08(d, 2H), 6.08(b, 1H), 4.52–4.58(m, 1H), 2.71–2.79(m, 1H), 1.80–1.95(m, 6H), 1.30–1.36 (m, 2H); RP-HPLC (Delta Pak C18, 5 μm, 300 A, 15 cm; 5%–85% acetonitrile-0.1 M ammonium acetate over 20 min, 1 mL/min) R$_t$ 13.31 min.; MS: M$^+$ 429.

c.) trans-7-[4-Amino-4-(ammoniomethyl)cyclohexyl]-5-(4-phenoxyphenyl)-7H-pyrrolo[2,3-d]pyrimidin-4-amine Acetate The solvents were removed in vacuo from the more polar fraction from the above procedure. The residue was subjected to a second purification by preparative RP-HPLC (Rainin C18, 8 μm, 300 A, 25 cm; 20%–60% acetonitrile-0.1M ammonium acetate over 30 min, 21 ml/min). Acetonitrile was removed in vacuo and the aqueous solution was lyopholyzed to give trans-7-[4-amino-4-(ammoniomethyl)cyclohexyl]-5-(4-phenoxyphenyl)-7H-pyrrolo[2,3-d]pyrimidin-4-amine acetate as a white solid (0.037 g, 0.00008 mol):

$^1$H NMR (DMSO-d$_6$, 400 MHz) δ 8.13(s, 1H), 7.45–7.54 (m, 3H), 7.42(t, 2H), 7.16 (t, 1H), 7.06–7.13(m, 4H), 6.09(b, 1H), 4.52–4.60 (m, 1H), 1.91–2.07(m, 2H), 1.86(s, 3H), 1.71–1.84(m, 4H), 1.40–1.53 (m, 2H); RP-HPLC (Delta Pak C18, 5 μm, 300 A, 15 cm; 5%–85% acetonitrile-0.1 M ammonium acetate over 20 min, 1 mL/min) R$_t$, 12.18 min.; MS: M$^+$ 429.

Example 496

5-[4-(Benzyloxy)phenyl]-7-(1,4-dioxaspiro[4.5]dec-8-yl)-7H-pyrrolo[2,3-d]pyrimidin-4-amine 1,4-Dioxaspiro[4.5]decan-8-ol A solution of 1,4-dioxaspiro[4.5]decan-8-one (150 g, 962 mmol) in methanol (1 L) was treated with sodium borohydride (36.38 g, 962 mmol) portion-wise over 2 hours at 0° C. under a nitrogen atmosphere. The ice bath was removed after 2 hours, and the reaction mixture stirred over night at room temperature. After 24 hours, the solvent was removed under reduced pressure, dichlorormethane:iso-propanol (3:1, 1 L) solution and 2 N sodium hydroxide aqueous solution(400 mL) were added. The aqueous layer was extracted with the dichloromethane:iso-propanol solution (1 L). The organic layers were combined, washed water (500 mL), dried over magnesium sulfate, filtered and concentrated under reduced pressure. Residual solvent was removed under high vacuum pressure to give 144.18 g (94%) of the product 1,4-dioxaspiro[4.5]decan-8-ol. $^1$H NMR (DMSO-$d_6$, 400 MHz) 6 4.46–4.45(d, 1H, J=4 Hz), 3.83(s, 4H), 3.55(br s, 1H), 1.69–1.64(m, 4H), 1.49–1.40 (m, 4H). TLC (ethyl acetate/heptane=1:3, stain potassium permanganate) Rf=0.2

4-chloro-7-(1,4-dioxaspiro[4.5]dec-8-yl)-5-iodo-7H-pyrrolo[2,3-d]pyrimidine A solution of 4-chloro-5-iodo-7H-pyrrolo[2,3-d]pyrimidine (25 g, 89.46 mmol) in tetrahydrofuran (600 mL) was treated with 1,4-dioxaspiro[4.5]decan-8-ol (42.45 g, 268.5 mmol), triphenylphosphine (46.95 g, 179 mmol), and diethylazodicarboxyate (31.17 g, 179 mmol). The reaction mixture stirred for 24 hours at room temperature under a nitrogen atmosphere. The solid, which precipitated, was filtered and washed with ethyl acetate. The reaction solution was partially evaporated under reduced pressure. A solid precipitated and was filtered. The product contained reduced DEAD. Ethyl acetate (50–100 mL) was added to the solid. The product is not soluble in ethyl acetate, and was filtered. The trituration yielded 23.69 g (63%) of 4-chloro-7-(1,4-dioxaspiro[4.5]dec-8-yl)-5-iodo-7H-pyrrolo[2,3-d]pyrimidine. $^1$H NMR (DMSO-$d_6$, 400 MHz) δ 8.64(s, 1H), 8.10(s, 1H), 4.77–4.71(m, 1H), 3.95–3.88(m, 4H), 2.17–2.08(m, 2H), 1.93–1.90(d, 2H, J=12 Hz), 1.79–1.70(m, 4H); Waters 2690 Alliance HPLC (Symmetry Shield RP$_{18}$ 3.5 μm, 2.1×50 mm; 5%–95% acetonitrile-0.1 M ammonium acetate over 15 min, 0.5 mL/min) R$_t$ 6.99 min.

5-[4-(Benzyloxy)phenyl]-4-chloro-7-(1,4-dioxaspiro [4.5]dec-8-y)-7H-pyrrolo[2,3-d]pyrimidine A mixture of 4-chloro-7-(1,4-dioxaspiro[4.5]dec-8-yl)-5-iodo-7H-pyrrolo[2,3-d]pyrimidine (3.0 g, 7.15 mmol) in ethylene glycol dimethyl ether (100 mL) was treated with 4-(benzyloxy)phenylboronic acid (1.79 g, 7.87 mmol), tetrakis(triphenylphosphine)palladium (0.496 g, 0.429 mmol), and a solution of sodium carbonate (1.83 g, 17.16 mmol) in water (50 mL). A precipitate formed after 20 minutes. Reaction was stirred for 5 hours at 80° C. under a nitrogen atmosphere. The mixture was allowed to cool to room temperature and the organic solvent was removed under reduced pressure. The product was partitioned between the aqueous sodium carbonate layer and ethyl acetate. The aqueous layer was further extracted with ethyl acetate three times. The organic layers were combined, washed with water and brine, dried over magnesium sulfate, and partially concentrated until a precipitate formed. The solid was filtered, washed with ethyl acetate, and dried under a high vacuum. Yielded 2.06 g (61%) of 5-[4-(benzyloxy) phenyl]-4-chloro-7-(1,4-dioxaspiro[4.5]dec-8-yl)-7H-pyrrolo[2,3-d]pyrimidine. $^1$H NMR (DMSO-$d_6$, 400 MHz) δ 8.64(s, 1H), 7.88(s, 1H), 7.52–7.33(m, 7H), 7.08–7.05(d, 2H, J=12 Hz), 5.15(s, 2H), 4.82–4.78 (m, 1H), 3.95–3.89(m, 4H), 2.21–2.13(m, 2H), 1.98–1.96(m, 2H), 1.85–1.75(m, 4H); Waters 2690 Alliance HPLC (Symmetry Shield RP$_{18}$ 3.5 μm, 2.1×50 mm; 5%–95% acetonitrile-0.1 M ammonium acetate over 15 min, 0.5 mL/min) R$_t$ 8.356 min.

5-[4-(Benzyloxy)phenyl]-7-(1,4-dioxaspiro[4.5]dec-8-yl)-7H-pyrrolo[2,3-d]pyrimidin-4-amine A mixture of 5-[4-(benzyloxy)phenyl]-4-chloro-7-(1,4-dioxaspiro[4.5]dec-8-yl)-7H-pyrrolo[2,3-d]pyrimidine (1.925 g, 4.01 mmol) and concentrated ammonium hydroxide (50 ml) in dioxane (50 mL) was heated at 120° C. in a pressure vessel for 20 hours. The reaction mixture was allowed to cool to room temperature. Ethyl acetate (300 mL) and saturated sodium chloride aqueous solution (300 mL) were added. The layers were partitioned and the aqueous layer was extracted with ethyl acetate (700 mL). The organic layers were combined, washed with water, dried over magnesium sulfate, and the solvent removed under reduced pressure. The compound was purified by flash chromatography on silica using 5% methanol in dichloromethane to give 1.457 g (81%) of 5-[4-(benzyloxy)phenyl]-7-(1,4-dioxaspiro[4.5]dec-8-yl)-7H-pyrrolo[2,3-d]pyrimidin-4-amine. $^1$H NMR (DMSO-$d_6$, 400 MHz) δ 8.13(s, 1H), 7.49–7.31(m, 8H), 7.121–7.100(d, 2H, J=8 Hz), 6.02(br s, 2H), 5.149(s, 2H), 4.681–4.620 (m, 1H), 3.94–3.88(m, 4H), 2.12–2.03(m, 2H), 1.93–1.90(m, 2H), 1.82–1.71(m, 4H); Waters 2690 Alliance HPLC (Symmetry Shield RP$_{18}$ 3.5 μm, 2.1×50 mm; 5%–95% acetonitrile-0.1 M ammonium acetate over 15 min, 0.5 mL/min) R$_t$ 6.924 min.

Examples 497 and 498 cis-5–14-(Benzyloxy)phenyl[-7-,4-(4-methylpiperazino)cyclohexyl]-7H-pyrrolo[2,3-d] pyrimidin-4-amine and trans-5-[4-(Benzyloxy) phenyl]-7-[4-(4-methylpiperazino)cyclohexyl]-7H-pyrrolo[2,3-d]pyrimidin-4-amine 4-{4-Amino-5-[4-(benzyloxy)phenyl]-7H-pyrrolo[2,3-d] pyrimidin-7-yl}-1-cyclohexanone A suspension of 5-[4-(benzyloxy)phenyl]-7-(1,4-dioxaspiro[4.5]dec-8-yl)-7H-pyrrolo[2,3-d]pyrimidin-4-amine (1.447 g, 3.06 mmol) in acetone (100 mL) was treated with 5 N hydrochloric acid aqueous solution (25 mL) drop-wise over 10 min at 0° C. under a nitrogen atmosphere. The reaction mixture was stirred at 0° C. for 30 minutes and ice bath was removed. The reaction mixture was stirred for 72 hours then the organic layer was removed under reduced pressure. The aqueous layer was basified to approximately pH 8 with 50% sodium hydroxide aqueous solution. The aqueous layer was extracted with dichloromethane (600 mL). The organic layer was dried with magnesium sulfate, filtered, concentrated under reduced pressure, and dried under high vacuum for 3 hours to give 1.221 g (94%) of 4-4-amino-5-[4-(benzyloxy)phenyl]-7H-pyrrolo[2,3-d] pyrimidin-7-yl-1-cyclohexanone. $^1$H NMR (DMSO-$d_6$, 400 MHz) δ 8.15 (s, 1H), 7.48–7.34(m, 8H), 7.13–7.11 (d, 2H, J=8H), 6.13–6.04(br s, 2H), 5.19–5.15(s, 3H), 2.79–2.67(m, 2H), 2.33–2.30 (m, 4H), 2.30–2.20(m, 2H); Waters 2690 Alliance HPLC (Symmetry Shield RP$_{18}$ 3.5 μm, 2.1×50 mm; 5%–95% acetonitrile-0.1 M 25 ammonium acetate over 15 min, 0.5 mL/min) R$_t$ 6.51 min.

a. A suspension of the 4-{4-amino-5-[4-(benzyloxy) phenyl]-7H-pyrrolo[2,3-d]pyrimidin-7-yl}-1-cyclohexanone (1.22 g, 2.96 mmol) in dichloroethane (40 ml) was treated with N-methylpiperazine (0.889 g, 8.88 mmol) and glacial acetic acid (0.534 g, 8.88 mmol) at 0° C. for 1 hour. Subsequently, sodium triacetoxyborohydride (0.816 g, 3.85 mmol) was added and the reaction mixture was stirred overnight. Additional N-methylpiperazine (0.445 g, 4.44 mmol), sodium triaceoxyborohydride (0.407 g, 1.92 mmol), and glacial acetic acid (0.267 g, 4.44 mmol) were added and the reaction mixture was stirred for an additional 1.5 hour. To the reaction solution, a solution of sodium bicarbonate (1.49 g, 17.76 mmol) in 25 mL water was added and stirred for 1 hour. The aqueous layer was extracted with ethyl acetate (4×125 mL), The organic layers were combined, washed with water and brine (each 4×125 ml), dried over magnesium sulfate, filtered and concentrated under reduced pressure to give 1.6 g of crude material. The compound was purified by flash chromatography on silica gel using 10% methanol in dichloromethane, 20% methanol in dichloromethane, and then 30% methanol in dichloromethane. The column yielded 0.83 g (56%) of Cis-5-[4-(benzyloxy)phenyl]-7-[4-(4-methylpiperazino)cyclohexyl]-7H-pyrrolo[2,3-d]pyrimidin-4-amine, and 0.305 g (21%) of transs-5-[4-(benzyloxy)phenyl]-7-[4-(4-methylpiperazino) cyclohexyl]-7H-pyrrolo[2,3-d]pyrimidin-4-amine.

cis-5–14-(Benzyloxy)phenyl[-7-,4-(4-methylpiperazino)cyclohexyl]-7H-pyrrolo[2,3-d] pyrimidin-4-amine and trans-5-[4-(Benzyloxy) phenyl]-7-[4-(4-methylpiperazino)cyclohexyl]-7H-pyrrolo[2,3-d]pyrimidin-4-amine $^1$H NMR (DMSO-$d_6$, 400 MHz) δ 8.12(s, 1H), 7.49–4.47 (m, 2H), 7.43–7.34(m, 5H), 7.20(s, 1H), 7.13–7.11(d, 2H, J=8 Hz), 6.1–5.9(br s, 2H), 5.15(s, 2H), 4.70–4.64(m, 1H), 2.5–2.3(br s, 8H), 2.18(s, 4H), 2.11–2.05(m, 4H), 1.70–1.67 (m, 2H), 1.59–1.52 (m, 2H); Waters 2690 Alliance HPLC (Symmetry Shield RP$_{18}$ 3.5 μm, 2.1×50 mm; 5%–95% acetonitrile-0.1 M ammonium acetate over 15 min, 0.5 mL/min) R$_t$ 5.161 min.

trans-5-[4-(Benzyloxy)phenyl]-7-[4-(4-methylpiperazino) cyclohexyl]-7H-pyrrolo[2,3-d]pyrimidin-4-amine $^1$H NMR (DMSO-$d_6$, 400 MHz) 8.11(s, 1H), 7.48–7.46(d, 2H, J=7.6 Hz), 7.42–7.33(m, 6H), 7.12–7.10(d, 2H, J=8.8 Hz), 6.1–5.9(br s, 2H), 5.14(s, 2H), 4.55–4.50 (m, 1H), 2.6–2.4(br s, 4H), 2.40–2.25(m, 5H), 2.14(s, 3H), 2.0–1.8 (m, 6H), 1.5–1.3(m, 2H). Waters 2690 Alliance HPLC (Symmetry Shield RP$_{18}$ 3.5 m, 2.1×50 mm; 5%–95% acetonitrile-0.1 M ammonium acetate over 15 min, 0.5 mL/min) R$_t$ 5.129 min.

Example 499

4-Amino-5-(4-phenoxyphenyl)-7-[1-(1-methyl-4-piperidinyl)-4-piperidinyl]-7H-pyrrolo[2,3-d] pyrimidine tert-Butyl 4-Hydroxy-1-piperidinecarboxylate A solution of tert-butyl 4-oxo-1-piperidinecarboxylate (179.24 g, 899.62 mmol) in anhydrous methanol (1.5 L) at 0° C. under a nitrogen atmosphere was treated with sodium borohydride (34.03 g, 899.62 mmol). Sodium borohydride was added portion-wise (5 g every 10 minutes). The ice bath was removed 20 minutes after the last addition of sodium borohydride, and the reaction mixture stirred for 72 hours. To the reaction solution, 1 N sodium hydroxide aqueous solution (1 L) was added, and allowed to stir for 2 hours. The organic layer was removed under reduced pressure, and anhydrous diethyl ether (200 mL) was added. The aqueous layer was extracted with anhydrous diethyl ether (1.5 L). The organic layers were combined, washed with brine, dried over magnesium sulfate, filtered and evaporated under reduced pressure to give a yellow oil. The product was further dried under high vacuum to remove residual solvent to give 177.04 g (97%) of tert-butyl 4-hydroxy-1-piperidinecarboxylate as a white solid. $^1$H NMR (DMSO-$d_6$, 400 MHz) δ 4.688(s, 1H), 3.678–3.589(m, 3H), 2.940(m, 2H), 1.689–1.646(m, 2H), 1.385(s, 9H), 1.252–1.212(m, 2H).

tert-Butyl 4-(4-Chloro-5-iodo-7H-pyrrolo[2,3-d]pyrimidin-7-yl)-1-piperidinecarboxylate A solution of 4-chloro-5-iodo-7H-pyrrolo[2,3-d] pyrimidine (6.48 g, 21.78 mmol) in tetrahydrofuran (200 mL) at 0° C. under a nitrogen atmosphere was treated with tert-butyl 4-hydroxy-1-piperidinecarboxylate (13.147 g, 65.33 mmol) and triphenylphosphine (11.43 g, 43.56 mmol) and stirred for 30 minutes. Diethylazodicarboxyate (7.61 g, 43.56 mmol) was added drop-wise over 15 minutes to the reaction solution. The ice bath was removed after 15 minutes, and the reaction mixture was allowed to stir over night. The solvent was evaporated under reduced pressure, and then the yellow gummy solid dissolved in dichloromethane. The solid precipitated was filtered and discarded. The filtrate was evaporated under reduced pressure. Recrystallization from ethyl acetate/heptane yielded 4.82 g (47%) of tert-butyl 4-(4-chloro-5-iodo-7H-pyrrolo[2,3-d] pyrimidin-7-yl)-1-piperidinecarboxylate. $^1$H NMR (DMSO-$d_6$, 400 MHz) 8.64(s, 1H), 8.20 (s, 1H), 4.89–4.84(m, 1H), 4.13–4.10 (m, 2H), 3.00–2.80(br s, 2H), 2.01–1.88 (m, 4H), 1.43(s, 9H). Waters 2690 Alliance HPLC (Symmetry Shield RP$_{18\ 3.5}$ m, 2.1×50 mm; 5%–95% acetonitrile-0.1 M ammonium acetate over 15 min, 0.5 mL/min) R$_t$ 7.825 minutes.

4-Chloro-5-iodo-7-(4-piperidyl)-7H-pyrrolo[2,3-d] pyrimidine

A mixture of tert-butyl 4-(4-chloro-5-iodo-7H-pyrrolo[2, 3-d]pyrimidin-7-yl)-1-piperidinecarboxylate (1.0 g, 2.16 mmol) in dichloromethane (10 mL) at 0° C. was treated with a cold solution of trifluoroacetic acid (20%) in dichloromethane (total volume 56 mL). Reaction stirred at 0° C. under a nitrogen atmosphere for 3 hours. The solvent was evaporated under reduced pressure at ambient temperature. Ethyl acetate (50 mL) and 5 N hydrochloric acid (50 mL) were added to the solid. The layers were partitioned, and the organic layer was extracted with 5 N hydrochloric acid (150 mL). The aqueous layers were combined, cooled to 0° C., and basified using 50% sodium hydroxide aqueous solution at 0° C. The aqueous layer was extracted with dichloromethane (300 mL). The organic layers were combined, dried over magnesium sulfate, filtered, and evaporated under reduced pressure. The resulting product, 4-chloro-5-iodo-7-(4-piperidyl)-7H-pyrrolo[2,3-d]pyrimidine (0.520 g, 99%) was dried 5 under high vacuum. $^1$H NMR (DMSO-$d_6$, 400 MHz); 8.63(s, 1H), 8.12(s, 1H), 4.75–4.68 (m, 1H), 3.09–3.06(d, 2H, J=12 Hz), 2.70–2.60(m, 2H), 1.99–1.83(m, 4H); Waters 2690 Alliance HPLC (Symmetry Shield RP$_{18}$ 3.5 m, 2.1×50 mm; 5%–95% acetonitrile-0.1 M ammonium acetate over 15 min, 0.5 mL/min) R$_t$ 4.022 min.

4-Chloro-5-iodo-7-[1-(1-methyl-4-piperidinyl)-4-piperidinyl]-7H-pyrrolo[2,3-d]pyrimidine A mixture of 4-chloro-5-iodo-7-(4-piperidinyl)-7H-pyrrolo[2,3-d]pyrimidine (0.52 g, 1.43 mmol), 1-methyl-4-piperidone (0.178 g, 1.57 mmol), and glacial acetic acid (0.094 g, 1.57 mmol) in dichloroethane was stirred at 0° C. for 20 minutes. Sodium 15 triacetoxy borohydride (0.455 g, 2.15 mmol) was added and stirred for 15 minutes at 0° C., after which the ice bath was removed, allowed to warm to room temperature and stirred over night. Additional 1-methyl-4-piperidone (0.178 g, 1.57 mmol), glacial acetic acid (0.094 g, 1.57 mmol), and sodium triacetoxy borohydride (0.455 g, 2.15 mmol) were added and stirred at room temperature. To the reaction solution was added sodium bicarbonate (0.721 g, 8.58 mmol) in water (10 mL) and stirred for 1 hour. The organic layer was evaporated under reduced pressure. Ethyl acetate was added, the layers were partitioned, and the aqueous layer was extracted with ethyl acetate. The organic layers were combined, washed with water and brine, dried over magnesium sulfate, filtered and evaporated under reduced pressure. The compound was purified by flash chromatography on silica using dichloromethane/ethyl acetate (1:1), 10% methanol in dichloromethane, and then 20% methanol in dichloromethane to give 400 mg (61%) of 4-chloro-5-iodo-7-[1-(1-methyl-4-piperidinyl)-4-piperidinyl]-7H-pyrrolo[2,3-d] pyrimidine ¹H NMR (DMSO-d₆, 400 MHz) 8.62(s, 1H), 8.16(s, 1H), 4.66–4.58(m, 1H), 3.17(s, 1H), 3.02–3.00(d, 2H, J=8 Hz), 2.84–2.82 (d, 2H, J=8 Hz), 2.33–2.26(m, 2H), 2.17 (s, 3H), 2.08–2.04(m, 2H), 1.95–1.85 (m, 4H), 1.91–1.88(d, 2H, J=12 Hz), 1.49–1.45(m, 2H); Waters 2690 Alliance HPLC (Symmetry Shield RP₁₈ 3.5 μm, 2.1×50 mm; 5%–95% acetonitrile-0.1 M ammonium acetate over 15 min, 0.5 mL/min) R$_t$ 3.505 min. 4-chloro-5-(4-phenoxyphenyl)-7-1-(1-methyl-4-piperidinyl)-4-piperidinyl]-7H-pyrrolo[2,3-d]pyrimidine A mixture of 4-chloro-5-iodo-7-[ 1-(1-methyl-4-piperidinyl)-4-piperidinyl]-7H-pyrrolo[2,3-d]pyrimidine (0.390 g, 0.845 mmol), 4-phenoxyphenyl boronic acid (0.199 g, 0.93 mmol), tetrakis(triphenylphosphine)pallidium (0.058 g, 0.051 mmol), and sodium carbonate (0.215 g, 2.03 mmol) were heated in a mixture of ethylene glycol dimethyl ether (20 mL) and water (10 mL) at 80° C. for 7 hours under a nitrogen atmosphere. Reaction solution was allowed to cool to room temperature, and the organic layer was removed under reduced pressure. Ethyl acetate was added, the layers were partitioned and the aqueous layer was extracted with ethyl acetate (250 mL). The organic layers were combined, washed with water and brine, dried over magnesium sulfate, filtered and evaporated under reduced pressure. The residue was purified by flash chromatography on silica using 10% methanol in dichloromethane, then 20% methanol in dichloromethane as eluent to give 0.241 g (51%) of 4-chloro-5-(4-phenoxyphenyl)-7-[1-(1-methyl-4-piperidinyl)-4-piperidinyl]-7H-pyrrolo[2,3-d]pyrimidine.

¹H NMR (DMSO-d₆, 400 MHz) δ 8.99(s, 1H), 7.94(s, 1H), 7.55–7.53(d, 2H, J=8 Hz), 7.45–7.41(m, 2H), 7.20–7.05(m, 5H), 4.69(m, 1H), 3.06–3.03(m, 2H), 2.95–2.85 (m, 2H), 2.45–2.25(m, 4H), 2.16(s, 3H), 2.00–1.80(m, 5H), 1.75–1.70(m, 2H), 1.55–1.45(m, 2H); Waters 2690 Alliance HPLC (Symmetry Shield RP₁₈ 3.5 μm, 2.1×50 mm; 5%–95% acetonitrile-0.1 M ammonium acetate over 15 min, 0.5 mL/min) R$_t$ 5.583 min.
4-Amino-5-(4-phenoxyphenyl)-7-[1-(1-methyl-4-piperidinyl)-4-piperidinyl]-7H-pyrrolo[2,3-d]pyrimidine A mixture of 4-chloro-5-(4-phenoxyphenyl)-7-[1-(1-methyl-4-piperidinyl)-4-piperidinyl]-7H-pyrrolo[2,3-d]pyrimidine (0.241 g, 0.48 mmol) and concentrated ammonium hydroxide (20 mL) in dioxane (20 mL) was heated at 120° C. in a pressure vessel under a nitrogen atmosphere for 20 hours. The reaction mixture was allowed to cool to room temperature, and dioxane was removed under reduced pressure. The residue was partitioned between ethyl acetate and saturated sodium chloride aqueous solution. The aqueous layer was extracted with ethyl acetate (500 mL). The combined organic layers were washed with water, dried over magnesium sulfate, filtered and evaporated under reduced pressure. The compound was purified by flash chromatography on silica gel using 20% methanol in dichloromethane to 35% methanol in dichloromethane in 5% increments, yielding 0.119 g of product which was subsequently dissolved in ethylacetate. To this solution, maleic acid (0.087 g, 0.75 mmol) in ethyl acetate was added. The solid, which precipitated, was filtered under a nitrogen atmosphere, and dried under high vacuum. The product contained some impurity. Approximately 5 mL of saturated sodium bicarbonate aqueous solution and 10 mL of dichloromethane was added. The layers were separated using an Empore extraction cartridge. The remaining material was sent for preparative HPLC, 38 mg was received. The product (0.038 g, 0.079 mmol) was dissolved in ethyl acetate. To this solution, (0.027 g, 0.23 mmol) of maleic acid in ethyl acetate was added. The product (0.063 g) formed was a trimaleate salt.
¹H NMR (DMSO-d₆, 400 MHz) δ 8.18(s, 1H), 7.48–7.40(m, 5H), 7.19–7.08(m, 5H), 6.29(s, 6H), 4.80(m, 1H), 3.70–2.90 (m, 9H), 2.67(s, 3H), 2.40–2.20(m, 6H), 1.90–1.75(m, 2H); Waters 2690 Alliance HPLC (Symmetry Shield RP₁₈ 3.5 μm, 2.1×50 mm; 5%–95% acetonitrile-0.1 M ammonium acetate over 15 min, 0.5 mL/min) R$_t$ 4.629 min.

Examples 500 and 501 trans-5-[4-(Aminomethyl)phenyl]-7-[4-(4-methylpiperazino)cyclohexyl]-7H-pyrrolo[2,3-d]pyrimidin-4-amine Tetramaleate Salt
cis-5-[4-(Aminomethyl)phenyl]-7-[4-(4-methylpiperazino)cyclohexyl]-7H-pyrrolo[2,3-d]pyrimidin-4-amine Tetramaleate Salt
a)

A mixture of 4-(4-chloro-5-iodo-7H-pyrrolo[2,3-d]pyrimidin-7-yl)-1-cyclohexanone (20.0 g, 53.3 mmol), 1-methylpiperazine (6.42 g, 128 mmol) and acetic acid (7.7 g, 128 mmol) in 1,2-dichloromethane (1 L) was stirred for 15 minutes at ambient temperature. Sodium triacetoxyborohydride (14.7 g, 69.3 mmol) was added and stirring was continued for 20 hours. Water (400 mL) was added followed by sodium bicarbonate (26.0 g, 310 mmol). The mixture was transferred to a separatory funnel and the layers separated. The aqueous layer was extracted with dichloromethane (300 mL). The combined organic extracts were dried over magnesium sulfate, filtered and the filtrate concentrated under reduced pressure. The resulting oil was purified by flash chromatography on silica gel (275 g) using dichloromethane/methanol (9:1) as an eluent to give cis-4-chloro-5-iodo-7-[4-(4-methylpiperazino)cyclohexyl]-7H-pyrrolo[2,3-d]pyrimidine (10.2 g, 42%) and trans-4-chloro-5-iodo-7-[4-(4-methylpiperazino)cyclohexyl]-7H-pyrrolo[2,3-d]pyrimidine (5.8 g) which contained 10% of the cis isomer. This mixture was stirred in diethyl ether (100 mL) for 1.5 hours then the solid was collected by filtration to provide pure trans-4-chloro-5-iodo-7-[4-(4-methylpiperazino)cyclohexyl]-7H-pyrrolo[2,3-d]pyrimidine (5.0 g, 20.2%).

cis-4-Chloro-5-iodo-7-[4-(4-methylpiperazino)cyclohexyl]-7H-pyrrolo[2,3-d]pyrimidine: ¹H NMR (DMSO-d₆, 400 MHz) δ 8.60(s, 1H), 7.52(s, 1H), 4.84(m, 1H), 2.06–2.53(m, 16H), 1.79(m, 2H), 1.62 (m, 2H); RP-HPLC (Hypersil HS C18 Hypersil HS C18, 5 μm, 100 A, 250×4.6 mm; 25%–100% acetonitrile over 10 min, 1 mL/min) t$_r$ 7.3 min; MS:MH⁺ 460.2.

trans-4-chloro-5-iodo-7-[4-(4-methylpiperazino)cyclohexyl]-7H-pyrrolo[2,3-d]pyrimidine: ¹H NMR (DMSO-d₆, 400 MHz) δ 8.60(s, 1H), 7.43(s, 1H), 4.70(m, 1H), 2.42–2.67(m, 9H), 2.32(s, 3H), 2.09–2.18(m, 4H), 1.76–1.86(m, 2H), 1.53–1.61(m, 2H); RP-HPLC (Hypersil HS C18, 5 μm, 100 A, 250×4.6 mm; 25%–100% acetonitrile over 10 min, 1 mL/min) t$_r$ 6.7 min; MS:MH³⁰ 460.2.
b) tert-Butyl N-[4-(4,4,5,5-Tetramethyl-1,3,2-dioxaborolan-2-yl)benzyl]carbamate A mixture of 4-bromobenzylamine hydrochloride (10.0 g, 45.0 mmol), di-tert-butyl dicarbonate (11.8 g, 54.0 mmol) and diisopropylethyl amine (8.7 g, 68 mmol) in tetrahydrofuran (100 mL) was heated at reflux for 1 hour. The mixture was cooled and the solvent evaporated under reduced pressure. The material was dissolved in dichloromethane (200 mL) and then washed with water, dried over magnesium sulfate, filtered and the filtrate concentrated under reduced pressure to provide an oil (14.0 g). The oil was dissolved in N,N-dimethylformamide (250 mL) then treated with diboron pinacol ester (11.4 g, 45 mmol), potassium acetate (13.2 g, 135 mmol) and [1.1'-bis(diphenylphosphino)ferrocene] dichloropalladium (II) complex with dichloromethane (1:1) (1.1 g, 1.35 mmol). The mixture was heated at 85° C. for 18 hours then cooled and the solvent removed under reduced pressure. The residue was stirred with dichloromethane (250 mL) then filtered through a pad of celite. The filtrate was concentrated under reduced pressure and the residue purified by flash chromatography on silica gel using heptane/ethyl acetate (8:2) as an eluent to provide tert-butyl N-[4-(4,4,5,5-tetramethyl-1,3,2-dioxaborolan-2-yl)benzyl]carbamate (11.8 g, 78%): $^1$H NMR (DMSO-$d_6$, 400 MHz) δ 7.63(d, 2H), 7.40 (t, 1H), 7.23(d, 2H), 4.14(d, 2H), 1.39(s, 9H), 1.28(s, 12H); RP-HPLC (Hypersil HS C18, 5 μm, 100 A, 250×4.6 mm; 25%–100% acetonitrile over 10 min, 1 mL/min) $t_r$ 12.65 min.

c) trans-5-[4-(Aminomethyl)phenyl]-7-[4-(4-methylpiperazino)cyclohexyl]-7H-pyrrolo[2,3-d]pyrimidin-4-amine Tetramaleate Salt PH 4011342C A mixture of trans-4-chloro-5-iodo-7-[4-(4-methylpiperazino)cyclohexyl]-7H-pyrrolo[2,3-d]pyrimidine (1.0 g, 2.18 mmol), tert-butyl N-[4-(4,4,5,5-tetramethyl-1,3,2-dioxaborolan-2-yl)benzyl]carbamate (0.8 g, 2.40 mmol), sodium carbonate (0.56 g, 5.24 mmol) and tetrakis(triphenyl-phosphine)palladium (70 mg, 0.131 mmol) in ethylene glycol dimethyl ether (16 mL) and water (8 mL) was heated at 85° C. under an atmosphere of nitrogen for 18 hours. The mixture was cooled to ambient temperature and the solvent evaporated under reduced pressure. Water (25 mL) was added and the mixture was extracted with ethyl acetate (2×25 mL) and dichloromethane (25 mL). The combined organic extracts were washed with brine (25 mL), dried over magnesium sulfate then fitered and the filtrate concentrated under reduced pressure. The residue was purified by flash chromatography on silica using dichloromethane/methanol (85:15) as an eluent to yield an oil (1.0 g) which was dissolved in 1,4-dioxane (75 mL) and 30% aqueous ammonium hydroxide (75 mL). The mixture was heated at 120° C. in a sealed vessel for 18 hours then cooled to ambient temperatue and concentrated under reduced pressure. The residue was dissolved in acetone (50 mL) and 6N aqueous hydrochloric acid (25 mL). The solution was stirred at ambient temperature for 20 hours then concentrated and purified by preparative reverse-phase chromatography. Lyophilization provided a hydroscopic solid (750 mg). The solid (75 mg, 0.179 mmol) was dissolved in ethanol (1 mL) then treated with a solution of maleic acid (104 mg, 0.894 mmol) in ethanol (2 mL). The suspension which resulted was heated at 85° C. with stirring for 30 minutes then cooled to ambient temperatue and the solid collected by filtration to provide trans-5-[4-(aminomethyl) phenyl]-7-[4-(4-methylpiperazino)cyclohexyl]-7H-pyrrolo [2,3-d]pyrimidin-4-amine tetramaleate salt as a white solid: $^1$H NMR (DMSO-$d_6$, 400 MHz) δ 8.19(s, 1H), 8.15(bs, 2H), 7.54(m, 4H), 7.49(s, 1H), 6.30(bs, 2H), 6.14 (s, 8H), 4.60(m, 1H), 4.09(s, 2H), 2.5–3.5(m, 8H), 2.69(s, 3H), 1.91–2.00(m, 7H), 1.54–1.59(m, 2H); RP-HPLC (Hypersil HS C18, 5 μm, 100 A, 250×4.6 mm; 2%–25% acetonitrile over 25 min, 1 mL/min) $t_r$ 6.7 min.; MS:MH$^+$ 420.2.

A similar procedure using cis-4-chloro-5-iodo-7-[4-(4-methylpiperazino)cyclohexyl]-7H-pyrrolo[2,3-d] pyrimidine was used to prepare cis-5-[4-(aminomethyl) phenyl]-7-[4-(4-methylpiperazino)cyclohexyl]-7H-pyrrolo [2,3-d]pyrimidin-4-amine tetramaleate salt: $^1$H NMR (DMSO-$d_6$, 400 MHz) δ 8.19(s, 1H), 8.14(bs, 2H), 7.53(m, 4H), 7.38(s, 1H), 6.13(s, 8H), 4.72(m, 1H), 4.10 (s, 2H), 3.1–3.6(m, 8H), 2.77(s, 3H), 1.65–2.50 (m, 9H); RP-HPLC (Hypersil HS C18, 5 μm, 100 A, 250×4.6 mm; 5%–50% acetonitrile over 25 min, 1 mL/min) $t_r$ 10.18 min.; MS:MH$^{30}$ 420.2.

Examples 502 and 503 trans-N1-(4-{4-Amino-7-[4-(4-methylpiperazino) cyclohexyl]-7H-pyrrolo[2,3-d]pyrimidin-5-yl}benzyl)benzamide and cis-N1-(4-{4-Amino-7-[4-(4-methylpiperazino)cyclohexyl]-7H-pyrrolo[2,3-d] pyrimidin-5-yl}benzyl)benzamide A mixture of trans-5-[4-(aminomethyl)phenyl]-7-[4-(4-methylpiperazino)cyclohexyl]-7H-pyrrolo[2,3-d]pyrimidin-4-amine (50 mg, 0.119 mmol) in pyridine (2 mL) and dichloromethane (2 mL) was cooled to 0° C. then treated with benzoyl chloride (19 mg, 0.13 mmol). The mixture was allowed to warm to ambient temperature and stirred for 1 hour. The solvents were removed under reduced pressure then the residue was purified by preparative reverse phase chromatography to give trans-N1-(4-{4-amino-7-[4-(4-methylpiperazino)cyclohexyl]-7H-pyrrolo[2,3-d]pyrimidin-5-yl}benzyl)benzamide (50 mg) as a white solid: $^1$H NMR (DMSO-$d_6$, 400 MHz) δ 9.08(t, 1H), 8.13(s, 1H), 7.91(m, 2H), 7.4–7.54(m, 8H), 6.0(bs, 2H), 4.53(m, 3H), 2.30–2.40 (m, 5H), 2.15(s, 3H), 1.85–1.89(m, 10H), 1.43–1.46 (m, 2H); RP-HPLC (Hypersil HS C18, 5μm, 100 A, 250×4.6 mm; 5%–50% acetonitrile over 25 min, 1 mL/min) $t_r$ 18.20 min.; MS:MH$^+$ 524.3.

The cis isomer was prepared in a similar manner as described above: $^1$H NMR (DMSO-$d_6$, 400 MHz) δ 9.08(t, 1H), 8.14(s, 1H), 7.91(d, 2H), 7.41–7.56(m, 7H), 7.26 (s, 1H), 4.67(m, 1H), 4.54(d, 2H), 1.5–2.5(m, 20H); RP-HPLC (Hypersil HS C18, 5 μm, 100 A, 250×4.6 mm; 5%–50% acetonitrile over 25 min, 1 mL/min) $t_r$ 18.40 min.; MS:MH$^+$ 524.3.

Example 504 cis-N1-(4-{4-Amino-7-[4-(4-,ethylpiperazino) cyclohexyl]-7H-pyrrolo[2,3-d]pyrimidin-5-yl) benzyl)acetamide The title compound was prepared in a similar manner cis-N1-(4- {4-amino-7-[4-(4-methylpiperazino) cyclohexyl]-7H-pyrrolo[2,3-d]pyrimidin-5-yl}benzyl) benzamide: $^1$H NMR (DMSO-$d_6$, 400 MHz) δ 8.37(t, 1H), 8.14 (s, 1H), 7.44(d, 2H), 7.35(d, 2H), 7.25(s, 1H), 6.0(bs, 2H), 4.68(m, 1H), 4.30(d, 2H), 1.5–2.45(m, 23H); RP-HPLC (Hypersil HS C18, 5 tm, 100 A, 250×4.6 mm; 5%–50% acetonitrile over 25 min, 1 mL/min) $t_r$ 13.38 min.; MS:MH$^+$ 462.3.

Example 505 cis-5-{4-[(Benzylamino)methyl]phenyl}-7-[4-(4-methylpiperazino)cyclohexyl]-7H-pyrrolo[2,3-d] pyrimidin-4-amine A mixture of cis-5-[4-(aminomethyl)phenyl]-7-[4-(4-methylpiperazino)cyclohexyl]-7H-pyrrolo[2,3-d]pyrimidin-4-amine (100 mg, 0.238 mmol), benzaldehyde (28 mg, 0.262 mmol) and acetic acid (43 mg, 0.714 mmol) in 1,2 dichloroethane (4 mL) was stirred at ambient temperature for 1 hour. Sodium triacetoxyborohydride (100 mg, 2.6 mmol) was added and the mixture was stirring continued for 2 hours. Sodium borohydride (100 mg, 2.60 mmol) was added and stirring was continued for an additional 30 minutes, the solvents were removed under reduced pressure and the residue purified by preparative reverse phase chromatography to yield cis-5-{4-[(benzylamino)methyl] phenyl}-7-[4-(4-methylpiperazino)cyclohexyl]-7H-pyrrolo

[2,3-d]pyrimidin-4-amine: $^1$H NMR (DMSO-d$_6$, 400 MHz) δ 8.13(s, 1H), 7.2–7.50(m, 1OH), 6.03(bs, 2H), 4.67 (m, 1H), 3.71(d, 2H), 1.52–2.50(m, 20H); R-P-HPLC (Hypersil HS C18, 5 μm, 100 A, 250×4.6 mm; 5%–50% acetonitrile over 25 min, 1 mL/min) t$_r$ 14.42 min.; MS:MH$^+$ 510.3.

Examples 506 and 507 trans-Benzyl N-(4-{4-Amino-7-[4-(4-methylpiperazino)cyclohexyl]-7H-pyrrolo[2,3-d]pyrimidin-5-yl}benzyl)carbamate and cis-Benzyl N-(4-{4-Amino-7-[4-(4-methylpiperazino)cyclohexyl]-7H-pyrrolo[2,3-d]pyrimidin-5-yl}benzyl)carbamate A mixture of trans-5-[4-(aminomethyl)phenyl]-7-[4-(4-methylpiperazino)cyclohexyl]-7H-pyrrolo[2,3-d]pyrimidin-4-amine (50 mg, 0.119 mol) in pyridine (2 mL) and dichloromethane (2 mL) was cooled to 0° C. then treated with benzyl chloroformate (22 mg, 0.131 mmol). The mixture was warmed to ambient temperature and stirred an additional 2 hours, evaporated and the residue purified by preparative reverse-phase chromatography to give trans-benzyl N-(4-{4-amino-7-[4-(4-methylpiperazino)cyclohexyl]-7H-pyrrolo[2,3-d]pyrimidin-5-yl}benzyl)carbamate: $^1$H NMR (DMSO-d$_6$, 400 MHz) 8.13(s, 1H), 7.85(t, 1H), 7.3–7.42(m, 10H), 6.02(bs, 2H), 5.06(s, 2H), 4.54(m, 1H), 4.26(d, 2H), 1.44–2.37(m, 20H); RP-HPLC (Hypersil HS C18, 5 m, 100 A, 250×4.6 mm; 5%–50% acetonitrile over 25 min, 1 mL/min) t$_r$ 22.15 min.; MS:MH$^+$ 554.3.

cis-Benzyl N-(4-{4-Amino-7-[4-(4-methylpiperazino)cyclohexyl]-7H-pyrrolo[2,3-d]pyrimidin-5-yl}benzyl)carbamate $^1$H NMR (DMSO-d$_6$, 400 MHz) 8.14(s, 1H), 7.86 (t, 1H), 7.26–7.48(m, 10H), 6.04(bs, 2H), 5.10(s, 2H), 4.67(m, 1H), 4.26(d, 2H), 1.44–1.56–2.5(m, 20H); RP-HPLC (Hypersil HS C18, 5 m, 100 A, 250×4.6 mm; 5%–50% acetonitrile over 25 min, 1 mL/min) t$_r$ 22.72 min.; MS:MH$^+$ 554.3.

Examples 508 and 509 trans-N-(4-{4-Amino-7-[4-(4-methylpiperazino)cyclohexyl]-7H-pyrrolo[2,3-d]pyrimidin-5-yl}benzyl)-1-benzenesulfonamide and cis-N-(4-{4-Amino-7-[4-(4-ethylpiperazino)cyclohexyl]-7H-pyrrolo[2,3-d]pyrimidin-5-yl}benzyl)-1-benzenesulfonamide The compound was prepared from trans-5-[4-(aminomethyl)phenyl]-7-[4-(4-methylpiperazino)cyclohexyl]-7H-pyrrolo[2,3-d]pyrimidin-4-amine and benzene sulfonyl chloride in a manner similar as that described for the synthesis of Trans-N 1-(4-{4-amino-7-[4-(4-methylpiperazino)cyclohexyl]-7H-pyrrolo[2,3-d]pyrimidin-5-yl}benzyl)benzamide: $^1$H NMR (DMSO-d$_6$, 400 MHz) 8.13 (s, 1H), 7.79(d, 2H), 7.54–7.64 (m, 3H), 7.38(s, 1H), 7.28–7.35 (m, 4H), 6.0(bs, 2H), 4.54(m, 1H), 4.06(s, 2H), 2.3–2.5(m, 6H), 2.14(s, 3H), 1.86–1.94 (m, 9H); RP-HPLC (Hypersil HS C18, 5 m, 100 A, 250×4.6 mm; 5%–50% acetonitrile over 25 min, 1 mL/min) t$_r$ 19.9 min.; MS:MH$^+$ 560.3.
cis-N-(4-{4-Amino-7-[4-(4-methylpiperazino)cyclohexyl]-7H-pyrrolo[2,3-d]pyrimidin-5-yl)benzyl}-1-benzenesulfonamide:

$^1$H NMR (DMSO-d$_6$, 400 MHz) 8.22(s, 1H), 8.14 (s, 1H), 7.78(d, 2H), 7.54–7.62(m, 3H), 7.23–7.37(m, 5H), 5.98(bs, 2H), 4.67(m, 1H), 4.07(d, 2H), 2.05–2.55(m, 16H), 1.53–1.77(m, 4H)); RP-HPLC (Hypersil HS C18, 5 m, 100 A, 250×4.6 mm; 5%–50% acetonitrile over 25 min, 1 mL/min) t$_r$ 20.45 min.; MS:MH$^+$ 560.3.

Examples 510 and 511 trans-N-(4-{4-Amino-7-[4-(4-methylpiperazino)cyclohexyl]-7H-pyrrolo[2,3-d]pyrimidin-5-yl}benzyl)-N-phenylurea and cis-N-(4-{4-Amino-7-[4-(4-methylpiperazino)cyclohexyl]-7H-pyrrolo[2,3-d]pyrimidin-5-yl}benzyl)-N-phenylurea The trans-5-[4-(aminomethyl)phenyl]-7-[4-(4-methylpiperazino)cyclohexyl]-7H-pyrrolo[2,3-d]pyrimidin-4-amine (50 mg, 0.119 mmol) was dissolved in dichloromethane (2 mL) then treated with phenyl isocyanate (16 mg, 0.131 mmol) and stirred for 1 hour at ambient temperature. The solvent was removed under reduced pressure and the residue purified by preparative reverse phase chromatography to give trans-N-(4-{4-amino-7-[4-(4-methylpiperazino)cyclohexyl]-7H-pyrrolo[2,3-]pyrimidin-5-yl}benzyl)-N-phenylurea: $^1$H NMR (DMSO-d$_6$, 400 MHz) 8.67(s, 1H), 8.13(s, 1H), 7.38–7.44(m, 7H), 7.22(t, 2H), 6.91(t, 1H), 6.76(t, 1H), 6.02(bs, 2H), 4.54(m, 1H), 4.35(d, 2H), 2.37–2.50(m, 5H), 2.14(s, 3H), 1.86–1.95(m, 10H), 1.40–1.49(m, 2H); RP-HPLC (Hypersil HS C18, 5 m, 100 A, 250×4.6 mm; 5%–50% acetonitrile over 25 min, 1 mL/min) t$_r$ 18.8 min.; MS:MH$^+$ 539.3.
cis-N-(4-{4-Amino-7-[4-(4-methylpiperazino)cyclohexyl]-7H-pyrrolo[2,3-d]pyrimidin-5-yl}benzyl)-N-phenylurea:
$^1$H NMR (DMSO-d$_6$, 400 MHz) 8.67(s, 1H), 8.14(s, 1H), 7.40–7.47(m, 6H), 7.20–7.24(m, 3H), 6.89(t, 1H), 6.71(t, 1H), 6.0(bs, 2H), 4.67(m, 1H), 4.35(d, 2H), 2.05–2.5(m, 16H), 1.53–1.71(m, 4H); RP-HPLC (Hypersil HS C18, 5 m, 100 A, 250×4.6 mm; 5%–50% acetonitrile over 25 min, 1 mL/min) t 19.3 min.; MS:MH$^+$ 539.3.

Examples 512 and 513 cis-N1-Phenyl-2-(4-{4-amino-7-[4-(4-methylpiperazino)cyclohexyl]-7H-pyrrolo[2.3-d]pyrimidin-5-yl}phenyl)acetamide Trismaleate and trans-N1-Phenyl-2-(4-{4-amino-7-[4-(4-methylpiperazino)cyclohexyl]-7H-pyrrolo[2.3-d]pyrimidin-5-yl}phenyl)acetamide Trismaleate a) N1-Phenyl-2-[4-(4,4,5,5-tetramethyl-1,3,2-dioxaborolan-2-yl)phenyl]acetamide A mixture of 4-bromophenyl acetic acid (5.0 g, 23.3 mmol), and oxalyl chloride (3.25 g, 25.6 mmol) in dichloromethane (100 mL), was stirred at ambient temperature, treated with 3 drops of N,N-dimethylformamide, then stirred for 2.5 hours. The solvents were removed under reduced pressure then the residue was dissolved in dichloromethane (100 mL) and triethylamine (5.9 g, 58.3 mmol). Aniline (2.4 g, 25.6 mmol) was added and the mixture was stirred an additional 1 hour. The solution was washed with 1N aqueous hydrochloric acid (2×50 mL), saturated sodium bicarbonate (100 mL), brine (50 mL), then dried over magnesium sulfate, filtered and the filtrate evaporated under reduced pressure to give N1-phenyl-2-(4-bromophenyl)acetamide (4.62 g, 68%) [RP-HPLC (Hypersil HS C18, 5 m, 100 A, 250×4.6 mm; 25%–00% acetonitrile over 10 min, 1 mL/min) t$_r$ 10.85 min.] which was used without further purification. A mixture of N1-phenyl-2-(4-bromophenyl)acetamide (4.62 g, 15.9 mmol), diboron pinacol ester (4.45 g, 17.5 mmol), potassium acetate (4.68 g, 47.8 mmol) and [1.1'-bis(diphenylphosphino)ferrocene]dichloropalladium (II) complex with dichloromethane (1: 1) (0.39 g, 0.5 mmol)

in N,N-dimethylformamide (90 mL) was heated at 100° C. under an atmosphere of nitrogen for 18 hours then cooled to ambient temperature. The solvent was removed under reduced pressure and the residue was triturated with dichloromethane (100 mL). The insoluble material was removed by filtration through a pad of celite and then the filtrate was concentrated under reduced pressure and purified by flash chromatography on silica gel using dichloromethane/ethyl acetate (95:5) as an eluent to provide N1-phenyl-2-[4-(4,4,5,5-tetramethyl-1,3,2-dioxaborolan-2-yl)phenyl]acetamide (4.82 g, 89%):$^1$H NMR (DMSO-$d_6$, 400 MHz) 10.15(s, 1H), 7.64(d, 2H), 2.59(d, 2H), 7.36(d, 2H), 7.29(t, 2H), 7.03 (t, 1H), 3.67(s, 2H), 1.29(s, 12H); RP-HPLC (Hypersil HS C18, 5 m, 100 A, 250×4.6 mm; 5%–50% acetonitrile over 25 min, 1 mL/min) $t_r$ 11.7 min.

b) N1-Phenyl-2-(4-{4-chloro-7-[4-(4-methylpiperazino)cyclohexyl]-7H-pyrrolo[2,3-d]pyrimidine-5-yl}phenyl)acetamide A mixture of cis-4-chloro-5-iodo-7-[4-(4-methylpiperazino)cyclohexyl]-7H-pyrrolo[2,3-d]pyrimidine (1.0 g, 2.18 mmol), N1-phenyl -2-[4-(4,4,5,5-tetramethyl-1,3,2-dioxaborolan-2-yl)phenyl]acetamide (0.81 g, 2.40 mmol), tetrakis(triphenyl-phosphine)palladium (70 mg, 0.131 mmol) and sodium carbonate monohydrate (0.65 g, 2.40 mmol) in ethylene glycol dimethyl ether (16 mL) and water (8 mL) was heated at 85° C. under an atmosphere of nitrogen for 18 hours. The mixture was cooled to ambient temperature and the solvent was removed under reduced pressure. The residue was purified by flash chromatography on silica using dichloromethane/methanol (9:1) as an eluent to give N1-phenyl-2-(4-{4-chloro-7-[4-(4-methylpiperazino)cyclohexyl]-7H-pyrrolo[2,3-d]pyrimidine-5-yl}phenyl)acetamide (0.74 g, 62%): $^1$H NMR (DMSO-$d_6$, 400 MHz) 10.20(s, 1H), 8.66(s, 1H), 7.81(s, 1H), 7.62(d, 2H), 7.52(d, 2H), 7.41(d, 2H), 7.31(t, 2H), 7.04(t, 1H), 4.83(m, 1H), 3.70(s, 2H)<2.05–2.5(m, 13H), 2.17(s, 3H), 1.59–1.77(m, 4H); RP-HPLC (Hypersil HS C18, 5 m, 100 A, 250×4.6 mm; 25%–100% acetontrile over 10 min, 1 mL/min) $t_r$ 8.23 min.; MS:MH$^+$ 543.2.

c) N-Phenyl-2-(4-{4-amino-7-[4-(4-methylpiperazino)cyclohexyl]-7H-pyrrolo[2,3-d]pyrimidin-5-yl}phenyl)acetamide Trismaleate The N1-phenyl-2-(4-{4-chloro-7-[4-(4-methylpiperazino)cyclohexyl]-7H-pyrrolo[2,3-d]pyrimidine-5-yl}phenyl)acetamide (0.74 g, 1.41 mmol) in 1,4-dioxane (50 mL) and concentrated ammonium hydroxide (50 mL) was heated in a pressure vessel at 120° C. for 18 hours. The mixture was cooled to ambient temperature and the solvents evaporated under reduced pressure. The residue was purified by reverse-phase preparative chromatography then lyophilized to give a light yellow solid (485 mg, 68%). The material was dissolved in ethyl acetate (25 mL) and ethanol (5 mL) then treated with a hot solution of maleic acid (325 mg, 2.79 mmol) in ethyl acetate (20 mL). The slurry was cooled and the solid collected by filtration to give the cis-N-phenyl-2-(4-{ 4-amino-7-[4-(4-methylpiperazino)cyclohexyl ]-7H-pyrrolo[2,3-d]pyrimidin-5-yl}phenyl)acetamide trismaleate as a white solid (630 mg, 80%): $^1$H NMR (DMSO-$d_6$, 400 MHz) 10.18(s, 1H), 8.21(s, 1H), 7.61(d, 2H), 7.28–7.47(m, 7H), 7.05(dd, 1H), 6.34(bs, 2H), 6.16(s, 6H), 4.74(m, 1H), 3.70(s, 2H), 1.6–3.6(20H); RP-HPLC (Hypersil HS C18, 5 m, 100 A, 250×4.6 mm; 25%–100% acetonitrile over 10 min, 1 mL/min) $t_r$ 6.33 min.; MS:MH$^+$ 524.2.

trans-N-phenyl-2-(4-{4-amino-7-[4-(4-methylpiperazino)cyclohexyl]-7H-pyrrolo[2,3-d]pyrimidin-5-yl}phenyl)acetamide trismaleate was prepared from trans-4-chloro-5-iodo-7-[4-(4-methylpiperazino)cyclohexyl]-7H-pyrrolo[2,3-d]pyrimidine (1.0 g, 2.18 mmol) and N1-phenyl -2-[4-(4,4,5,5-tetramethyl-1,3,2-dioxaborolan-2-yl)phenyl]acetamide in a similar method to that described for the cis-isomer: $^1$H NMR (DMSO-$d_6$, 400 MHz) 10.18(s, 1H), 8.18(s, 1H), 7.61(d, 2H), 7.51(m, 5H), 7.31(t, 2H), 7.04(t, 1H), 6.3(bs, 2H), 6.11(s, 6H), 4.58(m, 1H), 3.69(s, 2H), 2.6–3.6(bm, 9H), 2.68(s, 3H), 1.91–2.04(m, 6H), 1.51–1.59(m, 2H);); RP-HPLC (Hypersil HS C18, 5 m, 100 A, 250×4.6 mm; 25%–100% acetonitrile over 10 min, 1 mL/min) $t_r$ 6.07 min.; MS:MH$^+$ 524.3.

General Procedure of the Preparation of Urea Variants

The appropriately substituted isocyanate (1.2 equiv., 0.142 mmol) was added to a solution of the corresponding trans- or cis-5-(4-amino-3-fluorophenyl)-7-[4-(4-methylpiperazino)cyclohexyl]-7H-pyrrolo[2,3-d]pyrimidin-4-amine (50 mg, 0.11 8 mmol) in DMF (2.5 ml) at room temperature and the solution was shaken for 2.5 days. Water (1 ml) was added to each reaction and then concentrated in vacuo. The residues were then purified by mass actuated preparative RP-HPLC (Micromass/Gilson, Hypersil BDS C18, 5 μm, 100×21.2 mm; 100–100% ammonium acetate (0.05 M, pH 4.5)-acetonitrile over 12.5 min, 25 mL/min) to afford products including those detailed in Table 1.

Each sample was analysed by LCMS and in each case the target ion was observed. The retention time is given in Table 1. The LCMS conditions used for the analysis of examples 1–20, 22, 25 and 26 are: LC Column: Hypersil BDS C18, 5 μm, (100×2.1 mm)

Mobile Phase: 0.1M NH$_4$OAc (pH 4.55): MeCN
  10% to 100% MeCN gradient over 8 min.
  100% MeCN for 1 min.
  100% to 10% MeCN over 2 min. at 1 ml/min throughout.

MS method:APCI observing both +ve and −ve ions.

TABLE 1

| Urea variants | | |
|---|---|---|
| Example | RP-HPLC RT (min) | m/z (MH$^-$) |
| Example 514. cis-N-(4-{4-Amino-7-[4-(4-methylpiperazino)cyclohexyl]-7H-pyrrolo[2,3-d]pyrimidin-5-yl}-2-fluorophenyl)-N'-(2,4-difluorophenyl)urea | 3.09 | 579.3 |
| Example 515. cis-N-(4-{4-Amino-7-[4-(4-methylpiperazino)cyclohexyl]-7H-pyrrolo[2,3-d]pyrimidin-5-yl}-2-fluorophenyl)-N'-(4-dimethylaminophenyl)-urea | 2.82 | 586.3 |
| Example 516. cis-N-(4-{4-Amino-7-[4-(4-methylpiperazino)cyclohexyl]-7H-pyrrolo[2,3-d]-pyrimidin-5-yl}-2-fluorophenyl)-N'-benzyl)urea | 2.84 | 557.3 |
| Example 517. cis-N-(4-{4-Amino-7-[4-(4-methylpiperazino)cyclohexyl]-7H-pyrrolo[2,3-d]-pyrimidin-5-yl}-2-fluorophenyl)-N'(3-methyl-benzyl)urea | 3.01 | 571.4 |
| Example 518. cis-N-(4-{4-Amino-7-[4-(4-methylpiperazino)cyclohexyl]-7H-pyrrolo[2,3-d]-pyrimidin-5-yl}-2-fluorophenyl)-N'-(4-phenoxyphenyl)urea | 3.49 | 635.1 |
| Example 519. cis-N-(4-{4-Amino-7-[4-(4-methylpiperazino)cyclohexyl]-7H-pyrrolo[2,3-d]-pyrimidin-5-yl}-2-fluorophenyl)-N'-(4-methylbenzyl)urea | 2.97 | 571.1 |
| Example 520. cis-N-(4-{4-Amino-7-[4-(4-methylpiperazino)cyclohexyl]-7H-pyrrolo[2,3-d]-pyrimidin-5-yl}-2-fluorophenyl)-N'-(3-methylphenyl)urea | 3.14 | 556.9 |

TABLE 1-continued

Urea variants

| Example | RP-HPLC RT (min) | m/z (MH⁻) |
|---|---|---|
| Example 521. cis-N-(4-{4-Amino-7-[4-(4-methyl-piperazino)cyclohexyl]-7H-pyrrolo[2,3-d]-pyrimidin-5-yl}-2-fluorophenyl)-N'-(3,5-dimethoxyphenyl)urea | 3.08 | 603.1 |
| Example 522. cis-N-(4-{4-Amino-7-[4-(4-methyl-piperazino)cyclohexyl]-7H-pyrrolo[2,3-d]-pyrimidin-5-yl}-2-fluorophenyl)-N'-[2-(2-thienyl)ethyl]urea | 2.94 | 577.0 |
| Example 523. cis-N-(4-{4-Amino-7-[4-(4-methyl-piperazino)cyclohexyl]-7H-pyrrolo[2,3-d]-pyrimidin-5-yl}-2-fluorophenyl)-N'-(2-methyl-phenyl)urea | 3.08 | 557.0 |
| Example 524. cis-N-(4-{4-Amino-7-[4-(4-methyl-piperazino)cyclohexyl]-7H-pyrrolo[2,3-d]-pyrimidin-5-yl}-2-fluorophenyl)-N'-(3,5-dichlorophenyl)urea | 3.61 | 611.0 |
| Example 525. cis-N-(4-{4-Amino-7-[4-(4-methyl-piperazino)cyclohexyl]-7H-pyrrolo[2,3-d]-pyrimidin-5-yl}-2-fluorophenyl)-N'-(2,6-dichlorophenyl)urea | 3.02 | 610.9 |
| Example 526. cis-N-(4-{4-Amino-7-[4-(4-methyl-piperazino)cyclohexyl]-7H-pyrrolo[2,3-d]-pyrimidin-5-yl}-2-fluorophenyl)-N'-(3,5-bis-trifluoromethylphenyl)urea | 3.72 | 679.1 |
| Example 527. cis-N-(4-{4-Amino-7-[4-(4-methyl-piperazino)cyclohexyl]-7H-pyrrolo[2,3-d]-pyrimidin-5-yl}-2-fluorophenyl)-N'-(3-methoxy-phenyl)urea | 3.00 | 572.9 |
| Example 528. cis-N-(4-{4-Amino-7-[4-(4-methyl-piperazino)cyclohexyl]-7H-pyrrolo[2,3-d]-pyrimidin-5-yl}-2-fluorophenyl)-N'-(2,4,6-trichlorophenyl)urea | 3.33 | 645.0 |
| Example 529. cis-N-(4-{4-Amino-7-[4-(4-methyl-piperazino)cyclohexyl]-7H-pyrrolo[2,3-d]-pyrimidin-5-yl}-2-fluorophenyl)-N'-(1-biphen-2-yl)-urea | 5.20 | 619.2 |
| Example 530. cis-N-(4-{4-Amino-7-[4-(4-methyl-piperazino)cyclohexyl]-7H-pyrrolo[2,3-d]-pyrimidin-5-yl}-2-fluorophenyl)-N'-(4-methyl-phenyl)urea | 3.38 | 557.3 |
| Example 531. trans-N-(4-{4-Amino-7-[4-(4-methyl-piperazino)cyclohexyl]-7H-pyrrolo[2,3-d]-pyrimidin-5-yl}-2-fluorophenyl)-N'-(3-methyl-phenyl)urea | 2.66 | 557.3 |
| Example 532. cis-N-(4-{4-Amino-7-[4-(4-methyl-piperazino)cyclohexyl]-7H-pyrrolo[2,3-d]-pyrimidin-5-yl}-2-fluorophenyl)-N'-(2-phenoxy-phenyl)urea | 5.41 | 635.3 |
| Example 533. cis-N-(4-{4-Amino-7-[4-(4-methyl-piperazino)cyclohexyl]-7H-pyrrolo[2,3-d]-pynmidin-5-yl}-2-fluorophenyl)-N'-(2,5-dimethoxyphenyl)urea | 3.50 | 603.4 |

Example 534

N1-4-[4-Amino-7-(4-piperidyl)-7H-pyrrolo[2,3-d]pyrimidin-5-yl]-2-fluorophenyl-2,3-dichloro-1-benzenesulfonamide A solution containing N1-4-[4-amino-7-(1-benzyl-4-piperidyl)-7H-pyrrolo[2,3-d]pyrimidin-5-yl]-2-fluorophenyl-2,3-dichloro-1-benzenesulfonamide (0.156 g, 0.25 mmol) and α-chloroethylchloroformate (4 equiv., 1.0 mmol, 0.108 ml) and 1,2-dichloroethane (20 ml) was heated at reflux for a total of 24 h. The solvent was removed, methanol (10 ml) added and the reaction was heated at reflux for a further 24 h. The methanol was removed in vacuo and the residue was purified by column chromatography using neat ethyl acetate (100 ml) followed by 79:19:2 ethyl acetate: methanol: aq NH₄OH as the eluent to afford N1-4-[4-amino-7-(4-piperidyl)-7H-pyrrolo[2,3-d]pyrimidin-5-yl]-2-fluorophenyl-2,3-dichloro-1-benzenesulfonamide (0.105 g, 82%), RP-HPLC RT=2.64 min and m/z 534.9.

Example 535

N1-(4-{4-Amino-7-(4-oxo-cyclohexyl)-7H-pyrrolo[2,3-d]pyrimidin-5-yl}-2-fluorophenyl)-2,3-dichloro-1-benzenesulfonamide tert-Butyl N-4-[4-Chloro-7-(1,4-dioxaspiro[4.5]dec-8-yl)-7H-pyrrolo[2,3-d]pyrimidin-5-yl]-2-chlorophenylcarbamate A suspension of the 4-chloro-7-(1,4-dioxaspiro[4.5]dec-8-yl)-5-iodo-7H-pyrrolo[2,3-d]pyrimidine (6.8 g, 16.2 mmol), tert-butyl N-[2-chloro-4-(4,4,5,5-tetramethyl-1,3,2-dioxaborolan-2-yl)phenyl]carbamate (1.5 equiv, 8.59 g, 24.3 mmol), sodium carbonate (2.5 equiv, 4.30 g, 40.5 mmol) and Pd(PPh₃)₄(4 mol%, 0.76 g, 0.65 mmol) in DME (280 ml) and degassed H₂O (50 mL) was heated at 80° C. under nitrogen for 16 h. The reaction was concentrated under reduced pressure and the residue dissolved in CH₂Cl₂ (500 mL) and washed with water (300 ml). The aqueous layer was re-extracted with CH₂Cl₂(3×300 mL) and the combined organic extracts were combined, dried (MgSO₄) and concentrated in vacuo. Column chromatography purification over silica gel using 1:1 EtOAc:heptane afforded tert-butyl N-4-[4-chloro-7-(1,4-dioxaspiro[4.5]dec-8-yl)-7H-pyrrolo[2,3-d]pyrimidin-5-yl]-2-chlorophenylcarbamate as yellow oil (5.38 g), RP-HPLC RT=4.51 min and m/z 519.2(MH³⁰).

5-(4-Amino-3-chlorophenyl)-7-(1,4-dioxaspiro[4.5]dec-8-yl)-7H-pyrrolo]2,3-d]pyrimidin-4-amine A cloudy mixture of tert-butyl N-4-[4-chloro-7-(1,4-dioxaspiro[4.5]dec-8-yl)-7H-pyrrolo[2,3-d]pyrimidin-5-yl]-2-chlorophenylcarbamate (5.38 g, 10.35 mmol), aq. ammonium hydroxide (28–30%, 100 mL) and dioxane (100 mL) was placed in a sealed vessel at ambient temperature then heated to 120° C. with stirring for 24 h. The reaction was concentrated in vacuo, diluted with EtOAc (300 mL), washed with brine (2×150 mL), dried (MgSO₄) and concentrated under reduced pressure and scrupulously dried to afford 5-(4-amino-3-chlorophenyl)-7-(1,4-dioxaspiro[4.5]dec-8-yl)-7H-pyrrolo[2,3-d]pyrimidin-4-amine as a brown solid (4.0 g), RP-HPLC (5 to 85% CH₃CN in 0.1 N aqueous ammonium acetate over 30 min at 1 mL/min using a Waters Deltapak C18, 300 Å, 150×3.9 mm column) RT=14.049 min., 72%.

4-[4-Amino-5-(4-amino-3-chlorophenyl)-7H-pyrrolo[2,3-d]pyrimidin-7-yl]-1-cyclohexanone 5M HCl (700 mL) was added slowly to a solution of 5-(4-amino-3-chlorophenyl)-7-(1,4-dioxaspiro[4.5]dec-8-yl)-7H-pyrrolo[2,3-d]pyrimidin-4-amine (4.0 g, 10.0 mmol) in acetone (300 mL) at 0° C. then allowed to warm to ambient temperature for 24 h. The acetone was removed under reduced pressure and the acidic layer was basified to approx. pH 8 using sat. aq. Na₂CO₃. After extraction with CH₂Cl₂(4×300 mL), the combined organic layers were dried (MgSO₄) and concentrated to afford 4-[4-amino-5-(4-amino-3-chlorophenyl)-7H-pyrrolo[2,3-d]pyrimidin-7-yl]-1-cyclohexanone as a biege solid (1.71 g), RP-HPLC (5 to 85% CH₃CN in 0.1 N aqueous ammonium acetate over 30 min at 1 mL/min using a Waters Deltapak C18, 300 Å, 150×3.9 mm column) RT=12.392 min., 75%.

N1-(4-{4-Amino-7-(4-oxo-cyclohexyl)-7H-pyrrolo[2,3-d]pyrimidin-5-yl}-2-fluorophenyl)-2,3-dichloro-1-benzenesulfonamide 2,3-Dichlorobenzenesulfonyl chloride (1.1 equiv., 1.04 g, 4.26 mmol) was added to a solution of 4-[4-amino-5-(4-amino-3-chlorophenyl)-7H-pyrrolo[2,3-d]pyrimidin-7-yl]-

1-cyclohexanone (1.38 g, 3.87 mmol) in pyridine (25 mL) at 40° C. After 3 h. at 40° C. and 14 h at ambient temperature, additional 2,3-dichlorobenzenesulfonyl chloride (1.2 g) was added and the reaction stirred at 40° C. for a further 24 h. The reaction was concentrated in vacuo, dissolved in $CH_2Cl_2$(500 ml) and washed with sat. aq. $Na_2CO_3$ (2×100 ml). The organic layer was dried (MgSO$_4$) and concentrated in vacuo to afford a brown solid. Purification by column chromatography over silica gel using 1% MeOH in dichloromethane as the eluent afforded as a white solid (60% pure). Trituration with hot ethyl acetate gave N1-(4-{4-amino-7-(4-oxo-cyclohexyl)-7H-pyrrolo[2,3-d]pyrimidin-5-yl)-2-fluorophenyl)-2,3-dichloro-1-benzenesulfonamide as a white solid (70 mg), ), RP-HPLC RT=3.14 min and m/z 564.2(MH$^{30}$).

Example 536 trans-N1-(4-{4-Amino-7-[4-(4-methylpiperazino)cyclohexyl]-7H-pyrrolo[2,3-d]pyrimidin-5-yl}-2-fluorophenyl)-2,3-dichloro-1-benzenesulfonamide To a solution of N1-(4-{4-amino-7-(4-oxo-cyclohexyl)-7H-pyrrolo[2,3-d]pyrimidin-5-5 yl}-2-fluorophenyl)-2,3-dichloro-1-benzenesulfonamide (0.2 g, 0.35 mmol), N-methylpiperazine (3 equiv, 1.05 mmol, 0.116 mL) and glacial acetic acid (3 equiv., 0.061 mL, 1.05 mmol) in 1,2-dichloroethane (20 mL) under nitrogen was added sodium triacetoxyborohydride (1.3 equiv., 0.096 g, 0.455 mmol). The solution was stirred for 18 hr then additional sodium triacetoxyborohydride (0.10 g) was added and the reaction continued for a further 48 h. The reaction was concentrated in vacuo, partitioned between dichloromethane (100 mL) and sat. aq. NaHCO$_3$ (100 mL). The aqueous layer was re-extracted with dichloromethane (4×100 mL) and the combined organic layers were dried over magnesium sulfate and evaporated to dryness. Purification by column chromatography over silica gel using dichloromethane:methanol (19:1) as the eluent afforded trans-N1-(4-{4-amino-7-[4-(4-methylpiperazino)cyclohexyl]-7H-pyrrolo[2,3-d]pyrimidin-5-yl}-2-fluorophenyl)-2,3-dichloro-1-benzenesulfonamide as a white solid (10 mg), RP-HPLC (5 to 85% CH$_3$CN in 0.1 N aqueous ammonium acetate over 30 min at 1 mL/min using a Waters Deltapak C18, 300 Å, 150×3.9 mm column) RT=14.475 min., 100% and m/z 648.1(MH$^+$)

Example 537

1. 4-Chloro-5-iodo-7-(8-methyl-8-aza[3.2.1]bicyclooctan-3-yl)-7H-pyrrolo[2,3-d]pyrimidine 4-chloro-5-iodo-7H-pyrrolo[2,3-d]pyrimidine (9.78 g, 0.035mol) was dissolved in tetrahydrofuran (400 ml) at room temperature under a nitrogen atmosphere. Tropine (10 g, 0.071 mol) and triphenylphosphine (18.6 g, 0.071 mol) were added to this solution.

The reaction mixture was cooled to 0° C. and diethyl azodicarboxylate (12.35 g, 0.071 mol) was added slowly. Stirring was continued at 0° C. for one hour then the reaction mixture was warmed to room temperature and stirred for 20 hours. The reaction mixture was concentrated under reduced pressure. The residue was dissolved in ethyl acetate (250–300 ml) and concentrated again under reduced pressure. A precipitate formed which was collected by filtration and washed with ethyl acetate to give 4-chloro-5-iodo-7-(8-methyl-8-aza[3.2.1]bicyclooctan-3-yl)-7H-pyrrolo[2,3-d] pyrimidine as a light yellow solid (43%, 6.09 g, 0.015 mol): $^1$H NMR (DMSO-d$_6$, 400 MHz) δ 8.64(s, 1H), 8.13(s, 1H), 4.98(m, 1H), 3.23 (m, 2H), 2.29(s, 3H), 2.22(m, 2H), 2.04(m, 2H), 1.70(m, 4H). TLC (dichloromethane/methanol=9:1) R$_f$ 0.68; LC/MS: MH$^{30}$ =402.9.

2. tert-Butyl N-[4-(4-Chloro-7-(8-methyl-8-aza[3.2.1]bicyclooctan-3-yl)-7H-pyrrolo[2,3-d]pyrimidin-5-yl)-2-fluorophenyl]carbamate A suspension of 4-chloro-5-iodo-7-(8-methyl-8-aza[3.2.1]bicyclooctan-3-yl)-7H-pyrrolo[2,3-d]pyrimidine (6.09 g, 0.015 mol), tert-butyl N-[2-fluoro-4-(4,4,5,5-tetramethyl-1,3,2-dioxaborolan-2-yl)phenyl]carbamate (7.64 g, 0.023 mol), tetrakis(triphenylphosphine)palladium (0) (699 mg, 0.605 mmol) and sodium carbonate (4.01 g, 0.039 mol) in degassed water (45 mL) and dimethoxyethane (240 mL) was heated at 80° C. for 36 h. The reaction mixture was concentrated under reduced pressure, then diluted with dichloromethane and washed with 10% aqueous sodium carbonate, followed by brine. The organic layer was dried over sodium sulfate and concentrated under reduced pressure. The filtrate was purified by column chromatography on silica gel eluting with 5% methanol/dichloromethane/2% ammonium hydroxide to afford tert-butyl N-[4-(4-chloro-7-(8-methyl-8-aza[3.2.1]bicyclooctan-3-yl)-7H-pyrrolo[2,3-d]pyrimidin-5-yl)-2-fluorophenyl]carbamate as a white foam (6.62 g, 0.014 mol): $^1$H NMR (DMSO-d$_6$, 400 MHz) 9.02(brs, 1H), 8.66(m, 1H), 8.03(s, 1H), 7.65(m, 1H), 7.39 (m, 1H), 7.30 (m, 1H), 5.76(s, 1H), 5.05(m, 2H), 3.26(brs, 3H), 2.26(m, 6H), 2.06(m, 2H), 1.73(m, 5H), 1.47(s, 9H). LC/MS: MH$^+$=486.2.

3. 5-(4-Amino-3-fluorophenyl)-7-(8-methyl-8-aza[3.2.1]bicyclooctan-3-yl)-7H-pyrrolo[2,3-d]pyrimidin-4-amine A solution of tert-butyl N-[4-(4-chloro-7-(8-methyl-8-aza[3.2.1]bicyclooctan-3-yl)-7H-pyrrolo[2,3-d]pyrimidin-5-yl)-2-fluorophenyl]carbamate (6.62 g, 0.014 mol) in dioxane (100 mL) and ammonium hydroxide (100 mL) was heated at 120° C. in a stainless steel bomb for 18 hours. The reaction mixture was concentrated under reduced pressure, then diluted with ethyl acetate and washed with water. The aqueous layer was concentrated under reduced pressure at 60° C. and the remaining solid was dried on the lyophilizer. Isolated 5-(4-amino-3-fluorophenyl)-7-(8-methyl-8-aza[3.2.1]bicyclooctan-3-yl)-7H1-pyrrolo[2,3-d]pyrimidin-4-amine as a brown solid (5.73 g, 0.016 mol):); TLC (dichloromethane/methanol 9:1) R$_f$ 0.147. LC/MS: MH$^+$= 367.1.

4. N1-[4-(4-Amino-7-(8-methyl-8-aza[3.2.1]bicyclooctan-3-yl)-7H-pyrrolo[2,3-d]pyrimidin-5-yl)-2-fluorophenyl]-2,3-dichloro-1-benzenesulfonamide 2,3-Dichlorobenzensulfonic Acid Salt A mixture of 5-(4-amino-3-fluorophenyl)-7-(8-methyl-8-aza[3.2.1]bicyclooctan-3-yl)-7H-pyrrolo[2,3-d]pyrimidin-4-amine (4.0 g, 0.011 mol) and 2,3-dichlorobenzenesulfonyl chloride (2.95 g, 0.012 mol) in pyridine (55 mL) was heated at 40° C. for 18 hours. Additional 2,3-dichlorobenzenesulfonyl chloride (429 mg, 1.75 mmol and 671 mg, 2.73 mmol) was added over approximately 3 days. The reaction mixture was concentrated under reduced pressure to give an orange oil/foam (10 g, 0.017 mol). The crude material was purified twice by column chromatography on silica gel. The first column was eluted with 10% methanol/dichloromethane, followed by 10% methanol/dichloromethane/2% ammonium hydroxide to afford N1-[4-

(4-amino-7-(8-methyl-8-aza[3.2.1]bicyclooctan-3-yl)-7H-pyrrolo[2,3-d]pyrimidin-5-yl)-2-fluorophenyl]-2,3-dichloro-1-benzenesulfonamide as an orange oil (7.2 g, 80% purity by HPLC). The second column was eluted with a 0% to 10% methanol/dichloromethane/2% ammonium hydroxide gradient to afford N1-[4-(4-amino-7-(8-methyl-8-aza[3.2.1]bicyclooctan-3-yl)-7H-pyrrolo[2,3-d]pyrimidin-5-yl)-2-fluorophenyl]-2,3-dichloro-1-benzenesulfonamide as a light yellow foam (1.77 g, 3.08 mmol, 99% purity by HPLC): 1H NMR (DMSO-d6, 400 MHz) 8.15 (s, 1H), 7.95(d, 1H), 7.86(m, 2H), 7.58(m, 1H), 7.50(m, 1H), 7.30 (m, 3H), 7.13(m, 2H), 6.18(br s, 2H), 5.05(m, 1H), 3.91(m, 2H), 3.21(s, 1H), 2.75(s, 3H), 2.26(m, 2H), 2.04(m, 4H). LC/MS: MH$^{30}$ =575.0.

5. N1-(4-(4-Amino-7-(8-methyl-8-aza[3.2.1]bicyclooctan-3-yl)-7H-pyrrolo[2,3-d]pyrimidin-5-yl)-2-fluorophenyl]-2,3-dichloro-1-benzenesulfonamide A solution of N1-[4-(4-amino-7-(8-methyl-7H-pyrrolo[2,3-d]pyrimidin-5-yl)-2-fluorophenyl]-2,3-dichloro-1-benzenesulfonamide$_{23}$ dichlorobenzensulfonic acid salt (106 mg, 0.133 mmol) in dichloromethane (30 mL) and a minimal amount of methanol was washed with saturated aqueous sodium bicarbonate. The organic layer was dried over sodium sulfate then concentrated under reduced pressure to afford N1-[4-(4-amino-7-(8-methyl-8-aza[3.2.1]bicyclooctan-3-yl)-7H-pyrrolo[2,3-d]pyrimidin-5-yl)-2-fluorophenyl]-2,3-dichloro-1-benzenesulfonamide as an off-white solid (74 mg, 0.129 mmol): 1H NMR (DMSO-d6, 400 MHz) δ 8.13(s, 1H), 7.99(d, 1H), 7.77(d, 1H), 7.44(t, 1H), 7.28 (t, 1H), 7.06(m, 3H), 6.12(br s, 2H), 5.01 (m, 1H), 3.69(br s, 2H), 2.62(s, 3H), 2.35 (m, 2H), 2.21(m, 2H), 1.94(m, 4H). LC/MS: MH$^{30}$ =575.1.

Example 538

N1-4-(4-Amino-7-}4-[4-(1-methylpiperidyl)piperidyl]-7H-pyrrolo[2,3-d]pyrimidin-5-yl])-2-fluorophenyl-4-fluoro-1-benzenesulfonamide To a solution containing N1-4-[4-amino-7-(4-piperidyl)-7H-pyrrolo[2,3-d]pyrimidin-5-yl]-2-fluorophenyl-4-fluoro-1-benzenesulfonamide (50 mg, 0.103 mmol), 1-methylpiperid-4-one (1.5 equiv., 17.5 mg, 0.019 ml) and glacial acetic acid (0.025 ml) in N-methyl-2-pyrrolidinone (3 ml) was added sodium triacetoxyborohydride (1.3 equiv., 28.1 mg). The reaction was stirred for 24 h at room temperature prior to the addition of extra sodium triacetoxyborohydride (1.3 equiv., 28.1 mg) was added and the reaction continued for a further 48 h. The reaction was concentrated in vacuo, partitioned between dichloromethane (100 mL) and sat. aq. NaHCO$_3$(100 mL). The aqueous layer was re-extracted with dichloromethane (4×100 mL) and the combined organic layers were dried over magnesium sulfate and evaporated to dryness. Purification by column chromatography over silica gel using dichloromethane:methanol:aqueous ammonium hydroxide (78:19:3) as the eluent afforded a biege solid (45 mg, 75%), RP-HPLC RT=2.28 min and m/z 582.1.

General Procedure for Substituted Pyrrolopyrimidine Aryl Sulfonamides

A 0.19 M solution of 5-(4-amino-3-fluorophenyl)-7-[4-(4-methylpiperazino)cyclohexyl]-7H-pyrrolo[2,3-d]pyrimidin-4-amine in pyridine was added one equivalent of substituted aryl sulfonyl chloride. The mixture was heated to 45° C. while being shaken in an Incubator Shaker for 24 h. The reaction mixture was purified by using mass actuated preparative RP-HPLC (Micromass/Gilson, Hypersil BDS C18, 5u, 100×21.2 mm; 100–100% ammonium acetate (0.05 M, pH 4.5)-acetonitrile over 12.5 min, 25 mL/min).

| Structure | RT/min | Example |
|---|---|---|
| 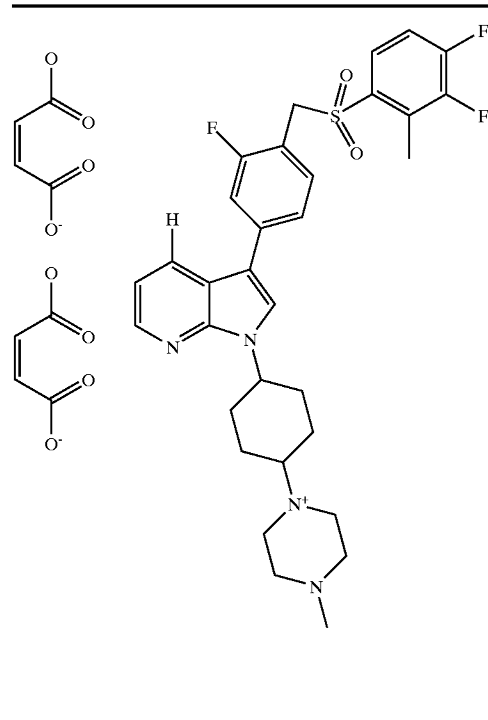 | LC, rt = 3.08  MH+ = 618.3 | 539 |

-continued
| Structure | RT/min | Example |
|---|---|---|
| 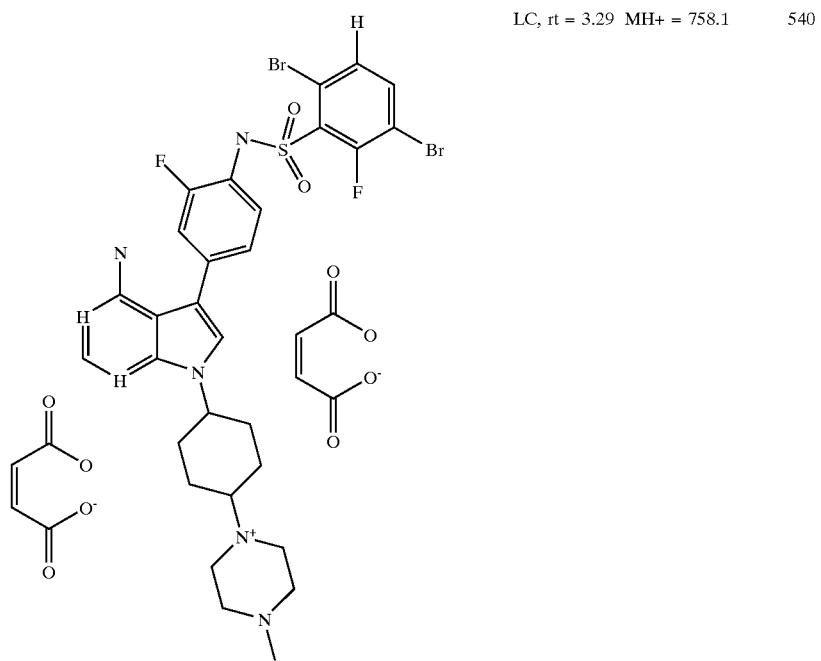 | LC, rt = 3.29  MH+ = 758.1 | 540 |
| 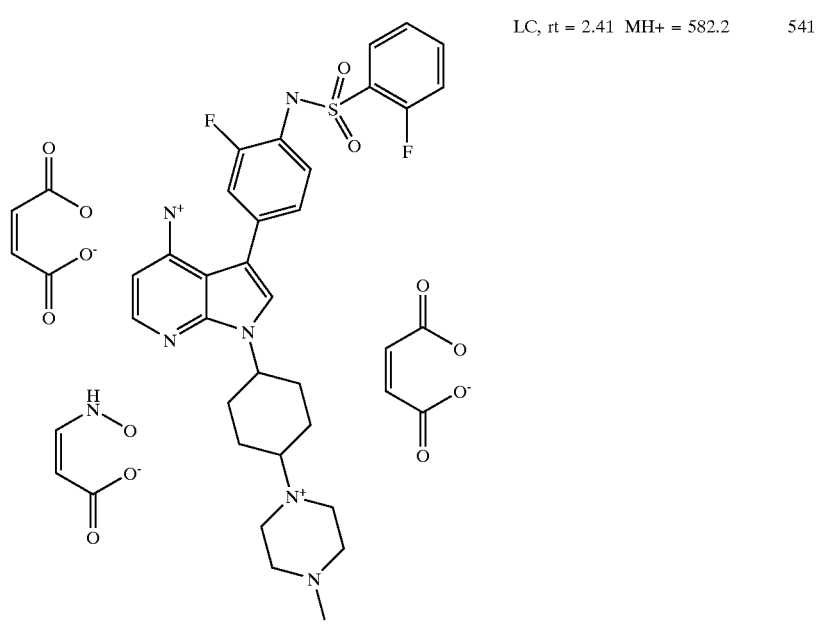 | LC, rt = 2.41  MH+ = 582.2 | 541 |

-continued
| Structure | RT/min | Example |
|---|---|---|
| 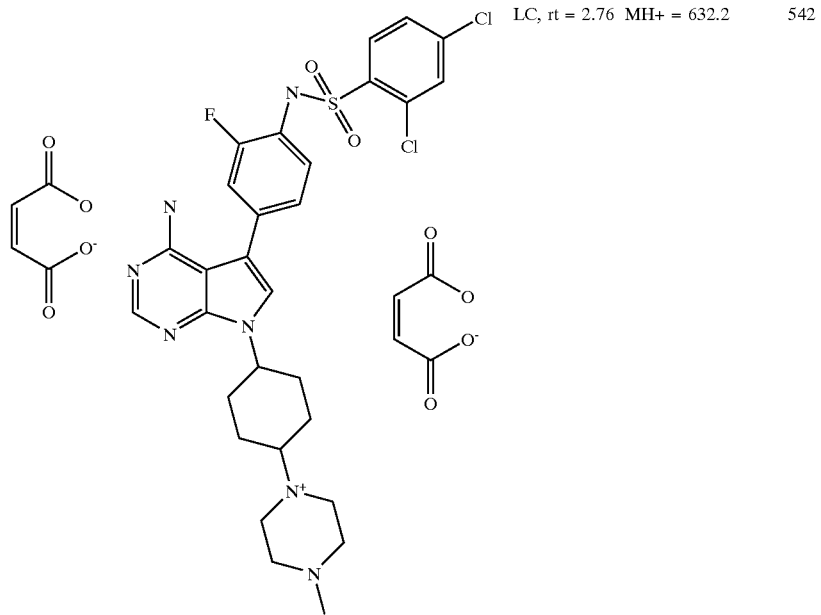 | LC, rt = 2.76  MH+ = 632.2 | 542 |
| 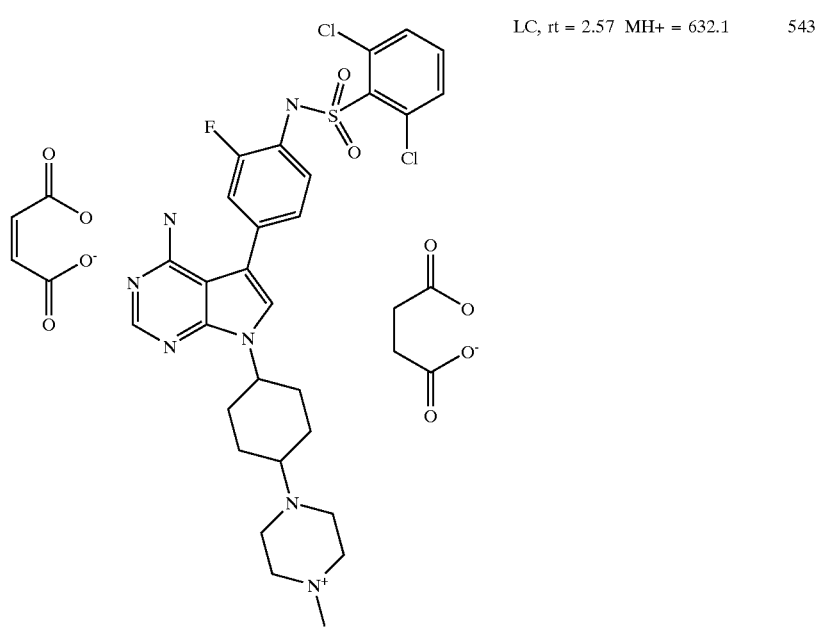 | LC, rt = 2.57  MH+ = 632.1 | 543 |

-continued

| Structure | RT/min | Example |
|---|---|---|
| 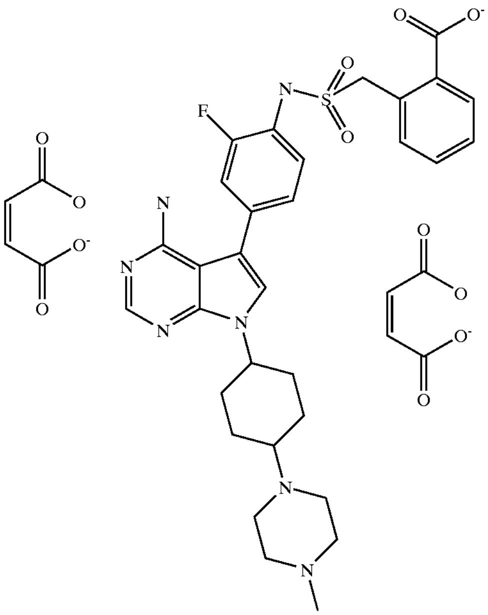 | LC, rt = 2.49 MH+ = 623.2 | 544 |
| 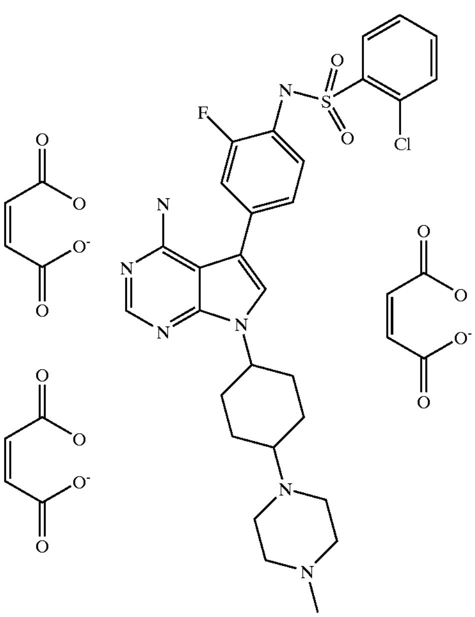 | LC, rt = MH+ | 545 |

-continued

| Structure | RT/min | Example |
|---|---|---|
| 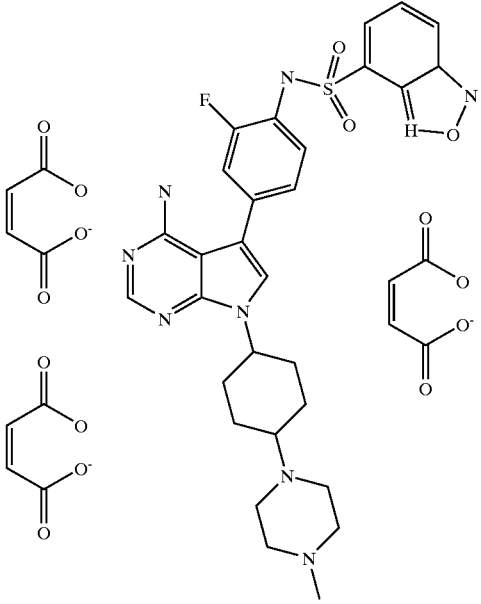 | LC, rt = 2.38  MH+ = 606.3 | 546 |

The following compounds are prepared using the general methods described above.

Trans-N2-(4-{4-amino-7-[4-(4-methylpiperazino)cyclohexyl]-7H-pyrrolo[2,3-d]pyrimidin-5-yl}phenyl)-1,3-benzoxazol-2-amine Trans-N2-(4-{4-amino-7-[4-(4-methylpiperazino)cyclohexyl]-7H-pyrrolo[2,3-d]pyrimidin-5-yl}phenyl)-1,3-(4-methylbenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(5-methylbenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(6-methylbenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(7-methylbenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(4,5-dimethylbenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(4,6-dimethylbenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(4,7-dimethylbenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(5,6-dimethylbenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(5,7-dimethylbenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(6,7-dimethylbenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(4-fluorobenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(5-fluorobenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(6-fluorobenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(7-fluorobenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(4,5-difluorobenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(4,6-di fluorobenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(4,7-difluorobenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(5,6-difluorolbenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(5,7-difluorobenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(6,7-difluorobenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(4-chlorobenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(5-chlorobenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(6-chlorobenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(7-chlorobenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(4,5-dichlorobenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(4,6-dichlorobenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(4,7-dichlorobenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(5,6-dichlorolbenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(5,7-dichlorobenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(6,7-dichlorobenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(5-chloro-4-methylbenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(5-fluoro-4-methylbenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(6-chloro-4-methylbenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(6-fluoro-4-methylbenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(7-chloro-4-methylbenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(7-fluoro-4-methylbenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(4-chloro-5-methylbenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(4-fluoro-5-methylbenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(6-chloro-5-methylbenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(6-fluoro-5-methylbenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(7-chloro-5-methylbenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(7-fluoro-5-methylbenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(4-chloro-6-methylbenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(4-fluoro-6-methylbenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(5-chloro-6-methylbenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(5-fluoro-6-methylbenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(7-chloro-6-methylbenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(7-fluoro-6-methylbenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(4-chloro-7-methylbenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-{4-fluoro-7-methylbenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(5-chloro-7-methylbenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(5-fluoro-7-methylbenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(6-chloro-7-methylbenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-(6-fluoro-7-methylbenzoxazol)-2-amine Trans-N2-(4-{4-amino-7-[4-(4-methylpiperazino)cyclohexyl]-7H-pyrrolo[2,3-d]pyrimidin-5-yl}phenyl)-1,3-benzothiazol-2-amine Trans-N2-(4-{4-amino-7-[4-(4-methylpiperazino)cyclohexyl]-7H-pyrrolo[2,3-d]pyrimidin-5-yl}phenyl)-1,3-(4-methylbenzothiazol)-2-amine Trans-N2-(4-{4-amino-7-[4-(4-methylpiperazino)cyclohexyl]-7H-pyrrolo[2,3-d]pyrimidin-5-yl}phenyl)-1,3-(5-methylbenzothiazol)-2-amine Trans-N2-(4-{4-amino-7-[4-(4-methylpiperazino)cyclohexyl]-7H-pyrrolo[2,3-d]pyrimidin-5-yl}phenyl)-1,3-(6-methylbenzothiazol)-2-amine Trans-N2-(4-{4-amino-7-[4-(4-methylpiperazino)cyclohexyl]-7H-pyrrolo[2,3-d]pyrimidin-5-yl}phenyl)-1,3-(7-methylbenzothiazol)-2-amine Trans-N2-(4-{4-amino-7-[4-(4-methylpiperazino)cyclohexyl]-7H-pyrrolo[2,3-d]pyrimidin-5-yl}phenyl)-1,3-(4,5-dimethylbenzothiazol)-2-amine Trans-N2-(4-{4-amino-7-[4-(4-methylpiperazino)cyclohexyl]-7H-pyrrolo[2,3-d]pyrimidin-5-yl}phenyl)-1,3-{4,6-dimethylbenzothiazol)-2-amine Trans-N2-(4-{4-amino-7-[4-(4-methylpiperazino)cyclohexyl]-7H-pyrrolo[2,3-d]pyrimidin-5-yl}phenyl)-1,3-(4,7-dimethylbenzothiazol)-2-amine Trans-N2-(4-{4-amino-7-[4-(4-methylpiperazino)cyclohexyl]-7H-pyrrolo[2,3-d]pyrimidin-5-yl}phenyl)-1,3-(5,6-dimethylbenzothiazol)-2-amine Trans-N2-(4-{4-amino-7-[4-(4-methylpiperazino)cyclohexyl]-7H-pyrrolo[2,3-d]pyrimidin-5-yl}phenyl)-1,3-(5,7-dimethylbenzothiazol)-2-amine Trans-N2-(4-{4-amino-7-[4-(4-methylpiperazino)cyclohexyl]-7H-pyrrolo[2,3-d]pyrimidin-5-yl}phenyl)-1,3-(6,7-dimethylbenzothiazol)-2-amine Trans-N2-(4-{4-amino-7-[4-(4-methylpiperazino)cyclohexyl]-7H-pyrrolo[2,3-d]pyrimidin-5-yl}phenyl)-1,3-(4-fluorobenzothiazol)-2-amine Trans-N2-(4-{4-amino-7-[4-(4-methylpiperazino)cyclohexyl]-7H-pyrrolo[2,3-d]pyrimidin-5-yl}phenyl)-1,3-(5-fluorobenzothiazol)-2-amine Trans-N2-(4-{4-amino-7-[4-(4-methylpiperazino)cyclohexyl]-7H-pyrrolo[2,3-d]pyrimidin-5-yl}phenyl)-1,3-(6-fluorobenzothiazol)-2-amine Trans-N2-(4-{4-amino-7-[4-(4-methylpiperazino)cyclohexyl]-7H-pyrrolo[2,3-d]pyrimidin-5-yl}phenyl)-1,3-(7-fluorobenzothiazol)-2-amine Trans-N2-(4-{4-amino-7-[4-(4-methylpiperazino)cyclohexyl]-7H-pyrrolo[2,3-d]pyrimidin-5-yl}phenyl)-1,3-(4,5-difluorobenzothiazol)-2-amine Trans-N2-(4-{4-amino-7-[4-(4-methylpiperazino)cyclohexyl]-7H-pyrrolo[2,3-d]pyrimidin-5-yl}phenyl)-1,3-(4,6-difluorobenzothiazol)-2-amine Trans-N2-(4-{4-amino-7-[4-(4-methylpiperazino)cyclohexyl]-7H-pyrrolo[2,3-d]pyrimidin-5-yl}phenyl)-1,3-(4,7-difluorobenzothiazol)-2-amine Trans-N2-(4-{4-amino-7-[4-(4-methylpiperazino)cyclohexyl]-7H-pyrrolo[2,3-d]pyrimidin-5-yl}phenyl)-1,3-(5,6-difluorolbenzothiazol)-2-amine Trans-N2-(4-{4-amino-7-[4-(4-methylpiperazino)cyclohexyl]-7H-pyrrolo[2,3-d]pyrimidin-5-yl}phenyl)-1,3-(5,7-difluorobenzothiazol)-2-amine Trans-N2-(4-{4-amino-7-[4-(4-methylpiperazino)cyclohexyl]-7H-pyrrolo[2,3-d]pyrimidin-5-yl}phenyl)-1,3-(6,7-difluorobenzothiazol)-2-amine Trans-N2-(4-{4-amino-7-[4-(4-methylpiperazino)cyclohexyl]-7H-pyrrolo[2,3-d]pyrimidin-5-yl}phenyl)-1,3-(4-chlorobenzothiazol)-2-amine Trans-N2-(4-{4-amino-7-[4-(4-methylpiperazino)cyclohexyl]-7H-pyrrolo[2,3-d]pyrimidin-5-yl}phenyl)-1,3-(5-chlorobenzothiazol)-2-amine Trans-N2-(4-{4-amino-7-[4-(4-methylpiperazino)cyclohexyl]-7H-pyrrolo[2,3-d]pyrimidin-5-yl}phenyl)-1,3-(6-chlorobenzothiazol)-2-amine Trans-N2-(4-{4-amino-7-[4-(4-methylpiperazino)cyclohexyl]-7H-pyrrolo[2,3-d]pyrimidin-5-yl}phenyl)-1,3-(7-chlorobenzothiazol)-2-amine Trans-N2-(4-{4-amino-7-[4-(4-methylpiperazino)cyclohexyl]-7H-pyrrolo[2,3-d]pyrimidin-5-yl}phenyl)-1,3-(4,5-dichlorobenzothiazol)-2-amine Trans-N2-(4-{4-amino-7-[4-(4-methylpiperazino)cyclohexyl]-7H-pyrrolo[2,3-d]pyrimidin-5-yl}phenyl)-1,3-(4,6-dichlorobenzothiazol)-2-amine Trans-N2-(4-{4-amino-7-[4-(4-methylpiperazino)cyclohexyl]-7H-pyrrolo[2,3-d]pyrimidin-5-yl}phenyl)-1,3-(4,7-dichlorobenzothiazol)-2-amine Trans-N2-(4-{4-amino-7-[4-(4-methylpiperazino)cyclohexyl]-7H-pyrrolo[2,3-d]pyrimidin-5-yl}phenyl)-1,3-(5,6-dichlorolbenzothiazol)-2-amine Trans-N2-(4-{4-amino-7-[4-(4-methylpiperazino)cyclohexyl]-7H-pyrrolo[2,3-d]pyrimidin-5-yl}phenyl)-1,3-(5,7-dichlorobenzothiazol)-2-amine Trans-N2-(4-{4-amino-7-[4-(4-methylpiperazino)cyclohexyl]-7H-pyrrolo[2,3-d]pyrimidin-5-yl}phenyl)-1,3-(6,7-dichlorobenzothiazol)-2-amine Trans-N2-(4-{4-amino-7-[4-(4-methylpiperazino)cyclohexyl]-7H-pyrrolo[2,3-d]pyrimidin-5-yl}phenyl)-1,3-(5-chloro-4-methylbenzothiazol)-2-amine Trans-N2-(4-{4-amino-7-[4-(4-methylpiperazino)cyclohexyl]-7H-pyrrolo[2,3-d]pyrimidin-5-yl}phenyl)-1,3-(5-fluoro-4-methylbenzothiazol)-2-amine Trans-N2-(4-{4-amino-7-[4-(4-methylpiperazino)cyclohexyl]-7H-pyrrolo[2,3-d]pyrimidin-5-yl}phenyl)-1,3-(6-chloro-4-methylbenzothiazol)-2-amine Trans-N2-(4-{4-amino-7-[4-(4-methylpiperazino)cyclohexyl]-7H-pyrrolo[2,3-d]pyrimidin-5-yl}phenyl)-1,3-(6-fluoro-4-methylbenzothiazol)-2-amine Trans-N2-(4-{4-amino-7-[4-(4-methylpiperazino)cyclohexyl]-7H-pyrrolo[2,3-d]pyrimidin-5-yl}phenyl)-1,3-(7-chloro-4-methylbenzothiazol)-2-amine Trans-N2-(4-{4-amino-7-[4-(4-methylpiperazino)cyclohexyl]-7H-pyrrolo[2,3-d]pyrimidin-5-yl}phenyl)-1,3-(7-fluoro-4-methylbenzothiazol)-2-amine Trans-N2-(4-{4-amino-7-[4-(4-methylpiperazino)cyclohexyl]-7H-pyrrolo[2,3-d]pyrimidin-5-yl}phenyl)-1,3-(4-chloro-5-methylbenzothiazol)-2-amine Trans-N2-(4-{4-amino-7-[4-(4-methylpiperazino)cyclohexyl]-7H-pyrrolo[2,3-d]pyrimidin-5-yl}phenyl)-1,3-(4-fluoro-5-methylbenzothiazol)-2-amine Trans-N2-(4-{4-amino-7-[4-(4-methylpiperazino)cyclohexyl]-7H-pyrrolo[2,3-d]pyrimidin-5-yl}phenyl)-1,3-(6-chloro-5-methylbenzothiazol)-2-amine Trans-N2-(4-{4-amino-7-[4-(4-methylpiperazino)cyclohexyl]-7H-pyrrolo[2,3-d]pyrimidin-5-yl}phenyl)-1,3-(6-fluoro-5-methylbenzothiazol)-2-amine Trans-N2-(4-{4-amino-7-[4-(4-methylpiperazino)cyclohexyl]-7H-pyrrolo[2,3-d]pyrimidin-5-yl}phenyl)-1,3-(7-chloro-5-methylbenzothiazol)-2-amine Trans-N2-(4-{4-amino-7-[4-(4-methylpiperazino)cyclohexyl]-7H-pyrrolo[2,3-d]pyrimidin-5-yl}phenyl)-1,3-(7-fluoro-5-methylbenzothiazol)-2-amine Trans-N2-(4-{4-amino-7-[4-(4-methylpiperazino) cyclohexyl]-7H-pyrrolo[2,3-d]pyrimidin-5-yl}phenyl)-1,3-(4-chloro-6-methylbenzothiazol)-2-amine Trans-N2-(4-{4-amino-7-[4-(4-methylpiperazino) cyclohexyl]-7H-pyrrolo[2,3-d]pyrimidin-5-yl}phenyl)-1,3-(4-fluoro-6-methylbenzothiazol)-2-amine Trans-N2-(4-{4-amino-7-[4-(4-methylpiperazino) cyclohexyl]-7H-pyrrolo[2,3-d]pyrimidin-5-yl}phenyl)-1,3-(5-chloro-6-methylbenzothiazol)-2-amine Trans-N2-(4-{4-amino-7-[4-(4-methylpiperazino) cyclohexyl]-7H-pyrrolo[2,3-d]pyrimidin-5-yl}phenyl)-1,3-(5-fluoro-6-methylbenzothiazol)-2-amine Trans-N2-(4-{4-amino-7-[4-(4-methylpiperazino) cyclohexyl]-7H-pyrrolo[2,3-d]pyrimidin-5-yl}phenyl)-1,3-(7-chloro-6-methylbenzothiazol)-2-amine Trans-N2-(4-{4-amino-7-[4-(4-methylpiperazino) cyclohexyl]-7H-pyrrolo[2,3-d]pyrimidin-5-yl}phenyl)-1,3-(7-fluoro-6-methylbenzothiazol)-2-amine Trans-N2-(4-{4-amino-7-[4-(4-methylpiperazino) cyclohexyl]-7H-pyrrolo[2,3-d]pyrimidin-5-yl}phenyl)-1,3-(4-chloro-7-methylbenzothiazol)-2-amine Trans-N2-(4-{4-amino-7-[4-(4-methylpiperazino) cyclohexyl]-7H-pyrrolo[2,3-d]pyrimidin-5-yl}phenyl)-1,3-(4-fluoro-7-methylbenzothiazol)-2-amine Trans-N2-(4-{4-amino-7-[4-(4-methylpiperazino) cyclohexyl]-7H-pyrrolo[2,3-d]pyrimidin-5-yl}phenyl)-1,3-(5-chloro-7-methylbenzothiazol)-2-amine Trans-N2-(4-{4-amino-7-[4-(4-methylpiperazino) cyclohexyl]-7H-pyrrolo[2,3-d]pyrimidin-5-yl}phenyl)-1,3-(5-fluoro-7-methylbenzothiazol)-2-amine Trans-N2-(4-{4-amino-7-[4-(4-methylpiperazino) cyclohexyl]-7H-pyrrolo[2,3-d]pyrimidin-5-yl}phenyl)-1,3-(6-chloro-7-methylbenzothiazol)-2-amine Trans-N2-(4-{4-amino-7-[4-(4-methylpiperazino) cyclohexyl]-7H-pyrrolo[2,3-d]pyrimidin-5-yl}phenyl)-1,3-(6-fluoro-7-methylbenzothiazol)-2-amine Trans-N2-(4-{4-amino-7-[4-(4-methylpiperazino) cyclohexyl]-7H-pyrrolo[2,3-d]pyrimidin-5-yl}phenyl)-benzimidazol-2-amine Trans-N2-(4-{4-amino-7-[4-(4-methylpiperazino) cyclohexyl]-7H-pyrrolo[2,3-d]pyrimidin-5-yl}phenyl)-(4-methylbenzimidazol)-2-amine Trans-N2-(4-{4-amino-7-[4-(4-methylpiperazino) cyclohexyl]-7H-pyrrolo[2,3-d]pyrimidin-5-yl}phenyl)-(5-methylbenzimidazol)-2-amine Trans-N2-(4-{4-amino-7-[4-(4-methylpiperazino) cyclohexyl]-7H-pyrrolo[2,3-d]pyrimidin-5-yl}phenyl)-(6-methylbenzimidazol)-2-amine Trans-N2-(4-{4-amino-7-[4-(4-methylpiperazino) cyclohexyl]-7H-pyrrolo[2,3-d]pyrimidin-5-yl}phenyl)-(7-methylbenzimidazol)-2-amine Trans-N2-(4-{4-amino-7-[4-(4-methylpiperazino) cyclohexyl]-7H-pyrrolo[2,3-d]pyrimidin-5-yl}phenyl)-(4,5-dimethylbenzimidazol)-2-amine Trans-N2-(4-{4-amino-7-[4-(4-methylpiperazino) cyclohexyl]-7H-pyrrolo[2,3-d]pyrimidin-5-yl}phenyl)-(4,6-dimethylbenzimidazol)-2-amine Trans-N2-(4-{4-amino-7-[4-(4-methylpiperazino) cyclohexyl]-7H-pyrrolo[2,3-d]pyrimidin-5-yl}phenyl)-(4,7-dimethylbenzimidazol)-2-amine Trans-N2-(4-{4-amino-7-[4-(4-methylpiperazino) cyclohexyl]-7H-pyrrolo[2,3-d]pyrimidin-5-yl}phenyl)-(5,6-dimethylbenzimidazol)-2-amine Trans-N2-(4-{4-amino-7-[4-(4-methylpiperazino) cyclohexyl]-7H-pyrrolo[2,3-d]pyrimidin-5-yl}phenyl)-(5,7-dimethylbenzimidazol)-2-amine Trans-N2-(4-{4-amino-7-[4-(4-methylpiperazino) cyclohexyl]-7H-pyrrolo[2,3-d]pyrimidin-5-yl}phenyl)-(6,7-dimethylbenzimidazol)-2-amine Trans-N2-(4-{4-amino-7-[4-(4-methylpiperazino) cyclohexyl]-7H-pyrrolo[2,3-d]pyrimidin-5-yl}phenyl)-(4-fluorobenzimidazol)-2-amine Trans-N2-(4-{4-amino-7-[4-(4-methylpiperazino) cyclohexyl]-7H-pyrrolo[2,3-d]pyrimidin-5-yl}phenyl)-(5-fluorobenzimidazol)-2-amine Trans-N2-(4-{4-amino-7-[4-(4-methylpiperazino) cyclohexyl]-7H-pyrrolo[2,3-d]pyrimidin-5-yl}phenyl)-(6-fluorobenzimidazol)-2-amine Trans-N2-(4-{4-amino-7-[4-(4-methylpiperazino) cyclohexyl]-7H-pyrrolo[2,3-d]pyrimidin-5-yl}phenyl)-(7-fluorobenzimidazol)-2-amine Trans-N2-(4-{4-amino-7-[4-(4-methylpiperazino) cyclohexyl]-7H-pyrrolo[2,3-d]pyrimidin-5-yl}phenyl)-(4,5-difluorobenzimidazol)-2-amine Trans-N2-(4-{4-amino-7-[4-(4-methylpiperazino) cyclohexyl]-7H-pyrrolo[2,3-d]pyrimidin-5-yl}phenyl)-(4,6-difluorobenzimidazol)-2-amine Trans-N2-(4-{4-amino-7-[4-(4-methylpiperazino) cyclohexyl]-7H-pyrrolo[2,3-d]pyrimidin-5-yl}phenyl)-(4,7-difluorobenzimidazol)-2-amine Trans-N2-(4-{4-amino-7-[4-(4-methylpiperazino) cyclohexyl]-7H-pyrrolo[2,3-d]pyrimidin-5-yl}phenyl)-(5,6-difluorolbenzimidazol)-2-amine Trans-N2-(4-{4-amino-7-[4-(4-methylpiperazino) cyclohexyl]-7H-pyrrolo[2,3-d]pyrimidin-5-yl}phenyl)-(5,7-difluorobenzimidazol)-2-amine Trans-N2-(4-{4-amino-7-[4-(4-methylpiperazino) cyclohexyl]-7H-pyrrolo[2,3-d]pyrimidin-5-yl}phenyl)-(6,7-difluorobenzimidazol)-2-amine Trans-N2-(4-{4-amino-7-[4-(4-methylpiperazino) cyclohexyl]-7H-pyrrolo[2,3-d]pyrimidin-5-yl}phenyl)-(4-chlorobenzimidazol)-2-amine Trans-N2-(4-{4-amino-7-[4-(4-methylpiperazino) cyclohexyl]-7H-pyrrolo[2,3-d]pyrimidin-5-yl}phenyl)-(5-chlorobenzimidazol)-2-amine Trans-N2-(4-{4-amino-7-[4-(4-methylpiperazino) cyclohexyl]-7H-pyrrolo[2,3-d]pyrimidin-5-yl}phenyl)-(6-chlorobenzimidazol)-2-amine Trans-N2-(4-{4-amino-7-[4-(4-methylpiperazino) cyclohexyl]-7H-pyrrolo[2,3-d]pyrimidin-5-yl}phenyl)-(7-chlorobenzimidazol)-2-amine Trans-N2-(4-{4-amino-7-[4-(4-methylpiperazino) cyclohexyl]-7H-pyrrolo[2,3-d]pyrimidin-5-yl}phenyl)-(4,5-dichlorobenzimidazol)-2-amine Trans-N2-(4-{4-amino-7-[4-(4-methylpiperazino) cyclohexyl]-7H-pyrrolo[2,3-d]pyrimidin-5-yl}phenyl)-(4,6-dichlorobenzimidazol)-2-amine Trans-N2-(4-{4-amino-7-[4-(4-methylpiperazino)cyclohexyl]-7H-pyrrolo[2,3-d]pyrimidin-5-yl}phenyl)-(4,7-dichlorobenzimidazol)-2-amine Trans-N2-(4-{4-amino-7-[4-(4-methylpiperazino)cyclohexyl]-7H-pyrrolo[2,3-d]pyrimidin-5-yl}phenyl)-(5,6-dichlorolbenzimidazol)-2-amine Trans-N2-(4-{4-amino-7-[4-(4-methylpiperazino)cyclohexyl]-7H-pyrrolo[2,3-d]pyrimidin-5-yl}phenyl)-(5,7-dichlorobenzimidazol)-2-amine Trans-N2-(4-{4-amino-7-[4-(4-methylpiperazino)cyclohexyl]-7H-pyrrolo[2,3-d]pyrimidin-5-yl}phenyl)-(6,7-dichlorobenzimidazol)-2-amine Trans-N2-(4-{4-amino-7-[4-(4-methylpiperazino)cyclohexyl]-7H-pyrrolo[2,3-d]pyrimidin-5-yl}phenyl)-(5-chloro-4-methylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(5-fluoro-4-methylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(6-chloro-4-methylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(6-fluoro-4-methylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(7-chloro-4-methylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(7-fluoro-4-methylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(4-chloro-5-methylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(4-fluoro-5-methylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(6-chloro-5-methylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(6-fluoro-5-methylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(7-chloro-5-methylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(7-fluoro-5-methylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(4-chloro-6-methylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(4-fluoro-6-methylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(5-chloro-6-methylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(5-fluoro-6-methylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(7-chloro-6-methylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(7-fluoro-6-methylbenzimidazol)-5-yl}phenyl)-(4-chloro-7-methylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(4-fluoro-7-methylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(5-chloro-7-methylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(5-fluoro-7-methylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(6-chloro-7-methylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(6-fluoro-7-methylbenzimidazol)-2-amine Trans-N2-(4-{4-amino-7-[4-(4-methylpiperazino)cyclohexyl]-7H-pyrrolo[2,3-d]pyrimidin-5-yl}phenyl)-1-methylbenzimidazol-2-amine Trans-N2-(4-{4-amino-7-[4-(4-methylpiperazino)cyclohexyl]-7H-pyrrolo[2,3-d]pyrimidin-5-yl}phenyl)-(1,4-dimethylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(1,5-dimethylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(1,6-dimethylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(1,7-dimethylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(1,4,5-trimethylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(1,4,6-trimethylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(1,4,7-trimethylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(1,5,6-trimethylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(1,5,7-trimethylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(1,6,7-trimethylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(4-fluoro-1-methylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(5-fluoro-1-methylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(6-fluoro-1-methylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(7-fluoro-1-methylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(4,5-difluoro-1-methylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(4,6-difluoro-1-methylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(4,7-difluoro-1-methylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(5,6-difluoro-1-methylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(5,7-difluoro-1-methylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(6,7-difluoro-1-methylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(4-chloro-1-methylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(5-chloro-1-methylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(6-chloro-1-methylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(7-chloro-1-methylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(4,5-dichloro-1-methylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(4,6-dichloro-1-methylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(4,7-dichlorobenzimidazol)-2-amine Trans-N2-(4-{4-amino-7-[4-(4-methylpiperazino)cyclohexyl]-7H-pyrrolo[2,3-d]pyrimidin-5-yl}phenyl)-(5,6-dichloro-1-methylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(5,7-dichloro-1-methylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(6,7-dichloro-1-methylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(5-chloro-1,4-dimethylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(1,4-dimethyl-5-fluorobenzimidazol)-2-amine Trans-N2-(4-{4-amino-7-[4-(4-methylpiperazino)cyclohexyl]-7H-pyrrolo[2,3-d]pyrimidin-5-yl}phenyl)-(6-chloro-1,4-dimethylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(1,4-dimethyl-6-fluorobenzimidazol)-2-amine Trans-N2-(4-{4-amino-7-[4-(4-methylpiperazino)cyclohexyl]-7H-pyrrolo[2,3-d]pyrimidin-5-yl}phenyl)-(7-chloro-1,4-dimethylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(1,4-dimethyl-7-fluorobenzimidazol)-2-amine Trans-N2-(4-{4-amino-7-[4-(4-methylpiperazino)cyclohexyl]-7H-pyrrolo[2,3-d]pyrimidin-5-yl}phenyl)-(4-chloro-1,5-dimethylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(1,5-dimethyl-4-fluorobenzimidazol)-2-amine Trans-N2-(4-{4-amino-7-[4-(4-methylpiperazino)cyclohexyl]-7H-pyrrolo[2,3-d]pyrimidin-5-yl}phenyl)-(6-chloro-1,5-dimethylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(1,5-dimethyl-6-fluorobenzimidazol)-2-amine Trans-N2-(4-{4-amino-7-[4-(4-methylpiperazino)cyclohexyl]-7H-pyrrolo[2,3-d]pyrimidin-5-yl}phenyl)-(7-chloro-1,5-dimethylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(1,5-dimethyl-7-fluorobenzimidazol)-2-amine Trans-N2-(4-{4-amino-7-[4-(4-methylpiperazino)cyclohexyl]-7H-pyrrolo[2,3-d]pyrimidin-5-yl}phenyl)-(4-chloro-1,6-dimethylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(1,6-dimethyl-4-fluorobenzimidazol)-2-amine Trans-N2-(4-{4-amino-7-[4-(4-methylpiperazino)cyclohexyl]-7H-pyrrolo[2,3-d]pyrimidin-5-yl}phenyl)-(5-chloro-1,6-dimethylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(1,6-dimethyl-5-fluorobenzimidazol)-2-amine Trans-N2-(4-{4-amino-7-[4-(4-methylpiperazino)cyclohexyl]-7H-pyrrolo[2,3-d]pyrimidin-5-yl}phenyl)-(7-chloro-1,6-dimethylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(1,6-dimethyl-7-fluorobenzimidazol)-2-amine Trans-N2-(4-{4-amino-7-[4-(4-methylpiperazino)cyclohexyl]-7H-pyrrolo[2,3-d]pyrimidin-5-yl}phenyl)-(4-chloro-1,7-dimethylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(1,7-dimethyl-4-fluorobenzimidazol)-2-amine Trans-N2-(4-{4-amino-7-[4-(4-methylpiperazino)cyclohexyl]-7H-pyrrolo[2,3-d]pyrimidin-5-yl}phenyl)-(5-chloro-1,7-dimethylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(1,7-dimethyl-5-fluorobenzimidazol)-2-amine Trans-N2-(4-{4-amino-7-[4-(4-methylpiperazino)cyclohexyl]-7H-pyrrolo[2,3-d]pyrimidin-5-yl}phenyl)-(6-chloro-1,7-dimethylbenzimidazol)-2-amine Trans-N2-(4-{4-amino-7-[4-(4-methylpiperazino)cyclohexyl]-7H-pyrrolo[2,3-d]pyrimidin-5-yl}phenyl)-(1,7-dimethyl-6-fluorobenzimidazol)-2-amine Trans-N2-(4-{4-amino-7-[4-(4-methylpiperazino)cyclohexyl]-7H-pyrrolo[2,3-d]pyrimidin-5-yl}phenyl)-quinazolino-2-amine Trans-N2-(4-{4-amino-7-[4-(4-methylpiperazino)cyclohexyl]-7H-pyrrolo[2,3-d]pyrimidin-5-yl}phenyl)-(4-methylquinazolino)-2-amine Trans-N2-(4-{4-amino-7-[4-(4-methylpiperazino)cyclohexyl]-7H-pyrrolo[2,3-d]pyrimidin-5-yl}phenyl)-(5-methylquinazolino)-2-amine Trans-N2-(4-{4-amino-7-[4-(4-methylpiperazino)cyclohexyl]-7H-pyrrolo[2,3-d]pyrimidin-5-yl}phenyl)-(6-methylquinazolino)-2-amine Trans-N2-(4-{4-amino-7-[4-(4-methylpiperazino)cyclohexyl]-7H-pyrrolo[2,3-d]pyrimidin-5-yl}phenyl)-(7-methylquinazolino)-2-amine Trans-N2-(4-{4-amino-7-[4-(4-methylpiperazino)cyclohexyl]-7H-pyrrolo[2,3-d]pyrimidin-5-yl}phenyl)-(4,5-dimethylquinazolino)-2-amine Trans-N2-(4-{4-amino-7-[4-(4-methylpiperazino)cyclohexyl]-7H-pyrrolo[2,3-d]pyrimidin-5-yl}phenyl)-(4,6-dimethylquinazolino)-2-amine Trans-N2-(4-{4-amino-7-[4-(4-methylpiperazino)cyclohexyl]-7H-pyrrolo[2,3-d]pyrimidin-5-yl}phenyl)-(4,7-dimethylquinazolino)-2-amine Trans-N2-(4-{4-amino-7-[4-(4-methylpiperazino)cyclohexyl]-7H-pyrrolo[2,3-d]pyrimidin-5-yl}phenyl)-(5,6-dimethylquinazolino)-2-amine Trans-N2-(4-{4-amino-7-[4-(4-methylpiperazino)cyclohexyl]-7H-pyrrolo[2,3-d]pyrimidin-5-yl}phenyl)-(5,7-dimethylquinazolino)-2-amine Trans-N2-(4-{4-amino-7-[4-(4-methylpiperazino)cyclohexyl]-7H-pyrrolo[2,3-d]pyrimidin-5-yl}phenyl)-(6,7-dimethylquinazolino)-2-amine Trans-N2-(4-{4-amino-7-[4-(4-methylpiperazino)cyclohexyl]-7H-pyrrolo[2,3-d]pyrimidin-5-yl}phenyl)-(4-fluoroquinazolino)-2-amine Trans-N2-(4-{4-amino-7-[4-(4-methylpiperazino)cyclohexyl]-7H-pyrrolo[2,3-d]pyrimidin-5-yl}phenyl)-(5-fluoroquinazolino)-2-amine Trans-N2-(4-{4-amino-7-[4-(4-methylpiperazino)cyclohexyl]-7H-pyrrolo[2,3-d]pyrimidin-5-yl}phenyl)-(6-fluoroquinazolino)-2-amine Trans-N2-(4-{4-amino-7-[4-(4-methylpiperazino)cyclohexyl]-7H-pyrrolo[2,3-d]pyrimidin-5-yl}phenyl)-(7-fluoroquinazolino)-2-amine Trans-N2-(4-{4-amino-7-[4-(4-methylpiperazino)cyclohexyl]-7H-pyrrolo[2,3-d]pyrimidin-5-yl}phenyl)-(4,5-difluoroquinazolino)-2-amine Trans-N2-(4-{4-amino-7-[4-(4-methylpiperazino)cyclohexyl]-7H-pyrrolo[2,3-d]pyrimidin-5-yl}phenyl)-(4,6-difluoroquinazolino)-2-amine Trans-N2-(4-{4-amino-7-[4-(4-methylpiperazino)cyclohexyl]-7H-pyrrolo[2,3-d]pyrimidin-5-yl}phenyl)-(4,7-difluoroquinazolino)-2-amine Trans-N2-(4-{4-amino-7-[4-(4-methylpiperazino)cyclohexyl]-7H-pyrrolo[2,3-d]pyrimidin-5-yl}phenyl)-(5,6-difluorolquinazolino)-2-amine Trans-N2-(4-{4-amino-7-[4-(4-methylpiperazino)cyclohexyl]-7H-pyrrolo[2,3-d]pyrimidin-5-yl}phenyl)-(5,7-difluoroquinazolino)-2-amine Trans-N2-(4-{4-amino-7-[4-(4-methylpiperazino)cyclohexyl]-7H-pyrrolo[2,3-d]pyrimidin-5-yl}phenyl)-(6,7-difluoroquinazolino)-2-amine Trans-N2-(4-{4-amino-7-[4-(4-methylpiperazino)cyclohexyl]-7H-pyrrolo[2,3-d]pyrimidin-5-yl}phenyl)-(4-chloroquinazolino)-2-amine Trans-N2-(4-{4-amino-7-[4-(4-methylpiperazino)cyclohexyl]-7H-pyrrolo[2,3-d]pyrimidin-5-yl}phenyl)-(5-chloroquinazolino)-2-amine Trans-N2-(4-{4-amino-7-[4-(4-methylpiperazino)cyclohexyl]-7H-pyrrolo[2,3-d]pyrimidin-5-yl}phenyl)-(6-chloroquinazolino)-2-amine Trans-N2-(4-{4-amino-7-[4-(4-methylpiperazino)cyclohexyl]-7H-pyrrolo[2,3-d]pyrimidin-5-yl}phenyl)-(7-chloroquinazolino)-2-amine Trans-N2-(4-{4-amino-7-[4-(4-methylpiperazino)cyclohexyl]-7H-pyrrolo[2,3-d]pyrimidin-5-yl}phenyl)-(4,5-dichloroquinazolino)-2-amine Trans-N2-(4-{4-amino-7-[4-(4-methylpiperazino)cyclohexyl]-7H-pyrrolo[2,3-d]pyrimidin-5-yl}phenyl)-(4,6-dichloroquinazolino)-2-amine Trans-N2-(4-{4-amino-7-[4-(4-methylpiperazino)cyclohexyl]-7H-pyrrolo[2,3-d]pyrimidin-5-yl}phenyl)-(4,7-dichloroquinazolino)-2-amine Trans-N2-(4-{4-amino-7-[4-(4-methylpiperazino)cyclohexyl]-7H-pyrrolo[2,3-d]pyrimidin-5-yl}phenyl)-(5,6-dichloroquinazolino)-2-amine Trans-N2-(4-{4-amino-7-[4-(4-methylpiperazino)cyclohexyl]-7H-pyrrolo[2,3-d]pyrimidin-5-yl}phenyl)-(5,7-dichloroquinazolino)-2-amine Trans-N2-(4-{4-amino-7-[4-(4-methylpiperazino)cyclohexyl]-7H-pyrrolo[2,3-d]pyrimidin-5-yl}phenyl)-(6,7-dichloroquinazolino)-2-amine Trans-N2-(4-{4-amino-7-[4-(4-methylpiperazino)cyclohexyl]-7H-pyrrolo[2,3-d]pyrimidin-5-yl}phenyl)-(5-chloro-4-methylquinazolino)-2-amine Trans-N2-(4-{4-amino-7-[4-(4-methylpiperazino)cyclohexyl]-7H-pyrrolo[2,3-d]pyrimidin-5-yl}phenyl)-(5-fluoro-4-methylquinazolino)-2-amine Trans-N2-(4-{4-amino-7-[4-(4-methylpiperazino)cyclohexyl]-7H-pyrrolo[2,3-d]pyrimidin-5-yl}phenyl)-(6-chloro-4-methylquinazolino)-2-amine Trans-N2-(4-{4-amino-7-[4-(4-methylpiperazino)cyclohexyl]-7H-pyrrolo[2,3-d]pyrimidin-5-yl}phenyl)-(6-fluoro-4-methylquinazolino)-2-amine Trans-N2-(4-{4-amino-7-[4-(4-methylpiperazino)cyclohexyl]-7H-pyrrolo[2,3-d]pyrimidin-5-yl}phenyl)-(7-chloro-4-methylquinazolino)-2-amine Trans-N2-(4-{4-amino-7-[4-(4-methylpiperazino)cyclohexyl]-7H-pyrrolo[2,3-d]pyrimidin-5-yl}phenyl)-(7-fluoro-4-methylquinazolinol)-2-amine Trans-N2-(4-{4-amino-7-[4-(4-methylpiperazino)cyclohexyl]-7H-pyrrolo[2,3-d]pyrimidin-5-yl}phenyl)-(4-chloro-5-methylquinazolino)-2-amine Trans-N2-(4-{4-amino-7-[4-(4-methylpiperazino)cyclohexyl]-7H-pyrrolo[2,3-d]pyrimidin-5-yl}phenyl)-(4-fluoro-5-methylquinazolino)-2-amine Trans-N2-(4-{4-amino-7-[4-(4-methylpiperazino)cyclohexyl]-7H-pyrrolo[2,3-d]pyrimidin-5-yl}phenyl)-(6-chloro-5-methylquinazolino)-2-amine Trans-N2-(4-{4-amino-7-[4-(4-methylpiperazino)cyclohexyl]-7H-pyrrolo[2,3-d]pyrimidin-5-yl}phenyl)-(6-fluoro-5-methylquinazolino)-2-amine Trans-N2-(4-{4-amino-7-[4-(4-methylpiperazino)cyclohexyl]-7H-pyrrolo[2,3-d]pyrimidin-5-yl}phenyl)-(7-chloro-5-methylquinazolino)-2-amine Trans-N2-(4-{4-amino-7-[4-(4-methylpiperazino)cyclohexyl]-7H-pyrrolo[2,3-d]pyrimidin-5-yl}phenyl)-(7-fluoro-5-methylquinazolino)-2-amine Trans-N2-(4-{4-amino-7-[4-(4-methylpiperazino)cyclohexyl]-7H-pyrrolo[2,3-d]pyrimidin-5-yl}phenyl)-(4-chloro-6-methylquinazolino)-2-amine Trans-N2-(4-{4-amino-7-[4-(4-methylpiperazino)cyclohexyl]-7H-pyrrolo[2,3-d]pyrimidin-5-yl}phenyl)-(4-fluoro-6-methylquinazolino)-2-amine Trans-N2-(4-{4-amino-7-[4-(4-methylpiperazino)cyclohexyl]-7H-pyrrolo[2,3-d]pyrimidin-5-yl}phenyl)-(5-chloro-6-methylquinazolino)-2-amine Trans-N2-(4-{4-amino-7-[4-(4-methylpiperazino)cyclohexyl]-7H-pyrrolo[2,3-d]pyrimidin-5-yl}phenyl)-(5-fluoro-6-methylquinazolino)-2-amine Trans-N2-(4-{4-amino-7-[4-(4-methylpiperazino)cyclohexyl]-7H-pyrrolo[2,3-d]pyrimidin-5-yl}phenyl)-(7-chloro-6-methylquinazolino)-2-amine Trans-N2-(4-{4-amino-7-[4-(4-methylpiperazino)cyclohexyl]-7H-pyrrolo[2,3-d]pyrimidin-5-yl}phenyl)-(7-fluoro-6-methylquinazolino)-2-amine Trans-N2-(4-{4-amino-7-[4-(4-methylpiperazino)cyclohexyl]-7H-pyrrolo[2,3-d]pyrimidin-5-yl}phenyl)-(4-chloro-7-methylquinazolino)-2-amine Trans-N2-(4-{4-amino-7-[4-(4-methylpiperazino)cyclohexyl]-7H-pyrrolo[2,3-d]pyrimidin-5-yl}phenyl)-(4-fluoro-7-methylquinazolino)-2-amine Trans-N2-(4-{4-amino-7-[4-(4-methylpiperazino)cyclohexyl]-7H-pyrrolo[2,3-d]pyrimidin-5-yl}phenyl)-(5-chloro-7-methylquinazolino)-2-amine Trans-N2-(4-{4-amino-7-[4-(4-methylpiperazino)cyclohexyl]-7H-pyrrolo[2,3-d]pyrimidin-5-yl}phenyl)-(5-fluoro-7-methylquinazolino)-2-amine Trans-N2-(4-{4-amino-7-[4-(4-methylpiperazino)cyclohexyl]-7H-pyrrolo[2,3-d]pyrimidin-5-yl}phenyl)-(6-chloro-7-methylquinazolino)-2-amine Trans-N2-(4-{4-amino-7-[4-(4-methylpiperazino)cyclohexyl]-7H-pyrrolo[2,3-d]pyrimidin-5-yl}phenyl)-(6-fluoro-7-methylquinazolino)-2-amine Cis-N2-(4-{4-amino-7-[4-(4-methylpiperazino)cyclohexyl]-7H-pyrrolo[2,3-d]pyrimidin-5-yl}phenyl)-1,3-benzoxazol-2-amine Cis-N2-(4-{4-amino-7-[4-(4-methylpiperazino)cyclohexyl]-7H-pyrrolo[2,3-d]pyrimidin-5-yl}phenyl)-1,3-(4-methylbenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(5-methylbenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(6-methylbenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(7-methylbenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(4,5-dimethylbenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(4,6-dimethylbenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(4,7-dimethylbenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(5,6-dimethylbenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(5,7-dimethylbenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(6,7-dimethylbenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(4-fluorobenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(5-fluorobenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(6-fluorobenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(7-fluorobenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(4,5-difluorobenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(4,6-difluorobenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(4,7-difluorobenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(5,6-difluorolbenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(5,7-difluorobenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(6,7-difluorobenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(4-chlorobenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(5-chlorobenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(6-chlorobenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(7-chlorobenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(4,5-dichlorobenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(4,6-dichlorobenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(4,7-dichlorobenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(5,6-dichlorolbenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(5,7-dichlorobenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(6,7-dichlorobenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(5-chloro-4-methylbenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(5-fluoro-4-methylbenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(6-chloro-4-methylbenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(6-fluoro-4-methylbenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(7-chloro-4-methylbenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(7-fluoro-4-methylbenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(4-chloro-5-methylbenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(4-fluoro-5-methylbenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(6-fluoro-5-methylbenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(6-fluoro-5-methylbenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(7-chloro-5-methylbenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(7-chloro-5-methylbenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(4-fluoro-6-methylbenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(4-chloro-6-methylbenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(5-chloro-6-methylbenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(5-fluoro-6-methylbenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(7-chloro-6-methylbenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(7-fluoro-6-methylbenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(4-chloro-7-methylbenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(4-fluoro-7-methylbenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(5-chloro-7-methylbenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(5-fluoro-7-methylbenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(6-chloro-7-methylbenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-(6-fluoro-7-methylbenzoxazol)-2-amine Cis-N2-(4-{4-amino-7-[4-(4-methylpiperazino)cyclohexyl]-7H-pyrrolo[2,3-d]pyrimidin-5-yl}phenyl)-1,3-benzothiazol-2-amine Cis-N2-(4-{4-amino-7-[4-(4-methylpiperazino)cyclohexyl]-7H-pyrrolo[2,3-d]pyrimidin-5-yl}phenyl)-1,3-(4-methylbenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(5-methylbenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(6-methylbenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(7-methylbenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(4,5-dimethylbenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(4,6-dimethylbenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(4,7-dimethylbenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(5,6-dimethylbenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(5,7-dimethylbenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(6,7-dimethylbenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(4-fluorobenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(5-fluorobenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(6-fluorobenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(7-fluorobenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(4,5-difluorobenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(4,6-difluorobenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(4,7-difluorobenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(5,6-difluorolbenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(5,7-difluorobenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(6,7-difluorobenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(4-chlorobenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(5-chlorobenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(6-chlorobenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(7-chlorobenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(4,5-dichlorobenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(4,6-dichlorobenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(4,7-dichlorobenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(5,6-dichlorobenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(5,7-dichlorobenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(6,7-dichlorobenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(5-chloro-4-methylbenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(5-fluoro-4-methylbenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(6-chloro-4-methylbenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(6-fluoro-4-methylbenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(7-chloro-4-methylbenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(7-fluoro-4-methylbenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(4-chloro-5-methylbenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(4-fluoro-5-methylbenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(6-chloro-5-methylbenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(6-fluoro-5-methylbenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(7-chloro-5-methylbenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(7-fluoro-5-methylbenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(4-chloro-6-methylbenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(4-fluoro-6-methylbenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(5-chloro-6-methylbenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(5-fluoro-6-methylbenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(7-chloro-6-methylbenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(7-fluoro-6-methylbenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(4-chloro-7-methylbenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(4-fluoro-7-methylbenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(5-chloro-7-methylbenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(5-fluoro-7-methylbenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(6-chloro-7-methylbenzothiazol)-2-amine Cis-N2-(4-{4-amino-7-[4-(4-methylpiperazino)cyclohexyl]-7H-pyrrolo[2,3-d]pyrimidin-5-yl}phenyl)-1,3-(6-fluoro-7-methylbenzothiazol)-2-amine Cis-N2-(4-{4-amino-7-[4-(4-methylpiperazino)cyclohexyl]-7H-pyrrolo[2,3-d]pyrimidin-5-yl}phenyl)-benzimidazol-2-amine Cis-N2-(4-{4-amino-7-[4-(4-methylpiperazino)cyclohexyl]-7H-pyrrolo[2,3-d]pyrimidin-5-yl}phenyl)-(4-methylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(5-methylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(6-methylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(7-methylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(4,5-dimethylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(4,6-dimethylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(4,7-dimethylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(5,6-dimethylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(5,7-dimethylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(6,7-dimethylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(4-fluorobenzimidazol)-2-amine Cis-N2-(4-{4-amino-7-[4-(4-methylpiperazino)cyclohexyl]-7H-pyrrolo[2,3-d]pyrimidin-5-yl}phenyl)-(5-fluorobenzimidazol)-2-amine Cis-N2-(4-{4-amino-7-[4-(4-methylpiperazino)cyclohexyl]-7H-pyrrolo[2,3-d]pyrimidin-5-yl}phenyl)-(6-fluorobenzimidazol)-2-amine Cis-N2-(4-{4-amino-7-[4-(4-methylpiperazino)cyclohexyl]-7H-pyrrolo[2,3-d]pyrimidin-5-yl}phenyl)-(7-fluorobenzimidazol)-2-amine Cis-N2-(4-{4-amino-7-[4-(4-methylpiperazino)cyclohexyl]-7H-pyrrolo[2,3-d]pyrimidin-5-yl}phenyl)-(4,5-difluorobenzimidazol)-2-amine Cis-N2-(4-{4-amino-7-[4-(4-methylpiperazino)cyclohexyl]-7H-pyrrolo[2,3-d]pyrimidin-5-yl}phenyl)-(4,6-difluorobenzimidazol)-2-amine Cis-N2-(4-{4-amino-7-[4-(4-methylpiperazino)cyclohexyl]-7H-pyrrolo[2,3-d]pyrimidin-5-yl}phenyl)-(4,7-difluorobenzimidazol)-2-amine Cis-N2-(4-{4-amino-7-[4-(4-methylpiperazino)cyclohexyl]-7H-pyrrolo[2,3-d]pyrimidin-5-yl}phenyl)-(5,6-difluorolbenzimidazol)-2-amine Cis-N2-(4-{4-amino-7-[4-(4-methylpiperazino)cyclohexyl]-7H-pyrrolo[2,3-d]pyrimidin-5-yl}phenyl)-(5,7-difluorobenzimidazol)-2-amine Cis-N2-(4-{4-amino-7-[4-(4-methylpiperazino)cyclohexyl]-7H-pyrrolo[2,3-d]pyrimidin-5-yl}phenyl)-(6,7-difluorobenzimidazol)-2-amine Cis-N2-(4-{4-amino-7-[4-(4-methylpiperazino)cyclohexyl]-7H-pyrrolo[2,3-d]pyrimidin-5-yl}phenyl)-(4-chlorobenzimidazol)-2-amine Cis-N2-(4-{4-amino-7-[4-(4-methylpiperazino)cyclohexyl]-7H-pyrrolo[2,3-d]pyrimidin-5-yl}phenyl)-(5-chlorobenzimidazol)-2-amine Cis-N2-(4-{4-amino-7-[4-(4-methylpiperazino)cyclohexyl]-7H-pyrrolo[2,3-d]pyrimidin-5-yl}phenyl)-(6-chlorobenzimidazol)-2-amine Cis-N2-(4-{4-amino-7-[4-(4-methylpiperazino)cyclohexyl]-7H-pyrrolo[2,3-d]pyrimidin-5-yl}phenyl)-(7-chlorobenzimidazol)-2-amine Cis-N2-(4-{4-amino-7-[4-(4-methylpiperazino)cyclohexyl]-7H-pyrrolo[2,3-d]pyrimidin-5-yl}phenyl)-(4,5-dichlorobenzimidazol)-2-amine Cis-N2-(4-{4-amino-7-[4-(4-methylpiperazino)cyclohexyl]-7H-pyrrolo[2,3-d]pyrimidin-5-yl}phenyl)-(4,6-dichlorobenzimidazol)-2-amine Cis-N2-(4-{4-amino-7-[4-(4-methylpiperazino)cyclohexyl]-7H-pyrrolo[2,3-d]pyrimidin-5-yl}phenyl)-(4,7-dichlorobenzimidazol)-2-amine Cis-N2-(4-{4-amino-7-[4-(4-methylpiperazino)cyclohexyl]-7H-pyrrolo[2,3-d]pyrimidin-5-yl}phenyl)-(5,6-dichlorolbenzimidazol)-2-amine Cis-N2-(4-{4-amino-7-[4-(4-methylpiperazino)cyclohexyl]-7H-pyrrolo[2,3-d]pyrimidin-5-yl}phenyl)-(5,7-dichlorobenzimidazol)-2-amine Cis-N2-(4-{4-amino-7-[4-(4-methylpiperazino)cyclohexyl]-7H-pyrrolo[2,3-d]pyrimidin-5-yl}phenyl)-(6,7-dichlorobenzimidazol)-2-amine Cis-N2-(4-{4-amino-7-[4-(4-methylpiperazino)cyclohexyl]-7H-pyrrolo[2,3-d]pyrimidin-5-yl}phenyl)-(5-chloro-4-methylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(5-fluoro-4-methylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(6-chloro-4-methylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(6-fluoro-4-methylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(7-chloro-4-methylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(7-fluoro-4-methylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(4-chloro-5-methylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(4-fluoro-5-methylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(6-chloro-5-methylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(6-fluoro-5-methylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(7-chloro-5-methylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(7-fluoro-5-methylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(4-chloro-6-methylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(4-fluoro-6-methylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(5-chloro-6-methylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(5-fluoro-6-methylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(7-chloro-6-methylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(7-fluoro-6-methylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(4-chloro-7-methylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(4-fluoro-7-methylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(5-chloro-7-methylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(5-fluoro-7-methylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(6-chloro-7-methylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(6-fluoro-7-methylbenzimidazol)-2-amine Cis-N2-(4-{4-amino-7-[4-(4-methylpiperazino)cyclohexyl]-7H-pyrrolo[2,3-d]pyrimidin-5-yl}phenyl)-1-methylbenzimidazol-2-amine Cis-N2-(4-{4-amino-7-[4-(4-methylpiperazino)cyclohexyl]-7H-pyrrolo[2,3-d]pyrimidin-5-yl}phenyl)-(1,4-dimethylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(1,5-dimethylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(1,6-dimethylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(1,7-dimethylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(1,4,5-trimethylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(1,4,6-trimethylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(1,4,7-trimethylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(1,5,6-trimethylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(1,5,7-trimethylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(1,6,7-trimethylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(4-fluoro-1-methylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(5-fluoro-1-methylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(6-fluoro-1-methylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(7-fluoro-1-methylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(4,5-difluoro-1-methylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(4,6-difluoro-1-methylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(4,7-difluoro-1-methylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(5,6-difluoro-1-methylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(5,7-difluoro-1-methylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(6,7-difluoro-1-methylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(4-chloro-1-methylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(5-chloro-1-methylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(6-chloro-1-methylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(7-chloro-1-methylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(4,5-dichloro-1-methylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(4,6-dichloro-1-methylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(4,7-dichlorobenzimidazol)-2-amine Cis-N2-(4-{4-amino-7-[4-(4-methylpiperazino)cyclohexyl]-7H-pyrrolo[2,3-d]pyrimidin-5-yl}phenyl)-(5,6-dichloro-1-methylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(5,7-dichloro-1-methylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(6,7-dichloro-1-methylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(5-chloro-1,4-dimethylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(1,4-dimethyl-5-fluorobenzimidazol)-2-amine Cis-N2-(4-{4-amino-7-[4-(4-methylpiperazino)cyclohexyl]-7H-pyrrolo[2,3-d]pyrimidin-5-yl}phenyl)-(6-chloro-1,4-dimethylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(1,4-dimethyl-6-fluorobenzimidazol)-2-amine Cis-N2-(4-{4-amino-7-[4-(4-methylpiperazino)cyclohexyl]-7H-pyrrolo[2,3-d]pyrimidin-5-yl}phenyl)-(7-chloro-1,4-dimethylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(1,4-dimethyl-7-fluorobenzimidazol)-2-amine Cis-N2-(4-{4-amino-7-[4-(4-methylpiperazino)cyclohexyl]-7H-pyrrolo[2,3-d]pyrimidin-5-yl}phenyl)-(4-chloro-1,5-dimethylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(1,5-dimethyl-4-fluorobenzimidazol)-2-amine Cis-N2-(4-{4-amino-7-[4-(4-methylpiperazino)cyclohexyl]-7H-pyrrolo[2,3-d]pyrimidin-5-yl}phenyl)-(6-chloro-1,5-dimethylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(1,5-dimethyl-6-fluorobenzimidazol)-2-amine Cis-N2-(4-{4-amino-7-[4-(4-methylpiperazino)cyclohexyl]-7H-pyrrolo[2,3-d]pyrimidin-5-yl}phenyl)-(7-chloro-1,5-dimethylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(1,5-dimethyl-7-fluorobenzimidazol)-2-amine Cis-N2-(4-{4-amino-7-[4-(4-methylpiperazino)cyclohexyl]-7H-pyrrolo[2,3-d]pyrimidin-5-yl}phenyl)-(4-chloro-1,6-dimethylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(1,6-dimethyl-4-fluorobenzimidazol)-2-amine Cis-N2-(4-{4-amino-7-[4-(4-methylpiperazino)cyclohexyl]-7H-pyrrolo[2,3-d]pyrimidin-5-yl}phenyl)-(5-chloro-1,6-dimethylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(1,6-dimethyl-5-fluorobenzimidazol)-2-amine Cis-N2-(4-{4-amino-7-[4-(4-methylpiperazino)cyclohexyl]-7H-pyrrolo[2,3-d]pyrimidin-5-yl}phenyl)-(7-chloro-1,6-dimethylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(1,6-dimethyl-7-fluorobenzimidazol)-2-amine Cis-N2-(4-{4-amino-7-[4-(4-methylpiperazino)cyclohexyl]-7H-pyrrolo[2,3-d]pyrimidin-5-yl}phenyl)-(4-chloro-1,7-dimethylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(1,7-dimethyl-4-fluorobenzimidazol)-2-amine Cis-N2-(4-{4-amino-7-[4-(4-methylpiperazino)cyclohexyl]-7H-pyrrolo[2,3-d]pyrimidin-5-yl}phenyl)-(5-chloro-1,7-dimethylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(1,7-dimethyl-5-fluorobenzimidazol)-2-amine Cis-N2-(4-{4-amino-7-[4-(4-methylpiperazino)cyclohexyl]-7H-pyrrolo[2,3-d]pyrimidin-5-yl}phenyl)-(6-chloro-1,7-dimethylbenzimidazol)-2-amine Cis-N2-(4-{4-amino-7-[4-(4-methylpiperazino)cyclohexyl]-7H-pyrrolo[2,3-d]pyrimidin-5-yl}phenyl)-(1,7-dimethyl-6-fluorobenzimidazol)-2-amine Cis-N2-(4-{4-amino-7-[4-(4-methylpiperazino)cyclohexyl]-7H-pyrrolo[2,3-d]pyrimidin-5-yl}phenyl)-quinazolino-2-amine Cis-N2-(4-{4-amino-7-[4-(4-methylpiperazino)cyclohexyl]-7H-pyrrolo[2,3-d]pyrimidin-5-yl}phenyl)-(4-methylquinazolino)-2-amine Cis-N2-(4-{4-amino-7-[4-(4-methylpiperazino)cyclohexyl]-7H-pyrrolo[2,3-d]pyrimidin-5-yl}phenyl)-(5-methylquinazolino)-2-amine Cis-N2-(4-{4-amino-7-[4-(4-methylpiperazino)cyclohexyl]-7H-pyrrolo[2,3-d]pyrimidin-5-yl}phenyl)-(6-methylquinazolino)-2-amine Cis-N2-(4-{4-amino-7-[4-(4-methylpiperazino)cyclohexyl]-7H-pyrrolo[2,3-d]pyrimidin-5-yl}phenyl)-(7-methylquinazolino)-2-amine Cis-N2-(4-{4-amino-7-[4-(4-methylpiperazino)cyclohexyl]-7H-pyrrolo[2,3-d]pyrimidin-5-yl}phenyl)-(4,5-dimethylquinazolino)-2-amine Cis-N2-(4-{4-amino-7-[4-(4-methylpiperazino)cyclohexyl]-7H-pyrrolo[2,3-d]pyrimidin-5-yl}phenyl)-(4,6-dimethylquinazolino)-2-amine Cis-N2-(4-{4-amino-7-[4-(4-methylpiperazino)cyclohexyl]-7H-pyrrolo[2,3-d]pyrimidin-5-yl}phenyl)-(4,7-dimethylquinazolino)-2-amine Cis-N2-(4-{4-amino-7-[4-(4-methylpiperazino)cyclohexyl]-7H-pyrrolo[2,3-d]pyrimidin-5-yl}phenyl)-(5,6-dimethylquinazolino)-2-amine Cis-N2-(4-{4-amino-7-[4-(4-methylpiperazino)cyclohexyl]-7H-pyrrolo[2,3-d]pyrimidin-5-yl}phenyl)-(5,7-dimethylquinazolino)-2-amine Cis-N2-(4-{4-amino-7-[4-(4-methylpiperazino)cyclohexyl]-7H-pyrrolo[2,3-d]pyrimidin-5-yl}phenyl)-(6,7-dimethylquinazolino)-2-amine Cis-N2-(4-{4-amino-7-[4-(4-methylpiperazino)cyclohexyl]-7H-pyrrolo[2,3-d]pyrimidin-5-yl}phenyl)-(4-fluoroquinazolino)-2-amine Cis-N2-(4-{4-amino-7-[4-(4-methylpiperazino)cyclohexyl]-7H-pyrrolo[2,3-d]pyrimidin-5-yl}phenyl)-(5-fluoroquinazolino)-2-amine Cis-N2-(4-{4-amino-7-[4-(4-methylpiperazino)cyclohexyl]-7H-pyrrolo[2,3-d]pyrimidin-5-yl}phenyl)-(6-fluoroquinazolino)-2-amine Cis-N2-(4-{4-amino-7-[4-(4-methylpiperazino)cyclohexyl]-7H-pyrrolo[2,3-d]pyrimidin-5-yl}phenyl)-(7-fluoroquinazolino)-2-amine Cis-N2-(4-{4-amino-7-[4-(4-methylpiperazino)cyclohexyl]-7H-pyrrolo[2,3-d]pyrimidin-5-yl}phenyl)-(4,5-difluoroquinazolino)-2-amine Cis-N2-(4-{4-amino-7-[4-(4-methylpiperazino)cyclohexyl]-7H-pyrrolo[2,3-d]pyrimidin-5-yl}phenyl)-(4,6-difluoroquinazolino)-2-amine Cis-N2-(4-{4-amino-7-[4-(4-methylpiperazino)cyclohexyl]-7H-pyrrolo[2,3-d]pyrimidin-5-yl}phenyl)-(4,7-difluoroquinazolino)-2-amine Cis-N2-(4-{4-amino-7-[4-(4-methylpiperazino)cyclohexyl]-7H-pyrrolo[2,3-d]pyrimidin-5-yl}phenyl)-(5,6-difluorolquinazolino)-2-amine Cis-N2-(4-{4-amino-7-[4-(4-methylpiperazino)cyclohexyl]-7H-pyrrolo[2,3-d]pyrimidin-5-yl}phenyl)-(5,7-difluoroquinazolino)-2-amine Cis-N2-(4-{4-amino-7-[4-(4-methylpiperazino)cyclohexyl]-7H-pyrrolo[2,3-d]pyrimidin-5-yl}phenyl)-(6,7-difluoroquinazolino)-2-amine Cis-N2-(4-{4-amino-7-[4-(4-methylpiperazino)cyclohexyl]-7H-pyrrolo[2,3-d]pyrimidin-5-yl}phenyl)-(4-chloroquinazolino)-2-amine Cis-N2-(4-{4-amino-7-[4-(4-methylpiperazino)cyclohexyl]-7H-pyrrolo[2,3-d]pyrimidin-5-yl}phenyl)-(5-chloroquinazolino)-2-amine Cis-N2-(4-{4-amino-7-[4-(4-methylpiperazino)cyclohexyl]-7H-pyrrolo[2,3-d]pyrimidin-5-yl}phenyl)-(6-chloroquinazolino)-2-amine Cis-N2-(4-{4-amino-7-[4-(4-methylpiperazino)cyclohexyl]-7H-pyrrolo[2,3-d]pyrimidin-5-yl}phenyl)-(7-chloroquinazolino)-2-amine Cis-N2-(4-{4-amino-7-[4-(4-methylpiperazino)cyclohexyl]-7H-pyrrolo[2,3-d]pyrimidin-5-yl}phenyl)-(4,5-dichloroquinazolino)-2-amine Cis-N2-(4-{4-amino-7-[4-(4-methylpiperazino)cyclohexyl]-7H-pyrrolo[2,3-d]pyrimidin-5-yl}phenyl)-(4,6-dichloroquinazolino)-2-amine Cis-N2-(4-{4-amino-7-[4-(4-methylpiperazino)cyclohexyl]-7H-pyrrolo[2,3-d]pyrimidin-5-yl}phenyl)-(4,7-dichloroquinazolino)-2-amine Cis-N2-(4-{4-amino-7-[4-(4-methylpiperazino)cyclohexyl]-7H-pyrrolo[2,3-d]pyrimidin-5-yl}phenyl)-(5,6-dichlorolquinazolino)-2-amine Cis-N2-(4-{4-amino-7-[4-(4-methylpiperazino)cyclohexyl]-7H-pyrrolo[2,3-d]pyrimidin-5-yl}phenyl)-(5,7-dichloroquinazolino)-2-amine Cis-N2-(4-{4-amino-7-[4-(4-methylpiperazino)cyclohexyl]-7H-pyrrolo[2,3-d]pyrimidin-5-yl}phenyl)-(6,7-dichloroquinazolino)-2-amine Cis-N2-(4-{4-amino-7-[4-(4-methylpiperazino)cyclohexyl]-7H-pyrrolo[2,3-d]pyrimidin-5-yl}phenyl)-(5-chloro-4-methylquinazolino)-2-amine Cis-N2-(4-{4-amino-7-[4-(4-methylpiperazino)cyclohexyl]-7H-pyrrolo[2,3-d]pyrimidin-5-yl}phenyl)-(5-fluoro-4-methylquinazolino)-2-amine Cis-N2-(4-{4-amino-7-[4-(4-methylpiperazino)cyclohexyl]-7H-pyrrolo[2,3-d]pyrimidin-5-yl}phenyl)-(6-chloro-4-methylquinazolino)-2-amine Cis-N2-(4-{4-amino-7-[4-(4-methylpiperazino)cyclohexyl]-7H-pyrrolo[2,3-d]pyrimidin-5-yl}phenyl)-(6-fluoro-4-methylquinazolino)-2-amine Cis-N2-(4-{4-amino-7-[4-(4-methylpiperazino)cyclohexyl]-7H-pyrrolo[2,3-d]pyrimidin-5-yl}phenyl)-(7-chloro-4-methylquinazolino)-2-amine Cis-N2-(4-{4-amino-7-[4-(4-methylpiperazino)cyclohexyl]-7H-pyrrolo[2,3-d]pyrimidin-5-yl}phenyl)-(7-fluoro-4-methylquinazolinol)-2-amine Cis-N2-(4-{4-amino-7-[4-(4-methylpiperazino)cyclohexyl]-7H-pyrrolo[2,3-d]pyrimidin-5-yl}phenyl)-(4-chloro-5-methylquinazolino)-2-amine Cis-N2-(4-{4-amino-7-[4-(4-methylpiperazino)cyclohexyl]-7H-pyrrolo[2,3-d]pyrimidin-5-yl}phenyl)-(4-fluoro-5-methylquinazolino)-2-amine Cis-N2-(4-{4-amino-7-[4-(4-methylpiperazino)cyclohexyl]-7H-pyrrolo[2,3-d]pyrimidin-5-yl}phenyl)-(6-chloro-5-methylquinazolino)-2-amine Cis-N2-(4-{4-amino-7-[4-(4-methylpiperazino)cyclohexyl]-7H-pyrrolo[2,3-d]pyrimidin-5-yl}phenyl)-(6-fluoro-5-methylquinazolino)-2-amine Cis-N2-(4-{4-amino-7-[4-(4-methylpiperazino)cyclohexyl]-7H-pyrrolo[2,3-d]pyrimidin-5-yl}phenyl)-(7-chloro-5-methylquinazolino)-2-amine Cis-N2-(4-{4-amino-7-[4-(4-methylpiperazino)cyclohexyl]-7H-pyrrolo[2,3-d]pyrimidin-5-yl}phenyl)-(7-fluoro-5-methylquinazolino)-2-amine Cis-N2-(4-{4-amino-7-[4-(4-methylpiperazino)cyclohexyl]-7H-pyrrolo[2,3-d]pyrimidin-5-yl}phenyl)-(4-chloro-6-methylquinazolino)-2-amine Cis-N2-(4-{4-amino-7-[4-(4-methylpiperazino)cyclohexyl]-7H-pyrrolo[2,3-d]pyrimidin-5-yl}phenyl)-(4-fluoro-6-methylquinazolino)-2-amine Cis-N2-(4-{4-amino-7-[4-(4-methylpiperazino)cyclohexyl]-7H-pyrrolo[2,3-d]pyrimidin-5-yl}phenyl)-(5-chloro-6-methylquinazolino)-2-amine Cis-N2-(4-{4-amino-7-[4-(4-methylpiperazino)cyclohexyl]-7H-pyrrolo[2,3-d]pyrimidin-5-yl}phenyl)-(5-fluoro-6-methylquinazolino)-2-amine Cis-N2-(4-{4-amino-7-[4-(4-methylpiperazino)cyclohexyl]-7H-pyrrolo[2,3-d]pyrimidin-5-yl}phenyl)-(7-chloro-6-methylquinazolino)-2-amine Cis-N2-(4-{4-amino-7-[4-(4-methylpiperazino)cyclohexyl]-7H-pyrrolo[2,3-d]pyrimidin-5-yl}phenyl)-(7-fluoro-6-methylquinazolino)-2-amine Cis-N2-(4-{4-amino-7-[4-(4-methylpiperazino)cyclohexyl]-7H-pyrrolo[2,3-d]pyrimidin-5-yl}phenyl)-(4-chloro-7-methylquinazolino)-2-amine Cis-N2-(4-{4-amino-7-[4-(4-methylpiperazino)cyclohexyl]-7H-pyrrolo[2,3-d]pyrimidin-5-yl}phenyl)-(4-fluoro-7-methylquinazolino)-2-amine Cis-N2-(4-{4-amino-7-[4-(4-methylpiperazino)cyclohexyl]-7H-pyrrolo[2,3-d]pyrimidin-5-yl}phenyl)-(5-chloro-7-methylquinazolino)-2-amine Cis-N2-(4-{4-amino-7-[4-(4-methylpiperazino)cyclohexyl]-7H-pyrrolo[2,3-d]pyrimidin-5-yl}phenyl)-(5-fluoro-7-methylquinazolino)-2-amine Cis-N2-(4-{4-amino-7-[4-(4-methylpiperazino)cyclohexyl]-7H-pyrrolo[2,3-d]pyrimidin-5-yl}phenyl)-(6-chloro-7-methylquinazolino)-2-amine Cis-N2-(4-{4-amino-7-[4-(4-methylpiperazino)cyclohexyl]-7H-pyrrolo[2,3-d]pyrimidin-5-yl}phenyl)-(6-fluoro-7-methylquinazolino)-2-amine In addition to the foregoing compounds, the corresponding 2-fluorophynyl analogs of the above list of compounds are also preferred, e.g., cis-N2-(4-{4-amino-7-[4-(4-methylpiperazino)-cyclohexyl]-7H-pyrrolo[2,3-d]pyrimidin-5-yl}-3-fluorophynyl)-(6-fluoro-7-methylquinazolino)-2-amine.

We claim:

1. A compound represented by the following structural formula:

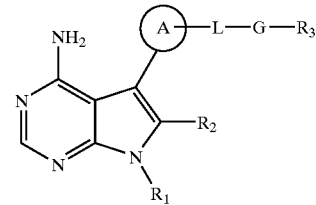

and pharmaceutically acceptable salts thereof, wherein:

Ring A is a six membered aromatic ring or a five or six membered heteroaromatic ring which is optionally substituted with one or more substituents selected from the group consisting of a substituted or unsubstituted aliphatic group, a halogen, a substituted or unsubstituted aromatic group, substituted or unsubstituted heteroaromatic group, substituted or unsubstituted cycloalkyl, substituted or unsubstituted heterocycloalkyl, substituted or unsubstituted aralkyl, substituted or unsubstituted heteroaralkyl, cyano, nitro, —NR$_4$R$_5$, —C(O)$_2$H, —OH, a substituted or unsubstituted alkoxycarbonyl, —C(O)$_2$-haloalkyl, a substituted or unsubstituted alkylthio ether, a substituted or unsubstituted alkylsulfoxide, a substituted or unsubstituted alkylsulfone, a substituted or unsubstituted arylthio ether, a substituted or unsubstituted arylsulfoxide, a substituted or unsubstituted arylsulfone, a substituted or unsubstituted alkyl carbonyl, —C(O)-haloalkyl, a substituted or unsubstituted alkoxy group, a substituted or unsubstituted aryloxy group, carboxamido, tetrazolyl, trifluoromethylsulphonamido, trifluoromethylcarbonylamino, a substituted or unsubstituted alkynyl, a substituted or unsubstituted alkenyl, a substituted or unsubstituted alkyl amido, a substituted or unsubstituted aryl amido, —NR$_{95}$C(O)R$_{95}$, a substituted or unsubstituted styryl and a substituted or unsubstituted aralkyl amido, wherein R$_{95}$ is an aliphatic group or an aromatic group;

L is —O—; —S—; —S(O)—; —S(O)$_2$—; —N(R)—; —N(C(O)OR)—; —N(C(O)R)—; —N(SO$_2$R); —CH$_2$O—; —CH$_2$S—; —CH$_2$N(R)—; —C(NR)—; —CH$_2$N(C(O)R))—; —CH$_2$N(C(O)OR)—; —CH$_2$N(SO$_2$R)—; —CH(NHR)—; —CH(NHC(O)R)—; —CH(NHSO$_2$R); —CH(NHC(O)OR)—; —CH(OC(O)R)—; —CH(OC(O)NHR)—; —CH=CH—; —C(=NOR)—; —C(O)—; —CH(OR)—; —C(O)N(R)—; N(R)C(O)—; —N(R)S(O)—; —N(R)S(O)$_2$—;

—OC(O)N(R)—; —N(R)C(O)N(R)—; —NRC(O)O—; —S(O)N(R)—; —S(O)$_2$N(R)—; N(C(O)R)S(O)—; N(C(O)R)S(O)$_2$—; —N(R)S(O)N(R); —N(R)S(O)$_2$N(R); —C(O)N(R)C(O)—; —S(O)N(R)C(O)—; —S(O)$_2$N(R)C(O)—; —OS(O)N(R)—; —OS(O)$_2$N(R)—; —N(R)S(O)O—; —N(R)S(O)$_2$O—; —N(R)S(O)C(O)—; —NR)S(O)$_2$C(O)—; —SON(C(O)R)—; —SO$_2$N(C(O)R)—; —N(R)SON(R)—; —N(R)SO$_2$N(R); —C(O)O—; CHR)S(O)—; —CH(R)S(O)$_2$—; —CH(R)N(C(O)OR)—; —CH(R)N(C(O)R)—; —CH(R)N(SO$_2$R); —CH(R)O—; —CH(R)S—; —CH(R)N(R)—; —CH(R)N(C(O)R))—; —CH(R)N(C(O)OR)—; —CH(R)N(SO$_2$R)—; —CH(R)C(=NOR)—; —CH(R)C(O)—; —CH(R)CH(OR)—; —CH(R)C(O)N(R)—; —CH(R)N(R)C(O)—; —CH(R)N(R)S(O)—; —CH(R)N(R)S(O)$_2$—; —CH(R)OC(O)N(R)—; —CH(R)N(R)C(O)N(R)—; —CH(R)N(R)C(O)O—; —CH(R)S(O)N(R)—; —CH(R)S(O)$_2$N(R)—; —CH(R)N(C(O)R)S(O)—; —CH(R)N(C(O)R)S(O)$_2$—; —CH(R)N(R)S(O)N(R)—; —CH(R)N(R)S(O)$_2$N(R)—; —CH(R)C(O)N(R)C(O)—; —CH(R)S(O)N(R)C(O)—; —CH(R)S(O)$_2$N(R)C(O)—; —CH(R)OS(O)N(R)—; —CH(R)OS(O)$_2$N(R)—; —CH(R)N(R)S(O)O—; —CH(R)N(R)S(O)$_2$O—; —CH(R)N(R)S(O)C(O)—; —CH(R)N(R)S(O)$_2$C(O)—; —CH(R)SON(C(O)R)—; —CH(R)S(O)$_2$N(C(O)R)—; —CH(R)N(R)SON(R)—; —CH(R)N(R)S(O)$_2$N(R)—; or —CH(R)C(O)O—, wherein each R and R' is, independently, —H, an acyl group, a substituted or unsubstituted aliphatic group, a substituted or unsubstituted aromatic group, a substituted or unsubstituted arylalkyl group, a substituted or unsubstituted heteroaromatic group, or a substituted or unsubstituted cycloalkyl group or a substituted or unsubstituted arylalkyl group; or L is —R$_b$N(R)S(O)$_2$— wherein R$_b$ is an alkylene group which when taken together with the sulphonamide group to which it is bound forms a five or six membered ring fused to ring A;

G is a direct bond; —(CH$_2$)$_j$—, wherein j is 1 to 6; a C$_2$–C$_6$-alkenylene group, a C$_3$–C$_8$-cycloalkylene group or a C$_1$–C$_6$-oxaalkylene group;

R$_1$ is a substituted aliphatic group, a substituted cycloalkyl, a substituted bicycloalkyl, a substituted cycloalkenyl, an optionally substituted aromatic group, an optionally substituted heteroaromatic group, an optionally substituted heteroaralkyl, an optionally substituted heterocycloalkyl, an optionally substituted heterobicycloalkyl, an optionally substituted alkylamido, and optionally substituted arylamido, an optionally substituted —S(O)$_2$-alkyl or optionally substituted —S(O)$_2$-cycloalkyl, a —C(O)-alkyl or an optionally substituted —(O)-alkyl, provided that when R$_1$ is an aliphatic group or cycloalkyl group, R$_1$ is not exclusively substituted with one or more substitutents selected from the group consisting of hydroxyl and lower alkyl ethers, provided that the heterocycloalkyl is not 2-phenyl-1,3-dioxan-5-yl and provided that an aliphatic group is not substituted exclusively with one or more aliphatic groups;

wherein one or more substituents are selected from the group consisting of a substituted or unsubstituted aliphatic group, a substituted or unsubstituted aromatic group, a substituted or unsubstituted heteroaromatic, a substituted or unsubstituted aralkyl, a substituted or unsubstituted heteroaralkyl, a substituted or unsubstituted cycloalkyl, a substituted or unsubstituted heterocycloalkyl, a substituted or unsubstituted aromatic ether, a substituted or unsubstituted aliphatic ether, a substituted or unsubstituted alkoxycarbonyl, a substituted or unsubstituted alkylcarbonyl, a substituted or unsubstituted arylcarbonyl, a substituted or unsubstituted heteroarylcarbonyl, substituted or unsubstituted aryloxycarbonyl, —OH, a substituted or unsubstituted aminocarbonyl, an oxime, a substituted or unsubstituted azabicycloalkyl, heterocycloalkyl, oxo, aldehyde, a substituted or unsubstituted alkyl sulfonamido group, a substituted or unsubstituted aryl sulfonamido group, a substituted or unsubstituted bicycloalkyl, a substituted or unsubstituted heterobicycloalkyl, cyano, —NH$_2$, an alkylamino, ureido, thioureido; or R$_1$ is —B—E, wherein
  B is a substituted or unsubstituted cycloalkyl, a substituted or unsubstituted heterocycloalkyl, a substituted or unsubstituted aromatic, a substituted or unsubstituted heteroaromatic, an alkylene, an aminoalkyl, an alkylenecarbnonyl, or an aminoalkylcarbonyl; and
  E is a substituted or unsubstituted azacycloalkyl, a substituted or unsubstituted azacycloalkylcarbonyl, a substituted or unsubstituted azacycloalkylsulfonyl, a substituted or unsubstituted azacycloalkylalkyl, a substituted or unsubstituted heteroaryl, a substituted or unsubstituted heteroarylcarbonyl, a substituted or unsubstituted heteroarylsulfonyl, a substituted or unsubstituted heteroaralkyl, a substituted or unsubstituted alkyl sulfonamido, a substituted or unsubstituted aryl sulfonamido, a substituted or unsubstituted bicycloalkyl, a substituted or unsubstituted ureido, a substituted or unsubstituted thioureido or a substituted or unsubstituted aryl;

R$_2$ is —H, a substituted or unsubstituted aliphatic group, a substituted or unsubstituted cycloalkyl, a halogen, —OH, cyano, a substituted or unsubstituted aromatic group, a substituted or unsubstituted heteroaromatic group, a substituted or unsubstituted heterocycloalkyl, a substituted or unsubstituted aralkyl, a substituted or unsubstituted heteroaralkyl, —(CH$_2$)$_{0-3}$NR$_4$R$_5$, or —(CH$_2$)$_{0-3}$C(O)NR$_4$R$_5$;

R$_3$ is an unsubstituted aliphatic group, a substituted or unsubstituted alkenyl group, a substituted or unsubstituted cycloalkyl, a substituted or unsubstituted aromatic group, a substituted or unsubstituted heteroaromatic group, or a substituted or unsubstituted heterocycloalkyl;

provided that L is —SN(R)—, —S(O)N(R)—, —S(O)$_2$N(R)—, —N(R)S—, —N(R)S(O)—, —N(R)S(O)$_2$—, —N(R)SN(R')—, —N(R)S(O)N(R')—, or —N(R)S(O)$_2$N(R')13 when R$_3$ is an unsubstituted aliphatic group, a substituted or unsubstituted alkenyl group;

provided that when L is —O—, —CH$_2$NR—, —C(O)NR— or —NRC(O)— and R$_3$ is azacycloalkyl or azaheteroaryl, G is a direct bond; a C$_2$–C$_6$-alkenylene group, a C$_3$–C$_8$-cycloalkylene group or a C$_1$–C$_6$-oxaalkylene; and provided that when L is —O— and R$_3$ is phenyl, G is a direct bond; a C$_2$–C$_6$-alkenylene group, a C$_3$–C$_8$-cycloalkylene group or a C$_1$–C$_6$-oxaalkylene;

R$_4$, R$_5$ and the nitrogen atom together form a 3, 4, 5, 6 or 7-membered, substituted or unsubstituted heterocycloalkyl, substituted or unsubstituted heterobicycloalkyl or a substituted or unsubstituted heteroaromatic; or R$_4$ and R$_5$ are each, independently, —H, azabicycloalkyl, heterocycloalkyl, a substituted or unsubstituted alkyl group or Y—Z;

Y is selected from the group consisting of —C(O)—, —CH$_2$)$_p$—, —S(O)$_2$—, —C(O)O—, —SO$_2$NH—, —CONH—, —(CH$_2$)$_p$O—, —(CH$_2$)$_p$NH—, —(CH$_2$)$_p$S—, —(CH$_2$)$_p$S(O)—, and —(CH2)$_p$S(O)$_2$—;

p is an integer from 0 to 6; and

Z is —H, a substituted or unsubstituted alkyl, substituted or unsubstituted amino, substituted or unsubstituted aryl, substituted or unsubstituted heteroaryl or substituted or unsubstituted heterocycloalkyl group.

2. The compound of claim 1, wherein R$_3$ is selected from the group consisting of a substituted or unsubstituted phenyl, a substituted or unsubstituted naphthyl, a substituted or unsubstituted pyridyl, a substituted or unsubstituted thienyl, a substituted or unsubstituted benzotriazole, a substituted or unsubstituted tetrahydropyranyl, a substituted or unsubstituted tetrahydrofuranyl, a substituted or unsubstituted dioxane, a substituted or unsubstituted dioxolane, a substituted or unsubstituted quinoline, a substituted or unsubstituted thiazole, substituted or unsubstituted isoxazole, substituted or unsubstituted cyclopentyl, a substituted or unsubstituted benzofuran, substituted or unsubstituted benzothiophene, substituted or unsubstituted benzisoxazole, substituted or unsubstituted benzisothiazole, substituted or unsubstituted benzothiazole, substituted or unsubstituted benzoxazole, substituted or unsubstituted benzoxazole, substituted or unsubstituted benzimidazole, substituted or unsubstituted benzoxadiazole, substituted or unsubstituted benzothiadiazole, substituted or unsubstituted isoquinoline, substituted or unsubstituted quinoxaline, substituted or unsubstituted indole and substituted or unsubstituted pyrazole.

3. The compound of claim 2 wherein R$_3$ is substituted with one or more substituent selected from the group consisting of F, Cl, Br, I, CH$_3$, NO$_2$, OCF$_3$, OCH$_3$, CN, CO$_2$CH$_3$, CF$_3$, t-butyl, pyridyl, substituted or unsubstituted oxazolyl, substituted or unsubstituted benzyl, substituted or unsubstituted benzenesulfonyl, substituted or unsubstituted phenoxy, substituted or unsubstituted phenyl, substituted or unsubstituted amino, carboxyl, substituted or unsubstituted tetrazolyl, styryl, —S-(substituted or unsubstituted aryl), —S-(substituted or unsubstituted heteroaryl), substituted or unsubstituted heteroaryl, substituted or unsubstituted heterocycloalkyl, —NR$_f$R$_g$, alkynyl, —C(O)NR$_f$R$_g$, R$_c$, and CH$_2$OR$_c$;

R$_f$, R$_g$ and the nitrogen atom together form a 3, 4, 5, 6 or 7-membered, substituted or unsubstituted heterocycloalkyl, substituted or unsubstituted heterobicycloalkyl or a substituted or unsubstituted heteroaromatic; or R$_f$ and R$_g$ are each, independently, —H, a substituted or unsubstituted aliphatic group, or a substituted or unsubstituted aromatic group; and R$_c$ is hydrogen, or substituted or unsubstituted alkyl or substituted or unsubstituted aryl, —W—(CH$_2$)$_t$—NR$_d$R$_e$, —W—(CH$_2$)$_t$—O-alkyl, —W—(CH$_2$)$_t$—S-alkyl, —W—(CH$_2$)$_t$—OH; or —W—(CH$_2$)$_t$—OR$_f$;

t is an integer from 0 to 6;

W is a bond or —O—, —S—, —S(O)—, —S(O)$_2$—, or —NR$_k$—;

R$_k$ is —H or alkyl; and

R$_d$, R$_e$ and the nitrogen atom to which they are attached together form a 3, 4, 5, 6 or 7-membered substituted or unsubstituted heterocycloalkyl or substituted or unsubstituted heterobicyclic group; or R$_d$ and R$_e$ are each, independently, —H, alkyl, alkanoyl or —K—D;

K is —S(O)$_2$—, —C(O)—, —C(O)NH—, —C(O)$_2$—, or a direct bond;

D is a substituted or unsubstituted aryl, a substituted or unsubstituted heteroaryl, a substituted or unsubstituted aralkyl, a substituted or unsubstituted heteroaromatic group, a substituted or unsubstituted heteroaralkyl, a substituted or unsubstituted cycloalkyl, a substituted or unsubstituted heterocycloalkyl, a substituted or unsubstituted amino, a substituted or unsubstituted aminoalkyl, a substituted or unsubstituted aminocycloalkyl, COOR$_i$, or substituted or unsubstituted alkyl; and R$_i$ is a substituted or unsubstituted aliphatic group or a substituted or unsubstituted aromatic group.

4. The compound of claim 1, wherein R$_3$ is a substituted or unsubstituted phenyl or pheny used to a five- or six-membered heterocyclic group.

5. The compound of claim 4 wherein R$_3$ is selected from the group

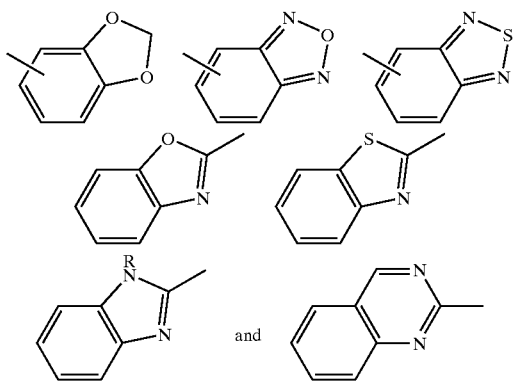

wherein R is hydrogen or alkyl.

6. The compound of claim 5 wherein ring A is a 1,4-phenylene group substituted with methoxy or fluoro.

7. The compound of claim 1, wherein ring A is selected from the group consisting of a substituted or unsubstituted phenyl, a substituted or unsubstituted naphthyl, a substituted or unsubstituted pyridyl, and a substituted or unsubstituted indole.

8. The compound of claim 7 wherein ring A is substituted with one or more substituent selected from the group consisting of —F, —Cl, —Br, —I, —OH, —CH$_3$, —NO$_2$, —OCF$_3$, —OCH$_3$, —CN, —CO$_2$CH$_3$, —CF$_3$, —CH$_2$OH, —CH$_2$NMe$_2$, —CH$_2$NHMe, CH$_2$NH$_2$, t-butyl, pyridyl, methylenedioxy; substituted or unsubstituted oxazolyl, substituted or unsubstituted benzyl, substituted or unsubstituted benzenesulfonyl, substituted or unsubstituted phenoxy, substituted or unsubstituted phenyl, substituted or unsubstituted amino, carboxyl, substituted or unsubstituted tetrazolyl, styryl, —S-(substituted or unsubstituted aryl), —S-(substituted or unsubstituted heteroaryl), substituted or unsubstituted heteroaryl, substituted or unsubstituted heterocycloalkyl, —NR$_f$R$_g$, alkynyl, —C(O)NR$_f$R$_g$, R$_c$ and CH$_2$OR$_c$;

R$_f$, R$_g$ and the nitrogen atom together form a 3, 4, 5, 6 or 7-membered, substituted or unsubstituted heterocycloalkyl, substituted or unsubstituted heterobicycloalkyl or a substituted or unsubstituted heteroaromatic; or R$_f$ and R$_g$ are each, independently, —H, a substituted or unsubstituted aliphatic group or a substituted or unsubstituted aromatic group; and $R_c$ is hydrogen, substituted or unsubstituted alkyl, substituted or unsubstituted aryl, —W—$(CH_2)_t$—$NR_dR_e$, —W—$(CH_2)_t$—O-alkyl, —W—$(CH_2)_t$—S-alkyl, —W—$(CH_2)_t$—OH; or —W—$(CH_2)_t$—$OR_j$;

t is an integer from 0 to 6;

W is a bond or —O—, —S—, —S(O)—, —S(O)$_2$—, or —$NR_k$—;

$R_k$ is —H or alkyl; and $R_d$, $R_e$ and the nitrogen atom to which they are attached together form a 3, 4, 5, 6 or 7-membered substituted or unsubstituted heterocycloalkyl, substituted or unsubstituted heterobicycloalkyl or a substituted or unsubstituted heteroaromatic; or $R_d$ and $R_e$ are each, independently, —H, alkyl, alkanoyl or —K—D;

K is —S(O)$_2$—, —C(O)—, —C(O)NH—, —C(O)$_2$—, or a direct bond;

D is a substituted or unsubstituted aryl, a substituted or unsubstituted heteroaryl, a substituted or unsubstituted aralkyl, a substituted or unsubstituted heteroaromatic group, a substituted or unsubstituted heteroaralkyl, a substituted or unsubstituted cycloalkyl, a substituted or unsubstituted heterocycloalkyl, a substituted or unsubstituted amino, a substituted or unsubstituted aminoalkyl, a substituted or unsubstituted aminocycloalkyl, $COOR_i$, or a substituted or unsubstituted alkyl; and $R_i$ is a substituted or unsubstituted aliphatic group or a substituted or unsubstituted aromatic group.

9. The compound of claim 8, wherein ring A is a substituted phenyl.

10. The compound of claim 9 wherein ring A is a substituted 1,4-phenylene group.

11. The compound of claim 1 wherein $R_1$ is of the formula

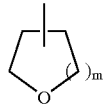

wherein m is an integer from 0 to 3.

12. The compound of claim 1 wherein $R_1$ is of the formula

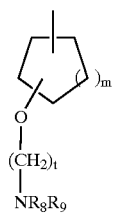

wherein:

m is an integer from 0 to 3;

t is an integer from 1 to 6; and $R_8$, $R_9$ and the nitrogen atom together form a 3, 4, 5, 6 or 7-membered, substituted or unsubstituted heterocycloalkyl, a substituted or unsubstituted heteroaromatic or substituted or unsubstituted heterobicyclicalkyl group; or $R_8$ and $R_9$ are each, independently, —H, azabicycloalkyl, heterocycloalkyl or $Y_2$—$Z_2$;

$Y_2$ is selected from the group consisting of —C(O)—, —$(CH_2)_q$—, —S(O)$_2$—, —C(O)O—, —SO$_2$NH—, —CONH—, $(CH_2)_qO$—, —$(CH_2)_qNH$—, —$(CH_2)_qS$—, —$(CH_2)_qS(O)$—, and —$(CH_2)_qS(O)_2$—;

q is an integer from 0 to 6; and $Z_2$ is —H, a substituted or unsubstituted alkyl, a substituted or unsubstituted amino, a substituted or unsubstituted aryl, a substituted or unsubstituted heteroaryl or a substituted or unsubstituted heterocycloalkyl group.

13. The compound of claim 1 wherein $R_1$ is of the formula

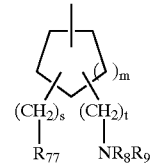

wherein:

m is an integer from 1 to 3;

s and t are each, independently, an integer from 0 to 6; and $R_8$, $R_9$ and the nitrogen atom together form a 3, 4, 5, 6 or 7-membered, substituted or unsubstituted heterocycloalkyl group, substituted or unsubstituted heteroaryl group, or a substituted heterobicyclicalkyl group; or $R_8$ and $R_9$ are each, independently, —H, azabicycloalkyl, heterocycloalkyl; alkyl; hydroxyalkyl; dihydroxyalkyl; or —$Y_2$—$Z_2$;

$Y_2$ is selected from the group consisting of —C(O)—, —$(CH_2)_q$—, —S(O)$_2$—, —C(O)O—, —SO$_2$NH—, —CONH—, $(CH_2)_qO$—, —$(CH_2)_qNH$—, —$(CH_2)_qS$—, —$(CH_2)_qS(O)$— and —$(CH_2)_qS(O)_2$—;

q is an integer from 0 to 6;

$Z_2$ is —H, a substituted or unsubstituted alkyl, a substituted or unsubstituted amino, a substituted or unsubstituted aryl, a substituted or unsubstituted heteroaryl or a substituted or unsubstituted heterocycloalkyl;

$R_{77}$ is —H, —$OR_{78}$, or —$NR_{79}R_{80}$;

$R_{78}$ is —H or a substituted or unsubstituted aliphatic group;

$R_{79}$, $R_{80}$ and the nitrogen atom together form a 3, 4, 5, 6 or 7-membered, substituted or unsubstituted heterocycloalkyl group, substituted or unsubstituted heteroaryl group, or a substituted heterobicyclicalkyl group; or $R_{79}$ and $R_{80}$ are each, independently, —H, azabicycloalkyl, heterocycloalkyl or —$Y_3$—$Z_3$;

$Y_3$ is selected from the group consisting of —C(O)—, —$(CH_2)_q$—, —S(O)$_2$—, —C(O)O—, —SO$_2$NH—, —CONH—, $(CH_2)_qO$—, $(CH_2)_qNH$—, $(CH_2)_qS$—, $(CH_2)_qS(O)$—, —$(CH_2)_qN(C_1$-$C_6$-alkyl)-, —$(CH_2)_q$—C(O)O—$(CH_2)_q$— and —$(CH_2)_qS(O)_2$—;

q is an integer from 0 to 6;

$Z_3$ is —H, a substituted or unsubstituted alkyl, a substituted or unsubstituted amino, a substituted or unsubstituted aryl, a substituted or unsubstituted heteroaryl or a substituted or unsubstituted heterocycloalkyl.

14. The compound of claim 13 wherein m is 2; s is 0; and $R_{77}$ is —OH.

15. The compound of claim 14 wherein $R_1$ is selected from the group consisting of:
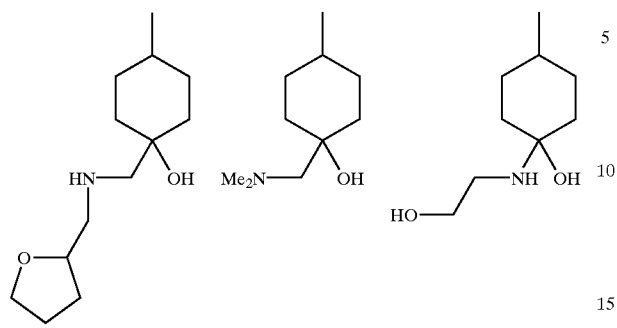
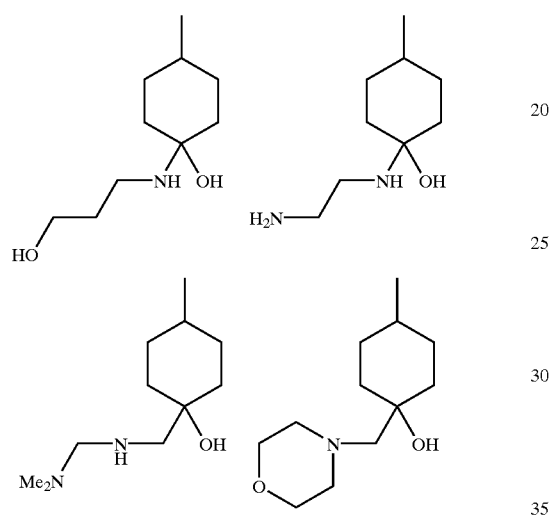
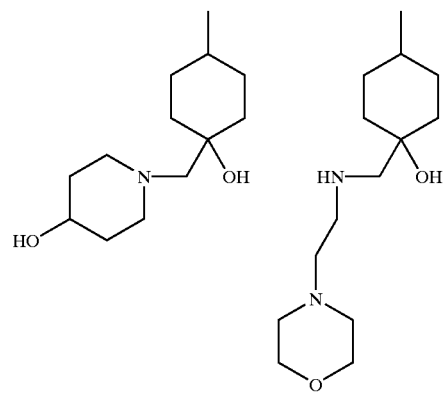
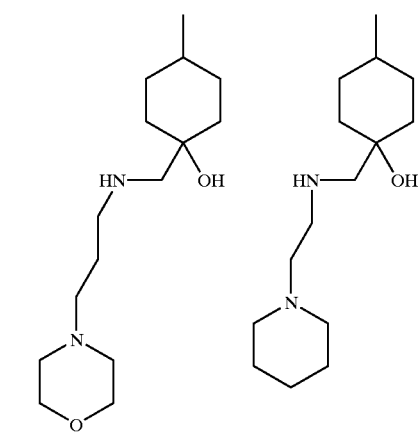
-continued
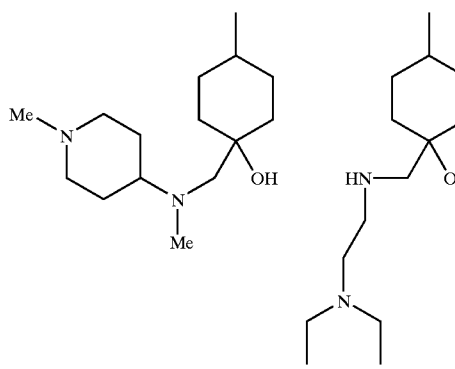
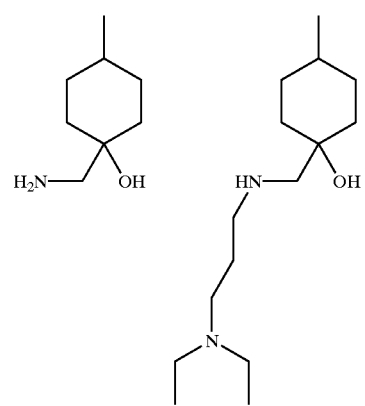
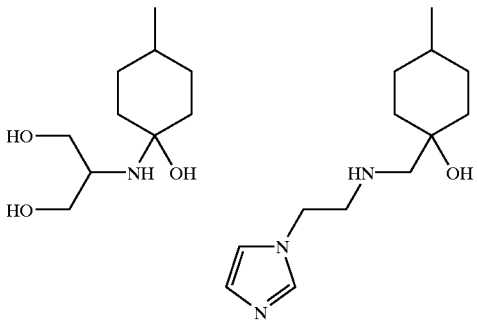
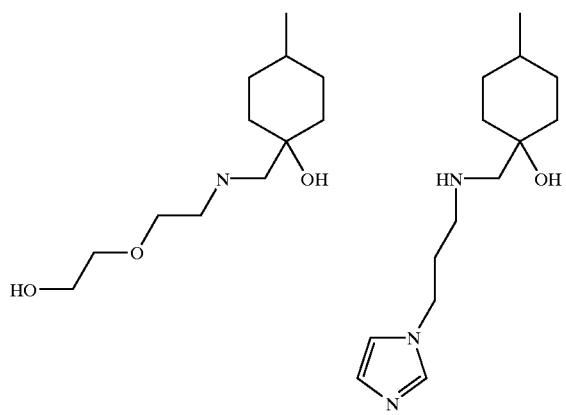

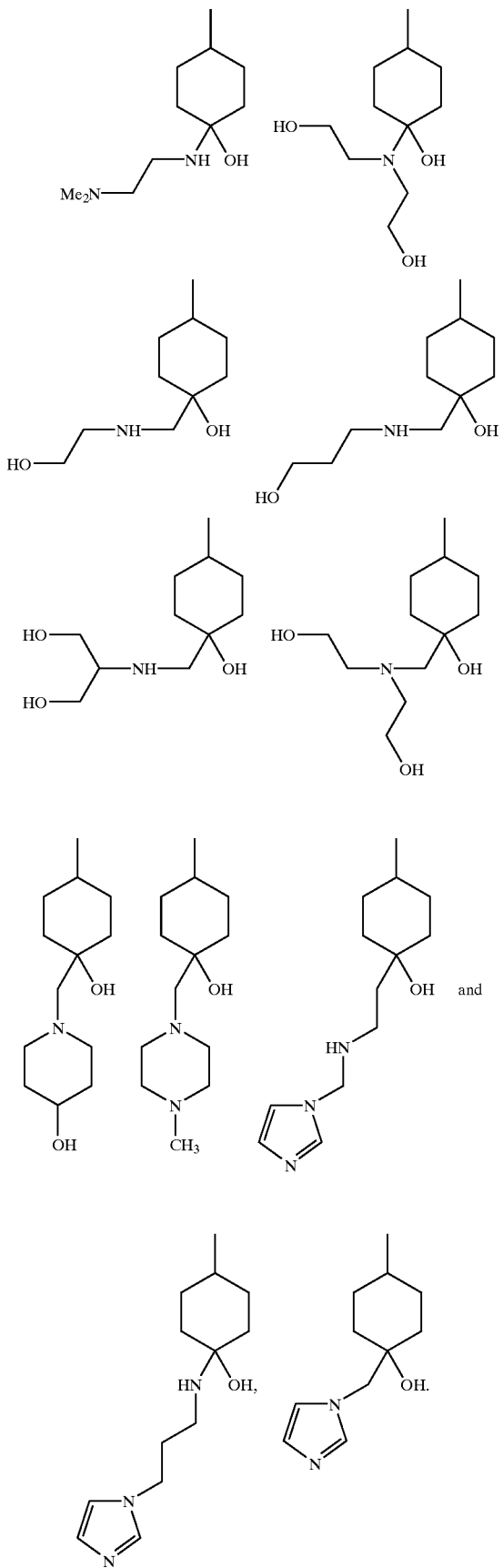

16. The compound of claim 1 wherein $R_1$ is of the formula

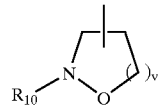

wherein:

v is an integer from 1 to 3

$R_{10}$ is —H, azabicycloalkyl, heterocycloalkyl or $Y_2$—$Z_2$;
$Y_2$ is selected from the group consisting of —C(O)—, —(CH$_2$)$_q$—, —S(O)$_2$—, —C(O)O—, —SO$_2$NH—, —CONH—, —(CH$_2$)$_q$O—, —(CH$_2$)$_q$NH—, —(CH$_2$)$_q$S—, —(CH$_2$)$_q$S(O)—, and —(CH$_2$)$_q$S(O)$_2$—;

q is an integer from 0 to 6; and $Z_2$ is —H, a substituted or unsubstituted alkyl, a substituted or unsubstituted amino, a substituted or unsubstituted aryl, a substituted or unsubstituted heteroaryl or a substituted or unsubstituted heterocycloalkyl.

17. The compound of claim 1 wherein $R_1$ is of the formula

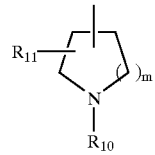

wherein:

m is an integer from 0 to 3;

$R_{10}$ is —H, azabicycloalkyl, heterocycloalkyl or $Y_2$—$Z_2$;
$Y_2$ is selected from the group consisting of —C(O)—, —(CH$_2$)$_p$—, —S(O)$_2$—, C(O)O—, —SO$_2$NH—, —CONH—, —(CH$_2$)$_q$O—, (CH$_2$)$_q$NH—, —(CH$_2$)$_q$S—, —(CH$_2$)$_q$S(O)—, and —(CH$_2$)$_q$S(O)$_2$—;

q is an integer from 0 to 6; and $Z_2$ is —H, a substituted or unsubstituted alkyl, a substituted or unsubstituted amino, a substituted or unsubstituted aryl, a substituted or unsubstituted heteroaryl or a substituted or unsubstituted heterocycloalkyl; and $R_{11}$ represents one or more substituents independently selected from the group consisting of hydrogen, hydroxy, oxo, a substituted or unsubstituted aliphatic group, a substituted or unsubstituted aromatic group, a substituted or unsubstituted heteroaromatic group, a substituted or unsubstituted alkoxycarbonyl, a substituted or unsubstituted alkoxyalkyl, a substituted or unsubstituted aminocarbonyl, a substituted or unsubstituted alkylcarbonyl, a substituted or unsubstituted arylcarbonyl, a substituted or unsubstituted heteroarylcarbonyl, a substituted or unsubstituted aminoalkyl and a substituted or unsubstituted aralkyl groups, provided that the carbon atoms adjacent to the nitrogen atom are not substituted by a hydroxy group.

18. The compound of claim 17 wherein $Z_2$ is of the formula $N(R_{35})R_{36}$, wherein $R_{35}$ and $R_{36}$ are each, independently, hydrogen, alkyl, alkoxycarbonyl, alkoxyalkyl, hydroxyalkyl, aminocarbonyl, cyano, alkylcarbonyl or aralkyl.

19. The compound of claim 17 wherein $Z_2$ is of the formula

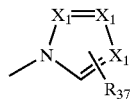

wherein:
each $X_1$ is, independently, CH or N; and
$R_{37}$ is hydrogen, cyano or a substituted or unsubstituted alkyl, a substituted or unsubstituted alkoxycarbonyl, a substituted or unsubstituted alkoxyalkyl, a substituted or unsubstituted hydroxyalkyl, a substituted or unsubstituted aminocarbonyl, a substituted or unsubstituted alkylcarbonyl or a substituted or unsubstituted aralkyl group.

20. The compound of claim 17 wherein $Z_2$ is of the formula

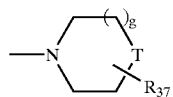

wherein
g is an integer from 0 to 3;
T is —O—, —C(O)—, —S—, —SO—, —SO$_2$—, —CH$_2$—, —CH(OR$_{34}$)— or —N(R$_{34}$)—;
$R_{34}$ is hydrogen, substituted or unsubstituted alkyl, a substituted or unsubstituted aryl or a substituted or unsubstituted aralkyl; and
$R_{37}$ is hydrogen, cyano or a substituted or unsubstituted alkyl, a substituted or unsubstituted alkoxycarbonyl, a substituted or unsubstituted alkoxyalkyl, a substituted or unsubstituted hydroxyalkyl, a substituted or unsubstituted aminocarbonyl, a substituted or unsubstituted alkylcarbonyl or a substituted or unsubstituted aralkyl group.

21. The compound of claim 17 wherein $Z_2$ is of the formula

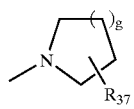

wherein:
g is an integer from 0 to 3; and
$R_{37}$ is hydrogen, cyano or a substituted or unsubstituted alkyl, a substituted or unsubstituted alkoxycarbonyl, a substituted or unsubstituted alkoxyalkyl, a substituted or unsubstituted hydroxyalkyl, a substituted or unsubstituted aminocarbonyl, a substituted or unsubstituted alkylcarbonyl or a substituted or unsubstituted aralkyl group.

22. The compound of claim 17 wherein $Z_2$ is of the formula

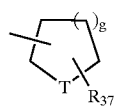

wherein:
T is —O—, —C(O)—, —S—, —SO—, —SO$_2$—, —CH$_2$—, —CH(OR$_{34}$)— or —N(R$_{34}$)—;

$R_{34}$ is hydrogen, substituted or unsubstituted alkyl, a substituted or unsubstituted aryl or a substituted or unsubstituted aralkyl; and
g is an integer from 0 to 3; and
$R_{37}$ is hydrogen, cyano or a substituted or unsubstituted alkyl, a substituted or unsubstituted alkoxycarbonyl, a substituted or unsubstituted alkoxyalkyl, a substituted or unsubstituted hydroxyalkyl, a substituted or unsubstituted aminocarbonyl, a substituted or unsubstituted alkylcarbonyl or a substituted or unsubstituted aralkyl.

23. The compound of claim 17 wherein $Z_2$ is of the formula

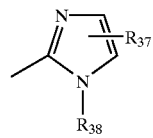

wherein:
$R_{37}$ is hydrogen, cyano, a substituted or unsubstituted alkyl, a substituted or unsubstituted alkoxycarbonyl, a substituted or unsubstituted alkoxyalkyl, a substituted or unsubstituted hydroxyalkyl, a substituted or unsubstituted aminocarbonyl, a substituted or unsubstituted alkylcarbonyl , a substituted or unsubstituted thioalkoxy or a substituted or unsubstituted aralkyl; and
$R_{38}$ is hydrogen, substituted or unsubstituted alkyl, a substituted or unsubstituted alkoxycarbonyl, a substituted or unsubstituted alkoxyalkyl, a substituted or unsubstituted aminocarbonyl, perhaloalkyl, a substituted or unsubstituted alkenyl, a substituted or unsubstituted alkylcarbonyl or a substituted or unsubstituted aralkyl.

24. The compound of claim 1 wherein $R_1$ is of the formula

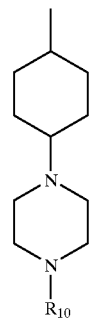

wherein:
$R_{10}$ is H, azabicycloalkyl, heterocycloalkyl or $Y_2$—$Z_2$;
$Y_2$ is selected from the group consisting of —C(O)—, —(CH$_2$)$_q$—, —S(O)$_2$—, —C(O)O—, —SO$_2$NH—, —CONH—, (CH$_2$)$_q$O—, —(CH$_2$)$_q$NH—, —(CH$_2$)$_q$S—, —(CH$_2$)$_q$S(O)—, and —(CH$_2$)$_q$S(O)$_2$—;
q is an integer from 0 to 6; and
$Z_2$ is —H, a substituted or unsubstituted alkyl, a substituted or unsubstituted amino, a substituted or unsubstituted aryl, a substituted or unsubstituted heteroaryl or a substituted or unsubstituted heterocycloalkyl.

25. A compound of claim 24 wherein $R_{10}$ is methyl; ring A is

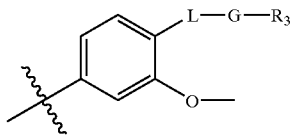

L is —N(R)C(O)—, where R is H;
G is a direct bond, —$CH_2$—O—, —O—$CH_2$— cyclopropylene, —$CH_2$—O—$CH_2$— or —$(CH_2)_3$—;
$R_3$ is phenyl, 2,6-difluorophenyl, 2-methoxyphenyl, 2,6-dimethoxyphenyl, 3,4-dichlorophenyl, 3-methoxyphenyl, 4-fluorophenyl, 4-chlorophenyl, 4-methoxyphenyl, 4-trifluoromethylphenyl, 3-nitrophenyl, 2,5-difluorophenyl, 3-cyanophenyl, 2,3-difluorophenyl, 2-chloropyridin-5-yl, 4-trifluoromethoxyphenyl, 2,4,6-trifluorophenyl, 2-fluoro-6-chlorophenyl, 4-dimethylaminophenyl, 4-cyanophenyl, 3-fluorophenyl, 2,5-dimethoxyphenyl, 3,4-methylenedioxyphenyl, 2,6-dimethylphenyl, 2-chloro-4-fluorophenyl, 4-nitrophenyl,

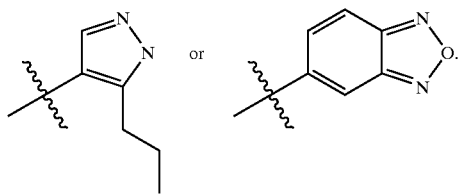

26. The compound of claim 1 wherein $R_1$ is of the formula

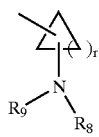

wherein:
r is an integer from 1 to 6; and
$R_8$, $R_9$ and the nitrogen atom together form a 3, 4, 5, 6 or 7-membered, substituted or unsubstituted heterocycloalkyl group, substituted or unsubstituted heteroaryl group, or a substituted heterobicyclicalkyl group; or
$R_8$ and $R_9$ are each, independently, —H, azabicycloalkyl, heterocycloalkyl or $Y_2$—$Z_2$;
$Y_2$ is selected from the group consisting of —C(O)—, —$(CH_2)_q$—, —$S(O)_2$—, —C(O)O—, —$SO_2NH$—, —CONH—, $(CH_2)_qO$—, —$(CH_2)_qNH$—, $(CH_2)_qS$—, $(CH_2)_qS(O)$—, and —$(CH_2)_qS(O)_2$—;
q is an integer from 0 to 6; and
$Z_2$ is —H, a substituted or unsubstituted alkyl, a substituted or unsubstituted amino, a substituted or unsubstituted aryl, a substituted or unsubstituted heteroaryl or a substituted or unsubstituted heterocycloalkyl group.

27. The compound of claim 26 wherein $R_8$, $R_9$ and the nitrogen atom together form a heterocycloalkyl group; of the formula

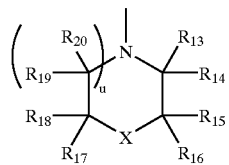

wherein:
$R_{13}$, $R_{14}$, $R_{15}$, $R_{16}$, $R_{17}$, $R_{18}$, $R_{19}$ and $R_{20}$ are each, independently, lower alkyl or hydrogen; or
at least one pair of substituents $R_{13}$ and $R_{14}$; $R_{15}$ and $R_{16}$; $R_{17}$ and $R_{18}$; or $R_{19}$ and $R_{20}$ together are an oxygen atom; or
at least one of $R_{13}$ and $R_{15}$ is cyano, $CONHR_{21}$, $COOR_{21}$, $CH_2OR_{21}$ or $CH_2NR_{21}(R_{22})$;
$R_{21}$, $R_{22}$ and the nitrogen atom together form a 3, 4, 5, 6 or 7-membered, substituted or unsubstituted heterocycloalkyl group, substituted or unsubstituted heteroaryl group, or a substituted heterobicyclicalkyl group; or
$R_{21}$ and $R_{22}$ are each, independently, —H, azabicycloalkyl, heterocycloalkyl or $Y_3$—$Z_3$;
$Y_3$ is selected from the group consisting of —C(O)—, —$(CH_2)_q$—, —$S(O)_2$, —C(O)O—, —$SO_2NH$—, —CONH—, $(CH_2)_qO$—, —$(CH_2)_qNH$—, —$(CH_2)_qS$—, —$(CH_2)_qS(O)$—; and —$(CH_2)_qS(O)_2$—;
q is an integer from 0 to 6; and
$Z_3$ is —H, a substituted or unsubstituted alkyl, a substituted or unsubstituted amino, a substituted or unsubstituted aryl, a substituted or unsubstituted heteroaryl or a substituted or unsubstituted heterocycloalkyl;
X is —O—, —S—, —SO—, —$SO_2$—, —$CH_2$—, —CH($OR_{23}$)— or $NR_{23}$;
$R_{23}$ is —H, substituted or unsubstituted alkyl, a substituted or unsubstituted aryl, a substituted or unsubstituted aralkyl, —C(NH)$NH_2$, —C(O)$R_{24}$, or —C(O)$OR_{24}$;
$R_{24}$ is hydrogen, substituted or unsubstituted alkyl, a substituted or unsubstituted aryl or a substituted or unsubstituted aralkyl; and
u is 0 or 1.

28. The compound of claim 26 wherein $R_8$, $R_9$ and the nitrogen atom together form a heterocycloalkyl of the formula

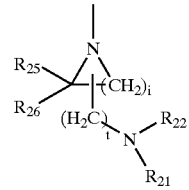

wherein:
$R_{25}$ and $R_{26}$ are each, independently, hydrogen or lower alkyl; or
$R_{25}$ and $R_{26}$ together are an oxygen atom; and
$R_{21}$, $R_{22}$ and the nitrogen atom together form a 3, 4, 5 or 6-membered, substituted or unsubstituted heterocycloalkyl group; or
$R_{21}$ and $R_{22}$ are each, independently, —H, azabicycloalkyl, heterocycloalkyl or $Y_3$—$Z_3$;
$Y_3$ is —H, selected from the group consisting of —C(O)—, —$(CH_2)_s$—, —$S(O)_2$—, —C(O)O—, —SO₂NH—, —CONH—, (CH₂)ₛO—, —(CH₂)ₛNH—, —(CH₂)ₛS—, —(CH₂)ₛS(O)—, and —(CH₂)ₛS(O)₂—;

s is an integer from 0 to 6; and

Z₃ is a substituted or unsubstituted alkyl, a substituted or unsubstituted amino, a substituted or unsubstituted aryl, a substituted or unsubstituted heteroaryl or a substituted or unsubstituted heterocycloalkyl;

i is an integer from 1 to 6; and t is an integer from 0 to 6.

29. The compound of claim 26 wherein R₈, R₉ and the nitrogen atom together form a heterocycloalkyl group; of the formula

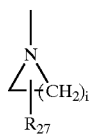

wherein:

i is an integer from 1 to 6; and

R₂₇ is OH, CH₂OH, C(O)NR₂₄R₂₈ or COOR₂₄;

R₂₄ and R₂₈ are each, independently, hydrogen or a substituted or unsubstituted alkyl, a substituted or unsubstituted aryl or a substituted or unsubstituted aralkyl group.

30. The compound of claim 26 wherein R₈, R₉ and the nitrogen atom together form a heteroaromatic group of the formula

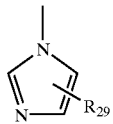

wherein:

R₂₉ is a —Cl, substituted or unsubstituted alkyl, a substituted or unsubstituted aryl or a substituted or unsubstituted aralkyl group, carboxylic acid, cyano, C(O)OR₃₀, CH₂OR₃₀, CH₂NR₂₁R₂₂ or C(O)NR₂₁R₂₂;

R₃₀ is —H, a substituted or unsubstituted alkyl, a substituted or unsubstituted aryl, a substituted or unsubstituted aralkyl, a substituted or unsubstituted heterocycloalkyl or heterocycloaryl group; and R₂₁, R₂₂ and the nitrogen atom together form a 3, 4, 5 or 6-membered, substituted or unsubstituted heterocycloalkyl group, a substituted or unsubstituted heteroaromatic or a substitutituted or unsubstituted heterobicycloalkyl; or R₂₁ and R₂₂ are each, independently, H, azabicycloalkyl, heterocycloalkyl or Y₃—Z3;

Y₃ is selected from the group consisting of —C(O)—, —(CH₂)ₜ—, —S(O)₂—, —C(O)O—, —SO₂NH—, —CONH—, (CH₂)ₜ—, —(CH₂)ₜNH—, —(CH₂)ₜS—, —(CH₂)ₜS(O)—, and —(CH₂)ₜS(O)₂—;

t is an integer from 0 to 6; and

Z₃ is —H, a substituted or unsubstituted alkyl, a substituted or unsubstituted amino, a substituted or unsubstituted aryl, a substituted or unsubstituted heteroaryl or a substituted or unsubstituted heterocycloalkyl.

31. The compound of claim 26 wherein at least one of R₈ and R₉ is of the formula Y₃—D, wherein D is of the formula

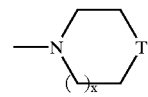

wherein:

Y₃ is selected from the group consisting of —C(O)—, —(CH₂)ₜ—, —S(O)₂—, —C(O)O—, —SO₂NH—, —CONH—, (CH₂)ₜO—, —(CH₂)ₜNH—, —(CH₂)ₜS—, —(CH₂)ₜS(O)—, and —(CH₂)ₜS(O)₂—;

t is an integer from 0 to 6;

T is —O—, —C(O)—, —S—, —SO—, —SO₂—, —CH₂—, —CH(OR₂₄)— or —N(R₂₄)—;

R₂₄ is hydrogen or a substituted or unsubstituted alkyl, aryl or aralkyl group; and x is 0, 1 or 2.

32. The compound of claim 26 wherein at least one of R₈ and R₉ is of the formula Y₃—N(R₃₁)R₃₂, wherein:

Y₃ is selected from the group consisting of —C(O)—, —(CH₂)ₜ—, —S(O)₂—, —C(O)O—, —SO₂NH—, —CONH—, (CH₂)ₜO—, —(CH₂)ₜNH—, —(CH₂)ₜS—, —(CH₂)ₜS(O)—, and —(CH₂)ₜS(O)₂—;

t is an interger from 0 to 6;

R₃₁ and R₃₂ are each, independently, substituted or unsubstituted carboxyalkyl, a substituted or unsubstituted alkoxycarbonylalkyl, a substituted or unsubstituted hydroxyalkyl, a substituted or unsubstituted alkylsulfonyl, a substituted or unsubstituted alkylcarbonyl or a substituted or unsubstituted cyanoalkyl; or R₃₁ and R₃₂, together with the nitrogen atom, form a five- or six-membered heterocycloalkyl group, a substituted or unsubstituted heteroaromatic or a substituted or unsubstituted heterobicycloalkyl.

33. The compound of claim 1 wherein R₁ is of the formula

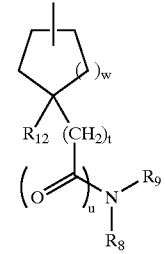

wherein:

w is an integer from 0 to 4;

t is an integer from 0 to 6;

u is 0 or 1;

R₁₂ is hydrogen, hydroxy or a substituted or unsubstituted alkoxy group;

R₈, R₉ and the nitrogen atom together form a 3, 4, 5 or 6-membered, substituted or unsubstituted heterocycloalkyl, a substituted or unsubstituted heteroaromatic, or a substituted or unsubstituted heterobicycloatkyl; or R₈ and R₉ are each, independently, —H, azabicycloalkyl, heterocycloalkyl or Y₂—Z₂;

Y₂ is selected from the group consisting of —C(O)—, —(CH₂)q—, —S(O)₂—, —C(O)O—, —SO₂NH—, —CONH—, (CH₂)qO—, —(CH₂)qNH—, —(CH₂)qS—, —(CH₂)qS(O)—, and —(CH₂)qS(O)₂—;

q is an integer from 0 to 6; and $Z_2$ is —H, a substituted or unsubstituted alkyl, a substituted or unsubstituted amino, a substituted or unsubstituted aryl, a substituted or unsubstituted heteroaryl or a substituted or unsubstituted heterocycloalkyl.

34. The compound of claim 33 wherein $R_8$, $R_9$ and the nitrogen atom together form a heterocycloalkyl of the formula

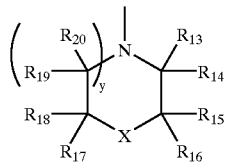

wherein
$R_{13}$, $R_{14}$, $R_{15}$, $R_{16}$, $R_{17}$, $R_{18}$, $R_{19}$ and $R_{20}$ are each, independently, lower alkyl or hydrogen; or at least one pair of substituents $R_{13}$ and $R_{14}$; $R_{15}$ and $R_{16}$; $R_{17}$ and $R_{18}$; or $R_{19}$ and $R_{20}$ together are an oxygen atom; or at least one of $R_{13}$ and $R_{15}$ is cyano, $CONHR_{21}$, $COOR_{21}$, $CH_2OR_{21}$ or $CH_2NR_{21}(R_{22})$;

$R_{21}$, $R_{22}$ and the nitrogen atom together form a 3, 4, 5, 6 or 7-membered, substituted or unsubstituted heterocycloalkyl group, substituted or unsubstituted heteroaryl group, or a substituted heterobicyclicalkyl group; or $R_{21}$ and $R_{22}$ are each, independently, —H, azabicycloalkyl, heterocycloalkyl or $Y_3$—$Z_3$;

$Y_3$ is selected from the group consisting of —C(O)—, —(CH$_2$)$_s$—, —S(O)$_2$—, —C(O)O—, —SO$_2$NH—, —CONH—, (CH$_2$)$_s$O—, —(CH$_2$)$_s$NH—, —(CH$_2$)$_s$S—, —(CH$_2$)$_s$S(O)— and —(CH$_2$)$_s$S(O)$_2$—;

s is an integer from 0 to 6; and $Z_3$ is —H, a substituted or unsubstituted alkyl, a substituted or unsubstituted amino, a substituted or unsubstituted aryl, a substituted or unsubstituted heteroaryl or a substituted or unsubstituted heterocycloalkyl;

X is —O—, —S—, —SO—, —SO$_2$—, —CH$_2$—, —CH(OR$_{23}$)— or NR$_{23}$;

$R_{23}$ is hydrogen, substituted or unsubstituted alkyl, a substituted or unsubstituted aryl, a substituted or unsubstituted aralkyl, —C(NH)NH$_2$, —C(O)R$_{24}$, or —C(O)OR$_{24}$;

$R_{24}$ is hydrogen, substituted or unsubstituted alkyl, a substituted or unsubstituted aryl or a substituted or unsubstituted aralkyl; and y is 0 or 1.

35. The compound of claim 33 wherein $R_8$, $R_9$ and the nitrogen atom together form a heterocycloalkyl of the formula

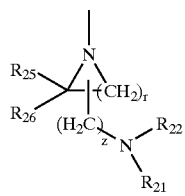

wherein
$R_{25}$ and $R_{26}$ are each, independently, hydrogen or lower alkyl; or $R_{25}$ and $R_{26}$ together are an oxygen atom;

$R_{21}$, $R_{22}$ and the nitrogen atom together form a 3, 4, 5 or 6-membered, substituted or unsubstituted heterocycloalkyl group, a substituted or unsubstituted heteroaromatic or a substitutituted or unsubstituted heterobicycloalkyl; or $R_{21}$ and $R_{22}$ are each, independently, —H, azabicycloalkyl, heterocycloalkyl or $Y_3$—$Z_3$;

$Y_3$ is selected from the group consisting of —C(O)—, —(CH$_2$)$_s$—, —S(O)$_2$—, —C(O)O—, —SO$_2$NH—, —CONH—, (CH$_2$)$_s$—, —(CH$_2$)$_s$NH—, —(CH$_2$)$_s$S—, —(CH$_2$)$_s$S(O)—, and —(CH$_2$)$_s$S(O)$_2$—;

s is an integer from 0 to 6; and $Z_3$ is —H, a substituted or unsubstituted alkyl, a substituted or unsubstituted amino, a substituted or unsubstituted aryl, a substituted or unsubstituted heteroaryl or a substituted or unsubstituted heterocycloalkyl group; or r is an integer from 1 to 6; and z is an integer from 0 to 6.

36. The compound of claim 33 wherein $R_8$, $R_9$ and the nitrogen atom together form a heterocycloalkyl group of the formula

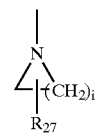

wherein
i is an integer from 1 to 6; and $R_{27}$ is $CH_2OH$ $C(O)NR_{24}R_{28}$, or $COOR_{24}$;

$R_{24}$ and $R_{28}$ are each, independently, hydrogen or a substituted or unsubstituted alkyl, a substituted or unsubstituted aryl or a substituted or unsubstituted aralkyl group.

37. The compound of claim 33 wherein $R_8$, $R_9$ and the nitrogen atom together form a heteroaromatic group of the formula

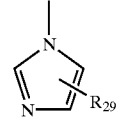

wherein:
$R_{29}$ is a substituted or unsubstituted alkyl, a substituted or unsubstituted aryl or a substituted or unsubstituted aralkyl group, carboxyl, cyano, $C(O)OR_{30}$, $CH_2OR_{30}$, $CH_2NR_{21}R_{22}$ or $C(O)NR_{21}R_{22}$;

$R_{30}$ is a —H, substituted or unsubstituted alkyl, a substituted or unsubstituted aryl, a substituted or unsubstituted aralkyl, a substituted or unsubstituted heterocycloalkyl or a substituted or unsubstituted heterocycloaryl group;

$R_{21}$, $R_{22}$ and the nitrogen atom together form a 3, 4, 5 or 6-membered, substituted or unsubstituted heterocycloalkyl group, a substituted or unsubstituted heteroaromatic or a substitutituted or unsubstituted heterobicycloalkyl; or $R_{21}$ and $R_{22}$ are each, independently, —H, azabicycloalkyl, heterocycloalkyl or $Y_3$—$Z_3$;

Y$_3$ is selected from the group consisting of —C(O)—, —(CH$_2$)$_s$—, —S(O)$_2$—, —C(O)O—, —SO$_2$NH—, —CONH—, (CH$_2$)$_s$O—, —(CH$_2$)$_s$NH—, —(CH$_2$)$_s$S—, —(CH$_2$)$_s$S(O)—, and —(CH$_2$)$_s$S(O)$_2$—;

s is an integer from 0 to 6; and

Z$_3$ is —H, a substituted or unsubstituted alkyl group, a substituted or unsubstituted amino, a substituted or unsubstituted aryl group, a substituted or unsubstituted heteroaryl group or a substituted or unsubstituted heterocycloalkyl group.

38. The compound of claim 33 wherein at least one of R$_8$ and R$_9$ is of the formula Y$_3$—D, wherein D is of the formula

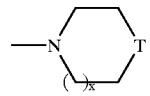

wherein:

Y$_3$ is selected from the group consisting of —C(O)—, —(CH$_2$)$_s$—, —S(O)$_2$—, —C(O)O—, —SO$_2$NH—, —CONH—, (CH$_2$)$_s$O—, —(CH$_2$)$_s$NH—, —(CH$_2$)$_s$S—, —(CH$_2$)$_s$S(O)—, and —(CH$_2$)$_s$S(O)$_2$—;

s is an integer from 0 to 6;

T is —O—, —C(O)—, —S—, —SO—, —SO$_2$—, —CH$_2$—, —CH(OR$_{33}$)— or —NR$_{33}$—;

R$_{33}$ is hydrogen, a substituted or unsubstituted alkyl, a substituted or unsubstituted aryl, a substituted or unsubstituted aralkyl, —C(NH)NH$_2$, —C(O)R$_{34}$, or —C(O)OR$_{34}$;

R$_{34}$ is hydrogen, substituted or unsubstituted alkyl, aryl or aralkyl,; and x is 0, 1 or 2.

39. The compound of claim 33 wherein at least one of R$_8$ and R$_9$ is of the formula Y$_3$—N(R$_{31}$)R$_{32}$, wherein:

Y$_3$ is selected from the group consisting of —C(O)—, —(CH$_2$)$_s$—, —S(O)$_2$—, —C(O)O—, —SO$_2$NH—, —CONH—, (CH$_2$)$_s$O—, —(CH$_2$)$_s$NH—, —(CH$_2$)$_s$S—, —(CH$_2$)$_s$S(O)—, and —(CH$_2$)$_s$S(O)$_2$—;

s is an integer from 0 to 6;

R$_{31}$ and R$_{32}$ are each, independently, substituted or unsubstituted carboxyalkyl, a substituted or unsubstituted alkoxycarbonylalkyl, a substituted or unsubstituted hydroxyalkyl, a substituted or unsubstituted alkylsulfonyl, a substituted or unsubstituted alkylcarbonyl or a substituted or unsubstituted cyanoalkyl; or R$_{31}$ and R$_{32}$, together with the nitrogen atom, form a five- or six-membered heterocycloalkyl group, a substituted or unsubstituted heteroaromatic or a substitutituted or unsubstituted heterobicycloalkyl.

40. The compound of claim 1 wherein R$_1$ is of the formula

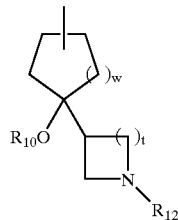

wherein:

w is an integer from 0 to 4;

t is an integer from 0 to 6;

R$_{10}$ is hydrogen or a substituted or unsubstituted alkyl group;

R$_{12}$ is —H, azabicycloalkyl, heteocycloalkyl or Y$_2$—Z$_2$;

Y$_2$ is selected from the group consisting of —C(O)—, —(CH$_2$)$_q$—, —S(O)$_2$—, —C(O)O—, —SO$_2$NH—, —CONH—, (CH$_2$)$_q$O—, —(CH$_2$)$_q$NH—, —(CH$_2$)$_q$S—, —(CH$_2$)$_q$S(O)—, and —(CH$_2$)$_q$S(O)$_2$—;

q is an integer from 0 to 6; and

Z$_2$ is —H, a substituted or unsubstituted alkyl, a substituted or unsubstituted amino, a substituted or unsubstituted aryl, a substituted or unsubstituted heteroaryl or a substituted or unsubstituted heterocycloalkyl.

41. The compound of claim 1 wherein R$_1$ is of the formula

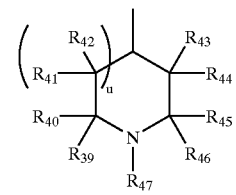

wherein:

u is 0 or 1;

R$_{39}$, R$_{40}$, R$_{41}$, R$_{42}$, R$_{43}$, R$_{44}$, R$_{45}$ and R$_{46}$ are each, independently, methyl or hydrogen; or at least one pair of substituents R$_{39}$ and R$_{40}$; R$_{41}$ and R$_{42}$; R$_{43}$ and R$_{44}$; or R$_{45}$ and R$_{46}$ together are an oxygen atom; and R$_{47}$ is H, azabicycloalkyl, heterocycloalkyl or Y$_2$—Z$_2$;

Y$_2$ is selected from the group consisting of —C(O)—, —(CH$_2$)$_q$—, —S(O)$_2$—, —C(O)O—, —SO$_2$NH—, —CONH—, (CH$_2$)$_q$O—, —(CH$_2$)$_q$NH—, —(CH$_2$)$_q$S—, —(CH$_2$)$_q$S(O)—, and —(CH$_2$)$_q$S(O)$_2$—;

q is an integer from 0 to 6; and

Z$_2$ is —H, a substituted or unsubstituted alkyl, a substituted or unsubstituted amino, a substituted or unsubstituted aryl, a substituted or unsubstituted heteroaryl or a substituted or unsubstituted heterocycloalkyl group; or R$_{47}$ is of the formula

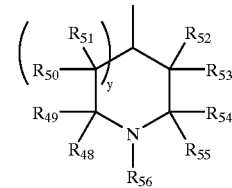

wherein:

y is 0 or 1;

R$_{48}$, R$_{49}$, R$_{50}$, R$_{51}$, R$_{52}$, R$_{53}$, R$_{54}$ and R$_{55}$ are each, independently, methyl or hydrogen; or at least one pair of substituents R$_{48}$ and R$_{49}$; R$_{50}$ and R$_{51}$; R$_{52}$ and R$_{53}$; or R$_{54}$ and R$_{55}$ together are an oxygen atom; and R$_{56}$ is —H, azabicycloalkyl, heterocycloalkyl or Y$_3$—Z$_3$, Y$_3$ is selected from the group consisting of —C(O)—, —(CH$_2$)$_t$—, —S(O)$_2$—, —C(O)O—, —SO$_2$NH—, —CONH—, (CH$_2$)$_t$O—, —(CH$_2$)$_t$NH—, —(CH$_2$)$_t$S—, —(CH$_2$)$_t$S(O)—; and —(CH$_2$)$_t$S(O)$_2$—;

t is an integer from 0 to 6; and $Z_3$ is —H, a substituted or unsubstituted alkyl, a substituted or unsubstituted amino, a substituted or unsubstituted aryl, a substituted or unsubstituted heteroaryl or a substituted or unsubstituted heterocycloalkyl.

42. The compound of claim 1 wherein $R_1$ is of the formula wherein:

e, f, h, u and y are independently 0 or 1;

$R_{57}$, $R_{58}$, $R_{59}$, $R_{60}$, $R_{61}$, $R_{62}$, $R_{63}$, $R_{64}$, $R_{65}$ and $R_{66}$ are each, independently, methyl or hydrogen; or at least one pair of substituents $R_{57}$ and $R_{58}$; $R_{59}$ and $R_{60}$; $R_{61}$ and $R_{62}$; or $R_{63}$ and R64 together are an oxygen atom; and $R_{67}$ is H, azabicycloalkyl, heterocycloalkyl or $Y_2$—$Z_2$;

$Y_2$ is selected from the group consisting of —C(O)—, —(CH$_2$)$_q$—, —S(O)$_2$—, —C(O)O—, —SO$_2$NH—, —CONH—, (CH$_2$)$_q$O—, —(CH$_2$)$_q$NH—, —(CH$_2$)$_q$S—, (CH$_2$)$_q$S(O)—, and —(CH$_2$)$_q$S(O)$_2$—;

p is an integer from 0 to 6; and $Z_2$ is —H, a substituted or unsubstituted alkyl, a substituted or unsubstituted amino, a substituted or unsubstituted aryl, a substituted or unsubstituted heteroaryl or a substituted or unsubstituted heterocycloalkyl; or $R_{67}$ is of the formula wherein:

d is 0 or 1;

$R_{68}$, $R_{69}$, $R_{70}$, $R_{71}$, $R_{72}$, $R_{73}$, $R_{74}$ and $R_{75}$ are each, independently, lower alkyl or hydrogen; or at least one pair of substituents $R_{68}$ and $R_{69}$; $R_{70}$ and $R_{71}$; $R_{72}$ and $R_{73}$; and $R_{74}$ and $R_{75}$ together are an oxygen atom; and $R_{76}$ is —H, azabicycloalkyl, heterocycloalkyl or $Y_3$—$Z_3$;

$Y_3$ is selected from the group consisting of —C(O)—, —(CH$_2$)$_t$—, —S(O)$_2$—, —C(O)O—, —SO$_2$NH—, —CONH—, (CH$_2$)$_t$O—, —(CH$_2$)$_t$NH—, —(CH$_2$)$_t$S—, —(CH$_2$)$_t$S(O)—, and —(CH$_2$)$_t$S(O)$_2$—;

p is an integer from 0 to 6;

$Z_3$ is —H, a substituted or unsubstituted alkyl, a substituted or unsubstituted amino, a substituted or unsubstituted aryl, a substituted or unsubstituted heteroaryl or a substituted or unsubstituted heterocycloalkyl group.

43. The compound of claim 1, wherein $R_2$ is —H.

44. The compound of claim 1, wherein L is —O—, —NHSO$_2$R—, —NC(O)O—, or NHC(O)—.

45. The compound of claim 1 wherein $R_1$ is of the formula wherein m is 0, 1 or 2;

$R_{81}$ and $R_{82}$ are each, independently, selected from the group consisting of hydrogen, hydroxyl, cyanomethyl, carboxymethyl, aminocarbonylmethyl, aminocarbonyl, aminomethyl, hydroxymethyl and amino, provided that no more than one of $R_{81}$ and $R_{82}$ is hydrogen; or $R_{81}$ and $R_{82}$ together are oxo; —O—(CH$_2$)$_i$—O, wherein i is 2 or 3;

—NH—C(O)—NH—C(O)—; or —NH—C(O)—NH—CH$_2$— provided that m is not 1 when $R_{82}$ is hydroxy.

46. The compound of claim 45 wherein $R_1$ is selected from the group consisting of 47. The compound of claim 1 wherein G is selected from the group consisting of a direct bond; —(CH$_2$)$_j$—, wherein j is 1 or 2; trans —CH=CH—; -cycloC$_3$H$_4$—; and CH$_2$O—.

48. The compound of claim 13 wherein m is 2.

49. The compound of claim 48 wherein S is O and $R_{77}$ is hydrogen.

50. The compound of claim 49 wherein the —(CH$_2$)$_t$—NR$_8$R$_9$ group is

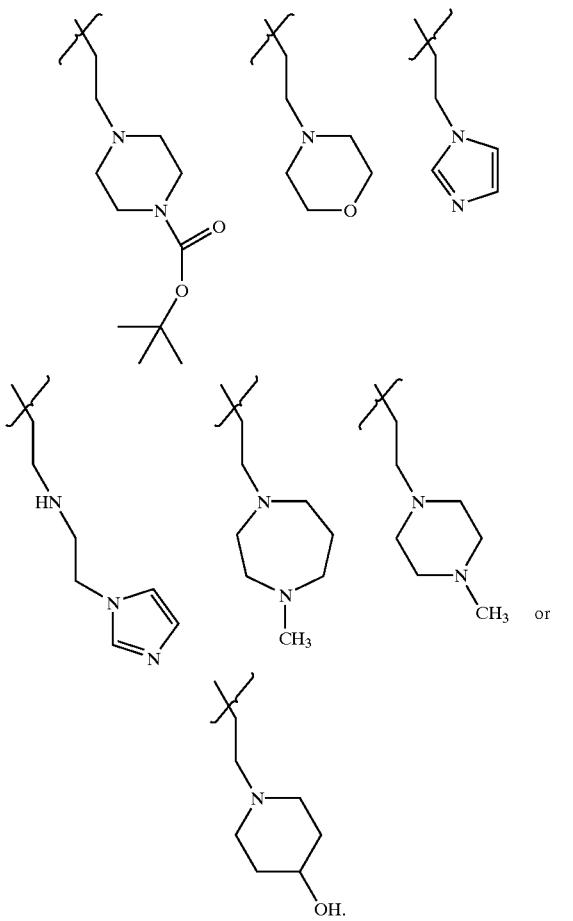

51. The compound of claim 49 wherein L is —O—, j is 0 or 1 and $R_3$ is phenyl.

52. The compound of claim 48 wherein
L is —CH$_2$NHC(O)—; —CH$_2$NHC(O)NH—; —CH$_2$NHC(O)O—; —CH$_2$C(O)NH—; —CH$_2$NHS(O)$_2$—; —NHC(O)—; —NHC(O)NH—; —NHC(O)O—; —C(O)NH—; or —NS(O)$_2$—;
A is 1,4-phenylene or 1,4-phenylene substituted with one or more methoxy groups or fluorine atoms;
$R_3$ is phenyl or phenyl substituted with one or more substituents selected from the group consisting of chloro, cyano, bromo, fluoro, trifluoromethoxy, methoxy, methylenedioxy, methyl, amino, dimethylamino and nitro;
$R_2$ is hydrogen; and
G is a direct bond or —(CH$_2$)$_j$—, wherein j is 0 to 4.

53. The compound of claim 24 wherein $R_{10}$ is methyl, isopropyl or methoxyethyl.

54. A compound of claim 24, 26, 27, 28, 29, 30, 31, 45 or 47 wherein ring A is

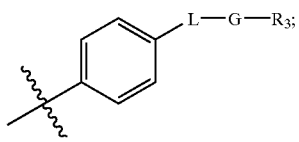

L is —O—;
G is a direct bond; and
$R_3$ is phenyl.

55. A compound according to claim 1 selected from the group consisting of:
Cis-5-(4-phenoxyphenyl)-7-(4-pyrrolidinocyclohex-1-yl)-7H-pyrrolo[2,3-d]pyrimidin-4-ylamine,
Trans-5-(4-phenoxyphenyl)-7-(4-pyrrolidinocyclohex-1-yl)-7H-pyrrolo[2,3-d]pyrimidin-4-ylamine,
Cis-5-(4-phenoxyphenyl)-7-(4-piperidinocyclohex-1-yl)-7H-pyrrolo[2,3-d]pyrimidin-4-ylamine hydrochloride,
Trans-5-(4-phenoxyphenyl)-7-(4-piperidinocyclohex-1-yl)-7H-pyrrolo[2,3-d]pyrimidin-4-ylamine,
Trans-7-(4-dimethylaminocyclohexyl)-5-(4-phenoxyphenyl)-7H-pyrrolo [2,3-d]pyrimidin-4-ylamine,
Cis-7-(4-dimethylaminocyclohexyl)-5-(4-phenoxyphenyl)-7H-pyrrolo[2,3-d]pyrimidin-4-ylamine,
5-(4-phenoxyphenyl)-7-(4-piperidyl)-7H-pyrrolo[2,3-d]pyrimidin-4-ylamine dihydrochloride,
5-(4-phenoxyphenyl)-7-(3-pyrrolidinyl)-7H-pyrrolo[2,3-d]pyrimidin-4-ylamine dihydrochloride,
Cis-7-[4-(4-isopropylpiperazino)cyclohexyl]-5-(4-phenoxyphenyl)-7H-pyrrolo[2,3-d]pyrimidin-4-amine,
Trans-7-[4-(4-isopropylpiperazino)cyclohexyl]-5-(4-phenoxyphenyl)-7h-pyrrolo[2,3-d]pyrimidin-4-amine,
Cis-7-{4-[4-(2-methoxyethyl)piperazino]cyclohexyl}-5-(4-phenoxyphenyl)-7H-pyrrolo[2,3-d]pyrimidin-4-amine,
Trans-7-{4-[4-(2-methoxyethyl)piperazino]cyclohexyl}-5-(4-phenoxyphenyl)-7H-pyrrolo[2,3-d]pyrimidin-4-amine,
Cis-7-[-4-(4-ethylpiperazino)cyclohexyl]-5-(4-phenoxyphenyl)-7H-pyrrolo[2,3-d]pyrimidin-4-amine,
Trans-7-[4-(4-ethylpiperazino)cyclohexyl]-5-(4-phenoxyphenyl)-7H-pyrrolo[2,3-d]pyrimidin-4-amine,
Cis-7-[4-(4-isopropylpiperazino)cyclohexyl]-5-(4-phenoxyphenyl)-7H-pyrrolo[2,3-d]pyrimidin-4-amine tris maleate,
Trans-7-[4-(4-isopropylpiperazino)cyclohexyl]-5-(4-phenoxyphenyl)-7H-pyrrolo[2,3-d]pyrimidin-4-amine tris maleate,
Cis-7-(4-[4-(2-methoxyethyl)piperazino]cyclohexyl}-5-(4-phenoxyphenyl)-7H-pyrrolo[2,3-d]pyrimidin-4-amine tris maleate,
Trans-7-{4-[4-(2-methoxyethyl)piperazino]cyclohexyl}-5-(4-phenoxyphenyl)-7H-pyrrolo[2,3-d]pyrimidin-4-amine tris maleate,
Cis-7-(4-{[3-(1H-1-imidazolyl)propyl]amino}cyclohexyl)-5-(4-phenoxyphenyl)-7H-pyrrolo[2,3-d]pyrimidin-4-amine trimaleate salt, and
Trans-7-(4-{[3-(1H-1-imidazolyl)propyl]amino}cyclohexyl)-5-(4-phenoxyphenyl)-7H-pyrrolo[2,3-d]pyrimidin-4-amine dimaleate salt.

56. A compound according to claim 1 selected from the group consisting of:
Cis-7-[4-(dimethylamino)cyclohexyl]-5-(4-phenoxyphenyl)-7H-pyrrolo[2,3-d]pyrimidin-4-amine dimaleate salt,
Trans-5-(4-phenoxyphenyl)-7-(4-piperidinocyclohexyl)-7H-pyrrolo[2,3-d]pyrimidin-4-amine dimaleate salt,
Trans-5-(4-phenoxyphenyl)-7-(4-tetrahydro-1H-1-pyrrolylcyclohexyl)-7H-pyrrolo[2,3-d]pyrimidin-4-amine dimaleate salt, Cis-5-(4-phenoxyphenyl)-7-(4-piperazinocyclohexyl)-7H-pyrrolo[2,3-d]pyrimidin-4-amine trimaleate salt, Trans-5-(4-phenoxyphenyl)-7-(4-piperazinocyclohexyl)-7H-pyrrolo[2,3-d]pyrimidin-4-amine trimaleate salt, 7-[3-(4-methylpiperazino)cyclopentyl]-5-(4-phenoxyphenyl)-7H-pyrrolo[2,3-d]pyrimidin-4-amine tri-maleate, Trans-7-[3-(4-methylpiperazino)cyclohexyl]-5-(4-phenoxyphenyl)-7H-pyrrolo[2,3-d]pyrimidin-4-amine, Trans-7-[3-(4-methylpiperazino)cyclohexyl]-5-(4-phenoxyphenyl)-7H-pyrrolo[2,3-d]pyrimidin-4-amine tri-maleate, trans-7-[3-(4-methylpiperazino)cyclohexyl]-5-(4-phenoxyphenyl)-7H-pyrrolo[2,3-d]pyrimidin-4-amine tri-hydrochloride, cis-7-[3-(4-methylpiperazino)cyclohexyl]-5-(4-phenoxyphenyl)-7H-pyrrolo[2,3-d]pyrimidin-4-amine tri-maleate salt, cis-7-[3-(4-methylpiperazino)cyclohexyl]-5-(4-phenoxyphenyl)-7H-pyrrolo[2,3-d]pyrimidin-4-amine tri-hydrochloride, Trans-5-(2-methyl-4-phenoxyphenyl)-7-[4-(4-methylpiperazino)cyclohexyl]-7H-pyrrolo[2,3-d]pyrimidin-4-amine trimaleate, Cis-benzyl N-(4-{4-amino-7-[4-(4-methylpiperazino)cyclohexyl]-7H-pyrrolo[2,3-d]pyrimidin-5-yl}2-methoxyphenyl)carbamate tri-maleate, Trans-benzyl N-(4-{4-amino-7-[4-(4-methylpiperazino)cyclohexyl]-7H-pyrrolo[2,3-d]pyrimidin-5-yl}-2-methoxyphenyl)carbamate tri-maleate, Trans-N1-(4-{4-amino-7-[4-(4-methylpiperazino)cyclohexyl]-7H-pyrrolo[2,3-d]pyrimidin-5-yl}-2-methoxyphenyl)benzamide, Trans-N1-(4-{4-amino-7-[4-(4-methylpiperazino)cyclohexyl]-7H-pyrrolo[2,3-d]pyrimidin-5-yl}-2-methoxyphenyl)benzamide tri-maleate, Cis-N1-(4-{4-amino-7-[4-(4-methylpiperazino)cyclohexyl]-7H-pyrrolo[2,3-d]pyrimidin-5-yl}-2-methoxyphenyl)-3-phenylpropanamide, Trans-N1-(4-{4-amino-7-[4-(4-methylpiperazino)cyclohexyl]-7H-pyrrolo[2,3-d]pyrimidin-5-yl}-2-methoxyphenyl)-3-phenylpropanamide, cis-N1-(4-4-amino-7-[4-(4-methylpiperazino)cyclohexyl]-7H-pyrrolo[2,3-d]pyrimidin-5-yl-2-methoxyphenyl)-3-phenylpropanamide trimaleate salt, and trans-N1-(4-4-amino-7-[4-(4-methylpiperazino)cyclohexyl]-7H-pyrrolo[2,3-d]pyrimidin-5-yl-2-methoxyphenyl)-3-phenylpropanamide tri-maleate.

57. A compound according to claim 1 selected from the group consisting of:

cis-2-(4-4-amino-7-[4-(4-methylpiperazino)cyclohexyl]-7H-pyrrolo[2,3-d]pyrimidin-5-ylphenoxy)-6-[(3-methoxypropyl)amino]benzonitrile tri-maleate, trans-2-(4-4-amino-7-[4-(4-methylpiperazino)cyclohexyl]-7H-pyrrolo[2,3-d]pyrimidin-5-ylphenoxy)-6-[(3-methoxypropyl)amino]benzonitrile tri-maleate, cis-2-amino-6-(4-4-amino-7-[4-(4-methylpiperazino)cyclohexyl]-7H-pyrrolo[2,3-d]pyrimidin-5-ylphenoxy)benzonitrile tri-maleate, trans-2-amino-6-(4-4-amino-7-[4-(4-methylpiperazino)cyclohexyl]-7H-pyrrolo[2,3-d]pyrimidin-5-ylphenoxy)benzonitrile tri-maleate, cis-2-(4-4-amino-7-[4-(4-methylpiperazino)cyclohexyl]-7H-pyrrolo[2,3-d]pyrimidin-5-ylphenoxy)-6-[(4-methylphenyl)sulfanyl]benzonitrile tri-maleate, trans-2-(4-4-amino-7-[4-(4-methylpiperazino)cyclohexyl]-7H-pyrrolo[2,3-d]pyrimidin-5-ylphenoxy)-6-[(4-methylphenyl)sulfanyl]benzonitrile tri-maleate, cis-2-(4-4-amino-7-[4-(4-methylpiperazino)cyclohexyl]-7H-pyrrolo[2,3-d]pyrimidin-5-ylphenoxy)-6-(2-pyridylsulfanyl)benzonitrile tri-maleate, trans-2-(4-4-amino-7-[4-(4-methylpiperazino)cyclohexyl]-7H-pyrrolo[2,3-d]pyrimidin-5-ylphenoxy)-6-(2-pyridylsulfanyl)benzonitrile tri-maleate, cis-5-(2-methyl-4-phenoxyphenyl)-7-[4-(4-methylpiperazino)cyclohexyl]-7H-pyrrolo[2,3-d]pyrimidin-4-amine tri-maleate, trans-5-(2-methyl-4-phenoxyphenyl)-7-[4-(4-methylpiperazino)cyclohexyl]-7H-pyrrolo[2,3-d]pyrimidin-4-amine tri-maleate, cis-N 1-(4-{4-amino-7-[4-(4-methylpiperazino)cyclohexyl]-7H-pyrrolo[2,3-d]pyrimidin-5-yl}-2-fluorophenyl)-4-fluoro-1-benzenesulfonamide tri-maleate, trans-N1-(4-{4-amino-7-[4-(4-methylpiperazino)cyclohexyl]-7H-pyrrolo[2,3-d]pyrimidin-5-yl}-2-fluorophenyl)-4-fluoro-1-benzenesulfonamide tri-maleate, N1-4-[4-amino-7-(1-benzyl-4-piperidyl)-7H-pyrrolo[2,3-d]pyrimidin-5-yl]-2-fluorophenyl-4-fluoro-1-benzenesulfonamide, N1-4-[4-amino-7-(1-benzyl-4-piperidyl)-7H-pyrrolo[2,3-d]pyrimidin-5-yl]-2-fluorophenyl-2,3-dichloro-1-benzenesulfonamide, N1-4-[4-amino-7-(4-piperidyl)-7H-pyrrolo[2,3-d]pyrimidin-5-yl]-2-fluorophenyl-4-fluoro-1-benzenesulfonamide, N1-4-[4-amino-7-(1-formyl-4-piperidyl)-7H-pyrrolo[2,3-d]pyrimidin-5-yl]-2-fluorophenyl-4-fluoro-1-benzenesulfonamide, N1-[4-(4-amino-7-1-[(1-methyl-1H-4-imidazolyl)sulfonyl]-4-piperidyl-7H-pyrrolo[2,3-d]pyrimidin-5-yl)-2-fluorophenyl]-4-fluoro-1-benzenesulfonamide dimaleate, N1-[4-(4-amino-7-1-[(1,2-dimethyl-1H-4-imidazolyl)sulfonyl]-4-piperidyl-7H-pyrrolo[2,3-d]pyrimidin-5-yl)-2-fluorophenyl]-4-fluoro-1-benzenesulfonamide, N1-[4-(4-amino-7-1-[(1,3-dimethyl-1H-5-pyrazolyl)carbonyl]-4-piperidyl-7H-pyrrolo[2,3-d]pyrimidin-5-yl)-2-fluorophenyl]-4-fluoro-1-benzenesulfonamide, and N1-(4-{4-amino-7-[1-(2-pyridylcarbonyl)-4-piperidyl]-7H-pyrrolo[2,3-d]pyrimidin-5-yl}-2-fluorophenyl)-4-fluoro-1-benzenesulfonamide.

58. A compound according to claim 1 selected from the group consisting of:

N1-4-(4-amino-7-{4-[1-(1-methylpiperid-4-yl)piperidyl]-7H-pyrrolo[2,3-d]pyrimidin-5-yl})-2-fluorophenyl-4-fluoro-1-benzenesulfonamide tri-maleate, Trans-N-1-(4-{4-amino-7-[4-(4-methylpiperazino)cyclohexyl]-7H-pyrrolo[2,3-d]pyrimidin-5-yl}-2-fluorophenyl)-2-(trifluoromethoxy)-1-benzenesulfonamide trimaleate, Trans-N-1-(4-{4-amino-7-[4-(4-methylpiperazino)cyclohexyl]-7H-pyrrolo[2,3-d]pyrimidin-5-yl}-2-fluorophenyl)-5-chloro-2-thiophenesulfonamide benzenesulfonamide trimaleate, Trans-N-1-(4-{4-amino-7-[4-(4-methylpiperazino)cyclohexyl]-7H-pyrrolo[2,3-d]pyrimidin-5-yl}-2-fluorophenyl)-2-chloro-4-fluoro-1-benzenesulfonamide benzenesulfonamide trimaleate, Trans-N-1-(4-{4-amino-7-[4-(4-methylpiperazino)cyclohexyl]-7H-pyrrolo[2,3-d]pyrimidin-5-yl}-2-fluorophenyl)-2,3-dichloro-1-benzenesulfonamide trimaleate, cis-N-1-(4-{4-amino-7-[4-(4-methylpiperazino)cyclohexyl]-7H-pyrrolo[2,3-d]pyrimidin-5-yl}-2-fluorophenyl)-2-chloro-4-fluoro-1-benzenesulfonamide trimaleate, cis-N-1-(4-4-amino-7-[4-(4-methylpiperazino)cyclohexyl]-7H-pyrrolo[2,3-d]pyrimidin-5-yl-2-fluorophenyl)-2,5-difluoro-1-benzenesulfonamide trimaleate, Trans-N-1-(4-{4-amino-7-[4-(4-methylpiperazino)cyclohexyl]-7H-pyrrolo[2,3-d]pyrimidin-5-yl}-2-fluorophenyl)-2,6-difluoro-1-benzenesulfonamide trimaleate, Trans-N-4-(4-{4-amino-7-[4-(4-methylpiperazino)cyclohexyl]-7H-pyrrolo[2,3-d]pyrimidin-5-yl}-2-fluorophenyl)-2,1,3-benzothiadiazole-4-sulfonamide trimaleate, Trans-N-1-(4-{4-amino-7-[4-(4-methylpiperazino)cyclohexyl]-7H-pyrrolo[2,3-d]pyrimidin-5-yl}-2-fluorophenyl)-2,3,4-trifluoro-1-benzenesulfonamide trimaleate, cis-N-1-(4-{4-amino-7-[4-(4-methylpiperazino)cyclohexyl]-7H-pyrrolo[2,3-d]pyrimidin-5-yl}-2-fluorophenyl)-2-nitro-1-benzenesulfonamide trimaleate, cis-N-1-(4-{4-amino-7-[4-(4-methylpiperazino)cyclohexyl]-7H-pyrrolo[2,3-d]pyrimidin-5-yl}-2-fluorophenyl)-2-fluoro-1-benzenesulfonamide trimaleate, cis-N-1-(4-{4-amino-7-[4-(4-methylpiperazino)cyclohexyl]-7H-pyrrolo[2,3-d]pyrimidin-5-yl}-2-fluorophenyl)-2,4,6-trichloro-1-benzenesulfonamide trimaleate, cis-N-1-(4-{4-amino-7-[4-(4-methylpiperazino)cyclohexyl]-7H-pyrrolo[2,3-d]pyrimidin-5-yl}-2-fluorophenyl)-2,6-dichloro-1-benzenesulfonamide trimaleate, cis-N-1-(4-{4-amino-7-[4-(4-methylpiperazino)cyclohexyl]-7H-pyrrolo[2,3-d]pyrimidin-5-yl}-2-fluorophenyl)-2-chloro-1-benzenesulfonamide trimaleate, cis-N-1-(4-{4-amino-7-[4-(4-methylpiperazino)cyclohexyl]-7H-pyrrolo[2,3-d]pyrimidin-5-yl}-2-fluorophenyl)-3-fluoro-1-benzenesulfonamide dimaleate, cis-N-1-(4-{4-amino-7-[4-(4-methylpiperazino)cyclohexyl]-7H-pyrrolo[2,3-d]pyrimidin-5-yl}-2-fluorophenyl)-5-chloro-2-thiophenesulfonamide dimaleate, cis-N-1-(4-{4-amino-7-[4-(4-methylpiperazino)cyclohexyl]-7H-pyrrolo[2,3-d]pyrimidin-5-yl}-2-fluorophenyl)-4-bromo-2,6-difluoro-1-benzenesulfonamide trimaleate, cis-N-1-(4-{4-amino-7-[4-(4-methylpiperazino)cyclohexyl]-7H-pyrrolo[2,3-d]pyrimidin-5-yl}-2-fluorophenyl)-3-chloro-4-fluoro-1-benzenesulfonamide trimaleate, and cis-N-1-(4-{4-amino-7-[4-(4-methylpiperazino)cyclohexyl]-7H-pyrrolo[2,3-d]pyrimidin-5-yl}-2-fluorophenyl-2-iodo-1-benzenesulfonamide trimaleate.

59. A compound according to claim 1 selected from the group consisting of:

cis-N-1-(4-{4-amino-7-[4-(4-methylpiperazino)cyclohexyl]-7H-pyrrolo[2,3-d]pyrimidin-5-yl}-2-fluorophenyl)-2-(trifluoromethoxy)-1-benzenesulfonamide trimaleate, cis-N-1-(4-{4-amino-7-[4-(4-methylpiperazino)cyclohexyl]-7H-pyrrolo[2,3-d]pyrimidin-5-yl}-2-fluorophenyl)-2,3-dichloro-1-benzenesulfonamide trimaleate, cis-N-1-(4-{4-amino-7-[4-(4-methylpiperazino)cyclohexyl]-7H-pyrrolo[2,3-d]pyrimidin-5-yl}-2-fluorophenyl)-2-chloro-6-methyl-1-benzenesulfonamide trimaleate, cis-N-1-(4-{4-amino-7-[4-(4-methylpiperazino)cyclohexyl]-7H-pyrrolo[2,3-d]pyrimidin-5-yl}-2-fluorophenyl)-2-chloro-4-cyano-1-benzenesulfonamide trimaleate, cis-N-1-(4-{4-amino-7-[4-(4-methylpiperazino)cyclohexyl]-7H-pyrrolo[2,3-d]pyrimidin-5-yl}-2-fluorophenyl)-2,3,4-trifluoro-1-benzenesulfonamide trimaleate, cis-N-1-(4-{4-amino-7-[4-(4-methylpiperazino)cyclohexyl]-7H-pyrrolo[2,3-d]pyrimidin-5-yl}-2-fluorophenyl)-3,4-difluoro-1-benzenesulfonamide trimaleate, cis-N-1-(4-{4-amino-7-[4-(4-methylpiperazino)cyclohexyl]-7H-pyrrolo[2,3-d]pyrimidin-5-yl}-2-fluorophenyl)-4-bromo-2-fluoro-1-benzenesulfonamide trimaleate, cis-N-1-(4-{4-amino-7-[4-(4-methylpiperazino)cyclohexyl]-7H-pyrrolo[2,3-d]pyrimidin-5-yl}-2-fluorophenyl)-5-bromo-2-thiophenesulfonamide trimaleate, cis-N-1-(4-{4-amino-7-[4-(4-methylpiperazino)cyclohexyl]-7H-pyrrolo[2,3-d]pyrimidin-5-yl}-2-fluorophenyl)-2,4-dichloro-1-benzenesulfonamide trimaleate, cis-N-1-(4-{4-amino-7-[4-(4-methylpiperazino)cyclohexyl]-7H-pyrrolo[2,3-d]pyrimidin-5-yl}-2-fluorophenyl)-2,3,4-trichloro-1-benzenesulfonamide trimaleate, cis-N-1-(4-{4-amino-7-[4-(4-methylpiperazino)cyclohexyl]-7H-pyrrolo[2,3-d]pyrimidin-5-yl}-2-fluorophenyl)-3-bromo-5-chloro-2-thiophenesulfonamide trimaleate, cis-N-4-(4-{4-amino-7-[4-(4-methylpiperazino)cyclohexyl]-7H-pyrrolo[2,3-d]pyrimidin-5-yl}-2-fluorophenyl)-2,1,3-benzothiadiazole-4-sulfonamide trimaleate, cis-N-4-(4-{4-amino-7-[4-(4-methylpiperazino)cyclohexyl]-7H-pyrrolo[2,3-d]pyrimidin-5-yl}-2-fluorophenyl)-2,1,3-benzoxadiazole-4-sulfonamide trimaleate, cis-N-1-(4-{4-amino-7-[4-(4-methylpiperazino)cyclohexyl]-7H-pyrrolo[2,3-d]pyrimidin-5-yl}-2-fluorophenyl)-2,5-dichloro-1-thiophenesulfonamide trimaleate, cis-N-4-(4-{4-amino-7-[4-(4-methylpiperazino)cyclohexyl]-7H-pyrrolo[2,3-d]pyrimidin-5-yl}-2-fluorophenyl)-(7-chloro-2,1,3-benzoxadiazole)-4-sulfonamide trimaleate, cis-N-4-(4-{4-amino-7-[4-(4-methylpiperazino)cyclohexyl]-7H-pyrrolo[2,3-d]pyrimidin-5-yl}-2-fluorophenyl)-(7-methyl-2,1,3-benzothiadiazole)-4-sulfonamide trimaleate, cis-N-4-(4-{4-amino-7-[4-(4-methylpiperazino)cyclohexyl]-7H-pyrrolo[2,3-d]pyrimidin-5-yl}-2-fluorophenyl)-(5-methyl-2,1,3-benzothiadiazole)-4-sulfonamide trimaleate, cis-N-4-(4-{4-amino-7-[4-(4-methylpiperazino)cyclohexyl]-7H-pyrrolo[2,3-d]pyrimidin-5-yl}-2-fluorophenyl)-(5-chloro-2,1,3-benzothiadiazole)-4-sulfonamide trimaleate, cis-N-1-(4-{4-amino-7-[4-(4-methylpiperazino)cyclohexyl]-7H-pyrrolo[2,3-d]pyrimidin-5-yl}-2-fluorophenyl)-3-chloro-2-methyl-1-benzenesulfonamide trimaleate, cis-N-1-(4-{4-amino-7-[4-(4-methylpiperazino)cyclohexyl]-7H-pyrrolo[2,3-d]pyrimidin-5-yl}-2-fluorophenyl)-2-bromo-1-benzenesulfonamide trimaleate, and cis-N-1-(4-{4-amino-7-[4-(4-methylpiperazino)cyclohexyl]-7H-pyrrolo[2,3-d]pyrimidin-5-yl}-2-fluorophenyl)-2,5-dibromo-3,6-difluoro-1-benzenesulfonamide trimaleate.

60. A compound according to claim 1 selected from the group consisting of:

cis-N-1-(4-{4-amino-7-[4-(4-methylpiperazino)cyclohexyl]-7H-pyrrolo[2,3-d]pyrimidin-5-yl}-2-fluorophenyl)-2,3-dichloro-1-benzenesulfonamide trimaleate, cis-N-1-(4-{4-amino-7-[4-(4-methylpiperazino)cyclohexyl]-7H-pyrrolo[2,3-d]pyrimidin-5-yl}-2-fluorophenyl)-(2-nitrophenyl)methanesulfonamide trimaleate, Trans-N-1-(4-{4-amino-7-[4-(4-methylpiperazino)cyclohexyl]-7H-pyrrolo[2,3-d]pyrimidin-5-yl}-2-fluorophenyl)-2-nitro-1-benzenesulfonamide trimaleate, Trans-N-1-(4-{4-amino-7-[4-(4-methylpiperazino)cyclohexyl]-7H-pyrrolo[2,3-d]pyrimidin-5-yl}-2-fluorophenyl)-2-fluoro-1-benzenesulfonamide trimaleate, Trans-N-1-(4-{4-amino-7-[4-(4-methylpiperazino)cyclohexyl]-7H-pyrrolo[2,3-d]pyrimidin-5-yl}-2-fluorophenyl)-2,4,6-trichloro-1-benzenesulfonamide trimaleate, Trans-N-1-(4-{4-amino-7-[4-(4-methylpiperazino)cyclohexyl]-7H-pyrrolo[2,3-d]pyrimidin-5-yl}-2-fluorophenyl)-2,6-dichloro-1-benzenesulfonamide trimaleate, Trans-N-1-(4-{4-amino-7-[4-(4-methylpiperazino)cyclohexyl]-7H-pyrrolo[2,3-d]pyrimidin-5-yl}-2-fluorophenyl)-2-chloro-1-benzenesulfonamide trimaleate, Trans-N-1-(4-{4-amino-7-[4-(4-methylpiperazino)cyclohexyl]-7H-pyrrolo[2,3-d]pyrimidin-5-yl}-2-fluorophenyl)-3-fluoro-1-benzenesulfonamide dimaleate, Trans-N-1-(4-{4-amino-7-[4-(4-methylpiperazino)cyclohexyl]-7H-pyrrolo[2,3-d]pyrimidin-5-yl}-2-fluorophenyl)-4-bromo-2,5-difluoro-1-benzenesulfonamide trimaleate, Trans-N-1-(4-{4-amino-7-[4-(4-methylpiperazino)cyclohexyl]-7H-pyrrolo[2,3-d]pyrimidin-5-yl}-2-fluorophenyl)-3-chloro-4-fluoro-1-benzenesulfonamide trimaleate, Trans-N-1-(4-{4-amino-7-[4-(4-methylpiperazino)cyclohexyl]-7H-pyrrolo[2,3-d]pyrimidin-5-yl}-2-fluorophenyl-2-iodo-1-benzenesulfonamide trimaleate, Trans-N-1-(4-{4-amino-7-[4-(4-methylpiperazino)cyclohexyl]-7H-pyrrolo[2,3-d]pyrimidin-5-yl}-2-fluorophenyl)-2,3-dichloro-1-benzenesulfonamide trimaleate, Trans-N-1-(4-{4-amino-7-[4-(4-methylpiperazino)cyclohexyl]-7H-pyrrolo[2,3-d]pyrimidin-5-yl}-2-fluorophenyl)-2-chloro-6-methyl-1-benzenesulfonamide trimaleate, Trans-N-1-(4-{4-amino-7-[4-(4-methylpiperazino)cyclohexyl]-7H-pyrrolo[2,3-d]pyrimidin-5-yl}-2-fluorophenyl)-2-chloro-4-cyano-1-benzenesulfonamide trimaleate, Trans-N-1-(4-{4-amino-7-[4-(4-methylpiperazino)cyclohexyl]-7H-pyrrolo[2,3-d]pyrimidin-5-yl}-2-fluorophenyl)-3,4-difluoro-1-benzenesulfonamide trimaleate, Trans-N-1-(4-{4-amino-7-[4-(4-methylpiperazino)cyclohexyl]-7H-pyrrolo[2,3-d]pyrimidin-5-yl}-2-fluorophenyl)-4-bromo-2-fluoro-1-benzenesulfonamide trimaleate, Trans-N-1-(4-{4-amino-7-[4-(4-methylpiperazino)cyclohexyl]-7H-pyrrolo[2,3-d]pyrimidin-5-yl}-2-fluorophenyl)-5-bromo-2-thiophenesulfonamide trimaleate, and Trans-N-1-(4-{4-amino-7-[4-(4-methylpiperazino)cyclohexyl]-7H-pyrrolo[2,3-d]pyrimidin-5-yl}-2-fluorophenyl)-2,4-dichloro-1-benzenesulfonamide trimaleate.

61. A compound according to claim 1 selected from the group consisting of:

Trans-N-1-(4-{4-amino-7-[4-(4-methylpiperazino)cyclohexyl]-7H-pyrrolo[2,3-d]pyrimidin-5-yl}-2-fluorophenyl)-2,3,4-trichloro-1-benzenesulfonamide trimaleate, Trans-N-1-(4-{4-amino-7-[4-(4-methylpiperazino)cyclohexyl]-7H-pyrrolo[2,3-d]pyrimidin-5-yl}-2-fluorophenyl)-3-bromo-5-chloro-2-thiophenesulfonamide trimaleate, Trans-N-4-(4-{4-amino-7-[4-(4-methylpiperazino)cyclohexyl]-7H-pyrrolo[2,3-d]pyrimidin-5-yl}-2-fluorophenyl)-2,1,3-benzoxadiazole-4-sulfonamide trimaleate, Trans-N-1-(4-{4-amino-7-[4-(4-methylpiperazino)cyclohexyl]-7H-pyrrolo[2,3-d]pyrimidin-5-yl}-2-fluorophenyl)-2,5-dichloro-1-thiophenesulfonamide trimaleate, Trans-N-4-(4-{4-amino-7-[4-(4-methylpiperazino)cyclohexyl]-7H-pyrrolo[2,3-d]pyrimidin-5-yl}-2-fluorophenyl)-(7-chloro-2,1,3-benzoxadiazole)-4-sulfonamide trimaleate, Trans-N-4-(4-{4-amino-7-[4-(4-methylpiperazino)cyclohexyl]-7H-pyrrolo[2,3-d]pyrimidin-5-yl}-2-fluorophenyl)-(7-methyl-2,1,3-benzothiadiazole)-4-sulfonamide trimaleate, Trans-N-4-(4-{4-amino-7-[4-(4-methylpiperazino)cyclohexyl]-7H-pyrrolo[2,3-d]pyrimidin-5-yl}-2- fluorophenyl)-(5-methyl-2,1,3-benzothiadiazole)-4-sulfonamide trimaleate,

Trans-N-4-(4-{4-amino-7-[4-(4-methylpiperazino)cyclohexyl]-7H-pyrrolo[2,3-d]pyrimidin-5-yl}-2-fluorophenyl)-(5-chloro-2,1,3-benzothiadiazole)-4-sulfonamide trimaleate, Trans-N-1-(4-{4-amino-7-[4-(4-methylpiperazino)cyclohexyl]-7H-pyrrolo[2,3-d]pyrimidin-5-yl}-2-fluorophenyl)-3-chloro-2-methyl-1-benzenesulfonamide trimaleate, Trans-N-1-(4-{4-amino-7-[4-(4-methylpiperazino)cyclohexyl]-7H-pyrrolo[2,3-d]pyrimidin-5-yl}-2-fluorophenyl)-2-bromo-1-benzenesulfonamide trimaleate, Trans-N-1-(4-{4-amino-7-[4-(4-methylpiperazino)cyclohexyl]-7H-pyrrolo[2,3-d]pyrimidin-5-yl}-2-fluorophenyl)-2,5-dibromo-3,6-difluoro-1-benzenesulfonamide trimaleate, and Trans-N-1-(4-{4-amino-7-[4-(4-methylpiperazino)cyclohexyl]-7H-pyrrolo[2,3-d]pyrimidin-5-yl}-2-fluorophenyl)-(2-nitrophenyl)methanesulfonamide trimaleate.

62. A compound represented by the following structural formula:

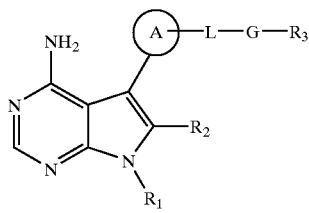

and pharmaceutically acceptable salts thereof, wherein:

Ring A is a five or six membered heteroaromatic ring which is optionally substituted with one or more substituents selected from the group consisting of a substituted or unsubstituted aliphatic group, a halogen, a substituted or unsubstituted aromatic group, substituted or unsubstituted heteroaromatic group, substituted or unsubstituted cycloalkyl, substituted or unsubstituted heterocycloalkyl, substituted or unsubstituted aralkyl, substituted or unsubstituted heteroaralkyl, cyano, nitro, —$NR_4R_5$, —$C(O)_2H$, —OH, a substituted or unsubstituted alkoxycarbonyl, —$C(O)_2$-haloalkyl, a substituted or unsubstituted alkylthio ether, a substituted or unsubstituted alkylsulfoxide, a substituted or unsubstituted alkylsulfone, a substituted or unsubstituted arylthio ether, a substituted or unsubstituted arylsulfoxide, a substituted or unsubstituted arylsulfone, a substituted or unsubstituted alkyl carbonyl, —C(O)-haloalkyl, a substituted or unsubstituted alkoxy group, a substituted or unsubstituted aryloxy group, carboxamido, tetrazolyl, trifluoromethylsulphonamido, trifluoromethylcarbonylamino, a substituted or unsubstituted alkynyl, a substituted or unsubstituted alkenyl, a substituted or unsubstituted alkyl amido, a substituted or unsubstituted aryl amido, —$NR_{95}C(O)R_{95}$, a substituted or unsubstituted styryl and a substituted or unsubstituted aralkyl amido, wherein $R_{95}$ is an aliphatic group or an aromatic group;

L is —N(C(O)OR)—; —N(C(O)R)—; —N($SO_2$R); —$CH_2$S—; —$CH_2$N(R)—; —C(NR)—; —$CH_2$N(C(O)R))—; —$CH_2$N(C(O)OR)—; —$CH_2$N($SO_2$R)—; —CH(NHR)—; —CH(NHC(O)R)—; —CH(NH$SO_2$R)—; —CH(NHC(O)OR)—; —CH(OC(O)R)—; —CH(OC(O)NHR)—; —CH═CH—; —C(═NOR)—; —C(O)—; —CH(OR)—; —N(R)S(O)—; —OC(O)N(R)—; —NRC(O)O—; —S(O)N(R)—; —S(O)$_2$N(R)—; N(C(O)R)S(O)—; N(C(O)R)S(O)$_2$—; —N(R)S(O)N(R)—; —N(R)S(O)$_2$N(R)—; —C(O)N(R)C(O)—; —S(O)N(R)C(O)—; —S(O)$_2$N(R)C(O)—; —OS(O)$_2$N(R)—; —N(R)S(O)O—; —N(R)S(O)$_2$O—; —N(R)S(O)C(O)—; —N(R)S(O)$_2$C(O)—; —SON(C(O)R)—; —$SO_2$N(C(O)R)—; —N(R)SON(R)—; —N(R)$SO_2$N(R)—; —CH(R)S(O)—; —CH(R)S(O)$_2$—; —CH(R)N(C(O)OR)—; —CH(R)N(C(O)R)—; —CH(R)N($SO_2$R); —CH(R)O—; —CH(R)S—; —CH(R)N(R)—; —CH(R)N(C(O)R))—; —CH(R)N(C(O)OR)—; —CH(R)N($SO_2$R)—; —CH(R)C(═NOR)—; —CH(R)C(O)—; —CH(R)CH(OR)—; —CH(R)C(O)N(R)—; —CH(R)N(R)C(O)—; —CH(R)N(R)S(O)—; —CH(R)N(R)S(O)$_2$—; —CH(R)OC(O)N(R)—; —CH(R)N(R)C(O)N(R)—; —CH(R)N(R)C(O)O—; —CH(R)S(O)N(R)—; —CH(R)S(O)$_2$N(R)—; —CH(R)N(C(O)R)S(O)—; —CH(R)N(C(O)R)S(O)$_2$—; —CH(R)N(R)S(O)N(R)—; —CH(R)N(R)S(O)$_2$N(R)—; —CH(R)C(O)N(R)C(O)—; —CH(R)S(O)N(R)C(O)—; —CH(R)S(O)$_2$N(R)C(O)—; —CH(R)OS(O)N(R)—; —CH(R)OS(O)$_2$N(R)—; —CH(R)N(R)S(O)O—; —CH(R)N(R)S(O)$_2$O—; —CH(R)N(R)S(O)C(O)—; —CH(R)N(R)S(O)$_2$C(O)—; —CH(R)SON(C(O)R)—; —CH(R)S(O)$_2$N(C(O)R)—; —CH(R)N(R)SON(R)—; —CH(R)N(R)S(O)$_2$N(R)—; or —CH(R)C(O)O—, wherein each R and R' is, independently, —H, an acyl group, a substituted or unsubstituted aliphatic group, a substituted or unsubstituted aromatic group, a substituted or unsubstituted arylalkyl group, a substituted or unsubstituted heteroaromatic group, or a substituted or unsubstituted cycloalkyl group or a substituted or unsubstituted arylalkyl group; or L is —$R_b$N(R)S(O)$_2$— wherein $R_b$ is an alkylene group which when taken together with the sulphonamide group to which it is bound forms a five or six membered ring fused to ring A;

G is a direct bond; —$CH_2$)$_j$—, wherein j is 1 to 6; a $C_2$–$C_6$-alkenylene group, a $C_3$–$C_8$—cycloalkylene group or a $C_1$–$C_6$-oxaalkylene group;

$R_1$ is a substituted aliphatic group, a substituted cycloalkyl, a substituted bicycloalkyl, a substituted cycloalkenyl, an optionally substituted aromatic group, an optionally substituted heteroaromatic group, an optionally substituted heteroaralkyl, an optionally substituted heterocycloalkyl, an optionally substituted heterobicycloalkyl, an optionally substituted alkylamido, and optionally substituted arylamido, an optionally substituted —S(O)$_2$-alkyl or optionally substituted —S(O)$_2$-cycloalkyl, a —C(O)-alkyl or an optionally substituted —C(O)-alkyl, provided that when $R_1$ is an aliphatic group or cycloalkyl group, $R_1$ is not exclusively substituted with one or more substitutents selected from the group consisting of hydroxyl and lower alkyl ethers, provided that the heterocycloalkyl is not 2-phenyl-1,3-dioxan-5-yl and provided that an aliphatic group is not substituted exclusively with one or more aliphatic groups;

wherein one or more substituents are selected from the group consisting of a substituted or unsubstituted aliphatic group, a substituted or unsubstituted aromatic group, a substituted or unsubstituted heteroaromatic, a substituted or unsubstituted aralkyl, a substituted or unsubstituted heteroaralkyl, a substituted or unsubstituted cycloalkyl, a substituted or unsubstituted heterocycloalkyl, a substituted or unsubstituted aromatic ether, a substituted or unsubstituted aliphatic ether, a substituted or unsubstituted alkoxycarbonyl, a substituted or unsubstituted alkylcarbonyl, a substituted or unsubstituted arylcarbonyl, a substituted or unsubstituted heteroarylcarbonyl, substituted or unsubstituted aryloxycarbonyl, —OH, a substituted or unsubstituted aminocarbonyl, an oxime, a substituted or unsubstituted azabicycloalkyl, heterocycloalkyl, oxo, aldehyde, a substituted or unsubstituted alkyl sulfonamido group, a substituted or unsubstituted aryl sulfonamido group, a substituted or unsubstituted bicycloalkyl, a substituted or unsubstituted heterobicycloalkyl, cyano, —$NH_2$, an alkylamino, ureido, thioureido; or $R_1$ is —B—E, wherein
 B is a substituted or unsubstituted cycloalkyl, a substituted or unsubstituted heterocycloalkyl, a substituted or unsubstituted aromatic, a substituted or unsubstituted heteroaromatic, an alkylene, an aminoalkyl, an alkylenecarbnonyl, or an aminoalkylcarbonyl; and
 E is a substituted or unsubstituted azacycloalkyl, a substituted or unsubstituted azacycloalkylcarbonyl, a substituted or unsubstituted azacycloalkylsulfonyl, a substituted or unsubstituted azacycloalkylalkyl, a substituted or unsubstituted heteroaryl, a substituted or unsubstituted heteroarylcarbonyl, a substituted or unsubstituted heteroarylsulfonyl, a substituted or unsubstituted heteroaralkyl, a substituted or unsubstituted alkyl sulfonamido, a substituted or unsubstituted aryl sulfonamido, a substituted or unsubstituted bicycloalkyl, a substituted or unsubstituted ureido, a substituted or unsubstituted thioureido or a substituted or unsubstituted aryl;

$R_2$ is —H, a substituted or unsubstituted aliphatic group, a substituted or unsubstituted cycloalkyl, a halogen, —OH, cyano, a substituted or unsubstituted aromatic group, a substituted or unsubstituted heteroaromatic group, a substituted or unsubstituted heterocycloalkyl, a substituted or unsubstituted aralkyl, a substituted or unsubstituted heteroaralkyl, —$(CH_2)_{0-3}NR_4R_5$, or —$CH_2)_{3-3}C(O)NR_4R_5$;

$R_3$ is an unsubstituted aliphatic group, a substituted or unsubstituted alkenyl group, a substituted or unsubstituted cycloalkyl, a substituted or unsubstituted aromatic group, a substituted or unsubstituted heteroaromatic group, or a substituted or unsubstituted heterocycloalkyl;

provided that L is —SN(R)—, —S(O)N(R)—, —$S(O)_2$N(R)—, —N(R)S—, —N(R)S(O)—, —N(R)S$(O)_2$—, —N(R)SN(R')—, —N(R)S(O)N(R')—, or —N(R)S(O)$_2$N(R')— when $R_3$ is a substituted aliphatic group, a substituted or unsubstituted alkenyl group;
 provided that when L is —O—, —$CH_2$NR—, —C(O) NR— or —NRC(O)— and $R_3$ is azacycloalkyl or azaheteroaryl, G is a direct bond; a $C_2$-$C_6$-alkenylene group, a $C_3$-$C_8$-cycloalkylene group or a $C_3$-$C_6$-oxaalkylene; and
 provided that when L is —O— and $R_3$ is phenyl, G is a direct bond; a $C_2$-$C_6$-alkenylene group, a $C_3$-$C_8$-cycloalkylene group or a $C_1$-$C_6$-oxaalkylene;

$R_4$, $R_5$ and the nitrogen atom together form a 3, 4, 5, 6 or 7-membered, substituted or unsubstituted heterocycloalkyl, substituted or unsubstituted heterobicycloalkyl or a substituted or unsubstituted heteroaromatic; or
 $R_4$ and $R_5$ are each, independently, —H, azabicycloalkyl, heterocycloalkyl, a substituted or unsubstituted alkyl group or Y—Z;
 Y is selected from the group consisting of —C(O)—, —$(CH_2)_p$—, —$S(O)_2$—, —C(O)O—, —$SO_2NH$—, —CONH—, —$(CH_2)_pO$—, —$(CH_2)_pNH$—, —$(CH_2)_pS$—, —$(CH_2)_pS(O)$—, and —$(CH_2)_pS(O)_2$—;
 p is an integer from 0 to 6; and
 Z is —H, a substituted or unsubstituted alkyl, substituted or unsubstituted amino, substituted or unsubstituted aryl, substituted or unsubstituted heteroaryl or substituted or unsubstituted heterocycloalkyl group.

63. A compound represented by the following structural formula:

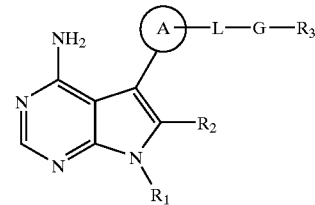

and pharmaceutically acceptable salts thereof, wherein:
 Ring A is a six membered aromatic ring or a five or six membered heteroaromatic ring which is optionally substituted with one or more substituents selected from the group consisting of a substituted or unsubstituted aliphatic group, a halogen, a substituted or unsubstituted aromatic group, substituted or unsubstituted heteroaromatic group, substituted or unsubstituted cycloalkyl, substituted or unsubstituted heterocycloalkyl, substituted or unsubstituted aralkyl, substituted or unsubstituted heteroaralkyl, cyano, nitro, —$NR_4R_5$, —$C(O)_2H$, —OH, a substituted or unsubstituted alkoxycarbonyl, —$C(O)_2$—haloalkyl, a substituted or unsubstituted alkylthio ether, a substituted or unsubstituted alkylsulfoxide, a substituted or unsubstituted alkylsulfone, a substituted or unsubstituted arylthio ether, a substituted or unsubstituted arylsulfoxide, a substituted or unsubstituted arylsulfone, a substituted or unsubstituted alkyl carbonyl, —C(O)-haloalkyl, a substituted or unsubstituted alkoxy group, a substituted or unsubstituted aryloxy group, carboxamido, tetrazolyl, tri fluoromethylsulphonamido, trifluoromethylcarbonylamino, a substituted or unsubstituted alkynyl, a substituted or unsubstituted alkenyl, a substituted or unsubstituted alkyl amido, a substituted or unsubstituted aryl amido, —$NR_{95}C(O)R_{95}$, a substituted or unsubstituted styryl and a substituted or unsubstituted aralkyl amido, wherein $R_{95}$ is an aliphatic group or an aromatic group;

L is —O—; —S—; —S(O)—; —$S(O)_2$—; —N(R)—; —N(C(O)OR)—; —N(C(O)R)—; —N($SO_2$R); —$CH_2$S—; —$CH_2$N(R)—; —C(NR)—; —$CH_2$N(C(O)R)—; —$CH_2$N(C(O)OR)—; —$CH_2$N($SO_2$R)—; —CH(NHR)—; —CH(NHC(O)R)—; —CH(NH$SO_2$R)—; —CH(NHC(O)OR)—; —CH(OC(O)R)—; —CH(OC(O)NHR)—; —CH=CH—; —C(=NOR)—; —C(O)—; —CH(OR)—; —C(O)N(R)—; —N(R)C(O)—; —N(R)S(O)—; —N(R)S (O)₂—; —OC(O)N(R)—; —N(R)C(O)N(R)—; —NRC(O)O—; —S(O)N(R)—; —S(O)N(R)—; N(C(O)R)S(O)—; N(C(O)R)S(O)₂—; —N(R)S(O)N(R)—; —N(R)S(O)₂N(R)—; —C(O)N(R)C(O)—; —S(O)N(R)C(O)—; —S(O)₂N(R)C(O)—; —OS(O)N(R)—; —OS(O)₂N(R)—; —N(R)S(O)O—; —N(R)S(O)₂O—; —N(R)S(O)C(O)—; —N(R)S(O)₂C(O)—; —SON(C(O)R)—; —SO₂N(C(O)R)—; —N(R)SON(R)—; —N(R)SO₂N(R)—; —C(O)O—; —CH(R)S(O)—; —CH(R)S(O)₂—; —CH(R)N(C(O)OR)—; —CH(R)N(C(O)R)—; —CH(R)N(SO₂R); —CH(R)O—; —CH(R)S—; —CH(R)N(R)—; —CH(R)N(C(O)R))—; —CH(R)N(C(O)OR)—; —CH(R)N(SO₂R)—; —CH(R)C(=NOR)—; —CH(R)C(O)—; —CH(R)CH(OR)—; —CH(R)C(O)N(R)—; —CH(R)N(R)C(O)—; —CH(R)N(R)S(O)—; —CH(R)N(R)S(O)₂—; —CH(R)OC(O)N(R)—; —CH(R)N(R)C(O)N(R)—; —CH(R)N(R)C(O)O—; —CH(R)S(O)N(R)—; —CH(R)S(O)₂N(R)—; —CH(R)N(C(O)R)S(O)—; —CH(R)N(C(O)R)S(O)₂—; —CH(R)N(R)S(O)N(R)—; —CH(R)N(R)S(O)₂N(R)—; —CH(R)C(O)N(R)C(O)—; —CH(R)S(O)N(R)C(O)—; —CH(R)S(O)₂N(R)C(O)—; —CH(R)OS(O)N(R)—; —CH(R)OS(O)₂N(R)—; —CH(R)N(R)S(O)O—; —CH(R)N(R)S(O)₂O—; —CH(R)N(R)S(O)C(O)—; —CH(R)N(R)S(O)₂C(O)—; —CH(R)SON(C(O)R)—; —CH(R)S(O)₂N(C(O)R)—; —CH(R)N(R)SON(R)—; —CH(R)N(R)S(O)₂N(R)—; or —CH(R)C(O)O—, wherein each R and R' is, independently, —H, an acyl group, a substituted or unsubstituted aliphatic group, a substituted or unsubstituted aromatic group, a substituted or unsubstituted arylalkyl group, a substituted or unsubstituted heteroaromatic group, or a substituted or unsubstituted cycloalkyl group or a substituted or unsubstituted arylalkyl group; or L is —R_bN(R)S(O)₂— wherein R_b is an alkylene group which when taken together with the sulphonamide group to which it is bound forms a five or six membered ring fused to ring A;

G is a direct bond; —CH₂)_j—, wherein j is 1 to 6; a C₂–C₆-alkenylene group, a C₃–C₈-cycloalkylene group or a C₁–C₆-oxaalkylene group;

R₁ is a substituted aliphatic group, a substituted cycloalkyl, a substituted bicycloalkyl, a substituted cycloalkenyl, an optionally substituted aromatic group, an optionally substituted heteroaromatic group, an optionally substituted heteroaralkyl, an optionally substituted heterocycloalkyl, an optionally substituted heterobicycloalkyl, an optionally substituted alkylamido, and optionally substituted arylamido, an optionally substituted —S(O)₂-alkyl or optionally substituted —S(O)₂-Cycloalkyl, a —C(O)-alkyl or an optionally substituted —(O)-alkyl, provided that when R₁ is an aliphatic group or cycloalkyl group, R₁ is not exclusively substituted with one or more substitutents selected from the group consisting of hydroxyl and lower alkyl ethers, provided that the heterocycloalkyl is not 2-phenyl-1,3-dioxan-5-yl and provided that an aliphatic group is not substituted exclusively with one or more aliphatic groups;

wherein one or more substituents are selected from the group consisting of a substituted or unsubstituted aliphatic group, a substituted or unsubstituted aromatic group, a substituted or unsubstituted heteroaromatic, a substituted or unsubstituted aralkyl, a substituted or unsubstituted heteroaralkyl, a substituted or unsubstituted cycloalkyl, a substituted or unsubstituted heterocycloalkyl, a substituted or unsubstituted aromatic ether, a substituted or unsubstituted aliphatic ether, a substituted or unsubstituted alkoxycarbonyl, a substituted or unsubstituted alkylcarbonyl, a substituted or unsubstituted arylcarbonyl, a substituted or unsubstituted heteroarylcarbonyl, substituted or unsubstituted aryloxycarbonyl, —OH, a substituted or unsubstituted aminocarbonyl, an oxime, a substituted or unsubstituted azabicycloalkyl, heterocycloalkyl, oxo, aldehyde, a substituted or unsubstituted alkyl sulfonamido group, a substituted or unsubstituted aryl sulfonamido group, a substituted or unsubstituted bicycloalkyl, a substituted or unsubstituted heterobicycloalkyl, cyano, —NH₂, an alkylamino, ureido, thioureido; or R₁ is —B—E, wherein
  B is a substituted or unsubstituted cycloalkyl, a substituted or unsubstituted heterocycloalkyl, a substituted or unsubstituted aromatic, a substituted or unsubstituted heteroaromatic, an alkylene, an aminoalkyl, an alkylenecarbnonyl, or an aminoalkylcarbonyl; and
  E is a substituted or unsubstituted azacycloalkyl, a substituted or unsubstituted azacycloalkylcarbonyl, a substituted or unsubstituted azacycloalkylsulfonyl, a substituted or unsubstituted azacycloalkylalkyl, a substituted or unsubstituted heteroaryl, a substituted or unsubstituted heteroarylcarbonyl, a substituted or unsubstituted heteroarylsulfonyl, a substituted or unsubstituted heteroaralkyl, a substituted or unsubstituted alkyl sulfonamido, a substituted or unsubstituted aryl sulfonamido, a substituted or unsubstituted bicycloalkyl, a substituted or unsubstituted ureido, a substituted or unsubstituted thioureido or a substituted or unsubstituted aryl;

R₂ is —H, a substituted or unsubstituted aliphatic group, a substituted or unsubstituted cycloalkyl, a halogen, —OH, cyano, a substituted or unsubstituted aromatic group, a substituted or unsubstituted heteroaromatic group, a substituted or unsubstituted heterocycloalkyl, a substituted or unsubstituted aralkyl, a substituted or unsubstituted heteroaralkyl, —(CH₂)₀₋₃NR₄R₅, or CH₂)₀₋₃C(O)NR₄R₅;

R₃ is selected from the group consisting of

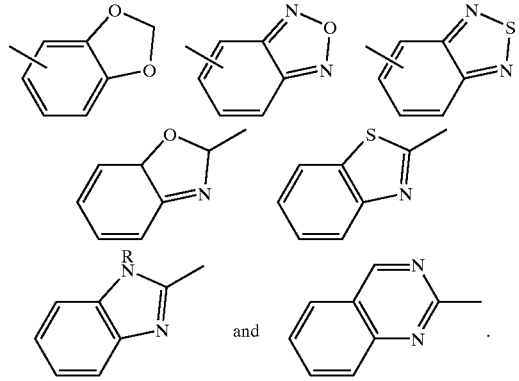

wherein R is hydrogen or alkyl;
provided that when L is —O—, —CH₂NR—, —C(O)NR— or —NRC(O)— and R₃ is azacycloalkyl or azaheteroaryl, G is a direct bond; a C₂–C₆-alkenylene group, a C₃–C₈-cycloalkylene group or a C₁–C₆-oxaalkylene;
R₄, R₅ and the nitrogen atom together form a 3, 4, 5, 6 or 7-membered, substituted or unsubstituted heterocycloalkyl, substituted or unsubstituted heterobicycloalkyl or a substituted or unsubstituted heteroaromatic; or $R_4$ and $R_5$ are each, independently, —H, azabicycloalkyl, heterocycloalkyl, a substituted or unsubstituted alkyl group or Y—Z;

Y is selected from the group consisting of —C(O)—, —(CH$_2$)$_p$—, —S(O)$_2$—, —C(O)O—, —SO$_2$NH—, —CONH—, —(CH$_2$)$_p$O—, —(CH$_2$)$_p$NH—, —(CH$_2$)$_p$S—, —(CH$_2$)$_p$S(O)—, and —(CH$_2$)$_p$S(O)$_2$—;

p is an integer from 0 to 6; and

Z is —H, a substituted or unsubstituted alkyl, substituted or unsubstituted amino, substituted or unsubstituted aryl, substituted or unsubstituted heteroaryl or substituted or unsubstituted heterocycloalkyl group.

64. A method of affecting angiogenesis or vascular permeability in a patient, comprising the step of administering to the patient a therapeutically effective amount of a compound of claim 1 or a physiologically acceptable salt thereof.

65. A method of treating a patient having a condition by promoting angiogenesis or vasculogenesis, comprising the step of administering to the patient a therapeutically effective amount of a compound of claim 1 or a physiologically acceptable salt wherein the condition is selected from the group consisting of anemia, ischemia, infarct, transplant rejection, a wound, gangrene and necrosis.

66. The method of claim 65 wherein the compound of Formula I, or physiologically acceptable salt thereof, is administered in combination with a pro-angiogenic growth factor.

67. The method of claim 66 wherein the pro-angiogenic growth factor is selected from the group consisiting of VEGF, VEGF-B, VEGF-C, VEGF-D, VEGF-E, HGF, FGF-1, FGF-2, derivatives thereof and antiiodotypic antibodies.

68. A method of decreasing fertility in a patient, said method comprising the step of administering to the patient an effective amount of a compound of claim 1 or a physiologically acceptable salt thereof.

69. A method of treating a patient having a condition, comprising the step of administering to the patient a therapeutically effective amount of a compound of claim 1 wherein the condition is selected from the group consisting of one or more ulcers, an ulcer or ulcers caused by a bacterial or fungal infection, an ulcer or ulcers that are a symptom of ulcerative colitis, Lyme disease, sepsis, septic shock, infection by Herpes simplex, Herpes Zoster, human immunodeficiency virus, parapoxvirus, protozoa or toxopasmosis, von Hippel Lindau disease, pemphigoid, psoriasis, Paget's disease, polycycstic kidney disease, fibrosis, sarcoidosis, cirrhosis, thyroiditis, hyperviscosity syndrome, Osler-Weber-Rendu disease, chronic occlusive pulmonary disease, asthma, exudtaes, ascites, pleural effusions, pulmonary edema, cerebral edema or edema following bums, trauma, radiation, stroke, hypoxia, iscbemia, ovarian hyperstimulation syndrome, preeclampsia, menometrorrhagia, endometriosis, glomemlonephritis, synovitis, inflammatory bowel disease, rheumatoid arthritis, osteoarthritis, graft rejection, sickle cell anaemia, ocular or macular edema, ocular neovascular disease, scleritis, uveitis, vitritis, myopia, optic pits, chronic retinal detachment, post-laser treatment complications, conjunctivitis, Stargardt's disease, Eales disease, retinopathy, macular degeneration, atherosclerosis, restenosis, ischemia/reperfusion injury, vascular occlusion, venous malformation, carotid obstructive disease, fibrosarcoma, osteoma, melanoma, retinoblastoma, a rhabdomyosarcoma, glioblastoma, neuroblastoma, teratocarcinoma, hematopoietic malignancy, malignant ascites, Kaposi's sarcoma, Hodgkin's disease, lymphoma, myeloma, leukemia, Crow-Fukase (POEMS) syndrome, insulin-dependent diabetes mellitus glaucoma, diabetic retinopathy or microangiopathy.

70. The method of claim 60, further comprising the step of administering to the patient a therapeutically effective amount of a compound of Formula I or physiologically acceptable salt thereof administered in combination with a proangiogenic growth factor selected from the group consisting of VEGF, VEGF-B, VEFG-C, VEGF-D, VEGF-E, HGF, FGF-1, FGF-2, derivatives thereof and antiiodotypic antibodies.

* * * * *